US012552803B2

(12) United States Patent
Yamamoto et al.

(10) Patent No.: US 12,552,803 B2
(45) **Date of Patent: *Feb. 17, 2026**

(54) ORGANIC ELECTROLUMINESCENT ELEMENT, MATERIAL FOR ORGANIC ELECTROLUMINESCENT ELEMENT, LIGHT EMITTING DEVICE, DISPLAY DEVICE AND LIGHTING DEVICE EACH USING SAID ELEMENT, AND COMPOUND USED FOR SAID ELEMENT

(71) Applicant: UDC IRELAND LIMITED, Dublin (IE)

(72) Inventors: Yosuke Yamamoto, Kanagawa (JP); Kousuke Watanabe, Kanagawa (JP); Yuichiro Itai, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 305 days.

This patent is subject to a terminal disclaimer.

(21) Appl. No.: 17/173,532

(22) Filed: Feb. 11, 2021

(65) Prior Publication Data

US 2022/0336752 A1 Oct. 20, 2022

Related U.S. Application Data

(63) Continuation of application No. 14/351,151, filed as application No. PCT/JP2012/080131 on Nov. 21, 2012, now Pat. No. 11,171,293.

(30) Foreign Application Priority Data

Nov. 22, 2011 (JP) ................................ 2011-254821

(51) Int. Cl.
*C07D 487/06* (2006.01)
*C07D 487/16* (2006.01)
(Continued)

(52) U.S. Cl.
CPC ......... *C07D 487/06* (2013.01); *C07D 487/16* (2013.01); *C07D 491/16* (2013.01);
(Continued)

(58) Field of Classification Search
CPC ............. H01L 51/0071; H01L 51/0072; H01L 51/5016; C07D 487/06; C07D 487/16;
(Continued)

(56) References Cited

U.S. PATENT DOCUMENTS

2002/0121638 A1 9/2002 Grushin
2007/0034863 A1 2/2007 Fortte
(Continued)

FOREIGN PATENT DOCUMENTS

JP 2010087496 4/2010
JP 2010087496 A 4/2010
(Continued)

OTHER PUBLICATIONS

Claude Niebel et al, Dibenzo[2,3:5,6]pyrrolizino[1,7-bc]indolo[1,2,3-lm]car-bazole: a new electron donor, New Journal of Chemistry, New J. Chem., 2010, vol. 34, p. 1243-1246, Compounds 3, 6 and 7, 5 pages.
(Continued)

*Primary Examiner* — Elizabeth M. Dahlburg
(74) *Attorney, Agent, or Firm* — Riverside Law LLP

(57) ABSTRACT

An organic electroluminescent element including a substrate, a pair of electrodes including an anode and a cathode, disposed on the substrate, and at least one organic layer including a light emitting layer, disposed between the electrodes, in which at least one layer of the organic layer(s) contains a compound represented by the following formula, has low driving voltage and excellent durability.
(Continued)

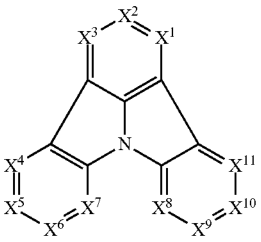

($X^1$ to $X^{11}$ represent $CR^0$ or N, and $R^0$ represents a hydrogen atom or a substituent. Adjacent two of $X^1$ to $X^{11}$ each independently represent at least $CR^0$, $R^0$s of the adjacent two $CR^0$s are bonded to each other to form a ring, and only one $R^0$ of the adjacent two $CR^0$s represents an aryl group or a heteroaryl group.)

13 Claims, 1 Drawing Sheet

(51) Int. Cl.

| | |
|---|---|
| ***C07D 491/16*** | (2006.01) |
| ***C07D 495/16*** | (2006.01) |
| ***C07D 519/00*** | (2006.01) |
| ***H10K 50/11*** | (2023.01) |
| ***H10K 85/60*** | (2023.01) |
| *H10K 85/30* | (2023.01) |
| *H10K 101/10* | (2023.01) |

(52) U.S. Cl.
CPC ......... *C07D 495/16* (2013.01); *C07D 519/00* (2013.01); *H10K 85/654* (2023.02); *H10K 85/657* (2023.02); *H10K 85/6572* (2023.02); *H10K 50/11* (2023.02); *H10K 85/324* (2023.02); *H10K 85/342* (2023.02); *H10K 85/622* (2023.02); *H10K 85/631* (2023.02); *H10K 2101/10* (2023.02)

(58) Field of Classification Search
CPC .. C07D 491/06; C07D 491/16; C07D 495/06; C07D 495/16; C07D 517/06; C07D 517/16; C07D 519/00; H10K 85/657; H10K 85/6572; H10K 2101/10; C09K 11/06
See application file for complete search history.

(56) References Cited

U.S. PATENT DOCUMENTS

| | | | | |
|---|---|---|---|---|
| 2010/0051928 | A1 | 3/2010 | Fukuzaki | |
| 2011/0062429 | A1 | 3/2011 | Kai | |
| 2012/0326141 | A1 | 12/2012 | Pflumm | |
| 2013/0001542 | A1 | 1/2013 | Okajima | |
| 2013/0026422 | A1* | 1/2013 | Parham ................ | C07D 498/16 544/31 |

FOREIGN PATENT DOCUMENTS

| | | | |
|---|---|---|---|
| JP | 2011216640 | | 9/2011 |
| JP | 2012049523 | A | 3/2012 |
| JP | 2012072099 | A | 4/2012 |
| JP | 2012191031 | A | 10/2012 |
| JP | 2013507330 | | 3/2013 |
| JP | 2013523847 | | 6/2013 |
| JP | 2017128415 | | 7/2017 |
| JP | 2017199925 | | 11/2017 |
| JP | 6582018 | | 9/2019 |
| JP | 2020004964 | A | 1/2020 |
| JP | 6830511 | | 2/2021 |
| JP | 6830511 | B2 | 2/2021 |
| KR | 101161598 | B1 | 4/2012 |
| WO | 0202714 | A2 | 1/2002 |
| WO | 0215645 | A1 | 2/2002 |
| WO | 2005033244 | | 4/2005 |
| WO | 2010131855 | | 11/2010 |
| WO | 2011042107 | | 4/2011 |
| WO | 2011060867 | A1 | 5/2011 |
| WO | 2011088877 | A1 | 7/2011 |
| WO | 2011110262 | | 9/2011 |
| WO | 2011128017 | | 10/2011 |
| WO | 2011128017 | A1 | 10/2011 |
| WO | 2013077344 | | 5/2013 |

OTHER PUBLICATIONS

The International Preliminary Report on Patentability for International Patent Application No. PCT/JP2012/080131, dated May 27, 2014, 6 pages.
The International Search Report for International Patent Application No. PCT/JP2012/080131, dated Feb. 26, 2013, 3 pages.
The Written Opinion for International Patent Application No. PCT/JP2012/080131, dated Feb. 26, 2013, 5 pages.
German Office Action for Application No. 112012004870.9, dated Dec. 4, 2019, 7 pages.
Japanese Office Action (with English language translation) issued May 12, 2020, in App. No. JP2019-115225, 10 pages.
Korean Office Action (with English language translation) for Application No. KR10-2019-7035479, dated Feb. 11, 2020, 12 pages.
Korean Office Action for App. No. KR10-2020-7032189, dated Nov. 26, 2020, 7 pages.
Notice of Allowance dated Jul. 13, 2020 for U.S. Appl. No. 14/351,151 (pp. 1-8).
Notice of Allowance dated Nov. 5, 2020 for U.S. Appl. No. 14/351,151 (pp. 1-8).
Office Action dated Jan. 10, 2019 for U.S. Appl. No. 14/351,151 (pp. 1-13).
Office Action dated Jul. 12, 2018 for U.S. Appl. No. 14/351,151 (pp. 1-11).
Office Action dated Mar. 3, 2020 for U.S. Appl. No. 14/351,151 (pp. 1-18).
Niebel, Claude et al., "Dibenzo[2,3:5,6]pyrrolizino[1,7-bc]indolo[1,2,3-m]carbazole: a new electron donor". In: New journal of chemistry, vol. 34, 2010, No. 7, S. 1243-1246, ISSN 0398-9836.

* cited by examiner

ORGANIC ELECTROLUMINESCENT ELEMENT, MATERIAL FOR ORGANIC ELECTROLUMINESCENT ELEMENT, LIGHT EMITTING DEVICE, DISPLAY DEVICE AND LIGHTING DEVICE EACH USING SAID ELEMENT, AND COMPOUND USED FOR SAID ELEMENT

CROSS REFERENCE TO RELATED APPLICATIONS

This application is a continuation of pending application U.S. application Ser. No. 14/351,151, filed Jul. 7, 2014, which is a U.S. national phase application filed under 35 U.S.C. § 371 claiming benefit to PCT International Patent Application No. PCT/JP2012/080131, filed Nov. 21, 2012, which claims the benefit of and priority to Japanese Patent Application No. 2011-254821, filed Nov. 22, 2011, each of which disclosures is incorporated herein by reference in its entirety.

TECHNICAL FIELD

The present invention relates to an organic electroluminescent element, a material for an organic electroluminescent element, alight emitting device, a display device, and an illumination device each using the element, and a compound used in the element.

BACKGROUND ART

Since organic electroluminescent elements (which may hereinafter also be referred to as "elements" or "organic EL elements") are capable of high-luminance light emitting with driving at a low voltage, they have been actively researched and developed. The organic electroluminescent elements have organic layers between a pair of electrodes, and utilize, for light emitting, energy of an exciton generated as a result of recombination of electrons injected from a cathode and holes injected from an anode in the organic layer.

In recent years, by using phosphorescent light emitting materials, the efficiency of organic electroluminescent elements is being enhanced. For practical use, however, improvements are required in terms of reduction in driving voltage, durability, and the like.

Meanwhile, an organic electroluminescent element which uses, as a host material of the light emitting layer, a compound having a structure obtained from triphenylamine by allowing the phenyl groups therein to be connected to each other to undergo ring fusion, and thus, form a carbazole ring, has been known.

PTL 1 describes an organic electroluminescent element, which uses a compound of a structure obtained from triphenylamine by allowing two or three phenyl groups therein to be connected to each other to undergo ring fusion as a host material of the light emitting layer, and is combined with a phosphorescent light emitting material. Further, it can be seen from Examples in this document that the element is excellent in driving voltage and luminous efficiency.

On the other hand, PTL 2 describes a polycyclic fused compound further having a fused ring in a carbazole ring, and also describes that the compound is used in an organic electroluminescent element. However, the document does not describe a compound of a fused structure obtained from triphenylamine by allowing two or more phenyl groups therein to be connected to each other to undergo ring fusion.

PTL 3 describes a compound of a fused structure obtained from triphenylamine by allowing two phenyl groups therein to be connected to each other to undergo ring fusion, and also describes that an organic electroluminescent element having good luminous efficiency and low driving voltage can be provided by using the compound as a host material of a light emitting layer.

CITATION LIST

Patent Literature

[PTL 1] WO2011/042107
[PTL 2] WO2010/131855
[PTL 3] JP-A-2010-087496

SUMMARY OF INVENTION

Technical Problem

In view of the above description, the present inventors have conducted studies on the characteristics of the organic electroluminescent elements described in PTLs 1 to 3, and as a result, they have found that the elements of the PTLs 1 to 3 were not satisfactory in the reduction in driving voltage and also not satisfactory in durability.

It is an object of the present invention to provide an organic electroluminescent element which has low driving voltage and excellent durability by solving the aforementioned problems.

Solution to Problem

The present inventors have conducted extensive investigations, and as a result, they have found that an organic electroluminescent element having low driving voltage and excellent durability is provided by using a compound obtained by allowing aryl groups or heteroaryl groups of two 6-membered rings of an amine tri-substituted with aryl groups or heteroaryl groups of a 6-membered ring to be connected to each other to undergo ring fusion, and having aryl groups or heteroaryl groups as a substituent, in which the substituents are fused at a specific position.

That is, the present invention which is a specific means for solving the problem described above is as follows.

[1] An organic electroluminescent element including a substrate, a pair of electrodes including an anode and a cathode, disposed on the substrate, and at least one organic layer including a light emitting layer, disposed between the electrodes, in which at least one layer of the organic layer(s) contains a compound represented by the following general formula (1).

General Formula (1)

[Chem. 1]

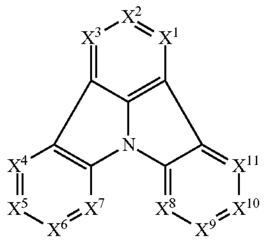

(In the general formula (1), $X^1$ to $X^{11}$ each independently represent $CR^0$ or N, and $R^0$s each independently represent a hydrogen atom or a substituent. Adjacent two of $X^1$ to $X^{11}$ each independently represent at least $CR^0$, $R^0$s of the adjacent two $CR^0$s are bonded to each other to form a ring, and only one $R^0$ of the adjacent two $CR^0$s represents an aryl group or a heteroaryl group. However, in the case where $X^7$ and $X^8$ each independently represent $CR^0$, $R^0$ contained in $X^7$ and $R^0$ contained in $X^8$ are not bonded to each other to form a ring.)

[2] In the organic electroluminescent element as described in [1], in the general formula (1), one $R^0$ of the adjacent two $CR^0$s, in which $R^0$s are bonded to each other to forma ring, preferably represents an aryl group or a heteroaryl group of a 6-membered ring.

[3] In the organic electroluminescent element as described in [1] or [2], the compound represented by the general formula (1) is preferably a compound represented by any one of the following general Formulae (2) to (9).

[Chem. 2]

(2)

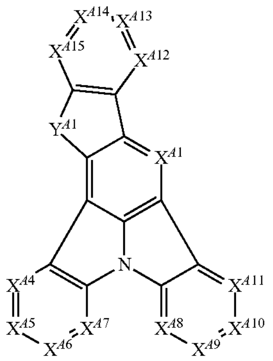

(3)

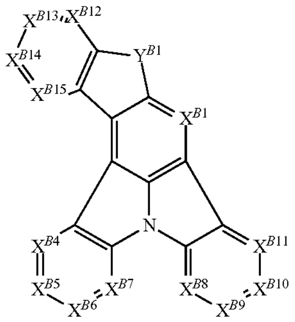

(4)

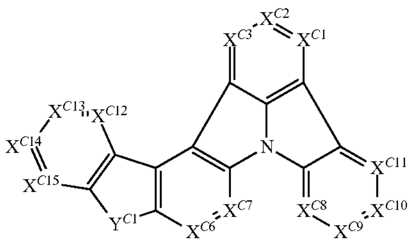

-continued (5)

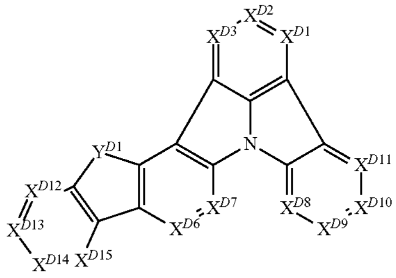

(6)

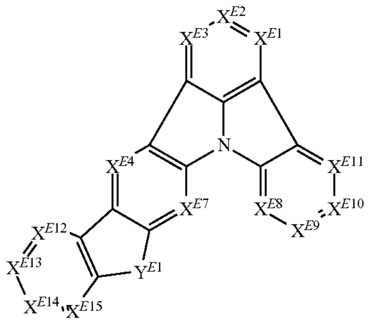

(7)

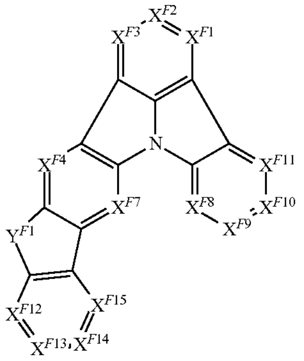

(8)

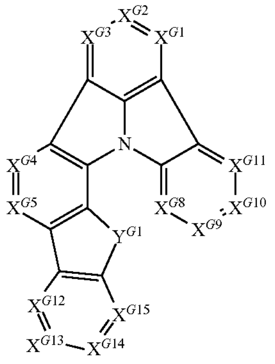

-continued (9)

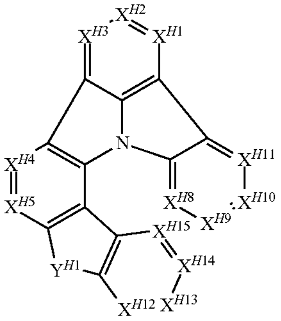

(In the general formulae (2) to (9), $Y^{A1}$ to $Y^{H1}$ each independently represent $CR^1R^2$, $NR^3$, O, S, or Se, $R^1$ to $R^3$ each independently represent a substituent, $X^{A1}$ to $X^{A15}$, $X^{B1}$ to $X^{B15}$, $X^{C1}$ to $X^{C15}$, $X^{D1}$ to $X^{D15}$, $X^{E1}$ to $X^{E15}$, $X^{F1}$ to $X^{F15}$, $X^{G1}$ to $X^{G15}$ and $X^{H1}$ to $X^{H15}$ each independently represent $CR^4$ or N, and $CR^4$s each independently represent a hydrogen atom or a substituent.)

[4] In the organic electroluminescent element as described in [1] or [2], the compound represented by the general formula (1) is preferably a compound represented by any one of the following general formulae (10) to (17).

(10)

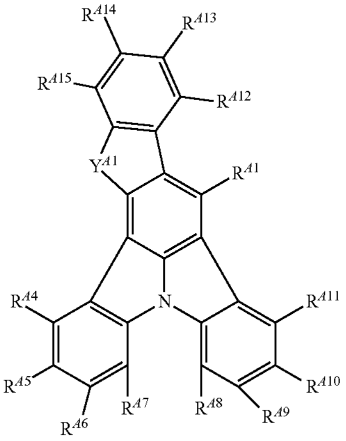

(11)

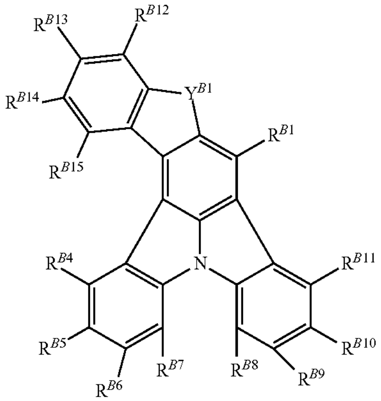

-continued (12)

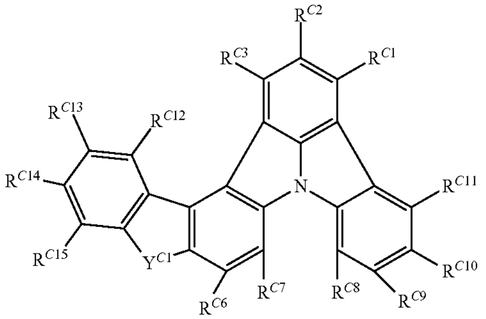

(13)

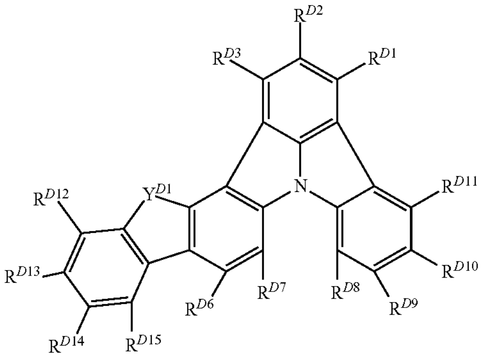

(14)

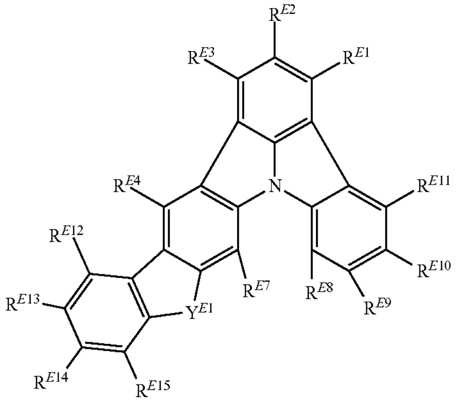

(15)

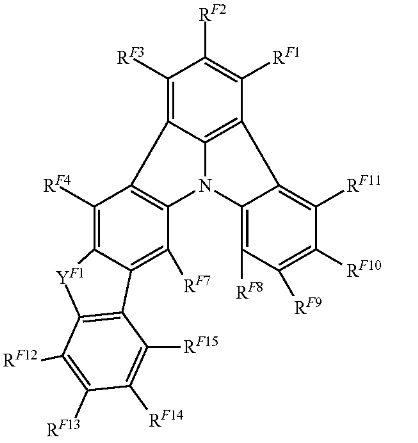

-continued (16)

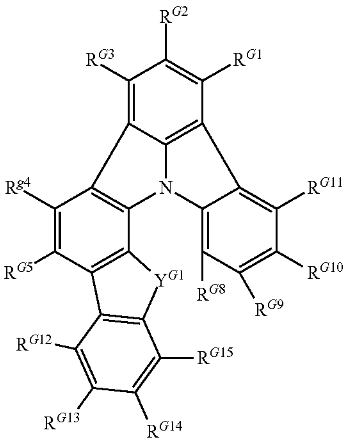

(17)

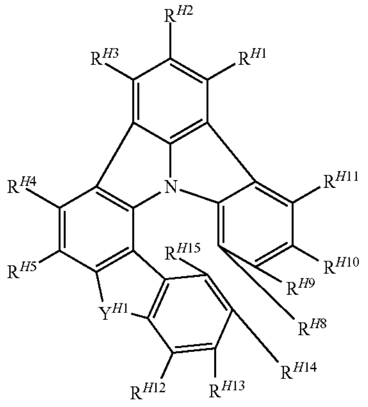

(In the general formulae (10) to (17), $Y^{A1}$ to $Y^{H1}$ each independently represent $CR^1R^2$, $NR^3$, O, S, or Se, and $R^1$ to $R^3$ each independently represent a substituent. $R^{A1}$ to $R^{A15}$, $R^{B1}$ to $R^{B15}$, $R^{C1}$ to $R^{C15}$ to $R^{D1}$ to $R^{D15}$, $R^{E1}$ to $R^{E15}$, $R^{F1}$ to $R^{F15}$, $R^{G1}$ to $R^{G15}$ and $R^{H1}$ to $R^{H15}$ each independently represent a hydrogen atom or a substituent.)

[5] In the organic electroluminescent element as described in any one of [1] to [4], the value of LUMO of the compound represented by the general formula (1), as determined by an electron density functional theory (B3LYP/6-31G (d) level), is preferably more than 1.25.

[6] In the organic electroluminescent element as described in any one of [1] to [5], the compound represented by the general formula (1) preferably has a substituent containing at least one of a pyridine ring, a pyrimidine ring, a triazine ring, a cyano group, and a carbonyl group.

[7] In the organic electroluminescent element as described in any one of [1] to [6], the light emitting layer preferably contains at least one kind of phosphorescent light emitting material.

[8] In the organic electroluminescent element as described in any one of [1] to [6], the phosphorescent light emitting material is preferably an iridium complex represented by the following general formula (E-1).

[Chem. 4]

(E-1)

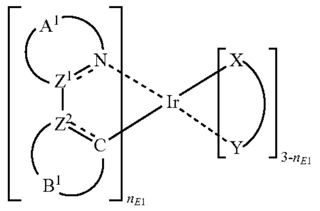

(In the general formula (E-1), $Z^1$ and $Z^2$ each independently represent a carbon atom or a nitrogen atom.

$A^1$ represents an atomic group that forms a 5- or 6-membered hetero ring together with $Z^1$ and a nitrogen atom.

$B^1$ represents an atomic group that forms a 5- or 6-membered ring together with $Z^2$ and a carbon atom.

(X—Y) represents a mono-anionic bidentate ligand.

$n_{E1}$ represents an integer of 1 to 3.)

[9] In the organic electroluminescent element as described in [8], the iridium complex represented by the general formula (E-1) is preferably represented by the following general formula (E-2).

[Chem. 5]

(E-2)

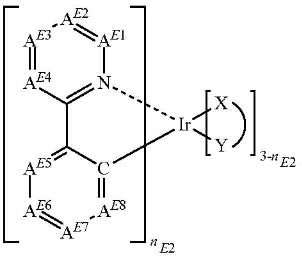

(In the general formula (E-2), $A^{E1}$ to $A^{E8}$ each independently represents a nitrogen atom or C—$R^E$.

$R^E$ represents a hydrogen atom or a substituent.

(X—Y) represents a mono-anionic bidentate ligand.

$n_{E2}$ represents an integer of 1 to 3.)

[10] In the organic electroluminescent element as described in any one of [1] to [9], the light emitting layer preferably contains the compound as described in any one of [1] to [6].

[11] A light emitting device using the organic electroluminescent element as described in any one of [1] to [10].

[12] A display device using the organic electroluminescent element as described in any one of [1] to [10].

[13] An illumination device using the organic electroluminescent element as described in any ore of [1] to [10].

[14] A compound represented by the following general formula (1).

[Chem. 6]

General Formula (1)

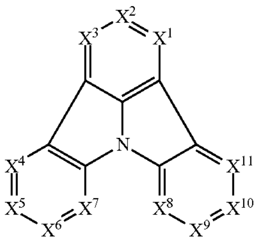

(In the general formula (1), $X^1$ to $X^{11}$ each independently represent $CR^0$ or N, and $R^0$s each independently represent a hydrogen atom or a substituent. Adjacent two of $X^1$ to $X^{11}$ each independently represent at least $CR^0$, $R^0$s of the adjacent two $CR^0$s are bonded to each other to form a ring, and only one $R^0$ of the adjacent two $CR^0$s represents an aryl group or a heteroaryl group. However, in the case where $X^7$ and $X^8$ each independently represent $CR^0$, $R^0$ contained in $X^7$ and $R^0$ contained in $X^8$ are not bonded to each other to form a ring.)

[15] The compound as described in [14] is preferably represented by any one of the following general formulae (2) to (9).

[Chem. 7]

(2)

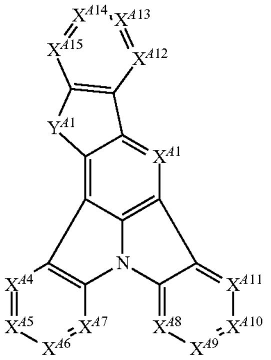

(3)

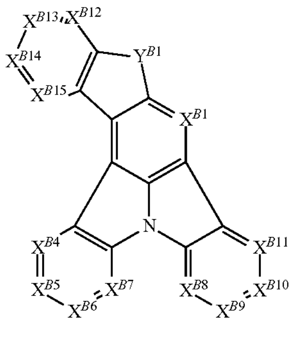

-continued (4)

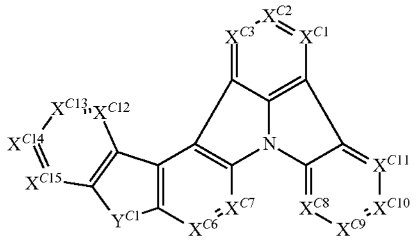

(5)

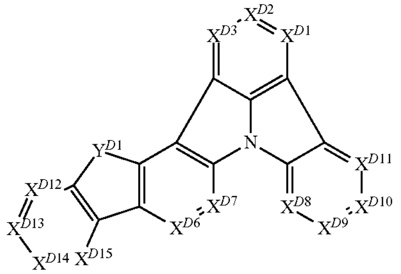

(6)

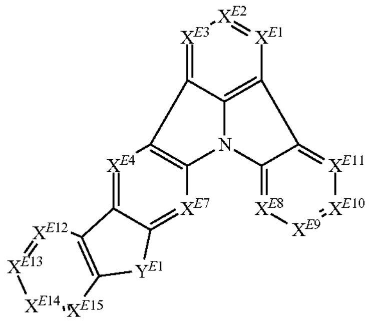

(7)

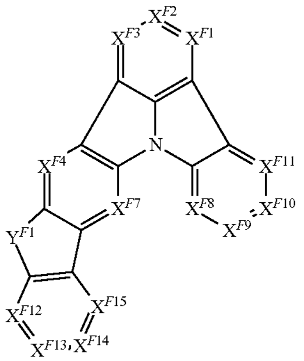

(8)

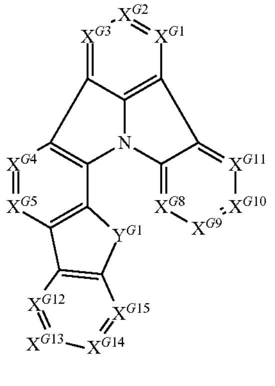

-continued (9)

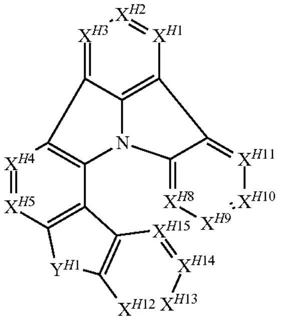

(In the general formulae (2) to (9), $Y^{A1}$ to $Y_{H1}$ each independently represent $CR^1R^2$, $NR^3$, O, S, or Se, and $R^1$ to $R^3$ each independently represent a substituent. $X^{A1}$ to $X^{A15}$, $X^{B1}$ to $X^{B15}$, $X^{C1}$ to $X^{C15}$, $X^{D1}$ to $X^{D15}$, $X^{E1}$ to $X^{E15}$, $X^{F1}$ to $X^{F15}$, $X^{G1}$ to $X^{G15}$ and $X^{H1}$ to $X^{H15}$ each independently represent $CR^4$ or N, and $CR^4$s each independently represent a hydrogen atom or a substituent.)

[16] The compound as described in [14] or [15] is preferably represented by anyone of the following general formulae (10) to (17).

[Chem. 8]

(10)

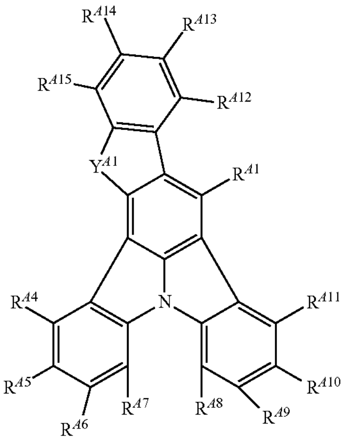

(11)

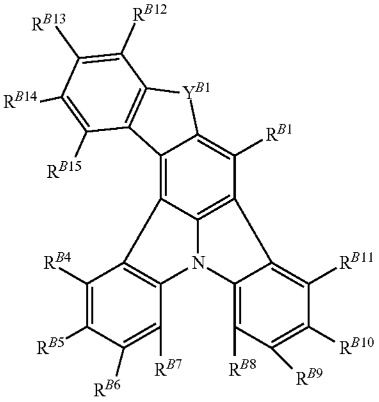

-continued (12)

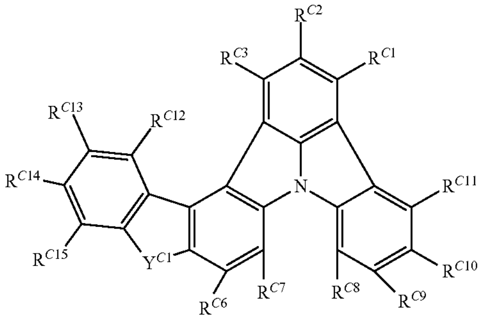

(13)

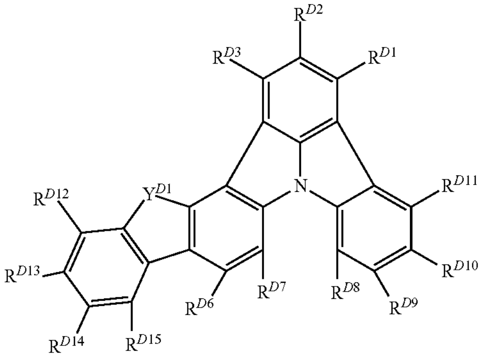

(14)

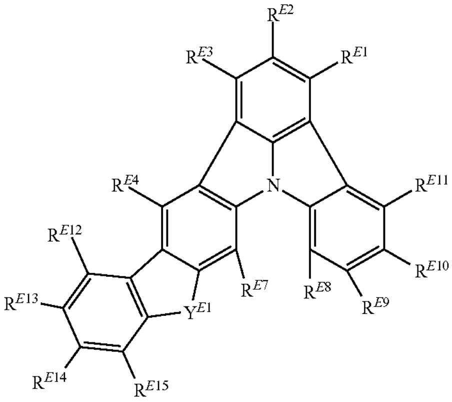

(15)

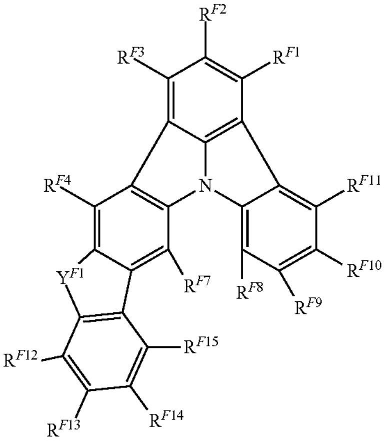

-continued (16)

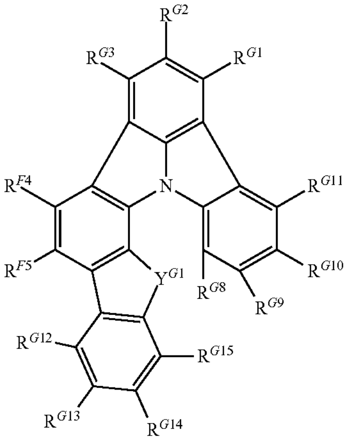

(17)

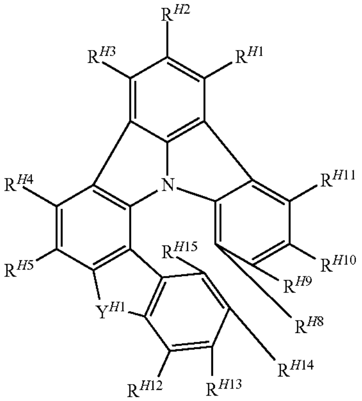

(In the general formulae (10) to (17), $Y^{A1}$ to $Y^{H1}$ each independently represent $CR^1R^2$, $NR^3$, O, S, or Se, and $R^1$ to $R^3$ each independently represent a substituent. $R^{A1}$ to $R^{A15}$, $R^{B1}$ to $R^{B15}$, $R^{C1}$ to $R^{C15}$, $R^{D1}$ to $R^{D15}$, $R^{E1}$ to $R^{E15}$, $R^{F1}$ to $R^{F15}$, $R^{G1}$ to $R^{G15}$ and $R^{H1}$ to $R^{H15}$ each independently represent a hydrogen atom or a substituent.)

[17] A material for an organic electroluminescent element, represented by the following general formula (1).

General Formula (1)

[Chem. 9]

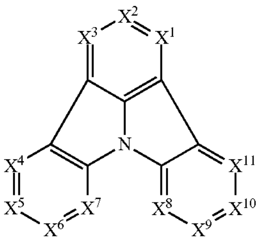

(In the general formula (1), $X^1$ to $X^{11}$ each independently represent $CR^0$ or N, and $R^0$s each independently represent a hydrogen atom or a substituent. Adjacent two of $X^1$ to $X^{11}$ each independently represent at least $CR^0$, $R^0$ s of the adjacent two $CR^0$s are bonded to each other to form a ring, and only one $R^0$ of the adjacent two $CR^0$s represents an aryl group or a heteroaryl group. However, in the case where $X^7$ and $X^8$ each independently represent $CR^0$, $R^0$ contained in $X^7$ and $R^0$ contained in $X^8$ are not bonded to each other to form a ring.)

[18] The material for an organic electroluminescent element as described in [17] is preferably represented by any one of the following general formulae (2) to (9).

[Chem. 10]

(2)

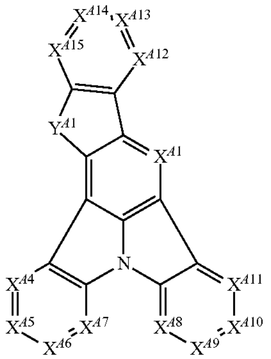

(3)

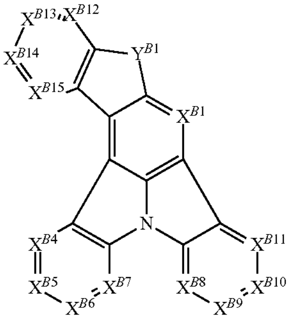

(4)

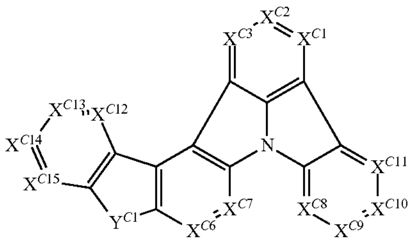

(5)

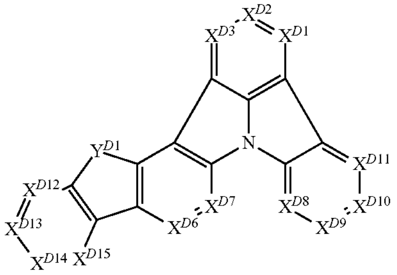

-continued (6)

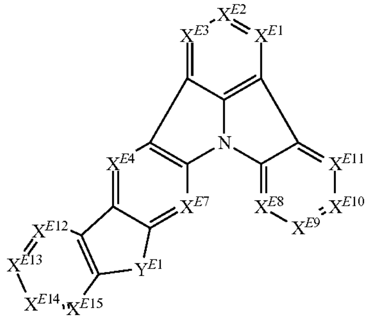

(7)

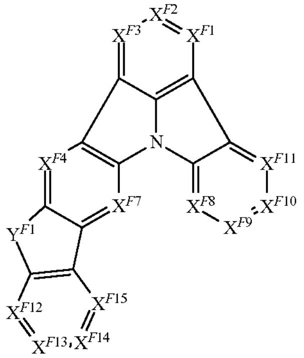

(8)

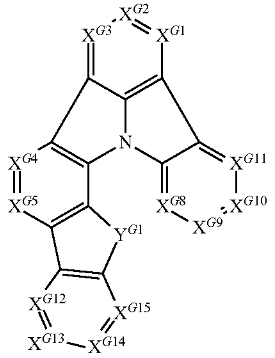

(9)

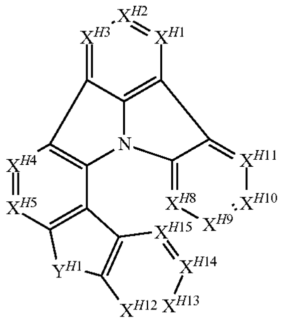

(In the general formulae (2) to (9), $Y^{A1}$ to $Y^{H1}$ each independently represent $CR^1R^2$, $NR^3$, O, S, or Se, and $R^1$ to $R^3$ each independently represent a substituent. $X^{A1}$ to $X^{A15}$, $X^{B1}$ to $X^{B15}$, $X^{C1}$ to $X^{C15}$, $X^{D1}$ to $X^{D15}$, $X^{E1}$ to $X^{E15}$, $X^{F1}$ to $X^{F15}$, $X^{G1}$ to $X^{G15}$ and $X^{H1}$ to $X^{H15}$ each independently represent $CR^4$ or N, and $CR^4$s each independently represent a hydrogen atom or a substituent.)

[19] The material for an organic electroluminescent element as described in [17] or [18] is preferably represented by any one of the following general formulae (10) to (17).

[Chem. 11]

(10)

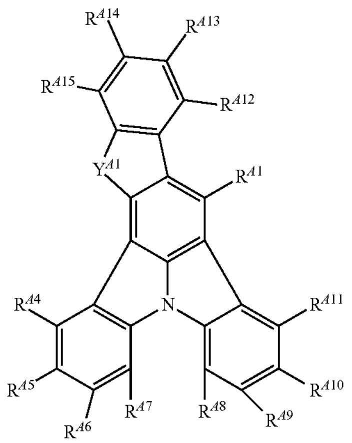

(11)

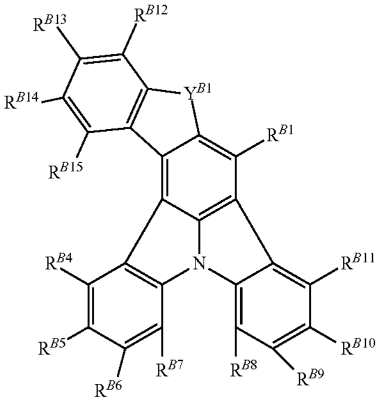

(12)

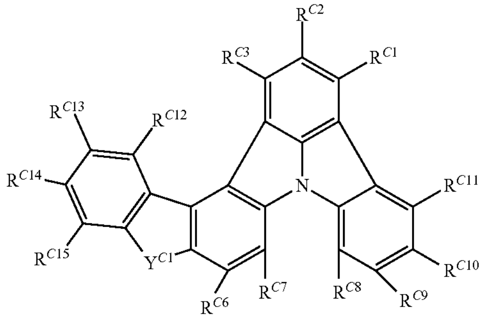

(13)

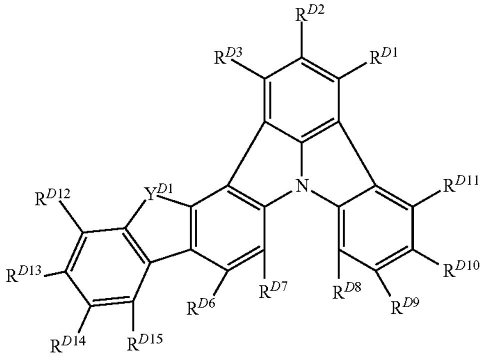

-continued (14)

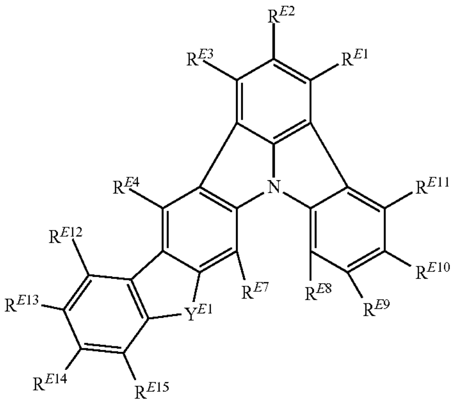

(15)

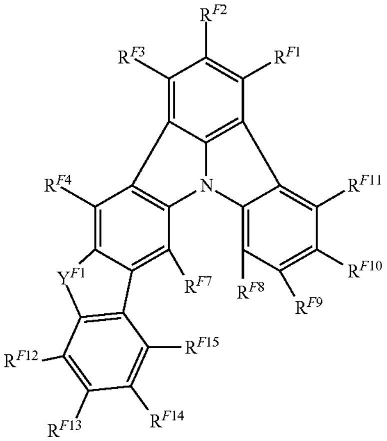

(16)

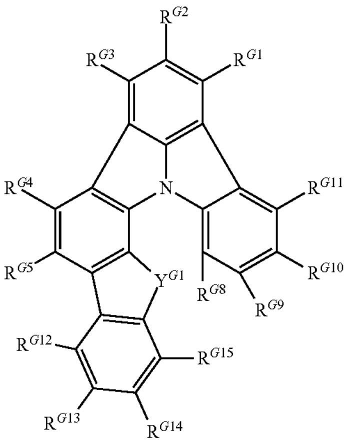

-continued (17)

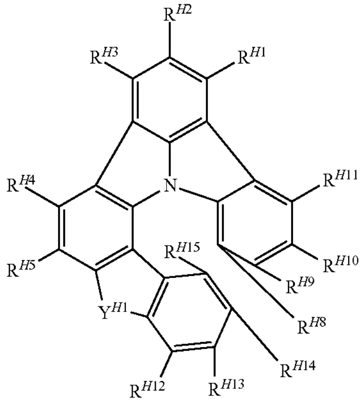

(In the general formula (10) to (17), $Y^{A1}$ to $Y^{H1}$ each independently represent $CR^1R^2$, $NR^3$, O, S, or Se, and $R^1$ to $R^3$ each independently represent a substituent. $R^{A1}$ to $R^{A15}$, $R^{B1}$ to $R^{B15}$, $R^{C1}$ to $R^{C15}$, $R^{D1}$ to $R^{D15}$, $R^{E1}$ to $R^{E15}$, $R^{F1}$ to $R^{F15}$, $R^{G1}$ to $R^{G15}$ and $R^{H1}$ to $R^{H15}$ each independently represent a hydrogen atom or a substituent.)

Advantageous Effects of Invention

According to the present invention, an organic electroluminescent element having low driving voltage and excellent durability can be provided.

In addition, according to the present invention, a light emitting device, a display device, and an illumination device each using the organic electroluminescent element can also be provided.

DESCRIPTION OF EMBODIMENTS

Hereinbelow, the details of the present invention will be described. The description of the configuration requirements as described below may be based on representative embodiments of the present invention, but the present invention is not limited to these embodiments. Incidentally, in the present specification, the range expressed with "to" means a range including the numerical values before and after "to" as the lower limit and the upper limit, respectively.

[Organic Electroluminescent Element, Compound, and Material for Organic Electroluminescent Element]

The compound of the present invention and the material for an organic electroluminescent element of the present invention may be represented by the general formula (1).

The organic electroluminescent element of the present invention may include a substrate, a pair of electrodes including an anode and a cathode, disposed on the substrate, and at least one organic layer including a light emitting layer, disposed between the electrodes, in which at least one layer of the organic layer(s) may contain the compound represented by the general formula (1).

Figure 1:
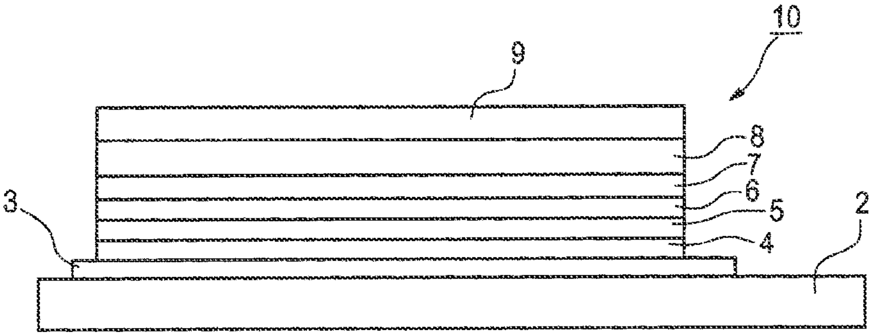
FIG. 1 is a schematic view showing one example of the configuration of an organic electroluminescent element according to the present invention.

The configuration of the organic electroluminescent element of the present invention is not particularly limited. FIG. 1 shows an example of the configuration of the organic electroluminescent element of the present invention. An organic electroluminescent element 10 in FIG. 1 includes organic layers between a pair of electrodes (an anode 3, and a cathode 9) on a substrate 2.

The element configuration, and the substrate, the anode, and the cathode of the organic: electroluminescent element are described in detail, for example, in JP-A-2008-270736, and the matters described in the patent publication can be applied to the present invention.

Hereinafter, preferred embodiments of the organic electroluminescent element of the present invention will be described, in the order of the substrate, the electrode, the organic layer, the protective layer, the sealing enclosure, the driving method, the light emitting wavelength, and applications thereof.

<Substrate>

The organic electroluminescent element of the present invention has a substrate.

The substrate used in the present invention is preferably a substrate that does not scatter or decay light emitted from the organic layer. In the case of an organic material, those having excellent heat resistance, dimensional stability, solvent resistance, electrical insulating properties, and processability are preferred.

<Electrodes>

The organic electroluminescent element of the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be typically one having a function as an electrode of supplying holes into an organic layer, and is not particularly limited in its shape, structure, size, or the like. Further, depending on the use and purpose of the light emitting element, the anode can be suitably selected from the known electrode materials. As described above, the anode is usually provided as a transparent anode.

(Cathode)

The cathode may be typically one having a function as an electrode of injecting electrons to an organic layer, and is not particularly limited in its shape, structure, size, or the like. Further, depending on the use and purpose of the light emitting element, the cathode can be suitably selected from the known electrode materials.

<Organic Layer>

The organic electroluminescent element of the present invention includes organic layers disposed between the electrodes, in which the organic layer(s) contains the compound represented by the general formula (1).

The organic layer is not particularly limited and can be suitably selected depending on the use and purpose of the organic electroluminescent element. However, the organic layer is preferably formed on the transparent electrode or the semi-transparent electrode. In that case, the organic layer is formed on the whole surface or one surface of the transparent electrode or the semi-transparent electrode.

The shape, the size, the thickness, and the like of the organic layer are not particularly limited and can be suitably selected depending on the purpose.

Hereinafter, the configuration of the organic layer, the method for forming an organic layer, preferred aspects of the respective layers constituting the organic layer, and the materials used in the respective layers in the organic electroluminescent element of the present invention will be described in detail in order.

(Configuration of Organic Layers)

In the organic electroluminescent element of the present invention, the organic layers preferably include a charge transporting layer. The charge transporting layer means a layer, in which charge transfer occurs when a voltage is applied to the organic electroluminescent element. Specific examples of the charge transporting layer include a hole injecting layer, a hole transporting layer, an electron blocking layer, a light emitting layer, a hole blocking layer, an electron transporting layer, and an electron injecting layer.

The organic electroluminescent element of the present invention includes a light emitting layer containing a phosphorescent light emitting material and other organic layers, the light emitting layer preferably containing a compound represented by the general formula (1). Here, the place where the compound represented by the general formula (1) is included is not particularly limited, but the light emitting layer preferably contains the compound represented by the general formula (1). Here, the compound represented by the general formula (1) is preferably used as a host compound of the light emitting layer. In addition, in the organic electroluminescent element of the present invention, the organic layers preferably include a light emitting layer containing the phosphorescent light emitting material and other organic layers. In the organic electroluminescent element of the present invention, however, even when the organic layers include a light emitting layer and other organic layers, the layers are not required to be clearly distinguished from one another.

Furthermore, preferably the organic electroluminescent element of the present invention has an electron transporting layer adjacent to the cathode between the pair of electrodes, optionally has an hole blocking layer adjacent to the cathode of the electron transporting layer, and the electron transporting layer or the hole blocking layer preferably contains the compound represented by the general formula (1).

Each of these organic layers may include a plurality of layers, and in the case of providing a plurality of layers, the layers may be formed from the same material or may be formed from different materials for respective layers.

(Method for Forming Organic Layer)

The respective organic layers in the organic electroluminescent element of the present invention can be suitably formed by any of dry film forming methods such as a deposition method and a sputtering method, and wet type film formation methods (solution coating methods) such as a transfer method, a printing method, a spin coating method, and a bar coating method.

In the organic electroluminescent element of the present invention, the organic layer disposed on the pair of electrodes preferably includes at least a layer formed by the deposition of a composition further including the compound represented by the general formula (1).

(Light Emitting Layer)

The light emitting layer is a layer having a function of, upon application of an electric field, receiving holes from the anode, the hole injecting layer or the hole transporting layer, receiving electrons from the cathode, the electron injecting layer or the electron transporting layer, providing a recombination site of the holes and the electrons, and thereby causing light emitting. However, the light emitting layer in the present invention is not necessarily limited to the light emitting by such a mechanism. The light emitting layer in the organic electroluminescent element of the present invention preferably contains at least one kind of phosphorescent light emitting material.

The light emitting layer in the organic electroluminescent element of the present invention may be constituted of only the phosphorescent light emitting material, or may be constituted as a mixed layer of a host material and the phosphorescent light emitting material. One kind or two or more kinds of phosphorescent light emitting materials may be used. The host material is preferably a charge transporting material. One kind or two or more kinds of materials may be used as the host material. Examples thereof include a configuration in which an electron transporting host material and a hole transporting host material are mixed. In addition, the light emitting layer may contain a material which does not have charge transporting property and does not emit light.

In addition, the light emitting layer may be made of a single layer or multiple layers including two or more layers. The layers may include the same light emitting material or host material, or also may include different materials for the respective layers. In the case where a plurality of light emitting layers are present, the light emitting layers may emit light in different luminous colors from one another.

The thickness of the light emitting layer is not particularly limited, but it is usually from 2 nm to 500 nm, and above all, from the viewpoint of external quantum efficiency, it is more preferably from 3 nm to 200 nm, and still more preferably from 5 nm to 100 nm.

In the organic electroluminescent element of the present invention, in a preferred embodiment, the light emitting layer preferably contains a compound represented by the general formula (1), and in a more preferred embodiment, the compound represented by the general formula (1) is used as a host material of the light emitting layer. Here, the host material as referred to in the present specification is a compound which chiefly plays a role in injecting or transporting charges in the light emitting layer and is also a compound which does not substantially emit light in itself. As used herein, it is meant by the terms "which does not substantially emit light" that the amount of light emission from the compound which does not substantially emit light is preferably 5% or less, more preferably 3% or less, and still more preferably 1% or less, with respect to the total amount of light emission in the whole of the element.

Hereinafter, as the materials of the light emitting layer, the compound represented by the general formula (1), the phosphorescent light emitting material, and host materials other than the compound represented by the general formula (1) will be described in this order. Further, the compound represented by the general formula (1) may be used as a material other than the light emitting layer in the organic electroluminescent element of the present invention.

(1) Compound Represented by General Formula (1)

It is reported that the phenylcarbazole described in WO2010/131855 and the like has cleavage of a bond between N of carbazole and C of a phenyl group cleaved, as a result of the analysis of decomposed products after element deterioration (J. Appl. Phys. 2007, 101, 024512). Meanwhile, a compound having an indolocarbazole skeleton represented by the following general formula (1), or a skeleton formed by substituting a specific position of a carbon atom in the indolocarbazole skeleton with a nitrogen atom can increase the durability of the obtained organic electroluminescent element. Not wishing to be restricted to any reason, the present inventors have contemplated that as suggested by the above articles, a cause of deteriorating the durability consists in the bond cleavage of the cause of deteriorating the durability, and a compound having an indolocarbazole skeleton represented by the following general formula (1), or a skeleton formed by substituting a specific position of a carbon atom in the indolocarbazole skeleton with a nitrogen atom has high durability by inhibiting the bond cleavage or promoting the rebonding after the bond cleavage.

Here, indolocarbazole compounds that have been well-known in the related art did not have an additional fused ring in indolocarbazole. Such the indolocarbazole compounds have a high ionization potential (=a high value of HOMO), and a hole injection barrier from a hole transporting layer is high, and thus, has not yet reached an element driving voltage at a level for practical use. In the present invention, by subjecting a compound having an indolocarbazole skeleton and a compound having a skeleton formed by substituting a specific position of a carbon atom in the indolocarbazole skeleton to ring fusion on a π plane, the element driving voltage can be reduced, as compared with indolocarbazole having no fused ring. Not wishing to be restricted to any reason, it is contemplated that it is possible to decrease the ionization potential (=to decrease value of HOMO), and as a result, a hole injection barrier from a hole transporting layer has been alleviated.

In addition, for the compound having an indolocarbazole skeleton described in WO2011/042107 and JP-A-2010-087496, there is a description that the indolocarbazole skeleton is further fused, but there is no exemplification of the specific compounds, and since there is a problem in the number of ring members constituting the skeleton and the positions of the fused rings, it can be seen that it is difficult to satisfy both of durability and reduction in a driving voltage.

A compound represented by the following general formula (1) will be described below.

General Formula (1)

[Chem. 12]

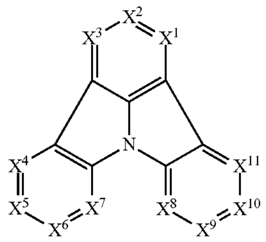

(In the general formula (1), $X^1$ to $X^{11}$ each independently represent $CR^0$ or N, and $R^0$s each independently represent a hydrogen atom or a substituent. Adjacent two of $X^1$ to $X^{11}$ each independently represent at least $CR^0$, $R^0$s of the adjacent two $CR^0$s are bonded to each other to forma ring, and only one $R^0$ of the adjacent two $CR^0$s represents an aryl group or a heteroaryl group. However, in the case where $X^7$ and $X^8$ each independently represent $CR^0$, $R^0$ contained in $X^7$ and $R^0$ contained in $X^8$ are not bonded to each other to form a ring.)

Incidentally, in the present invention, the hydrogen atoms in the description of the general formula (1) include isotopes (a deuterium atom and the like), and any atoms constituting the further substituent also include the isotopes thereof.

In the present invention, when referring to a "substituent", the substituent may be further substituted. For example, when the "alkyl group" is referred to in the present invention, it includes an alkyl group substituted with a fluorine atom (for example, a trifluoromethyl group) and an alkyl group substituted with an aryl group (for example, a triphenylmethyl group), but when "an alkyl group having 1 to 6 carbon atoms" is referred to herein, it represents any of alkyl groups having 1 to 6 carbon atoms, including the alkyl groups which are substituted.

In the general formula (1), $X^1$ to $X^{11}$ each independently represent $CR^0$ or N, and $R^0$s each independently represent a hydrogen atom or a substituent.

In the general formula (1), examples of the substituent represented by $R^0$ each independently the following Substituent Group A, the substituent may have an additional substituent, and examples of the additional substituent include the groups selected from the Substituent Group A.

<<Substituent Group A>>

An alkyl group (preferably having 1 to 30 carbon atoms, more preferably having 1 to 20 carbon atoms, and particularly preferably having 1 to 10 carbon atoms, for example, methyl, ethyl, n-propyl, isopropyl, L-butyl, n-octyl, n-hexyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms, for example, vinyl, allyl, 2-butenyl, and 3-pentenyl), an alkynylgroup (preferably having 2 to 30 carbon atoms, more preferably having 2 to 20 carbon atoms, and particularly preferably having 2 to 10 carbon atoms, for example, propargyl and 3-pentynyl), an aryl group (preferably having 6 to 30 carbon atoms, more preferably having 6 to 20 carbon atoms, and particularly preferably having 6 to 14 carbon atoms, for example, phenyl, p-methylphenyl, naphthyl, and anthranyl), amino group (preferably having 0 to 30 carbon atoms, more preferably having 0 to 20 carbon atoms, and particularly preferably having 0 to 10 carbon atoms, for example, amino, methylamino, dimethylamino, diethylamino, dibenzylamino, phenylamino, diphenylamino, and ditolylamino), an alkoxy group (preferably having 1 to 30 carbon atoms, more preferably having 1 to 20 carbon atoms, and particularly preferably having 1 to 10 carbon atoms, for example, methoxy, ethoxy, butoxy, and 2-ethylhexyloxy), and aryloxy group (preferably having 6 to 30 carbon atoms, more preferably having 6 to 20 carbon atoms, and particularly preferably having 6 to 12 carbon atoms, for example, phenyloxy, 1-naphthyloxy, and 2-naphthyloxy), a heterocyclic oxy group (preferably having 1 to 30 carbon atoms, more preferably having 1 to 20 carbon atoms, and particularly preferably having 1 to 12 carbon atoms, for example, pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms, for example, acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms, for example, methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms, for example, phenyloxycarbonyl), an acyloxy group (preferably having 2 to 30 carbon atoms, more preferably having 2 to 20 carbon atoms, and particularly preferably having 2 to 10 carbon atoms, for example, acetoxy and benzoyloxy), an acylamino group (preferably having 2 to 30 carbon atoms, more preferably having 2 to 20 carbon atoms, and particularly preferably having 2 to 10 carbon atoms, for example, acetylamino and benzoylamino), an alkoxycarbonylamino group (preferably having 2 to 30 carbon atoms, more preferably having 2 to 20 carbon atoms, and particularly preferably having 2 to 12 carbon atoms, for example, methoxycarbonylamino), an aryloxycarbonylamino group (preferably having 7 to 30 carbon atoms, more preferably having 7 to 20 carbon atoms, and particularly preferably having 7 to 12 carbon atoms, for example, phenyloxycarbonylamino), a sulfonylamino group (preferably having 1 to 30 carbon atoms, more preferably having 1 to 20 carbon atoms, and particularly preferably having 1 to 12 carbon atoms, for example, methanesulfonylamino and benzenesulfonylamino), a sulfamoyl group (preferably having 0 to 30 carbon atoms, more preferably having 0 to 20 carbon atoms, and particularly preferably having 0 to 12 carbon atoms, for example, sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms, for example, carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms, for example, methylthio and ethylthio), an arylthio group (preferably having 6 to 30 carbon atoms, more preferably having 6 to 20 carbon atoms, and particularly preferably having 6 to 12 carbon atoms, for example, phenylthio), a heterocyclic thio group (preferably having 1 to 30 carbon atoms, more preferably having 1 to 20 carbon atoms, and particularly preferably having 1 to 12 carbon atoms, for example, pyridylthio, 2-benzoimizolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms, for example, mesyl and tosyl), a sulfinyl group (preferably having 1 to 30 carbon atoms, more preferably having 1 to 20 carbon atoms, and particularly preferably having 1 to 12 carbon atoms, for example, methanesulfinyl and benzenesulfinyl), a ureido group (preferably having 1 to 30 carbon atoms, more preferably having 1 to 20 carbon atoms, and particularly preferably having 1 to 12 carbon atoms, for example, ureido, methylureido, and phenylureido), phosphoramide group (preferably having 1 to 30 carbon atoms, more preferably having 1 to 20 carbon atoms, and particularly preferably having 1 to 12 carbon atoms, for example, diethylphosphoramide and phenylphosphoramide), a hydroxy group, a mercapto group, a halogen atom (for example, a fluorine atom, a chlorine atom, a bromine atom, and an iodine atom), a sulfo group, a carboxyl group, a nitro group, a hydroxamic group, a sulfino group, a hydrazino group, an imino group, a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom, and specific examples thereof include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group), a silyl group (preferably having 3 to 40 carbon atoms, more preferably having 3 to 30 carbon atoms, and particularly preferably having 3 to 24 carbon atoms, for example, trimethylsilyl and triphenylsilyl), a silyloxy group (preferably having 3 to 40 carbon atoms, more preferably having 3 to 30 carbon atoms, and particularly preferably having 3 to 24 carbon atoms, for example, trimethylsilyloxy and triphenylsilyloxy), and a phosphoryl group (for example, a diphenylphosphoryl group and a dimethylphosphoryl group). These substituents may be further substituted, and examples of the additional substituent include the groups selected from the Substituent Group A as described above.

The $R^0$s included in $X^1$ to $X^{11}$ each independently represent, among the Substituent Group A, preferably a hydrogen Lom, an aryl group, or a heteroaryl group, and more preferably a hydrogen atom or an aryl group.

The aryl group represented by $R^0$ preferably has 6 to 30 carbon atoms, more preferably has 6 to 20 carbon atoms, and particularly preferably has 6 to 18 carbon atoms, and examples thereof include a phenyl group, a xylyl group, a biphenyl group, a terphenyl group, a naphthyl group, an anthranyl group, and a triphenylenyl group.

The heteroaryl group represented by $R^0$ preferably has 5 to 30 ring members, more preferably has 5 to 20 ring members, and particularly preferably has 5 to 15 ring members, and examples thereof include a pyridyl group, a pyrimidyl group, a triazyl group, a pyrazyl group, a pyridazyl group, a carbazolyl group, a dibenzothiophenyl group, and a dibenzofuranyl group.

$R^0$ contained in $X^1$ to $X^{11}$ may have an additional substituent represented by the Substituent Group A, but in the case where $R^0$ has the additional substituent, the substituent is preferably an aryl group, or a substituent containing at least one of a pyridine ring, a pyrimidine ring, a triazine ring, a cyano group, and a carbonyl group. Above all, an unsubstituted aryl group, a pyridinyl group, a pyrimidinyl group, a triazinyl group, a cyano group-substituted aryl group, and an arylcarbonyl group-substituted aryl group are more preferred, a unsubstituted aryl group, a triazinyl group, and a cyano group-substituted aryl group are still preferable, and an unsubstituted aryl group and a cyano group-substituted aryl group are particularly preferred.

However, itis preferable that the additional substituents which may be contained in $R^0$ be not connected to each other to form a fused ring, from the viewpoint of increasing the luminous efficiency of green phosphorescent light.

The additional substituents which may be contained in $R^0$ may be further substituted. In the case where the additional substituents which may be contained in $R^0$ are each a pyridinyl group, a pyrimidinyl group, or a triazinyl group, they are preferably all substituted with diaryl (preferably substituted with diphenyl).

Adjacent two of $X^1$ to $X^{11}$ each independently represent at least $CR^0$, $R^0$s of the adjacent two $CR^0$s are bonded to each other to form a ring and only one $R^0$ of the adjacent two $CR^0$s represents an aryl group or a heteroaryl group. However, in the case where $X^7$ and $X^8$ each independently represent $CR^0$, $R^0$ contained in $X^7$ and $R^0$ contained in $X^8$ are not bonded to each other to form a ring.

In the present invention, in the general formula (1), one $R^0$ of the adjacent two $CR^0$s, in which $R^0$s are bonded to each other to form a ring, preferably represents an aryl group of a 6-membered ring (that is, a phenyl group) or an heteroaryl group of a 6-membered ring, and more preferably a phenyl group.

In the present invention, in the general formula (1), the other $R^0$ other than $R^0$ representing an aryl group or a heteroaryl group, of the adjacent two $CR^0$s, in which $R^0$s are bonded to each other to form a ring, is not particularly limited as long as it is a substituent other than an aryl group or a heteroaryl group. Above all, the substituent is preferably one which is bonded to $R^0$ representing an aryl group or a heteroaryl group to form a ring which is a 5-membered ring, from the viewpoint of maintaining the luminous efficiency of green phosphorescent light.

As the substituent which is bonded to $R^0$ representing an aryl group or a heteroaryl group to form a ring which is a 5-membered ring, a substituent which can form $CR^1R^2$, $NR^3$ ($R^1$ to $R^3$ each independently represent a substituent), O, S, or Se as a linking group having one of an atom-linking chain length when forming a fused ring is preferred, a substituent which can form $CR^1R^2$, $NR^3$, O, or S is more preferred, a substituent which can form O or S is particularly preferred, and a substituent which can form O is more particularly preferred.

The number of $CR^0$s in $X^1$ to $X^{11}$ is from 2 to 11, preferably from 5 to 11, more preferably from 8 to 11, particularly preferably from 9 to 11, more particularly preferably 10 or 11, and still more particularly preferably 11.

Furthermore, the number of $CR^0$s in $X^1$ to $X^{11}$, in which $R^0$ is a substituent, inclusive of $R^0$s in which $R^0$s are bonded to each other to form a ring, is from 2 to 11, more preferably from 3 to 8, and still more preferably 3 or 4.

The position of $CR^0$s in $X^1$ to $X^{11}$, in which $R^0$ is a substituent, depends on the position of a ring formed by fusion of two $CR^0$s, but it is preferably at least one of $X^2$, $X^5$ and $X^{10}$, and more preferably at least two of $X^2$, $X^5$ and $X^{10}$.

The combination of the positions of the adjacent two $CR^0$s in $X^1$ to $X^{11}$, which are bonded to each other to form a ring, is not particularly limited as long as it is not a combination of $X^7$ and $X^8$, but a combination of $X^1$ and $X^2$, a combination of $X^2$ and $X^3$, a combination of $X^4$ and $X^5$, a combination of $X^5$ and $X^6$, a combination of $X^6$ and $X^7$, a combination of $X^8$ and $X^9$, a combination of $X^9$ and $X^{10}$, and a combination of $X^{10}$ and $X^{11}$ are preferred, and a combination of $X^1$ and $X^2$, a combination of $X^2$ and $X^3$, a combination of $X^4$ and $X^5$, a combination of $X^5$ and $X^6$, a combination of $X^9$ and $X^{10}$, and a combination of $X^{10}$ and $X^{11}$ are more preferred.

In the compound represented by the general formula (1), the number of the rings formed by the mutual bonding of the adjacent two $CR^0$s in $X^1$ to $X^{11}$ is preferably from 1 to 3, and particularly preferably 1 from the viewpoint of remarkably increasing the luminous efficiency of green phosphorescent light.

In the present invention, the compound represented by the general formula (1) is preferably a compound represented by any one of the following general formulae (2) to (9).

[Chem. 13-1]

(2)

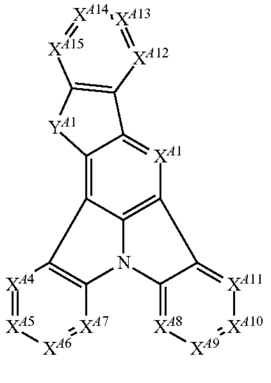

-continued (3)

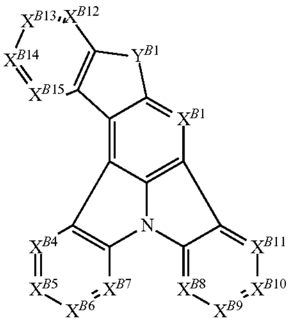

(4)

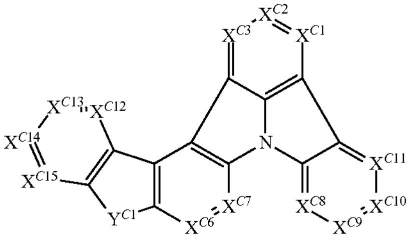

(5)

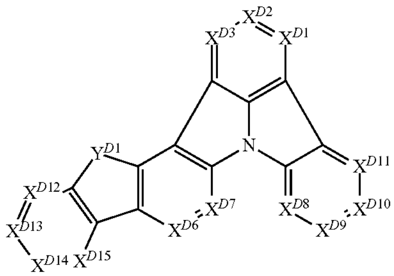

[Chem. 13-2]

(6)

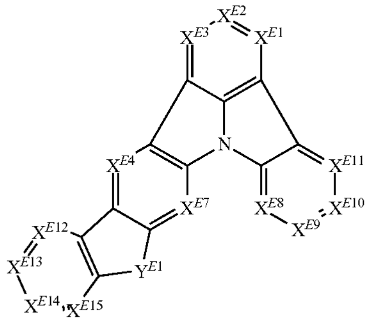

(7)

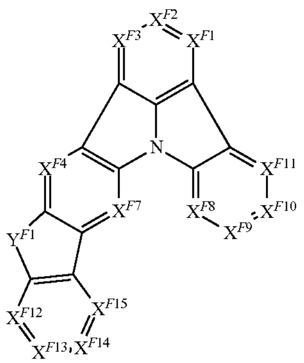

-continued (8)

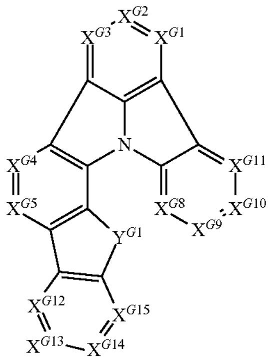

(9)

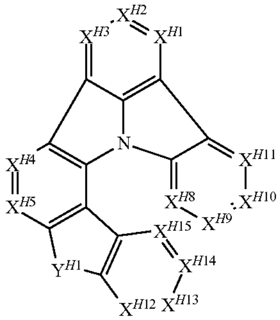

In the general formulae (2) to (9), $Y^{A1}$ to $Y^{H1}$ each independently represent $CR^1R^2$, $NR^3$, O, S, or Se, and $R^1$ to $R^3$ each independently represent a substituent.

$X^{A1}$ to $X^{A15}$, $X^{B1}$ to $X^{B15}$, $X^{C1}$ to $X^{C15}$, $X^{D1}$ to $X^{D15}$, $X^{E1}$ to $X^{E15}$, $X^{F1}$ to $X^{15}$, $X^{G1}$ to $X^{G15}$ and $X^{H1}$ to $X^{H15}$ each independently represent $CR^4$ or N, and $CR^4$s each independently represent a hydrogen atom or a substituent.

In the general formula (2), $Y^{A1}$ represents $CR^1R^2$, $NR^3$, O, S, or Se, and $R^1$ to $R^3$ each independently represent a substituent. The preferred range of $Y^{A1}$ is the same as the preferred range of the linking group having one of an atom-linking chain length, shown when the other $R^0$s other than $R^0$ representing an aryl group or a heteroaryl group, of the adjacent two $CR^0$s, in which $R^0$s are bonded to each other to form a ring, form a fused ring in the general formula (1).

Examples of the substituents represented by substituents $R^1$ and $R^2$ on carbon atoms include the substituent Group A as described above, and the substituent on the carbon atom is preferably an alkyl group, a perfluoroalkyl group, an aryl group, a heteroaryl group, a dialkylamino group, a diarylamino group, an alkoxy group, a cyano group, or a fluorine atom, more preferably an alkyl group or an aryl group, and particularly preferably a methyl group or a phenyl group.

Examples of the substituent represented by $R^3$ on the nitrogen atom include the following Substituent Group B.

<Substituent Group B>>

An alkyl group (preferably having 1 to 30 carbon atoms, more preferably having 1 to 20 carbon atoms, and particularly preferably having 1 to 10 carbon atoms, for example, methyl, ethyl, isopropyl, tert-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms, for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms, for example, propargyl and 3-pentynyl), an aryl group (preferably having 6 to 30 carbon atoms, more preferably having 6 to 20 carbon atoms, and particularly preferably having 6 to 12 carbon atoms, for example, phenyl, p-methylphenyl, naphthyl, and anthranyl), a cyano group, and a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom, and specific examples thereof include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzthiazolyl, a carbazolyl group, an azepinyl group, and a silolyl group) These substituents may be further substituted, and examples of the additional substituent include the groups selected from the Substituent Group B as described above.

The substituent represented by $R^3$ on the nitrogen atom is preferably an alkyl group, an aryl group, an aromatic hetero ring group, more preferably an aryl group, and particularly preferably a phenyl group, or a phenyl group substituted with a phenyl group (biphenyl group).

Furthermore, the substituent represented by $R^3$ of $Y^{A1}$ on the nitrogen atom may be connected to $X^{A15}$ to form a ring.

In the general formula (2), $X^{A1}$ to $X^{A15}$ each independently represent $CR^4$ or N, and $CR^4$s each independently represent a hydrogen atom or a substituent.

The preferred ranges of $X^{A1}$ to $X^{A11}$ are the same as the preferred ranges of $X^1$ to $X^{11}$ in the general formula (1).

In the general formula (2), examples of the substituent represented by $R^4$ in the case where $X^{A12}$ to $X^{A15}$ are $CR^4$s each independently include the Substituent Group A, and the substituent may have an additional substituent. Examples of the additional substituent include the groups selected from the Substituent Group A. Above all, $R^4$s are each independently preferably a hydrogen atom, an aryl group, or a heteroaryl group in the Substituent Group A, and more preferably a hydrogen atom or an aryl group.

The aryl group represented by $R^4$ preferably has 6 to 30 carbon atoms, more preferably has 6 to 20 carbon atoms, and particularly preferably has 6 to 18 carbon atoms, and examples thereof include a phenyl group, a xylyl group, a biphenyl group, a terphenyl group, a naphthyl group, an anthranyl group, and a triphenylenyl group.

The heteroaryl group represented by $R^4$ preferably has 5 to 30 ring members, more preferably has 5 to 20 ring members, and particularly preferably has 5 to 15 ring members, and examples thereof include a pyridyl group, a pyrimidyl group, a triazyl group, a pyrazyl group, a pyridazyl group, a carbazolyl group, a dibenzothiophenyl group, and a dibenzofuranyl group.

$R^4$ contained in $X^{A12}$ to $X^{A15}$ may have an additional substituent represented by the Substituent Group A as described above. In the case where $R^4$ has such an additional substituent, the substituent is preferably substituent containing an aryl group, or at least one of a pyridine ring, a pyrimidine ring, a triazine ring, a cyano group, and a carbonyl group. Above all, an aryl group-substituted aryl group is more preferred, and the additional substituent which may be contained in $R^4$ is particularly preferably further substituted. $R^4$ is preferably a phenyl group-substituted phenyl group (biphenyl group), or a cyano-substituted, phenyl group-substituted, or aryl group-substituted phenyl group.

The number of $CR^4$s in $X^{A12}$ to $X^{A15}$ is preferably from 1 to 4, more preferably from 2 to 4, particularly preferably 3 or 4, and more particularly preferably 4.

Furthermore, the number of $CR^4$s in $X^{A12}$ to $X^{A15}$, in which $R^4$ is a substituent, is preferably 0 or 1, and more preferably 0.

The position of $CR^4$s in $X^{A12}$ to $X^{A15}$, in which $R^4$ is a substituent, is preferably at least one of the positions adjacent to $Y^{A1}$ (the position of $X^{A15}$ in the general formula (2)), and more preferably only one of the positions adjacent to $Y^{A1}$.

The general formula (2) is more preferably represented by the general formula (10) as described later.

In the general formula (3), $Y^{B1}$ represents $CR^1R^2$, $NR^3$, O, S, or Se, and $R^1$ to $R^3$ each independently represent a substituent. The preferred range of $Y^{B1}$ is the same as the preferred range of $Y^{A1}$ in the general formula (2).

Furthermore, the substituent represented by $R^3$ of $Y^{B1}$ on the nitrogen atom may be connected to $X^{B1}$ or $X^{B12}$ to form a ring.

In the general formula (3), $X^{B1}$ to $X^{B15}$ each independently represent $CR^4$ or N, and $CR^4$s each independently represent a hydrogen atom or a substituent. The preferred ranges of $X^{B1}$ to $X^{B15}$ are the same as the preferred ranges of $X^{A1}$ to $X^{A15}$ in the general formula (2).

The preferred relationship between $Y^{B1}$ and $X^{B1}$ to $X^{B15}$ in the general formula (3) is the same as the preferred relationship between $Y^{A1}$ and $X^{A1}$ to $X^{A15}$ in the general formula (2), that is, the position of $CR^4$ in the case where $X^{B12}$ to $X^{B15}$ have $CR^4$ as a substituent is preferably a position adjacent to $Y^{B1}$ (the position of $X^{B12}$ in the general formula (3)).

The general formula (3) is more preferably represented by the general formula (11) as described later.

In the general formula (4), $Y^{C1}$ represents $CR^1R^2$, $NR^3$, O, S, or Se, and $R^1$ to $R^3$ each independently represent a substituent. The preferred range of $Y^{C1}$ is the same as the preferred range of $Y^{A1}$ in the general formula (2).

Furthermore, the substituent represented by $R^3$ of $Y^{C1}$ on the nitrogen atom may be connected to $X^{C6}$ or $X^{C15}$ to form a ring.

In the general formula (4), $X^{C1}$ to $X^{C15}$ each independently represent $CR^4$ or N, and $CR^4$s each independently represent a hydrogen atom or a substituent. The preferred ranges of $X^{C1}$ to $X^{C15}$ are the same as the preferred ranges of $X^{A1}$ to $X^{A15}$ in the general formula (2).

The preferred relationship between $Y^{C1}$ and $X^{C15}$ to $X^{C15}$ in the general formula (4) is the same as the preferred relationship between $Y^{A1}$ and $X^{A15}$ to $X^{A15}$ in the general formula (2), that is, the position of $CR^4$ in the case where $X^{C12}$ to $X^{C15}$ have $CR^4$ as a substituent is preferably a position adjacent to $Y^{C1}$ (the position of $X^{C15}$ in the general formula (4)).

The general formula (4) is more preferably represented by the general formula (12) as described later.

In the general formula (5), $Y^{D1}$ represents $CR^1R^2$, $NR^3$, O, S, or Se, and $R^1$ to $R^3$ each independently represent a substituent. The preferred range of $Y^{D1}$ is the same as the preferred range of $Y^{A1}$ in the general formula (2).

Furthermore, the substituent on the nitrogen atom represented by $R^3$ of $Y^{D1}$ may be connected to $X^{D12}$ to form a ring.

In the general formula (5), $X^{D1}$ to $X^{D15}$ each independently represent $CR^4$ or N, and $CR^4$s each independently represent a hydrogen atom or a substituent. The preferred ranges of $X^{D1}$ to $X^{D15}$ are the same as the preferred ranges of $X^{A1}$ to $X^{A15}$ in the general formula (2).

The preferred relationship between $Y^{D1}$ and $X^{D1}$ to $X^{D15}$ in the general formula (5) is the same as the preferred relationship between $Y^{A1}$ and $X^{A1}$ to $X^{A15}$ in the general formula (2), that is, the position of $CR^4$ in the case where $X^{D12}$ to $X^{D15}$ have $CR^4$ as a substituent is preferably a position adjacent to $Y^{D1}$ (the position of $X^{D12}$ in the general formula (5)).

The general formula (5) is more preferably represented by the general formula (13) as described later.

In the general formula (6), $Y^{E1}$ represents $CR^1R^2$, $NR^3$, O, S, or Se, and $R^1$ to $R^3$ each independently represent a substituent. The preferred range of $Y^{E1}$ is the same as the preferred range of $Y^{A1}$ in the general formula (2).

Furthermore, the substituent represented by $R^3$ of $Y^{E1}$ on the nitrogen atom may be connected to $X^{E7}$ or $X^{E15}$ to form a ring.

In the general formula (6), $X^{E1}$ to $X^{E15}$ each independently represent $CR^4$ or N, and $CR^4$s each independently represent a hydrogen atom or a substituent. The preferred ranges of $X^{E1}$ to $X^{E15}$ are the same as the preferred ranges of $X^{A1}$ to $X^{A15}$ in the general formula (2).

The preferred relationship between $Y^{E1}$ and $X^{E1}$ to $X^{E15}$ in the general formula (6) is the same as the preferred relationship between $Y^{A1}$ and $X^{A1}$ to $X^{A15}$ in the general formula (2), that is, the position of $CR^4$ in the case where $X^{E12}$ to $X^{E15}$ have $CR^4$ as a substituent is preferably a position adjacent to $Y^{E1}$ (the position of $X^{E15}$ in the general formula (6)).

The general formula (6) is more preferably represented by the general formula (14) as described later.

In the general formula (7), $Y^{F1}$ represents $CR^1R^2$, $NR^3$, O, S, or Se, and $R^1$ to $R^3$ each independently represent a substituent. The preferred range of $Y^{F1}$ is the same as the preferred range of $Y^{A1}$ in the general formula (2).

Furthermore, the substituent represented by $R^3$ of $Y^{F1}$ on the nitrogen atom may be connected to $X^{F4}$ or $X^{F12}$ to form a ring.

In the general formula (7), $X^{F1}$ to $X^{F15}$ each independently represent $CR^4$ or N, and $CR^4$s each independently represent a hydrogen atom or a substituent. The preferred ranges of $X^{F1}$ to $X^{F15}$ are the same as the preferred ranges of $X^{A1}$ to $X^{A15}$ in the general formula (2).

The preferred relationship between $Y^{F1}$ and $X^{F1}$ to $X^{F15}$ in the general formula (7) is the same as the preferred relationship between $Y^{A1}$ and $X^{A1}$ to $X^{A15}$ in the general formula (2), that is, the position of $CR^4$ in the case where $X^{F12}$ to $X^{F15}$ have $CR^4$ as a substituent is preferably a position adjacent to $Y^{F1}$ (the position of $X^{F12}$ in the general formula (7)).

The general formula (7) is more preferably represented by the general formula (15) as described later.

In the general formula (8), $Y^{G1}$ represents $CR^1R^2$, $NR^3$, O, S, or Se, and $R^1$ to $R^3$ each independently represent a substituent. The preferred range of $Y^{G1}$ is the same as the preferred range of $Y^{A1}$ in the general formula (2).

Furthermore, the substituent represented by $R^3$ of $Y^{G1}$ on the nitrogen atom may be connected to $X^{G15}$ to form a ring.

In the general formula (8), $X^{G1}$ to $X^{G15}$ each independently represent $CR^4$ or N, and $CR^4$s each independently represent a hydrogen atom or a substituent. The preferred ranges of $X^{G1}$ to $X^{G15}$ are the same as the preferred ranges of $X^{A1}$ to $X^{15}$ in the general formula (2).

The preferred relationship between $Y^{G1}$ and $X^{G1}$ to $X^{G15}$ in the general formula (8) is the same as the preferred relationship between $Y^{A1}$ and $X^{A1}$ to $X^{A15}$ in the general formula (2), that is, the position of $CR^4$ in the case where $X^{G12}$ to $X^{G15}$ have $CR^4$ as a substituent is preferably a position adjacent to $Y^{G1}$ (the position of $X^{G15}$ in the general formula (8)).

The general formula (8) is more preferably represented by the general formula (16) as described later.

In the general formula (9), $Y^{H1}$ represents $CR^1R^2$, $NR^3$, O, S, or Se, and $R^1$ to $R^3$ each independently represent a substituent. The preferred range of $Y^{H1}$ is the same as the preferred range of $Y^{A1}$ in the general formula (2).

Furthermore, the substituent represented by $R^3$ of $Y^{H1}$ on the nitrogen atom may be connected to $X^{H5}$ or $X^{H12}$ to form a ring.

In the general formula (9), $X^{H1}$ to $X^{H15}$ each independently represent $CR^4$ or N, and $CR^4$s each independently represent a hydrogen atom or a substituent. The preferred ranges of $X^{H1}$ to $X^{H15}$ are the same as the preferred ranges of $X^{A1}$ to $X^{A15}$ in the general formula (2).

The preferred relationship between $Y^{H1}$ and $X^{H15}$ to $X^{H15}$ in the general formula (9) is the same as the preferred relationship between $Y^{A1}$ and $X^{A1}$ to $X^{A15}$ in the general formula (2), that is, the position of $CR^4$ in the case where $X^{H12}$ to $X^{H15}$ have $CR^4$ as a substituent is preferably a position adjacent to $Y^{H1}$ (the position of $X^{H12}$ in the general formula (9)).

The general formula (9) is more preferably represented by the general formula (17) as described later.

In the present invention, the compound represented by the general formula (1) is preferably a compound represented by any one of the general formulae (2), (4) to (7), and (8) cut of the general formulae (2) to (9) from the viewpoints that the planarity and the stability of molecules are good, and the $T_1$ can be easily increased that a light emitting material as described later, and more preferably a compound represented by any one of the general formulae (2), (4) to (6), and (8) from the viewpoints that the $T_1$ can be easily increased that a light emitting material as described later.

In the present invention, the compound represented by the general formula (1) is preferably a compound represented by any one of the following general formulae (10) to (17).

[Chem. 14]

(10)

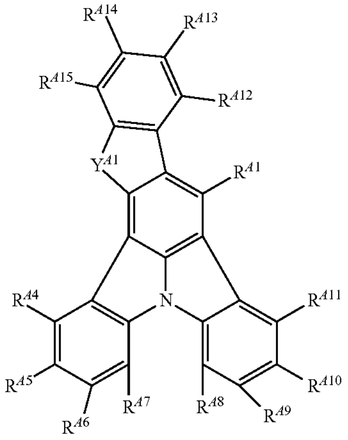

-continued (11)

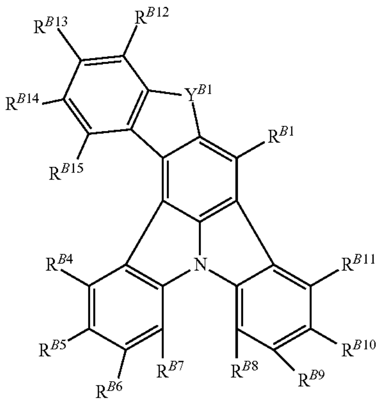

(12)

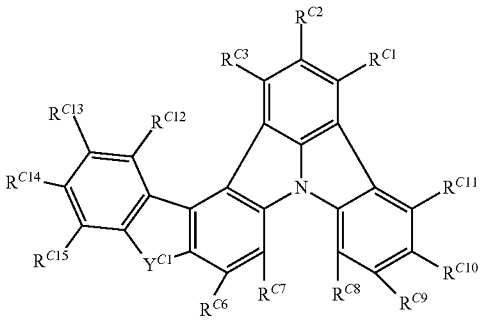

(13)

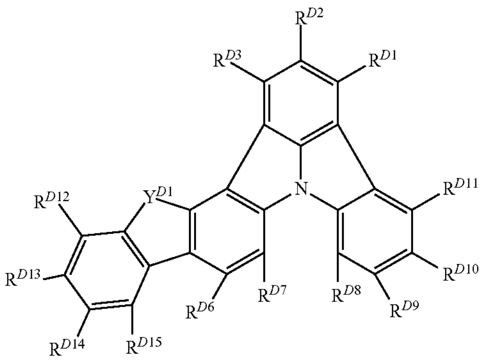

(14)

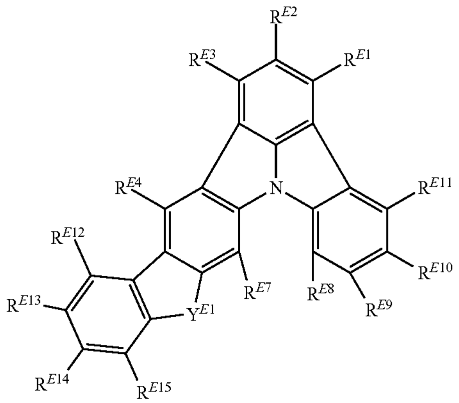

-continued (15)

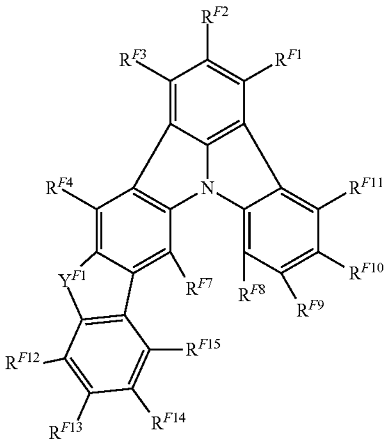

(16)

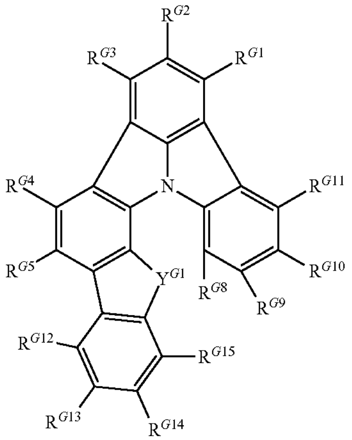

(17)

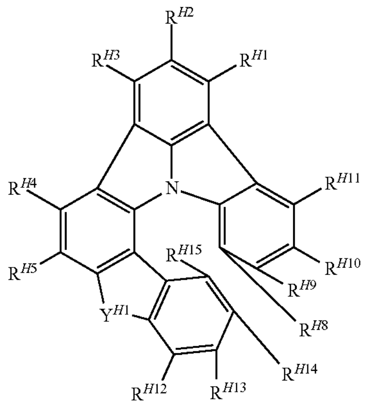

In the general formulae (10) to (17), $Y^{A1}$ to $Y^{H1}$ each independently represent $CR^1R^2$, $NR^3$, O, S, or Se, and $R^1$ to $R^3$ each independently represent a substituent. $R^{A1}$ to $R^{A15}$, $R^{B1}$ to $R^{B15}$, $R^{C1}$ to $R^{C15}$, $R^{D1}$ to $R^{D15}$, $R^{E1}$ to $R^{E15}$, $R^{F1}$ to $R^{F15}$, $R^{G1}$ to $R^{G15}$ and $R^{H1}$ to $R^{H15}$ each independently represent a hydrogen atom or a substituent.

In the general formula (10), the definition and the preferred range of $Y^{A1}$ are the same as the definition and the preferred range of $Y^{A1}$ in the general formula (2).

Furthermore, the substituent represented by $R^3$ of $Y^{A1}$ on the nitrogen atom may be connected to $R^{A15}$ to form a ring.

In the general formula (10), $R^{A1}$ to $R^{A15}$ each independently represent a hydrogen atom or a substituent, and the preferred ranges of $R^{A1}$ to $R^{A15}$ are the same as the preferred ranges of $R^4$ contained in each of $X^{A1}$ to $X^{A15}$ in the case where $X^{A1}$ to $X^{A15}$ in the general formula (2) represent all $CR^4$.

The preferred relationship between $Y^{A1}$ and $R^{A1}$ to $R^{A15}$ in the general formula (10) is the same as the preferred relationship between $Y^{A1}$ in the general formula (2) and $R^4$ contained in each of $X^{A1}$ to $X^{A15}$ in the case where $X^{A1}$ to $X^{A15}$ in the general formula (2) represent all $CR^4$, that is, the position of the substituent in the case where $R^{A12}$ to $R^{A15}$ have a substituent is preferably a position adjacent to $Y^{A1}$ (the position of $R^{A15}$ in the general formula (10)).

In the general formula (11), the definition and the preferred range of $Y^{B1}$ are the same as the definition and the preferred range of $Y^{B1}$ in the general formula (3).

Furthermore, the substituent represented by $R^3$ of $Y^{B1}$ on the nitrogen atom may be connected to $R^{B1}$ or $R^{B2}$ to form a zing. In the general formula (11), $R^{B1}$ to $R^{B15}$ each independently represent a hydrogen atom or a substituent, and the preferred ranges of $R^{B1}$ to $R^{B15}$ are the same as the preferred ranges of $R^4$ contained in each of $X^{B1}$ to $X^{B15}$ in the case where $X^{B1}$ to $X^{B15}$ in the general formula (3) represent all $CR^4$.

The preferred relationship between $Y^{B1}$ and $R^{B1}$ to $R^{B15}$ in the general formula (11) is the same as the preferred relationship between $Y^{B1}$ in the general formula (3) and $R^4$ contained in each of $X^{B1}$ to $X^{B15}$ in the case where $X^{B1}$ to $X^{B15}$ in the general formula (3) represent all $CR^4$, that is, the position of the substituent in the case where $R^{B12}$ to $R^{B15}$ have a substituent is preferably a position adjacent to $Y^{B1}$ (the position of $R^{B12}$ in the general formula (11)).

In the general formula (12), the definition and the preferred range of $Y^{C1}$ are the same as the definition and the preferred range of $Y^{C1}$ in the general formula (4).

Furthermore, the substituent represented by $R^3$ of $Y^{C1}$ on the nitrogen atom may be connected to $R^{C6}$ or $R^{C15}$ to form a ring.

In the general formula (12), $R^{C1}$ to $R^{C15}$ each independently represent a hydrogen atom or a substituent, and the preferred ranges of $R^{C1}$ to $R^{C15}$ are the same as the preferred ranges of $R^4$ contained in each of $X^{C1}$ to $X^{C15}$ in the case where $X^{C1}$ to $X^{C15}$ in the general formula (4) represent all $CR^4$.

The preferred relationship between $Y^{C1}$ and $R^{C1}$ to $R^{C15}$ in the general formula (12) is the same as the preferred relationship between $Y^{C1}$ in the general formula (4) and $R^4$ contained in each of $X^{C1}$ to $X^{C15}$ in the case where $X^{C1}$ to $X^{C15}$ in the general formula (4) represent all $CR^4$, that is, the position of the substituent in the case where $R^{C12}$ to $R^{C15}$ have a substituent is preferably a position adjacent to $Y^{C1}$ (the position of $R^{C15}$ in the general formula (12)).

In the general formula (13), the definition and the preferred range of $Y^{D1}$ are the same as the definition and the preferred range of $Y^{D1}$ in the general formula (5).

Furthermore, the substituent represented by $R^3$ of $Y^{D1}$ on the nitrogen atom may be connected to $R^{D12}$ to form a ring.

In the general formula (13), $R^{D1}$ to $R^{D15}$ each independently represent a hydrogen atom or a substituent, and the preferred ranges of $R^{D1}$ to $R^{D15}$ are the same as the preferred ranges of $R^4$ contained in each of $X^{D1}$ to $X^{D15}$ in the case where $X^{D1}$ to $X^{D12}$ in the general formula (5) represent all $CR^4$.

The preferred relationship between $Y^{D1}$ and $R^{D1}$ to $R^{D15}$ in the general formula (13) is the same as the preferred relationship between $Y^{D1}$ in the general formula (5) and $R^4$ contained in each of $X^{D1}$ to $X^{D15}$ in the case where $X^{D1}$ to $X^{D15}$ in the general formula (5) represent all $CR^4$, that is, the position of the substituent in the case where $R^{D12}$ to $R^{D15}$ have a substituent is preferably a position adjacent to $Y^{D1}$ (the position of $R^{D12}$ in the general formula (13)).

In the general formula (14), the definition and the preferred range of $Y^{E1}$ are the same as the definition and the preferred range of $Y^{E1}$ in the general formula (6).

Furthermore, the substituent, represented by $R^3$ of $Y^{E1}$ on the nitrogen atom may be connected to $R^{E7}$ or $R^{E15}$ to form a ring. In the general formula (14), $R^{E1}$ to $R^{E15}$ each independently represent a hydrogen atom or a substituent, and the preferred ranges of $R^{E1}$ to $R^{E15}$ are the same as the preferred ranges of $R^4$ contained in each of $X^{E1}$ to $X^{E15}$ in the case where $X^{E1}$ to $X^{E15}$ in the general formula (6) represent all $CR^4$.

The preferred relationship between $Y^{E1}$ and $R^{E1}$ to $R^{E15}$ in the general formula (14) is the same as the preferred relationship between $Y^{E1}$ in the general formula (6) and $R^4$ contained in each of $X^{E1}$ to $X^{E15}$ in the case where $X^{E1}$ to $X^{E15}$ in the general formula (6) represent all $CR^4$, that is, the position of the substituent in the case where $R^{E2}$ to $R^{E1}$ have a substituent is preferably a position adjacent to $Y^1$ (the position of $R^{E15}$ in the general formula (14)).

In the general formula (15), the definition and the preferred range of $Y^{F1}$ are the same as the definition and the preferred range of $Y^{F1}$ in the general formula (7).

Furthermore, the substituent represented by $R^3$ of $Y^{F1}$ on the nitrogen atom may be connected to $R^{F4}$ or $R^{E12}$ to form a ring.

In the general formula (15), $R^{F1}$ to $R^{15}$ each independently represent a hydrogen atom or a substituent, and the preferred ranges of $R^{F1}$ to $R^{F15}$ are the same as the preferred ranges of $R^4$ contained in each of $X^{F1}$ to $X^{F15}$ in the case where $X^{F1}$ to $X^{F15}$ in the general formula (7) represent all $CR^4$.

The preferred relationship between $Y^{F1}$ and $R^{F1}$ to $R^{F15}$ in the general formula (15) is the same as the preferred relationship between $Y^{F1}$ in the general formula (7) and $R^4$ contained in each of $X^{F1}$ to $X^{15}$ in the case where $X^{F1}$ to $X^{F15}$ in the general formula (7) represent all $CR^4$, that is, the position of the substituent in the case where $R^{F12}$ to $R^{F15}$ have a substituent is preferably a position adjacent to $Y^{F1}$ (the position of $R^{F12}$ in the general formula (15)).

In the general formula (16), the definition and the preferred range of $Y^{G1}$ are the same as the definition and the preferred range of $Y^{G1}$ in the general formula (8).

Furthermore, the substituent represented by $R^3$ of $Y^{G1}$ on the nitrogen atom may be connected to $X^{G15}$ to form a ring.

In the general formula (16), $R^{G1}$ to $R^{G15}$ each independently represent a hydrogen atom or a substituent, and the preferred ranges of $R^{G1}$ to $R^{G15}$ are the same as the preferred ranges of $R^4$ contained in each of $X^{G1}$ to $X^{G15}$ in the case where $X^{G1}$ to $X^{11}$ in the general formula (8) represent all $CR^4$.

The preferred relationship between $Y^{G1}$ and $R^{G1}$ to $R^{G15}$ in the general formula (16) is the same as the preferred relationship between $Y^{G1}$ in the general formula (8) and $R^4$ contained in each of $X^{G1}$ to $X^{G15}$ in the case where $X^{G1}$ to $X^{G15}$ in the general formula (8) represent all $CR^4$, that is, the position of the substituent in the case where $R^{G12}$ to $R^{G15}$ have a substituent is preferably a position adjacent to $Y^{G1}$ (the position of $R^{G15}$ in the general formula (16)).

In the general formula (17), the definition and the preferred range of $Y^{H1}$ are the same as the definition and the preferred range of $Y^{H1}$ in the general formula (9).

Furthermore, the substituent represented by $R^3$ of $Y^{H1}$ on the nitrogen atom may be connected to $R^{H5}$ or $R^{H12}$ to form a ring.

In the general formula (17), $R^{H1}$ to $R^{H15}$ each independently represent a hydrogen atom or a substituent, and the preferred ranges of $R^{H1}$ to $R^{H15}$ are the same as the preferred ranges of $R^4$ contained in each of $X^{H1}$ to $X^{H15}$ in the case where $X^{H1}$ to $X^{15}$ in the general formula (9) represent all $CR^4$.

The preferred relationship between $Y^{H1}$ and $R^{H1}$ to $R^{H15}$ in the general formula (17) is the same as the preferred relationship between $Y^{H1}$ in the general formula (9) and $R^4$ contained in each of $X^{H1}$ to $X^{H15}$ in the case where $X^{H1}$ to $X^{H15}$ in the general formula (9) represent all $CR^4$, that is, the position of the substituent in the case where $R^{H12}$ to $R^{H15}$ have a substituent is preferably a position adjacent to $Y^{H1}$ (the position of $R^{H12}$ in the general formula (17)).

In the present invention, the compound represented by the general formula (1) is preferably a compound represented by any one of the general formulae (10), (12) to (15), and (16) out of the general formulae (10) to (17) from the viewpoints that the planarity and the stability of molecules are good, and the $T_1$ can be easily increased that a light emitting material as described later, and more preferably a compound represented by any one of the general formulae (10), (12) to (14), and (16) from the viewpoints that the $T_1$ can be easily increased that a light emitting material as described later.

The molecular weight of the compound represented by the general formula (1) is usually from 400 to 1500, preferably from 450 to 1200, more preferably from 500 to 1100, and still more preferably from 550 to 1000. The molecular weight of 450 or more is advantageous in forming an amorphous thin film of good quality, and the molecular weight of 1200 or less is advantageous in improving solubility and sublimation properties, and thus improving the purity of the compound. In the organic electroluminescent element of the present invention, the molecular weight of the compound represented by the general formula (1) is preferably 550 or more from the viewpoint of a glass transition temperature. On the other hand, from the viewpoint of lamination of a composition including the compound represented by the general formula (1) by deposition, the molecular weight of the compound represented by the general formula (1) is preferably 1200 or less.

In the case where the hydrocarbon compound represented by the general formula (1) is used in a host material of a light emitting layer or in a charge transporting material of a layer adjacent to the light emitting layer, in an organic electroluminescent element, when the energy gap in the thin film state (the minimum excited triplet ($T_1$) energy in the thin film state in the case of the light emitting material being a phosphorescence emitting material) is larger than in the light emission material as described later, the quench of the light emission is prevented, which is advantageous in enhancing the efficiency. On the other hand, from the viewpoint of chemical stability of the compound, it is preferable that an energy gap and $T_1$ energy be not too large.

In the present invention, the value of LUMO of the compound represented by the general formula (1), as determined by an electron density functional theory (B3LYP/6-31G (d) level), is preferably more than 1.25, more preferably 1.4 or more, and particularly preferably from 1.4 to 1.9.

The minimum excited triplet ($T_1$) energy in the film state of the compound represented by the general formula (1) is preferably from 1.77 eV (40 kcal/mol) to 3.51 eV (81 kcal/mol), and more preferably from 2.39 eV (55 kcal/mol) to 3.25 eV (75 kcal/mol). In the organic electroluminescent element of the present invention, it is preferable that $T_1$ energy of the compound represented by the general formula (1) be more than $T_1$ energy of the above-mentioned phosphorescent light emitting material, from the viewpoint of luminous efficiency. In particular when the luminescent color from the organic electroluminescent element is green (the light emission peak wavelength is from 490 nm to 580 nm), from the viewpoint of luminous efficiency, $T_1$ energy is more preferably from 2.39 eV (55 kcal/mol) to 2.82 eV (65 kcal/mol).

By measuring the phosphorescent light emitting spectrum of a thin film of the material, the $T_1$ energy can be found from the short-wavelength end thereof. For instance, a film of the material is formed in a thickness of about 50 nm by a vacuum deposition method over a washed quartz glass substrate, and the phosphorescence spectrum of the thin film is measured using an F-7000 Hitachi spectrofluoro-photometer (Hitachi High-Technologies Corporation) at the temperature of liquid nitrogen. The $T_1$ energy can be found by converting the rising wavelength on the short-wavelength side of the light emission spectrum thus obtained to energy units.

From the viewpoint of stable operation of the organic electroluminescent element with respect to heat emission during high-temperature driving or element driving, the glass transition temperature of the compound represented by the general formula (1) in the organic electroluminescent element of the present invention is preferably a compound having a glass transition temperature of 100° C. or higher. The glass transition temperature (Tg) of the compound represented by the general formula (1) is more preferably from 100° C. to 400° C., particularly preferably from 120° C. to 400° C., and still more preferably from 140° C. to 400° C.

If the purity of the compound represented by the general formula (1) is low, impurities serve as a trap for charge transport or accelerate degradation of the element, and therefore, higher purity of the compound represented by the general formula (1) is preferred. The purity can be measured, for example, by high performance liquid chromatography (HPLC), and the surface area ratio of the compound represented by the general formula (1) as detected at an optical absorption intensity of 254 nm is preferably 95.0% or more, and more preferably 97.0% or more, particularly preferably 99.0% or more, and most preferably 99.9% or more. Examples of a method for increasing the purity of the compound represented by the general formula (1) include recrystallization and sublimation.

Specific examples of the compound represented by the general formula (1) are list, but the present invention is not limited thereto.

In the compounds represented by the following general formula (10), $R^{A1}$, $R^{A4}$, $R^{A6}$ to $R^{A9}$, $R^{A11}$ to $R^{A14}$ represent a hydrogen atom, and the other groups are groups described in Tables below.

[Chem. 15]
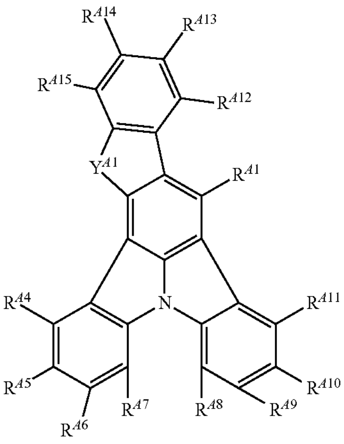
(10)
TABLE 1
| Compound No. | $Y^{A1}$ | $R^{A15}$ | $R^{A10}$ | $R^{A5}$ | $R^3$ | $R^1$ | $R^2$ |
|---|---|---|---|---|---|---|---|
| O-10-1 | O | H | H | H | — | — | — |
| O-10-2 | O | H | 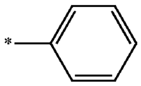 [SMILES: *c1ccccc1] | 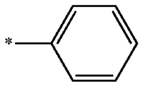 [SMILES: *c1ccccc1] | — | — | — |
| O-10-3 | O | H | 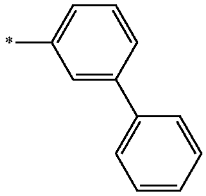 [SMILES: *c1cccc(-c2ccccc2)c1] | H | — | — | — |
| O-10-4 | O | H | 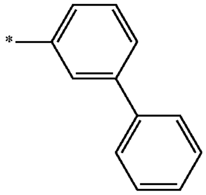 [SMILES: *c1cccc(-c2ccccc2)c1] | 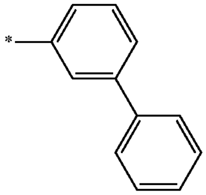 [SMILES: *c1cccc(-c2ccccc2)c1] | — | — | — |
| O-10-5 | O | 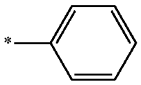 [SMILES: *c1ccccc1] | 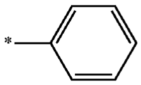 [SMILES: *c1ccccc1] | 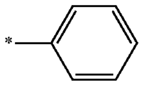 | — | — | — |
| O-10-6 | O | H | 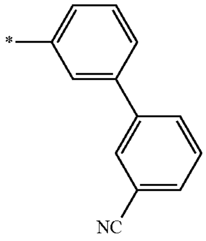 [SMILES: *c1cccc(-c2cccc(C#N)c2)c1] | H | — | — | — |

TABLE 1-continued
| Compound No. | $Y^{A1}$ | $R^{A15}$ | $R^{A10}$ | $R^{A5}$ | $R^3$ | $R^1$ | $R^2$ |
|---|---|---|---|---|---|---|---|
| O-10-7 | O | H | H | 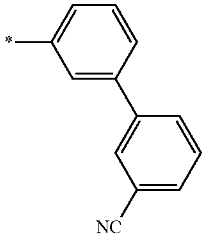 [SMILES: *c1cccc(-c2cccc(C#N)c2)c1] | — | — | — |
| O-10-8 | | H | 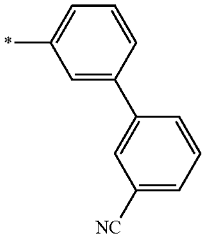 [SMILES: *c1cccc(-c2cccc(C#N)c2)c1] | 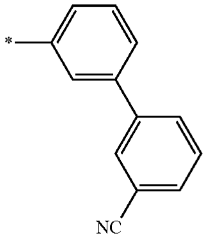 [SMILES: *c1cccc(-c2cccc(C#N)c2)c1] | — | — | — |
| O-10-9 | O | H | 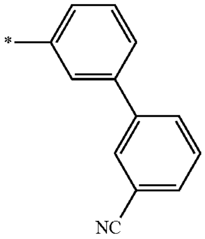 [SMILES: *c1cccc(-c2cccc(C#N)c2)c1] | 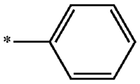 | — | — | — |
| O-10-10 | O | H | 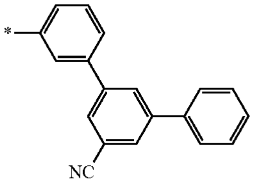 [SMILES: *c1cccc(-c2cc(C#N)cc(-c3ccccc3)c2)c1] | H | — | — | — |
| O-10-11 | O | H | 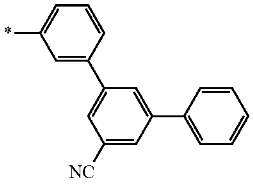 [SMILES: *c1cccc(-c2cc(C#N)cc(-c3ccccc3)c2)c1] | 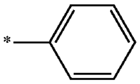 [SMILES: *c1ccccc1] | — | — | — |
| O-10-12 | O | 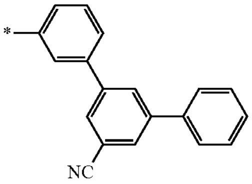 [SMILES: *c1cccc(-c2cc(C#N)cc(-c3ccccc3)c2)c1] | H | H | — | — | — |
| O-10-13 | O | H | 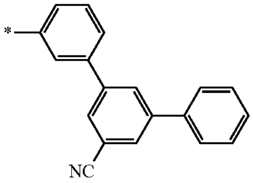 [SMILES: *c1cccc(-c2cc(C#N)cc(-c3ccccc3)c2)c1] | 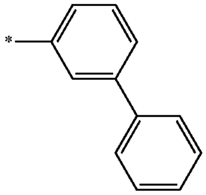 [SMILES: *c1cccc(-c2ccccc2)c1] | — | — | — |

TABLE 1-continued
| Compound No. | $Y^{A1}$ | $R^{A15}$ | $R^{A10}$ | $R^{A5}$ | $R^3$ | $R^1$ | $R^2$ |
|---|---|---|---|---|---|---|---|
| O-10-14 | O | H | 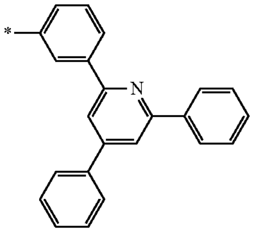 | H | — | — | — |
| O-10-15 | O | H | 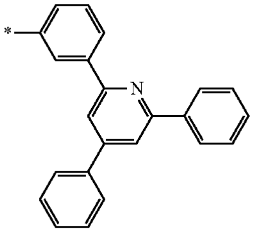 | 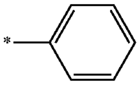 | — | — | — |
TABLE 2
| | | | | | | | |
|---|---|---|---|---|---|---|---|
| O-10-16 | O | H | 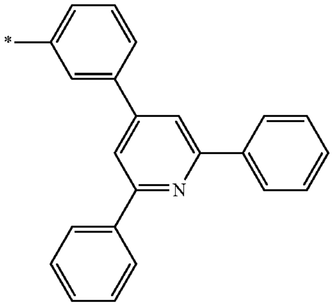 | H | — | — | — |
| O-10-17 | O | H | 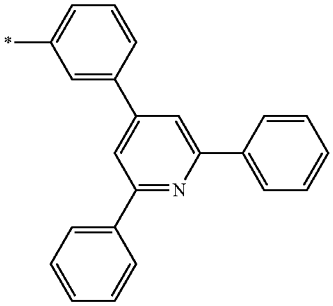 | 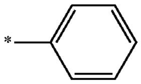 [SMILES: *c1ccccc1] | — | — | — |
| O-10-18 | O | H | 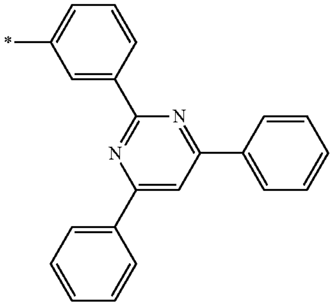 | H | — | — | — |

TABLE 2-continued
| | | | | | | | |
|---|---|---|---|---|---|---|---|
| O-10-19 | O | H | 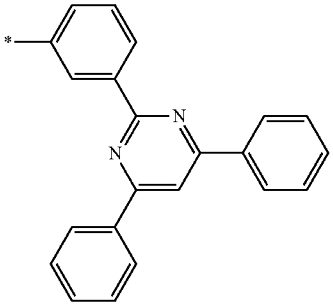 | 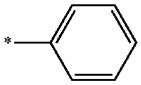 [SMILES: *c1ccccc1] | — | — | — |
| O-10-20 | O | H | 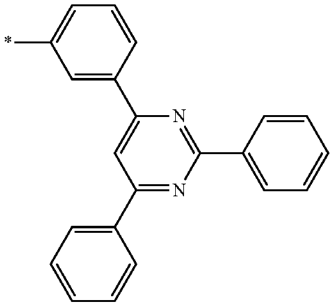 | H | — | — | — |
| O-10-21 | O | H | 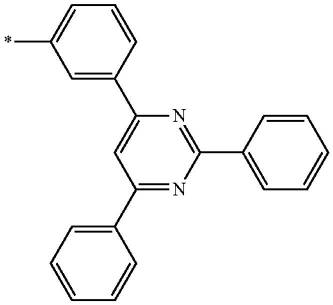 | 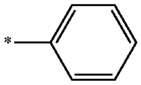 [SMILES: *c1ccccc1] | — | — | — |
| O-10-22 | O | H | 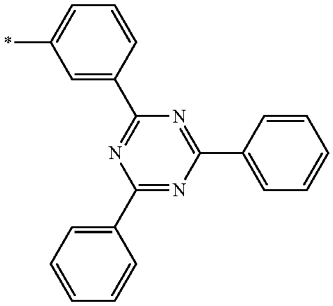 | H | — | — | — |
| O-10-23 | O | H | 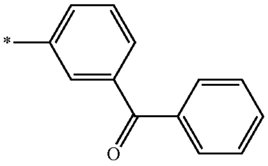 [SMILES: *c1cccc(C(=O)c2ccccc2)c1] | H | — | — | — |
| O-10-24 | O | H | 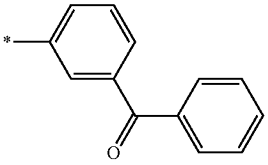 [SMILES: *c1cccc(C(=O)c2ccccc2)c1] | 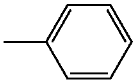 | — | — | — |

TABLE 2-continued
| | | | | | | | |
|---|---|---|---|---|---|---|---|
| O-10-25 | O | H | 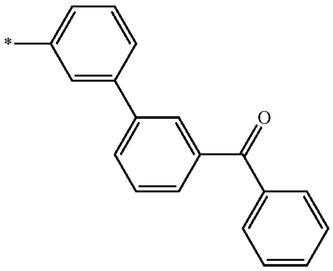 [SMILES: *c1cccc(-c2cccc(C(=O)c3ccccc3)c2)c1] | H | — | — | — |
| O-10-26 | O | H | 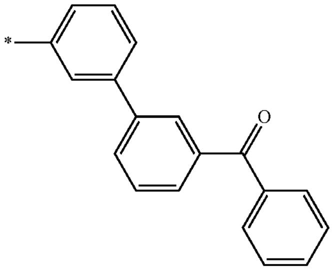 [SMILES: *c1cccc(-c2cccc(C(=O)c3ccccc3)c2)c1] | 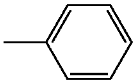 | — | — | — |
| S-10-1 | S | H | H | H | — | — | — |
| S-10-2 | S | H | 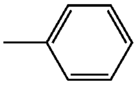 | 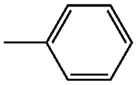 | — | — | — |
| S-10-3 | S | H | 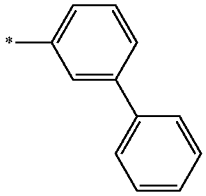 [SMILES: *c1cccc(-c2ccccc2)c1] | H | — | — | — |
| S-10-4 | S | H | 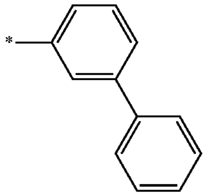 [SMILES: *c1cccc(-c2ccccc2)c1] | 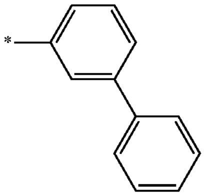 [SMILES: *c1cccc(-c2ccccc2)c1] | — | — | — |
TABLE 3
| | | | | | | | |
|---|---|---|---|---|---|---|---|
| S-10-5 | S | 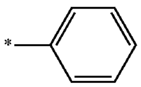 [SMILES: *c1ccccc1] | 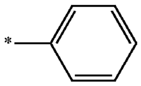 [SMILES: *c1ccccc1] | 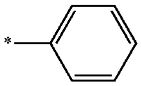 [SMILES: *c1ccccc1] | — | — | — |
| S-10-6 | S | H | 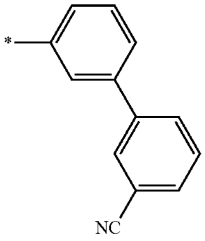 [SMILES: *c1cccc(-c2cccc(C#N)c2)c1] | H | — | — | — |

TABLE 3-continued
| | | | | | | | |
|---|---|---|---|---|---|---|---|
| S-10-7 | S | H | H | 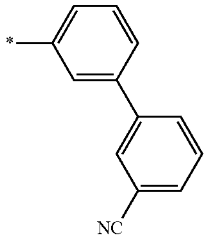 [SMILES: *c1cccc(-c2cccc(C#N)c2)c1] | — | — | — |
| S-10-8 | S | H | 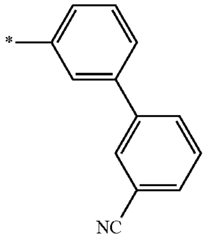 [SMILES: *c1cccc(-c2cccc(C#N)c2)c1] | 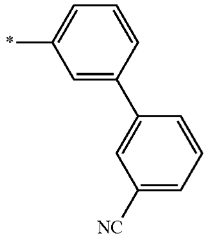 [SMILES: *c1cccc(-c2cccc(C#N)c2)c1] | — | — | — |
| S-10-9 | S | H | 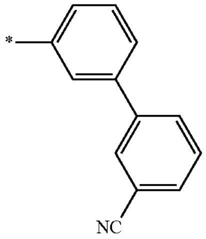 [SMILES: *c1cccc(-c2cccc(C#N)c2)c1] | 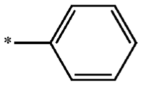 [SMILES: *c1ccccc1] | — | — | — |
| S-10-10 | S | H | 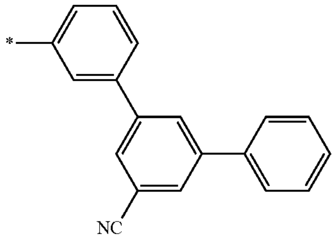 [SMILES: *c1cccc(-c2cc(C#N)cc(-c3ccccc3)c2)c1] | H | — | — | — |
| S-10-11 | S | H | 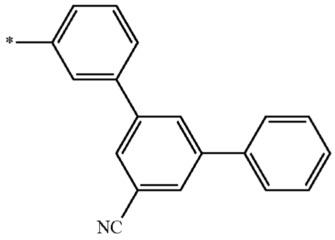 [SMILES: *c1cccc(-c2cc(C#N)cc(-c3ccccc3)c2)c1] | 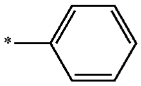 | — | — | — |
| S-10-12 | S | 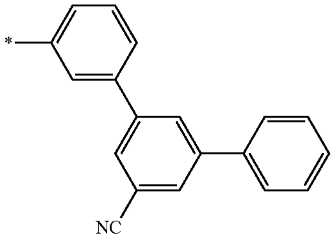 [SMILES: *c1cccc(-c2cc(C#N)cc(-c3ccccc3)c2)c1] | H | H | — | — | — |

TABLE 3-continued
| | | | | | | | |
|---|---|---|---|---|---|---|---|
| S-10-13 | S | H | 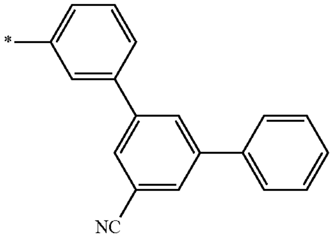 [SMILES: *c1cccc(-c2cc(C#N)cc(-c3ccccc3)c2)c1] | 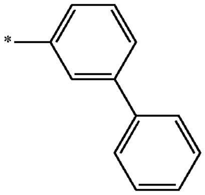 [SMILES: *c1cccc(-c2ccccc2)c1] | — | — | — |
| S-10-14 | S | H | 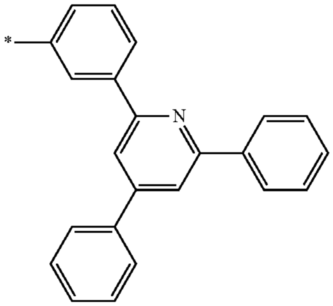 | H | — | — | — |
| S-10-15 | S | H | 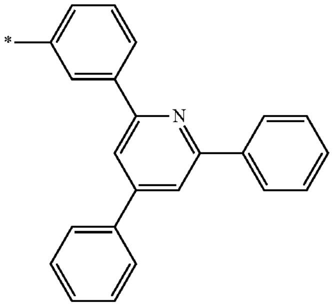 | 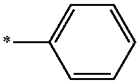 [SMILES: *c1ccccc1] | — | — | — |
| S-10-16 | S | H | 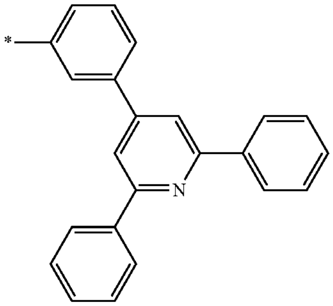 | H | — | — | — |
| S-10-17 | S | H | 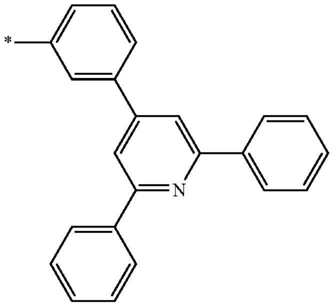 | 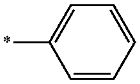 [SMILES: *c1ccccc1] | — | — | — |

TABLE 3-continued
| | | | | | | | |
|---|---|---|---|---|---|---|---|
| S-10-18 | S | H | 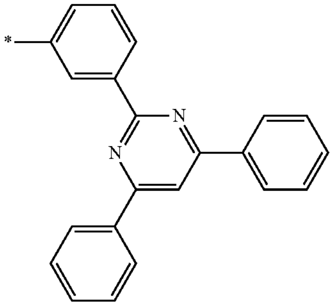 | H | — | — | — |
| S-10-19 | S | H | 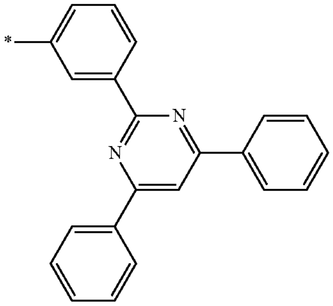 | 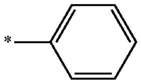 [SMILES: *c1ccccc1] | — | — | — |
TABLE 4
| | | | | | | | |
|---|---|---|---|---|---|---|---|
| S-10-20 | S | H | 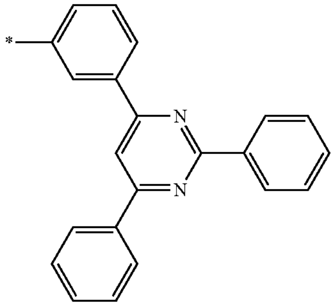 | H | — | — | — |
| S-10-21 | S | H | 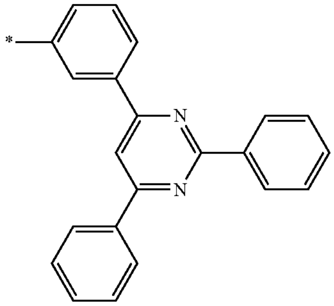 | 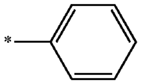 [SMILES: *c1ccccc1] | — | — | — |

TABLE 4-continued
| | | | | | | | |
|---|---|---|---|---|---|---|---|
| S-10-22 | S | H | 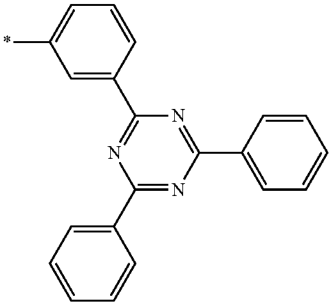 | H | — | — | — |
| S-10-23 | S | H | 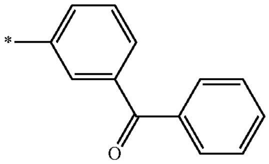 [SMILES: *c1cccc(C(=O)c2ccccc2)c1] | H | — | — | — |
| S-10-24 | S | H | 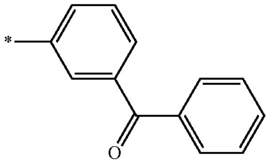 [SMILES: *c1cccc(C(=O)c2ccccc2)c1] | 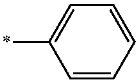 [SMILES: *c1ccccc1] | — | — | — |
| S-10-25 | S | H | 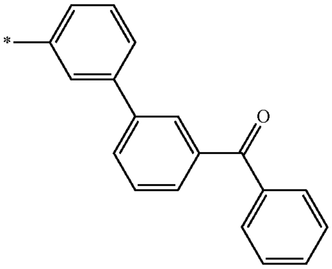 [SMILES: *c1cccc(-c2cccc(C(=O)c3ccccc3)c2)c1] | H | — | — | — |
| S-10-26 | S | H | 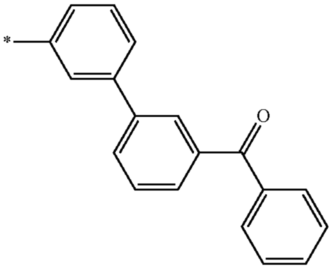 [SMILES: *c1cccc(-c2cccc(C(=O)c3ccccc3)c2)c1] | 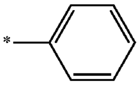 [SMILES: *c1ccccc1] | — | — | — |
| N-10-1 | $NR^3$ | H | H | H | 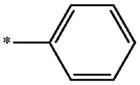 [SMILES: *c1ccccc1] | — | — |
| N-10-2 | $NR^3$ | H | 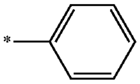 [SMILES: *c1ccccc1] | 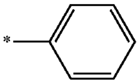 [SMILES: *c1ccccc1] | 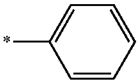 [SMILES: *c1ccccc1] | — | — |
| N-10-3 | NR3 | H | 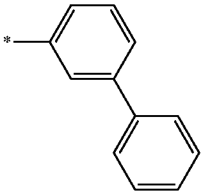 [SMILES: *c1cccc(-c2ccccc2)c1] | H | 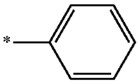 [SMILES: *c1ccccc1] | — | — |

TABLE 4-continued
| | | | | | | | |
|---|---|---|---|---|---|---|---|
| N-10-4 | $NR^3$ | H | 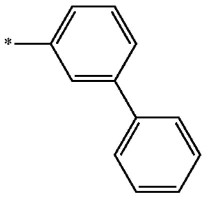 [SMILES: *c1cccc(-c2ccccc2)c1] | 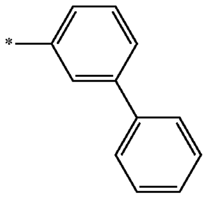 [SMILES: *c1cccc(-c2ccccc2)c1] | 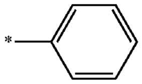 [SMILES: *c1ccccc1] | — | — |
| N-10-5 | $NR^3$ | H | 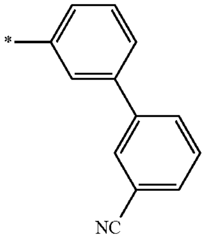 [SMILES: *c1cccc(-c2cccc(C#N)c2)c1] | H | 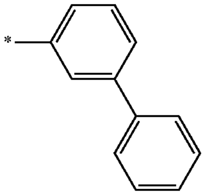 [SMILES: *c1cccc(-c2ccccc2)c1] | — | — |
| N-10-6 | $NR^3$ | H | H | 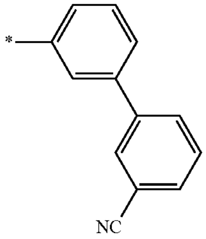 [SMILES: *c1cccc(-c2cccc(C#N)c2)c1] | 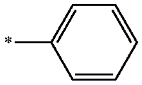 [SMILES: *c1ccccc1] | — | — |
| N-10-7 | $NR^3$ | H | 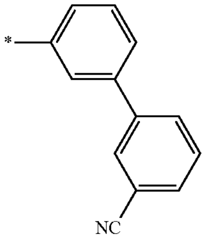 [SMILES: *c1cccc(-c2cccc(C#N)c2)c1] | 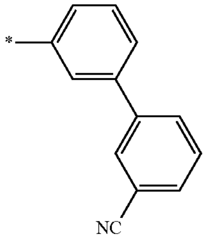 [SMILES: *c1cccc(-c2cccc(C#N)c2)c1] | 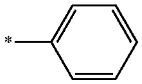 [SMILES: *c1ccccc1] | — | — |
| N-10-8 | $NR^3$ | H | 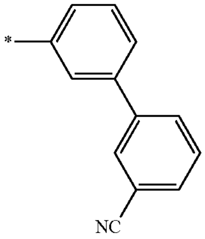 [SMILES: *c1cccc(-c2cccc(C#N)c2)c1] | 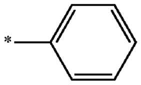 [SMILES: *c1ccccc1] | 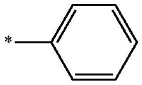 [SMILES: *c1ccccc1] | — | — |
TABLE 5
| | | | | | | | |
|---|---|---|---|---|---|---|---|
| N-10-9 | $NR^3$ | H | 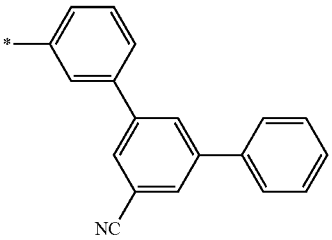 [SMILES: *c1cccc(-c2cc(C#N)cc(-c3ccccc3)c2)c1] | H | 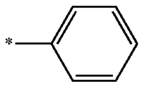 | — | — |

TABLE 5-continued
| | | | | | | | |
|---|---|---|---|---|---|---|---|
| N-10-10 | $NR^3$ | H | 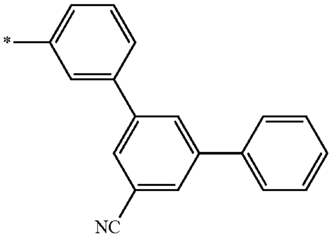 [SMILES: *c1cccc(-c2cc(C#N)cc(-c3ccccc3)c2)c1] | 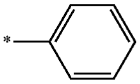 [SMILES: *c1ccccc1] | 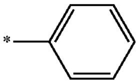 [SMILES: *c1ccccc1] | — | — |
| N-10-11 | $NR^3$ | H | 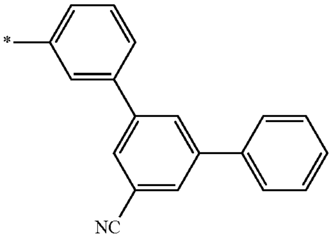 [SMILES: *c1cccc(-c2cc(C#N)cc(-c3ccccc3)c2)c1] | 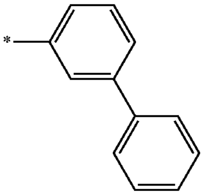 [SMILES: *c1cccc(-c2ccccc2)c1] | 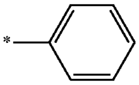 [SMILES: *c1ccccc1] | — | — |
| N-10-12 | $NR^3$ | H | 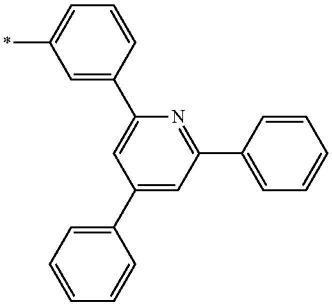 | H | 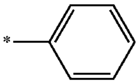 [SMILES: *c1ccccc1] | — | — |
| N-10-13 | $NR^3$ | H | 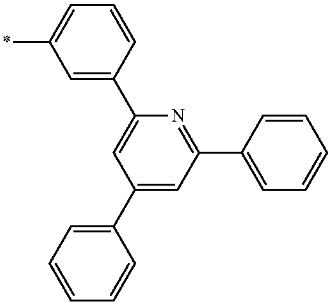 | 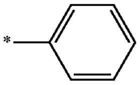 [SMILES: *c1ccccc1] | 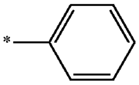 [SMILES: *c1ccccc1] | — | — |
| N-10-14 | $NR^3$ | H | 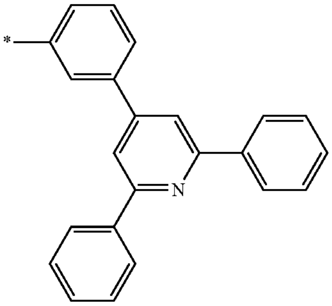 | H | 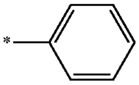 [SMILES: *c1ccccc1] | — | — |

TABLE 5-continued
| | | | | | | | |
|---|---|---|---|---|---|---|---|
| N-10-15 | $NR^3$ | H | 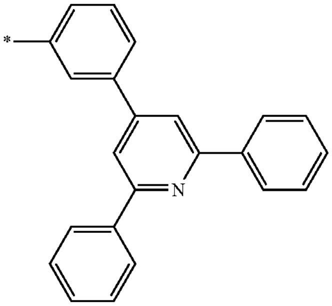 | 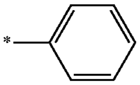 [SMILES: *c1ccccc1] | 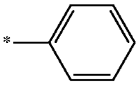 [SMILES: *c1ccccc1] | — | — |
| N-10-16 | $NR^3$ | H | 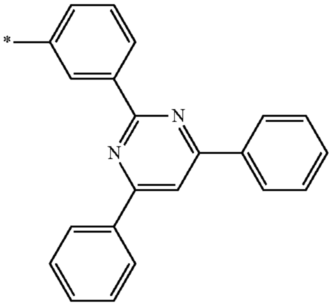 | H | 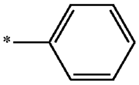 [SMILES: *c1ccccc1] | — | — |
| N-10-17 | $NR^3$ | H | 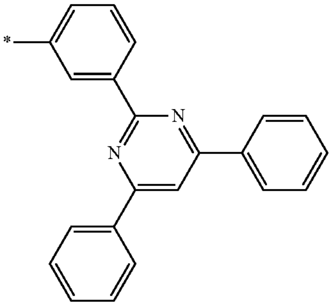 | 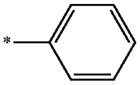 [SMILES: *c1ccccc1] | 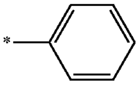 [SMILES: *c1ccccc1] | — | — |
| N-10-18 | $NR^3$ | H | 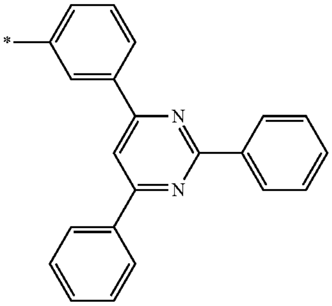 | H | 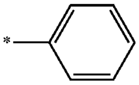 [SMILES: *c1ccccc1] | — | — |
| N-10-19 | $NR^3$ | H | 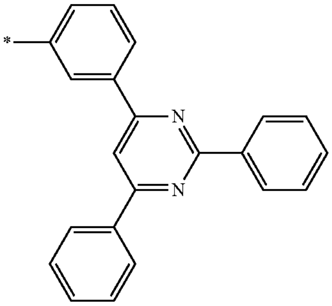 | 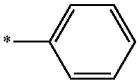 [SMILES: *c1ccccc1] | 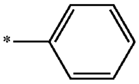 [SMILES: *c1ccccc1] | — | — |

TABLE 5-continued
| | | | | | | | |
|---|---|---|---|---|---|---|---|
| N-10-20 | $NR^3$ | H | 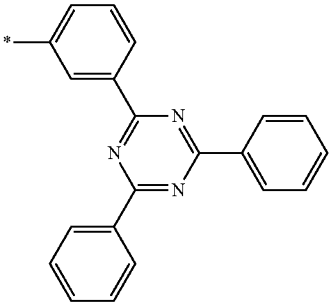 | H | 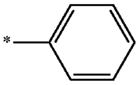 [SMILES: *c1ccccc1] | — | — |
| N-10-21 | $NR^3$ | H | 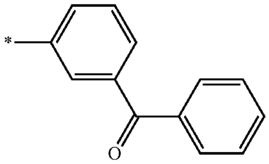 [SMILES: *c1cccc(C(=O)c2ccccc2)c1] | H | 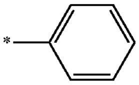 [SMILES: *c1ccccc1] | — | — |
| N-10-22 | $NR^3$ | H | 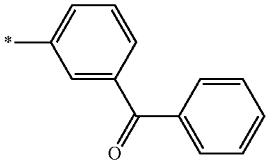 [SMILES: *c1cccc(C(=O)c2ccccc2)c1] | 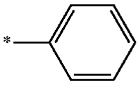 [SMILES: *c1ccccc1] | 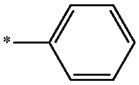 [SMILES: *c1ccccc1] | — | — |
| N-10-23 | $NR^3$ | H | 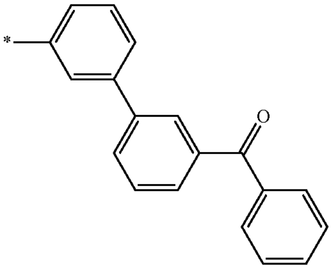 [SMILES: *c1cccc(-c2cccc(C(=O)c3ccccc3)c2)c1] | H | 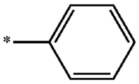 [SMILES: *c1ccccc1] | — | — |
TABLE 6
| | | | | | | | |
|---|---|---|---|---|---|---|---|
| N-10-24 | $NR^3$ | H | 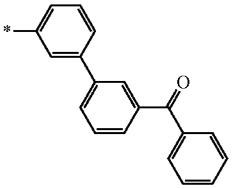 [SMILES: *c1cccc(-c2cccc(C(=O)c3ccccc3)c2)c1] | 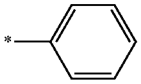 [SMILES: *c1ccccc1] | 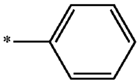 [SMILES: *c1ccccc1] | — | — |
| C-10-1 | $CR^1R^2$ | H | H | H | — | *—Me | *—Me |
| C-10-2 | $CR^1R^2$ | H | 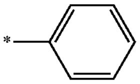 | 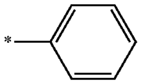 [SMILES: *c1ccccc1] | — | *—Me | *—Me |
| C-10-3 | $CR^1R^2$ | H | 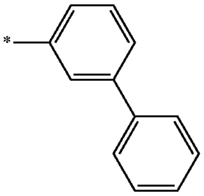 [SMILES: *c1cccc(-c2ccccc2)c1] | H | — | *—Me | *—Me |

TABLE 6-continued
| | | | | | | | |
|---|---|---|---|---|---|---|---|
| C-10-4 | $CR^1R^2$ | H | 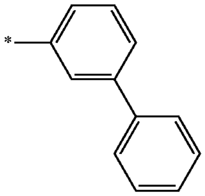 [SMILES: *c1cccc(-c2ccccc2)c1] | 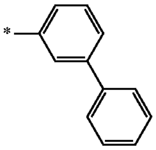 [SMILES: *c1cccc(-c2ccccc2)c1] | — | *—Me | *—Me |
| C-10-5 | $CR^1 R^2$ | H | 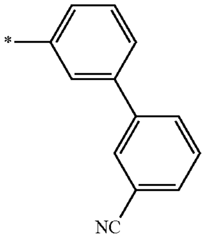 [SMILES: *c1cccc(-c2cccc(C#N)c2)c1] | H | — | 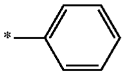 | 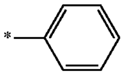 |
| C-10-6 | $CR^1R2$ | H | H | 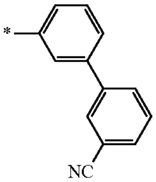 [SMILES: *c1cccc(-c2cccc(C#N)c2)c1] | — | *—Me | *—Me |
| C-10-7 | $CR^1 R^2$ | H | 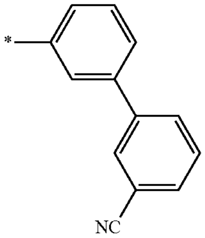 | 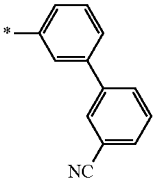 [SMILES: *c1cccc(-c2cccc(C#N)c2)c1] | — | 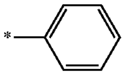 | 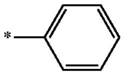 |
| C-10-8 | $CR^1 R^2$ | H | 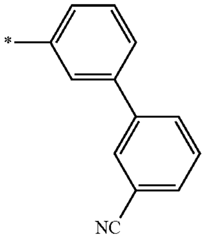 | 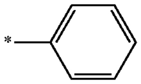 | — | *—Me | *—Me |
| C-10-9 | $CR^1 R^2$ | H | 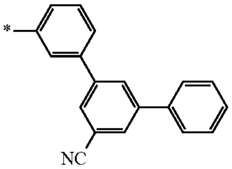 | H | — | 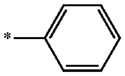 | 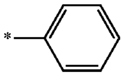 |
| C-10-10 | $CR^1R^2$ | H | 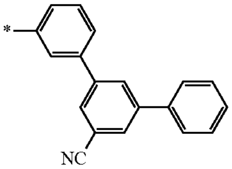 [SMILES: *c1cccc(-c2cc(C#N)cc(-c3ccccc3)c2)c1] | 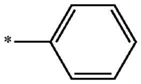 | — | *—Me | *—Me |

TABLE 6-continued
| | | | | | | | |
|---|---|---|---|---|---|---|---|
| C-10-11 | $CR^1R^2$ | H | 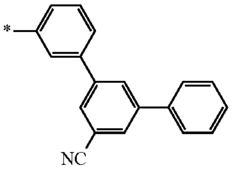 [SMILES: *c1cccc(-c2cc(C#N)cc(-c3ccccc3)c2)c1] | 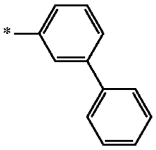 [SMILES: *c1cccc(-c2ccccc2)c1] | — | *—Me | *—Me |
| C-10-12 | $CR^1R^2$ | H | 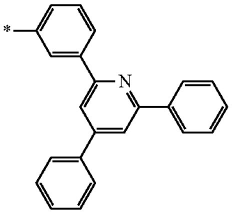 [SMILES: *c1cccc(-c2cc(-c3ccccc3)cc(-c3ccccc3)n2)c1] | H | — | *—Me | *—Me |
| C-10-13 | $CR^1R^2$ | H | 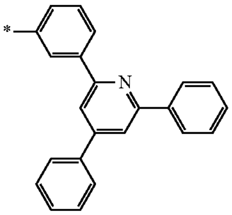 | 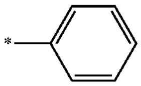 [SMILES: *c1ccccc1] | — | *—Me | *—Me |
| C-10-14 | $CR^1R^2$ | H | 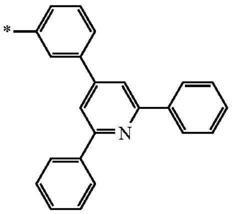 [SMILES: *c1cccc(-c2cc(-c3ccccc3)nc(-c3ccccc3)c2)c1] | H | — | *—Me | *—Me |
TABLE 7
| | | | | | | | |
|---|---|---|---|---|---|---|---|
| C-10-15 | $CR^1R^2$ | H | 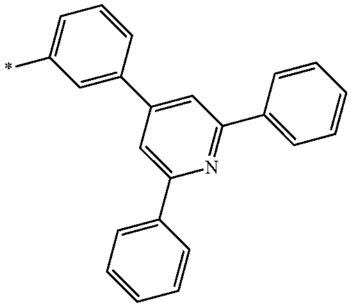 [SMILES: *c1cccc(-c2cc(-c3ccccc3)nc(-c3ccccc3)c2)c1] | 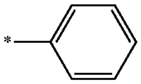 [SMILES: *c1ccccc1] | — | *—Me | *—Me |
| C-10-16 | $CR^1R^2$ | H | 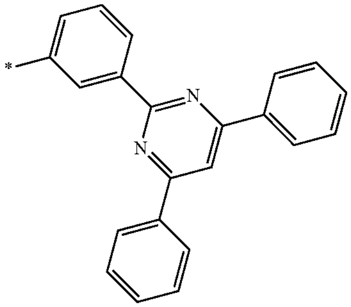 [SMILES: *c1cccc(-c2nc(-c3ccccc3)cc(-c3ccccc3)n2)c1] | H | — | 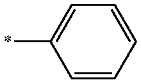 [SMILES: *c1ccccc1] | 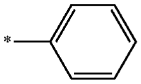 [SMILES: *c1ccccc1] |

TABLE 7-continued
| | | | | | | | |
|---|---|---|---|---|---|---|---|
| C-10-17 | $CR^1R^2$ | H | 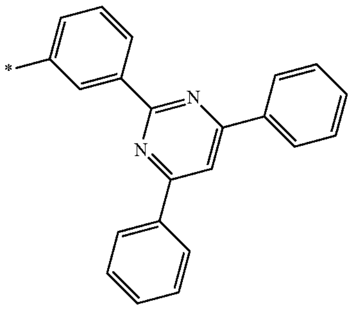 [SMILES: *c1cccc(-c2nc(-c3ccccc3)cc(-c3ccccc3)n2)c1] | 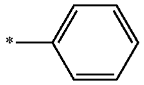 [SMILES: *c1ccccc1] | — | *—Me | *—Me |
| C-10-18 | $CR^1R^2$ | H | 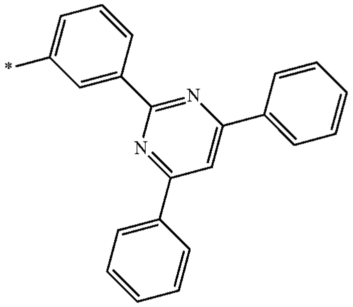 [SMILES: *c1cccc(-c2nc(-c3ccccc3)cc(-c3ccccc3)n2)c1] | H | — | *—Me | *—Me |
| C-10-19 | $CR^1R^2$ | H | 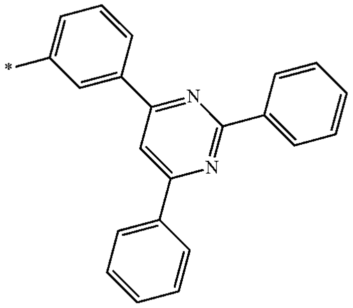 [SMILES: *c1cccc(-c2cc(-c3ccccc3)nc(-c3ccccc3)n2)c1] | 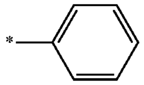 | — | *—Me | *—Me |
| C-10-20 | $CR^1R^2$ | H | 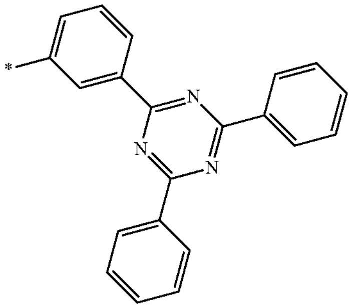 [SMILES: *c1cccc(-c2nc(-c3ccccc3)nc(-c3ccccc3)n2)c1] | H | — | *—Me | *—Me |
| C-10-21 | $CR^1R^2$ | H | 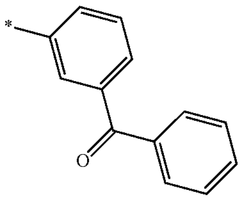 [SMILES: *c1cccc(C(=O)c2ccccc2)c1] | 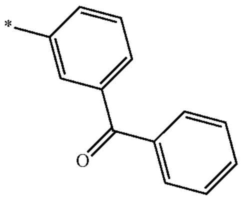 [SMILES: *c1cccc(C(=O)c2ccccc2)c1] | — | *—Me | *—Me |

TABLE 7-continued
| | | | | | | | |
|---|---|---|---|---|---|---|---|
| C-10-22 | $CR^1R^2$ | H | 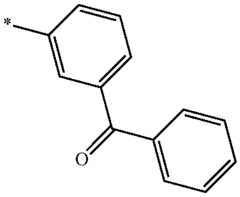 [SMILES: *c1cccc(C(=O)c2ccccc2)c1] | 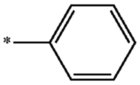 [SMILES: *c1ccccc1] | — | *—Me | *—Me |
| C-10-23 | $CR^1R^2$ | H | 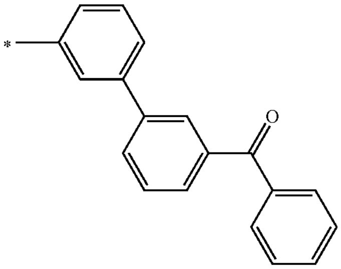 | H | — | 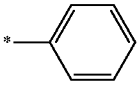 | 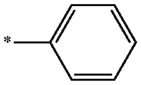 [SMILES: *c1ccccc1] |
| C-10-24 | $CR^1R2$ | H | 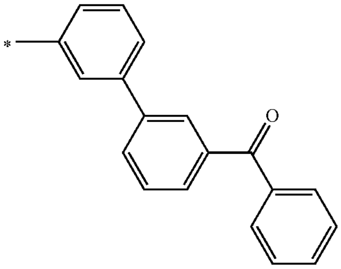 [SMILES: Cc1cccc(-c2cccc(C(=O)c3ccccc3)c2)c1] | 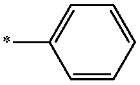 [SMILES: *c1ccccc1] | — | *—Me | *—Me |
TABLE 8
| Compound No. | Central skeleton | Substituent |
|---|---|---|
| O-10-27 | 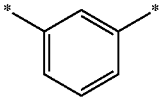 | 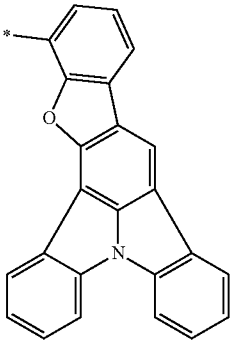 [SMILES: *c1cccc2c1oc1c2cc2c3ccccc3n3c4ccccc4c1c23] |
| O-10-28 | 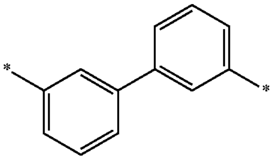 [SMILES: *c1cccc(-c2cccc(*)c2)c1] | 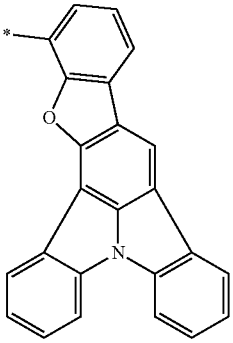 [SMILES: *c1cccc2c1oc1c2cc2c3ccccc3n3c4ccccc4c1c23] |

TABLE 8-continued
| Compound No. | Central skeleton | Substituent |
| --- | --- | --- |
| O-10-29 | 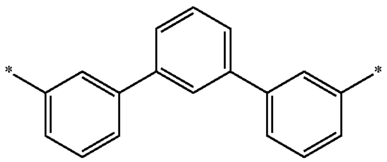 [SMILES: *c1cccc(-c2cccc(-c3cccc(*)c3)c2)c1] | 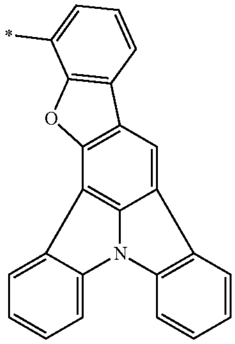 [SMILES: *c1cccc2c1oc1c2cc2c3ccccc3n3c4ccccc4c1c23] |
| O-10-30 | 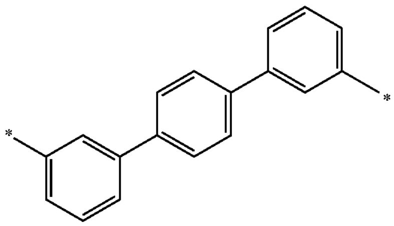 [SMILES: *c1cccc(-c2ccc(-c3cccc(C)c3)cc2)c1] | 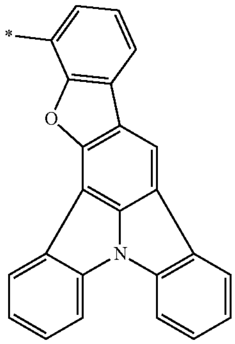 [SMILES: *c1cccc2c1oc1c2cc2c3ccccc3n3c4ccccc4c1c23] |
| O-10-31 | 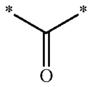 | 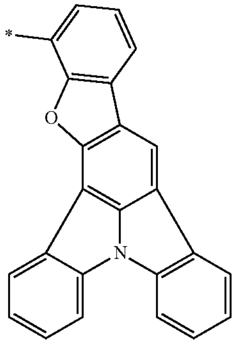 [SMILES: *c1cccc2c1oc1c2cc2c3ccccc3n3c4ccccc4c1c23] |
| O-10-32 | 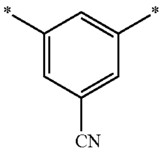 [SMILES: *c1cc(*)cc(C#N)c1] | 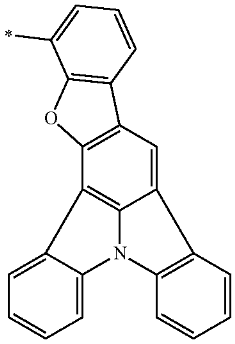 [SMILES: *c1cccc2c1oc1c2cc2c3ccccc3n3c4ccccc4c1c23] |

TABLE 8-continued
| Compound No. | Central skeleton | Substituent |
| --- | --- | --- |
| O-10-33 | 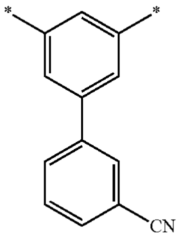 [SMILES: *c1cc(*)cc(-c2cccc(C#N)c2)c1] | 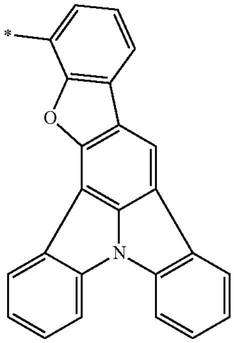 [SMILES: *c1cccc2c1oc1c2cc2c3ccccc3n3c4ccccc4c1c23] |
| O-10-34 | 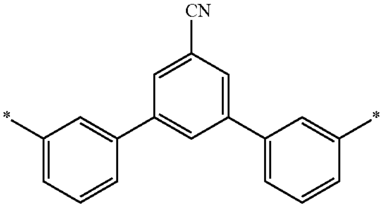 [SMILES: *c1cccc(-c2cc(C#N)cc(-c3cccc(*)c3)c2)c1] | 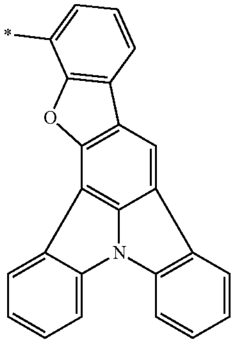 [SMILES: *c1cccc2c1oc1c2cc2c3ccccc3n3c4ccccc4c1c23] |
| O-10-35 | 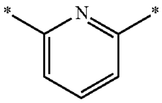 [SMILES: *c1cccc(*)n1] | 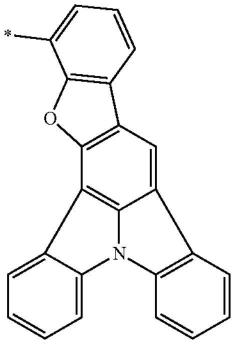 [SMILES: *c1cccc2c1oc1c2cc2c3ccccc3n3c4ccccc4c1c23] |
| O-10-36 | 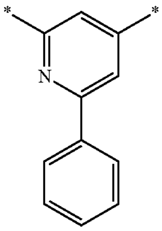 | 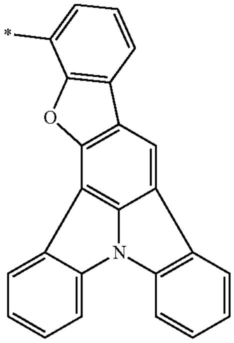 [SMILES: *c1cccc2c1oc1c2cc2c3ccccc3n3c4ccccc4c1c23] |

TABLE 8-continued
| Compound No. | Central skeleton | Substituent |
|---|---|---|
| O-10-37 | 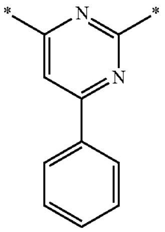 | 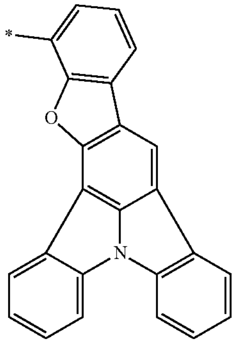 [SMILES: *c1cccc2c1oc1c2cc2c3ccccc3n3c4ccccc4c1c23] |
| O-10-38 | 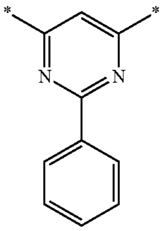 | 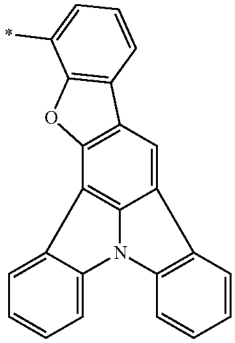 [SMILES: *c1cccc2c1oc1c2cc2c3ccccc3n3c4ccccc4c1c23] |
| O-10-39 | 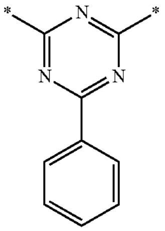 | 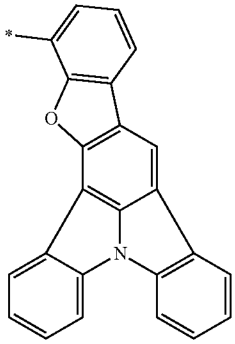 [SMILES: *c1cccc2c1oc1c2cc2c3ccccc3n3c4ccccc4c1c23] |
| O-10-40 | 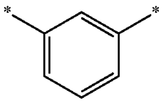 [SMILES: *c1cccc(*)c1] | 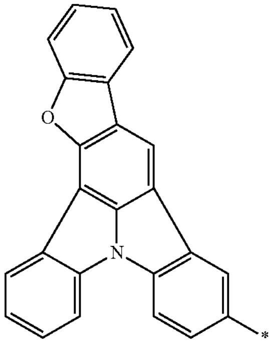 [SMILES: *c1ccc2c(c1)c1cc3c4ccccc4oc3c3c4ccccc4n2c13] |

TABLE 8-continued
| Compound No. | Central skeleton | Substituent |
|---|---|---|
| O-10-41 | 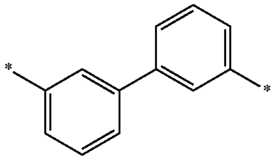 [SMILES: *c1cccc(-c2cccc(*)c2)c1] | 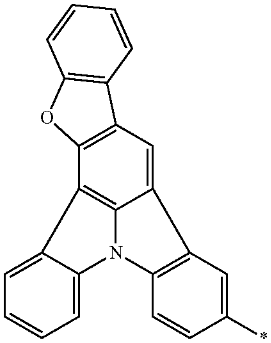 [SMILES: *c1ccc2c(c1)c1cc3c4ccccc4oc3c3c4ccccc4n2c13] |
| O-10-42 | 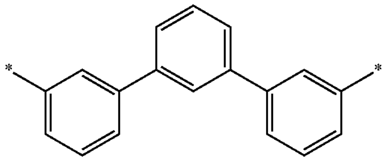 [SMILES: *c1cccc(-c2cccc(-c3cccc(*)c3)c2)c1] | 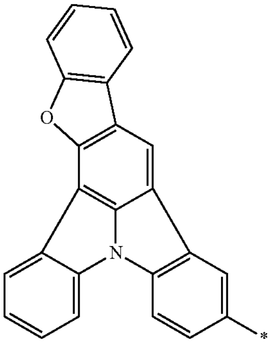 [SMILES: *c1ccc2c(c1)c1cc3c4ccccc4oc3c3c4ccccc4n2c13] |
| O-10-43 | 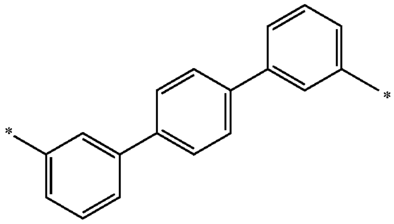 [SMILES: *c1cccc(-c2ccc(-c3cccc(C)c3)cc2)c1] | 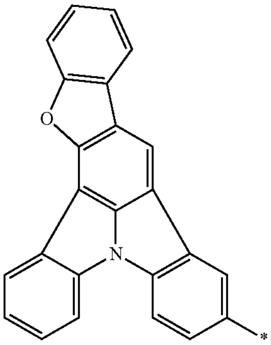 [SMILES: *c1ccc2c(c1)c1cc3c4ccccc4oc3c3c4ccccc4n2c13] |
| O-10-44 | 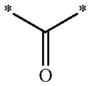 | 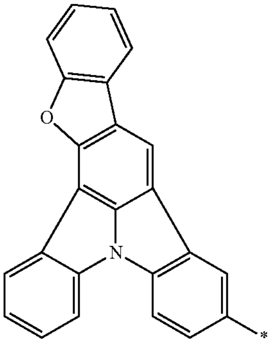 [SMILES: *c1ccc2c(c1)c1cc3c4ccccc4oc3c3c4ccccc4n2c13] |

TABLE 8-continued
| Compound No. | Central skeleton | Substituent |
|---|---|---|
| O-10-45 | 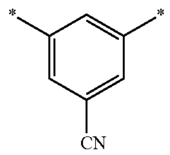 [SMILES: *c1cc(*)cc(C#N)c1] | 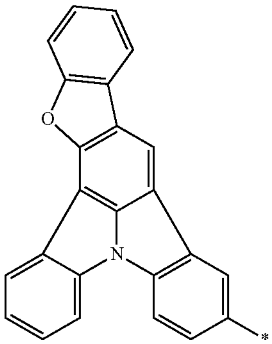 [SMILES: *c1ccc2c(c1)c1cc3c4ccccc4oc3c3c4ccccc4n2c13] |
| O-10-46 | 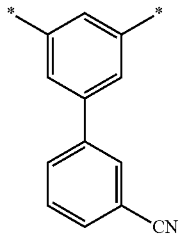 [SMILES: *c1cc(*)cc(-c2cccc(C#N)c2)c1] | 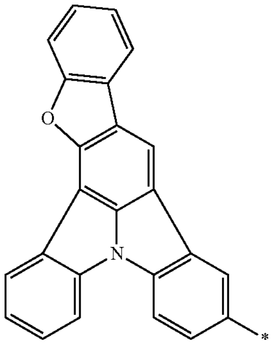 [SMILES: *c1ccc2c(c1)c1cc3c4ccccc4oc3c3c4ccccc4n2c13] |
| O-10-47 | 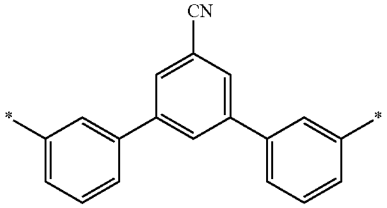 [SMILES: *c1cccc(-c2cc(C#N)cc(-c3cccc(*)c3)c2)c1] | 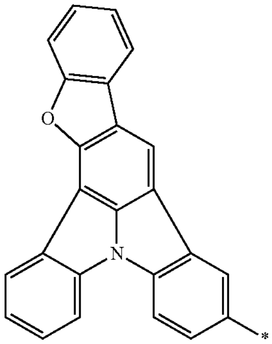 [SMILES: *c1ccc2c(c1)c1cc3c4ccccc4oc3c3c4ccccc4n2c13] |
| O-10-48 | 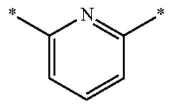 [SMILES: *c1cccc(*)n1] | 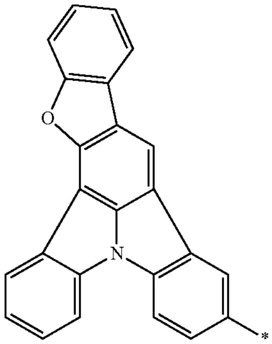 [SMILES: *c1ccc2c(c1)c1cc3c4ccccc4oc3c3c4ccccc4n2c13] |

TABLE 8-continued
| Compound No. | Central skeleton | Substituent |
| --- | --- | --- |
| O-10-49 | 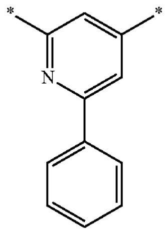 | 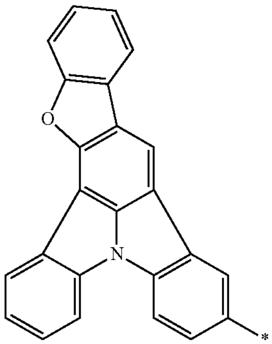 [SMILES: *c1ccc2c(c1)c1cc3c4ccccc4oc3c3c4ccccc4n2c13] |
| O-10-50 | 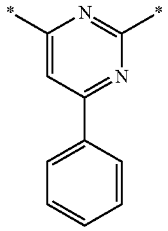 | 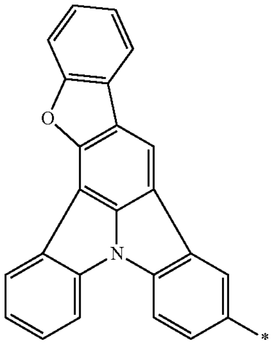 [SMILES: *c1ccc2c(c1)c1cc3c4ccccc4oc3c3c4ccccc4n2c13] |
| O-10-51 | 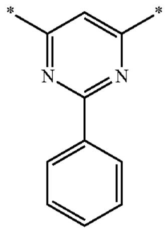 | 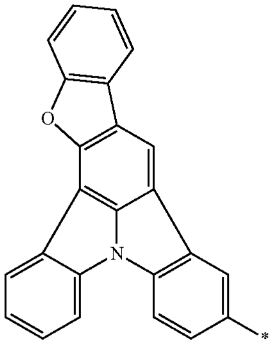 [SMILES: *c1ccc2c(c1)c1cc3c4ccccc4oc3c3c4ccccc4n2c13] |
| O-10-52 | 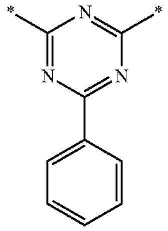 | 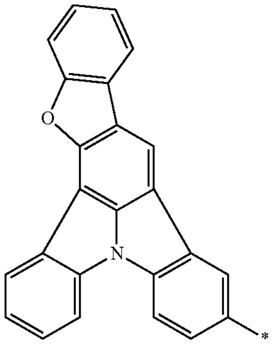 [SMILES: *c1ccc2c(c1)c1cc3c4ccccc4oc3c3c4ccccc4n2c13] |

TABLE 8-continued
| Compound No. | Central skeleton | Substituent |
|---|---|---|
| O-10-53 | 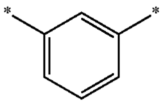 [SMILES: *c1cccc(*)c1] | 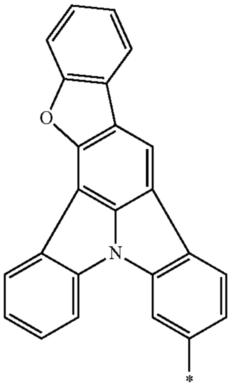 [SMILES: *c1ccc2c3cc4c5ccccc5oc4c4c5ccccc5n(c2c1)c34] |
| O-10-54 | 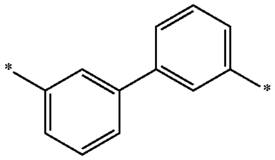 [SMILES: *c1cccc(-c2cccc(*)c2)c1] | 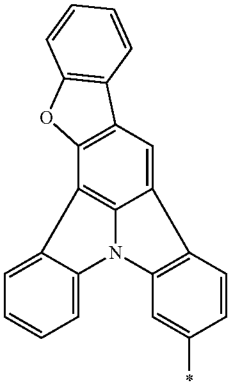 [SMILES: *c1ccc2c3cc4c5ccccc5oc4c4c5ccccc5n(c2c1)c34] |
| O-10-55 | 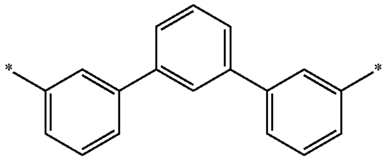 [SMILES: *c1cccc(-c2cccc(-c3cccc(*)c3)c2)c1] | 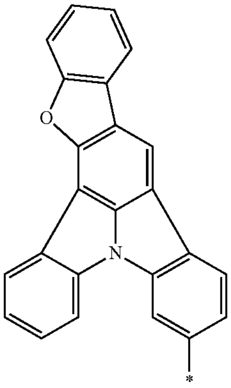 [SMILES: *c1ccc2c3cc4c5ccccc5oc4c4c5ccccc5n(c2c1)c34] |
| O-10-56 | 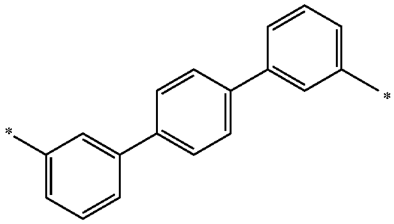 [SMILES: *c1cccc(-c2ccc(-c3cccc(C)c3)cc2)c1] | 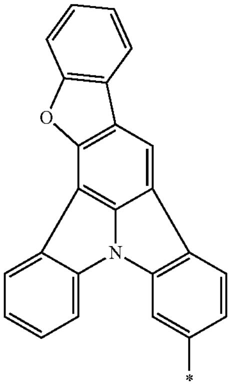 [SMILES: *c1ccc2c3cc4c5ccccc5oc4c4c5ccccc5n(c2c1)c34] |

TABLE 8-continued
| Compound No. | Central skeleton | Substituent |
| --- | --- | --- |
| O-10-57 | 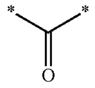 | 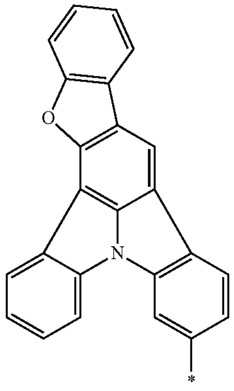 [SMILES: *c1ccc2c3cc4c5ccccc5oc4c4c5ccccc5n(c2c1)c34] |
| O-10-58 | 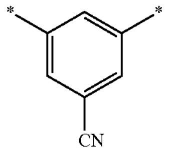 [SMILES: *c1cc(*)cc(C#N)c1] | 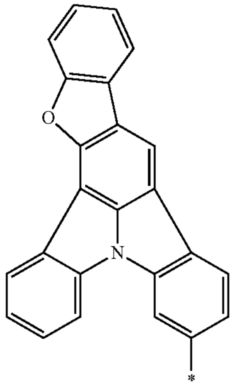 [SMILES: *c1ccc2c3cc4c5ccccc5oc4c4c5ccccc5n(c2c1)c34] |
| O-10-59 | 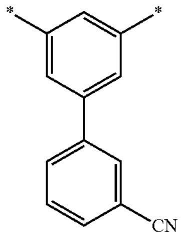 [SMILES: *c1cc(*)cc(-c2cccc(C#N)c2)c1] | 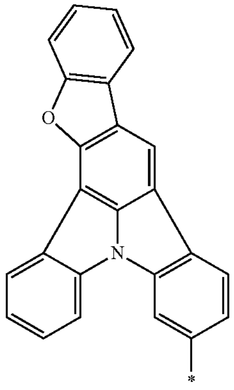 [SMILES: *c1ccc2c3cc4c5ccccc5oc4c4c5ccccc5n(c2c1)c34] |
| O-10-60 | 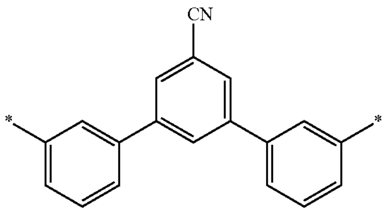 [SMILES: *c1cccc(-c2cc(C#N)cc(-c3cccc(*)c3)c2)c1] | 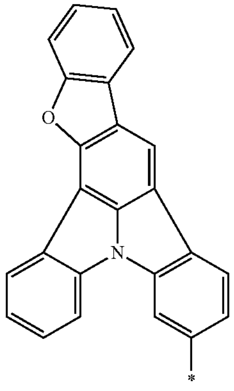 [SMILES: *c1ccc2c3cc4c5ccccc5oc4c4c5ccccc5n(c2c1)c34] |

TABLE 8-continued
| Compound No. | Central skeleton | Substituent |
| --- | --- | --- |
| O-10-61 | 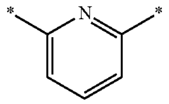 [SMILES: *c1cccc(*)n1] | 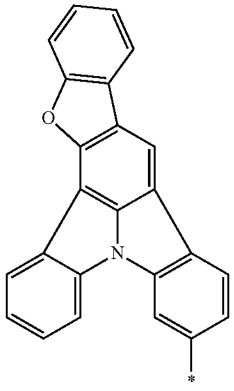 [SMILES: *c1ccc2c3cc4c5ccccc5oc4c4c5ccccc5n(c2c1)c34] |
| O-10-62 | 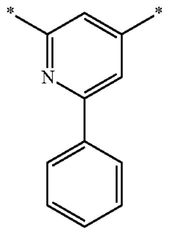 | 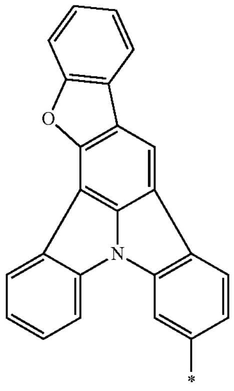 [SMILES: *c1ccc2c3cc4c5ccccc5oc4c4c5ccccc5n(c2c1)c34] |
| O-10-63 | 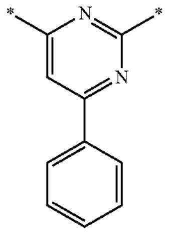 | 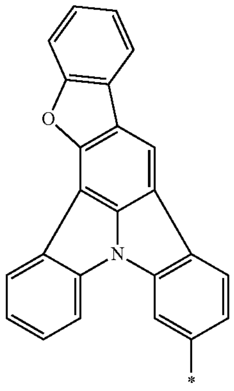 [SMILES: *c1ccc2c3cc4c5ccccc5oc4c4c5ccccc5n(c2c1)c34] |
| O-10-64 | 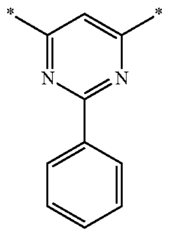 | 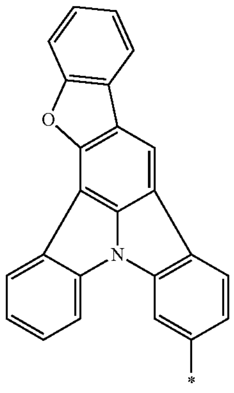 [SMILES: *c1ccc2c3cc4c5ccccc5oc4c4c5ccccc5n(c2c1)c34] |

TABLE 8-continued
| Compound No. | Central skeleton | Substituent |
|---|---|---|
| O-10-65 | 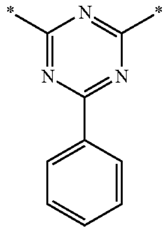 | 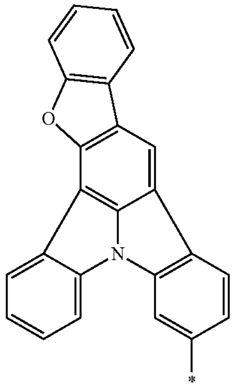 [SMILES: *c1ccc2c3cc4c5ccccc5oc4c4c5ccccc5n(c2c1)c34] |
In the compounds represented by the following general formula (11), $R^{B1}$, $R^{B4}$, $R^{B6}$ to $R^{B9}$, $R^{B11}$, $R^{B13}$ to $R^{B15}$ each represent a hydrogen atom, and the other groups are the groups described in Tables below.
[Chem. 16]
(11)
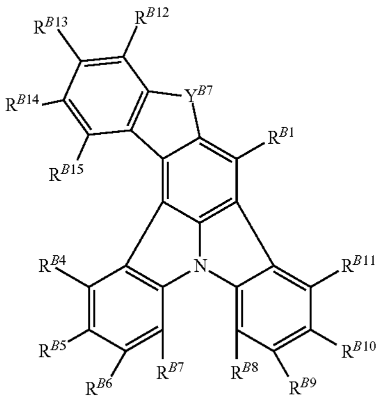
TABLE 9
| Compound No. | $Y^{B1}$ | $R^{B12}$ | $R^{B10}$ | $R^{B5}$ | $R^3$ | $R^1$ | $R^2$ |
|---|---|---|---|---|---|---|---|
| O-11-1 | O | H | H | H | — | — | — |
| O-11-2 | O | H | 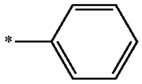 [SMILES: *c1ccccc1] | 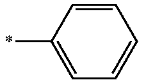 [SMILES: *c1ccccc1] | — | — | — |
| O-11-3 | O | H | 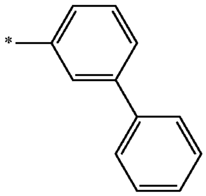 [SMILES: *c1cccc(-c2ccccc2)c1] | H | — | — | — |

TABLE 9-continued
| Compound No. | $Y^{B1}$ | $R^{B12}$ | $R^{B10}$ | $R^{B5}$ | $R^3$ | $R^1$ | $R^2$ |
|---|---|---|---|---|---|---|---|
| O-11-4 | O | H | 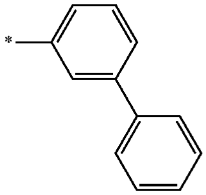 [SMILES: *c1cccc(-c2ccccc2)c1] | 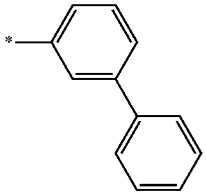 [SMILES: *c1cccc(-c2ccccc2)c1] | — | — | — |
| O-11-5 | O | 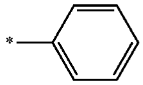 | 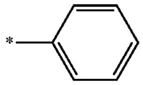 | 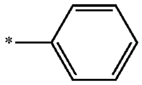 | — | — | — |
| O-11-6 | O | H | 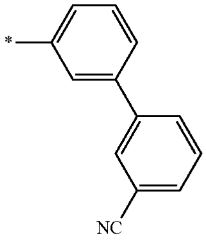 [SMILES: *c1cccc(-c2cccc(C#N)c2)c1] | H | — | — | — |
| O-11-7 | O | H | H | 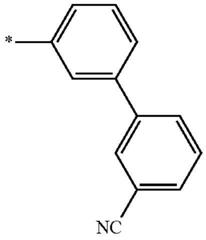 [SMILES: *c1cccc(-c2cccc(C#N)c2)c1] | — | — | — |
| O-11-8 | O | H | 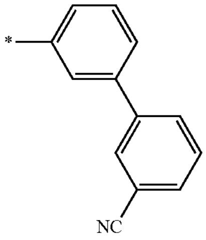 [SMILES: *c1cccc(-c2cccc(C#N)c2)c1] | 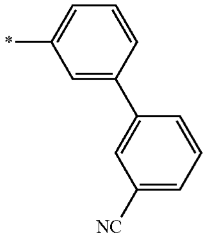 [SMILES: *c1cccc(-c2cccc(C#N)c2)c1] | — | — | — |
| O-11-9 | O | H | 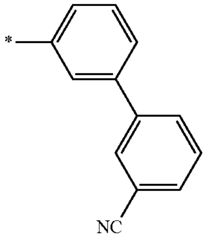 [SMILES: *c1cccc(-c2cccc(C#N)c2)c1] | 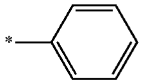 | — | — | — |
| O-11-10 | O | H | 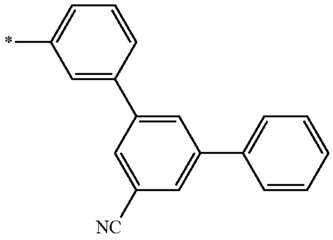 [SMILES: *c1cccc(-c2cc(C#N)cc(-c3ccccc3)c2)c1] | H | — | — | — |

TABLE 9-continued
| Compound No. | $Y^{B1}$ | $R^{B12}$ | $R^{B10}$ | $R^{B5}$ | $R^3$ | $R^1$ | $R^2$ |
|---|---|---|---|---|---|---|---|
| O-11-11 | O | H | 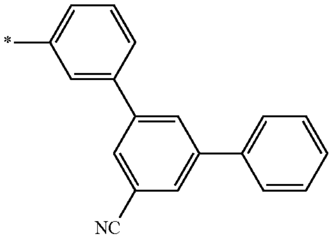 [SMILES: *c1cccc(-c2cc(C#N)cc(-c3ccccc3)c2)c1] | 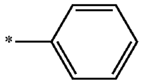 | — | — | — |
| O-11-12 | O | H | 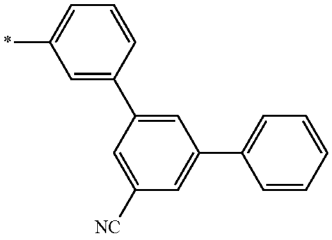 [SMILES: *c1cccc(-c2cc(C#N)cc(-c3ccccc3)c2)c1] | 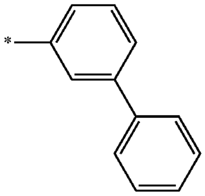 [SMILES: *c1cccc(-c2ccccc2)c1] | — | — | — |
| O-11-13 | O | 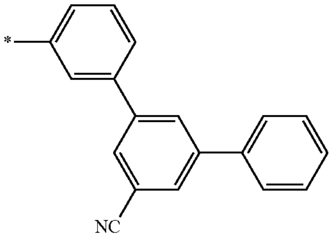 [SMILES: *c1cccc(-c2cc(C#N)cc(-c3ccccc3)c2)c1] | H | H | — | — | — |
| O-11-14 | O | H | 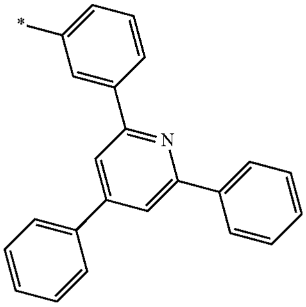 [SMILES: *c1cccc(-c2cc(-c3ccccc3)cc(-c3ccccc3)n2)c1] | H | — | — | — |
| O-11-15 | O | H | 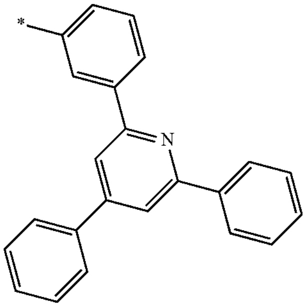 [SMILES: *c1cccc(-c2cc(-c3ccccc3)cc(-c3ccccc3)n2)c1] | 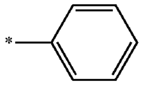 | — | — | — |

TABLE 10
| | | | | | | | |
|---|---|---|---|---|---|---|---|
| O-11-16 | O | H | 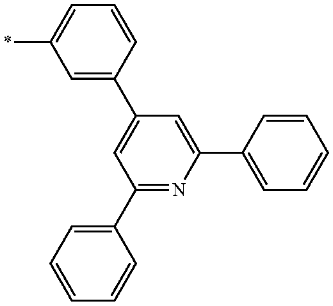 | H | — | — | — |
| O-11-17 | O | H | 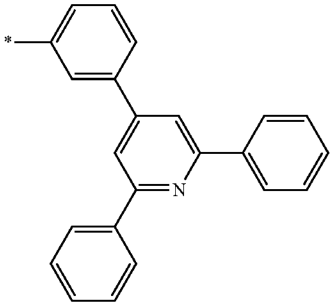 | 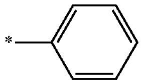 [SMILES: *c1ccccc1] | — | — | — |
| O-11-18 | O | H | 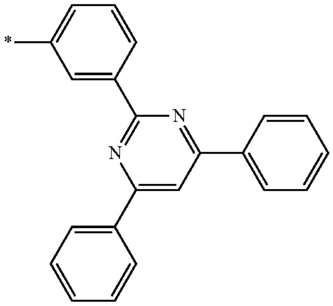 | H | — | — | — |
| O-11-19 | O | H | 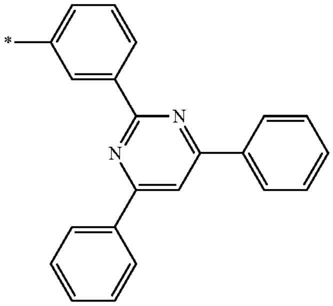 | 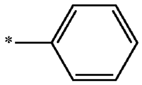 [SMILES: *c1ccccc1] | — | — | — |
| O-11-20 | O | H | 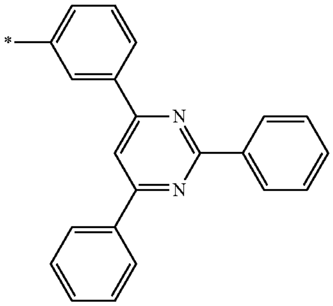 | H | — | — | — |

TABLE 10-continued
| | | | | | | | |
|---|---|---|---|---|---|---|---|
| O-11-21 | O | H | 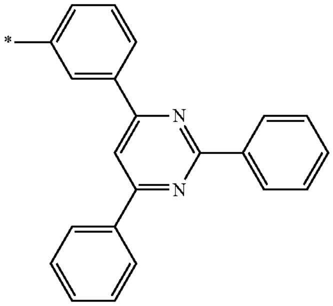 | 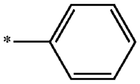 [SMILES: *c1ccccc1] | — | — | — |
| O-11-22 | O | H | 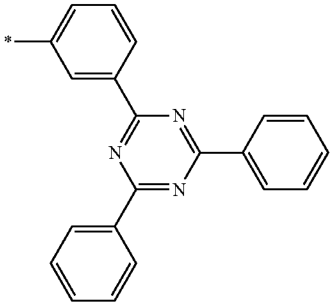 | H | — | — | — |
| O-11-23 | O | H | 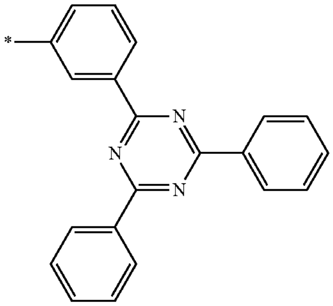 | 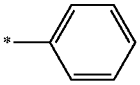 [SMILES: *c1ccccc1] | — | — | — |
| O-11-24 | O | H | 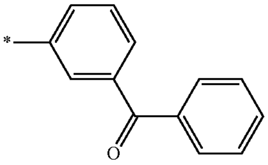 [SMILES: *c1cccc(C(=O)c2ccccc2)c1] | H | — | — | — |
| O-11-25 | O | H | 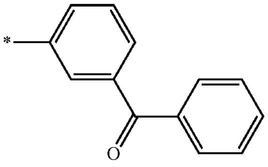 [SMILES: *c1cccc(C(=O)c2ccccc2)c1] | 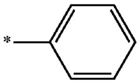 | — | — | — |
| O-11-26 | O | H | 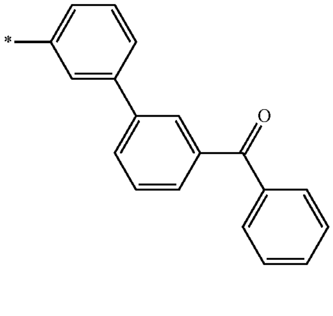 [SMILES: *c1cccc(-c2cccc(C(=O)c3ccccc3)c2)c1] | H | — | — | — |

TABLE 10-continued
| | | | | | | | |
|---|---|---|---|---|---|---|---|
| O-11-27 | O | H | 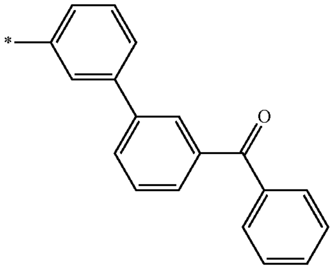 [SMILES: *c1cccc(-c2cccc(C(=O)c3ccccc3)c2)c1] | 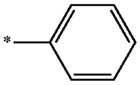 [SMILES: *c1ccccc1] | — | — | — |
| S-11-1 | S | H | H | H | — | — | — |
| S-11-2 | S | H | 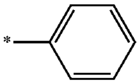 [SMILES: *c1ccccc1] | 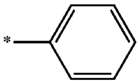 [SMILES: *c1ccccc1] | — | — | — |
| S-11-3 | S | H | 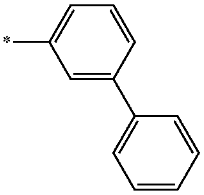 [SMILES: *c1cccc(-c2ccccc2)c1] | H | — | — | — |
TABLE 11
| | | | | | | | |
|---|---|---|---|---|---|---|---|
| S-11-4 | S | H | 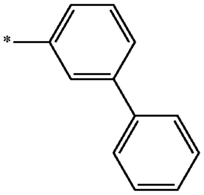 [SMILES: *c1cccc(-c2ccccc2)c1] | 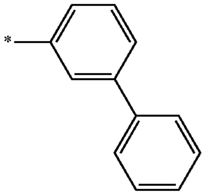 [SMILES: *c1cccc(-c2ccccc2)c1] | — | — | — |
| S-11-5 | S | 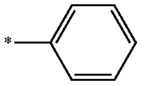 | 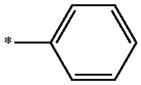 [SMILES: *c1ccccc1] | 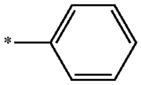 [SMILES: *c1ccccc1] | — | — | — |
| S-11-6 | S | H | 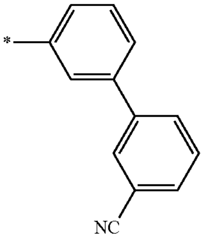 [SMILES: *c1cccc(-c2cccc(C#N)c2)c1] | H | — | — | — |
| S-11-7 | S | H | H | 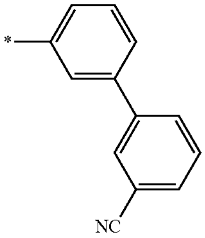 [SMILES: *c1cccc(-c2cccc(C#N)c2)c1] | — | — | — |

TABLE 11-continued
| | | | | | | | |
|---|---|---|---|---|---|---|---|
| S-11-8 | S | H | 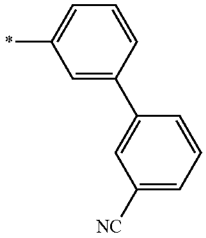 [SMILES: *c1cccc(-c2cccc(C#N)c2)c1] | 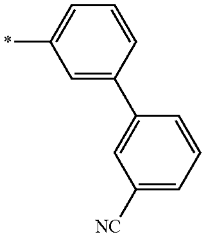 [SMILES: *c1cccc(-c2cccc(C#N)c2)c1] | — | — | — |
| S-11-9 | S | H | 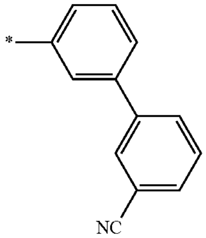 [SMILES: *c1cccc(-c2cccc(C#N)c2)c1] | 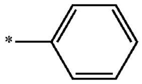 | — | — | — |
| S-11-10 | | H | 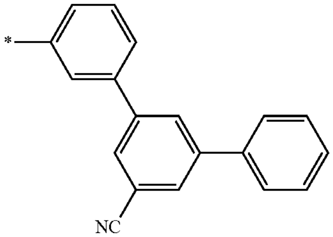 [SMILES: *c1cccc(-c2cc(C#N)cc(-c3ccccc3)c2)c1] | H | — | — | — |
| S-11-11 | S | H | 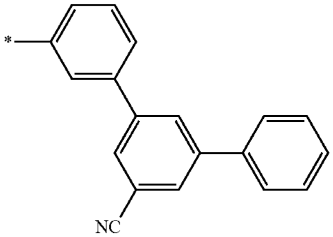 [SMILES: *c1cccc(-c2cc(C#N)cc(-c3ccccc3)c2)c1] | 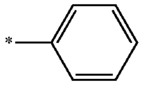 [SMILES: *c1ccccc1] | — | — | — |
| S-11-12 | S | H | 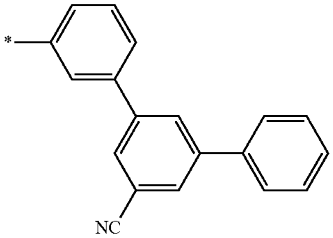 [SMILES: *c1cccc(-c2cc(C#N)cc(-c3ccccc3)c2)c1] | 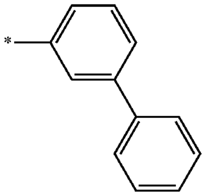 | — | — | — |
| S-11-13 | S | 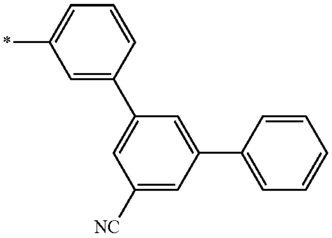 | H | H | — | — | — |

TABLE 11-continued
| | | | | | | | |
|---|---|---|---|---|---|---|---|
| S-11-14 | S | H | 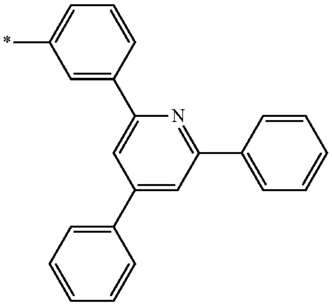 | H | — | — | — |
| S-11-15 | S | H | 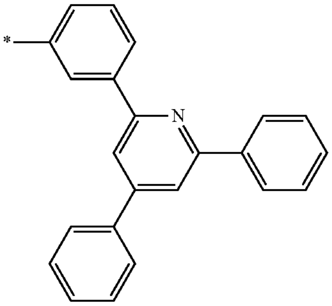 | 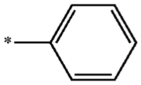 | — | — | — |
| S-11-16 | S | H | 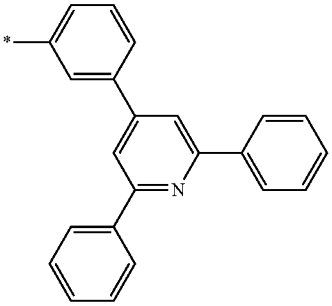 | H | — | — | — |
| S-11-17 | S | H | 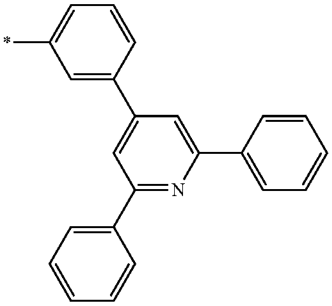 | 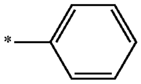 [SMILES: *c1ccccc1] | — | — | — |
| S-11-18 | S | H | 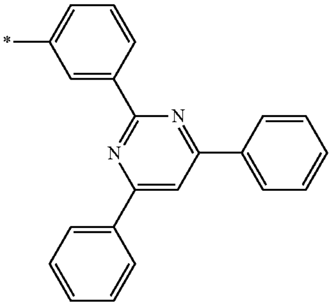 | H | — | — | — |

TABLE 12
| | | | | | | | |
|---|---|---|---|---|---|---|---|
| S-11-19 | S | H | 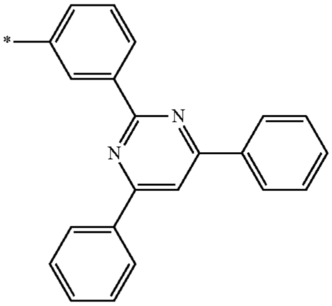 | 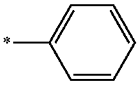 [SMILES: *c1ccccc1] | — | — | — |
| S-11-20 | S | H | 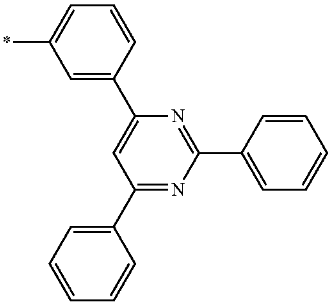 [SMILES: *c1cccc(-c2cc(-c3ccccc3)nc(-c3ccccc3)n2)c1] | H | — | — | — |
| S-11-21 | S | H | 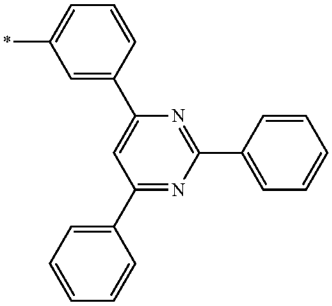 [SMILES: *c1cccc(-c2cc(-c3ccccc3)nc(-c3ccccc3)n2)c1] | 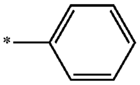 | — | — | — |
| S-11-22 | S | H | 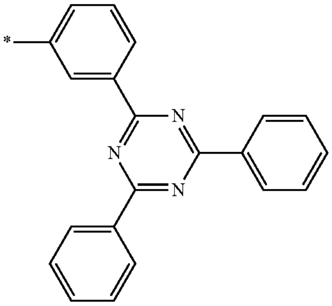 | H | — | — | — |
| S-11-23 | S | H | 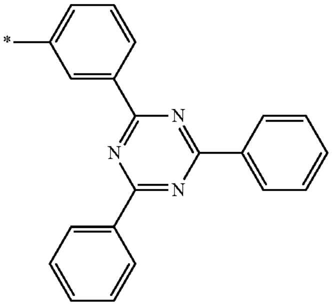 [SMILES: *c1cccc(-c2nc(-c3ccccc3)nc(-c3ccccc3)n2)c1] | 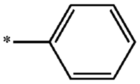 | — | — | — |

TABLE 12-continued
| | | | | | | | |
|---|---|---|---|---|---|---|---|
| S-11-24 | S | H | 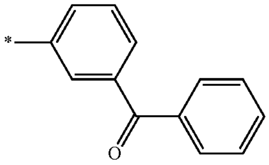 | H | — | — | — |
| S-11-25 | S | H | 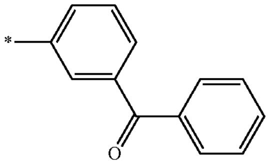 [SMILES: *c1cccc(C(=O)c2ccccc2)c1] | 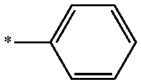 [SMILES: *c1ccccc1] | — | — | — |
| S-11-26 | S | H | 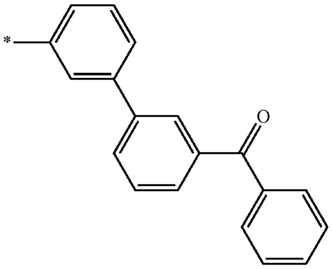 [SMILES: *c1cccc(-c2cccc(C(=O)c3ccccc3)c2)c1] | H | — | — | — |
| S-11-27 | S | H | 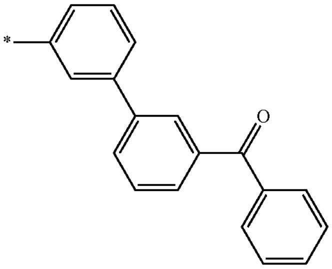 [SMILES: *c1cccc(-c2cccc(C(=O)c3ccccc3)c2)c1] | 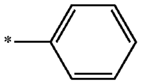 [SMILES: *c1ccccc1] | — | — | — |
| N-11-1 | $NR^3$ | H | H | H | 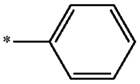 | — | — |
| N-11-2 | $NR^3$ | H | 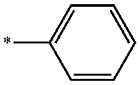 | 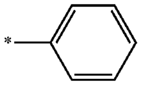 | 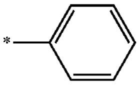 | — | — |
| N-11-3 | $NR^3$ | H | 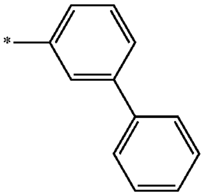 [SMILES: *c1cccc(-c2ccccc2)c1] | H | 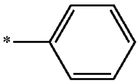 [SMILES: *c1ccccc1] | — | — |
| N-11-4 | $NR^3$ | H | 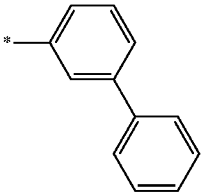 [SMILES: *c1cccc(-c2ccccc2)c1] | 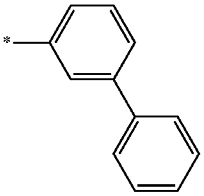 [SMILES: *c1cccc(-c2ccccc2)c1] | 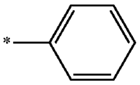 [SMILES: *c1ccccc1] | — | — |

TABLE 12-continued
| | | | | | | | |
|---|---|---|---|---|---|---|---|
| N-11-5 | $NR^3$ | H | 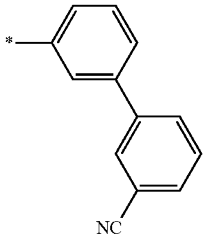 | H | 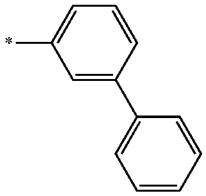 [SMILES: *c1cccc(-c2ccccc2)c1] | — | — |
| N-11-6 | $NR^3$ | H | H | 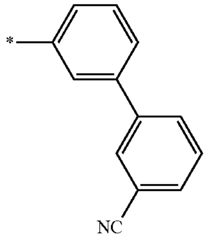 | 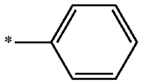 [SMILES: *c1ccccc1] | — | — |
TABLE 13
| | | | | | | | |
|---|---|---|---|---|---|---|---|
| N-11-7 | $NR^3$ | H | 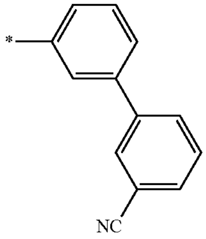 [SMILES: *c1cccc(-c2cccc(C#N)c2)c1] | 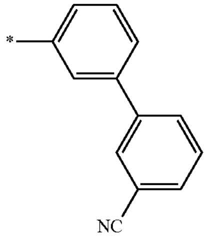 [SMILES: *c1cccc(-c2cccc(C#N)c2)c1] | 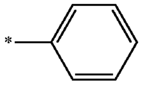 [SMILES: *c1ccccc1] | — | — |
| N-11-8 | $NR^3$ | H | 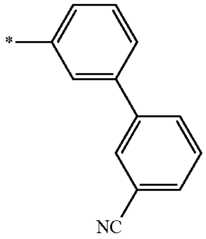 | 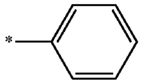 [SMILES: *c1ccccc1] | 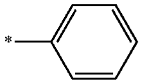 [SMILES: *c1ccccc1] | — | — |
| N-11-9 | $NR^3$ | H | 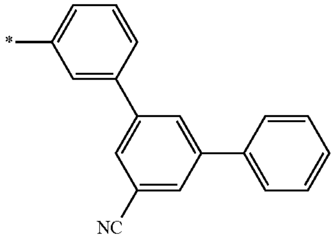 [SMILES: *c1cccc(-c2cc(C#N)cc(-c3ccccc3)c2)c1] | H | 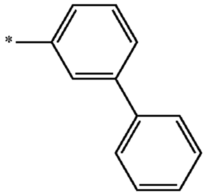 [SMILES: *c1cccc(-c2ccccc2)c1] | — | — |
| N-11-10 | $NR^3$ | H | 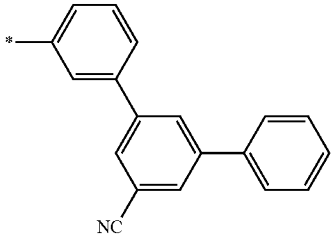 [SMILES: *c1cccc(-c2cc(C#N)cc(-c3ccccc3)c2)c1] | 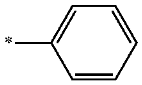 [SMILES: *c1ccccc1] | 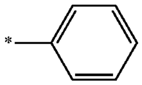 [SMILES: *c1ccccc1] | — | — |

TABLE 13-continued
| | | | | | | | |
|---|---|---|---|---|---|---|---|
| N-11-11 | $NR^3$ | H | 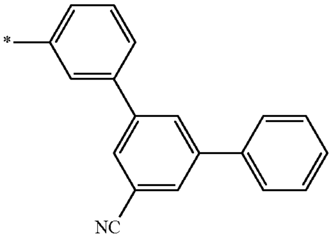 [SMILES: *c1cccc(-c2cc(C#N)cc(-c3ccccc3)c2)c1] | 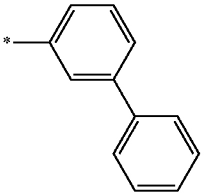 [SMILES: *c1cccc(-c2ccccc2)c1] | 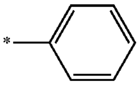 | — | — |
| N-11-12 | $NR^3$ | H | 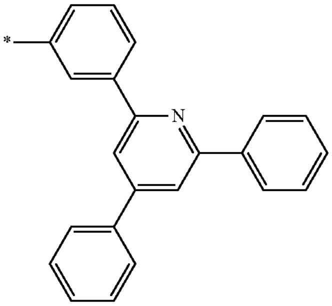 [SMILES: *c1cccc(-c2cc(-c3ccccc3)cc(-c3ccccc3)n2)c1] | H | 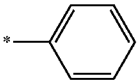 [SMILES: *c1ccccc1] | — | — |
| N-11-13 | $NR^3$ | H | 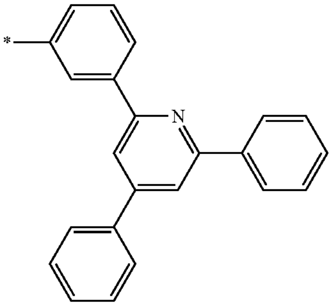 | 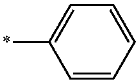 [SMILES: *c1ccccc1] | 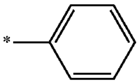 [SMILES: *c1ccccc1] | — | — |
| N-11-14 | $NR^3$ | H | 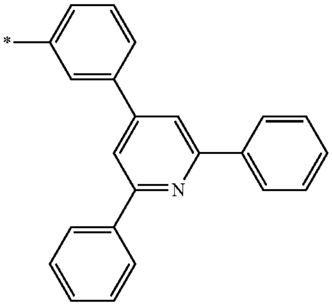 [SMILES: *c1cccc(-c2cc(-c3ccccc3)nc(-c3ccccc3)c2)c1] | H | 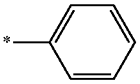 [SMILES: *c1ccccc1] | — | — |
| N-11-15 | $NR^3$ | H | 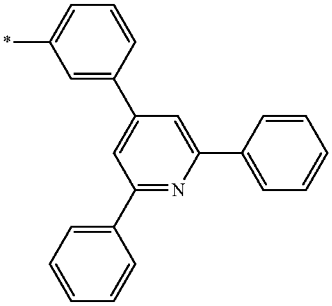 [SMILES: *c1cccc(-c2cc(-c3ccccc3)nc(-c3ccccc3)c2)c1] | 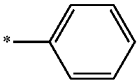 [SMILES: *c1ccccc1] | 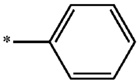 [SMILES: *c1ccccc1] | — | — |

TABLE 13-continued
| | | | | | | | |
|---|---|---|---|---|---|---|---|
| N-11-16 | NR$^3$ | H | 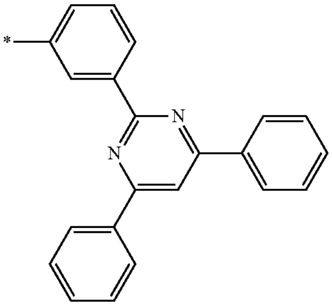 | H | 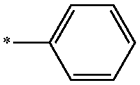 [SMILES: *c1ccccc1] | — | — |
| N-11-17 | NR$^3$ | H | 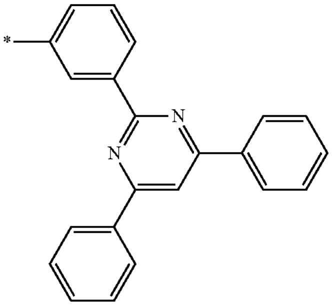 [SMILES: *c1cccc(-c2nc(-c3ccccc3)cc(-c3ccccc3)n2)c1] | 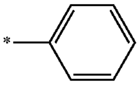 [SMILES: *c1ccccc1] | 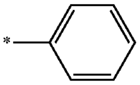 [SMILES: *c1ccccc1] | — | — |
| N-11-18 | NR$^3$ | H | 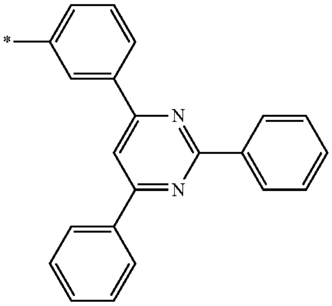 [SMILES: *c1cccc(-c2cc(-c3ccccc3)nc(-c3ccccc3)n2)c1] | H | 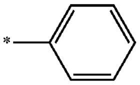 | — | — |
| N-11-19 | NR$^3$ | H | 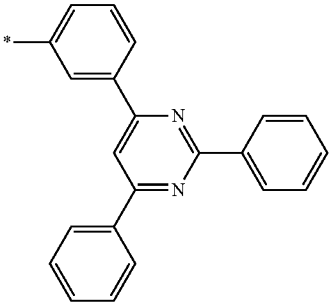 [SMILES: *c1cccc(-c2cc(-c3ccccc3)nc(-c3ccccc3)n2)c1] | 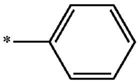 | 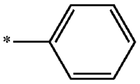 | — | — |
| N-11-20 | NR$^3$ | H | 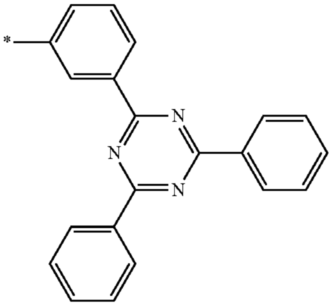 [SMILES: *c1cccc(-c2nc(-c3ccccc3)nc(-c3ccccc3)n2)c1] | H | 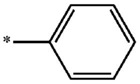 | — | — |

TABLE 13-continued
| | | | | | | | |
|---|---|---|---|---|---|---|---|
| N-11-21 | $NR^3$ | H | 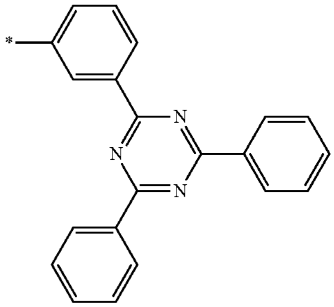 [SMILES: *c1cccc(-c2nc(-c3ccccc3)nc(-c3ccccc3)n2)c1] | 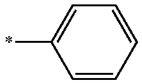 [SMILES: *c1ccccc1] | 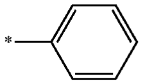 [SMILES: *c1ccccc1] | — | — |
TABLE 14
| | | | | | | | |
|---|---|---|---|---|---|---|---|
| N-11-22 | $NR^3$ | H | 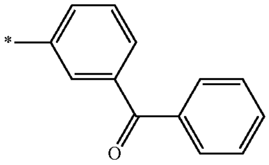 [SMILES: *c1cccc(C(=O)c2ccccc2)c1] | H | 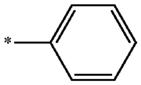 [SMILES: *c1ccccc1] | — | — |
| N-11-23 | $NR^3$ | H | 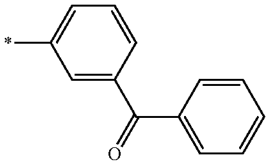 [SMILES: *c1cccc(C(=O)c2ccccc2)c1] | 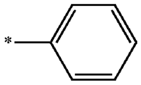 [SMILES: *c1ccccc1] | 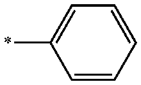 | — | — |
| N-11-24 | $NR^3$ | H | 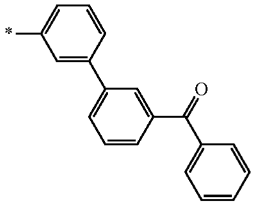 [SMILES: *c1cccc(-c2cccc(C(=O)c3ccccc3)c2)c1] | H | 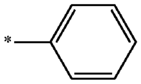 [SMILES: *c1ccccc1] | — | — |
| N-11-25 | $NR^3$ | H | 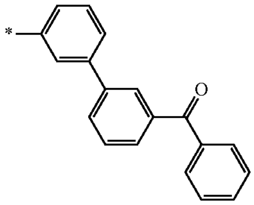 [SMILES: *c1cccc(-c2cccc(C(=O)c3ccccc3)c2)c1] | 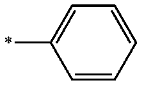 | 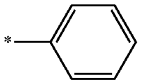 [SMILES: *c1ccccc1] | — | — |
| C-11-1 | $CR^1R^2$ | H | H | H | — | *—Me | *—Me |
| C-11-2 | $CR^1R^2$ | H | 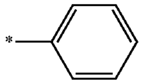 [SMILES: *c1ccccc1] | 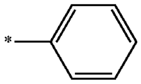 [SMILES: *c1ccccc1] | — | *—Me | *—Me |
| C-11-3 | $CR^1R^2$ | H | 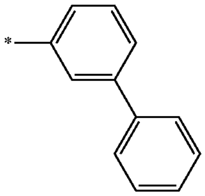 | H | — | *—Me | *—Me |

TABLE 14-continued
| | | | | | | | |
|---|---|---|---|---|---|---|---|
| C-11-4 | $CR^1R^2$ | H | 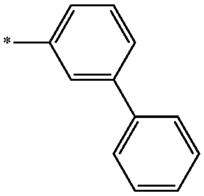 [SMILES: *c1cccc(-c2ccccc2)c1] | 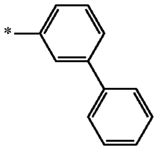 [SMILES: *c1cccc(-c2ccccc2)c1] | — | *—Me | *—Me |
| C-11-5 | $CR^1R^2$ | H | 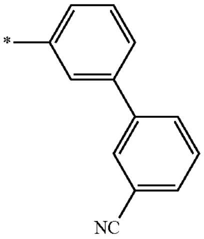 | H | — | 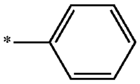 [SMILES: *c1ccccc1] | 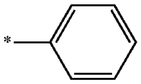 [SMILES: *c1ccccc1] |
| C-11-6 | $CR^1R^2$ | H | H | 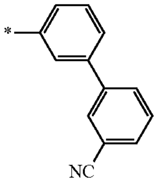 [SMILES: *c1cccc(-c2cccc(C#N)c2)c1] | — | *—Me | *—Me |
| C-11-7 | $CR^1R^2$ | H | 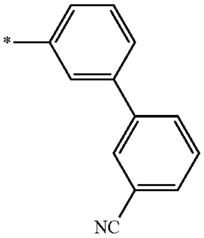 [SMILES: *c1cccc(-c2cccc(C#N)c2)c1] | 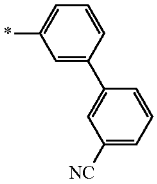 [SMILES: *c1cccc(-c2cccc(C#N)c2)c1] | — | 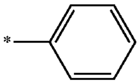 [SMILES: *c1ccccc1] | 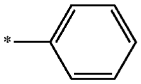 [SMILES: *c1ccccc1] |
| C-11-8 | $CR^1R^2$ | H | 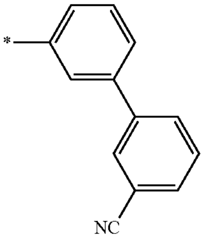 [SMILES: *c1cccc(-c2cccc(C#N)c2)c1] | 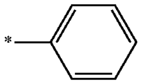 | — | *—Me | *—Me |
| C-11-9 | $CR^1R^2$ | H | 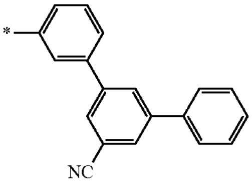 [SMILES: *c1cccc(-c2cc(C#N)cc(-c3ccccc3)c2)c1] | H | — | 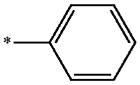 [SMILES: *c1ccccc1] | 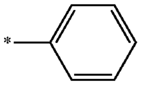 [SMILES: *c1ccccc1] |
| C-11-10 | $CR^1R^2$ | H | 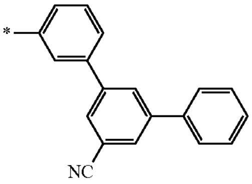 [SMILES: *c1cccc(-c2cc(C#N)cc(-c3ccccc3)c2)c1] | 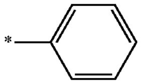 [SMILES: *c1ccccc1] | — | *—Me | *—Me |

TABLE 14-continued
| | | | | | | | |
|---|---|---|---|---|---|---|---|
| C-11-11 | $CR^1R^2$ | H | 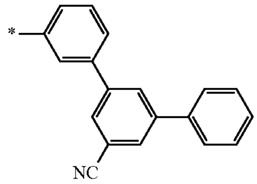 [SMILES: *c1cccc(-c2cc(C#N)cc(-c3ccccc3)c2)c1] | 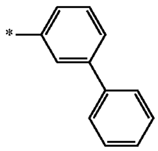 [SMILES: *c1cccc(-c2ccccc2)c1] | — | *—Me | *—Me |
TABLE 15
| | | | | | | | |
|---|---|---|---|---|---|---|---|
| C-11-12 | $CR^1R^2$ | H | 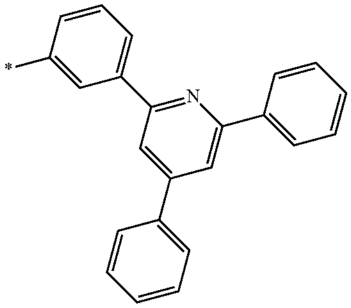 [SMILES: *c1cccc(-c2cc(-c3ccccc3)cc(-c3ccccc3)n2)c1] | H | — | *—Me | *—Me |
| C-11-13 | $CR^1R^2$ | H | 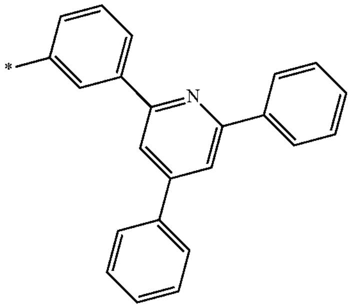 [SMILES: *c1cccc(-c2cc(-c3ccccc3)cc(-c3ccccc3)n2)c1] | 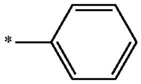 [SMILES: *c1ccccc1] | — | *—Me | *—Me |
| C-11-14 | $CR^1R^2$ | H | 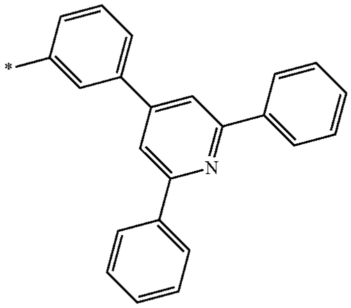 [SMILES: *c1cccc(-c2cc(-c3ccccc3)nc(-c3ccccc3)c2)c1] | H | — | *—Me | *—Me |
| C-11-15 | $CR^1R^2$ | H | 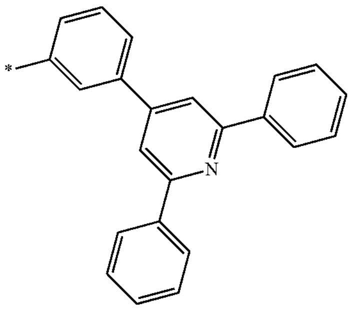 [SMILES: *c1cccc(-c2cc(-c3ccccc3)nc(-c3ccccc3)c2)c1] | 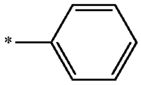 [SMILES: *c1ccccc1] | — | *—Me | *—Me |

TABLE 15-continued
| | | | | | | | |
|---|---|---|---|---|---|---|---|
| C-11-16 | $CR^1R^2$ | H | 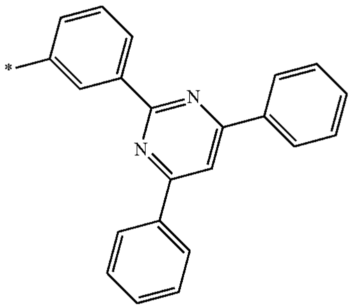 [SMILES: *c1cccc(-c2nc(-c3ccccc3)cc(-c3ccccc3)n2)c1] | H | — | 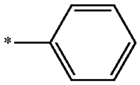 [SMILES: *c1ccccc1] | 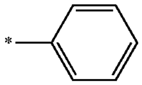 [SMILES: *c1ccccc1] |
| C-11-17 | $CR^1R^2$ | H | 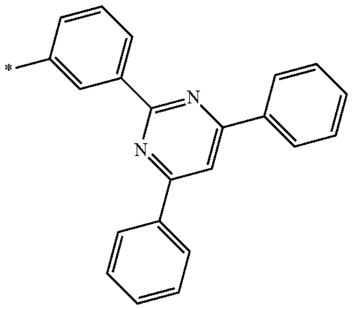 | 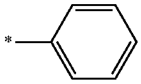 [SMILES: *c1ccccc1] | — | *—Me | *—Me |
| C-11-18 | $CR^1R^2$ | H | 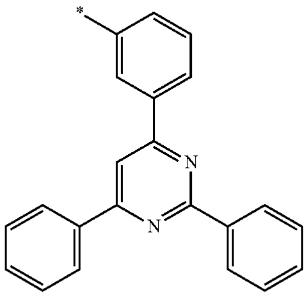 [SMILES: *c1cccc(-c2cc(-c3ccccc3)nc(-c3ccccc3)n2)c1] | H | — | *—Me | *—Me |
| C-11-19 | $CR^1R^2$ | H | 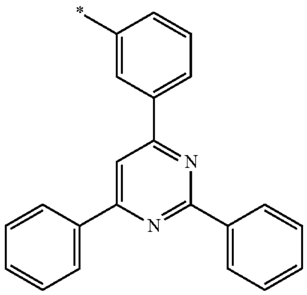 [SMILES: *c1cccc(-c2cc(-c3ccccc3)nc(-c3ccccc3)n2)c1] | 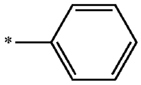 [SMILES: *c1ccccc1] | — | *—Me | *—Me |
| C-11-20 | $CR^1R^2$ | H | 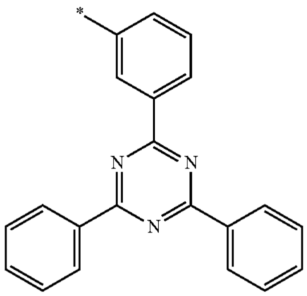 [SMILES: *c1cccc(-c2nc(-c3ccccc3)nc(-c3ccccc3)n2)c1] | H | — | *—Me | *—Me |

TABLE 15-continued
| | | | | | | | |
|---|---|---|---|---|---|---|---|
| C-11-21 | $CR^1R^2$ | H | 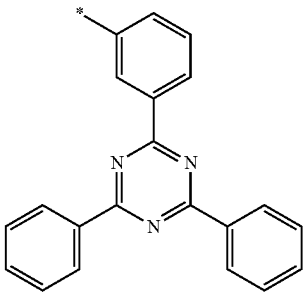 [SMILES: *c1cccc(-c2nc(-c3ccccc3)nc(-c3ccccc3)n2)c1] | 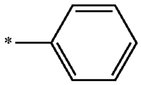 [SMILES: *c1ccccc1] | — | *—Me | *—Me |
| C-11-22 | $CR^1R^2$ | H | 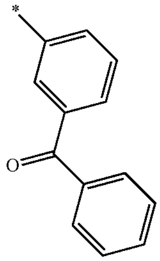 [SMILES: *c1cccc(C(=O)c2ccccc2)c1] | H | — | *—Me | *—Me |
| C-11-23 | $CR^1R^2$ | H | 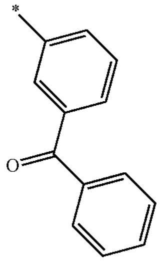 [SMILES: *c1cccc(C(=O)c2ccccc2)c1] | 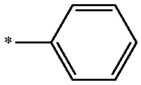 [SMILES: *c1ccccc1] | — | 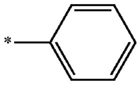 [SMILES: *c1ccccc1] | 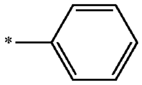 [SMILES: *c1ccccc1] |
| C-11-24 | $CR^1R^2$ | H | 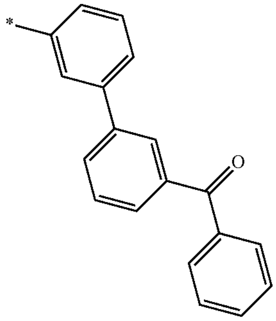 [SMILES: *c1cccc(-c2cccc(C(=O)c3ccccc3)c2)c1] | H | — | *—Me | *—Me |
| C-11-25 | $CR^1R^2$ | H | 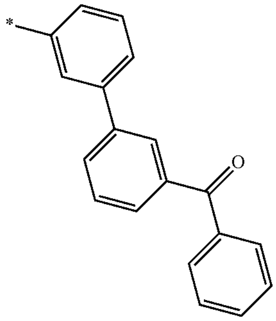 [SMILES: *c1cccc(-c2cccc(C(=O)c3ccccc3)c2)c1] | 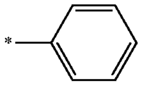 [SMILES: *c1ccccc1] | — | *—Me | *—Me |

In the compounds represented by the following general formula (12), $R^{C1}$, $R^{C3}$, $R^{C6}$ to $R^{C9}$, $R^{C11}$ to $R^{C14}$ each represent a hydrogen atom, and the other groups are the groups described in Tables below.
[Chem. 17]
(12)
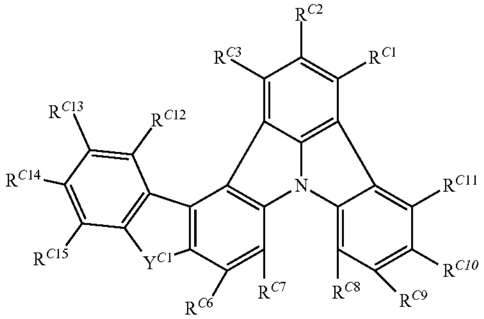

TABLE 16
| Compound No | $Y^{C1}$ | $R^{C15}$ | $R^{C10}$ | $R^{C2}$ | $R^3$ | $R^1$ | $R^2$ |
|---|---|---|---|---|---|---|---|
| O-12-1 | O | H | H | H | — | — | — |
| O-12-2 | O | H | 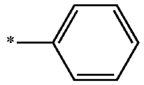 [SMILES: *c1ccccc1] | 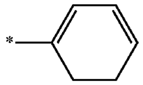 [SMILES: *C1=CC=CCC1] | — | — | — |
| O-12-3 | O | H | 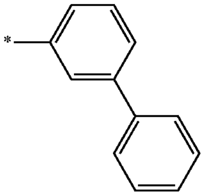 | H | — | — | — |
| O-12-4 | O | H | 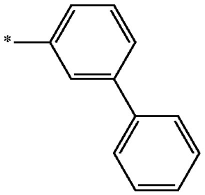 [SMILES: *c1cccc(-c2ccccc2)c1] | 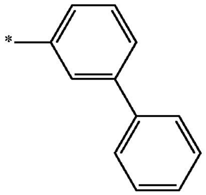 [SMILES: *c1cccc(-c2ccccc2)c1] | — | — | — |
| O-12-5 | O | 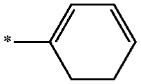 [SMILES: *C1=CC=CCC1] | 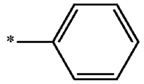 [SMILES: *c1ccccc1] | 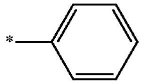 | — | — | — |
| O-12-6 | O | H | 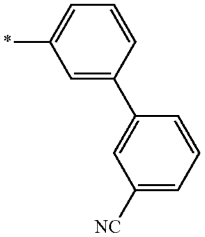 [SMILES: *c1cccc(-c2cccc(C#N)c2)c1] | H | — | — | — |

TABLE 16-continued
| Compound No | $Y^{C1}$ | $R^{C15}$ | $R^{C10}$ | $R^{C2}$ | $R^3$ | $R^1$ | $R^2$ |
|---|---|---|---|---|---|---|---|
| O-12-7 | O | H | H | 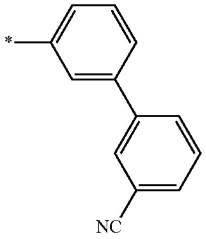 | — | — | — |
| O-12-8 | O | H | 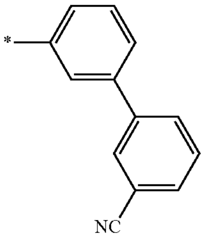 [SMILES: *c1cccc(-c2cccc(C#N)c2)c1] | 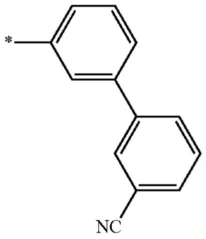 [SMILES: *c1cccc(-c2cccc(C#N)c2)c1] | — | — | — |
| O-12-9 | O | H | 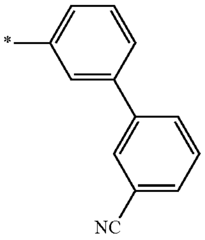 [SMILES: *c1cccc(-c2cccc(C#N)c2)c1] | 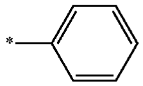 [SMILES: *c1ccccc1] | — | — | — |
| O-12-10 | O | H | 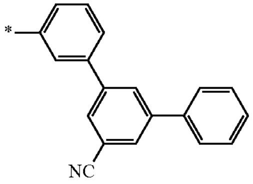 [SMILES: *c1cccc(-c2cc(C#N)cc(-c3ccccc3)c2)c1] | H | — | — | — |

TABLE 16-continued
| Compound No | $Y^{C1}$ | $R^{C15}$ | $R^{C10}$ | $R^{C2}$ | $R^3$ | $R^1$ | $R^2$ |
|---|---|---|---|---|---|---|---|
| O-12-11 | O | H | 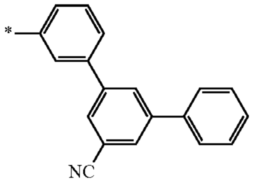 [SMILES: *c1cccc(-c2cc(C#N)cc(-c3ccccc3)c2)c1] | 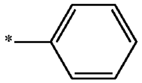 [SMILES: *c1ccccc1] | — | — | — |
| O-12-12 | O | H | 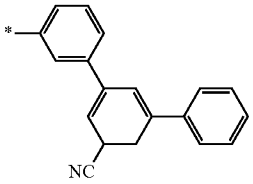 | 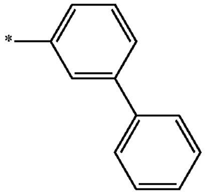 | — | — | — |
| O-12-13 | O | 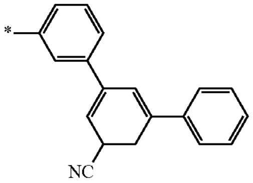 | H | H | — | — | — |
| O-12-14 | O | H | 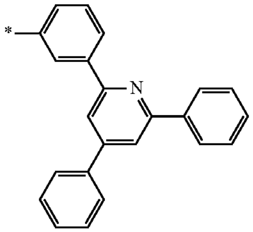 | H | — | — | — |

TABLE 16-continued
| Compound No | $Y^{C1}$ | $R^{C15}$ | $R^{C10}$ | $R^{C2}$ | $R^3$ | $R^1$ | $R^2$ |
|---|---|---|---|---|---|---|---|
| O-12-15 | O | H | 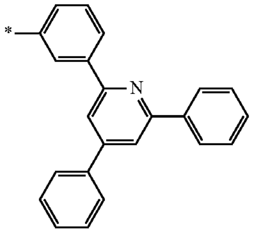 | 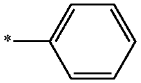 [SMILES: *c1ccccc1] | — | — | — |

TABLE 17
| | | | | | | | |
|---|---|---|---|---|---|---|---|
| O-12-16 | O | H | 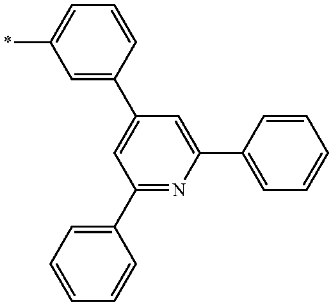 [SMILES: *c1cccc(-c2cc(-c3ccccc3)nc(-c3ccccc3)c2)c1] | H | — | — | — |
| O-12-17 | O | H | 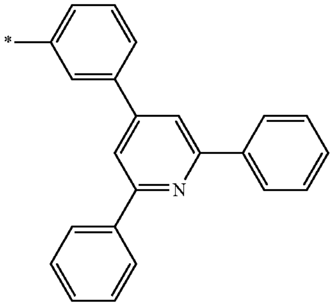 [SMILES: *c1cccc(-c2cc(-c3ccccc3)nc(-c3ccccc3)c2)c1] | 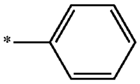 | — | — | — |
| O-12-18 | O | H | 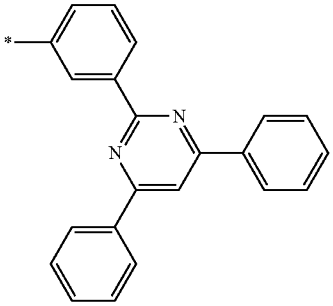 [SMILES: *c1cccc(-c2nc(-c3ccccc3)cc(-c3ccccc3)n2)c1] | H | — | — | — |
| O-12-19 | O | H | 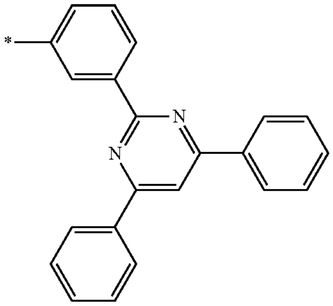 [SMILES: *c1cccc(-c2nc(-c3ccccc3)cc(-c3ccccc3)n2)c1] | 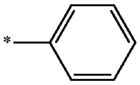 [SMILES: *c1ccccc1] | — | — | — |
| O-12-20 | O | H | 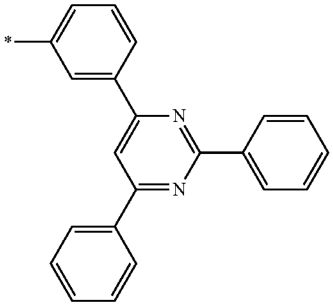 | H | — | — | — |

TABLE 17-continued
| | | | | | | | |
|---|---|---|---|---|---|---|---|
| O-12-21 | O | H | 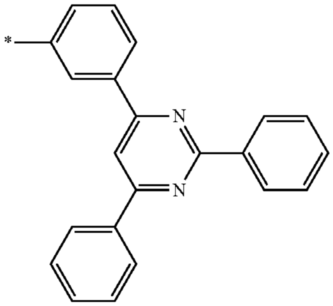 | 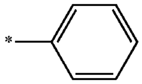 [SMILES: *c1ccccc1] | — | — | — |
| O-12-22 | O | H | 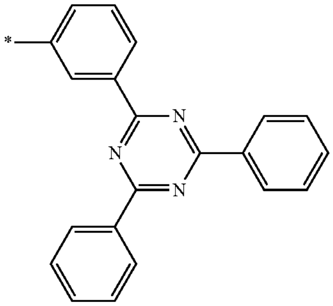 | H | — | — | — |
| O-12-23 | O | H | 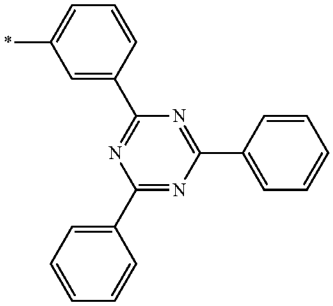 [SMILES: *c1cccc(-c2nc(-c3ccccc3)nc(-c3ccccc3)n2)c1] | 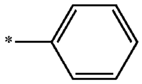 [SMILES: *c1ccccc1] | — | — | — |
| O-12-24 | O | H | 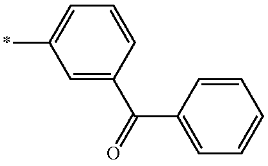 [SMILES: *c1cccc(C(=O)c2ccccc2)c1] | H | — | — | — |
| O-12-25 | O | H | 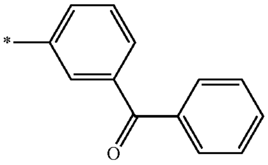 [SMILES: *c1cccc(C(=O)c2ccccc2)c1] | 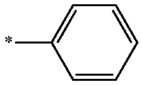 [SMILES: *c1ccccc1] | — | — | — |
| O-12-26 | O | H | 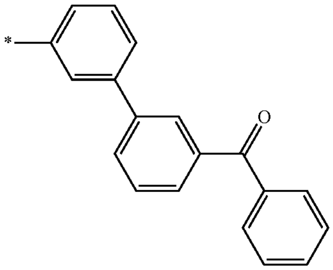 [SMILES: *c1cccc(-c2cccc(C(=O)c3ccccc3)c2)c1] | H | — | — | — |

TABLE 17-continued
| | | | | | | | |
|---|---|---|---|---|---|---|---|
| O-12-27 | O | H | 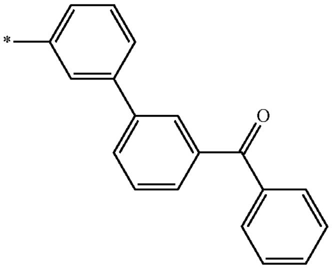 [SMILES: *c1cccc(-c2cccc(C(=O)c3ccccc3)c2)c1] | 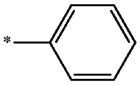 [SMILES: *c1ccccc1] | — | — | — |
| S-12-1 | S | H | H | H | — | — | — |
| S-12-2 | S | H | 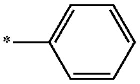 [SMILES: *c1ccccc1] | 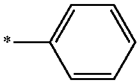 [SMILES: *c1ccccc1] | — | — | — |
| S-12-3 | S | H | 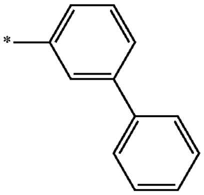 [SMILES: *c1cccc(-c2ccccc2)c1] | H | — | — | — |
TABLE 18
| | | | | | | | |
|---|---|---|---|---|---|---|---|
| S-12-4 | S | H | 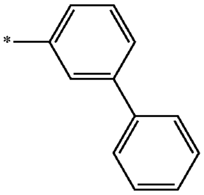 [SMILES: *c1cccc(-c2ccccc2)c1] | 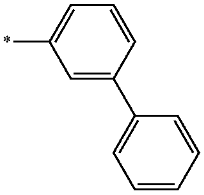 [SMILES: *c1cccc(-c2ccccc2)c1] | — | — | — |
| S-12-5 | S | 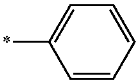 [SMILES: *c1ccccc1] | 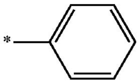 [SMILES: *c1ccccc1] | 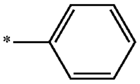 [SMILES: *c1ccccc1] | — | — | — |
| S-12-6 | S | H | 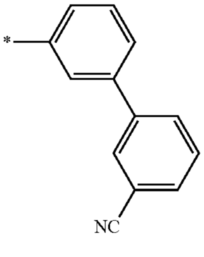 [SMILES: *c1cccc(-c2cccc(C#N)c2)c1] | H | — | — | — |
| S-12-7 | S | H | H | 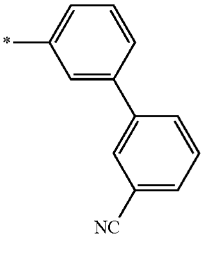 [SMILES: *c1cccc(-c2cccc(C#N)c2)c1] | — | — | — |

TABLE 18-continued
| | | | | | | | |
|---|---|---|---|---|---|---|---|
| S-12-8 | S | H | 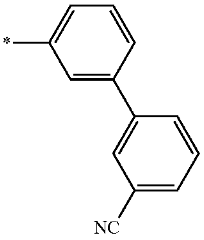 [SMILES: *c1cccc(-c2cccc(C#N)c2)c1] | 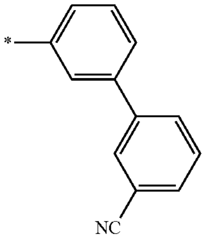 [SMILES: *c1cccc(-c2cccc(C#N)c2)c1] | — | — | — |
| S-12-9 | S | H | 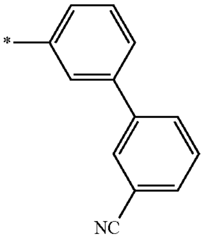 [SMILES: *c1cccc(-c2cccc(C#N)c2)c1] | 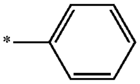 [SMILES: *c1ccccc1] | — | — | — |
| S-12-10 | S | H | 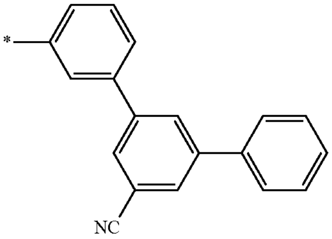 [SMILES: *c1cccc(-c2cc(C#N)cc(-c3ccccc3)c2)c1] | H | — | — | — |
| S- 12-11 | S | H | 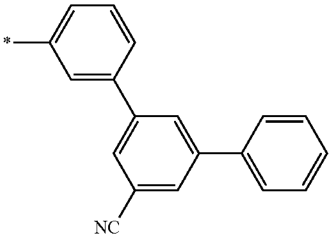 [SMILES: *c1cccc(-c2cc(C#N)cc(-c3ccccc3)c2)c1] | 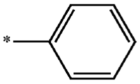 [SMILES: *c1ccccc1] | — | — | — |
| S-12-12 | S | H | 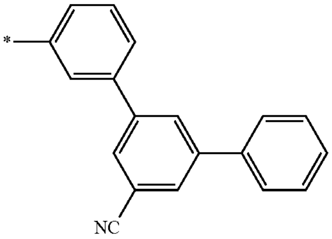 [SMILES: *c1cccc(-c2cc(C#N)cc(-c3ccccc3)c2)c1] | 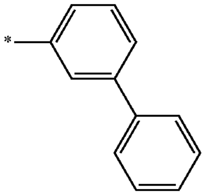 [SMILES: *c1cccc(-c2ccccc2)c1] | — | — | — |
| S-12-13 | S | 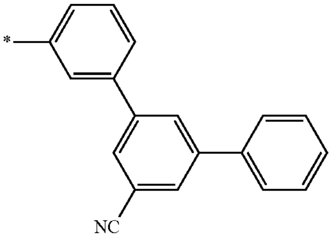 [SMILES: *c1cccc(-c2cc(C#N)cc(-c3ccccc3)c2)c1] | H | H | — | — | — |

TABLE 18-continued
| | | | | | | | |
|---|---|---|---|---|---|---|---|
| S-12-14 | S | H | 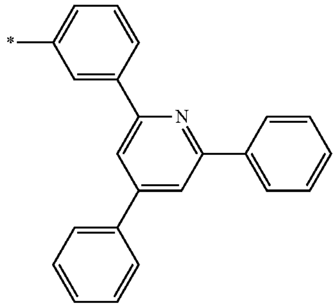 [SMILES: *c1cccc(-c2cc(-c3ccccc3)cc(-c3ccccc3)n2)c1] | H | — | — | — |
| S-12-15 | S | H | 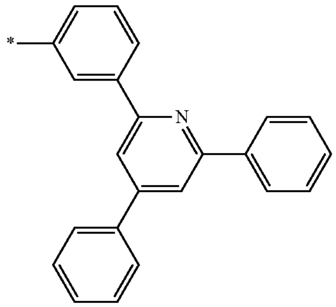 [SMILES: *c1cccc(-c2cc(-c3ccccc3)cc(-c3ccccc3)n2)c1] | 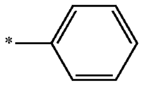 [SMILES: *c1ccccc1] | — | — | — |
| S-12-16 | S | H | 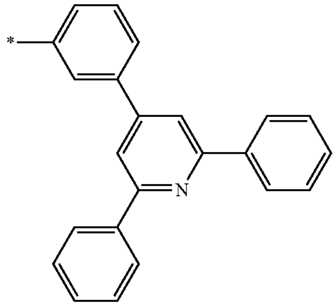 | H | — | — | — |
| S-12-17 | S | H | 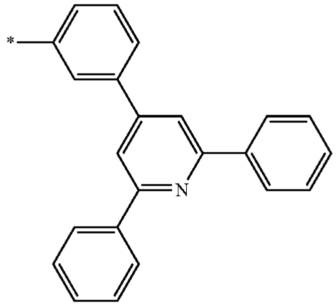 [SMILES: *c1cccc(-c2cc(-c3ccccc3)nc(-c3ccccc3)c2)c1] | 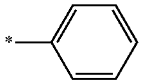 [SMILES: *c1ccccc1] | — | — | — |
| S-12-18 | S | H | 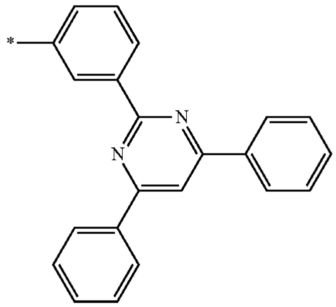 | H | — | — | — |

TABLE 19
| | | | | | | | |
|---|---|---|---|---|---|---|---|
| S-12-19 | S | H | 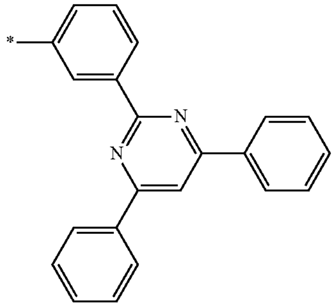 | 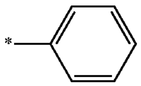 [SMILES: *c1ccccc1] | — | — | — |
| S-12-20 | S | H | 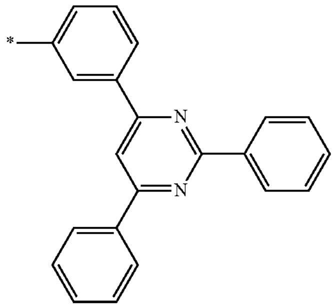 | H | — | — | — |
| S-12-21 | S | H | 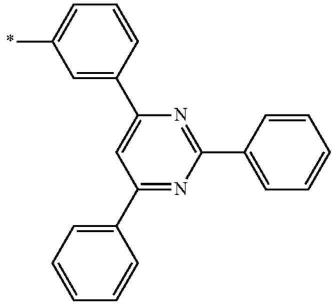 | 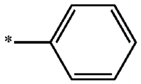 | — | — | — |

TABLE 19-continued
| | | | | | | | |
|---|---|---|---|---|---|---|---|
| S-12-22 | S | H | 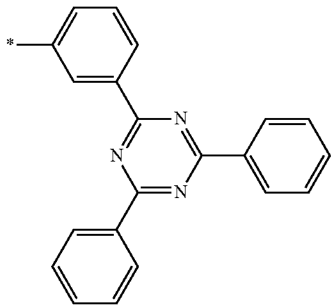 | H | — | — | — |
| S-12-23 | S | H | 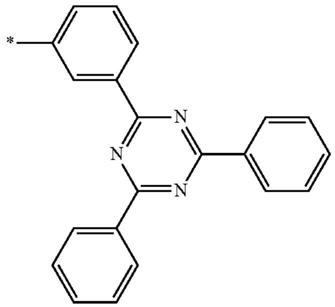 | 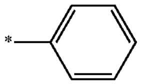 | — | — | — |
| S-12-24 | S | H | 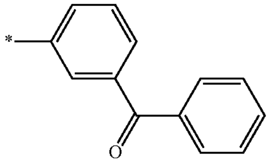 [SMILES: *c1cccc(C(=O)c2ccccc2)c1] | H | — | — | — |
| S-12-25 | S | H | 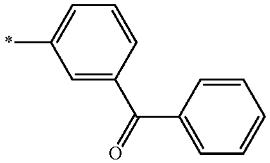 [SMILES: *c1cccc(C(=O)c2ccccc2)c1] | 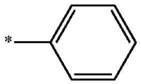 | — | — | — |

TABLE 19-continued
| | | | | | | | | |
|---|---|---|---|---|---|---|---|---|
| S-12-26 | S | H | 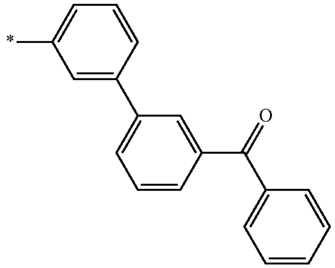 [SMILES: *c1cccc(-c2cccc(C(=O)c3ccccc3)c2)c1] | H | — | — | — | |
| S-12-27 | S | H | 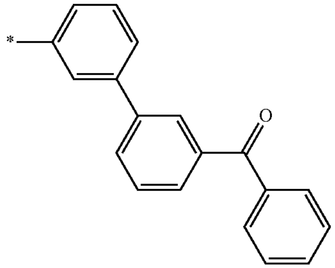 [SMILES: *c1cccc(-c2cccc(C(=O)c3ccccc3)c2)c1] | 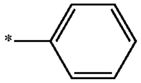 | — | — | — | |
| N-12-1 | $NR^3$ | H | H | H | 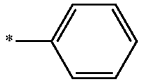 | — | — | |
| N-12-2 | $NR^3$ | H | 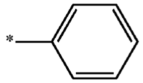 | 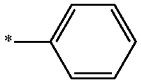 | 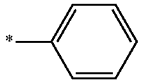 | — | — | |
| N-12-3 | $NR^3$ | H | 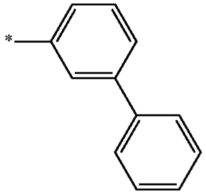 | H | 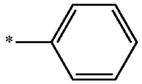 [SMILES: *c1ccccc1] | — | — | |

TABLE 19-continued
| | | | | | | | |
|---|---|---|---|---|---|---|---|
| N-12-4 | $NR^3$ | H | 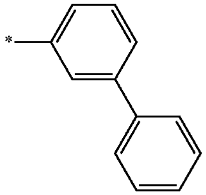 [SMILES: *c1cccc(-c2ccccc2)c1] | 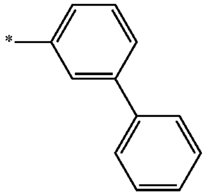 [SMILES: *c1cccc(-c2ccccc2)c1] | 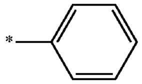 [SMILES: *c1ccccc1] | — | — |
| N-12-5 | $NR^3$ | H | 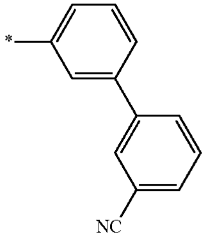 | H | 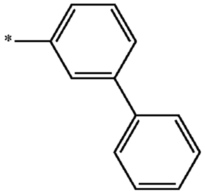 [SMILES: *c1cccc(-c2ccccc2)c1] | — | — |
| N-12-6 | $NR^3$ | H | H | 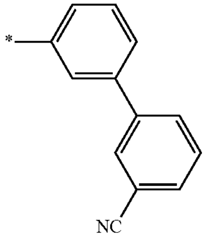 [SMILES: *c1cccc(-c2cccc(C#N)c2)c1] | 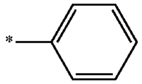 [SMILES: *c1ccccc1] | — | — |

TABLE 20
| | | | | | | | |
|---|---|---|---|---|---|---|---|
| N-12-7 | $NR^3$ | H | 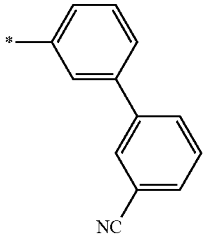 [SMILES: *c1cccc(-c2cccc(C#N)c2)c1] | 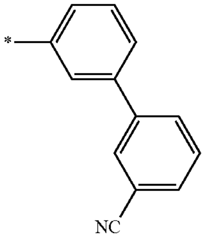 [SMILES: *c1cccc(-c2cccc(C#N)c2)c1] | 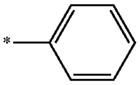 [SMILES: *c1ccccc1] | — | — |
| N-12-8 | $NR^3$ | H | 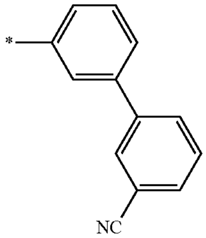 [SMILES: *c1cccc(-c2cccc(C#N)c2)c1] | 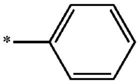 [SMILES: *c1ccccc1] | 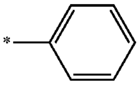 | — | — |
| N-12-9 | $NR^3$ | H | 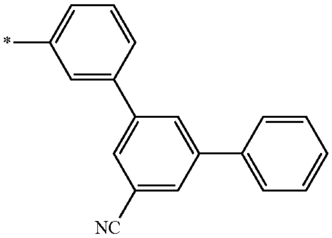 [SMILES: *c1cccc(-c2cc(C#N)cc(-c3ccccc3)c2)c1] | H | 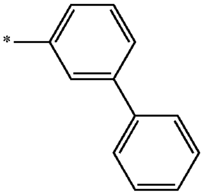 [SMILES: *c1cccc(-c2ccccc2)c1] | — | — |
| N-12-10 | $NR^3$ | H | 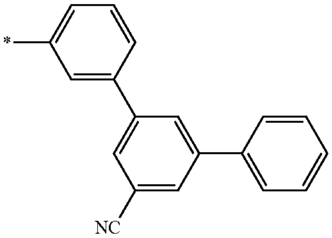 [SMILES: *c1cccc(-c2cc(C#N)cc(-c3ccccc3)c2)c1] | 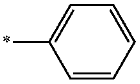 | 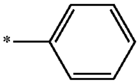 [SMILES: *c1ccccc1] | — | — |
| N-12-11 | $NR^3$ | H | 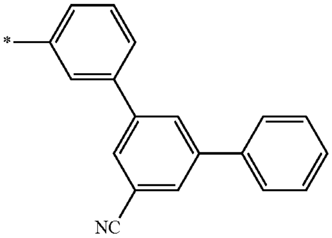 [SMILES: *c1cccc(-c2cc(C#N)cc(-c3ccccc3)c2)c1] | 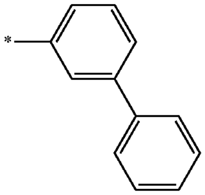 [SMILES: *c1cccc(-c2ccccc2)c1] | 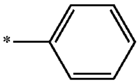 [SMILES: *c1ccccc1] | — | — |
| N-12-12 | $NR^3$ | H | 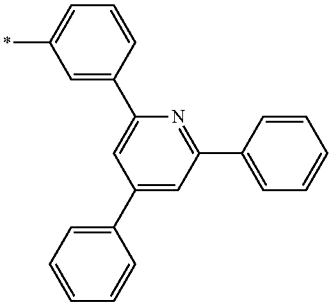 | H | 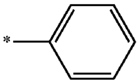 [SMILES: *c1ccccc1] | — | — |

TABLE 20-continued
| | | | | | | | |
|---|---|---|---|---|---|---|---|
| N-12-13 | $NR^3$ | H | 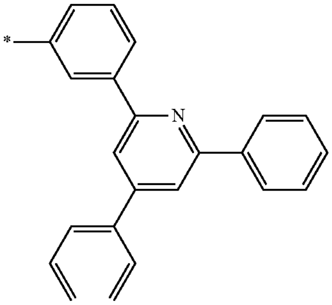 | 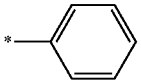 [SMILES: *c1ccccc1] | 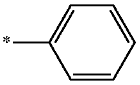 [SMILES: *c1ccccc1] | — | — |
| N-12-14 | $NR^3$ | H | 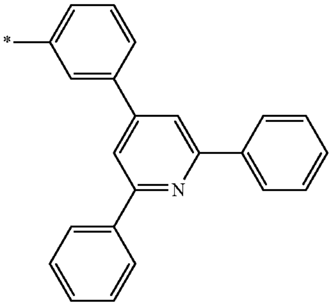 | H | 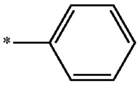 [SMILES: *c1ccccc1] | — | — |
| N-12-15 | $NR^3$ | H | 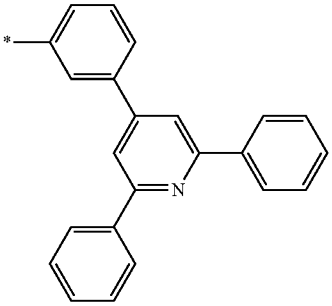 | 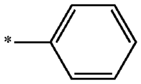 | 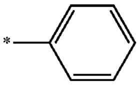 [SMILES: *c1ccccc1] | — | — |
| N-12-16 | $NR^3$ | H | 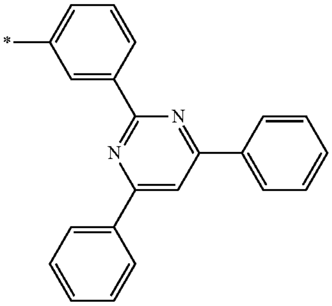 | H | 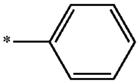 [SMILES: *c1ccccc1] | — | — |
| N-12-17 | $NR^3$ | H | 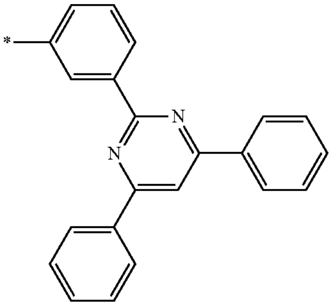 | 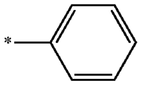 [SMILES: *c1ccccc1] | 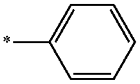 [SMILES: *c1ccccc1] | — | — |

TABLE 20-continued
| | | | | | | | |
|---|---|---|---|---|---|---|---|
| N-12-18 | $NR^3$ | H | 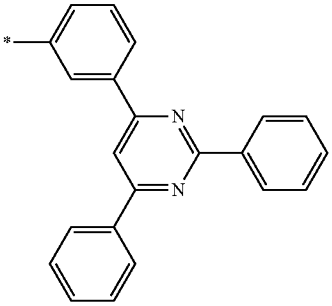 | H | 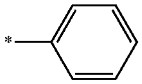 [SMILES: *c1ccccc1] | — | — |
| N-12-19 | $NR^3$ | H | 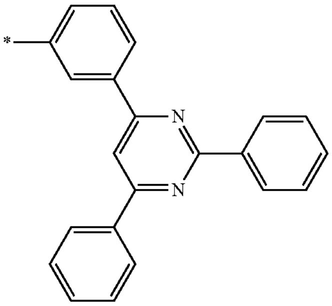 | 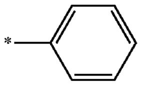 [SMILES: *c1ccccc1] | 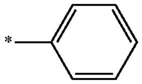 [SMILES: *c1ccccc1] | — | — |
| N-12-20 | $NR^3$ | H | 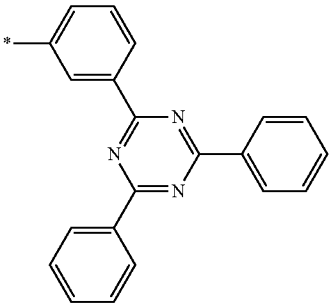 | H | 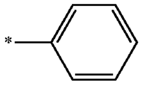 [SMILES: *c1ccccc1] | — | — |
| N-12-21 | $NR^3$ | H | 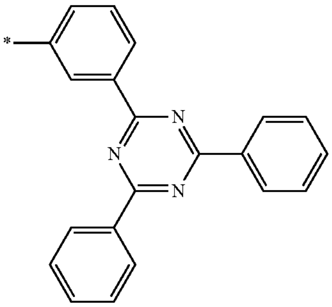 | 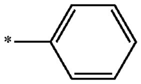 | 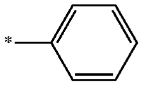 [SMILES: *c1ccccc1] | — | — |
TABLE 21
| | | | | | | | |
|---|---|---|---|---|---|---|---|
| N-12-22 | $NR^3$ | H | 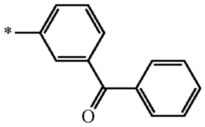 | H | 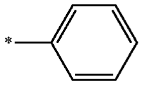 [SMILES: *c1ccccc1] | — | — |

TABLE 21-continued
| | | | | | | | |
|---|---|---|---|---|---|---|---|
| N-12-23 | $NR^3$ | H | 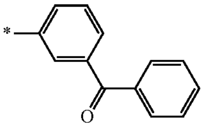 | 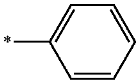 [SMILES: *c1ccccc1] | 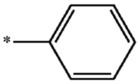 [SMILES: *c1ccccc1] | — | — |
| N-12-24 | $NR^3$ | H | 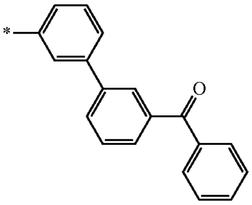 [SMILES: *c1cccc(-c2cccc(C(=O)c3ccccc3)c2)c1] | H | 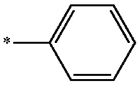 [SMILES: *c1ccccc1] | — | — |
| N-12-25 | $NR^3$ | H | 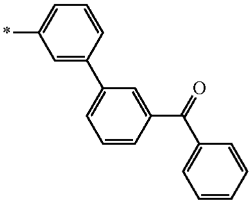 [SMILES: *c1cccc(-c2cccc(C(=O)c3ccccc3)c2)c1] | 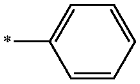 [SMILES: *c1ccccc1] | 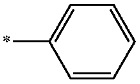 [SMILES: *c1ccccc1] | — | — |
| C-12-1 | $CR^1R^2$ | H | H | H | — | *—Me | *—Me |
| C-12-2 | $CR^1R^2$ | H | 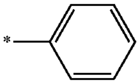 [SMILES: *c1ccccc1] | 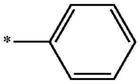 [SMILES: *c1ccccc1] | — | *—Me | *—Me |
| C-12-3 | $CR^1R^2$ | H | 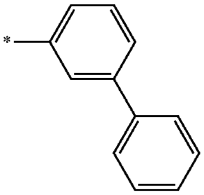 [SMILES: *c1cccc(-c2ccccc2)c1] | H | — | *—Me | *—Me |
| C-12-4 | $CR^1R^2$ | H | 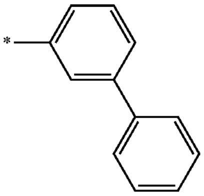 [SMILES: *c1cccc(-c2ccccc2)c1] | 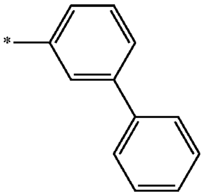 [SMILES: *c1cccc(-c2ccccc2)c1] | — | *—Me | *—Me |
| C-12-5 | $CR^1R^2$ | H | 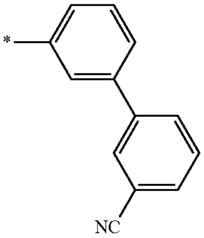 [SMILES: *c1cccc(-c2cccc(C#N)c2)c1] | H | — | 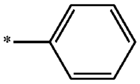 | 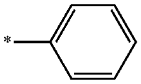 |
| C-12-6 | $CR^1R^2$ | H | H | 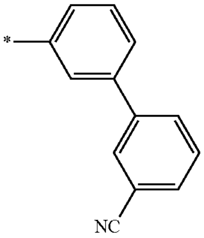 [SMILES: *c1cccc(-c2cccc(C#N)c2)c1] | — | *—Me | *—Me |

TABLE 21-continued
| | | | | | | | |
|---|---|---|---|---|---|---|---|
| C-12-7 | $CR^1R^2$ | H | 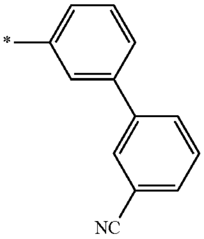 [SMILES: *c1cccc(-c2cccc(C#N)c2)c1] | 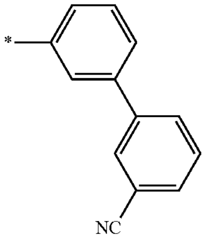 [SMILES: *c1cccc(-c2cccc(C#N)c2)c1] | — | 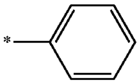 [SMILES: *c1ccccc1] | 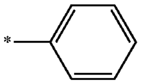 [SMILES: *c1ccccc1] |
| C-12-8 | $CR^1R^2$ | H | 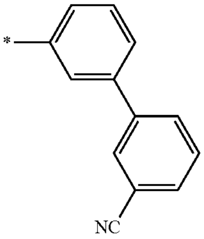 [SMILES: *c1cccc(-c2cccc(C#N)c2)c1] | 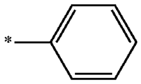 [SMILES: *c1ccccc1] | — | *—Me | *—Me |
| C-12-9 | $CR^1R^2$ | H | 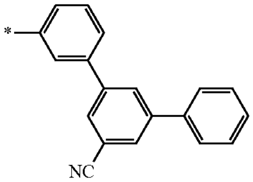 [SMILES: *c1cccc(-c2cc(C#N)cc(-c3ccccc3)c2)c1] | H | — | 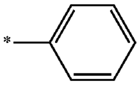 | 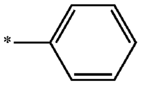 [SMILES: *c1ccccc1] |
| C-12-10 | $CR^1R^2$ | H | 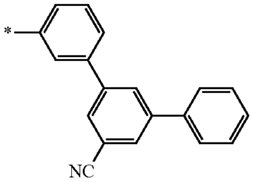 [SMILES: *c1cccc(-c2cc(C#N)cc(-c3ccccc3)c2)c1] | 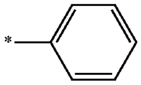 | — | *—Me | *—Me |
| C-12-11 | $CR^1R^2$ | H | 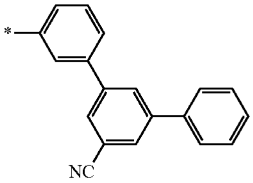 [SMILES: *c1cccc(-c2cc(C#N)cc(-c3ccccc3)c2)c1] | 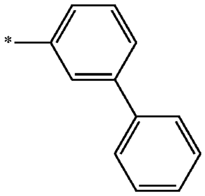 [SMILES: *c1cccc(-c2ccccc2)c1] | — | *—Me | *—Me |
TABLE 22
| | | | | | | | |
|---|---|---|---|---|---|---|---|
| C-12-12 | $CR^1R^2$ | H | 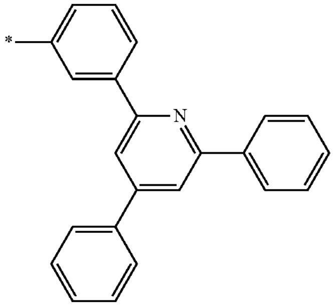 | H | — | *—Me | *—Me |

TABLE 22-continued
| | | | | | | | |
|---|---|---|---|---|---|---|---|
| C-12-13 | $CR^1R^2$ | H | 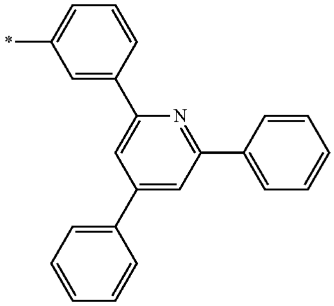 [SMILES: *c1cccc(-c2cc(-c3ccccc3)cc(-c3ccccc3)n2)c1] | 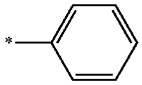 [SMILES: *c1ccccc1] | — | *—Me | *—Me |
| C-12-14 | $CR^1R^2$ | H | 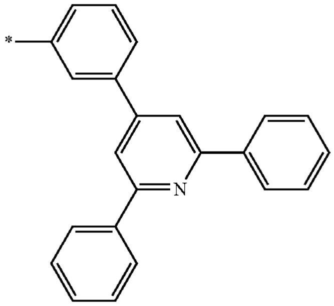 [SMILES: *c1cccc(-c2cc(-c3ccccc3)nc(-c3ccccc3)c2)c1] | H | — | *—Me | *—Me |
| C-12-15 | $CR^1R^2$ | H | 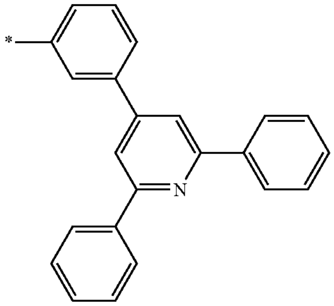 | 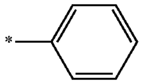 | — | *—Me | *—Me |
| C-12-16 | $CR^1R^2$ | H | 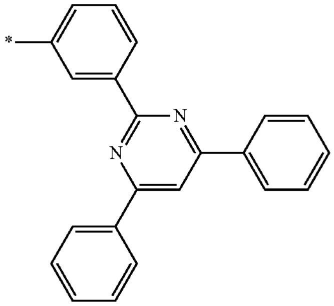 | H | — | 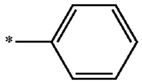 | 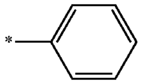 |
| C-12-17 | $CR^1R^2$ | H | 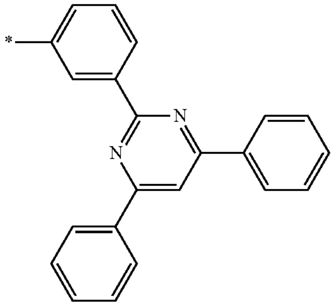 | 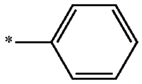 | — | *—Me | *—Me |

TABLE 22-continued
| | | | | | | | |
|---|---|---|---|---|---|---|---|
| C-12-18 | $CR^1R^2$ | H | 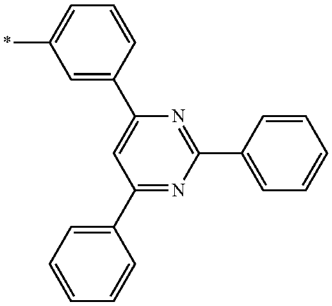 | H | — | *—Me | *—Me |
| C-12-19 | $CR^1R^2$ | H | 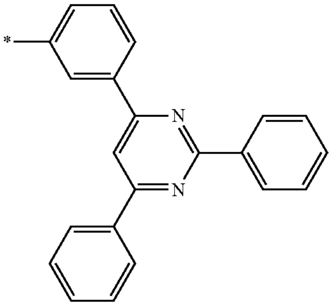 [SMILES: *c1cccc(-c2cc(-c3ccccc3)nc(-c3ccccc3)n2)c1] | 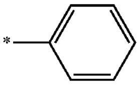 | — | *—Me | *—Me |
| C-12-20 | $CR^1R^2$ | H | 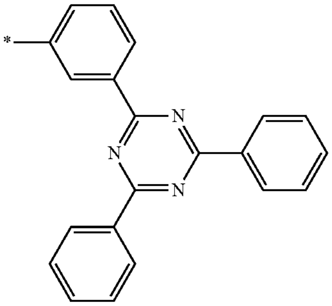 | H | — | *—Me | *—Me |
| C-12-21 | $CR^1R^2$ | H | 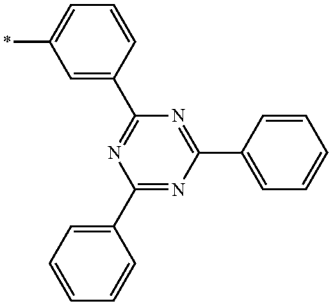 [SMILES: *c1cccc(-c2nc(-c3ccccc3)nc(-c3ccccc3)n2)c1] | 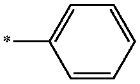 [SMILES: *c1ccccc1] | — | *—Me | *—Me |
| C-12-22 | $CR^1R^2$ | H | 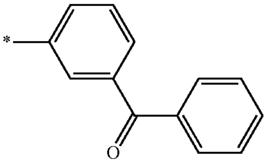 [SMILES: *c1cccc(C(=O)c2ccccc2)c1] | H | — | *—Me | *—Me |
| C-12-23 | $CR^1R^2$ | H | 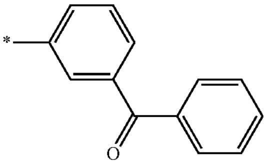 [SMILES: *c1cccc(C(=O)c2ccccc2)c1] | 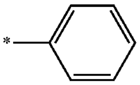 | — | 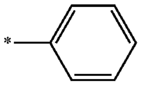 | 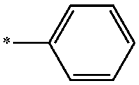 [SMILES: *c1ccccc1] |

TABLE 22-continued
| | | | | | | | |
|---|---|---|---|---|---|---|---|
| C-12-24 | $CR^1R^2$ | H | 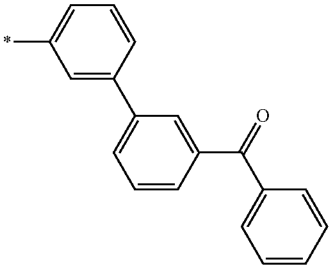 [SMILES: *c1cccc(-c2cccc(C(=O)c3ccccc3)c2)c1] | H | — | *—Me | *—Me |
| C-12-25 | $CR^1R^2$ | H | 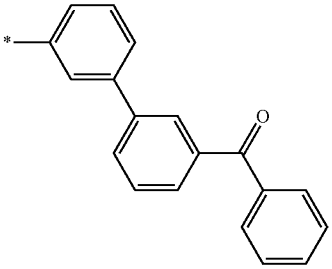 [SMILES: *c1cccc(-c2cccc(C(=O)c3ccccc3)c2)c1] | 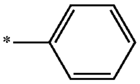 [SMILES: *c1ccccc1] | — | *—Me | *—Me |
TABLE 23
| Compound No. | Central Skeleton | Substituent |
|---|---|---|
| O-12-28 | 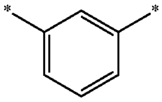 | 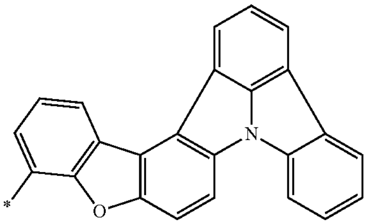 [SMILES: *c1cccc2c1oc1ccc3c(c4cccc5c6ccccc6n3c54)c12] |
| O-12-29 | 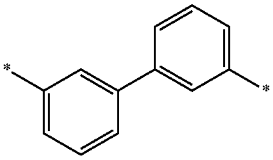 [SMILES: *c1cccc(-c2cccc(*)c2)c1] | 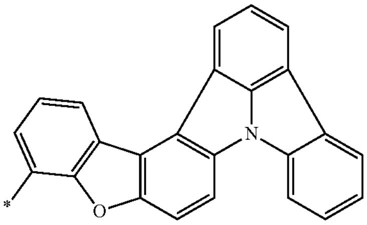 [SMILES: *c1cccc2c1oc1ccc3c(c4cccc5c6ccccc6n3c54)c12] |
| O-12-30 | 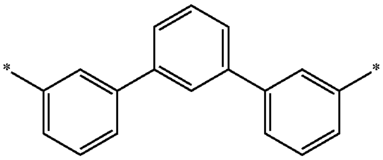 [SMILES: *c1cccc(-c2cccc(-c3cccc(*)c3)c2)c1] | 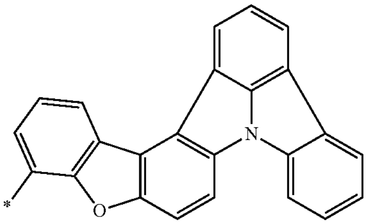 [SMILES: *c1cccc2c1oc1ccc3c(c4cccc5c6ccccc6n3c54)c12] |
| O-12-31 | 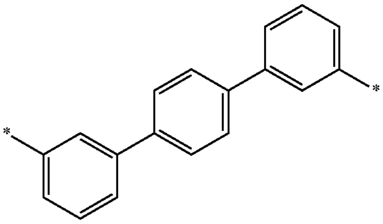 [SMILES: *c1cccc(-c2ccc(-c3cccc(*)c3)cc2)c1] | 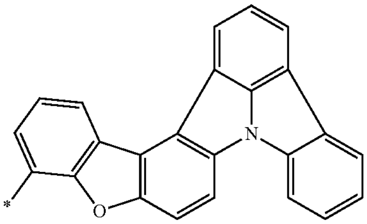 [SMILES: *c1cccc2c1oc1ccc3c(c4cccc5c6ccccc6n3c54)c12] |

TABLE 23-continued
| Compound No. | Central Skeleton | Substituent |
| --- | --- | --- |
| O-12-32 | 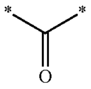 | 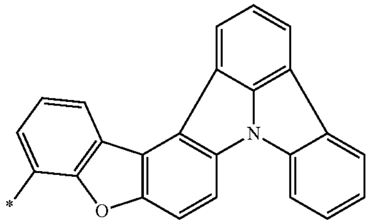 [SMILES: *c1cccc2c1oc1ccc3c(c4cccc5c6ccccc6n3c54)c12] |
| O-12-33 | 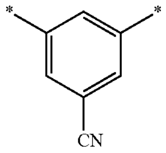 [SMILES: *c1cc(*)cc(C#N)c1] | 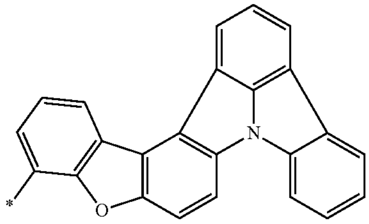 [SMILES: *c1cccc2c1oc1ccc3c(c4cccc5c6ccccc6n3c54)c12] |
| O-12-34 | 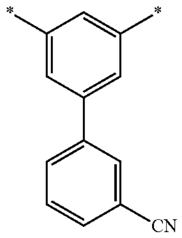 [SMILES: *c1cc(*)cc(-c2cccc(C#N)c2)c1] | 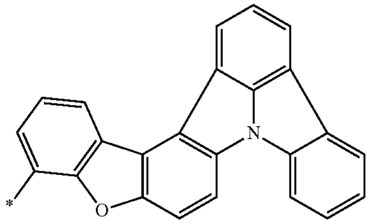 [SMILES: *c1cccc2c1oc1ccc3c(c4cccc5c6ccccc6n3c54)c12] |
| O-12-35 | 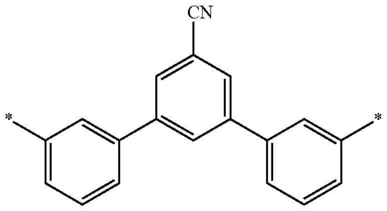 | 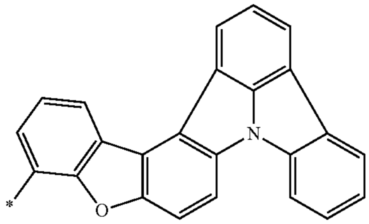 [SMILES: *c1cccc2c1oc1ccc3c(c4cccc5c6ccccc6n3c54)c12] |
| O-12-36 | 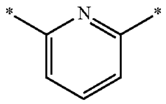 [SMILES: *c1cccc(*)n1] | 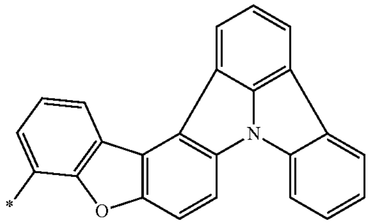 [SMILES: *c1cccc2c1oc1ccc3c(c4cccc5c6ccccc6n3c54)c12] |
| O-12-37 | 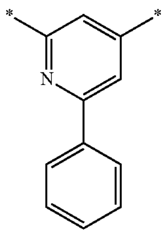 [SMILES: *c1cc(*)nc(-c2ccccc2)c1] | 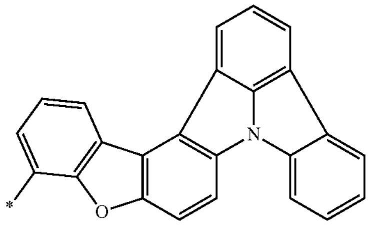 [SMILES: *c1cccc2c1oc1ccc3c(c4cccc5c6ccccc6n3c54)c12] |

TABLE 23-continued
| Compound No. | Central Skeleton | Substituent |
|---|---|---|
| O-12-38 | 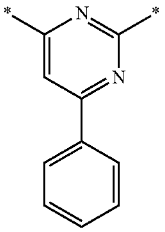 [SMILES: *c1cc(-c2ccccc2)nc(*)n1] | 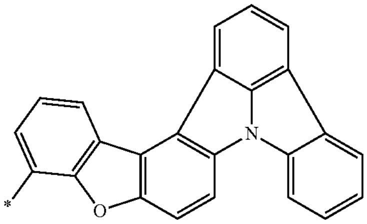 [SMILES: *c1cccc2c1oc1ccc3c(c4cccc5c6ccccc6n3c54)c12] |
| O-12-39 | 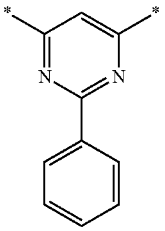 [SMILES: *c1cc(*)nc(-c2ccccc2)n1] | 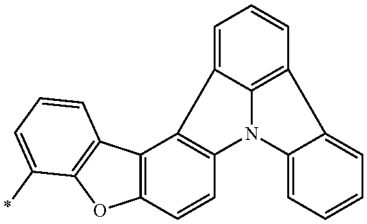 [SMILES: *c1cccc2c1oc1ccc3c(c4cccc5c6ccccc6n3c54)c12] |
| O-12-40 | 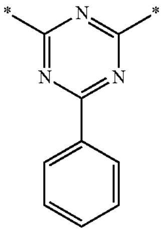 [SMILES: *c1nc(*)nc(-c2ccccc2)n1] | 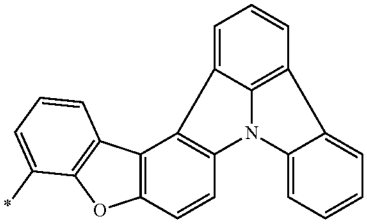 [SMILES: *c1cccc2c1oc1ccc3c(c4cccc5c6ccccc6n3c54)c12] |
| O-12-41 | 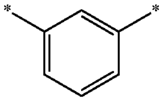 [SMILES: *c1cccc(*)c1] | 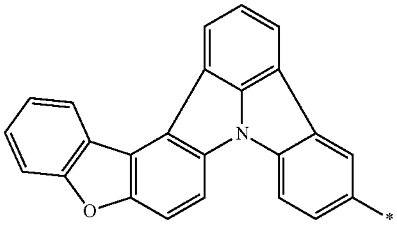 [SMILES: *c1ccc2c(c1)c1cccc3c4c5c(ccc4n2c13)oc1ccccc15] |
| O-12-42 | 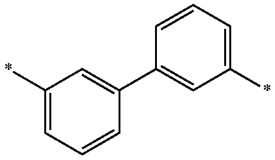 [SMILES: *c1cccc(-c2cccc(*)c2)c1] | 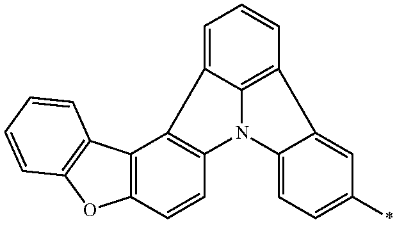 [SMILES: *c1ccc2c(c1)c1cccc3c4c5c(ccc4n2c13)oc1ccccc15] |
| O-12-43 | 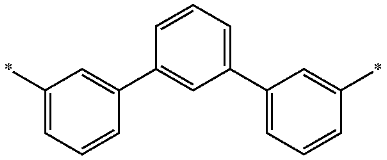 [SMILES: *c1cccc(-c2cccc(-c3cccc(*)c3)c2)c1] | 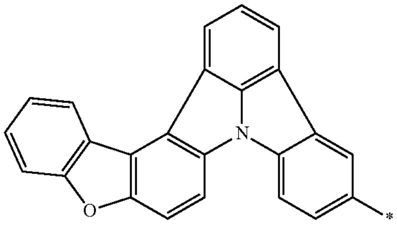 [SMILES: *c1ccc2c(c1)c1cccc3c4c5c(ccc4n2c13)oc1ccccc15] |

TABLE 23-continued
| Compound No. | Central Skeleton | Substituent |
| --- | --- | --- |
| O-12-44 | 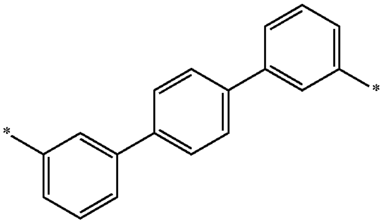 [SMILES: *c1cccc(-c2ccc(-c3cccc(*)c3)cc2)c1] | 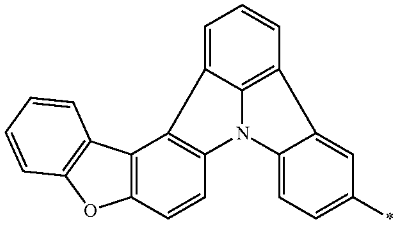 [SMILES: *c1ccc2c(c1)c1cccc3c4c5c(ccc4n2c13)oc1ccccc15] |
| O-12-45 | 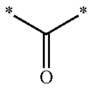 | 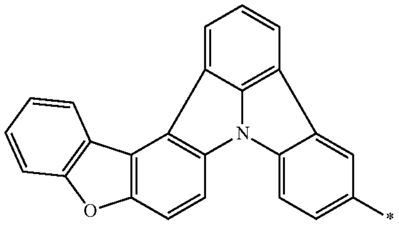 [SMILES: *c1ccc2c(c1)c1cccc3c4c5c(ccc4n2c13)oc1ccccc15] |
| O-12-46 | 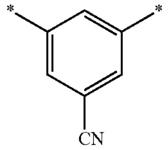 [SMILES: *c1cc(*)cc(C#N)c1] | 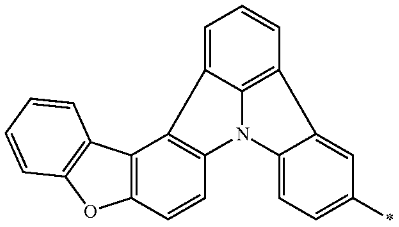 [SMILES: *c1ccc2c(c1)c1cccc3c4c5c(ccc4n2c13)oc1ccccc15] |
| O-12-47 | 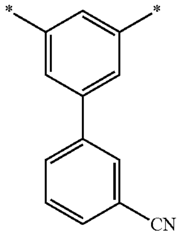 [SMILES: *c1cc(*)cc(-c2cccc(C#N)c2)c1] | 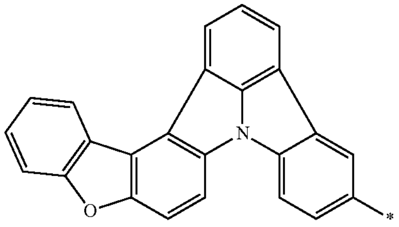 [SMILES: *c1ccc2c(c1)c1cccc3c4c5c(ccc4n2c13)oc1ccccc15] |
| O-12-48 | 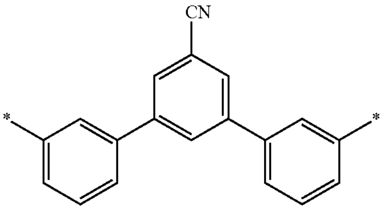 | 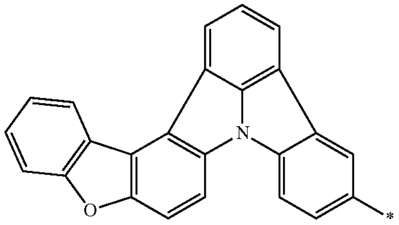 [SMILES: *c1ccc2c(c1)c1cccc3c4c5c(ccc4n2c13)oc1ccccc15] |
| O-12-49 | 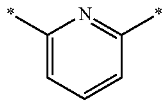 [SMILES: *c1cccc(*)n1] | 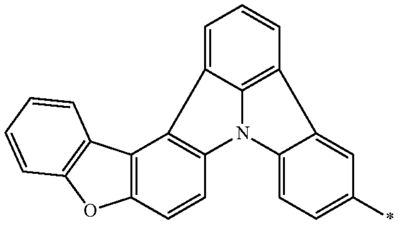 [SMILES: *c1ccc2c(c1)c1cccc3c4c5c(ccc4n2c13)oc1ccccc15] |

TABLE 23-continued
| Compound No. | Central Skeleton | Substituent |
| --- | --- | --- |
| O-12-50 | 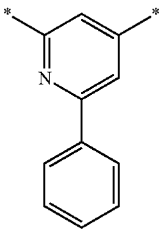 [SMILES: *c1cc(*)nc(-c2ccccc2)c1] | 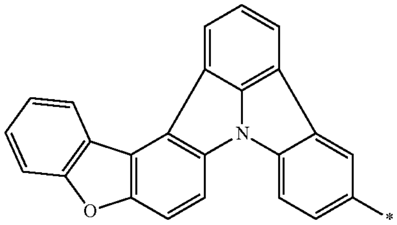 [SMILES: *c1ccc2c(c1)c1cccc3c4c5c(ccc4n2c13)oc1ccccc15] |
| O-12-51 | 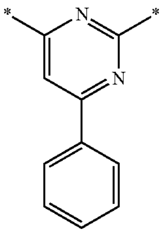 [SMILES: *c1cc(-c2ccccc2)nc(*)n1] | 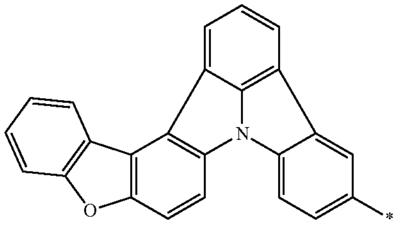 [SMILES: *c1ccc2c(c1)c1cccc3c4c5c(ccc4n2c13)oc1ccccc15] |
| O-12-52 | 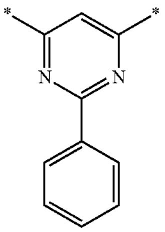 [SMILES: *c1cc(*)nc(-c2ccccc2)n1] | 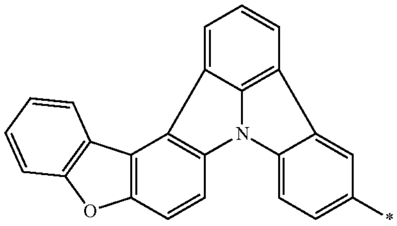 [SMILES: *c1ccc2c(c1)c1cccc3c4c5c(ccc4n2c13)oc1ccccc15] |
| O-12-53 | 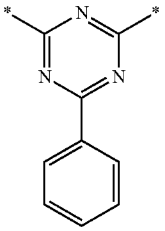 [SMILES: *c1nc(*)nc(-c2ccccc2)n1] | 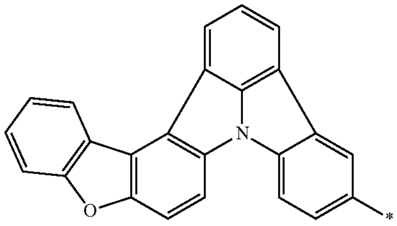 [SMILES: *c1ccc2c(c1)c1cccc3c4c5c(ccc4n2c13)oc1ccccc15] |
| O-12-54 | 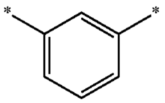 [SMILES: *c1cccc(*)c1] | 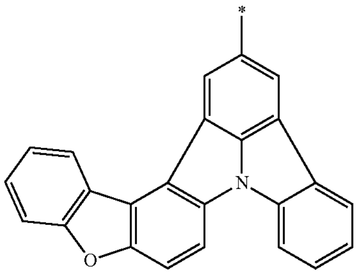 [SMILES: *c1cc2c3ccccc3n3c4ccc5oc6ccccc6c5c4c(c1)c23] |
| O-12-55 | 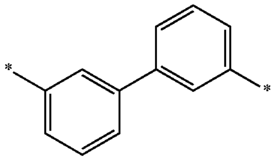 [SMILES: *c1cccc(-c2cccc(*)c2)c1] | 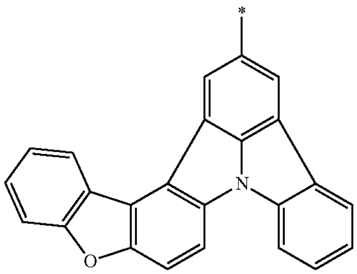 [SMILES: *c1cc2c3ccccc3n3c4ccc5oc6ccccc6c5c4c(c1)c23] |

TABLE 23-continued
| Compound No. | Central Skeleton | Substituent |
|---|---|---|
| O-12-56 | 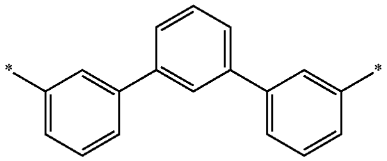 [SMILES: *c1cccc(-c2cccc(-c3cccc(*)c3)c2)c1] | 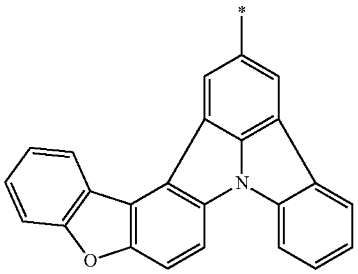 [SMILES: *c1cc2c3ccccc3n3c4ccc5oc6ccccc6c5c4c(c1)c23] |
| O-12-57 | 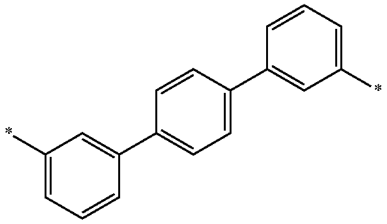 [SMILES: *c1cccc(-c2ccc(-c3cccc(*)c3)cc2)c1] | 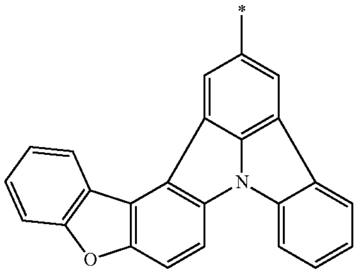 [SMILES: *c1cc2c3ccccc3n3c4ccc5oc6ccccc6c5c4c(c1)c23] |
| O-12-58 | 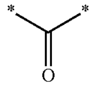 | 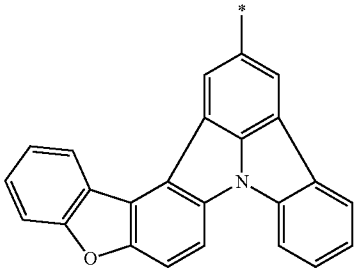 [SMILES: *c1cc2c3ccccc3n3c4ccc5oc6ccccc6c5c4c(c1)c23] |
| O-12-59 | 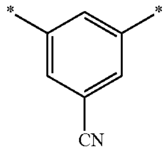 [SMILES: *c1cc(*)cc(C#N)c1] | 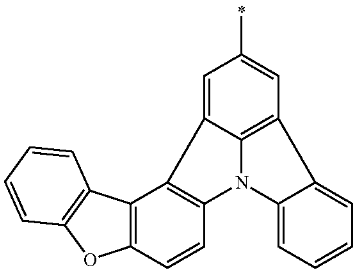 [SMILES: *c1cc2c3ccccc3n3c4ccc5oc6ccccc6c5c4c(c1)c23] |
| O-12-60 | 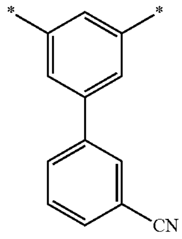 [SMILES: *c1cc(*)cc(-c2cccc(C#N)c2)c1] | 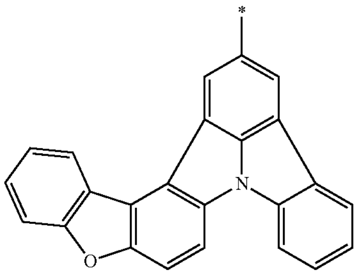 [SMILES: *c1cc2c3ccccc3n3c4ccc5oc6ccccc6c5c4c(c1)c23] |

TABLE 23-continued
| Compound No. | Central Skeleton | Substituent |
| --- | --- | --- |
| O-12-61 | 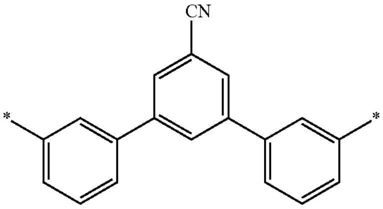 | 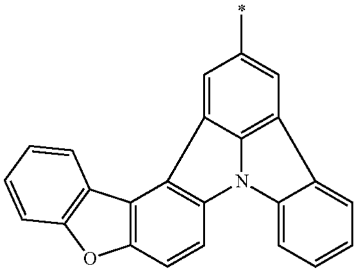 [SMILES: *c1cc2c3ccccc3n3c4ccc5oc6ccccc6c5c4c(c1)c23] |
| O-12-62 | 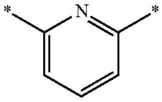 [SMILES: *c1cccc(*)n1] | 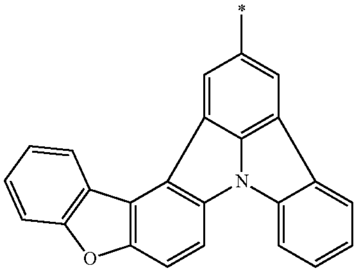 [SMILES: *c1cc2c3ccccc3n3c4ccc5oc6ccccc6c5c4c(c1)c23] |
| O-12-63 | 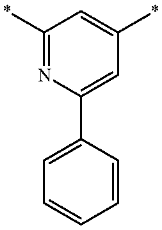 [SMILES: *c1cc(*)nc(-c2ccccc2)c1] | 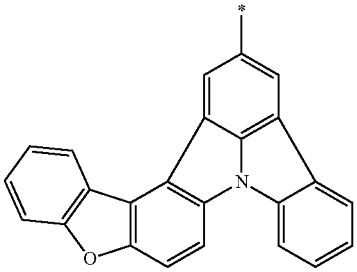 [SMILES: *c1cc2c3ccccc3n3c4ccc5oc6ccccc6c5c4c(c1)c23] |
| O-12-64 | 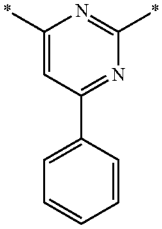 [SMILES: *c1cc(-c2ccccc2)nc(*)n1] | 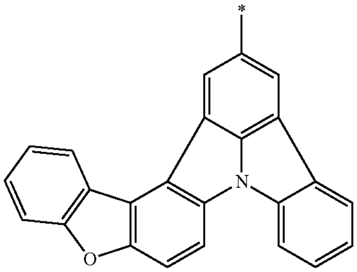 [SMILES: *c1cc2c3ccccc3n3c4ccc5oc6ccccc6c5c4c(c1)c23] |
| O-12-65 | 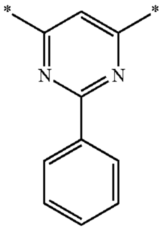 [SMILES: *c1cc(*)nc(-c2ccccc2)n1] | 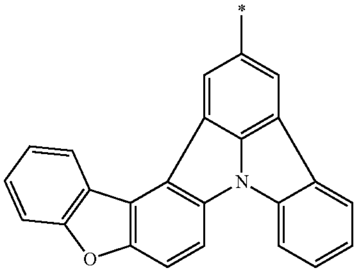 [SMILES: *c1cc2c3ccccc3n3c4ccc5oc6ccccc6c5c4c(c1)c23] |

TABLE 23-continued
| Compound No. | Central Skeleton | Substituent |
|---|---|---|
| O-12-66 | 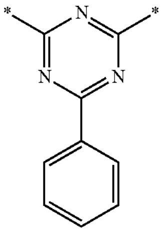 [SMILES: *c1nc(*)nc(-c2ccccc2)n1] | 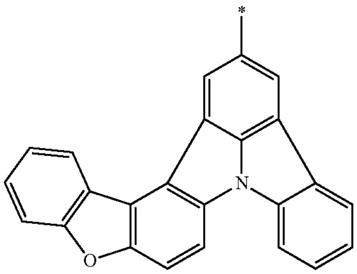 [SMILES: *c1cc2c3ccccc3n3c4ccc5oc6ccccc6c5c4c(c1)c23] |
In the compound represented by the following general formula (13), $R^{D1}$, $R^{D3}$, $R^{D6}$ to $R^{D9}$, $R^{D11}$, $R^{D13}$ to $R^{D15}$ each represent a hydrogen atom, and the other groups are the groups described in Tables below.
[Chem. 18]
(13)
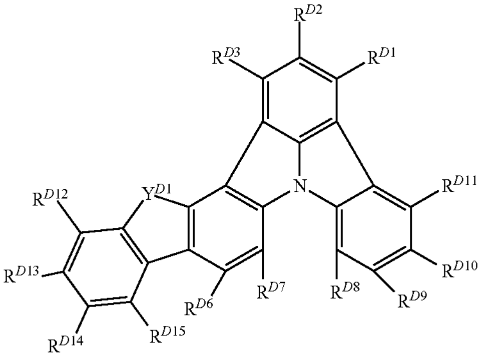
TABLE 24
| Compound No. | $Y^{D1}$ | $R^{D12}$ | $R^{D10}$ | $R^{D2}$ | $R^3$ | $R^1$ | $R^2$ |
|---|---|---|---|---|---|---|---|
| O-13-1 | O | H | H | H | — | — | — |
| O-13-2 | O | H | 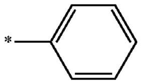 | 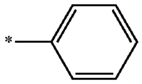 | — | — | — |
| O-13-3 | O | H | 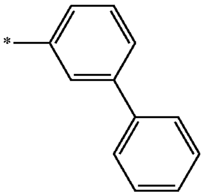 [SMILES: *c1cccc(-c2ccccc2)c1] | H | — | — | — |
| O-13-4 | O | H | 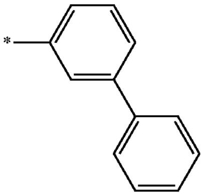 [SMILES: *c1cccc(-c2ccccc2)c1] | 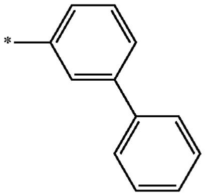 [SMILES: *c1cccc(-c2ccccc2)c1] | — | — | — |

TABLE 24-continued
| Compound No. | $Y^{D1}$ | $R^{D12}$ | $R^{D10}$ | $R^{D2}$ | $R^3$ | $R^1$ | $R^2$ |
|---|---|---|---|---|---|---|---|
| O-13-5 | O | 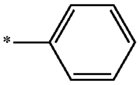 | 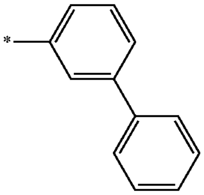 [SMILES: *c1cccc(-c2ccccc2)c1] | H | — | — | — |
| O-13-6 | O | H | 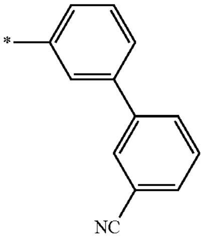 [SMILES: *c1cccc(-c2cccc(C#N)c2)c1] | H | — | — | — |
| O-13-7 | O | H | H | 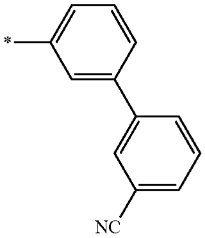 [SMILES: *c1cccc(-c2cccc(C#N)c2)c1] | — | — | — |
| O-13-8 | O | H | 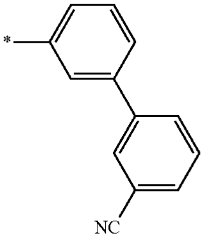 [SMILES: *c1cccc(-c2cccc(C#N)c2)c1] | 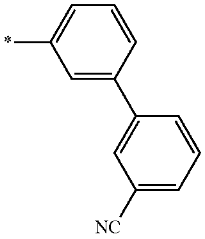 [SMILES: *c1cccc(-c2cccc(C#N)c2)c1] | — | — | — |
| O-13-9 | O | H | 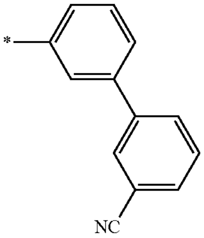 [SMILES: *c1cccc(-c2cccc(C#N)c2)c1] | 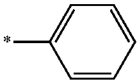 [SMILES: *c1ccccc1] | — | — | — |
| O-13-10 | O | H | 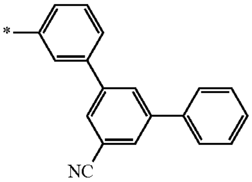 [SMILES: *c1cccc(-c2cc(C#N)cc(-c3ccccc3)c2)c1] | H | — | — | — |
| O-13-11 | O | H | 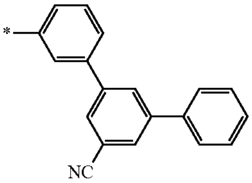 [SMILES: *c1cccc(-c2cc(C#N)cc(-c3ccccc3)c2)c1] | 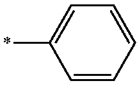 [SMILES: *c1ccccc1] | — | — | — |

TABLE 24-continued
| Compound No. | $Y^{D1}$ | $R^{D12}$ | $R^{D10}$ | $R^{D2}$ | $R^3$ | $R^1$ | $R^2$ |
|---|---|---|---|---|---|---|---|
| O-13-12 | O | H | 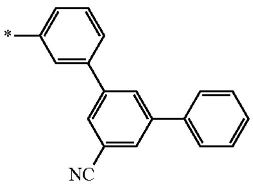 [SMILES: *c1cccc(-c2cc(C#N)cc(-c3ccccc3)c2)c1] | 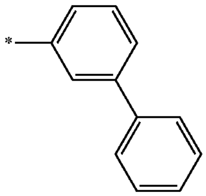 [SMILES: *c1cccc(-c2ccccc2)c1] | — | — | — |
| O-13-13 | O | 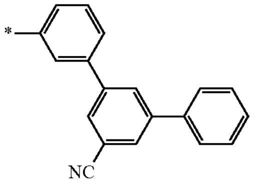 [SMILES: *c1cccc(-c2cc(C#N)cc(-c3ccccc3)c2)c1] | H | H | — | — | — |
| O-13-14 | O | H | 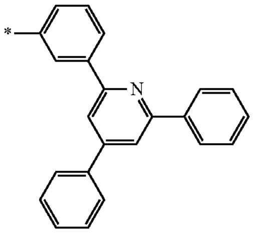 [SMILES: *c1cccc(-c2cc(-c3ccccc3)cc(-c3ccccc3)n2)c1] | H | — | — | — |
| O-13-15 | O | H | 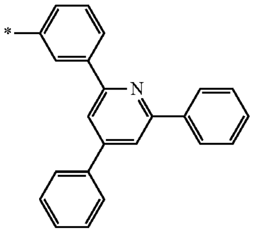 [SMILES: *c1cccc(-c2cc(-c3ccccc3)cc(-c3ccccc3)n2)c1] | 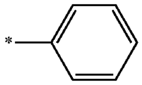 | — | — | — |
TABLE 25
| | | | | | | | |
|---|---|---|---|---|---|---|---|
| O-13-16 | O | H | 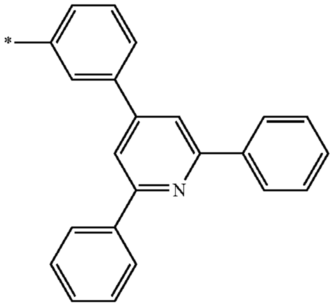 [SMILES: *c1cccc(-c2cc(-c3ccccc3)nc(-c3ccccc3)c2)c1] | H | — | — | — |

TABLE 25-continued
| | | | | | | | |
|---|---|---|---|---|---|---|---|
| O-13-17 | O | H | 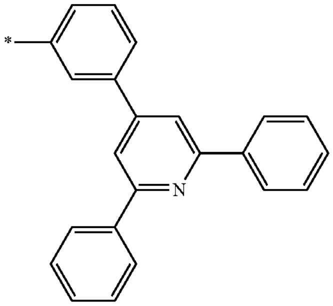 | 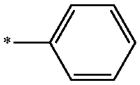 [SMILES: *c1ccccc1] | — | — | — |
| O-13-18 | O | H | 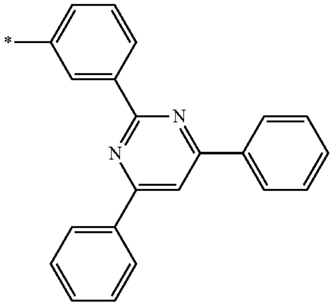 | H | — | — | — |
| O-13-19 | O | H | 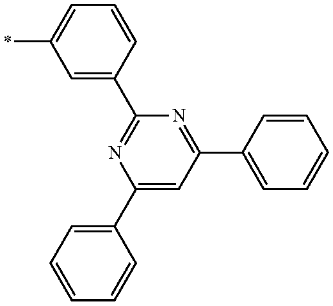 | 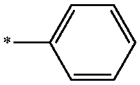 [SMILES: *c1ccccc1] | — | — | — |
| O-13-20 | O | H | 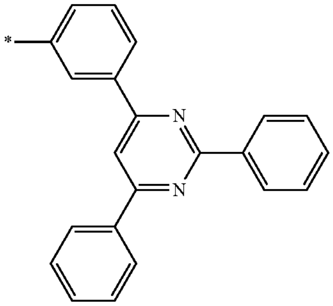 | H | — | — | — |
| O-13-21 | O | H | 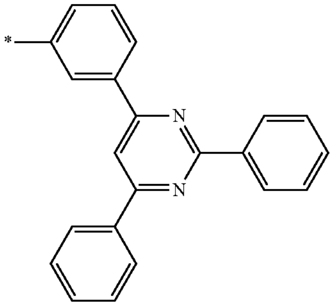 | 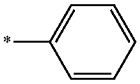 | — | — | — |

TABLE 25-continued
| | | | | | | | |
|---|---|---|---|---|---|---|---|
| O-13-22 | O | H | 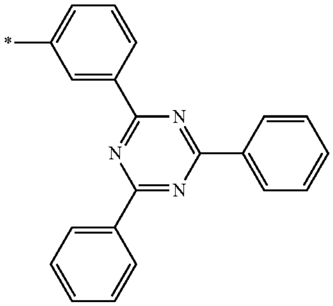 [SMILES: *c1cccc(-c2nc(-c3ccccc3)nc(-c3ccccc3)n2)c1] | H | — | — | — |
| O-13-23 | O | H | 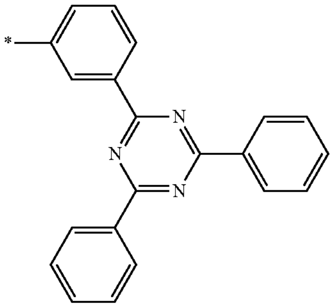 | 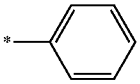 [SMILES: *c1ccccc1] | — | — | — |
| O-13-24 | O | H | 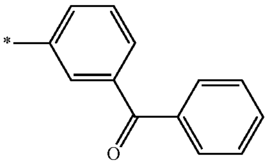 [SMILES: *c1cccc(C(=O)c2ccccc2)c1] | H | — | — | — |
| O-13-25 | O | H | 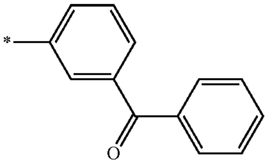 [SMILES: *c1cccc(C(=O)c2ccccc2)c1] | 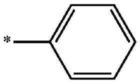 [SMILES: *c1ccccc1] | — | — | — |
| O-13-26 | O | H | 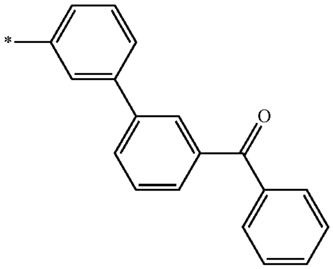 [SMILES: *c1cccc(-c2cccc(C(=O)c3ccccc3)c2)c1] | H | — | — | — |
| O-13-27 | O | H | 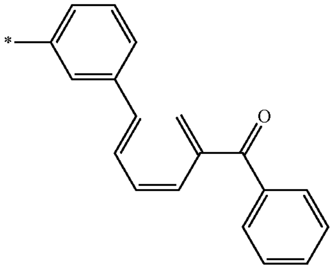 [SMILES: *c1cccc(/C=C/C=C\C(=C)C(=O)c2ccccc2)c1] | 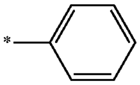 | — | — | — |
| S-13-1 | S | H | H | H | — | — | — |

TABLE 25-continued
| | | | | | | | |
|---|---|---|---|---|---|---|---|
| S-13-2 | S | H | 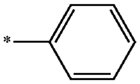 [SMILES: *c1ccccc1] | 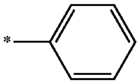 [SMILES: *c1ccccc1] | — | — | — |
| S-13-3 | S | H | 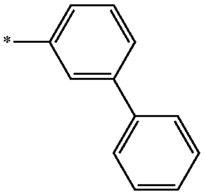 [SMILES: *c1cccc(-c2ccccc2)c1] | H | — | — | — |
TABLE 26
| | | | | | | | |
|---|---|---|---|---|---|---|---|
| S-13-4 | S | H | 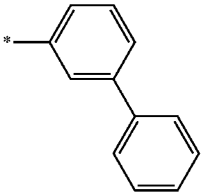 [SMILES: *c1cccc(-c2ccccc2)c1] | 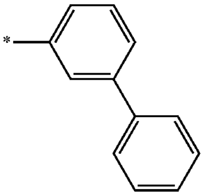 [SMILES: *c1cccc(-c2ccccc2)c1] | — | — | — |
| S-13-5 | S | 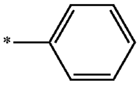 | 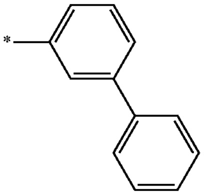 [SMILES: *c1cccc(-c2ccccc2)c1] | H | — | — | — |
| S-13-6 | S | H | 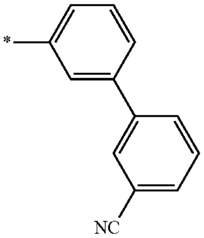 [SMILES: *c1cccc(-c2cccc(C#N)c2)c1] | H | — | — | — |
| S-13-7 | S | H | H | 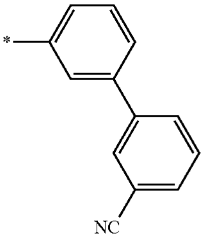 [SMILES: *c1cccc(-c2cccc(C#N)c2)c1] | — | — | — |
| S-13-8 | S | H | 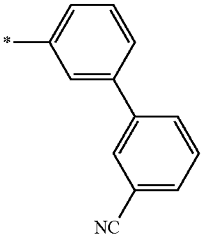 [SMILES: *c1cccc(-c2cccc(C#N)c2)c1] | 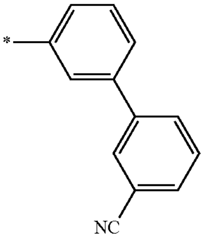 [SMILES: *c1cccc(-c2cccc(C#N)c2)c1] | — | — | — |

TABLE 26-continued
| | | | | | | | |
|---|---|---|---|---|---|---|---|
| S-13-9 | S | H | 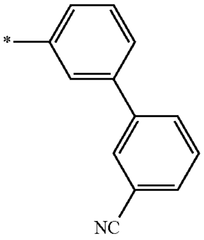 [SMILES: *c1cccc(-c2cccc(C#N)c2)c1] | 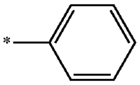 [SMILES: *c1ccccc1] | — | — | — |
| S-13-10 | S | H | 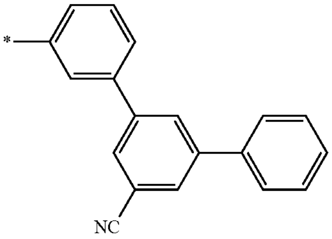 [SMILES: *c1cccc(-c2cc(C#N)cc(-c3ccccc3)c2)c1] | H | — | — | — |
| S-13-11 | S | H | 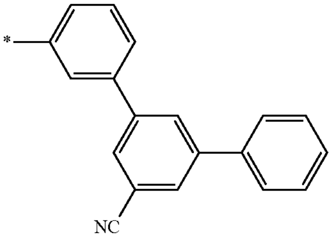 [SMILES: *c1cccc(-c2cc(C#N)cc(-c3ccccc3)c2)c1] | 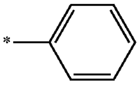 [SMILES: *c1ccccc1] | — | — | — |
| S-13-12 | S | H | 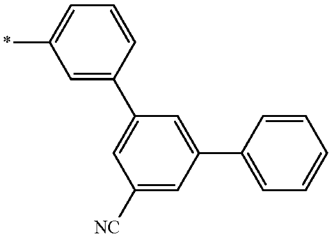 [SMILES: *c1cccc(-c2cc(C#N)cc(-c3ccccc3)c2)c1] | 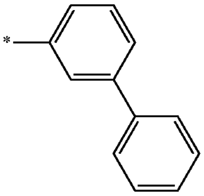 [SMILES: *c1cccc(-c2ccccc2)c1] | — | — | — |
| S-13-13 | S | 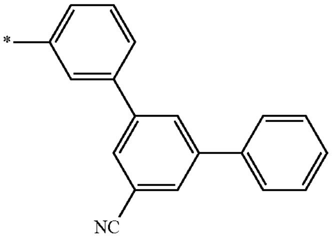 [SMILES: *c1cccc(-c2cc(C#N)cc(-c3ccccc3)c2)c1] | H | H | — | — | — |
| S-13-14 | S | H | 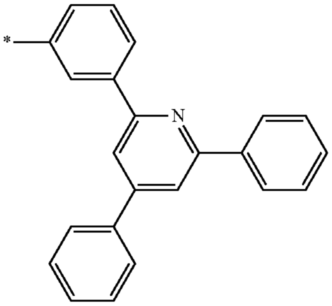 | H | — | — | — |

TABLE 26-continued
| | | | | | | | |
|---|---|---|---|---|---|---|---|
| S-13-15 | S | H | 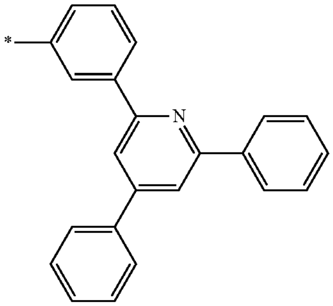 | 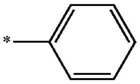 [SMILES: *c1ccccc1] | — | — | — |
| S-13-16 | S | H | 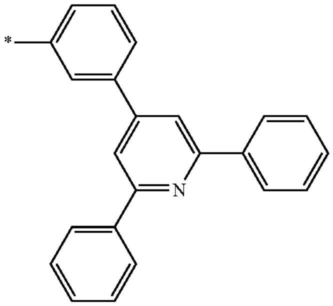 | H | — | — | — |
| S-13-17 | S | H | 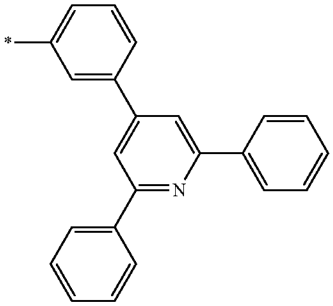 | 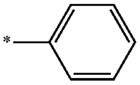 | — | — | — |
| S-13-18 | S | H | 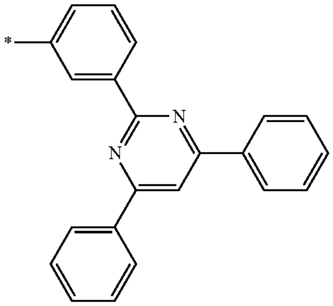 | H | — | — | — |

TABLE 27
| | | | | | | | |
|---|---|---|---|---|---|---|---|
| S-13-19 | S | H | 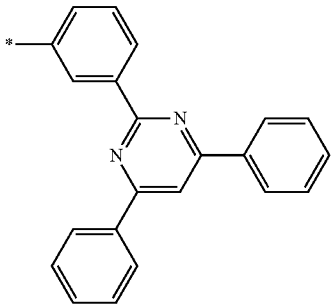 | 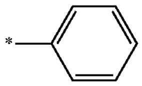 [SMILES: *c1ccccc1] | — | — | — |
| S-13-20 | S | H | 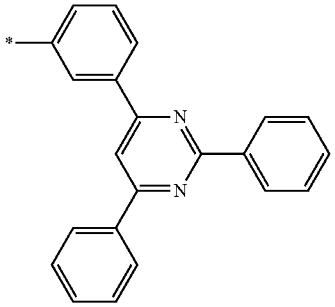 | H | — | — | — |
| S-13-21 | S | H | 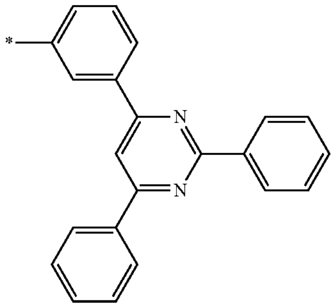 | 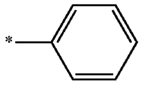 [SMILES: *c1ccccc1] | — | — | — |
| S-13-22 | S | H | 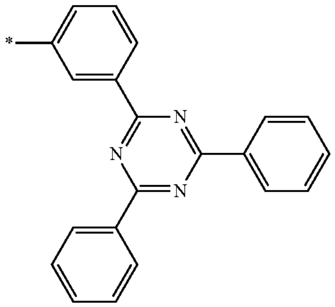 | H | — | — | — |
| S-13-23 | S | H | 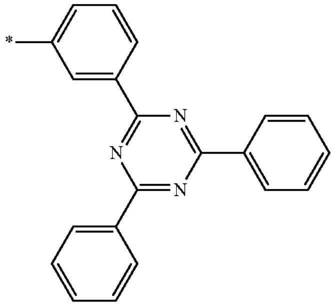 | 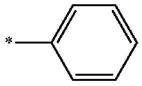 [SMILES: *c1ccccc1] | — | — | — |

TABLE 27-continued
| | | | | | | | |
|---|---|---|---|---|---|---|---|
| S-13-24 | S | H | 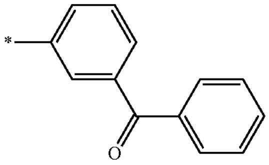 [SMILES: *c1cccc(C(=O)c2ccccc2)c1] | H | — | — | — |
| S-13-25 | S | H | 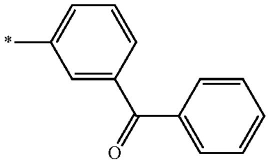 [SMILES: *c1cccc(C(=O)c2ccccc2)c1] | 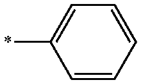 [SMILES: *c1ccccc1] | — | — | — |
| S-13-26 | S | H | 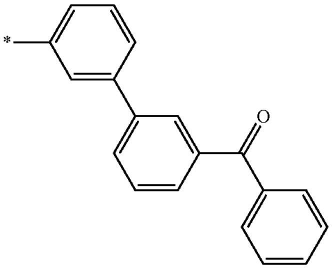 [SMILES: *c1cccc(-c2cccc(C(=O)c3ccccc3)c2)c1] | H | — | — | — |
| S-13-27 | S | H | 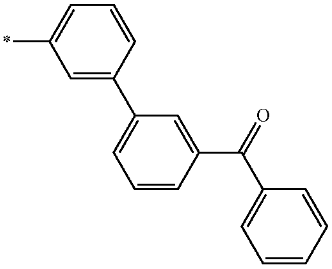 [SMILES: *c1cccc(-c2cccc(C(=O)c3ccccc3)c2)c1] | 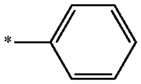 [SMILES: *c1ccccc1] | — | — | — |
| N-13-1 | $NR^3$ | H | H | H | 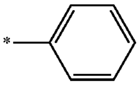 [SMILES: *c1ccccc1] | — | — |
| N-13-2 | $NR^3$ | H | 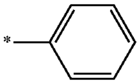 | 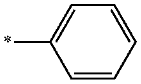 | 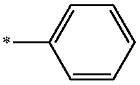 [SMILES: *c1ccccc1] | — | — |
| N-13-3 | $NR^3$ | H | 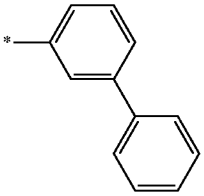 [SMILES: *c1cccc(-c2ccccc2)c1] | H | 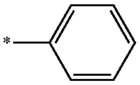 [SMILES: *c1ccccc1] | — | — |
| N-13-4 | $NR^3$ | H | 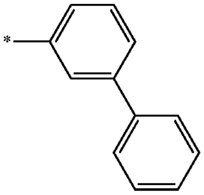 [SMILES: *c1cccc(-c2ccccc2)c1] | 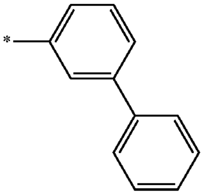 [SMILES: *c1cccc(-c2ccccc2)c1] | 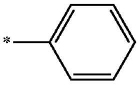 [SMILES: *c1ccccc1] | — | — |

TABLE 27-continued
| | | | | | | | |
|---|---|---|---|---|---|---|---|
| N-13-5 | $NR^3$ | H | 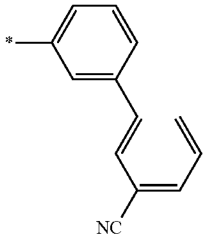 [SMILES: *c1cccc(/C=C/C(C#N)=C\C=C)c1] | H | 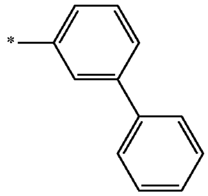 [SMILES: *c1cccc(-c2ccccc2)c1] | — | — |
| N-13-6 | $NR^3$ | H | H | 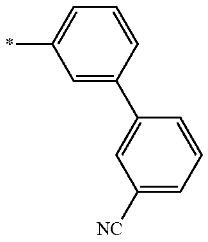 [SMILES: *c1cccc(-c2cccc(C#N)c2)c1] | 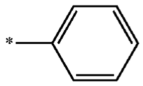 | — | — |
TABLE 28
| | | | | | | | |
|---|---|---|---|---|---|---|---|
| N-13-7 | $NR^3$ | H | 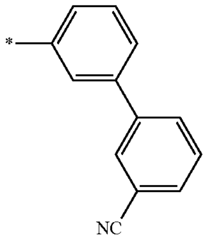 [SMILES: *c1cccc(-c2cccc(C#N)c2)c1] | 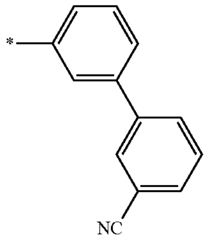 [SMILES: *c1cccc(-c2cccc(C#N)c2)c1] | 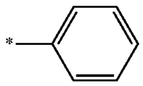 [SMILES: *c1ccccc1] | — | — |
| N-13-8 | $NR^3$ | H | 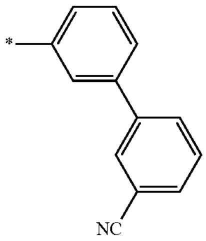 [SMILES: *c1cccc(-c2cccc(C#N)c2)c1] | 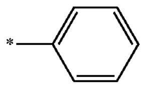 [SMILES: *c1ccccc1] | 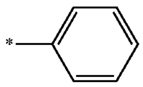 [SMILES: *c1ccccc1] | — | — |
| N-13-9 | $NR^3$ | H | 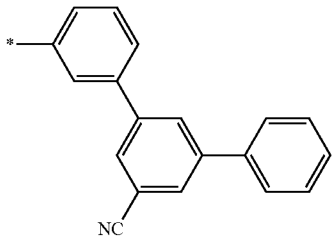 [SMILES: *c1cccc(-c2cc(C#N)cc(-c3ccccc3)c2)c1] | H | 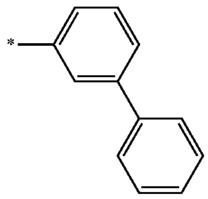 [SMILES: *c1cccc(-c2ccccc2)c1] | — | — |
| N-13-10 | $NR^3$ | H | 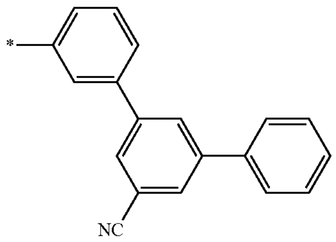 [SMILES: *c1cccc(-c2cc(C#N)cc(-c3ccccc3)c2)c1] | 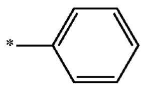 [SMILES: *c1ccccc1] | 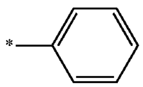 [SMILES: *c1ccccc1] | — | — |

TABLE 28-continued
| | | | | | | | |
|---|---|---|---|---|---|---|---|
| N-13-11 | $NR^3$ | H | 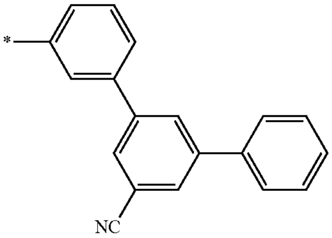 [SMILES: *c1cccc(-c2cc(C#N)cc(-c3ccccc3)c2)c1] | 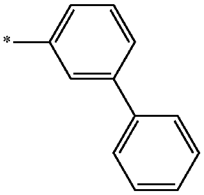 [SMILES: *c1cccc(-c2ccccc2)c1] | 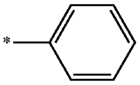 [SMILES: *c1ccccc1] | — | — |
| N-13-12 | $NR^3$ | H | 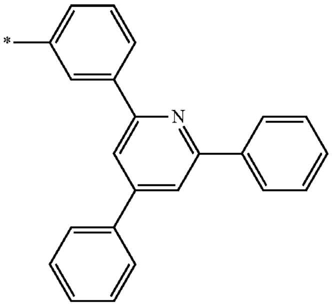 | H | 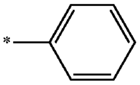 [SMILES: *c1ccccc1] | — | — |
| N-13-13 | $NR^3$ | H | 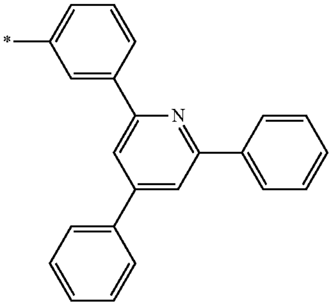 | 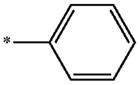 [SMILES: *c1ccccc1] | 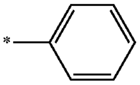 [SMILES: *c1ccccc1] | — | — |
| N-13-14 | $NR^3$ | H | 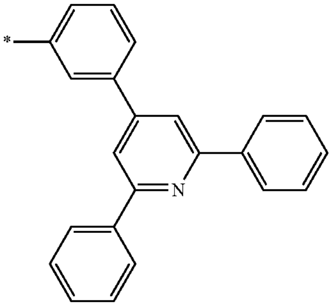 | H | 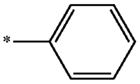 [SMILES: *c1ccccc1] | — | — |
| N-13-15 | $NR^3$ | H | 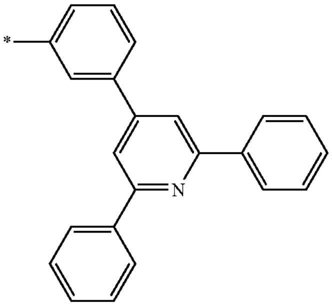 | 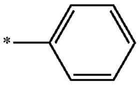 [SMILES: *c1ccccc1] | 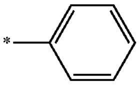 [SMILES: *c1ccccc1] | — | — |

TABLE 28-continued
| | | | | | | | |
|---|---|---|---|---|---|---|---|
| N-13-16 | $NR^3$ | H | 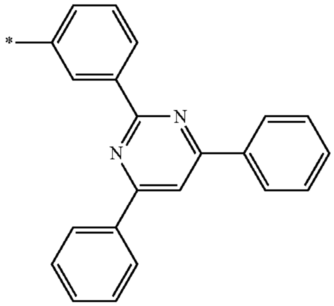 [SMILES: *c1cccc(-c2nc(-c3ccccc3)cc(-c3ccccc3)n2)c1] | H | 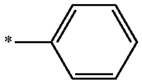 [SMILES: *c1ccccc1] | — | — |
| N-13-17 | $NR^3$ | H | 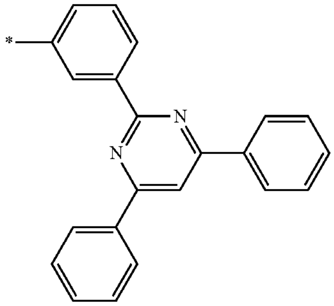 [SMILES: *c1cccc(-c2nc(-c3ccccc3)cc(-c3ccccc3)n2)c1] | 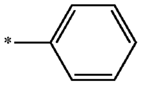 [SMILES: *c1ccccc1] | 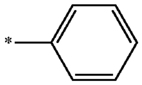 [SMILES: *c1ccccc1] | — | — |
| N-13-18 | $NR^3$ | H | 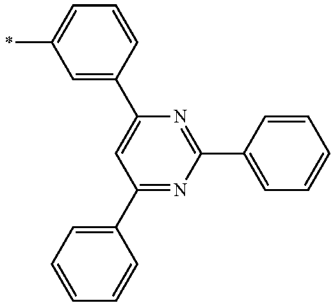 | H | 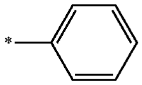 [SMILES: *c1ccccc1] | — | — |
| N-13-19 | $NR^3$ | H | 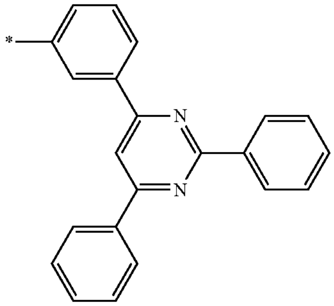 | 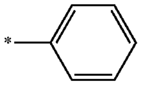 [SMILES: *c1ccccc1] | 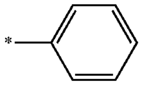 [SMILES: *c1ccccc1] | — | — |
| N-13-20 | $NR^3$ | H | 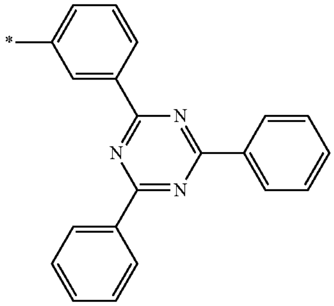 | H | 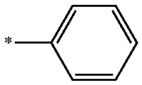 [SMILES: *c1ccccc1] | — | — |

TABLE 28-continued
| | | | | | | | |
|---|---|---|---|---|---|---|---|
| N-13-21 | $NR^3$ | H | 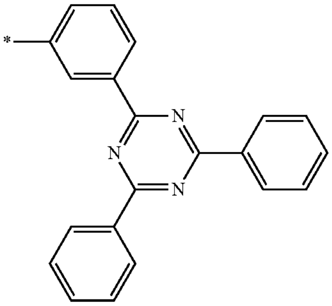 | 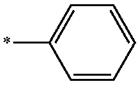 [SMILES: *c1ccccc1] | 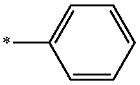 [SMILES: *c1ccccc1] | — | — |
TABLE 29
| | | | | | | | |
|---|---|---|---|---|---|---|---|
| N-13-22 | $NR^3$ | H | 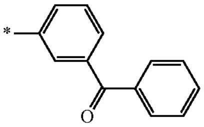 | H | 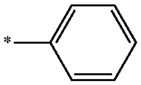 [SMILES: *c1ccccc1] | — | — |
| N-13-23 | $NR^3$ | H | 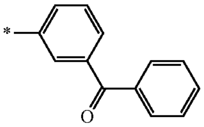 [SMILES: *c1cccc(C(=O)c2ccccc2)c1] | 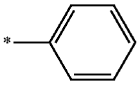 [SMILES: *c1ccccc1] | 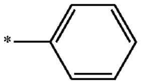 [SMILES: *c1ccccc1] | — | — |
| N-13-24 | $NR^3$ | H | 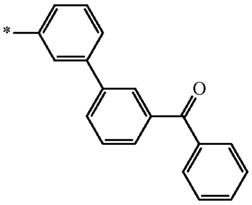 [SMILES: *c1cccc(-c2cccc(C(=O)c3ccccc3)c2)c1] | H | 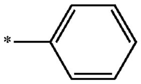 [SMILES: *c1ccccc1] | — | — |
| N-13-25 | $NR^3$ | H | 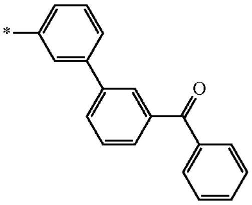 [SMILES: *c1cccc(-c2cccc(C(=O)c3ccccc3)c2)c1] | 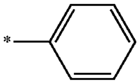 [SMILES: *c1ccccc1] | 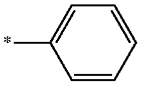 [SMILES: *c1ccccc1] | — | — |
| C-13-1 | $CR^1R^2$ | H | H | H | — | *—Me | *—Me |
| C-13-2 | $CR^1R^2$ | H | 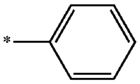 [SMILES: *c1ccccc1] | 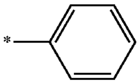 [SMILES: *c1ccccc1] | — | *—Me | *—Me |
| C-13-3 | $CR^1R^2$ | H | 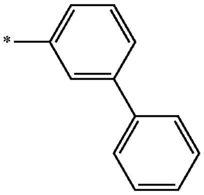 [SMILES: *c1cccc(-c2ccccc2)c1] | H | — | *—Me | *—Me |

TABLE 29-continued
| | | | | | | | |
|---|---|---|---|---|---|---|---|
| C-13-4 | $CR^1R^2$ | H | 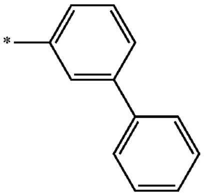 [SMILES: *c1cccc(-c2ccccc2)c1] | 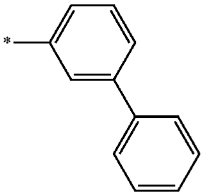 [SMILES: *c1cccc(-c2ccccc2)c1] | — | *—Me | *—Me |
| C-13-5 | $CR^1R^2$ | H | 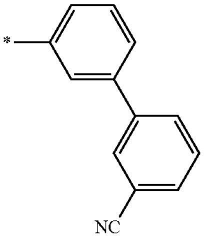 [SMILES: *c1cccc(-c2cccc(C#N)c2)c1] | H | — | 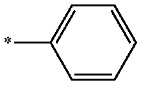 [SMILES: *c1ccccc1] | 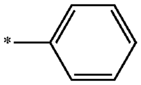 [SMILES: *c1ccccc1] |
| C-13-6 | $CR^1R^2$ | H | H | 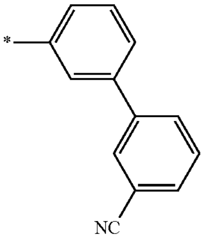 [SMILES: *c1cccc(-c2cccc(C#N)c2)c1] | — | *—Me | *—Me |
| C-13-7 | $CR^1R^2$ | H | 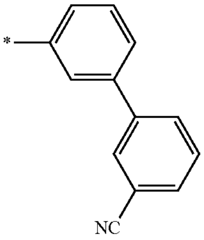 [SMILES: *c1cccc(-c2cccc(C#N)c2)c1] | 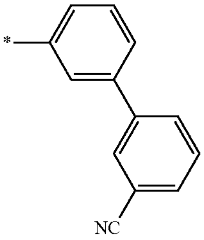 [SMILES: *c1cccc(-c2cccc(C#N)c2)c1] | — | 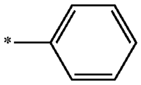 [SMILES: *c1ccccc1] | 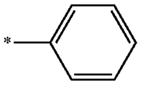 [SMILES: *c1ccccc1] |
| C-13-8 | $CR^1R^2$ | H | 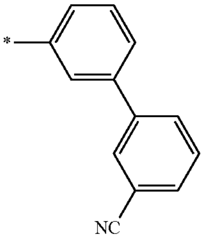 [SMILES: *c1cccc(-c2cccc(C#N)c2)c1] | 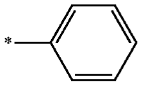 [SMILES: *c1ccccc1] | — | *—Me | *—Me |
| C-13-9 | $CR^1R^2$ | H | 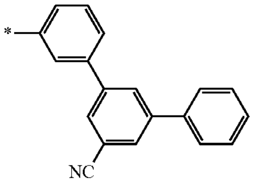 [SMILES: *c1cccc(-c2cc(C#N)cc(-c3ccccc3)c2)c1] | H | — | 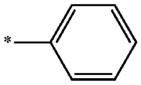 | 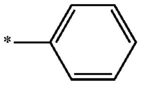 |
| C-13-10 | $CR^1R^2$ | H | 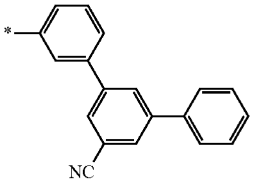 [SMILES: *c1cccc(-c2cc(C#N)cc(-c3ccccc3)c2)c1] | 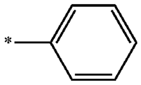 | — | *—Me | *—Me |

TABLE 29-continued
| | | | | | | | |
|---|---|---|---|---|---|---|---|
| C-13-11 | $CR^1R^2$ | H | 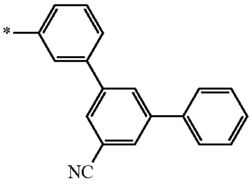 [SMILES: *c1cccc(-c2cc(C#N)cc(-c3ccccc3)c2)c1] | 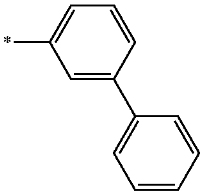 [SMILES: *c1cccc(-c2ccccc2)c1] | — | *—Me | *—Me |
TABLE 30
| | | | | | | | |
|---|---|---|---|---|---|---|---|
| C-13-12 | $CR^1R^2$ | H | 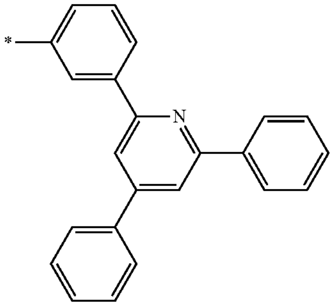 [SMILES: *c1cccc(-c2cc(-c3ccccc3)cc(-c3ccccc3)n2)c1] | H | — | *—Me | *—Me |
| C-13-13 | $CR^1R^2$ | H | 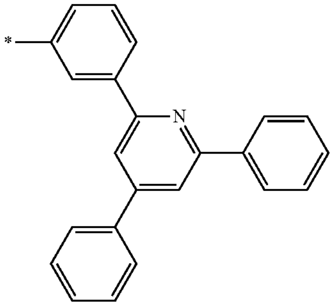 | 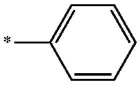 [SMILES: *c1ccccc1] | — | *—Me | *—Me |
| C-13-14 | $CR^1R^2$ | H | 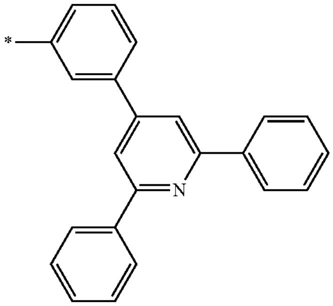 [SMILES: *c1cccc(-c2cc(-c3ccccc3)nc(-c3ccccc3)c2)c1] | H | — | *—Me | *—Me |
| C-13-15 | $CR^1R^2$ | H | 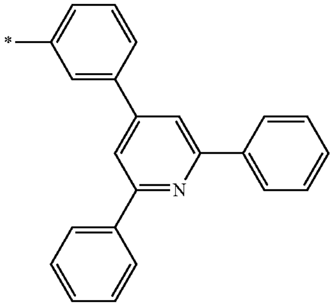 [SMILES: *c1cccc(-c2cc(-c3ccccc3)nc(-c3ccccc3)c2)c1] | 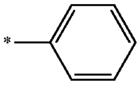 [SMILES: *c1ccccc1] | — | *—Me | *—Me |

TABLE 30-continued
| | | | | | | | |
|---|---|---|---|---|---|---|---|
| C-13-16 | $CR^1R^2$ | H | 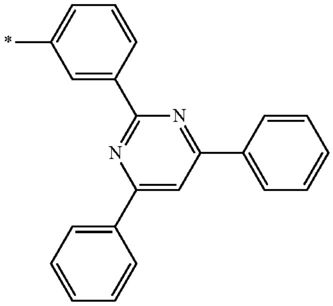 [SMILES: *c1cccc(-c2nc(-c3ccccc3)cc(-c3ccccc3)n2)c1] | H | — | 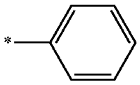 | 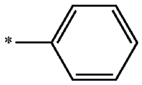 |
| C-13-17 | $CR^1R^2$ | H | 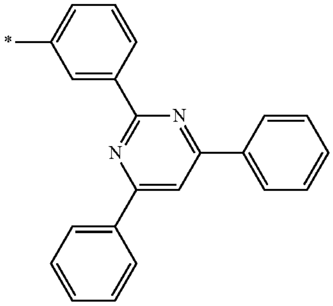 [SMILES: *c1cccc(-c2nc(-c3ccccc3)cc(-c3ccccc3)n2)c1] | 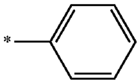 [SMILES: *c1ccccc1] | — | *—Me | *—Me |
| C-13-18 | $CR^1R^2$ | H | 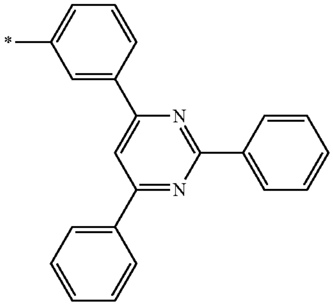 [SMILES: *c1cccc(-c2cc(-c3ccccc3)nc(-c3ccccc3)n2)c1] | H | — | *—Me | *—Me |
| C-13-19 | $CR^1R^2$ | H | 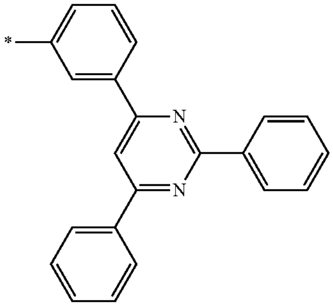 | 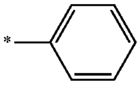 | — | *—Me | *—Me |
| C-13-20 | $CR^1R^2$ | H | 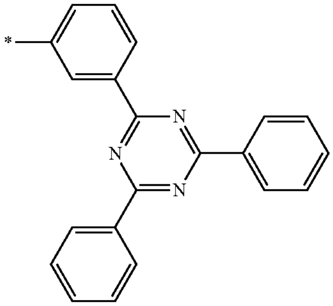 [SMILES: *c1cccc(-c2nc(-c3ccccc3)nc(-c3ccccc3)n2)c1] | H | — | *—Me | *—Me |

TABLE 30-continued
| | | | | | | | |
|---|---|---|---|---|---|---|---|
| C-13-21 | $CR^1R^2$ | H | 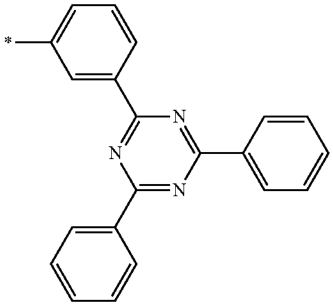 [SMILES: *c1cccc(-c2nc(-c3ccccc3)nc(-c3ccccc3)n2)c1] | 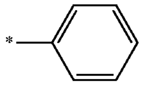 [SMILES: *c1ccccc1] | — | *—Me | *—Me |
| C-13-22 | $CR^1R^2$ | H | 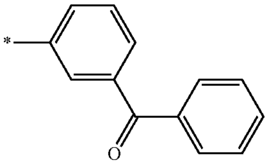 [SMILES: *c1cccc(C(=O)c2ccccc2)c1] | H | — | *—Me | *—Me |
| C-13-23 | $CR^1R^2$ | H | 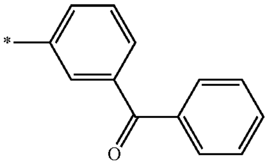 [SMILES: *c1cccc(C(=O)c2ccccc2)c1] | 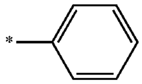 [SMILES: *c1ccccc1] | — | 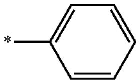 [SMILES: *c1ccccc1] | 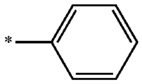 [SMILES: *c1ccccc1] |
| C-13-24 | $CR^1R^2$ | H | 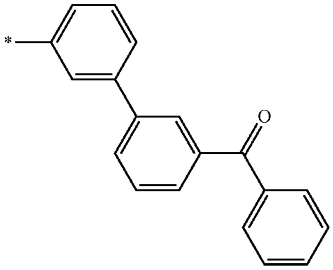 [SMILES: *c1cccc(-c2cccc(C(=O)c3ccccc3)c2)c1] | H | — | *—Me | *—Me |
| C-13-25 | $CR^1R^2$ | H | 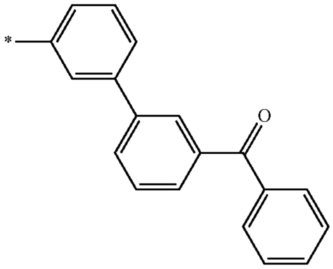 [SMILES: *c1cccc(-c2cccc(C(=O)c3ccccc3)c2)c1] | 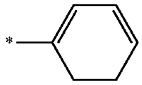 [SMILES: *C1=CC=CCC1] | — | *—Me | *—Me |
TABLE 31
| Compound No. | Central Skeleton | Substituent |
|---|---|---|
| O-13-28 | 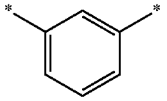 [SMILES: *c1cccc(*)c1] | 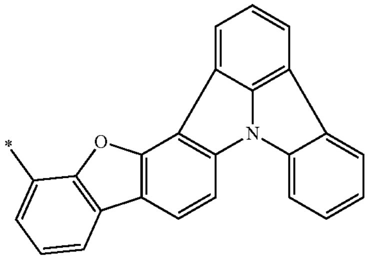 [SMILES: *c1cccc2c1oc1c2ccc2c1c1cccc3c4ccccc4n2c31] |

TABLE 31-continued
| Compound No. | Central Skeleton | Substituent |
| --- | --- | --- |
| O-13-23 | 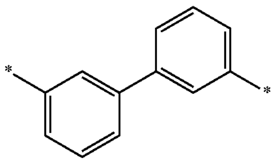 [SMILES: *c1cccc(-c2cccc(*)c2)c1] | 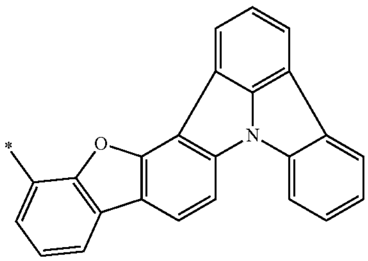 [SMILES: *c1cccc2c1oc1c2ccc2c1c1cccc3c4ccccc4n2c31] |
| O-13-30 | 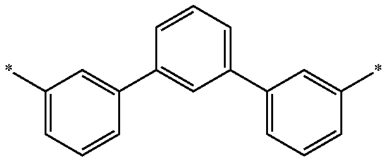 [SMILES: *c1cccc(-c2cccc(-c3cccc(*)c3)c2)c1] | 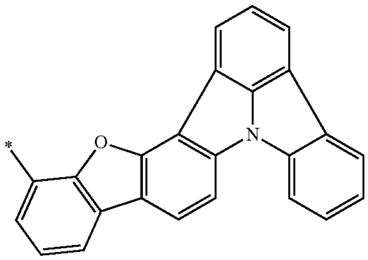 [SMILES: *c1cccc2c1oc1c2ccc2c1c1cccc3c4ccccc4n2c31] |
| O-13-31 | 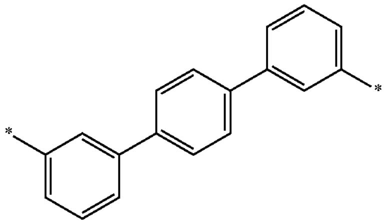 [SMILES: *c1cccc(-c2ccc(-c3cccc(*)c3)cc2)c1] | 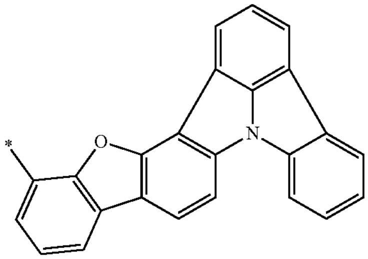 [SMILES: *c1cccc2c1oc1c2ccc2c1c1cccc3c4ccccc4n2c31] |
| O-13-32 | 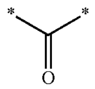 | 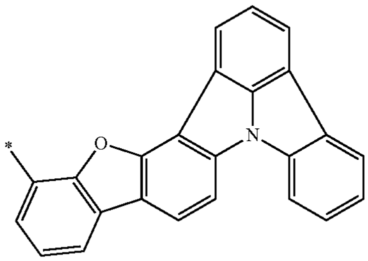 [SMILES: *c1cccc2c1oc1c2ccc2c1c1cccc3c4ccccc4n2c31] |
| O-13-33 | 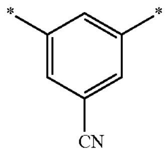 [SMILES: *c1cc(*)cc(C#N)c1] | 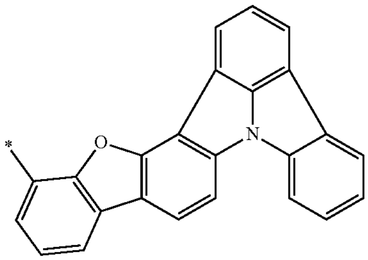 [SMILES: *c1cccc2c1oc1c2ccc2c1c1cccc3c4ccccc4n2c31] |
| O-13-34 | 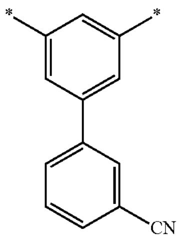 [SMILES: *c1cc(*)cc(-c2cccc(C#N)c2)c1] | 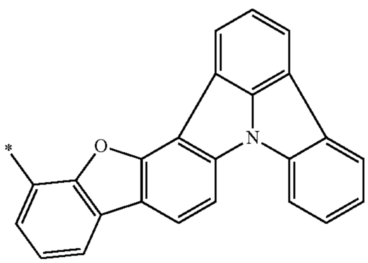 [SMILES: *c1cccc2c1oc1c2ccc2c1c1cccc3c4ccccc4n2c31] |

TABLE 31-continued
| Compound No. | Central Skeleton | Substituent |
|---|---|---|
| O-13-35 | 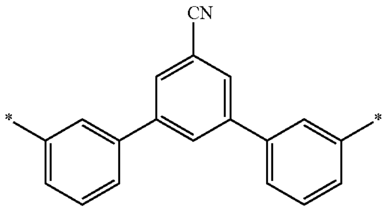 | 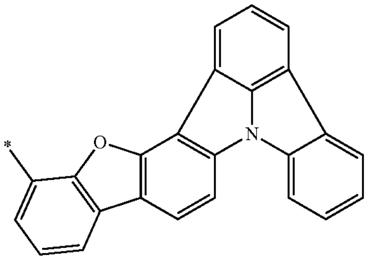 [SMILES: *c1cccc2c1oc1c2ccc2c1c1cccc3c4ccccc4n2c31] |
| O-13-36 | 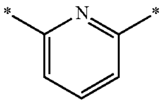 | 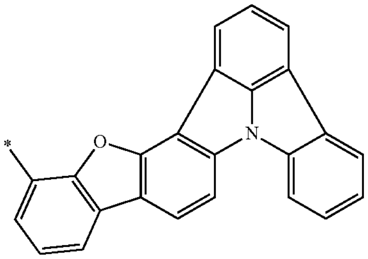 [SMILES: *c1cccc2c1oc1c2ccc2c1c1cccc3c4ccccc4n2c31] |
| O-13-37 | 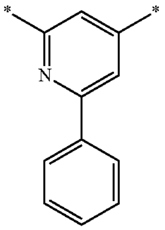 [SMILES: *c1cc(*)nc(-c2ccccc2)c1] | 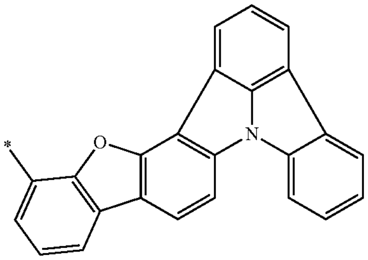 [SMILES: *c1cccc2c1oc1c2ccc2c1c1cccc3c4ccccc4n2c31] |
| O-13-38 | 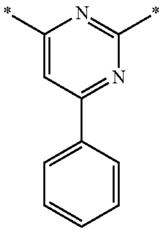 [SMILES: *c1cc(-c2ccccc2)nc(*)n1] | 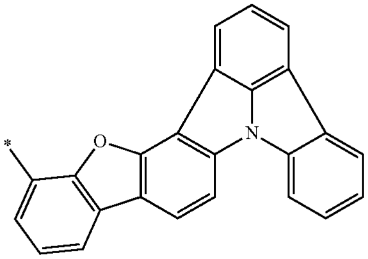 [SMILES: *c1cccc2c1oc1c2ccc2c1c1cccc3c4ccccc4n2c31] |
| O-13-39 | 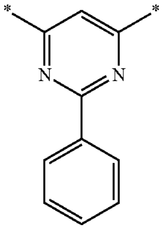 [SMILES: *c1cc(*)nc(-c2ccccc2)n1] | 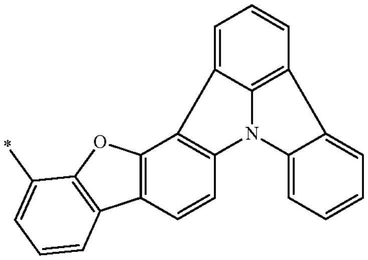 [SMILES: *c1cccc2c1oc1c2ccc2c1c1cccc3c4ccccc4n2c31] |

TABLE 31-continued
| Compound No. | Central Skeleton | Substituent |
| --- | --- | --- |
| O-13-40 | 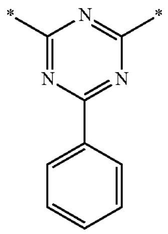 [SMILES: *c1nc(*)nc(-c2ccccc2)n1] | 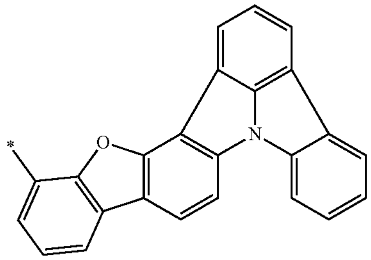 [SMILES: *c1cccc2c1oc1c2ccc2c1c1cccc3c4ccccc4n2c31] |
| O-13-41 | 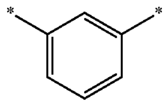 [SMILES: *c1cccc(*)c1] | 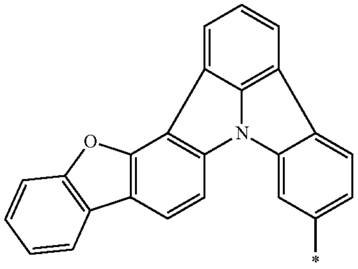 [SMILES: *c1ccc2c3cccc4c5c6oc7ccccc7c6ccc5n(c2c1)c34] |
| O-13-42 | 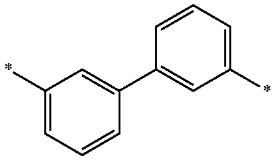 [SMILES: *c1cccc(-c2cccc(*)c2)c1] | 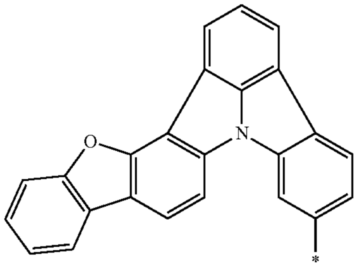 [SMILES: *c1ccc2c3cccc4c5c6oc7ccccc7c6ccc5n(c2c1)c34] |
| O-13-43 | 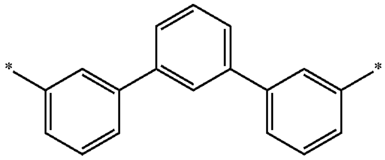 [SMILES: *c1cccc(-c2cccc(-c3cccc(*)c3)c2)c1] | 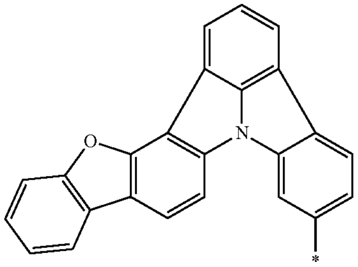 [SMILES: *c1ccc2c3cccc4c5c6oc7ccccc7c6ccc5n(c2c1)c34] |
| O-13-44 | 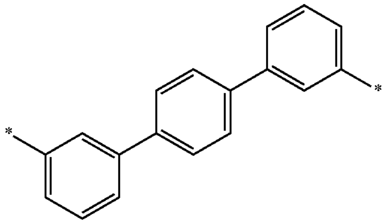 [SMILES: *c1cccc(-c2ccc(-c3cccc(*)c3)cc2)c1] | 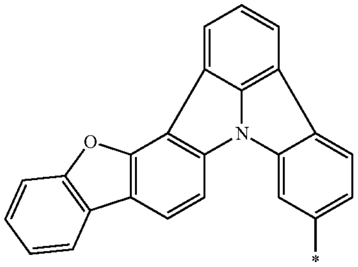 [SMILES: *c1ccc2c3cccc4c5c6oc7ccccc7c6ccc5n(c2c1)c34] |

TABLE 31-continued
| Compound No. | Central Skeleton | Substituent |
| --- | --- | --- |
| O-13-45 | 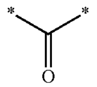 | 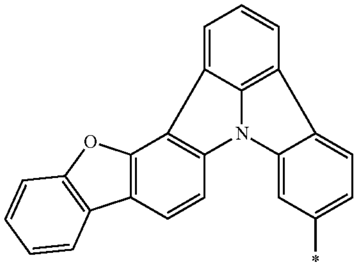 [SMILES: *c1ccc2c3cccc4c5c6oc7ccccc7c6ccc5n(c2c1)c34] |
| O-13-46 | 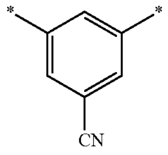 [SMILES: *c1cc(*)cc(C#N)c1] | 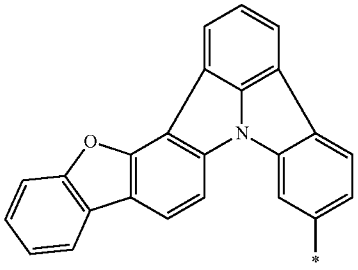 [SMILES: *c1ccc2c3cccc4c5c6oc7ccccc7c6ccc5n(c2c1)c34] |
| O-13-47 | 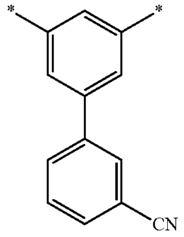 [SMILES: *c1cc(*)cc(-c2cccc(C#N)c2)c1] | 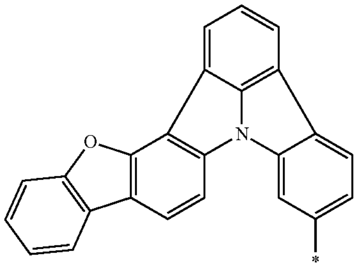 [SMILES: *c1ccc2c3cccc4c5c6oc7ccccc7c6ccc5n(c2c1)c34] |
| O-13-48 | 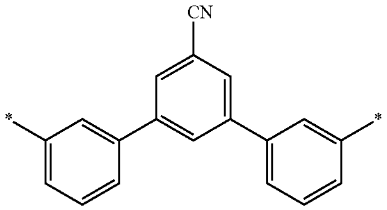 [SMILES: *c1cccc(-c2cc(C#N)cc(-c3cccc(*)c3)c2)c1] | 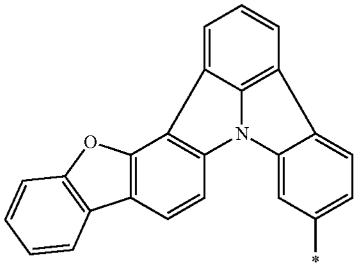 [SMILES: *c1ccc2c3cccc4c5c6oc7ccccc7c6ccc5n(c2c1)c34] |
| O-13-49 | 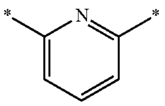 [SMILES: *c1cccc(*)n1] | 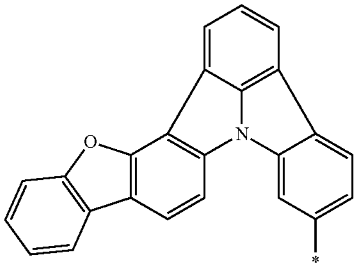 [SMILES: *c1ccc2c3cccc4c5c6oc7ccccc7c6ccc5n(c2c1)c34] |

TABLE 31-continued
| Compound No. | Central Skeleton | Substituent |
| --- | --- | --- |
| O-13-50 | 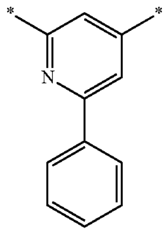 [SMILES: *c1cc(*)nc(-c2ccccc2)c1] | 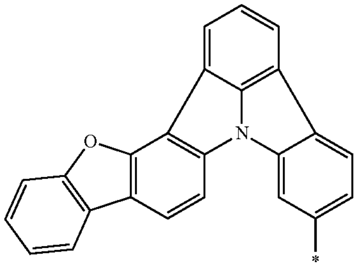 [SMILES: *c1ccc2c3cccc4c5c6oc7ccccc7c6ccc5n(c2c1)c34] |
| O-13-51 | 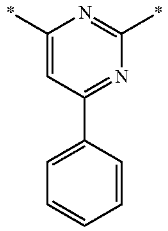 [SMILES: *c1cc(-c2ccccc2)nc(*)n1] | 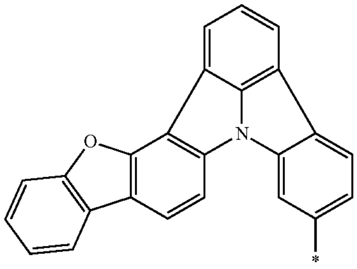 [SMILES: *c1ccc2c3cccc4c5c6oc7ccccc7c6ccc5n(c2c1)c34] |
| O-13-52 | 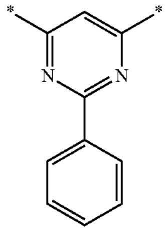 [SMILES: *c1cc(*)nc(-c2ccccc2)n1] | 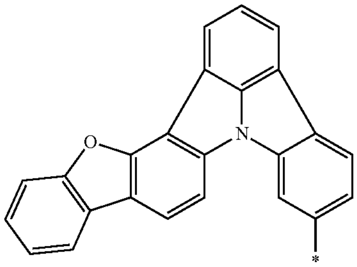 [SMILES: *c1ccc2c3cccc4c5c6oc7ccccc7c6ccc5n(c2c1)c34] |
| O-13-53 | 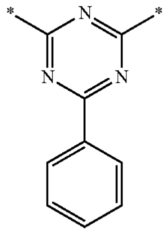 [SMILES: *c1nc(*)nc(-c2ccccc2)n1] | 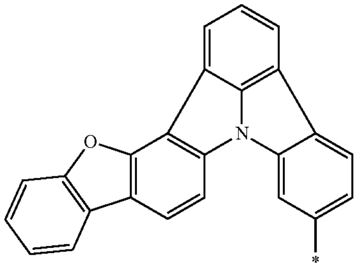 [SMILES: *c1ccc2c3cccc4c5c6oc7ccccc7c6ccc5n(c2c1)c34] |
| O-13-54 | 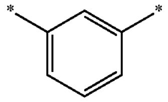 [SMILES: *c1cccc(*)c1] | 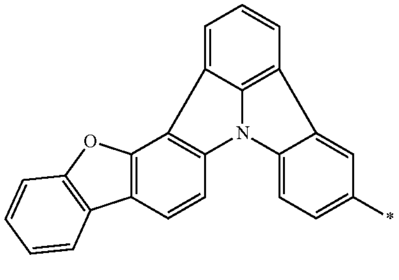 [SMILES: *c1ccc2c(c1)c1cccc3c4c5oc6ccccc6c5ccc4n2c13] |

TABLE 31-continued
| Compound No. | Central Skeleton | Substituent |
| --- | --- | --- |
| O-13-55 | 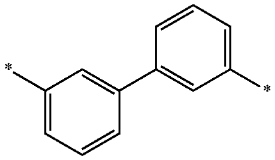 [SMILES: *c1cccc(-c2cccc(*)c2)c1] | 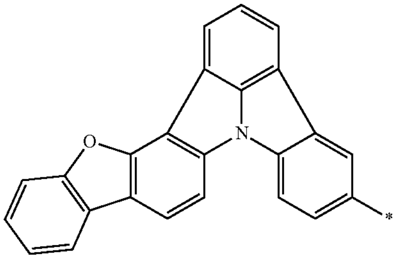 [SMILES: *c1ccc2c(c1)c1cccc3c4c5oc6ccccc6c5ccc4n2c13] |
| O-13-56 | 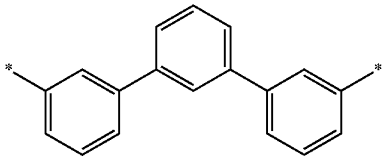 [SMILES: *c1cccc(-c2cccc(-c3cccc(*)c3)c2)c1] | 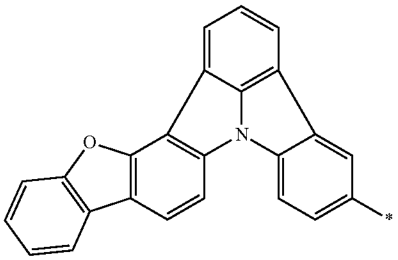 [SMILES: *c1ccc2c(c1)c1cccc3c4c5oc6ccccc6c5ccc4n2c13] |
| O-13-57 | 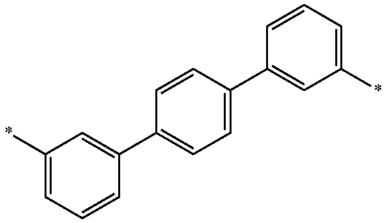 [SMILES: *c1cccc(-c2ccc(-c3cccc(*)c3)cc2)c1] | 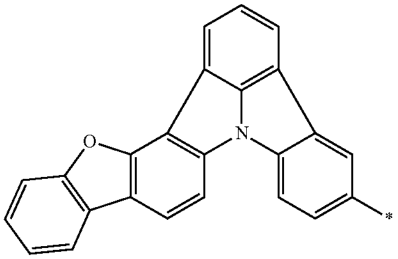 [SMILES: *c1ccc2c(c1)c1cccc3c4c5oc6ccccc6c5ccc4n2c13] |
| O-13-58 | 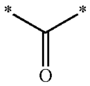 | 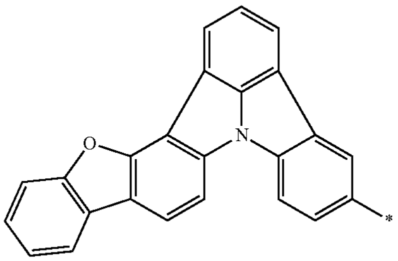 [SMILES: *c1ccc2c(c1)c1cccc3c4c5oc6ccccc6c5ccc4n2c13] |
| O-13-59 | 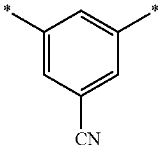 [SMILES: *c1cc(*)cc(C#N)c1] | 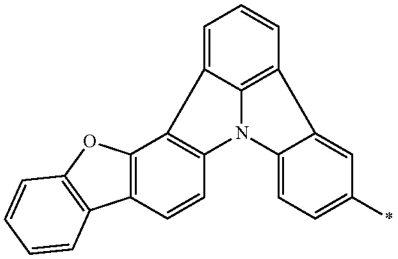 [SMILES: *c1ccc2c(c1)c1cccc3c4c5oc6ccccc6c5ccc4n2c13] |
| O-13-60 | 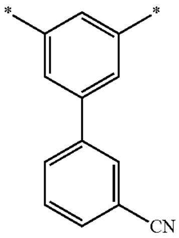 [SMILES: *c1cc(*)cc(-c2cccc(C#N)c2)c1] | 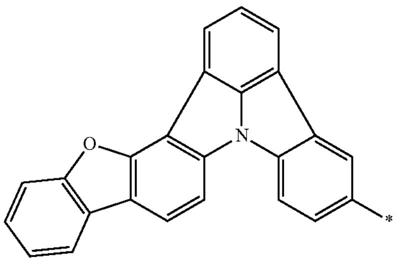 [SMILES: *c1ccc2c(c1)c1cccc3c4c5oc6ccccc6c5ccc4n2c13] |

TABLE 31-continued
| Compound No. | Central Skeleton | Substituent |
| --- | --- | --- |
| O-13-61 | 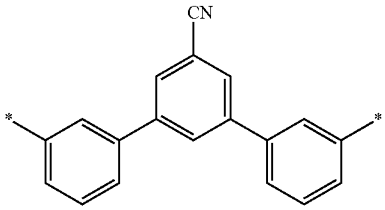 [SMILES: *c1cccc(-c2cc(C#N)cc(-c3cccc(*)c3)c2)c1] | 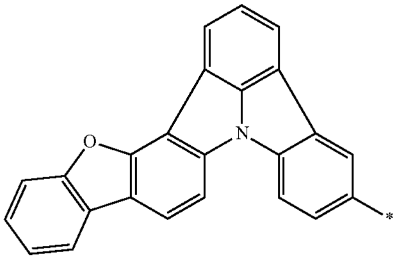 [SMILES: *c1ccc2c(c1)c1cccc3c4c5oc6ccccc6c5ccc4n2c13] |
| O-13-62 | 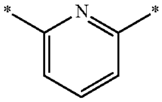 [SMILES: *c1cccc(*)n1] | 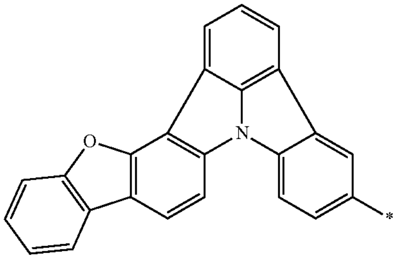 [SMILES: *c1ccc2c(c1)c1cccc3c4c5oc6ccccc6c5ccc4n2c13] |
| O-13-63 | 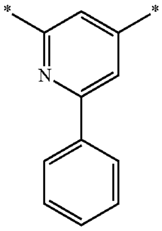 [SMILES: *c1cc(*)nc(-c2ccccc2)c1] | 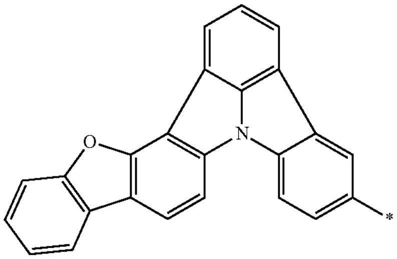 [SMILES: *c1ccc2c(c1)c1cccc3c4c5oc6ccccc6c5ccc4n2c13] |
| O-13-64 | 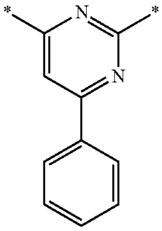 [SMILES: *c1cc(-c2ccccc2)nc(*)n1] | 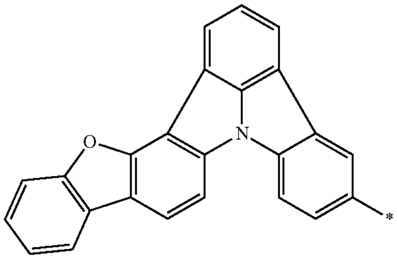 [SMILES: *c1ccc2c(c1)c1cccc3c4c5oc6ccccc6c5ccc4n2c13] |
| O-13-65 | 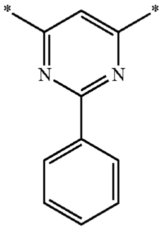 [SMILES: *c1cc(*)nc(-c2ccccc2)n1] | 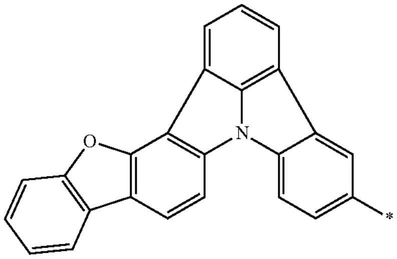 [SMILES: *c1ccc2c(c1)c1cccc3c4c5oc6ccccc6c5ccc4n2c13] |

TABLE 31-continued
| Compound No. | Central Skeleton | Substituent |
|---|---|---|
| O-13-66 | 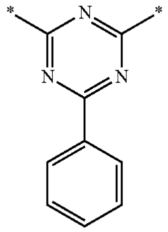 [SMILES: *c1nc(*)nc(-c2ccccc2)n1] | 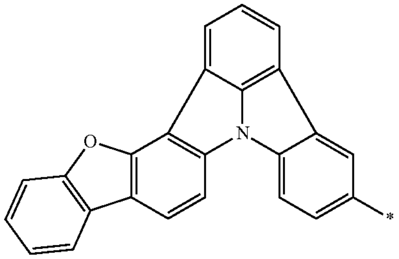 [SMILES: *c1ccc2c(c1)c1cccc3c4c5oc6ccccc6c5ccc4n2c13] |
In the compound represented by the following general formula (14), $R^{E1}$, $R^{E3}$, $R^{E4}$, $R^{E7}$ to $R^{E9}$, $R^{E11}$, $R^{E13}$ to $R^{E15}$ each represent a hydrogen atom, and the other groups are the groups described in Tables below.
[Chem. 19]
(14)
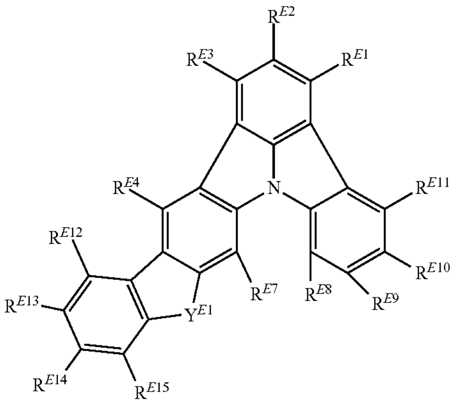
TABLE 32
| Compound No. | $Y^{E1}$ | $R^{E15}$ | $R^{E10}$ | $R^{E2}$ | $R^3$ | $R^1$ | $R^2$ |
|---|---|---|---|---|---|---|---|
| O-14-1 | O | H | H | H | — | — | — |
| O-14-2 | O | H | 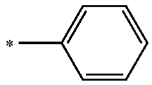 | 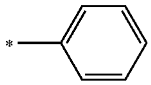 | — | — | — |
| O-14-3 | O | H | 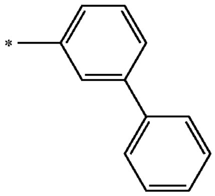 | H | — | — | — |

TABLE 32-continued
| Compound No. | $Y^{E1}$ | $R^{E15}$ | $R^{E10}$ | $R^{E2}$ | $R^3$ | $R^1$ | $R^2$ |
|---|---|---|---|---|---|---|---|
| O-14-4 | O | H | 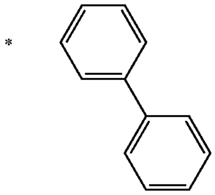 | 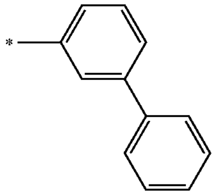 | — | — | — |
| O-14-5 | O | 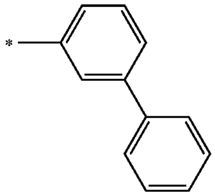 | H | H | — | — | — |
| O-14-6 | O | H | 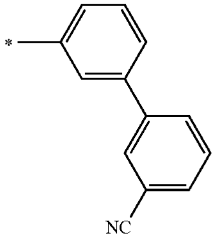 | H | — | — | — |
| O-14-7 | O | H | H | 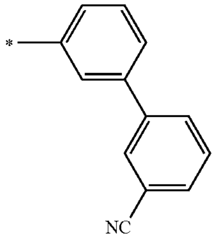 | — | — | — |
| O-14-8 | O | H | 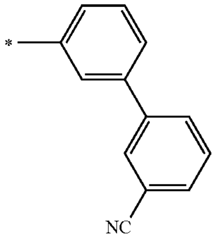 | 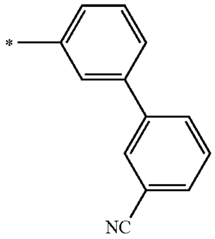 | — | — | — |
| O-14-9 | | H | 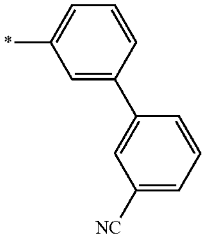 [SMILES: *c1cccc(-c2cccc(C#N)c2)c1] | 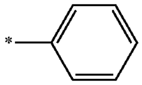 | — | — | — |
| O-14-10 | O | H | 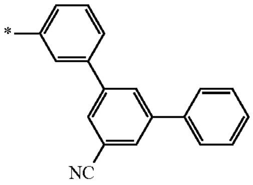 | H | — | — | — |

TABLE 32-continued
| Compound No. | $Y^{E1}$ | $R^{E15}$ | $R^{E10}$ | $R^{E2}$ | $R^3$ | $R^1$ | $R^2$ |
|---|---|---|---|---|---|---|---|
| O-14-11 | O | H | 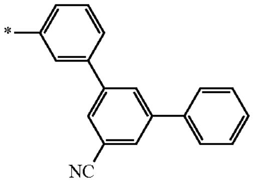 [SMILES: *c1cccc(-c2cc(C#N)cc(-c3ccccc3)c2)c1] | 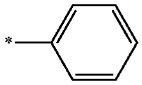 | — | — | — |
| O-14-12 | O | H | 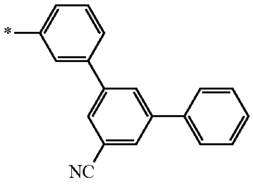 | 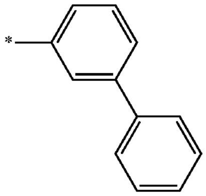 [SMILES: *c1cccc(-c2ccccc2)c1] | — | — | — |
| O-14-13 | O | 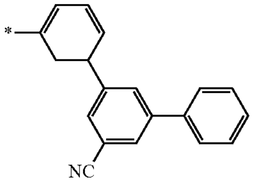 | 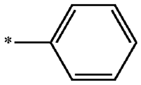 | H | — | — | — |
| O-14-14 | O | H | 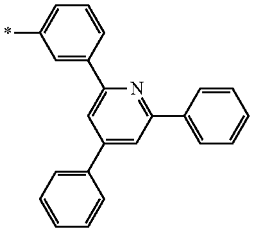 [SMILES: *c1cccc(-c2cc(-c3ccccc3)cc(-c3ccccc3)n2)c1] | H | — | — | — |
| O-14-15 | O | H | 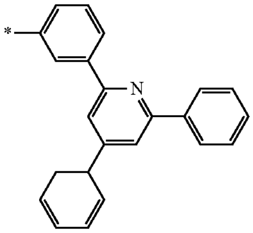 [SMILES: *c1cccc(-c2cc(C3C=CC=CC3)cc(-c3ccccc3)n2)c1] | 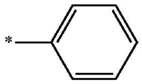 [SMILES: *c1ccccc1] | — | — | — |
TABLE 33
| | | | | | | | |
|---|---|---|---|---|---|---|---|
| O-14-16 | O | H | 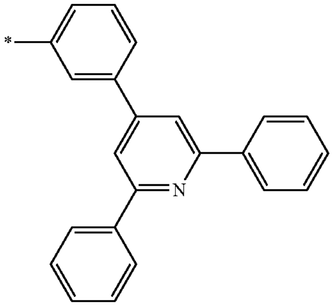 [SMILES: *c1cccc(-c2cc(-c3ccccc3)nc(-c3ccccc3)c2)c1] | H | — | — | — |

TABLE 33-continued
| | | | | | | | |
|---|---|---|---|---|---|---|---|
| O-14-17 | O | H | 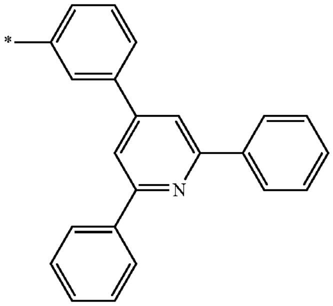 | 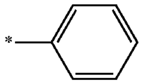 [SMILES: *c1ccccc1] | — | — | — |
| O-14-18 | O | H | 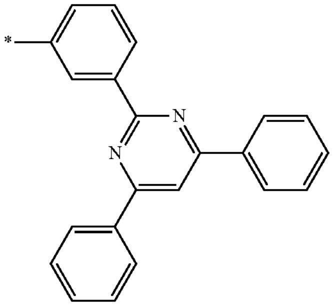 | H | — | — | — |
| O-14-19 | O | H | 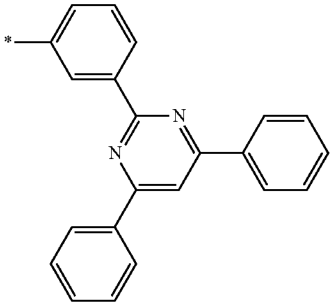 | 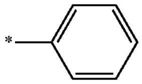 | — | — | — |
| O-14-20 | O | H | 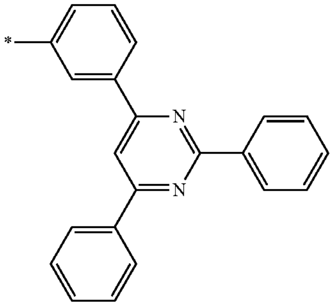 | H | — | — | — |
| O-14-21 | O | H | 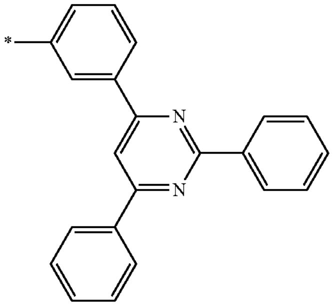 | 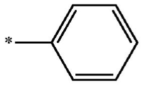 [SMILES: *c1ccccc1] | — | — | — |

TABLE 33-continued
| | | | | | | | |
|---|---|---|---|---|---|---|---|
| O-14-22 | O | H | 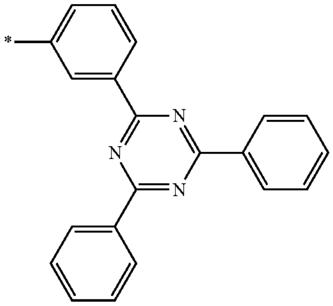 | H | — | — | — |
| O-14-23 | O | H | 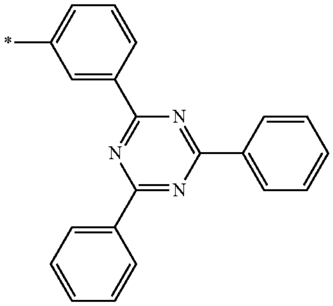 | 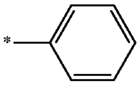 [SMILES: *c1ccccc1] | — | — | — |
| O-14-24 | O | H | 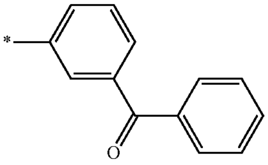 [SMILES: *c1cccc(C(=O)c2ccccc2)c1] | H | — | — | — |
| O-14-25 | O | H | 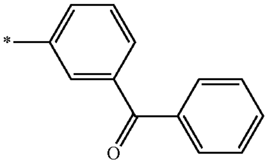 [SMILES: *c1cccc(C(=O)c2ccccc2)c1] | 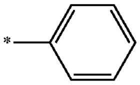 [SMILES: *c1ccccc1] | — | — | — |
| O-14-26 | O | H | 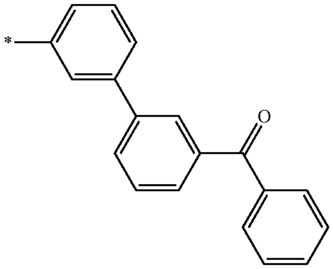 [SMILES: *c1cccc(-c2cccc(C(=O)c3ccccc3)c2)c1] | H | — | — | — |
| O-14-27 | O | H | 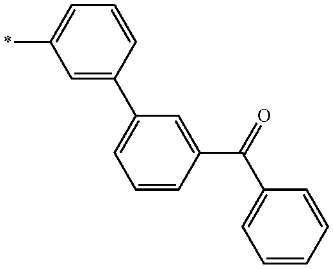 [SMILES: *c1cccc(-c2cccc(C(=O)c3ccccc3)c2)c1] | 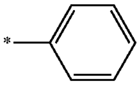 [SMILES: *c1ccccc1] | — | — | — |
| S-14-1 | S | H | H | H | — | — | — |

TABLE 33-continued
| | | | | | | | |
|---|---|---|---|---|---|---|---|
| S-14-2 | S | H | 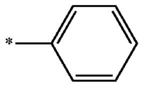 | 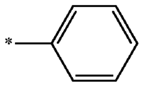 [SMILES: *c1ccccc1] | — | — | — |
| S-14-3 | S | H | 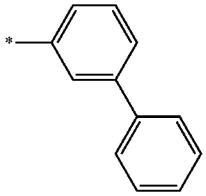 [SMILES: *c1cccc(-c2ccccc2)c1] | H | — | — | — |
TABLE 34
| | | | | | | | |
|---|---|---|---|---|---|---|---|
| S-14-4 | S | H | 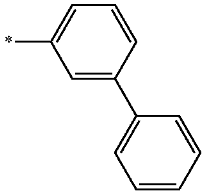 [SMILES: *c1cccc(-c2ccccc2)c1] | 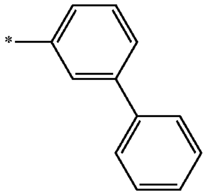 [SMILES: *c1cccc(-c2ccccc2)c1] | — | — | — |
| S-14-5 | S | 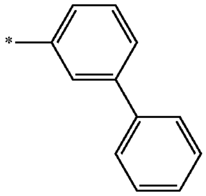 [SMILES: *c1cccc(-c2ccccc2)c1] | H | H | — | — | — |
| S-14-6 | S | H | 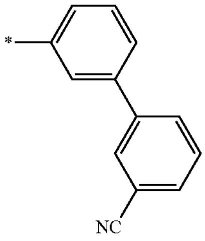 [SMILES: *c1cccc(-c2cccc(C#N)c2)c1] | H | — | — | — |
| S-14-7 | S | H | H | 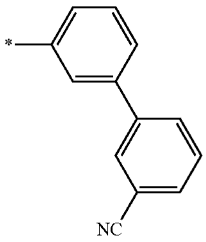 | — | — | — |
| S-14-8 | S | H | 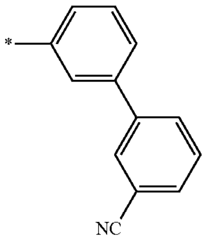 [SMILES: *c1cccc(-c2cccc(C#N)c2)c1] | 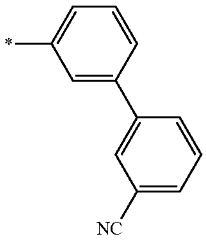 [SMILES: *c1cccc(-c2cccc(C#N)c2)c1] | — | — | — |

TABLE 34-continued
| | | | | | | | |
|---|---|---|---|---|---|---|---|
| S-14-9 | S | H | 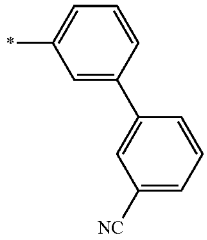 | 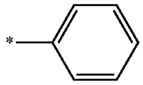 | — | — | — |
| S-14-10 | S | H | 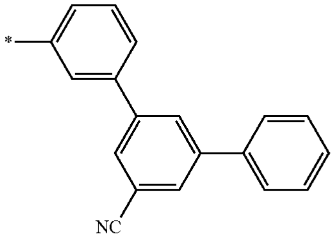 [SMILES: *c1cccc(-c2cc(C#N)cc(-c3ccccc3)c2)c1] | H | — | — | — |
| S-14-11 | S | H | 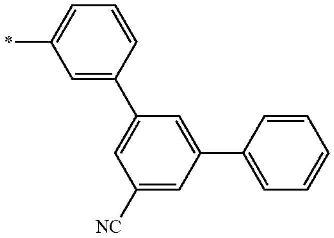 [SMILES: *c1cccc(-c2cc(C#N)cc(-c3ccccc3)c2)c1] | 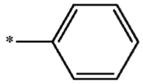 [SMILES: *c1ccccc1] | — | — | — |
| S-14-12 | S | H | 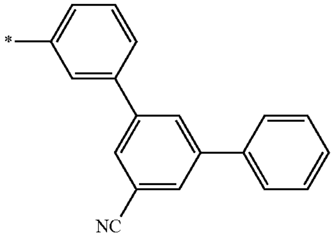 [SMILES: *c1cccc(-c2cc(C#N)cc(-c3ccccc3)c2)c1] | 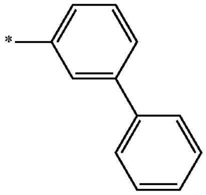 [SMILES: *c1cccc(-c2ccccc2)c1] | — | — | — |
| S-14-13 | S | 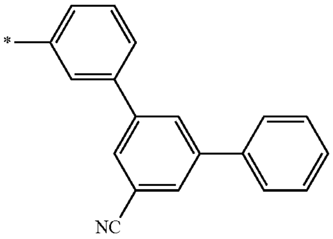 [SMILES: *c1cccc(-c2cc(C#N)cc(-c3ccccc3)c2)c1] | 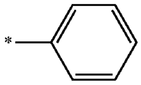 [SMILES: *c1ccccc1] | H | — | — | — |
| S-14-14 | S | H | 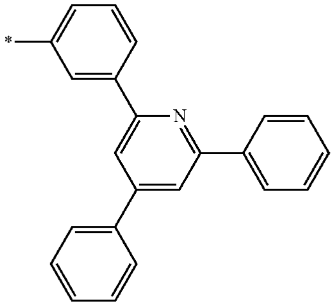 | H | — | — | — |

TABLE 34-continued
| | | | | | | | |
|---|---|---|---|---|---|---|---|
| S-14-15 | S | H | 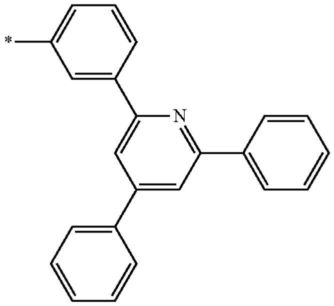 | 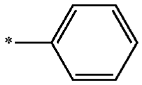 [SMILES: *c1ccccc1] | — | — | — |
| S-14-16 | S | H | 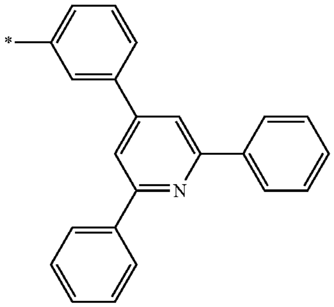 [SMILES: *c1cccc(-c2cc(-c3ccccc3)nc(-c3ccccc3)c2)c1] | H | — | — | — |
| S-14-17 | S | H | 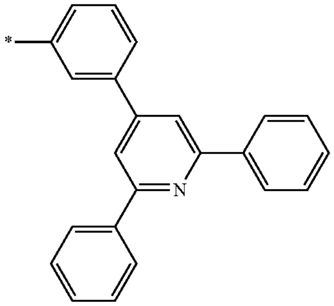 | 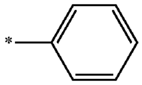 [SMILES: *c1ccccc1] | — | — | — |
| S-14-18 | S | H | 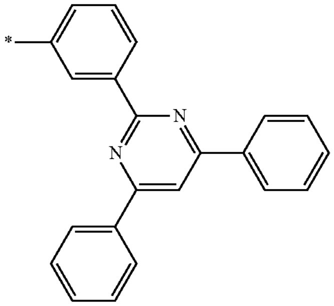 | H | — | — | — |

TABLE 35
| | | | | | | | |
|---|---|---|---|---|---|---|---|
| S-14-19 | S | H | 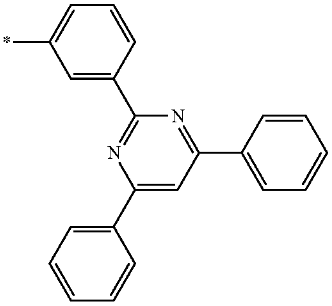 | 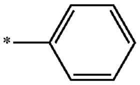 [SMILES: *c1ccccc1] | — | — | — |
| S-14-20 | S | H | 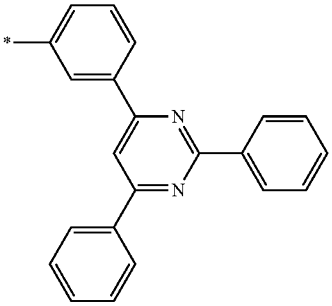 | H | — | — | — |
| S-14-21 | S | H | 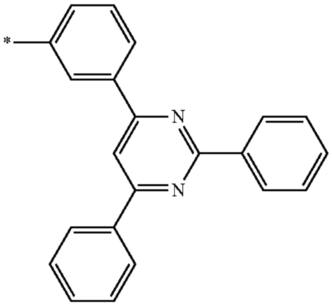 | 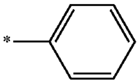 [SMILES: *c1ccccc1] | — | — | — |
| S-14-22 | S | H | 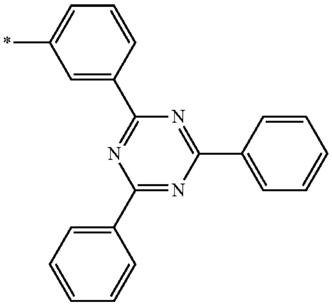 | H | — | — | — |
| S-14-23 | S | H | 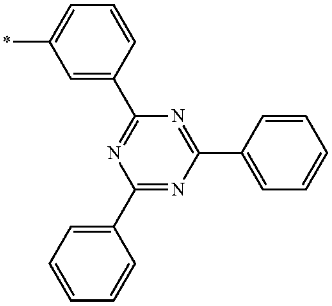 | 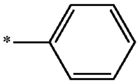 [SMILES: *c1ccccc1] | — | — | — |

TABLE 35-continued
| | | | | | | | |
|---|---|---|---|---|---|---|---|
| S-14-24 | S | H | 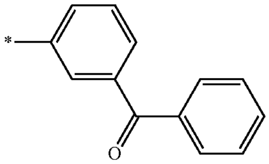 [SMILES: *c1cccc(C(=O)c2ccccc2)c1] | H | — | — | — |
| S-14-25 | S | H | 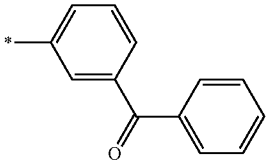 [SMILES: *c1cccc(C(=O)c2ccccc2)c1] | 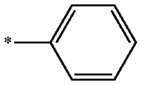 [SMILES: *c1ccccc1] | — | — | — |
| S-14-26 | S | H | 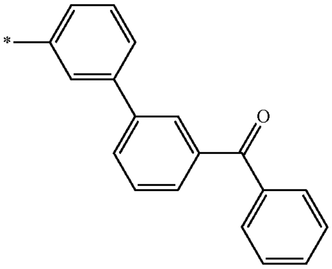 [SMILES: *c1cccc(-c2cccc(C(=O)c3ccccc3)c2)c1] | H | — | — | — |
| S-14-27 | S | H | 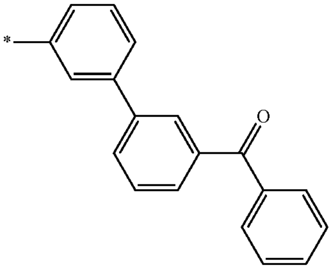 [SMILES: *c1cccc(-c2cccc(C(=O)c3ccccc3)c2)c1] | 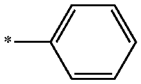 [SMILES: *c1ccccc1] | — | — | — |
| N-14-1 | $NR^3$ | H | H | H | 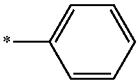 | — | — |
| N-14-2 | $NR^3$ | H | 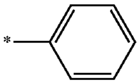 [SMILES: *c1ccccc1] | 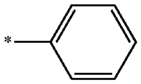 [SMILES: *c1ccccc1] | 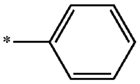 [SMILES: *c1ccccc1] | — | — |
| N-14-3 | $NR^3$ | H | 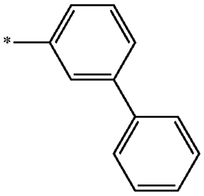 [SMILES: *c1cccc(-c2ccccc2)c1] | H | 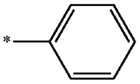 [SMILES: *c1ccccc1] | — | — |
| N-14-4 | $NR^3$ | H | 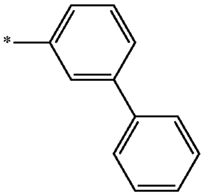 [SMILES: *c1cccc(-c2ccccc2)c1] | 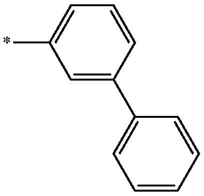 | 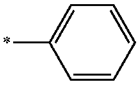 [SMILES: *c1ccccc1] | — | — |

TABLE 35-continued
| | | | | | | | |
|---|---|---|---|---|---|---|---|
| N-14-5 | $NR^3$ | H | 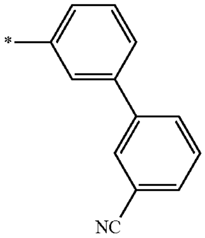 [SMILES: *c1cccc(-c2cccc(C#N)c2)c1] | H | 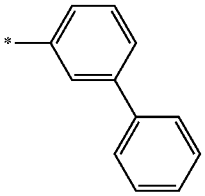 [SMILES: *c1cccc(-c2ccccc2)c1] | — | — |
| N-14-6 | $NR^3$ | H | H | 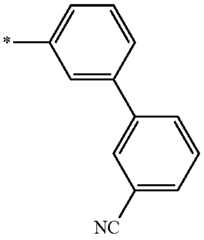 | 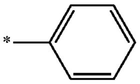 [SMILES: *c1ccccc1] | — | — |
TABLE 36
| | | | | | | | |
|---|---|---|---|---|---|---|---|
| N-14-7 | $NR^3$ | H | 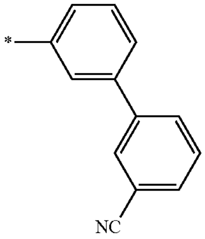 [SMILES: *c1cccc(-c2cccc(C#N)c2)c1] | 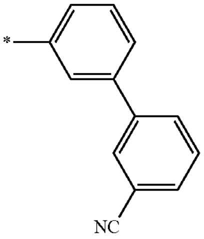 [SMILES: *c1cccc(-c2cccc(C#N)c2)c1] | 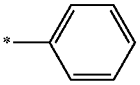 [SMILES: *c1ccccc1] | — | — |
| N-14-8 | $NR^3$ | H | 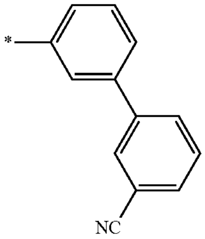 [SMILES: *c1cccc(-c2cccc(C#N)c2)c1] | 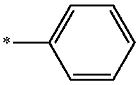 [SMILES: *c1ccccc1] | 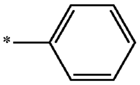 [SMILES: *c1ccccc1] | — | — |
| N-14-9 | $NR^3$ | H | 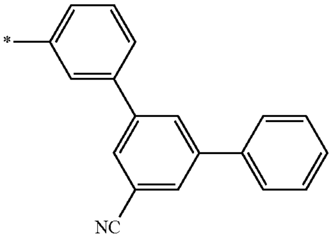 [SMILES: *c1cccc(-c2cc(C#N)cc(-c3ccccc3)c2)c1] | H | 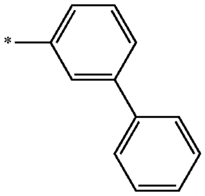 | — | — |
| N-14-10 | $NR^3$ | H | 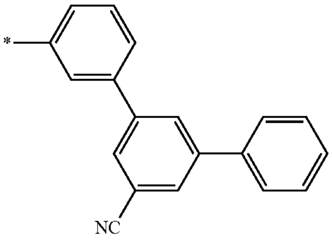 [SMILES: *c1cccc(-c2cc(C#N)cc(-c3ccccc3)c2)c1] | 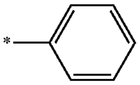 [SMILES: *c1ccccc1] | 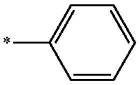 [SMILES: *c1ccccc1] | — | — |

TABLE 36-continued
| | | | | | | | |
|---|---|---|---|---|---|---|---|
| N-14-11 | $NR^3$ | H | 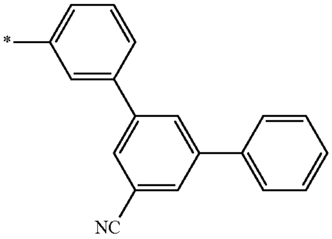 [SMILES: *c1cccc(-c2cc(C#N)cc(-c3ccccc3)c2)c1] | 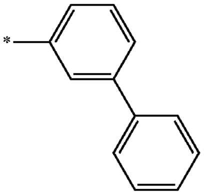 [SMILES: *c1cccc(-c2ccccc2)c1] | 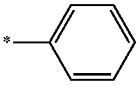 | — | — |
| N-14-12 | $NR^3$ | H | 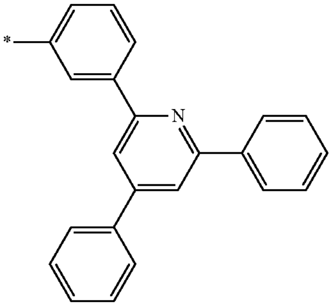 | H | 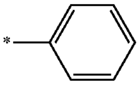 [SMILES: *c1ccccc1] | — | — |
| N-14-13 | $NR^3$ | H | 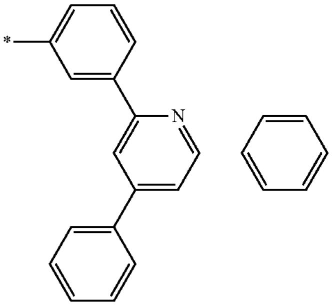 | 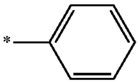 [SMILES: *c1ccccc1] | 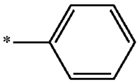 [SMILES: *c1ccccc1] | — | — |
| N-14-14 | $NR^3$ | H | 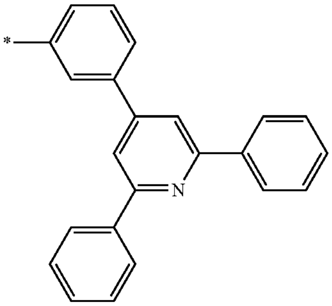 | H | 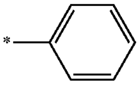 [SMILES: *c1ccccc1] | — | — |
| N-14-15 | $NR^3$ | H | 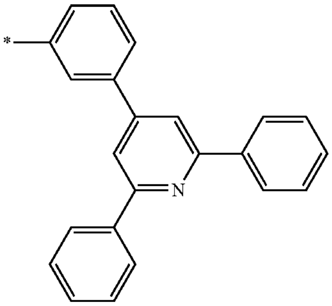 [SMILES: *c1cccc(-c2cc(-c3ccccc3)nc(-c3ccccc3)c2)c1] | 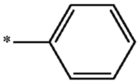 [SMILES: *c1ccccc1] | 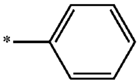 [SMILES: *c1ccccc1] | — | — |

TABLE 36-continued
| | | | | | | | |
|---|---|---|---|---|---|---|---|
| N-14-16 | $NR^3$ | H | 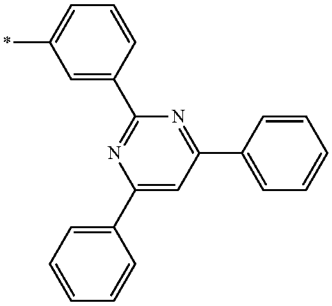 [SMILES: *c1cccc(-c2nc(-c3ccccc3)cc(-c3ccccc3)n2)c1] | H | 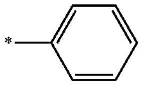 | — | — |
| N-14-17 | $NR^3$ | H | 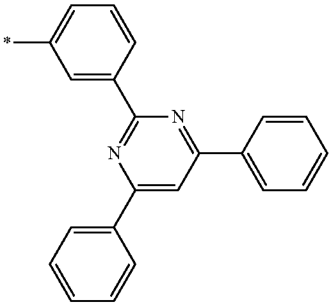 | 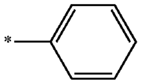 [SMILES: *c1ccccc1] | 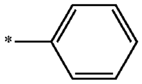 [SMILES: *c1ccccc1] | — | — |
| N-14-18 | $NR^3$ | H | 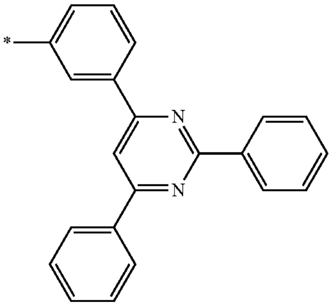 | H | 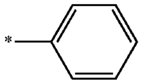 [SMILES: *c1ccccc1] | — | — |
| N-14-19 | $NR^3$ | H | 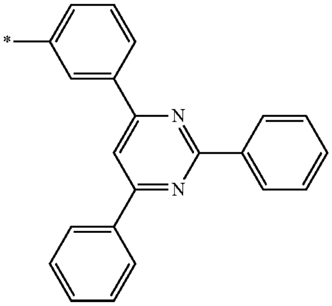 | 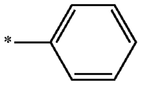 | 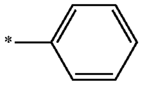 | — | — |
| N-14-20 | $NR^3$ | H | 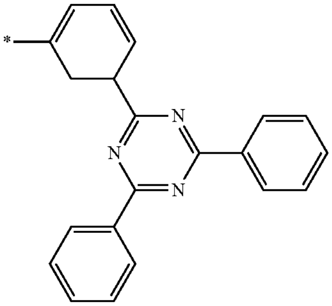 | H | 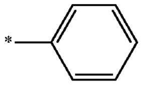 [SMILES: *c1ccccc1] | — | — |

TABLE 36-continued
| | | | | | | | |
|---|---|---|---|---|---|---|---|
| N-14-21 | $NR^3$ | H | 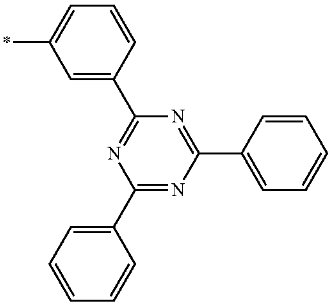 | 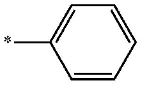 | 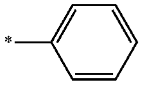 | — | — |
TABLE 37
| | | | | | | | |
|---|---|---|---|---|---|---|---|
| N-14-22 | $NR^3$ | H | 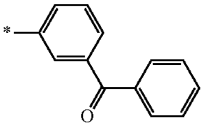 [SMILES: *c1cccc(C(=O)c2ccccc2)c1] | H | 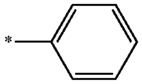 [SMILES: *c1ccccc1] | — | — |
| N-14-23 | $NR^3$ | H | 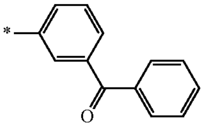 [SMILES: *c1cccc(C(=O)c2ccccc2)c1] | 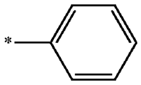 [SMILES: *c1ccccc1] | 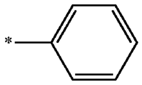 [SMILES: *c1ccccc1] | — | — |
| N-14-24 | $NR^3$ | H | 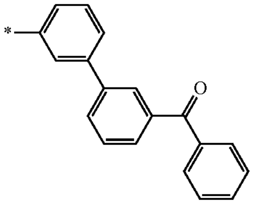 [SMILES: *c1cccc(-c2cccc(C(=O)c3ccccc3)c2)c1] | H | 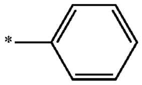 | — | — |
| N-14-25 | $NR^3$ | H | 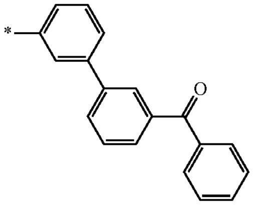 [SMILES: *c1cccc(-c2cccc(C(=O)c3ccccc3)c2)c1] | 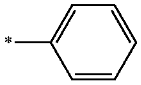 [SMILES: *c1ccccc1] | 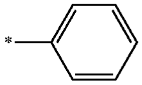 [SMILES: *c1ccccc1] | — | — |
| C-14-1 | $CR^1R^2$ | H | H | H | — | *—Me | *—Me |
| C-14-2 | $CR^1R^2$ | H | 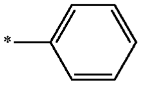 [SMILES: *c1ccccc1] | 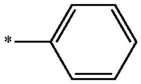 [SMILES: *c1ccccc1] | — | *—Me | *—Me |
| C-14-3 | $CR^1R^2$ | H | 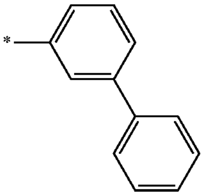 [SMILES: *c1cccc(-c2ccccc2)c1] | H | — | *—Me | *—Me |

TABLE 37-continued
| | | | | | | | |
|---|---|---|---|---|---|---|---|
| C-14-4 | $CR^1R^2$ | H | 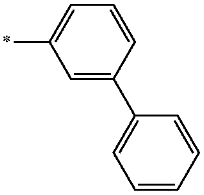 [SMILES: *c1cccc(-c2ccccc2)c1] | 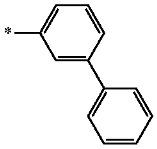 [SMILES: *c1cccc(-c2ccccc2)c1] | — | *—Me | *—Me |
| C-14-5 | $CR^1R^2$ | H | 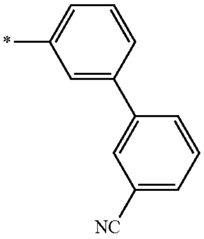 [SMILES: *c1cccc(-c2cccc(C#N)c2)c1] | H | — | 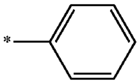 | 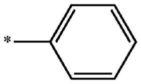 |
| C-14-6 | $CR^1R^2$ | H | H | 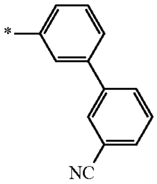 [SMILES: *c1cccc(-c2cccc(C#N)c2)c1] | — | * -Me | *-Me |
| C-14-7 | $CR^1R^2$ | H | 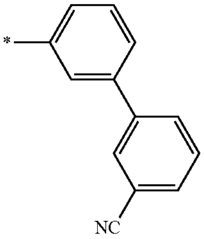 [SMILES: *c1cccc(-c2cccc(C#N)c2)c1] | 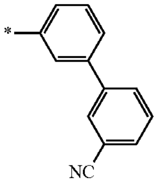 [SMILES: *c1cccc(-c2cccc(C#N)c2)c1] | — | 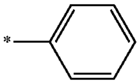 | 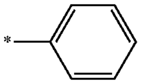 |
| C-14-8 | $CR^1R^2$ | H | 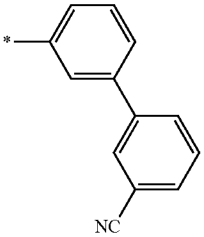 [SMILES: *c1cccc(-c2cccc(C#N)c2)c1] | 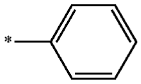 [SMILES: *c1ccccc1] | — | *—Me | *—Me |
| C-14-9 | $CR^1R^2$ | H | 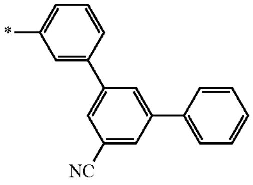 [SMILES: *c1cccc(-c2cc(C#N)cc(-c3ccccc3)c2)c1] | H | — | 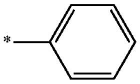 [SMILES: *c1ccccc1] | 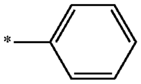 [SMILES: *c1ccccc1] |
| C-14-10 | $CR^1R^2$ | H | 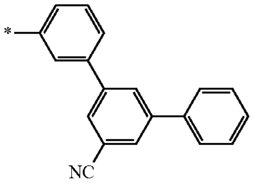 | 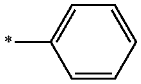 [SMILES: *c1ccccc1] | — | *—Me | *—Me |

TABLE 37-continued
| | | | | | | | |
|---|---|---|---|---|---|---|---|
| C-14-11 | $CR^1R^2$ | H | 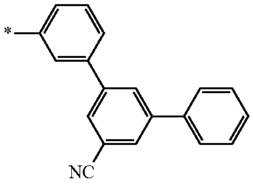 | 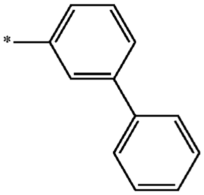 [SMILES: *c1cccc(-c2ccccc2)c1] | — | *—Me | *—Me |
TABLE 38
| | | | | | | | |
|---|---|---|---|---|---|---|---|
| C-14-12 | $CR^1R^2$ | H | 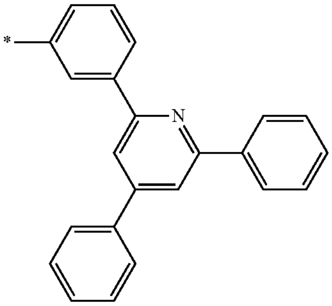 | H | — | *—Me | *—Me |
| C-14-13 | $CR^1R^2$ | H | 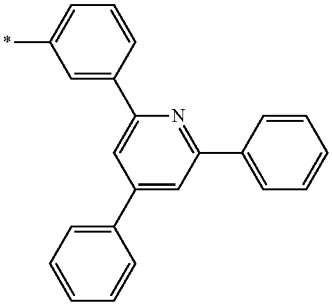 | 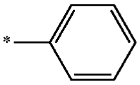 [SMILES: *c1ccccc1] | — | *—Me | *—Me |
| C-14-14 | $CR^1R^2$ | H | 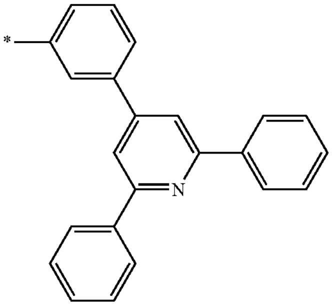 | H | — | *—Me | *—Me |
| C-14-15 | $CR^1R^2$ | H | 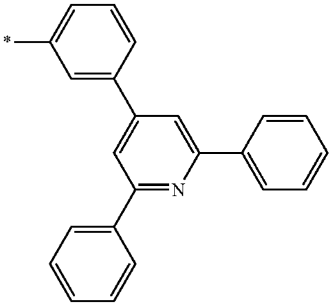 | 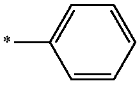 [SMILES: *c1ccccc1] | — | *—Me | *—Me |

TABLE 38-continued
| | | | | | | | |
|---|---|---|---|---|---|---|---|
| C-14-16 | $CR^1R^2$ | H | 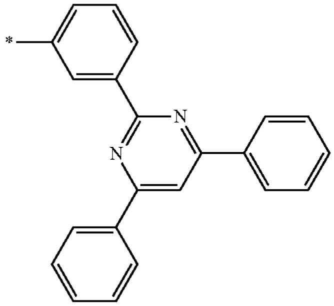 | H | — | 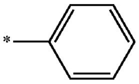 [SMILES: *c1ccccc1] | 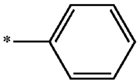 [SMILES: *c1ccccc1] |
| C-14-17 | $CR^1R^2$ | H | 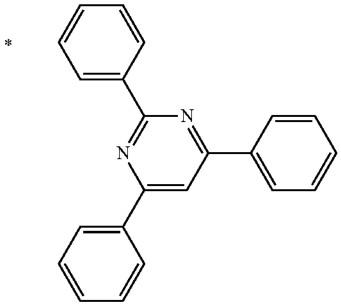 | 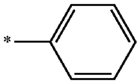 [SMILES: *c1ccccc1] | — | *—Me | *—Me |
| C-14-18 | $CR^1R^2$ | H | 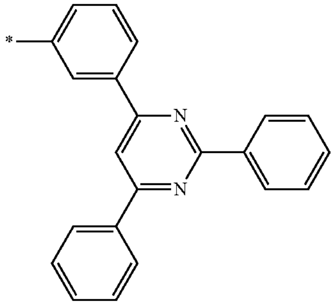 | H | — | *—Me | *—Me |
| C-14-19 | $CR^1R^2$ | H | 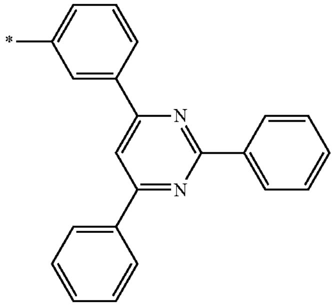 | 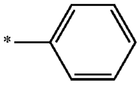 [SMILES: *c1ccccc1] | — | *—Me | *—Me |
| C-14-20 | $CR^1R^2$ | H | 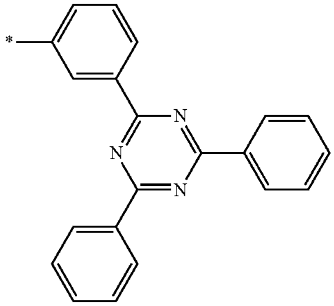 | H | — | *—Me | *—Me |

TABLE 38-continued
| | | | | | | | |
|---|---|---|---|---|---|---|---|
| C-14-21 | $CR^1R^2$ | H | 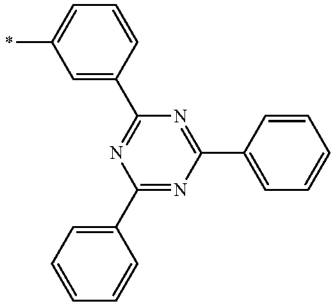 | 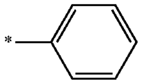 [SMILES: *c1ccccc1] | — | *—Me | *—Me |
| C-14-22 | $CR^1R^2$ | H | 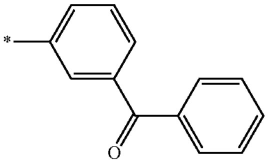 [SMILES: *c1cccc(C(=O)c2ccccc2)c1] | H | — | *—Me | *—Me |
| C-14-23 | $CR^1R^2$ | H | 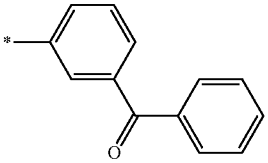 [SMILES: *c1cccc(C(=O)c2ccccc2)c1] | 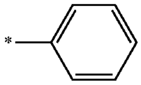 [SMILES: *c1ccccc1] | — | 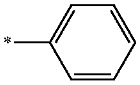 [SMILES: *c1ccccc1] | 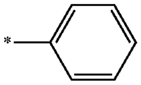 [SMILES: *c1ccccc1] |
| C-14-24 | $CR^1R^2$ | H | 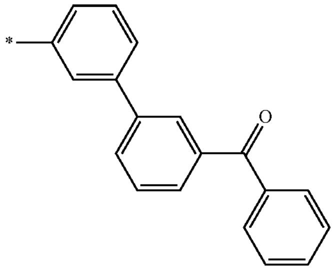 [SMILES: *c1cccc(-c2cccc(C(=O)c3ccccc3)c2)c1] | H | — | *—Me | *—Me |
| C-14-25 | $CR^1R^2$ | H | 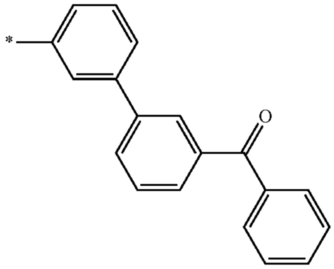 [SMILES: *c1cccc(-c2cccc(C(=O)c3ccccc3)c2)c1] | 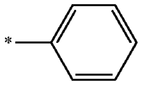 [SMILES: *c1ccccc1] | — | *—Me | *—Me |

TABLE 39
| Compound No. | Central Sketeton | Substituent |
| --- | --- | --- |
| O-14-28 | 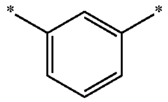 [SMILES: *c1cccc(*)c1] | 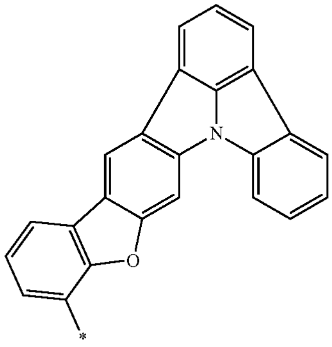 [SMILES: *c1cccc2c1oc1cc3c(cc12)c1cccc2c4ccccc4n3c21] |
| O-14-29 | 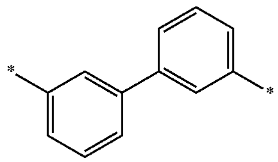 [SMILES: *c1cccc(-c2cccc(*)c2)c1] | 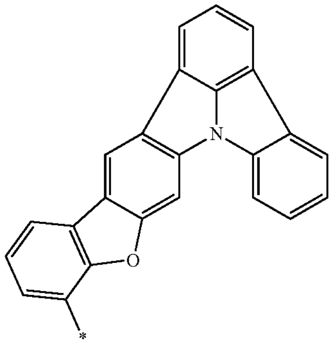 [SMILES: *c1cccc2c1oc1cc3c(cc12)c1cccc2c4ccccc4n3c21] |
| O-14-30 | 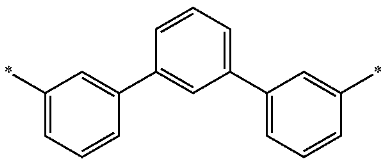 [SMILES: *c1cccc(-c2cccc(-c3cccc(*)c3)c2)c1] | 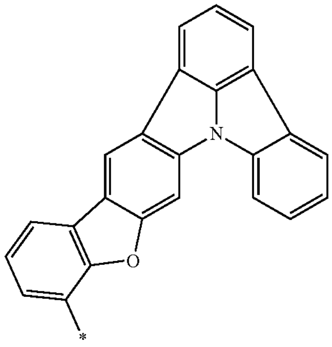 [SMILES: *c1cccc2c1oc1cc3c(cc12)c1cccc2c4ccccc4n3c21] |
| O-14-31 | 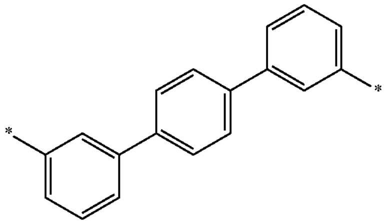 [SMILES: *c1cccc(-c2ccc(-c3cccc(*)c3)cc2)c1] | 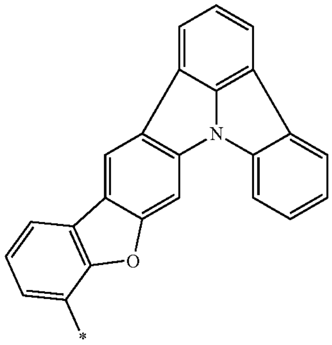 [SMILES: *c1cccc2c1oc1cc3c(cc12)c1cccc2c4ccccc4n3c21] |

TABLE 39-continued
| Compound No. | Central Sketeton | Substituent |
|---|---|---|
| O-14-32 | 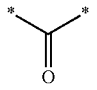 | 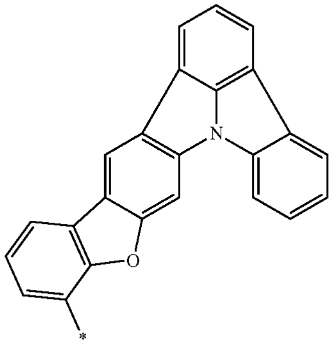 [SMILES: *c1cccc2c1oc1cc3c(cc12)c1cccc2c4ccccc4n3c21] |
| O-14-33 | 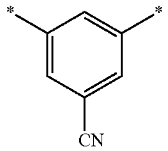 [SMILES: *c1cc(*)cc(C#N)c1] | 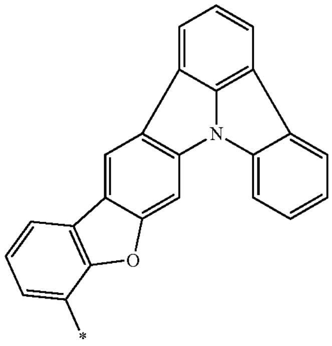 [SMILES: *c1cccc2c1oc1cc3c(cc12)c1cccc2c4ccccc4n3c21] |
| O-14-34 | 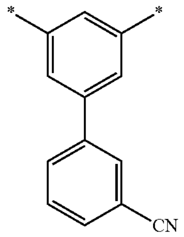 [SMILES: *c1cc(*)cc(-c2cccc(C#N)c2)c1] | 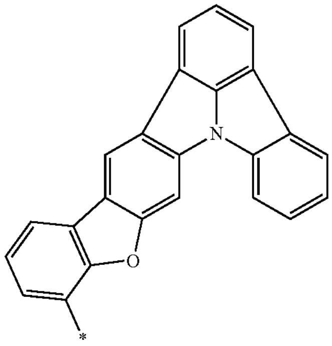 [SMILES: *c1cccc2c1oc1cc3c(cc12)c1cccc2c4ccccc4n3c21] |
| O-14-35 | 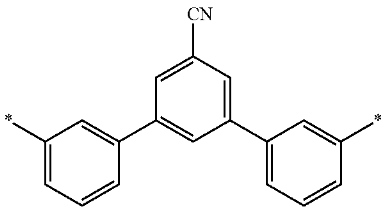 [SMILES: *c1cccc(-c2cc(C#N)cc(-c3cccc(*)c3)c2)c1] | 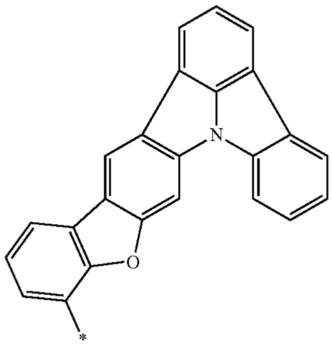 [SMILES: *c1cccc2c1oc1cc3c(cc12)c1cccc2c4ccccc4n3c21] |

TABLE 39-continued
| Compound No. | Central Sketeton | Substituent |
| --- | --- | --- |
| O-14-36 | 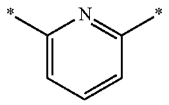 [SMILES: *c1cccc(*)n1] | 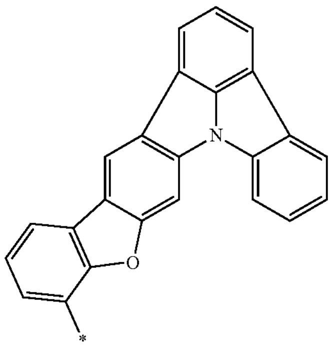 [SMILES: *c1cccc2c1oc1cc3c(cc12)c1cccc2c4ccccc4n3c21] |
| O-14-37 | 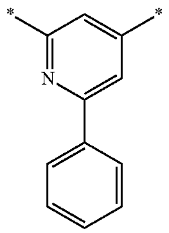 [SMILES: *c1cc(*)nc(-c2ccccc2)c1] | 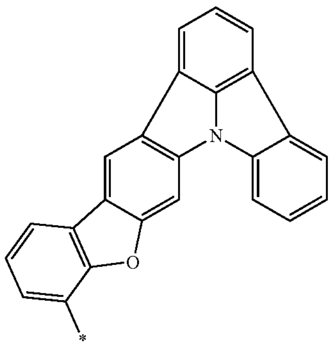 [SMILES: *c1cccc2c1oc1cc3c(cc12)c1cccc2c4ccccc4n3c21] |
| O-14-38 | 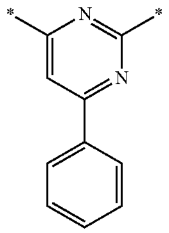 [SMILES: *c1cc(-c2ccccc2)nc(*)n1] | 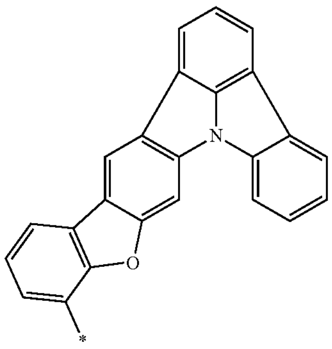 [SMILES: *c1cccc2c1oc1cc3c(cc12)c1cccc2c4ccccc4n3c21] |
| O-14-39 | 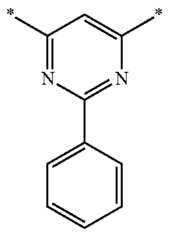 [SMILES: *c1cc(*)nc(-c2ccccc2)n1] | 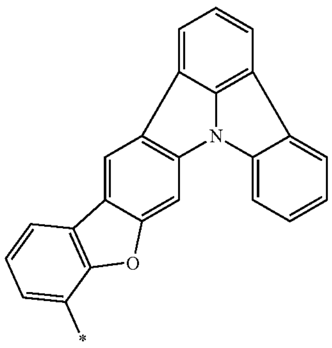 [SMILES: *c1cccc2c1oc1cc3c(cc12)c1cccc2c4ccccc4n3c21] |

TABLE 39-continued
| Compound No. | Central Sketeton | Substituent |
|---|---|---|
| O-14-40 | 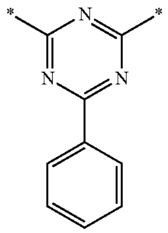 [SMILES: *c1nc(*)nc(-c2ccccc2)n1] | 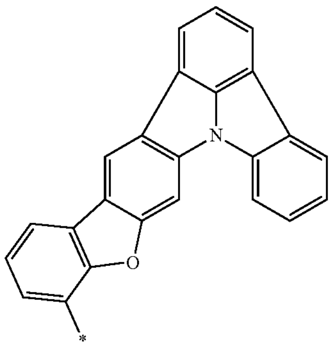 [SMILES: *c1cccc2c1oc1cc3c(cc12)c1cccc2c4ccccc4n3c21] |
| O-14-41 | 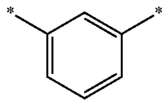 [SMILES: *c1cccc(*)c1] | 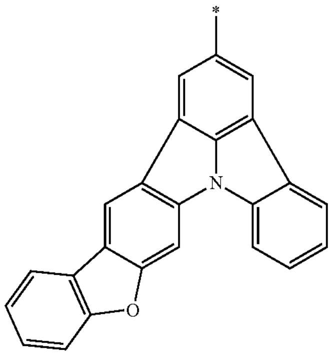 [SMILES: *c1cc2c3ccccc3n3c4cc5oc6ccccc6c5cc4c(c1)c23] |
| O-14-42 | 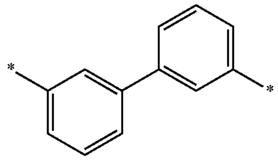 [SMILES: *c1cccc(-c2cccc(*)c2)c1] | 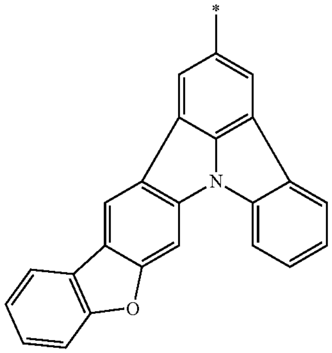 [SMILES: *c1cc2c3ccccc3n3c4cc5oc6ccccc6c5cc4c(c1)c23] |
| O-14-43 | 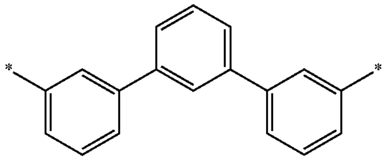 [SMILES: *c1cccc(-c2cccc(-c3cccc(*)c3)c2)c1] | 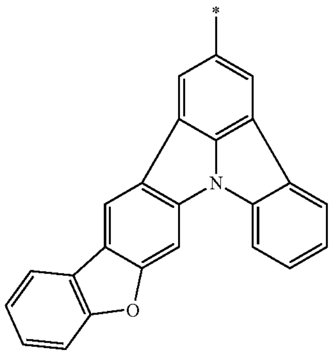 [SMILES: *c1cc2c3ccccc3n3c4cc5oc6ccccc6c5cc4c(c1)c23] |

TABLE 39-continued
| Compound No. | Central Sketeton | Substituent |
| --- | --- | --- |
| O-14-44 | 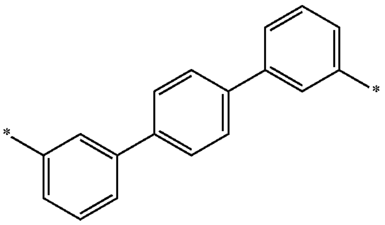 [SMILES: *c1cccc(-c2ccc(-c3cccc(*)c3)cc2)c1] | 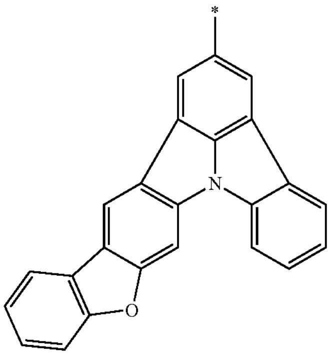 [SMILES: *c1cc2c3ccccc3n3c4cc5oc6ccccc6c5cc4c(c1)c23] |
| O-14-45 | 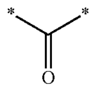 | 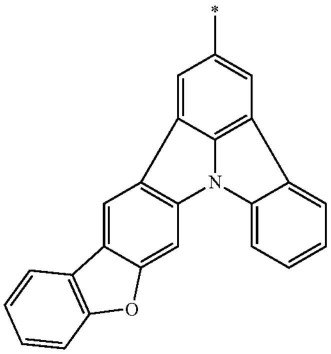 [SMILES: *c1cc2c3ccccc3n3c4cc5oc6ccccc6c5cc4c(c1)c23] |
| O-14-46 | 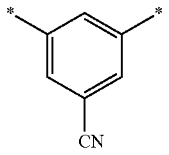 [SMILES: *c1cc(*)cc(C#N)c1] | 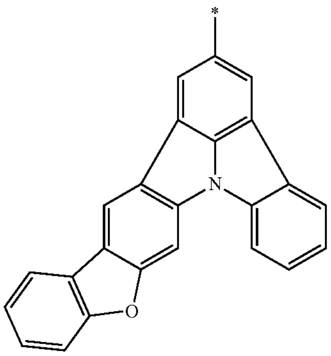 [SMILES: *c1cc2c3ccccc3n3c4cc5oc6ccccc6c5cc4c(c1)c23] |
| O-14-47 | 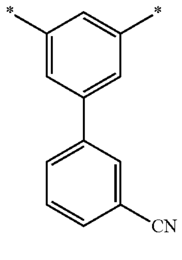 [SMILES: *c1cc(*)cc(-c2cccc(C#N)c2)c1] | 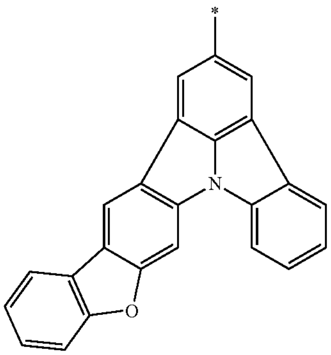 [SMILES: *c1cc2c3ccccc3n3c4cc5oc6ccccc6c5cc4c(c1)c23] |

TABLE 39-continued
| Compound No. | Central Sketeton | Substituent |
| --- | --- | --- |
| O-14-48 | 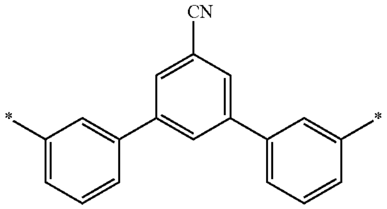 | 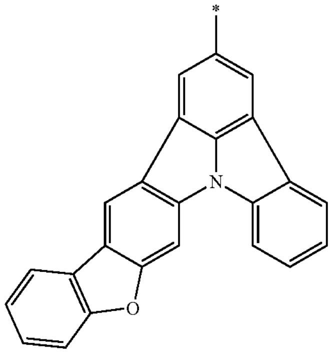 [SMILES: *c1cc2c3ccccc3n3c4cc5oc6ccccc6c5cc4c(c1)c23] |
| O-14-49 | 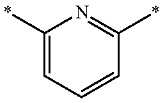 [SMILES: *c1cccc(*)n1] | 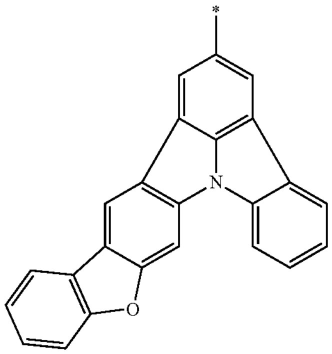 [SMILES: *c1cc2c3ccccc3n3c4cc5oc6ccccc6c5cc4c(c1)c23] |
| O-14-50 | 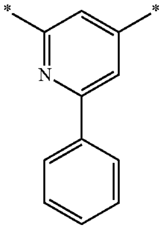 [SMILES: *c1cc(*)nc(-c2ccccc2)c1] | 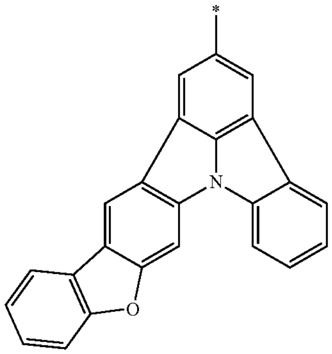 [SMILES: *c1cc2c3ccccc3n3c4cc5oc6ccccc6c5cc4c(c1)c23] |
| O-14-51 | 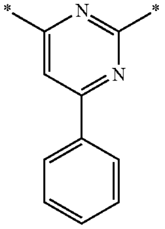 [SMILES: *c1cc(-c2ccccc2)nc(*)n1] | 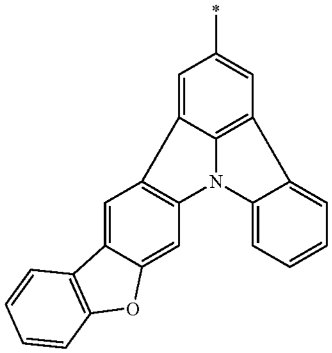 [SMILES: *c1cc2c3ccccc3n3c4cc5oc6ccccc6c5cc4c(c1)c23] |

TABLE 39-continued
| Compound No. | Central Sketeton | Substituent |
|---|---|---|
| O-14-52 | 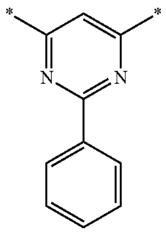 [SMILES: *c1cc(*)nc(-c2ccccc2)n1] | 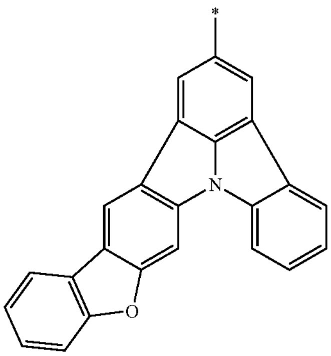 [SMILES: *c1cc2c3ccccc3n3c4cc5oc6ccccc6c5cc4c(c1)c23] |
| O-14-53 | 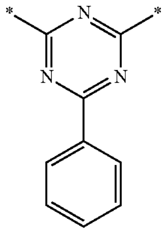 [SMILES: *c1nc(*)nc(-c2ccccc2)n1] | 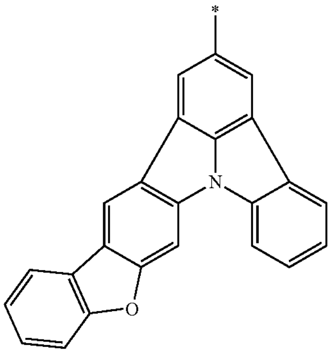 [SMILES: *c1cc2c3ccccc3n3c4cc5oc6ccccc6c5cc4c(c1)c23] |
TABLE 40
| Compound No. | Central Skeleton | Substituent |
|---|---|---|
| O-14-54 | 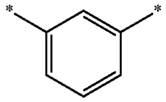 | 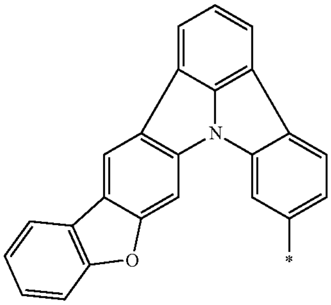 [SMILES: *c1ccc2c3cccc4c5cc6c(cc5n(c2c1)c34)oc1ccccc16] |
| O-14-55 | 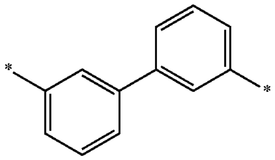 [SMILES: *c1cccc(-c2cccc(*)c2)c1] | 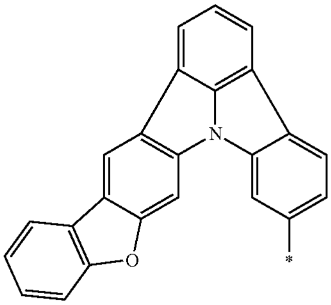 [SMILES: *c1ccc2c3cccc4c5cc6c(cc5n(c2c1)c34)oc1ccccc16] |

TABLE 40-continued
| Compound No. | Central Skeleton | Substituent |
| --- | --- | --- |
| O-14-56 | 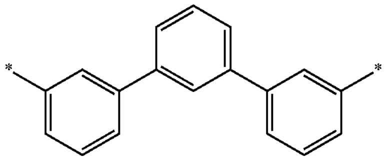 [SMILES: *c1cccc(-c2cccc(-c3cccc(*)c3)c2)c1] | 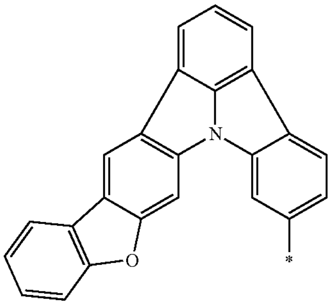 [SMILES: *c1ccc2c3cccc4c5cc6c(cc5n(c2c1)c34)oc1ccccc16] |
| O-14-57 | 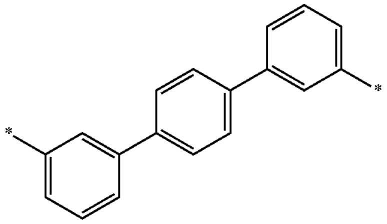 [SMILES: *c1cccc(-c2ccc(-c3cccc(*)c3)cc2)c1] | 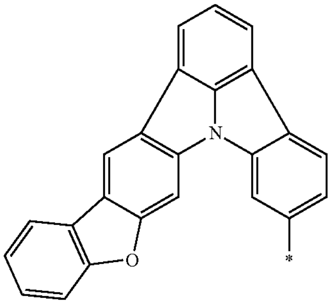 [SMILES: *c1ccc2c3cccc4c5cc6c(cc5n(c2c1)c34)oc1ccccc16] |
| O-14-58 | 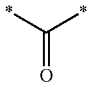 | 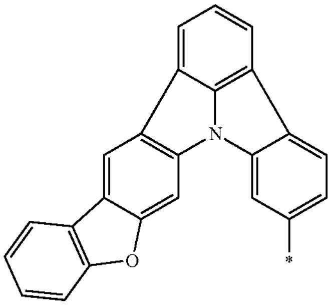 [SMILES: *c1ccc2c3cccc4c5cc6c(cc5n(c2c1)c34)oc1ccccc16] |
| O-14-59 | 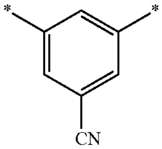 [SMILES: *c1cc(*)cc(C#N)c1] | 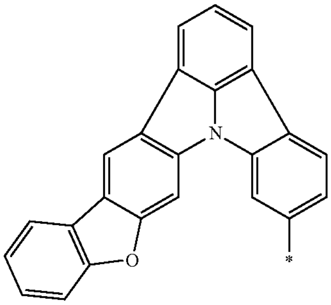 [SMILES: *c1ccc2c3cccc4c5cc6c(cc5n(c2c1)c34)oc1ccccc16] |
| O-14-60 | 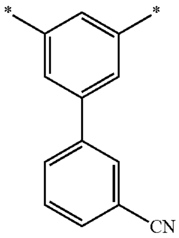 [SMILES: *c1cc(*)cc(-c2cccc(C#N)c2)c1] | 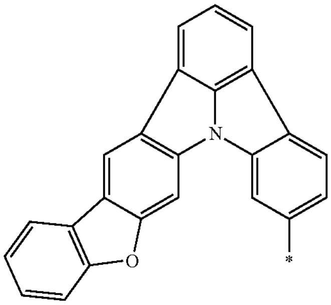 [SMILES: *c1ccc2c3cccc4c5cc6c(cc5n(c2c1)c34)oc1ccccc16] |

TABLE 40-continued
| Compound No. | Central Skeleton | Substituent |
| --- | --- | --- |
| O-14-61 | 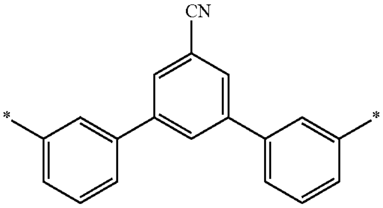 | 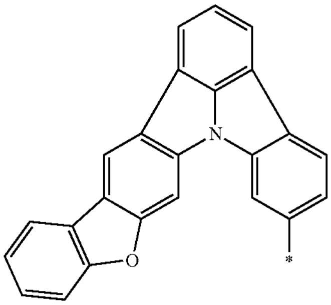 [SMILES: *c1ccc2c3cccc4c5cc6c(cc5n(c2c1)c34)oc1ccccc16] |
| O-14-62 | 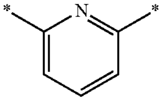 [SMILES: *c1cccc(*)n1] | 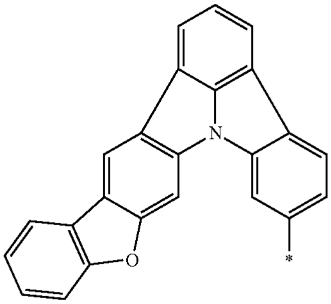 [SMILES: *c1ccc2c3cccc4c5cc6c(cc5n(c2c1)c34)oc1ccccc16] |
| O-14-63 | 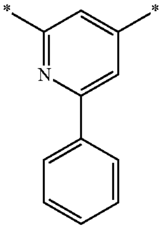 [SMILES: *c1cc(*)nc(-c2ccccc2)c1] | 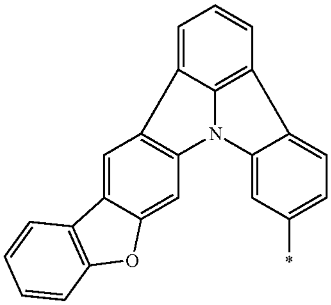 [SMILES: *c1ccc2c3cccc4c5cc6c(cc5n(c2c1)c34)oc1ccccc16] |
| O-14-64 | 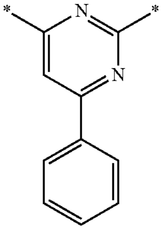 [SMILES: *c1cc(-c2ccccc2)nc(*)n1] | 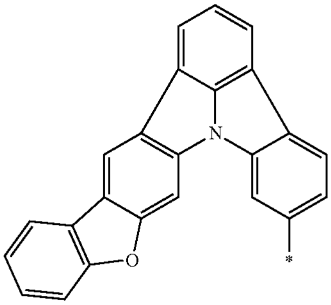 [SMILES: *c1ccc2c3cccc4c5cc6c(cc5n(c2c1)c34)oc1ccccc16] |
| O-14-65 | 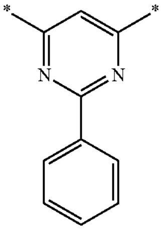 [SMILES: *c1cc(*)nc(-c2ccccc2)n1] | 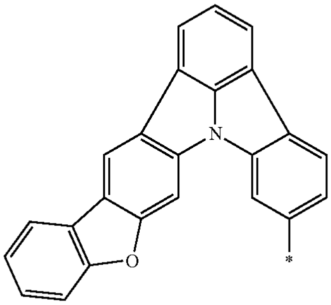 [SMILES: *c1ccc2c3cccc4c5cc6c(cc5n(c2c1)c34)oc1ccccc16] |

TABLE 40-continued
| Compound No. | Central Skeleton | Substituent |
| --- | --- | --- |
| O-14-66 | 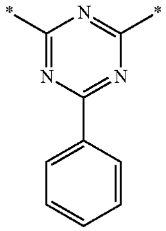 [SMILES: *c1nc(*)nc(-c2ccccc2)n1] | 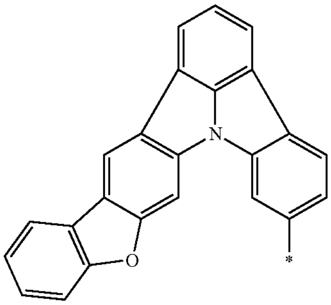 [SMILES: *c1ccc2c3cccc4c5cc6c(cc5n(c2c1)c34)oc1ccccc16] |
| O-14-67 | 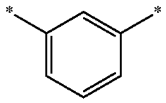 | 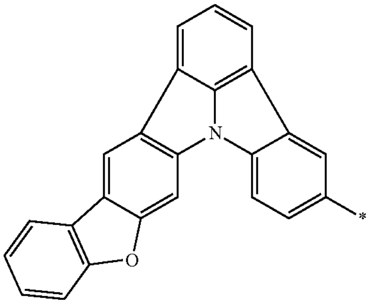 [SMILES: *c1ccc2c(c1)c1cccc3c4cc5c(cc4n2c13)oc1ccccc15] |
| O-14-68 | 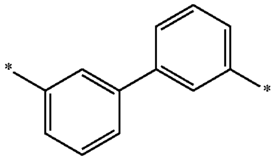 [SMILES: *c1cccc(-c2cccc(*)c2)c1] | 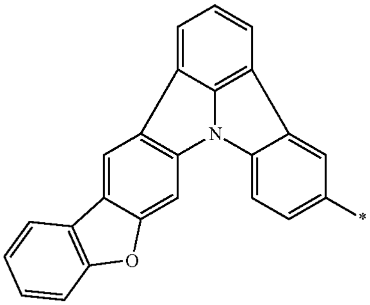 [SMILES: *c1ccc2c(c1)c1cccc3c4cc5c(cc4n2c13)oc1ccccc15] |
| O-14-69 | 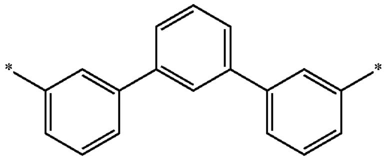 [SMILES: *c1cccc(-c2cccc(-c3cccc(*)c3)c2)c1] | 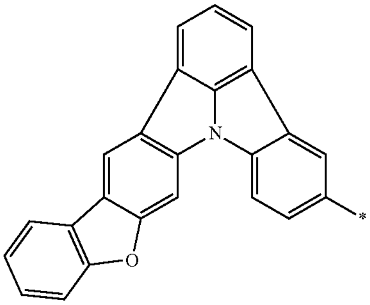 [SMILES: *c1ccc2c(c1)c1cccc3c4cc5c(cc4n2c13)oc1ccccc15] |
| O-14-70 | 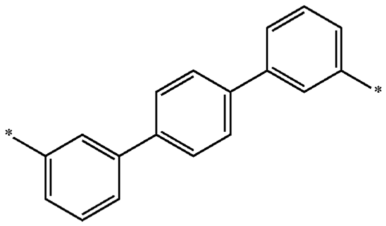 [SMILES: *c1cccc(-c2ccc(-c3cccc(*)c3)cc2)c1] | 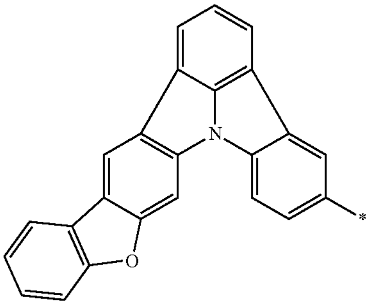 [SMILES: *c1ccc2c(c1)c1cccc3c4cc5c(cc4n2c13)oc1ccccc15] |

TABLE 40-continued
| Compound No. | Central Skeleton | Substituent |
| --- | --- | --- |
| O-14-71 | 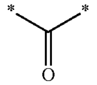 | 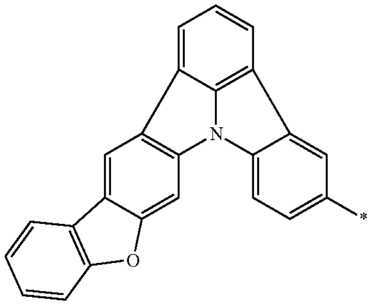 [SMILES: *c1ccc2c(c1)c1cccc3c4cc5c(cc4n2c13)oc1ccccc15] |
| O-14-72 | 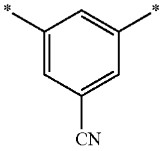 [SMILES: *c1cc(*)cc(C#N)c1] | 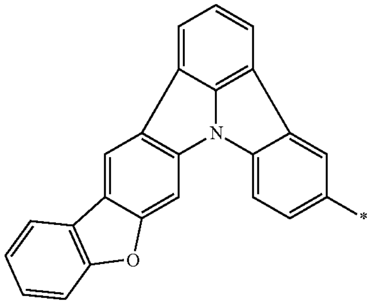 [SMILES: *c1ccc2c(c1)c1cccc3c4cc5c(cc4n2c13)oc1ccccc15] |
| O-14-73 | 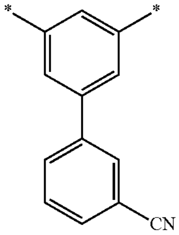 [SMILES: *c1cc(*)cc(-c2cccc(C#N)c2)c1] | 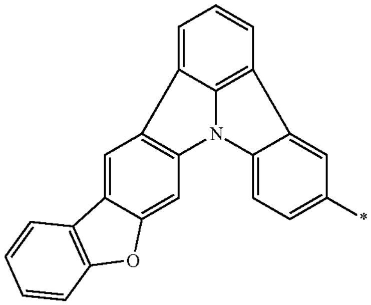 [SMILES: *c1ccc2c(c1)c1cccc3c4cc5c(cc4n2c13)oc1ccccc15] |
| O-14-74 | 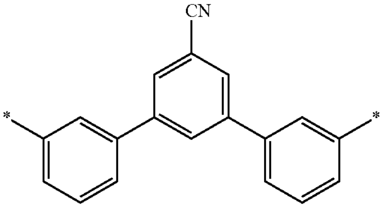 | 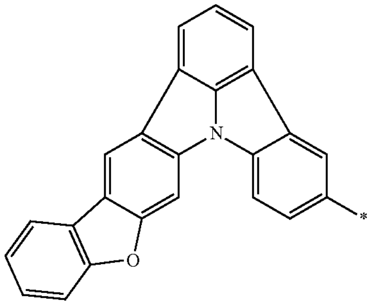 [SMILES: *c1ccc2c(c1)c1cccc3c4cc5c(cc4n2c13)oc1ccccc15] |
| O-14-75 | 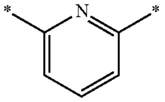 | 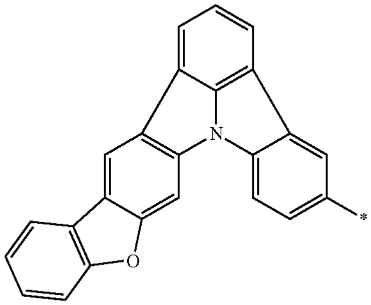 [SMILES: *c1ccc2c(c1)c1cccc3c4cc5c(cc4n2c13)oc1ccccc15] |

TABLE 40-continued
| Compound No. | Central Skeleton | Substituent |
| --- | --- | --- |
| O 14-76 | 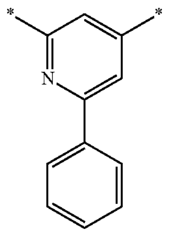 [SMILES: *c1cc(*)nc(-c2ccccc2)c1] | 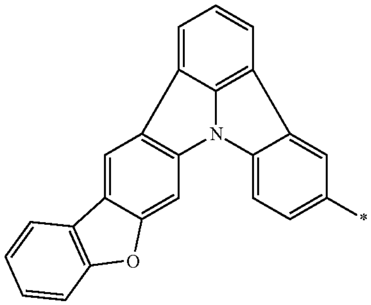 [SMILES: *c1ccc2c(c1)c1cccc3c4cc5c(cc4n2c13)oc1ccccc15] |
| O-14-77 | 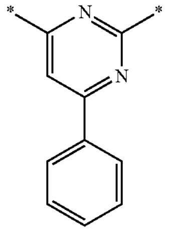 [SMILES: *c1cc(-c2ccccc2)nc(*)n1] | 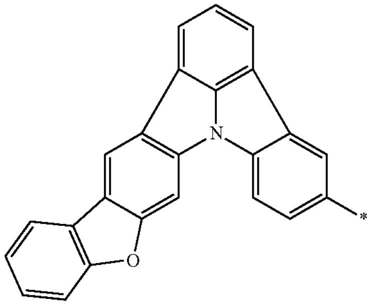 [SMILES: *c1ccc2c(c1)c1cccc3c4cc5c(cc4n2c13)oc1ccccc15] |
| O-14-78 | 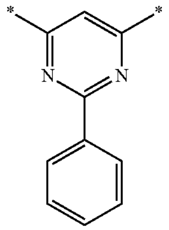 [SMILES: *c1cc(*)nc(-c2ccccc2)n1] | 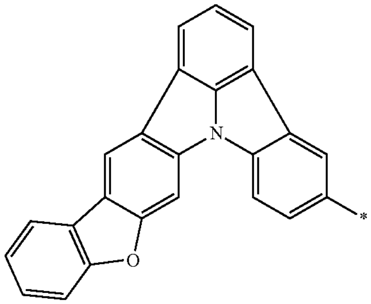 [SMILES: *c1ccc2c(c1)c1cccc3c4cc5c(cc4n2c13)oc1ccccc15] |
| O-14-79 | 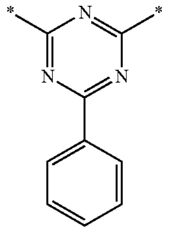 [SMILES: *c1nc(*)nc(-c2ccccc2)n1] | 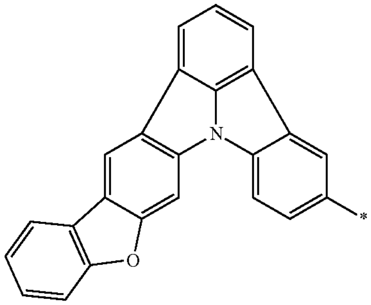 [SMILES: *c1ccc2c(c1)c1cccc3c4cc5c(cc4n2c13)oc1ccccc15] |

TABLE 41
| Compound No. | Central Skeleton | Substituent |
|---|---|---|
| N-14-26 | 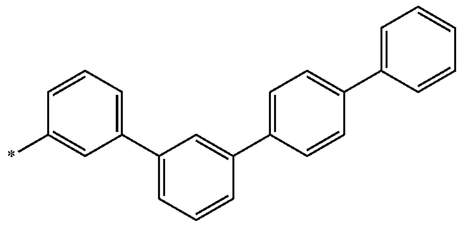 [SMILES: *c1cccc(-c2cccc(-c3ccc(-c4ccccc4)cc3)c2)c1] | 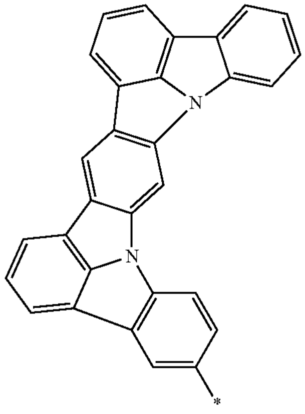 [SMILES: *c1ccc2c(c1)c1cccc3c4cc5c6cccc7c8ccccc8n(c5cc4n2c13)c76] |
| N-14-27 | 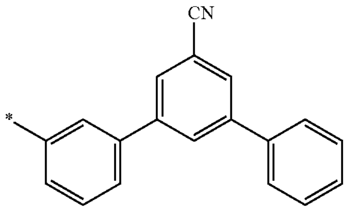 [SMILES: *c1cccc(-c2cc(C#N)cc(-c3ccccc3)c2)c1] | 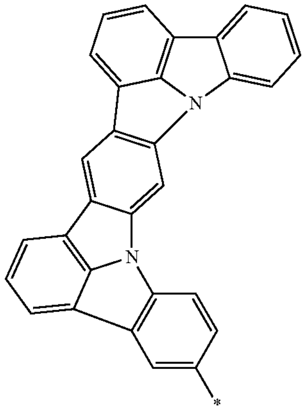 [SMILES: *c1ccc2c(c1)c1cccc3c4cc5c6cccc7c8ccccc8n(c5cc4n2c13)c76] |
| N-14-28 | 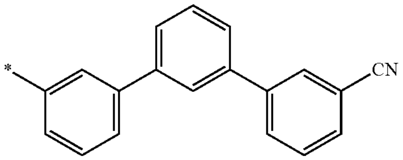 [SMILES: *c1cccc(-c2cccc(-c3cccc(C#N)c3)c2)c1] | 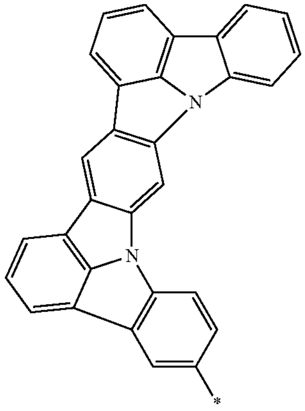 [SMILES: *c1ccc2c(c1)c1cccc3c4cc5c6cccc7c8ccccc8n(c5cc4n2c13)c76] |

TABLE 41-continued
| Compound No. | Central Skeleton | Substituent |
| --- | --- | --- |
| N-14-29 | 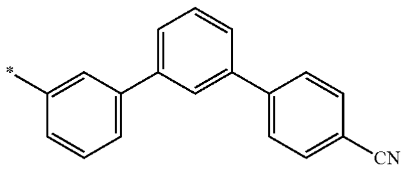 [SMILES: *c1cccc(-c2cccc(-c3ccc(C#N)cc3)c2)c1] | 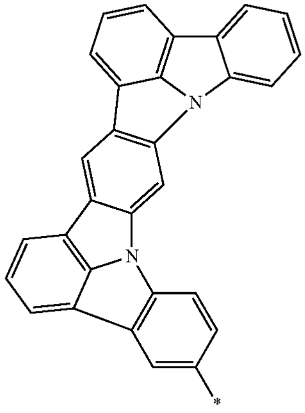 [SMILES: *c1ccc2c(c1)c1cccc3c4cc5c6cccc7c8ccccc8n(c5cc4n2c13)c76] |
| N-14-30 | 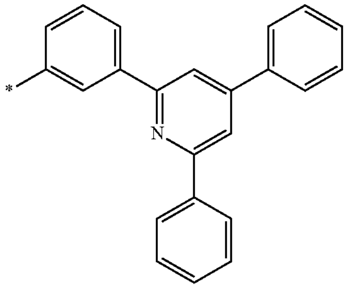 [SMILES: *c1cccc(-c2cc(-c3ccccc3)cc(-c3ccccc3)n2)c1] | 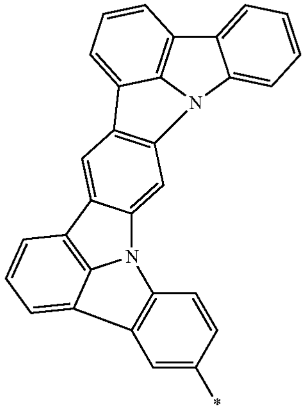 [SMILES: *c1ccc2c(c1)c1cccc3c4cc5c6cccc7c8ccccc8n(c5cc4n2c13)c76] |
| N-14-31 | 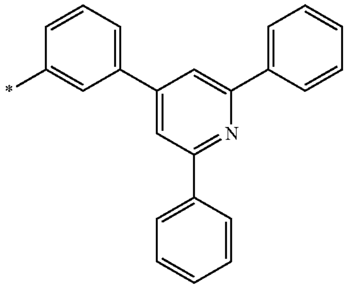 [SMILES: *c1cccc(-c2cc(-c3ccccc3)nc(-c3ccccc3)c2)c1] | 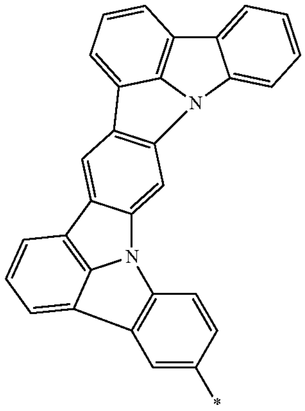 [SMILES: *c1ccc2c(c1)c1cccc3c4cc5c6cccc7c8ccccc8n(c5cc4n2c13)c76] |

TABLE 41-continued
| Compound No. | Central Skeleton | Substituent |
|---|---|---|
| N-14-32 | 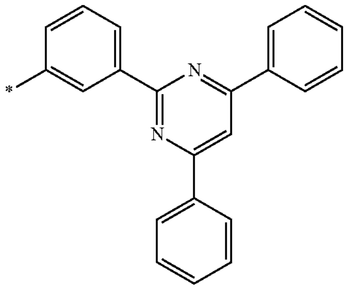 [SMILES: *c1cccc(-c2nc(-c3ccccc3)cc(-c3ccccc3)n2)c1] | 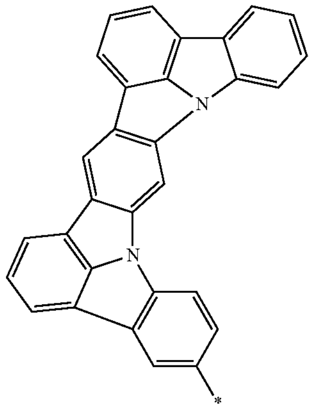 [SMILES: *c1ccc2c(c1)c1cccc3c4cc5c6cccc7c8ccccc8n(c5cc4n2c13)c76] |
| N-14-33 | 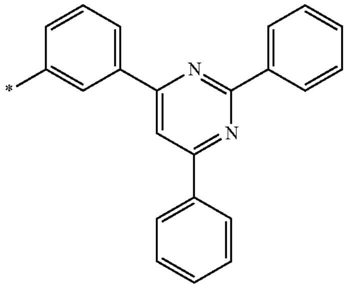 | 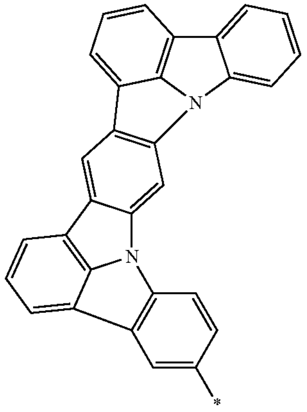 [SMILES: *c1ccc2c(c1)c1cccc3c4cc5c6cccc7c8ccccc8n(c5cc4n2c13)c76] |
| N-14-34 | 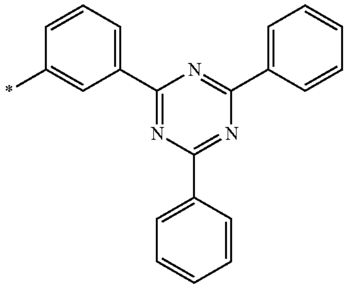 | 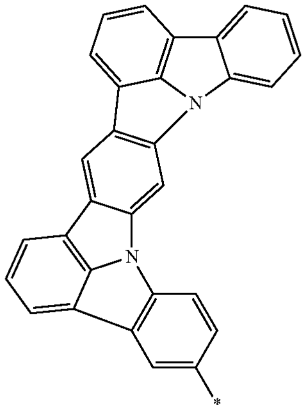 [SMILES: *c1ccc2c(c1)c1cccc3c4cc5c6cccc7c8ccccc8n(c5cc4n2c13)c76] |

TABLE 41-continued
| Compound No. | Central Skeleton | Substituent |
|---|---|---|
| N-14-35 | 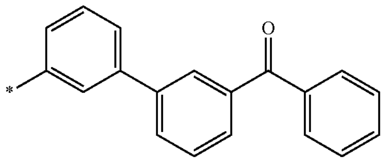 [SMILES: *c1cccc(-c2cccc(C(=O)c3ccccc3)c2)c1] | 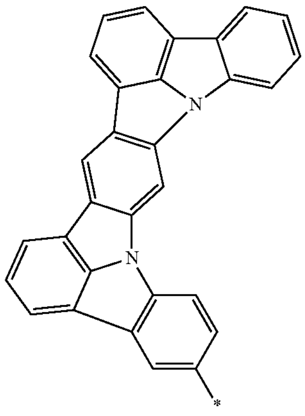 [SMILES: *c1ccc2c(c1)c1cccc3c4cc5c6cccc7c8ccccc8n(c5cc4n2c13)c76] |
| N-14-36 | 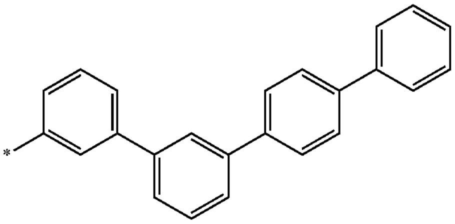 [SMILES: *c1cccc(-c2cccc(-c3ccc(-c4ccccc4)cc3)c2)c1] | 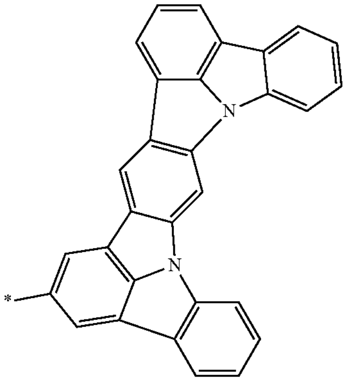 [SMILES: *c1cc2c3ccccc3n3c4cc5c(cc4c(c1)c23)c1cccc2c3ccccc3n5c21] |
| N-14-37 | 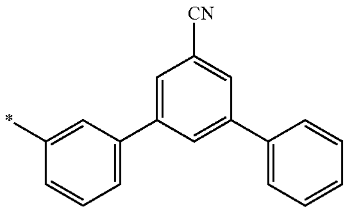 [SMILES: *c1cccc(-c2cc(C#N)cc(-c3ccccc3)c2)c1] | 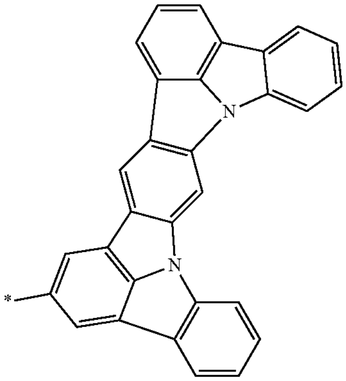 [SMILES: *c1cc2c3ccccc3n3c4cc5c(cc4c(c1)c23)c1cccc2c3ccccc3n5c21] |
| N-14-38 | 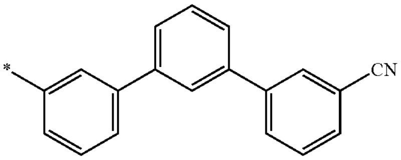 [SMILES: *c1cccc(-c2cccc(-c3cccc(C#N)c3)c2)c1] | 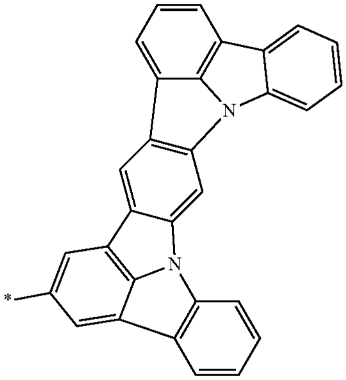 [SMILES: *c1cc2c3ccccc3n3c4cc5c(cc4c(c1)c23)c1cccc2c3ccccc3n5c21] |

TABLE 41-continued
| Compound No. | Central Skeleton | Substituent |
|---|---|---|
| N-14-39 | 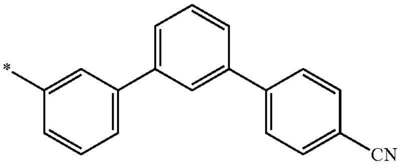 [SMILES: *c1cccc(-c2cccc(-c3ccc(C#N)cc3)c2)c1] | 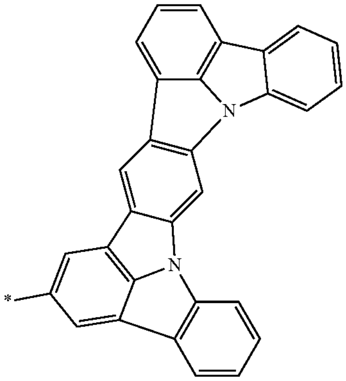 [SMILES: *c1cc2c3ccccc3n3c4cc5c(cc4c(c1)c23)c1cccc2c3ccccc3n5c21] |
| N-14-40 | 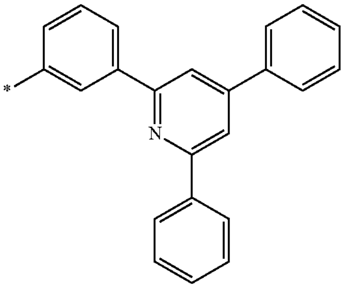 [SMILES: *c1cccc(-c2cc(-c3ccccc3)cc(-c3ccccc3)n2)c1] | 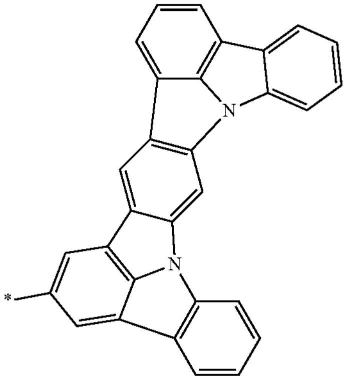 [SMILES: *c1cc2c3ccccc3n3c4cc5c(cc4c(c1)c23)c1cccc2c3ccccc3n5c21] |
| N-14-41 | 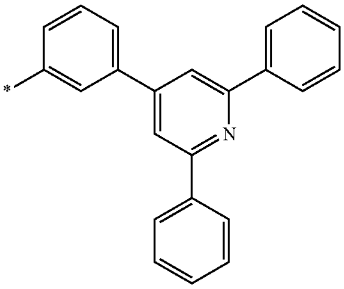 [SMILES: *c1cccc(-c2cc(-c3ccccc3)nc(-c3ccccc3)c2)c1] | 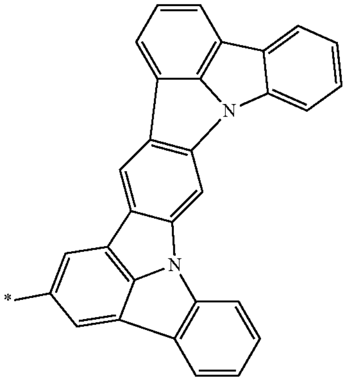 [SMILES: *c1cc2c3ccccc3n3c4cc5c(cc4c(c1)c23)c1cccc2c3ccccc3n5c21] |
| N-14-42 | 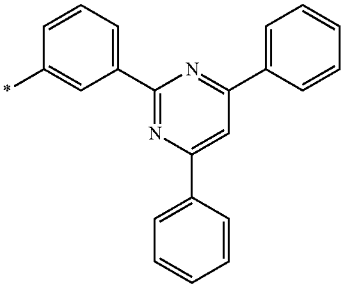 [SMILES: *c1cccc(-c2nc(-c3ccccc3)cc(-c3ccccc3)n2)c1] | 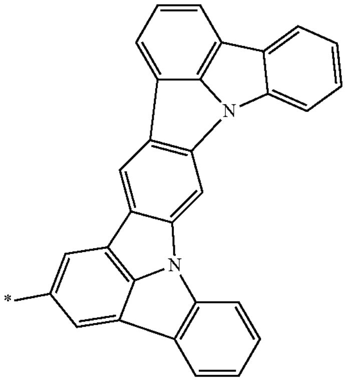 [SMILES: *c1cc2c3ccccc3n3c4cc5c(cc4c(c1)c23)c1cccc2c3ccccc3n5c21] |

TABLE 41-continued
| Compound No. | Central Skeleton | Substituent |
| --- | --- | --- |
| N-14-43 | 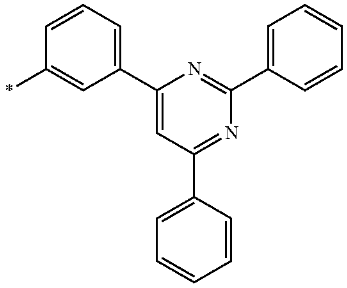 [SMILES: *c1cccc(-c2cc(-c3ccccc3)nc(-c3ccccc3)n2)c1] | 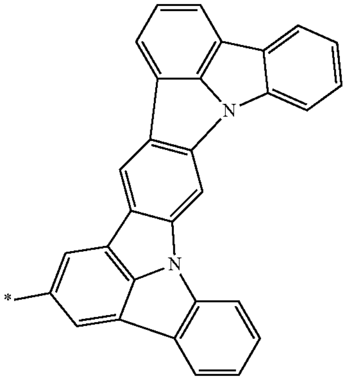 [SMILES: *c1cc2c3ccccc3n3c4cc5c(cc4c(c1)c23)c1cccc2c3ccccc3n5c21] |
| N-14-44 | 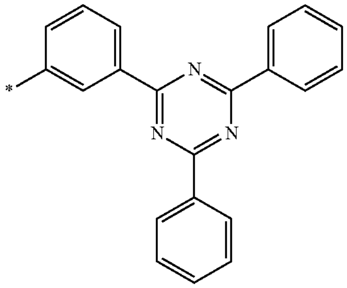 [SMILES: *c1cccc(-c2nc(-c3ccccc3)nc(-c3ccccc3)n2)c1] | 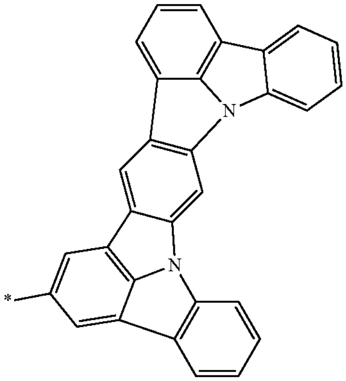 [SMILES: *c1cc2c3ccccc3n3c4cc5c(cc4c(c1)c23)c1cccc2c3ccccc3n5c21] |
| N-14-45 | 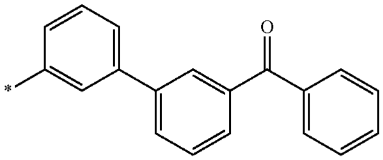 [SMILES: *c1cccc(-c2cccc(C(=O)c3ccccc3)c2)c1] | 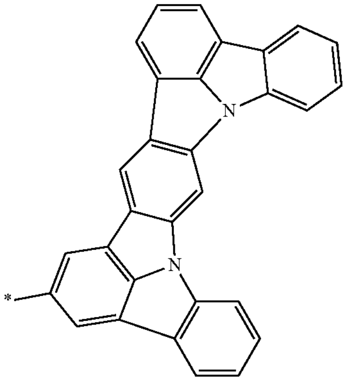 [SMILES: *c1cc2c3ccccc3n3c4cc5c(cc4c(c1)c23)c1cccc2c3ccccc3n5c21] |
| N-14-46 | 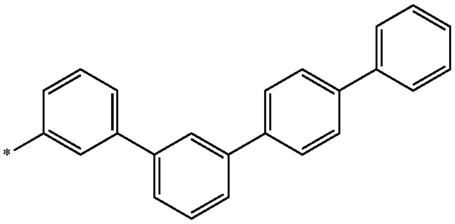 [SMILES: *c1cccc(-c2cccc(-c3ccc(-c4ccccc4)cc3)c2)c1] | 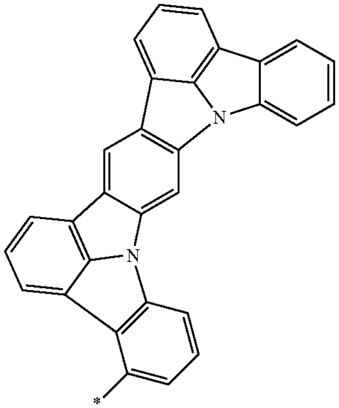 [SMILES: *c1cccc2c1c1cccc3c4cc5c6cccc7c8ccccc8n(c5cc4n2c31)c76] |

TABLE 41-continued
| Compound No. | Central Skeleton | Substituent |
|---|---|---|
| N-14-47 | 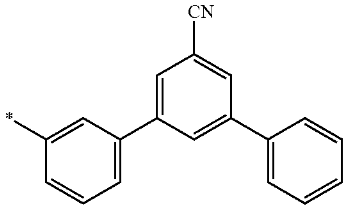 [SMILES: *c1cccc(-c2cc(C#N)cc(-c3ccccc3)c2)c1] | 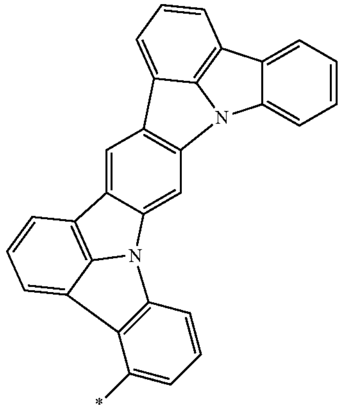 [SMILES: *c1cccc2c1c1cccc3c4cc5c6cccc7c8ccccc8n(c5cc4n2c31)c76] |
| N-14-48 | 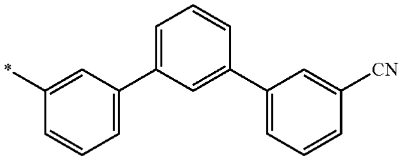 [SMILES: *c1cccc(-c2cccc(-c3cccc(C#N)c3)c2)c1] | 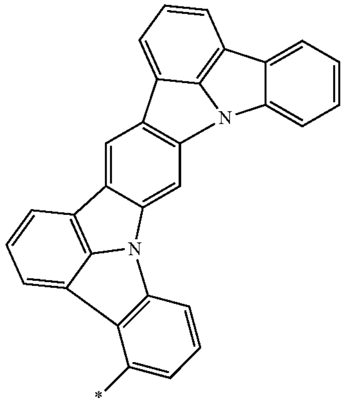 [SMILES: *c1cccc2c1c1cccc3c4cc5c6cccc7c8ccccc8n(c5cc4n2c31)c76] |
| N-14-49 | 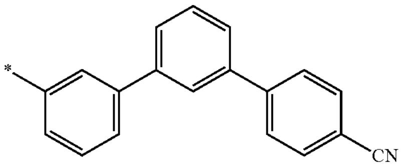 [SMILES: *c1cccc(-c2cccc(-c3ccc(C#N)cc3)c2)c1] | 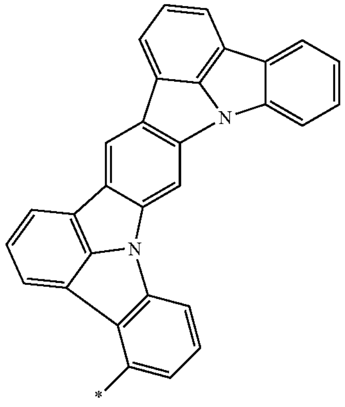 [SMILES: *c1cccc2c1c1cccc3c4cc5c6cccc7c8ccccc8n(c5cc4n2c31)c76] |

TABLE 41-continued
| Compound No. | Central Skeleton | Substituent |
| --- | --- | --- |
| N-14-50 | 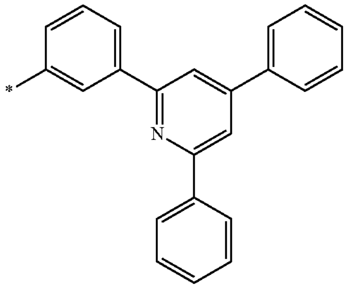 | 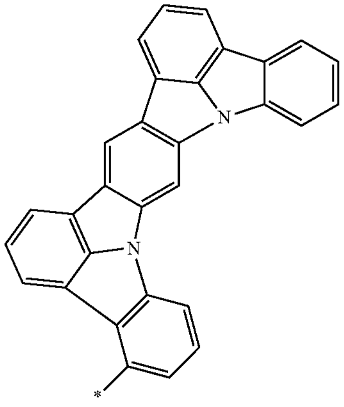 [SMILES: *c1cccc2c1c1cccc3c4cc5c6cccc7c8ccccc8n(c5cc4n2c31)c76] |
| N-14-51 | 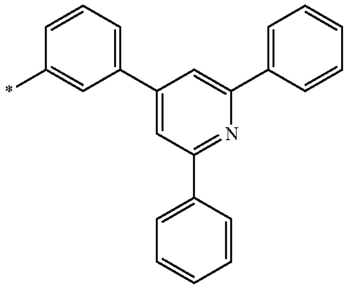 [SMILES: *c1cccc(-c2cc(-c3ccccc3)nc(-c3ccccc3)c2)c1] | 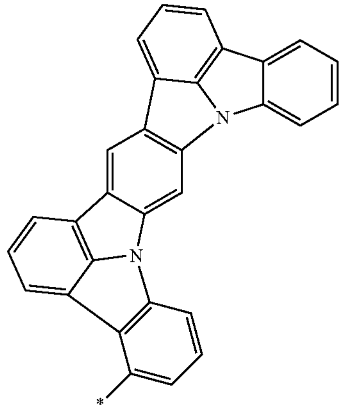 [SMILES: *c1cccc2c1c1cccc3c4cc5c6cccc7c8ccccc8n(c5cc4n2c31)c76] |
| N-14-52 | 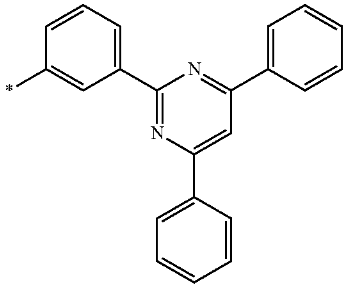 [SMILES: *c1cccc(-c2nc(-c3ccccc3)cc(-c3ccccc3)n2)c1] | 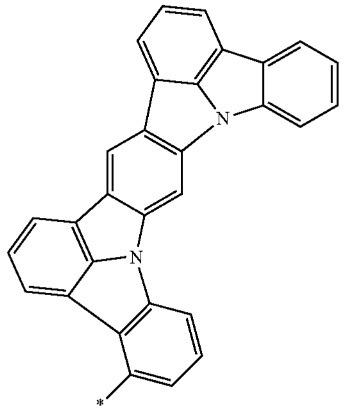 [SMILES: *c1cccc2c1c1cccc3c4cc5c6cccc7c8ccccc8n(c5cc4n2c31)c76] |

TABLE 41-continued
| Compound No. | Central Skeleton | Substituent |
| --- | --- | --- |
| N-14-53 | 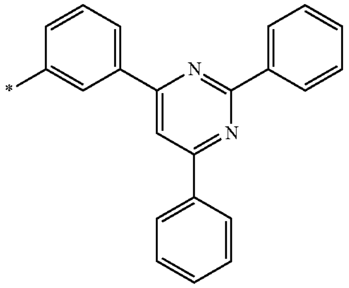 | 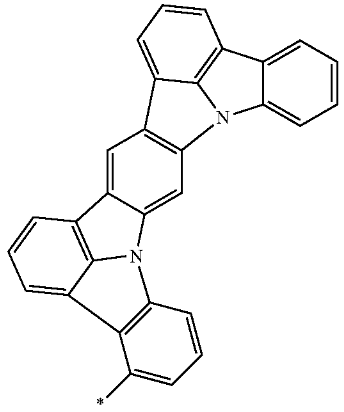 [SMILES: *c1cccc2c1c1cccc3c4cc5c6cccc7c8ccccc8n(c5cc4n2c31)c76] |
| N-14 54 | 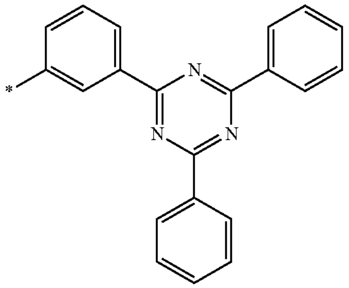 | 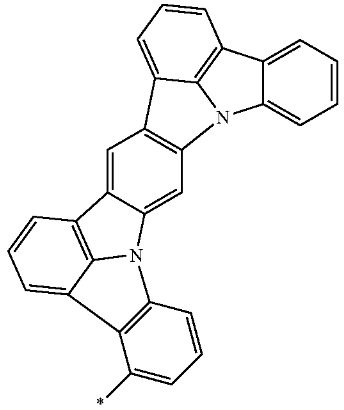 [SMILES: *c1cccc2c1c1cccc3c4cc5c6cccc7c8ccccc8n(c5cc4n2c31)c76] |
| N-14-55 | 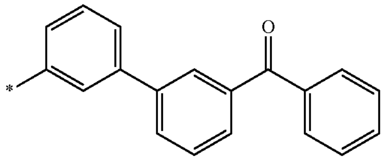 [SMILES: *c1cccc(-c2cccc(C(=O)c3ccccc3)c2)c1] | 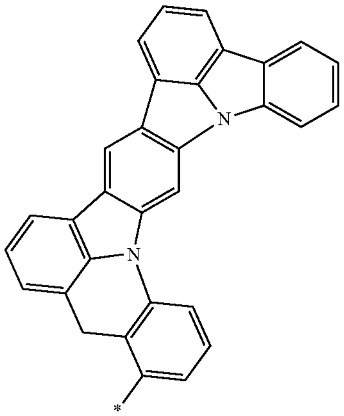 [SMILES: *c1cccc2c1Cc1cccc3c4cc5c6cccc7c8ccccc8n(c5cc4n-2c13)c76] |

TABLE 42
| Compound No. | Central Skeleton | Substituent |
|---|---|---|
| N-14-56 | 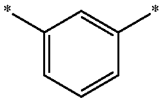 [SMILES: *c1cccc(*)c1] | 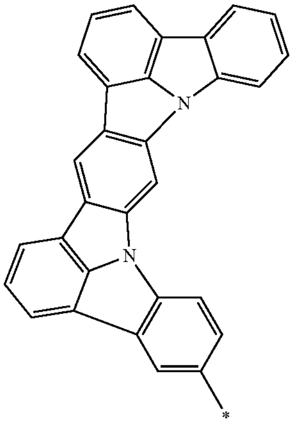 |
| N-14-57 | 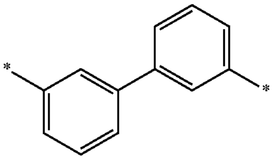 [SMILES: *c1cccc(-c2cccc(*)c2)c1] | 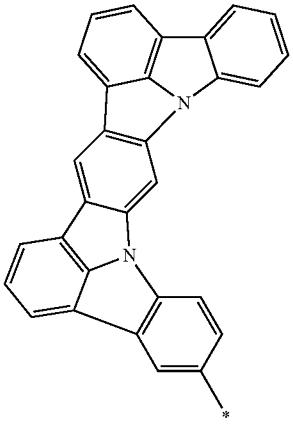 |
| N-14-58 | 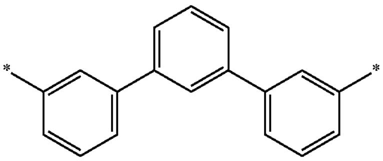 [SMILES: *c1cccc(-c2cccc(-c3cccc(*)c3)c2)c1] | 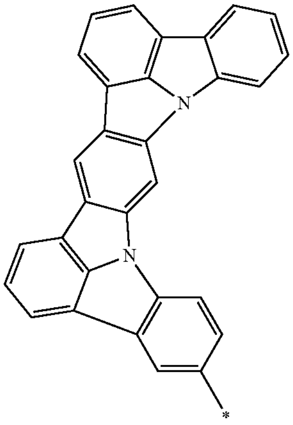 |

TABLE 42-continued
| Compound No. | Central Skeleton | Substituent |
| --- | --- | --- |
| N-14-59 | 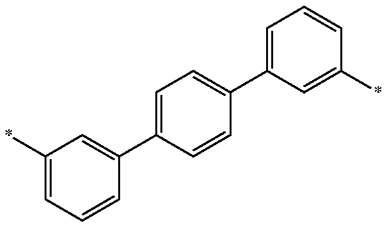 [SMILES: *c1cccc(-c2ccc(-c3cccc(*)c3)cc2)c1] | 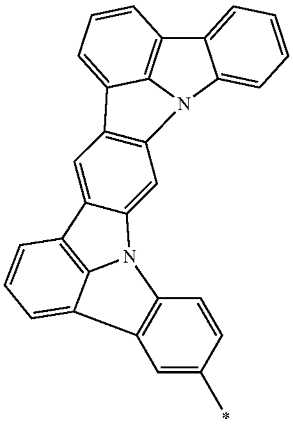 |
| N-14-60 | 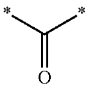 | 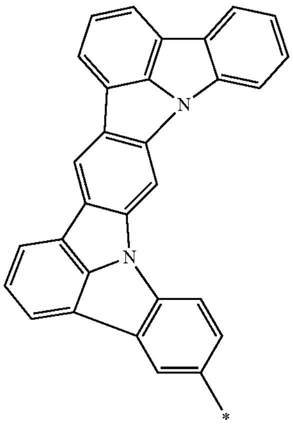 |
| N-14-61 | 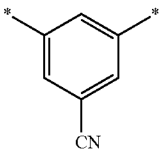 [SMILES: *c1cc(*)cc(C#N)c1] | 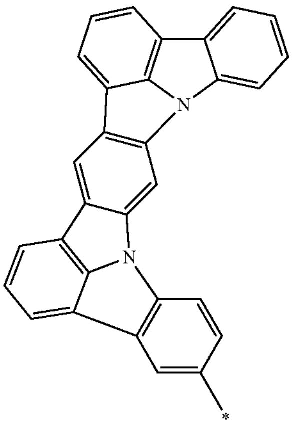 |

TABLE 42-continued
| Compound No. | Central Skeleton | Substituent |
| --- | --- | --- |
| N-14-62 | 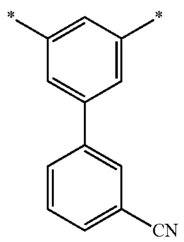 [SMILES: *c1cc(*)cc(-c2cccc(C#N)c2)c1] | 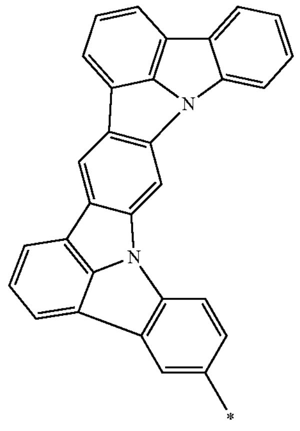 |
| N-14-63 | 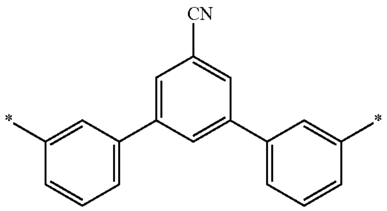 [SMILES: *c1cccc(-c2cc(C#N)cc(-c3cccc(*)c3)c2)c1] | 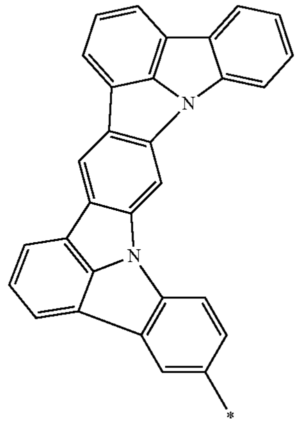 |
| N-14-64 | 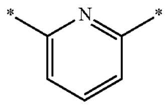 [SMILES: *c1cccc(*)n1] | 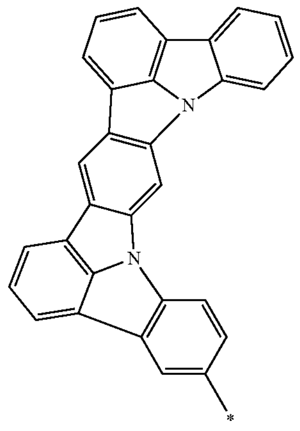 |

TABLE 42-continued
| Compound No. | Central Skeleton | Substituent |
|---|---|---|
| N-14-65 | 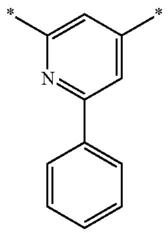 [SMILES: *c1cc(*)nc(-c2ccccc2)c1] | 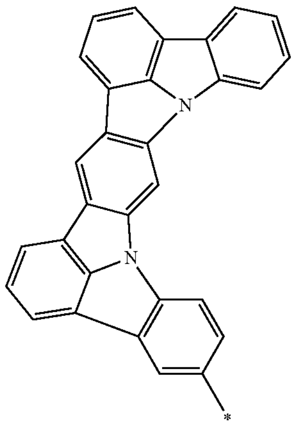 |
| N-14-66 | 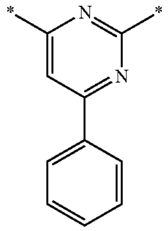 [SMILES: *c1cc(-c2ccccc2)nc(*)n1] | 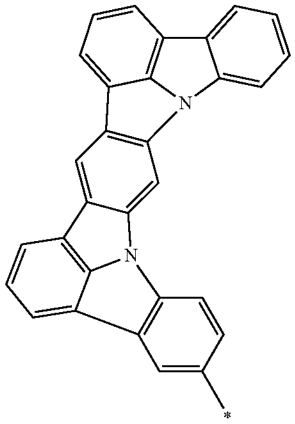 |
| N-14-67 | 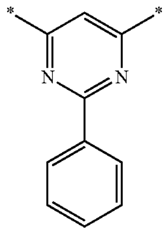 [SMILES: *c1cc(*)nc(-c2ccccc2)n1] | 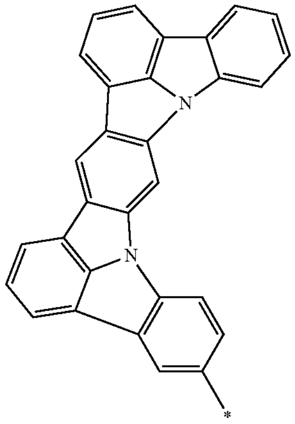 |

TABLE 42-continued
| Compound No. | Central Skeleton | Substituent |
| --- | --- | --- |
| N-14-68 | 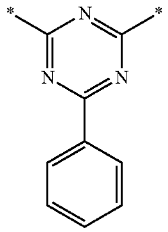 [SMILES: *c1nc(*)nc(-c2ccccc2)n1] | 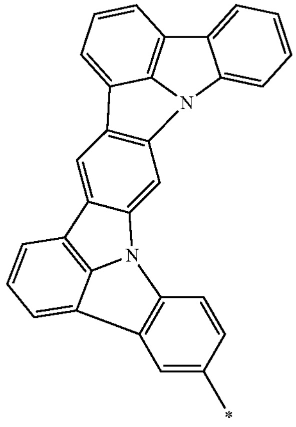 |
| N-14-69 | 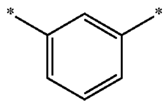 [SMILES: *c1cccc(*)c1] | 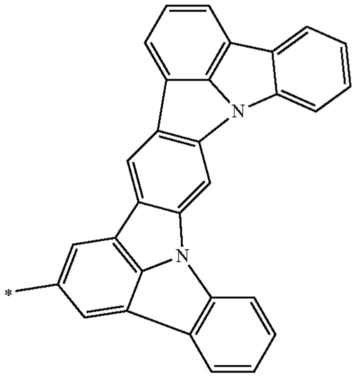 |
| N-14-70 | 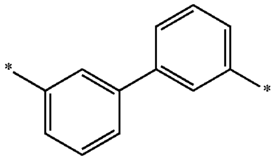 [SMILES: *c1cccc(-c2cccc(*)c2)c1] | 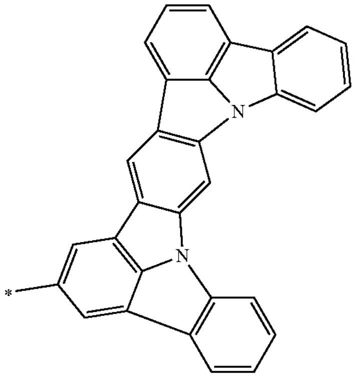 |
| N-14-71 | 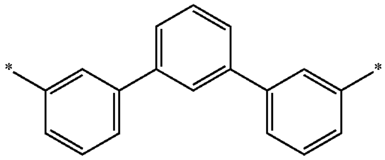 [SMILES: *c1cccc(-c2cccc(-c3cccc(*)c3)c2)c1] | 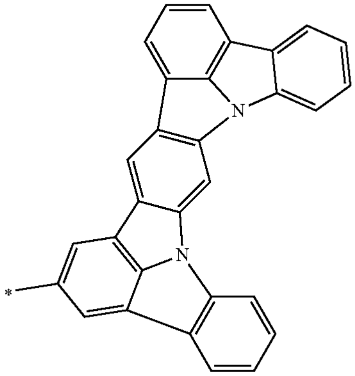 |

TABLE 42-continued
| Compound No. | Central Skeleton | Substituent |
|---|---|---|
| N-14-72 | 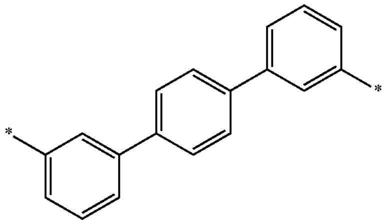 [SMILES: *c1cccc(-c2ccc(-c3cccc(*)c3)cc2)c1] | 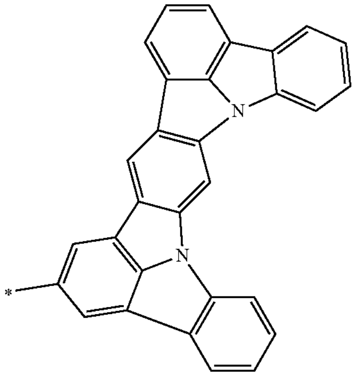 |
| N-14-73 | 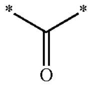 | 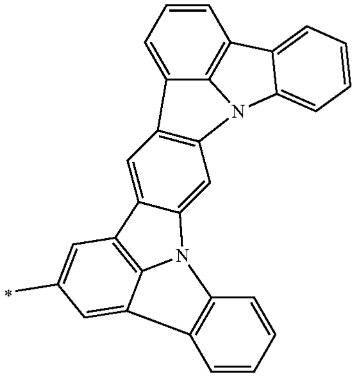 |
| N-14-74 | 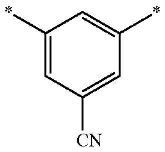 [SMILES: *c1cc(*)cc(C#N)c1] | 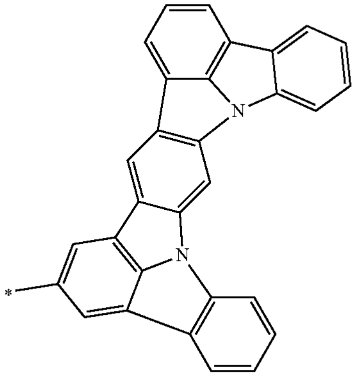 |
| N-14-75 | 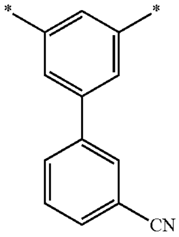 [SMILES: *c1cc(*)cc(-c2cccc(C#N)c2)c1] | 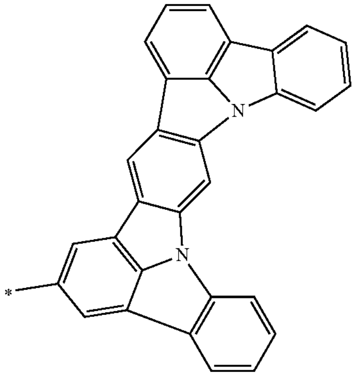 |

TABLE 42-continued
| Compound No. | Central Skeleton | Substituent |
|---|---|---|
| N-14-76 | 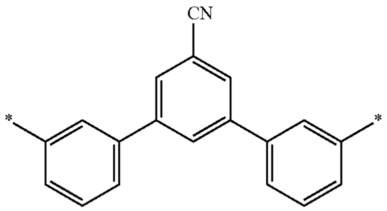 [SMILES: *c1cccc(-c2cc(C#N)cc(-c3cccc(*)c3)c2)c1] | 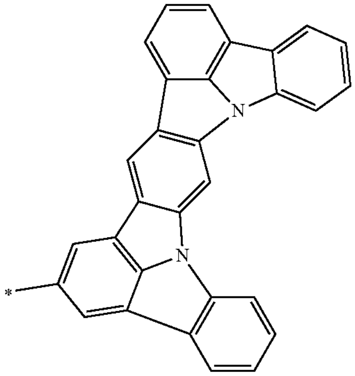 |
| N-14-77 | 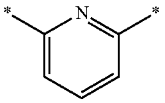 [SMILES: *c1cccc(*)n1] | 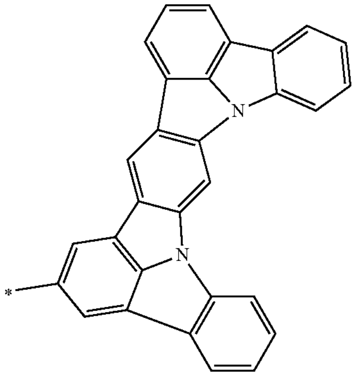 |
| N-14-78 | 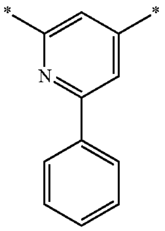 [SMILES: *c1cc(*)nc(-c2ccccc2)c1] | 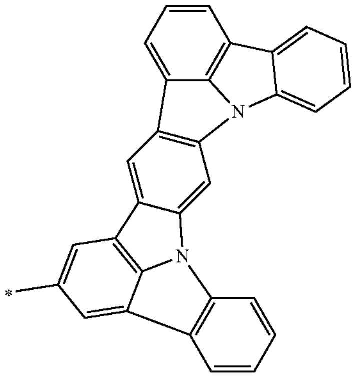 |
| N-14-79 | 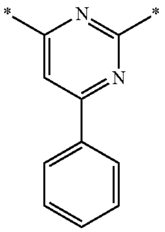 [SMILES: *c1cc(-c2ccccc2)nc(*)n1] | 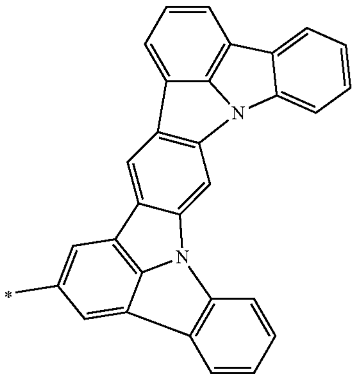 |

TABLE 42-continued
| Compound No. | Central Skeleton | Substituent |
| --- | --- | --- |
| N-14-80 | 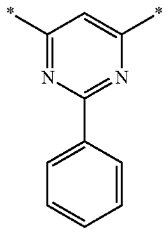 [SMILES: *c1cc(*)nc(-c2ccccc2)n1] | 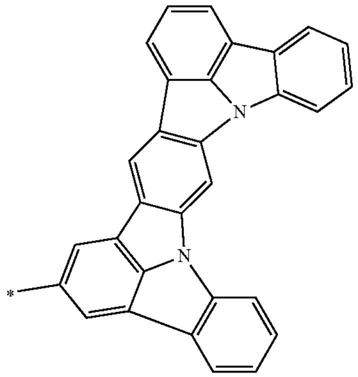 |
| N-14-81 | 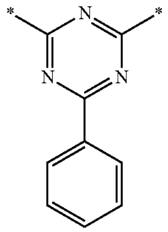 [SMILES: *c1nc(*)nc(-c2ccccc2)n1] | 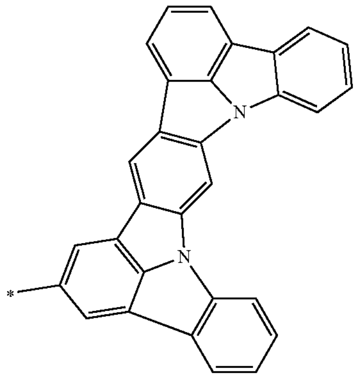 |
| N-14-82 | 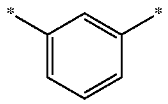 [SMILES: *c1cccc(*)c1] | 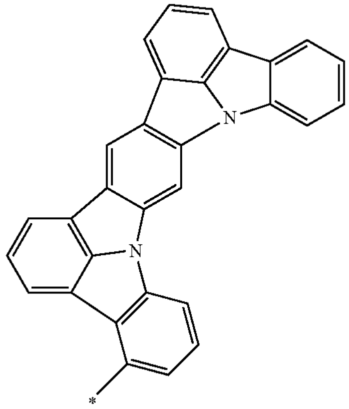 |
| N-14-83 | 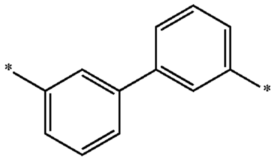 [SMILES: *c1cccc(-c2cccc(*)c2)c1] | 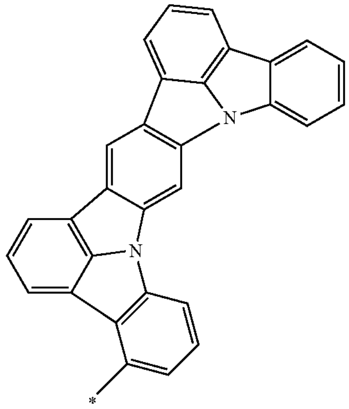 |

TABLE 42-continued
| Compound No. | Central Skeleton | Substituent |
| --- | --- | --- |
| N-14-84 | 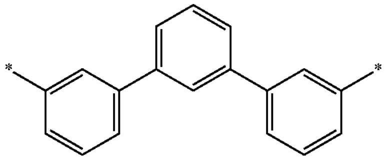 [SMILES: *c1cccc(-c2cccc(-c3cccc(*)c3)c2)c1] | 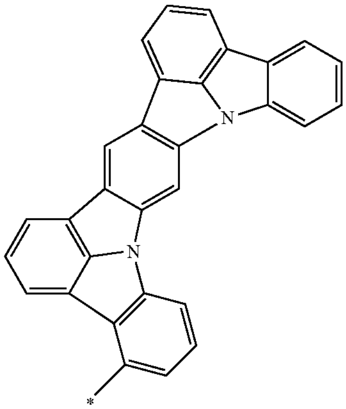 |
| N-14-85 | 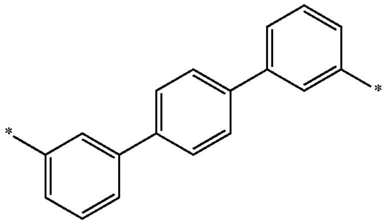 [SMILES: *c1cccc(-c2ccc(-c3cccc(*)c3)cc2)c1] | 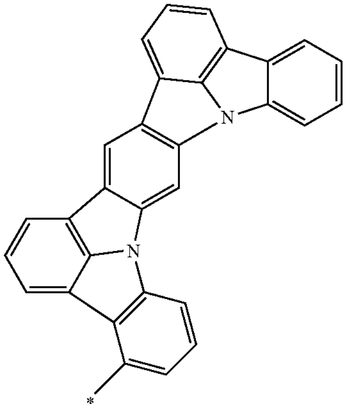 |
| N-14-86 | 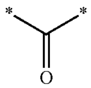 | 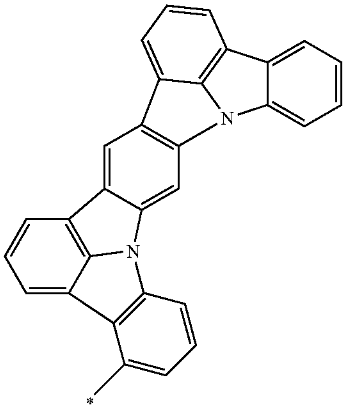 |

TABLE 42-continued
| Compound No. | Central Skeleton | Substituent |
|---|---|---|
| N-14-87 | 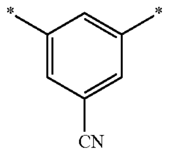 [SMILES: *c1cc(*)cc(C#N)c1] | 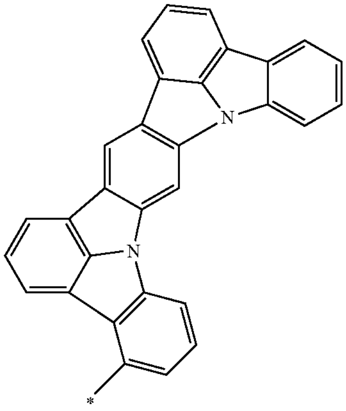 |
| N-14-88 | 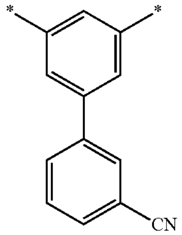 [SMILES: *c1cc(*)cc(-c2cccc(C#N)c2)c1] | 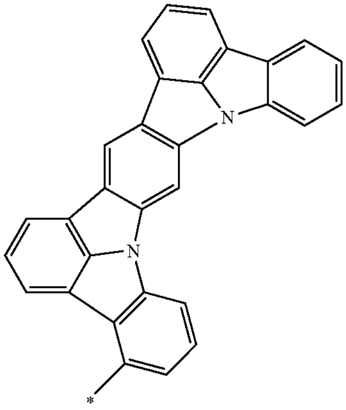 |
| N-14-89 | 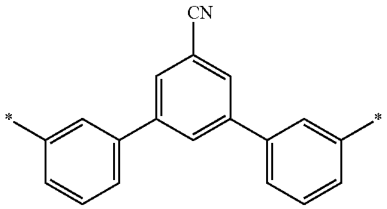 [SMILES: *c1cccc(-c2cc(C#N)cc(-c3cccc(*)c3)c2)c1] | 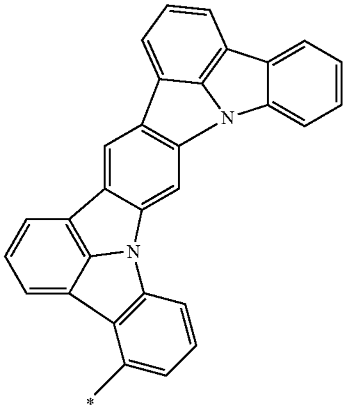 |

TABLE 42-continued
| Compound No. | Central Skeleton | Substituent |
| --- | --- | --- |
| N-14-90 | 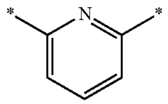 [SMILES: *c1cccc(*)n1] | 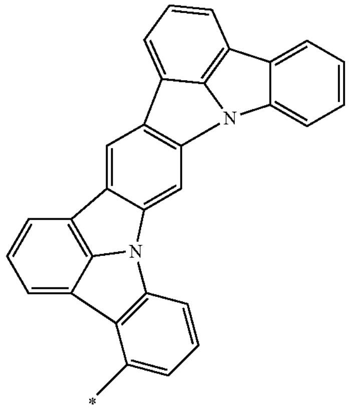 |
| N-14-91 | 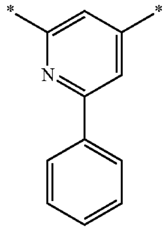 [SMILES: *c1cc(*)nc(-c2ccccc2)c1] | 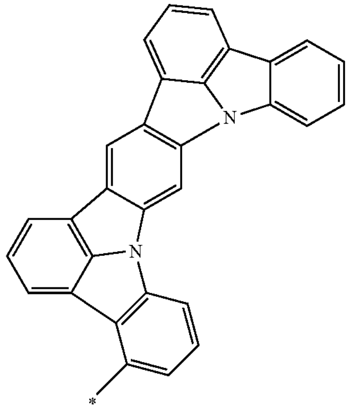 |
| N-14-92 | 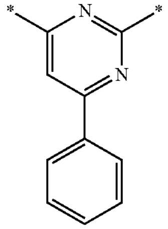 [SMILES: *c1cc(-c2ccccc2)nc(*)n1] | 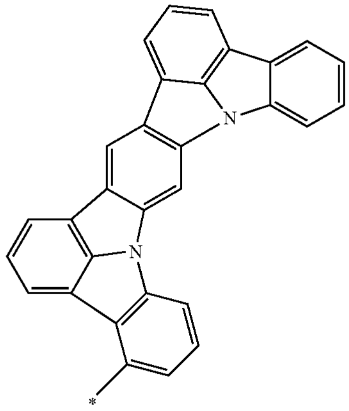 |

TABLE 42-continued
| Compound No. | Central Skeleton | Substituent |
| --- | --- | --- |
| N-14-93 | 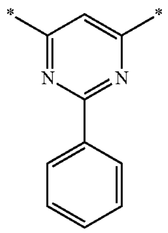 [SMILES: *c1cc(*)nc(-c2ccccc2)n1] | 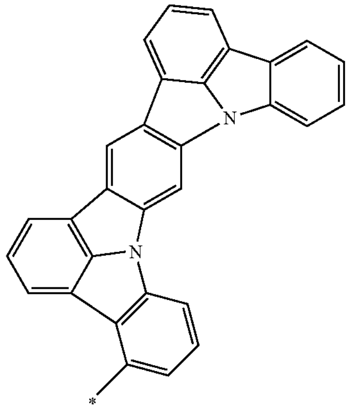 |
| N-14-94 | 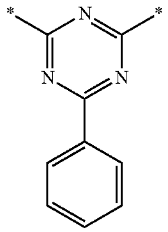 [SMILES: *c1nc(*)nc(-c2ccccc2)n1] | 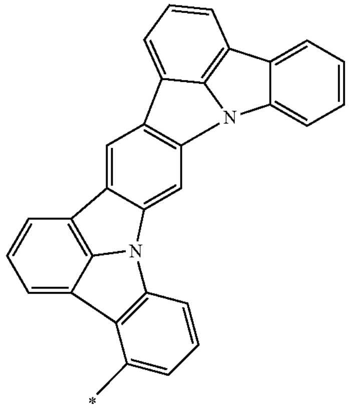 |
In the compound represented by the following general formula (15), $R^{F1}$, $R^{F3}$, $R^{F4}$, $R^{F7}$ to $R^{F9}$, $R^{F11}$, $R^{F13}$ to $R^{F15}$ each represent a hydrogen atom, and the other groups are the groups described in Tables below.
[Chem. 20]
(15)
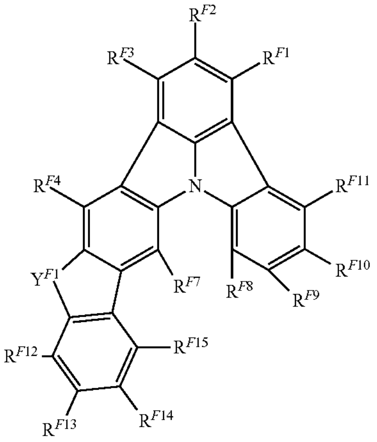

TABLE 43
| Compound No. | $Y^{F1}$ | $R^{F12}$ | $R^{F10}$ | $R^{F2}$ | $R^3$ | $R^1$ | $R^2$ |
|---|---|---|---|---|---|---|---|
| O-15-1 | O | H | H | H | — | — | — |
| O-15-2 | O | H | 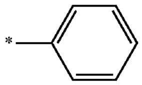 [SMILES: *c1ccccc1] | 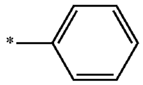 [SMILES: *c1ccccc1] | — | — | — |
| O-15-3 | O | H | 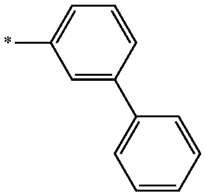 [SMILES: *c1cccc(-c2ccccc2)c1] | H | — | — | — |
| O-15-4 | O | H | 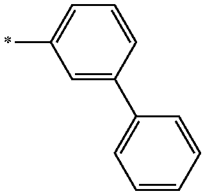 [SMILES: *c1cccc(-c2ccccc2)c1] | 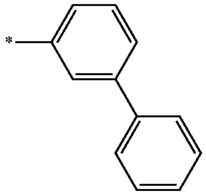 [SMILES: *c1cccc(-c2ccccc2)c1] | — | — | — |
| O-15-5 | O | 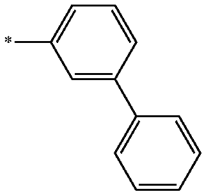 [SMILES: *c1cccc(-c2ccccc2)c1] | 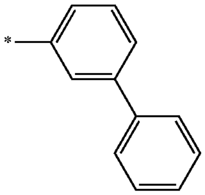 [SMILES: *c1cccc(-c2ccccc2)c1] | H | — | — | — |
| O-15-6 | O | H | 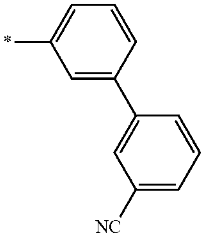 [SMILES: *c1cccc(-c2cccc(C#N)c2)c1] | H | — | — | — |
| O-15-7 | O | H | H | 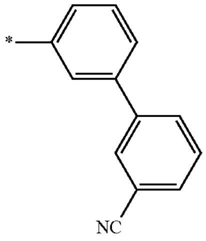 [SMILES: *c1cccc(-c2cccc(C#N)c2)c1] | — | — | — |
| O-15-8 | O | 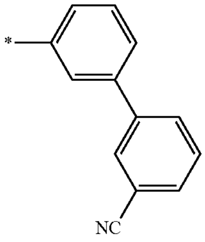 [SMILES: *c1cccc(-c2cccc(C#N)c2)c1] | 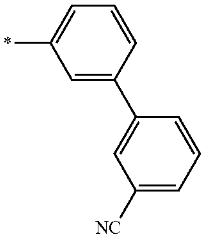 [SMILES: *c1cccc(-c2cccc(C#N)c2)c1] | — | — | — | |

TABLE 43-continued
| Compound No. | $Y^{F1}$ | $R^{F12}$ | $R^{F10}$ | $R^{F2}$ | $R^3$ | $R^1$ | $R^2$ |
|---|---|---|---|---|---|---|---|
| O-15-9 | O | H | 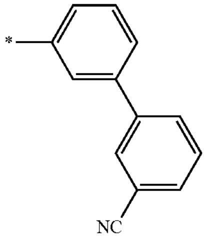 [SMILES: *c1cccc(-c2cccc(C#N)c2)c1] | 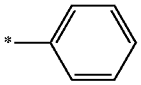 | — | — | — |
| O-15-10 | O | H | 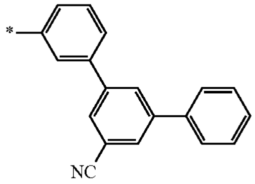 [SMILES: *c1cccc(-c2cc(C#N)cc(-c3ccccc3)c2)c1] | H | — | — | — |
| O-15-11 | O | H | 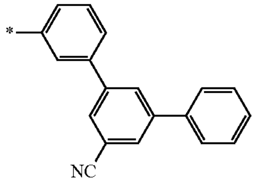 [SMILES: *c1cccc(-c2cc(C#N)cc(-c3ccccc3)c2)c1] | 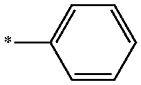 | | | |
| O-15-12 | O | H | 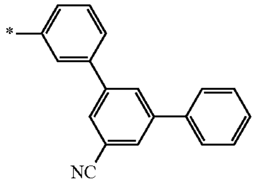 [SMILES: *c1cccc(-c2cc(C#N)cc(-c3ccccc3)c2)c1] | 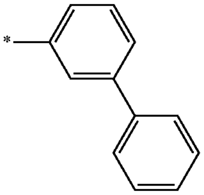 [SMILES: *c1cccc(-c2ccccc2)c1] | — | — | — |
| O-15-13 | O | 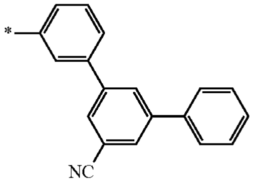 [SMILES: *c1cccc(-c2cc(C#N)cc(-c3ccccc3)c2)c1] | H | H | — | — | — |
| O-15-14 | O | H | 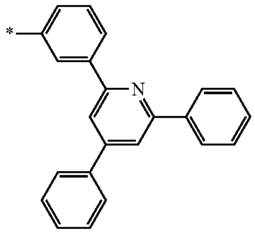 | H | — | — | — |
| O-15-15 | O | H | 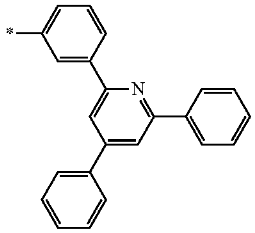 | 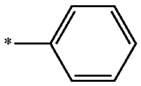 | — | — | — |

TABLE 44
| | | | | | | | |
|---|---|---|---|---|---|---|---|
| O-15-16 | O | H | 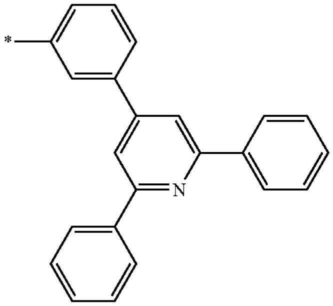 | H | — | — | — |
| O-15-17 | O | H | 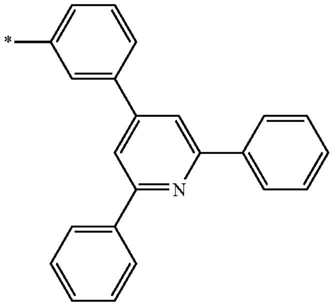 | 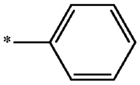 [SMILES: *c1ccccc1] | — | — | — |
| O-15-18 | O | H | 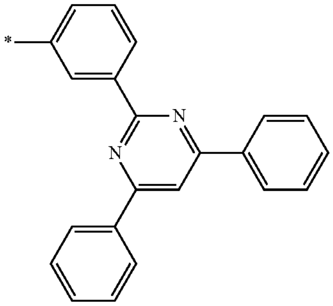 | H | — | — | — |
| O-15-19 | O | H | 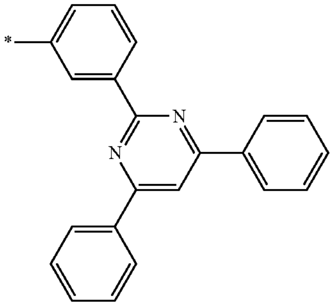 | 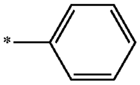 [SMILES: *c1ccccc1] | — | — | — |
| O-15-20 | O | H | 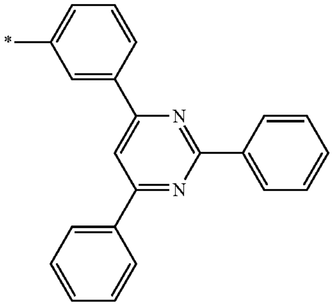 | H | — | — | — |

TABLE 44-continued
| | | | | | | | |
|---|---|---|---|---|---|---|---|
| O-15-21 | O | H | 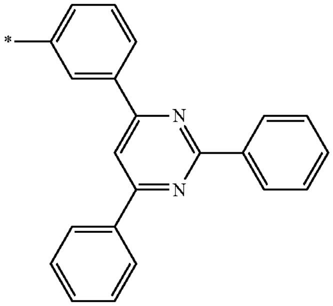 | 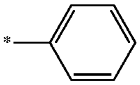 | — | — | — |
| O-15-22 | O | H | 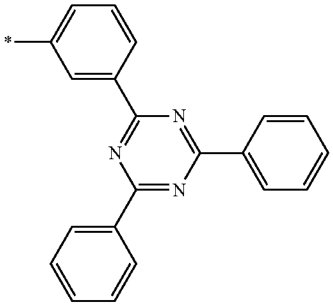 | H | — | — | — |
| O-15-23 | O | H | 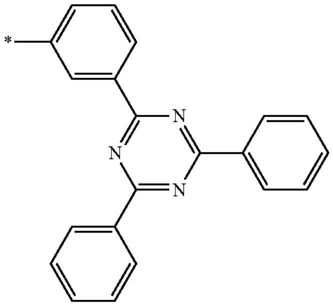 | 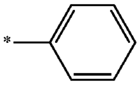 | — | — | — |
| O-15-24 | O | H | 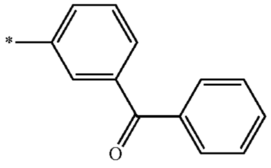 [SMILES: *c1cccc(C(=O)c2ccccc2)c1] | H | — | — | — |
| O-15-25 | O | H | 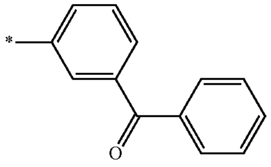 [SMILES: *c1cccc(C(=O)c2ccccc2)c1] | 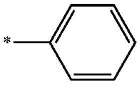 [SMILES: *c1ccccc1] | — | — | — |
| O-15-26 | O | H | 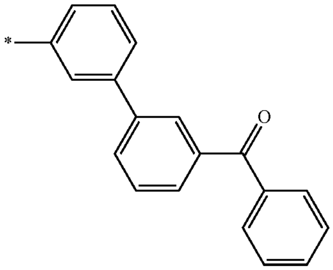 [SMILES: *c1cccc(-c2cccc(C(=O)c3ccccc3)c2)c1] | H | — | — | — |

TABLE 44-continued
| | | | | | |
|---|---|---|---|---|---|
| O-15-27 | O | H | 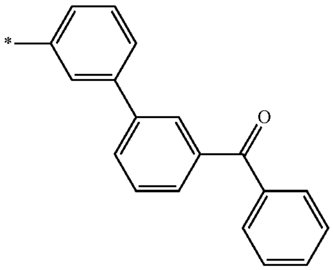 [SMILES: *c1cccc(-c2cccc(C(=O)c3ccccc3)c2)c1] | 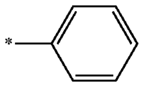 [SMILES: *c1ccccc1] | — — — |
| S-15-1 | S | H | H | H | — — — |
| S-15-2 | S | H | 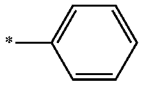 | 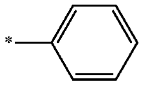 | — — — |
| S-15-3 | S | H | 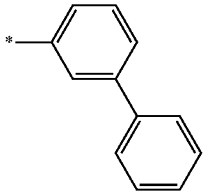 [SMILES: *c1cccc(-c2ccccc2)c1] | H | — — — |
TABLE 45
| | | | | | |
|---|---|---|---|---|---|
| S-15-4 | S | H | 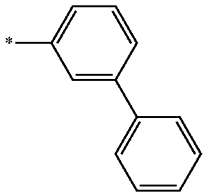 [SMILES: *c1cccc(-c2ccccc2)c1] | 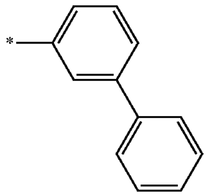 [SMILES: *c1cccc(-c2ccccc2)c1] | — — — |
| S-15-5 | S | 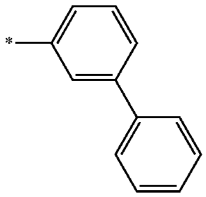 [SMILES: *c1cccc(-c2ccccc2)c1] | 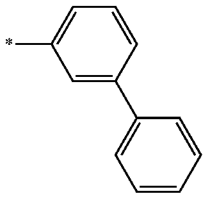 [SMILES: *c1cccc(-c2ccccc2)c1] | H | — — — |
| S-15-6 | S | H | 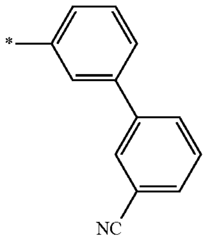 [SMILES: *c1cccc(-c2cccc(C#N)c2)c1] | H | — — — |
| S-15-7 | S | H | H | 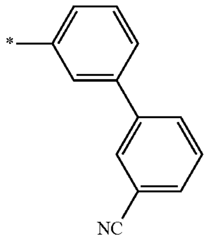 [SMILES: *c1cccc(-c2cccc(C#N)c2)c1] | — — — |

TABLE 45-continued
| | | | | | | | |
|---|---|---|---|---|---|---|---|
| S-15-8 | S | H | 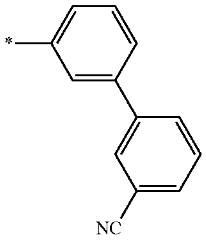 [SMILES: *c1cccc(-c2cccc(C#N)c2)c1] | 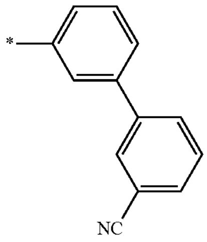 [SMILES: *c1cccc(-c2cccc(C#N)c2)c1] | — | — | — |
| S-15-9 | S | H | 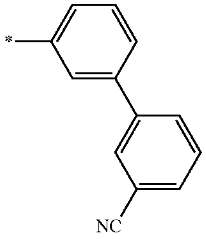 [SMILES: *c1cccc(-c2cccc(C#N)c2)c1] | 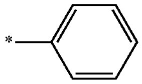 [SMILES: *c1ccccc1] | — | — | — |
| S-15-10 | S | H | 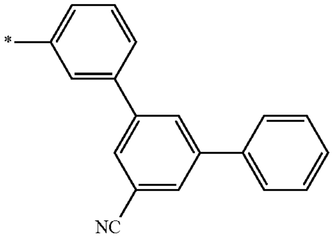 [SMILES: *c1cccc(-c2cc(C#N)cc(-c3ccccc3)c2)c1] | H | — | — | — |
| S-15-11 | S | H | 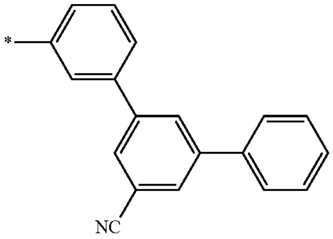 [SMILES: *c1cccc(-c2cc(C#N)cc(-c3ccccc3)c2)c1] | 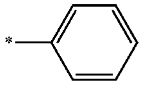 | — | — | — |
| S-15-12 | S | H | 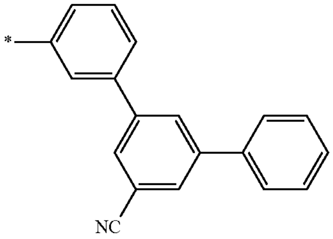 [SMILES: *c1cccc(-c2cc(C#N)cc(-c3ccccc3)c2)c1] | 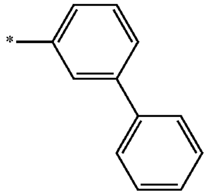 [SMILES: *c1cccc(-c2ccccc2)c1] | — | — | — |
| S-15-13 | S | 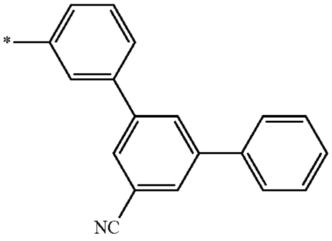 [SMILES: *c1cccc(-c2cc(C#N)cc(-c3ccccc3)c2)c1] | H | H | — | — | — |

TABLE 45-continued
| | | | | | | | |
|---|---|---|---|---|---|---|---|
| S-15-14 | S | H | 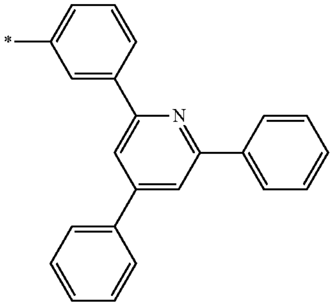 [SMILES: *c1cccc(-c2cc(-c3ccccc3)cc(-c3ccccc3)n2)c1] | H | — | — | — |
| S-15-15 | S | H | 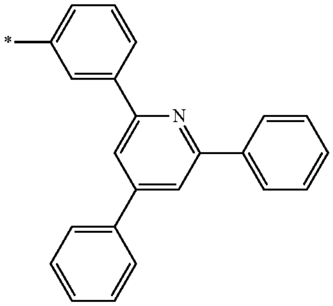 [SMILES: *c1cccc(-c2cc(-c3ccccc3)cc(-c3ccccc3)n2)c1] | 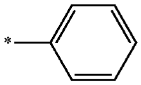 | — | — | — |
| S-15-16 | S | H | 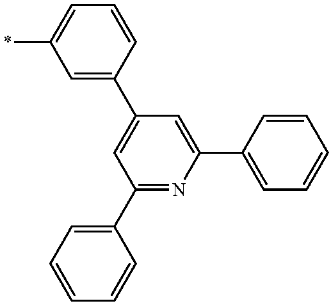 [SMILES: *c1cccc(-c2cc(-c3ccccc3)nc(-c3ccccc3)c2)c1] | H | — | — | — |
| S-15-17 | S | H | 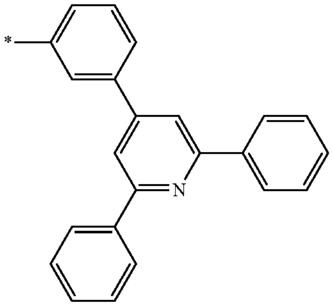 [SMILES: *c1cccc(-c2cc(-c3ccccc3)nc(-c3ccccc3)c2)c1] | 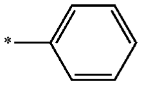 | — | — | — |
| S-15-18 | S | H | 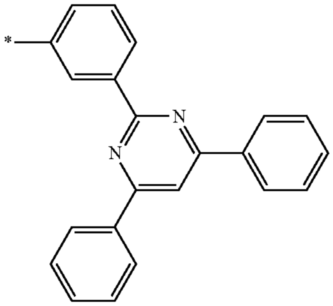 | H | — | — | — |

TABLE 46
| | | | | | | | |
|---|---|---|---|---|---|---|---|
| S-15-19 | S | H | 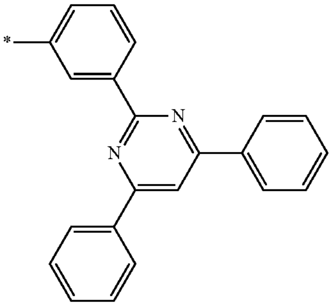 | 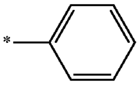 [SMILES: *c1ccccc1] | — | — | — |
| S-15-20 | S | H | 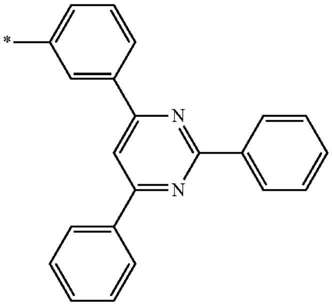 | H | — | — | — |
| S-15-21 | S | H | 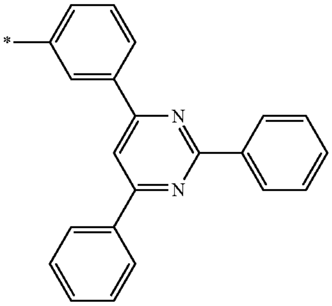 | 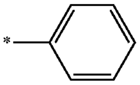 [SMILES: *c1ccccc1] | — | — | — |
| S-15-22 | S | H | 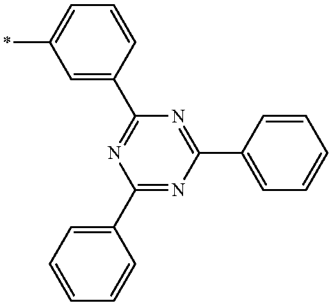 | H | — | — | — |
| S-15-23 | S | H | 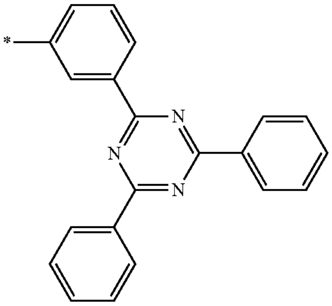 | 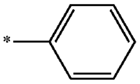 [SMILES: *c1ccccc1] | — | — | — |

TABLE 46-continued
| | | | | | | | |
|---|---|---|---|---|---|---|---|
| S-15-24 | S | H | 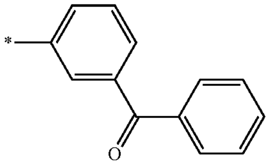 [SMILES: *c1cccc(C(=O)c2ccccc2)c1] | H | — | — | — |
| S-15-25 | S | H | 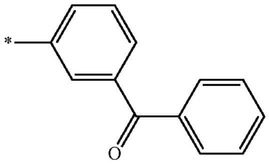 [SMILES: *c1cccc(C(=O)c2ccccc2)c1] | 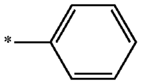 | — | — | — |
| S-15-26 | S | H | 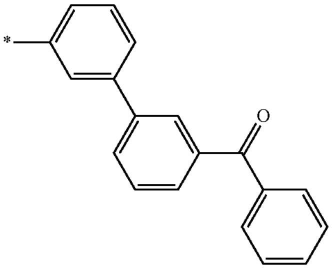 [SMILES: *c1cccc(-c2cccc(C(=O)c3ccccc3)c2)c1] | H | — | — | — |
| S-15-27 | S | H | 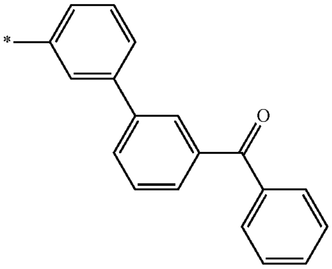 [SMILES: *c1cccc(-c2cccc(C(=O)c3ccccc3)c2)c1] | 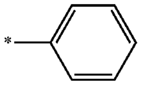 | — | — | — |
| N-15-1 | $NR^3$ | H | H | H | 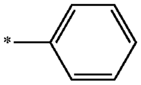 [SMILES: *c1ccccc1] | — | — |
| N-15-2 | $NR^3$ | H | 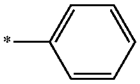 | 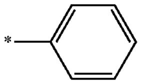 | 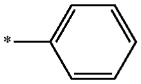 | — | — |
| N-15-3 | $NR^3$ | H | 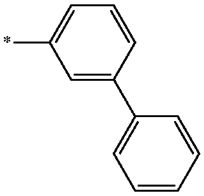 [SMILES: *c1cccc(-c2ccccc2)c1] | H | 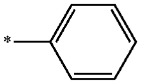 [SMILES: *c1ccccc1] | — | — |
| N-15-4 | $NR^3$ | H | 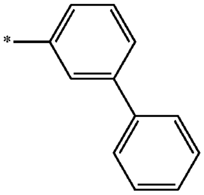 [SMILES: *c1cccc(-c2ccccc2)c1] | 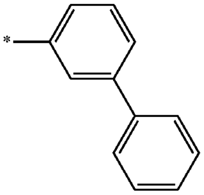 [SMILES: *c1cccc(-c2ccccc2)c1] | 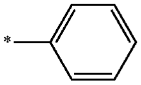 [SMILES: *c1ccccc1] | — | — |

TABLE 46-continued
| | | | | | | | |
|---|---|---|---|---|---|---|---|
| N-15-5 | $NR^3$ | H | 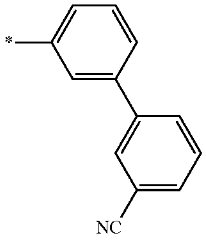 [SMILES: *c1cccc(-c2cccc(C#N)c2)c1] | H | 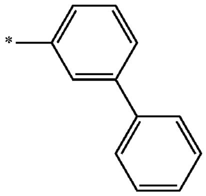 [SMILES: *c1cccc(-c2ccccc2)c1] | — | — |
| N-15-6 | $NR^3$ | H | H | 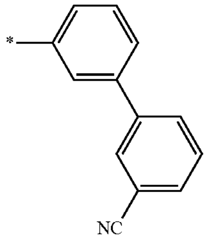 [SMILES: *c1cccc(-c2cccc(C#N)c2)c1] | 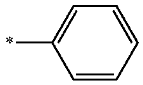 | — | — |
TABLE 47
| | | | | | | | |
|---|---|---|---|---|---|---|---|
| N-15-7 | $NR^3$ | H | 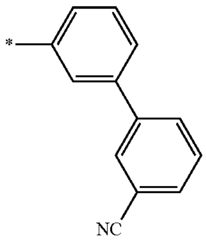 [SMILES: *c1cccc(-c2cccc(C#N)c2)c1] | 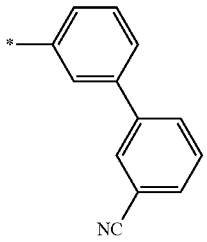 [SMILES: *c1cccc(-c2cccc(C#N)c2)c1] | 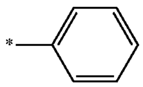 [SMILES: *c1ccccc1] | — | — |
| N-15-8 | $NR^3$ | H | 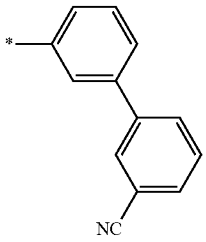 [SMILES: *c1cccc(-c2cccc(C#N)c2)c1] | 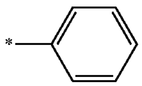 [SMILES: *c1ccccc1] | 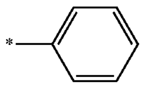 [SMILES: *c1ccccc1] | — | — |
| N-15-9 | $NR^3$ | H | 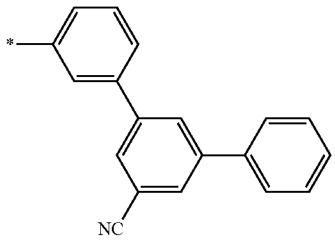 [SMILES: *c1cccc(-c2cc(C#N)cc(-c3ccccc3)c2)c1] | H | 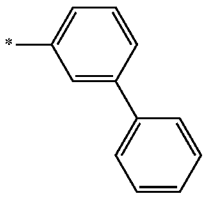 [SMILES: *c1cccc(-c2ccccc2)c1] | — | — |
| N-15-10 | $NR^3$ | H | 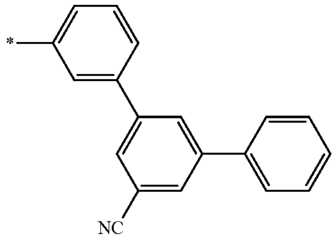 [SMILES: *c1cccc(-c2cc(C#N)cc(-c3ccccc3)c2)c1] | 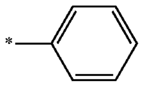 [SMILES: *c1ccccc1] | 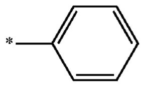 [SMILES: *c1ccccc1] | — | — |

TABLE 47-continued
| | | | | | | | |
|---|---|---|---|---|---|---|---|
| N-15-11 | $NR^3$ | H | 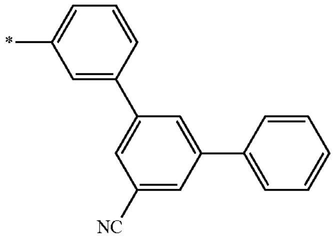 [SMILES: *c1cccc(-c2cc(C#N)cc(-c3ccccc3)c2)c1] | 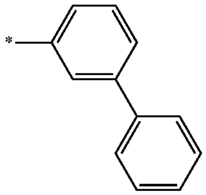 [SMILES: *c1cccc(-c2ccccc2)c1] | 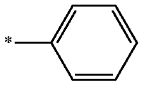 [SMILES: *c1ccccc1] | — | — |
| N-15-12 | $NR^3$ | H | 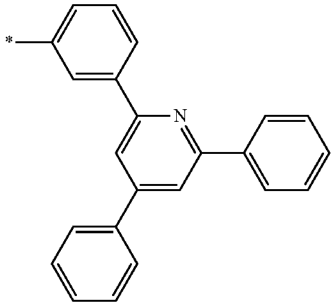 [SMILES: *c1cccc(-c2cc(-c3ccccc3)cc(-c3ccccc3)n2)c1] | H | 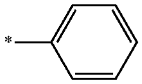 | — | — |
| N-15-13 | $NR^3$ | H | 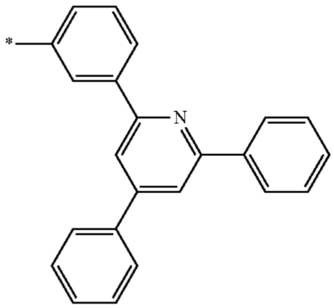 | 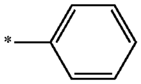 | 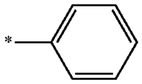 | — | — |
| N-15-14 | $NR^3$ | H | 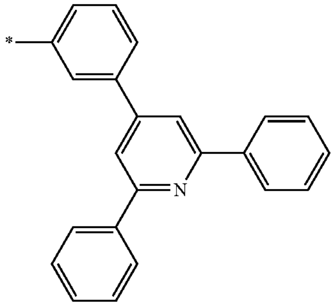 | H | 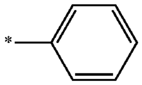 [SMILES: *c1ccccc1] | — | — |
| N-15-15 | $NR^3$ | H | 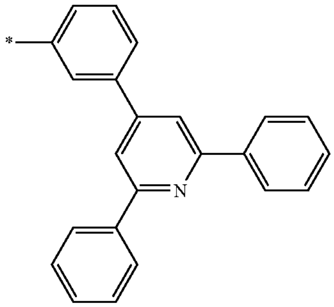 | 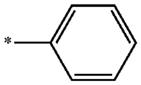 | 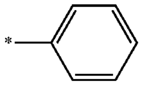 [SMILES: *c1ccccc1] | — | — |

TABLE 47-continued
| | | | | | | | |
|---|---|---|---|---|---|---|---|
| N-15-16 | $NR^3$ | H | 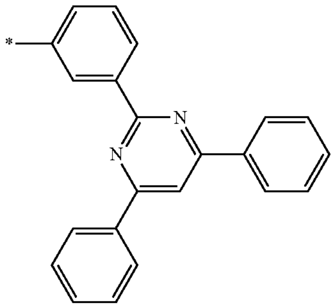 | H | 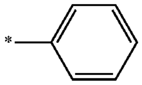 | — | — |
| N-15-17 | $NR^3$ | H | 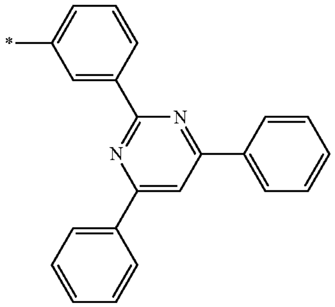 | 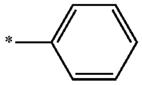 [SMILES: *c1ccccc1] | 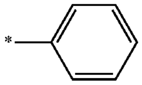 [SMILES: *c1ccccc1] | — | — |
| N-15-18 | $NR^3$ | H | 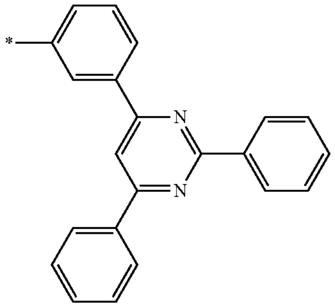 | H | 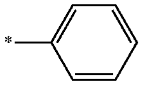 | — | — |
| N-15-19 | $NR^3$ | H | 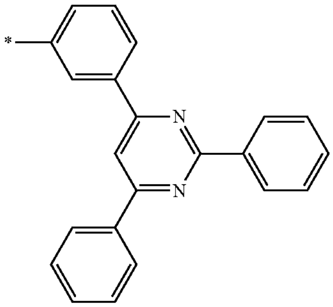 | 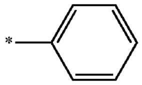 [SMILES: *c1ccccc1] | 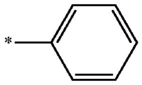 [SMILES: *c1ccccc1] | — | — |
| N-15-20 | $NR^3$ | H | 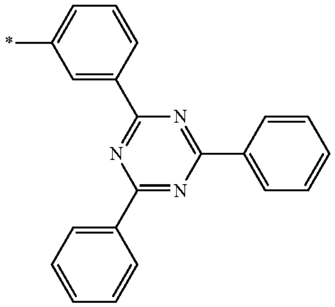 | H | 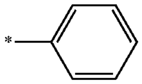 [SMILES: *c1ccccc1] | — | — |

TABLE 47-continued
| | | | | | | | |
|---|---|---|---|---|---|---|---|
| N-15-21 | $NR^3$ | H | 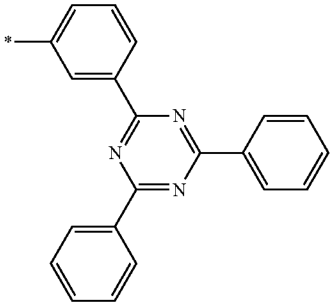 | 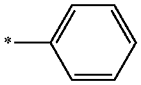 [SMILES: *c1ccccc1] | 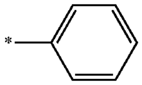 [SMILES: *c1ccccc1] | — | — |
TABLE 48
| | | | | | | | |
|---|---|---|---|---|---|---|---|
| N-15-22 | $NR^3$ | H | 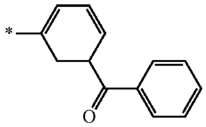 [SMILES: *C1=CC=CC(C(=O)c2ccccc2)C1] | H | 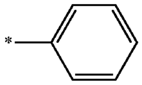 [SMILES: *c1ccccc1] | — | — |
| N-15-23 | $NR^3$ | H | 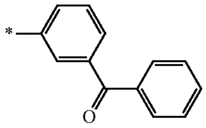 [SMILES: *c1cccc(C(=O)c2ccccc2)c1] | 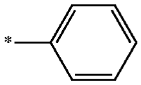 [SMILES: *c1ccccc1] | 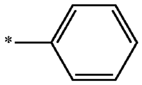 [SMILES: *c1ccccc1] | — | — |
| N-15-24 | $NR^3$ | H | 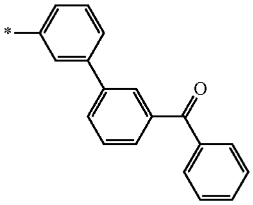 [SMILES: *c1cccc(-c2cccc(C(=O)c3ccccc3)c2)c1] | H | 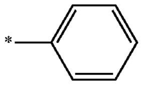 [SMILES: *c1ccccc1] | — | — |
| N-15-25 | $NR^3$ | H | 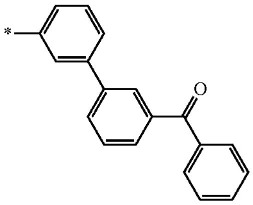 [SMILES: *c1cccc(-c2cccc(C(=O)c3ccccc3)c2)c1] | 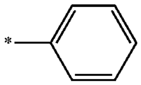 | 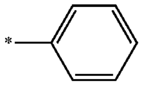 [SMILES: *c1ccccc1] | — | — |
| C-15-1 | $CR^1R^2$ | H | H | H | — | *—Me | *—Me |
| C-15-2 | $CR^1R^2$ | H | 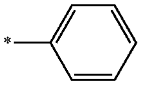 [SMILES: *c1ccccc1] | 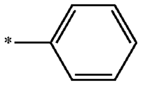 [SMILES: *c1ccccc1] | — | *—Me | *—Me |
| C-15-3 | $CR^1R^2$ | H | 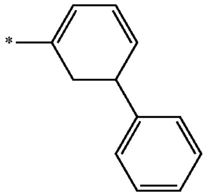 [SMILES: *C1=CC=CC(c2ccccc2)C1] | H | — | *—Me | *—Me |

TABLE 48-continued
| | | | | | | | |
|---|---|---|---|---|---|---|---|
| C-15-4 | $CR^1R^2$ | H | 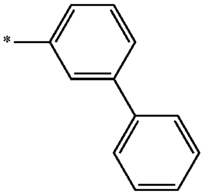 [SMILES: *c1cccc(-c2ccccc2)c1] | 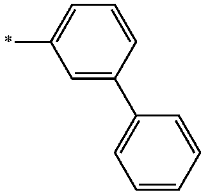 [SMILES: *c1cccc(-c2ccccc2)c1] | — | *—Me | *—Me |
| C-15-5 | $CR^1R^2$ | H | 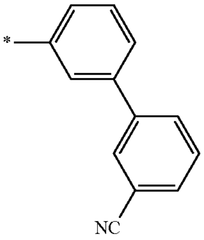 [SMILES: *c1cccc(-c2cccc(C#N)c2)c1] | H | — | 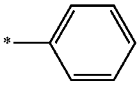 [SMILES: *c1ccccc1] | 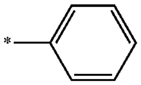 [SMILES: *c1ccccc1] |
| C-15-6 | $CR^1R^2$ | H | H | 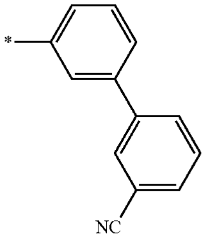 [SMILES: *c1cccc(-c2cccc(C#N)c2)c1] | — | *—Me | *—Me |
| C-15-7 | $CR^1R^2$ | H | 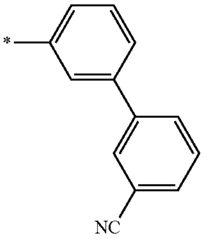 [SMILES: *c1cccc(-c2cccc(C#N)c2)c1] | 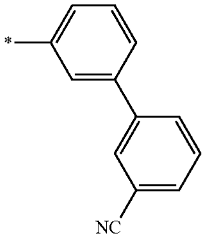 [SMILES: *c1cccc(-c2cccc(C#N)c2)c1] | — | 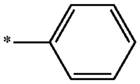 [SMILES: *c1ccccc1] | 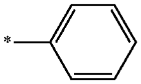 [SMILES: *c1ccccc1] |
| C-15-8 | $CR^1R^2$ | H | 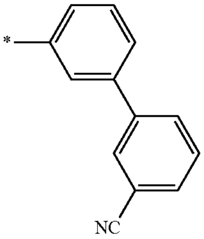 [SMILES: *c1cccc(-c2cccc(C#N)c2)c1] | 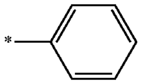 | — | *—Me | *—Me |
| C-15-9 | $CR^1R^2$ | H | 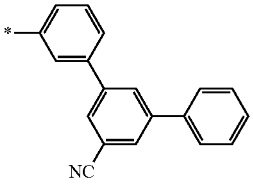 [SMILES: *c1cccc(-c2cc(C#N)cc(-c3ccccc3)c2)c1] | H | — | 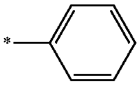 [SMILES: *c1ccccc1] | 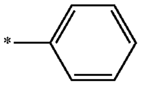 [SMILES: *c1ccccc1] |
| C-15-10 | $CR^1R^2$ | H | 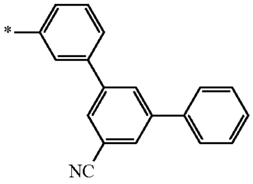 [SMILES: *c1cccc(-c2cc(C#N)cc(-c3ccccc3)c2)c1] | 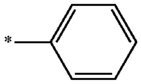 [SMILES: *c1ccccc1] | — | *—Me | *—Me |

TABLE 48-continued
| | | | | | | | |
|---|---|---|---|---|---|---|---|
| C-15-11 | $CR^1R^2$ | H | 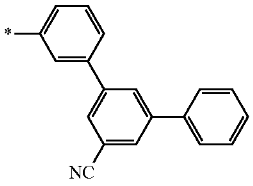 [SMILES: *c1cccc(-c2cc(C#N)cc(-c3ccccc3)c2)c1] | 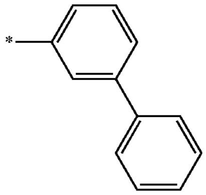 [SMILES: *c1cccc(-c2ccccc2)c1] | — | *—Me | *—Me |
TABLE 49
| | | | | | | | |
|---|---|---|---|---|---|---|---|
| C-15-12 | $CR^1R^2$ | H | 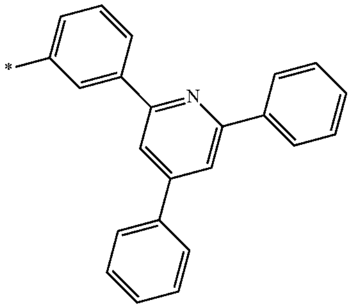 [SMILES: *c1cccc(-c2cc(-c3ccccc3)cc(-c3ccccc3)n2)c1] | H | — | *—Me | *—Me |
| C-15-13 | $CR^1R^2$ | H | 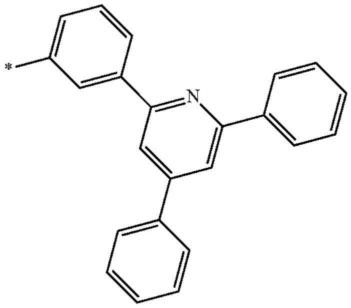 [SMILES: *c1cccc(-c2cc(-c3ccccc3)cc(-c3ccccc3)n2)c1] | 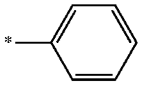 [SMILES: *c1ccccc1] | — | *—Me | *—Me |
| C-15-14 | $CR^1R^2$ | H | 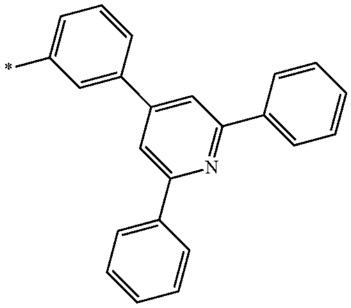 [SMILES: *c1cccc(-c2cc(-c3ccccc3)nc(-c3ccccc3)c2)c1] | H | — | *—Me | *—Me |
| C-15-15 | $CR^1R^2$ | H | 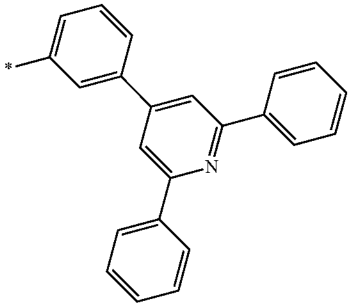 [SMILES: *c1cccc(-c2cc(-c3ccccc3)nc(-c3ccccc3)c2)c1] | 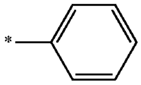 [SMILES: *c1ccccc1] | — | *—Me | *—Me |

TABLE 49-continued
| | | | | | | | |
|---|---|---|---|---|---|---|---|
| C-15-16 | $CR^1R^2$ | H | 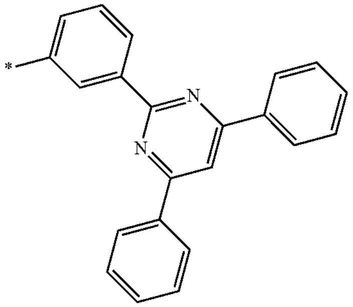 [SMILES: *c1cccc(-c2nc(-c3ccccc3)cc(-c3ccccc3)n2)c1] | H | — | 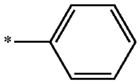 [SMILES: *c1ccccc1] | 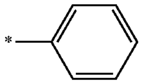 [SMILES: *c1ccccc1] |
| C-15-17 | $CR^1R^2$ | H | 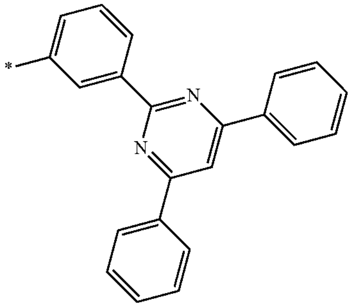 [SMILES: *c1cccc(-c2nc(-c3ccccc3)cc(-c3ccccc3)n2)c1] | 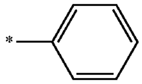 [SMILES: *c1ccccc1] | — | *—Me | *—Me |
| C-15-18 | $CR^1R^2$ | H | 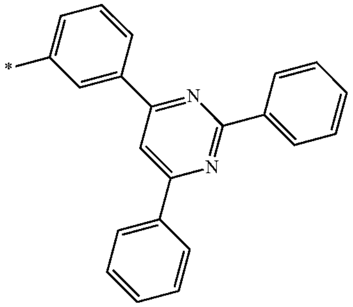 [SMILES: *c1cccc(-c2cc(-c3ccccc3)nc(-c3ccccc3)n2)c1] | H | — | *—Me | *—Me |
| C-15-19 | $CR^1R^2$ | H | 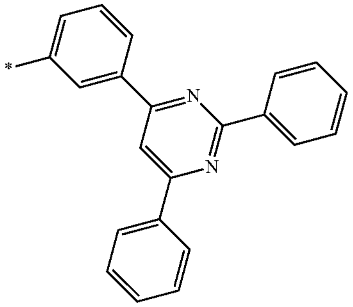 [SMILES: *c1cccc(-c2cc(-c3ccccc3)nc(-c3ccccc3)n2)c1] | 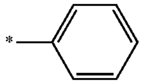 [SMILES: *c1ccccc1] | — | *—Me | *—Me |
| C-15-20 | $CR^1R^2$ | H | 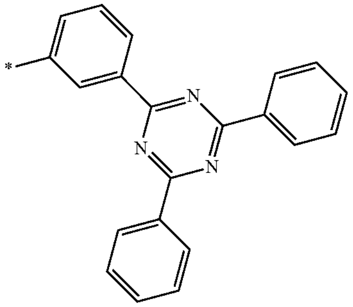 [SMILES: *c1cccc(-c2nc(-c3ccccc3)nc(-c3ccccc3)n2)c1] | H | — | *—Me | *—Me |

TABLE 49-continued
| | | | | | | | |
|---|---|---|---|---|---|---|---|
| C-15-21 | $CR^1R^2$ | H | 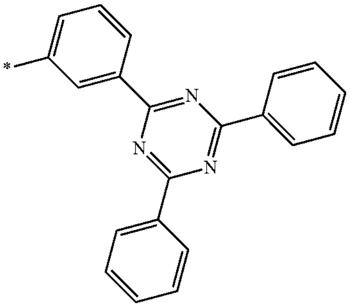 [SMILES: *c1cccc(-c2nc(-c3ccccc3)nc(-c3ccccc3)n2)c1] | 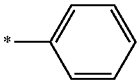 [SMILES: *c1ccccc1] | — | *—Me | *—Me |
| C-15-22 | $CR^1R^2$ | H | 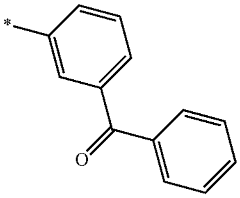 [SMILES: *c1cccc(C(=O)c2ccccc2)c1] | H | — | *—Me | *—Me |
| C-15-23 | $CR^1R^2$ | H | 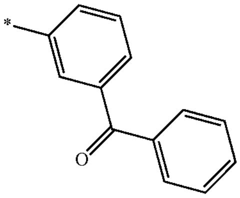 [SMILES: *c1cccc(C(=O)c2ccccc2)c1] | 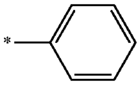 [SMILES: *c1ccccc1] | — | 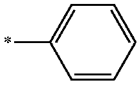 [SMILES: *c1ccccc1] | 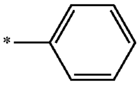 [SMILES: *c1ccccc1] |
| C-15-24 | $CR^1R^2$ | H | 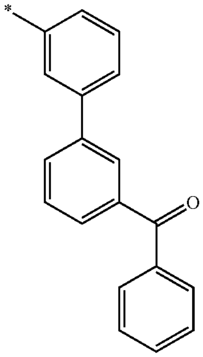 [SMILES: *c1cccc(-c2cccc(C(=O)c3ccccc3)c2)c1] | H | — | *—Me | *—Me |
| C-15-25 | $CR^1R^2$ | H | 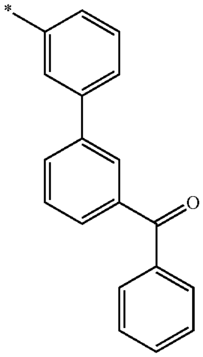 [SMILES: *c1cccc(-c2cccc(C(=O)c3ccccc3)c2)c1] | 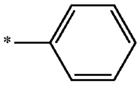 [SMILES: *c1ccccc1] | — | *—Me | *—Me |

In the following general formula (16), $R^{G1}$, $R^{G3}$, $R^{G4}$, $R^{G5}$, $R^{G8}$, $R^{G9}$, $R^{G11}$, and $R^{G12}$ to $R^{G14}$ each represent a hydrogen atom, and the other groups are the groups described in Tables below.
[Chem. 21]
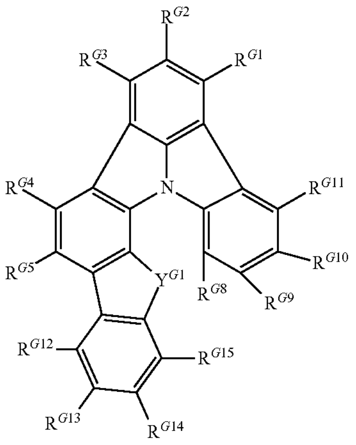
(16)
TABLE 50
| Compound No. | $Y^{G1}$ | $R^{G15}$ | $R^{G10}$ | $R^{G2}$ | $R^3$ | $R^1$ | $R^2$ |
|---|---|---|---|---|---|---|---|
| O-16-1 | O | H | H | H | — | — | — |
| O-16-2 | O | H | 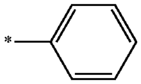 [SMILES: *c1ccccc1] | 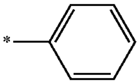 [SMILES: *c1ccccc1] | — | — | — |
| O-16-3 | O | H | 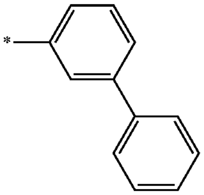 [SMILES: *c1cccc(-c2ccccc2)c1] | H | — | — | — |
| O-16-4 | O | H | 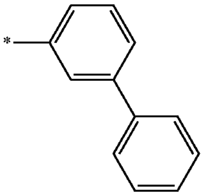 [SMILES: *c1cccc(-c2ccccc2)c1] | 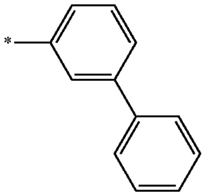 [SMILES: *c1cccc(-c2ccccc2)c1] | — | — | — |
| O-16-5 | O | 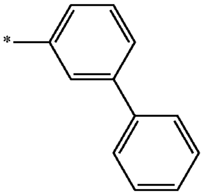 [SMILES: *c1cccc(-c2ccccc2)c1] | 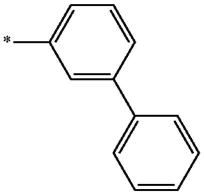 [SMILES: *c1cccc(-c2ccccc2)c1] | H | — | — | — |

TABLE 50-continued
| Compound No. | $Y^{G1}$ | $R^{G15}$ | $R^{G10}$ | $R^{G2}$ | $R^3$ | $R^1$ | $R^2$ |
|---|---|---|---|---|---|---|---|
| O-16-7 | O | H | H | 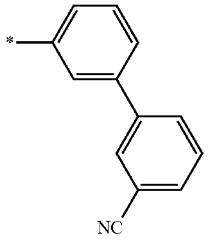 [SMILES: *c1cccc(-c2cccc(C#N)c2)c1] | — | — | — |
| O-16-8 | O | H | 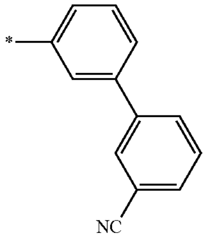 | 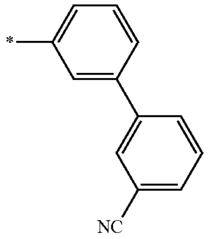 [SMILES: *c1cccc(-c2cccc(C#N)c2)c1] | — | — | — |
| O-16-9 | O | H | 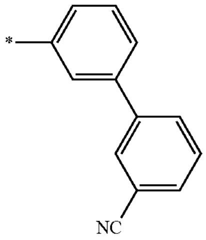 [SMILES: *c1cccc(-c2cccc(C#N)c2)c1] | 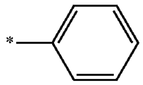 [SMILES: *c1ccccc1] | — | — | — |
| O-16-10 | O | H | 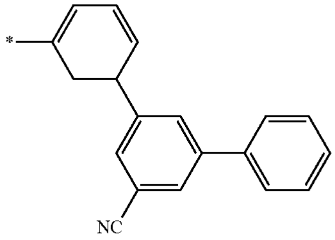 | H | — | — | — |
| O-16-11 | O | H | 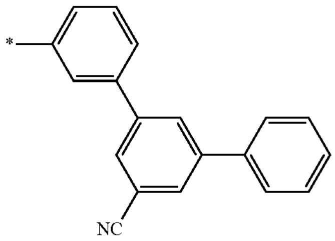 [SMILES: *c1cccc(-c2cc(C#N)cc(-c3ccccc3)c2)c1] | 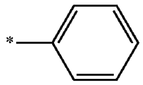 [SMILES: *c1ccccc1] | — | — | — |
| O-16-12 | O | H | 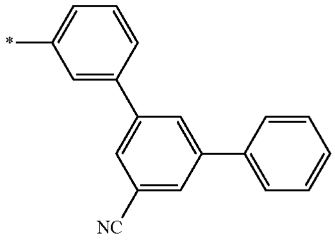 [SMILES: *c1cccc(-c2cc(C#N)cc(-c3ccccc3)c2)c1] | 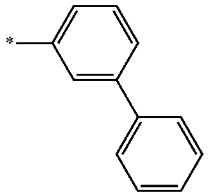 [SMILES: *c1cccc(-c2ccccc2)c1] | — | — | — |

TABLE 50-continued
| Compound No. | $Y^{G1}$ | $R^{G15}$ | $R^{G10}$ | $R^{G2}$ | $R^3$ | $R^1$ | $R^2$ |
|---|---|---|---|---|---|---|---|
| O-16-13 | O | 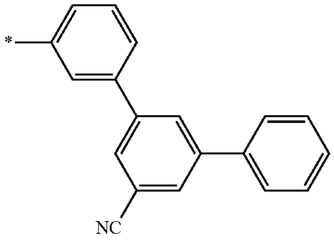 [SMILES: *c1cccc(-c2cc(C#N)cc(-c3ccccc3)c2)c1] | H | H | — | — | — |
| O-16-14 | O | H | 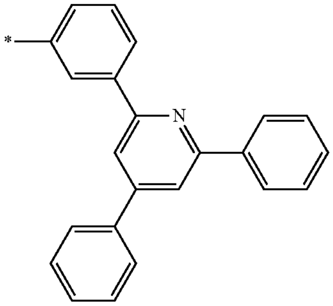 | H | — | — | — |
| O-16-15 | O | H | 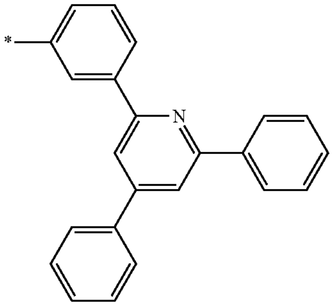 | 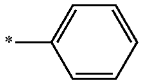 | — | — | — |
TABLE 51
| | | | | | | | |
|---|---|---|---|---|---|---|---|
| O-16-16 | O | H | 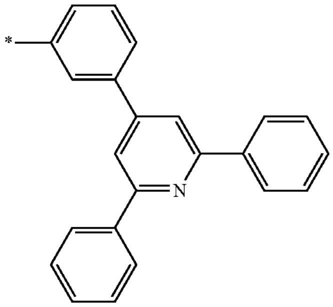 [SMILES: *c1cccc(-c2cc(-c3ccccc3)nc(-c3ccccc3)c2)c1] | H | — | — | — |

TABLE 51-continued
| | | | | | | | |
|---|---|---|---|---|---|---|---|
| O-16-17 | O | H | 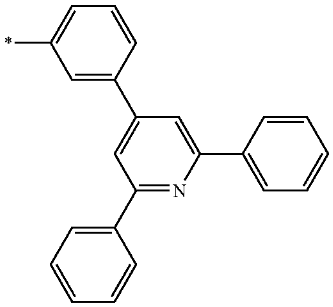 [SMILES: *c1cccc(-c2cc(-c3ccccc3)nc(-c3ccccc3)c2)c1] | 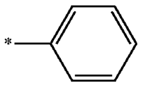 [SMILES: *c1ccccc1] | — | — | — |
| O-16-18 | O | H | 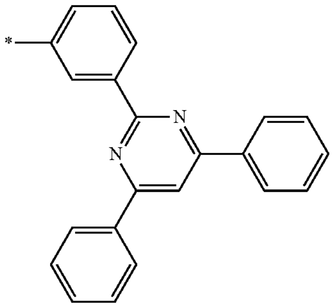 [SMILES: *c1cccc(-c2nc(-c3ccccc3)cc(-c3ccccc3)n2)c1] | H | — | — | — |
| O-16-19 | O | H | 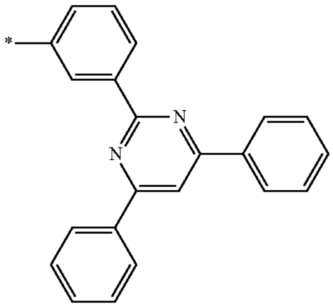 [SMILES: *c1cccc(-c2nc(-c3ccccc3)cc(-c3ccccc3)n2)c1] | 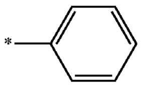 | — | — | — |
| O-16-20 | O | H | 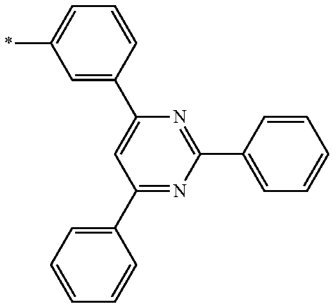 [SMILES: *c1cccc(-c2cc(-c3ccccc3)nc(-c3ccccc3)n2)c1] | H | — | — | — |
| O-16-21 | O | H | 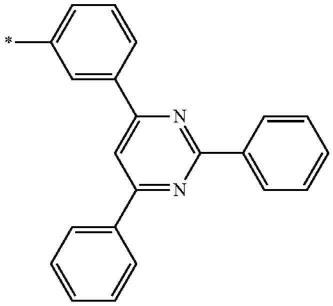 | 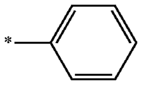 | — | — | — |

TABLE 51-continued
| | | | | | | | |
|---|---|---|---|---|---|---|---|
| O-16-22 | O | H | 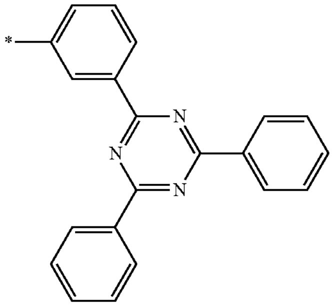 [SMILES: *c1cccc(-c2nc(-c3ccccc3)nc(-c3ccccc3)n2)c1] | H | — | — | — |
| O-16-23 | O | H | 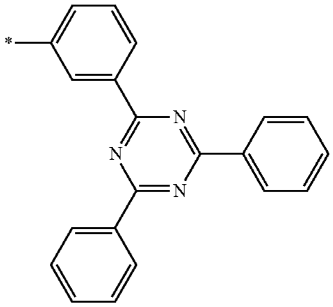 | 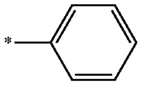 [SMILES: *c1ccccc1] | — | — | — |
| O-16-24 | O | H | 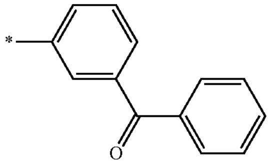 [SMILES: *c1cccc(C(=O)c2ccccc2)c1] | H | — | — | — |
| O-16-25 | O | H | 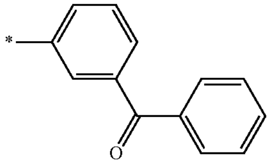 [SMILES: *c1cccc(C(=O)c2ccccc2)c1] | 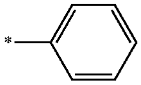 [SMILES: *c1ccccc1] | — | — | — |
| O-16-26 | O | H | 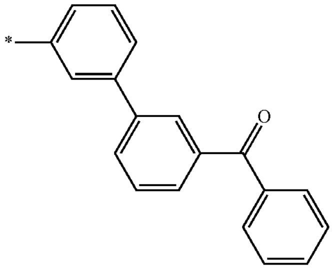 [SMILES: *c1cccc(-c2cccc(C(=O)c3ccccc3)c2)c1] | H | — | — | — |
| O-16-27 | O | H | 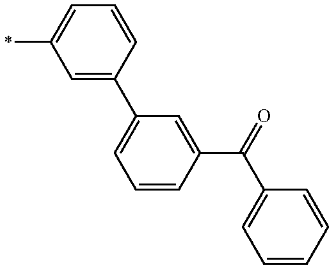 [SMILES: *c1cccc(-c2cccc(C(=O)c3ccccc3)c2)c1] | 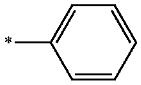 | — | — | — |
| S-16-1 | S | H | H | H | — | — | — |

TABLE 51-continued
| | | | | | | | |
|---|---|---|---|---|---|---|---|
| S-16-2 | S | H | 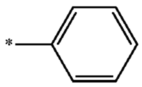 [SMILES: *c1ccccc1] | 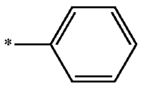 [SMILES: *c1ccccc1] | — | — | — |
| S-16-3 | S | H | 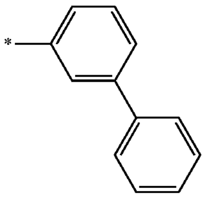 [SMILES: *c1cccc(-c2ccccc2)c1] | H | — | — | — |
TABLE 52
| | | | | | | | |
|---|---|---|---|---|---|---|---|
| S-16-4 | S | H | 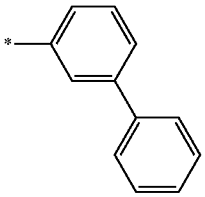 [SMILES: *c1cccc(-c2ccccc2)c1] | 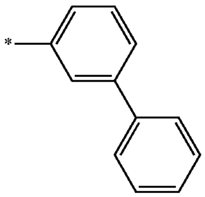 [SMILES: *c1cccc(-c2ccccc2)c1] | — | — | — |
| S-16-5 | S | 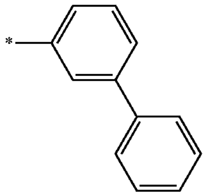 [SMILES: *c1cccc(-c2ccccc2)c1] | 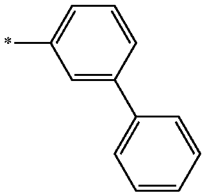 [SMILES: *c1cccc(-c2ccccc2)c1] | H | — | — | — |
| S-16-6 | S | H | 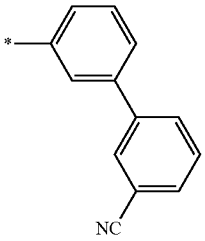 [SMILES: *c1cccc(-c2cccc(C#N)c2)c1] | H | — | — | — |
| S-16-7 | S | H | H | 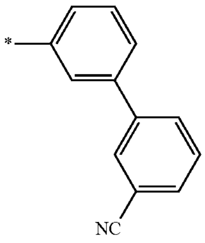 [SMILES: *c1cccc(-c2cccc(C#N)c2)c1] | — | — | — |
| S-16-8 | S | H | 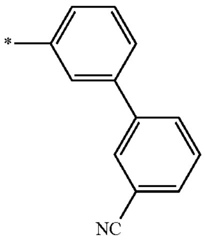 [SMILES: *c1cccc(-c2cccc(C#N)c2)c1] | 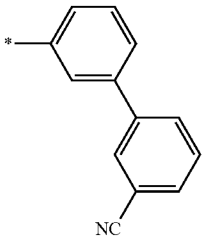 [SMILES: *c1cccc(-c2cccc(C#N)c2)c1] | — | — | — |

TABLE 52-continued
| | | | | | | | |
|---|---|---|---|---|---|---|---|
| S-16-9 | S | H | 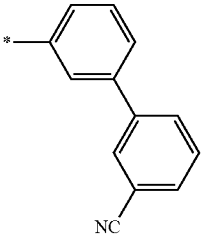 [SMILES: *c1cccc(-c2cccc(C#N)c2)c1] | 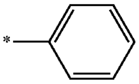 [SMILES: *c1ccccc1] | — | — | — |
| S-16-10 | S | H | 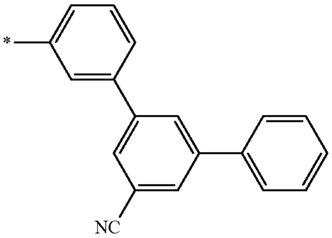 [SMILES: *c1cccc(-c2cc(C#N)cc(-c3ccccc3)c2)c1] | H | — | — | — |
| S-16-11 | S | H | 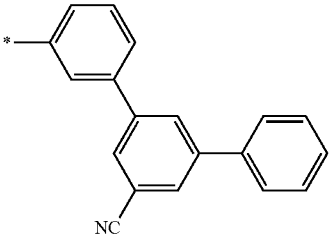 [SMILES: *c1cccc(-c2cc(C#N)cc(-c3ccccc3)c2)c1] | 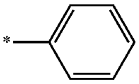 [SMILES: *c1ccccc1] | — | — | — |
| S-16-12 | S | H | 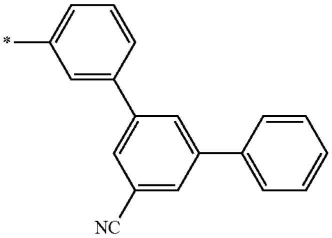 [SMILES: *c1cccc(-c2cc(C#N)cc(-c3ccccc3)c2)c1] | 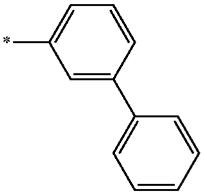 [SMILES: *c1cccc(-c2ccccc2)c1] | — | — | — |
| S-16-13 | S | 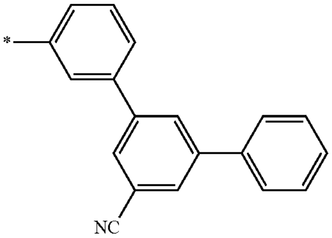 [SMILES: *c1cccc(-c2cc(C#N)cc(-c3ccccc3)c2)c1] | H | H | — | — | — |
| S-16-14 | S | H | 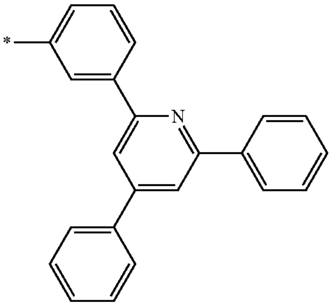 [SMILES: *c1cccc(-c2cc(-c3ccccc3)cc(-c3ccccc3)n2)c1] | H | — | — | — |

TABLE 52-continued
| | | | | | | | |
|---|---|---|---|---|---|---|---|
| S-16-15 | S | H | 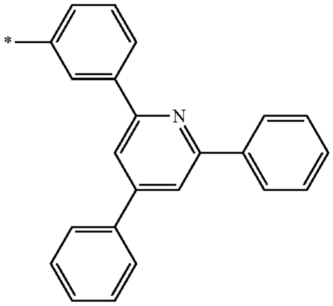 | 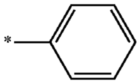 | — | — | — |
| S-16-16 | S | H | 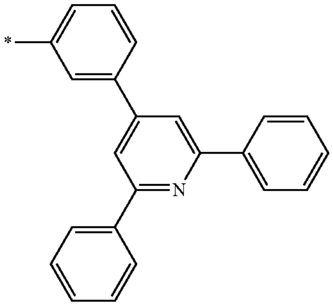 [SMILES: *c1cccc(-c2cc(-c3ccccc3)nc(-c3ccccc3)c2)c1] | H | — | — | — |
| S-16-17 | S | H | 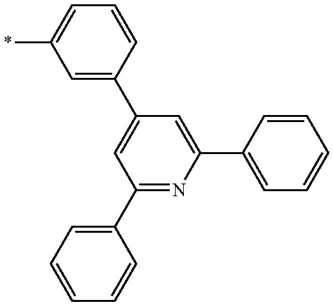 [SMILES: *c1cccc(-c2cc(-c3ccccc3)nc(-c3ccccc3)c2)c1] | 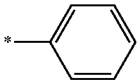 [SMILES: *c1ccccc1] | — | — | — |
| S-16-18 | S | H | 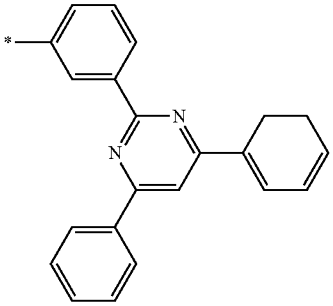 [SMILES: *c1cccc(-c2nc(C3=CC=CCC3)cc(-c3ccccc3)n2)c1] | H | — | — | — |
TABLE 53
| | | | | | | | |
|---|---|---|---|---|---|---|---|
| S-16-19 | S | H | 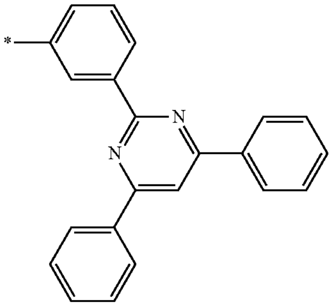 | 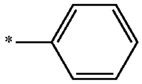 [SMILES: *c1ccccc1] | — | — | — |

TABLE 53-continued
| | | | | | | | |
|---|---|---|---|---|---|---|---|
| S-16-20 | S | H | 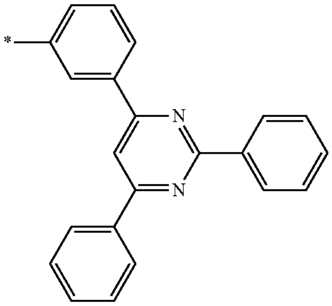 | H | — | — | — |
| S-16-21 | S | H | 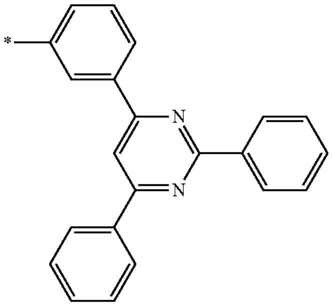 [SMILES: *c1cccc(-c2cc(-c3ccccc3)nc(-c3ccccc3)n2)c1] | 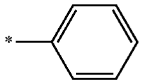 [SMILES: *c1ccccc1] | — | — | — |
| S-16-22 | S | H | 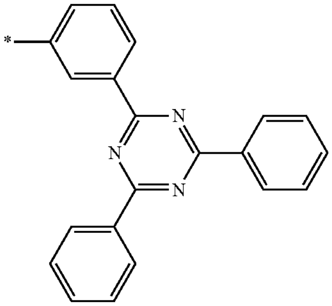 | H | — | — | — |
| S-16-23 | S | H | 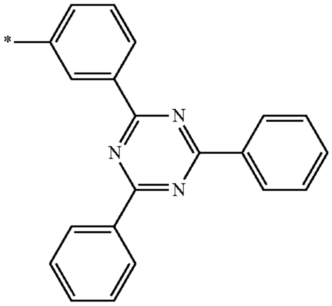 | 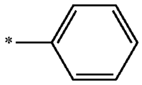 [SMILES: *c1ccccc1] | — | — | — |
| S-16-24 | S | H | 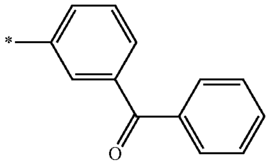 [SMILES: *c1cccc(C(=O)c2ccccc2)c1] | H | — | — | — |
| S-16-25 | S | H | 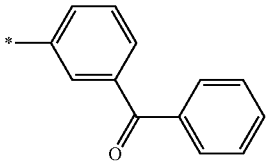 | 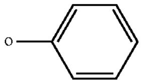 | — | — | — |

TABLE 53-continued
| | | | | | | | |
|---|---|---|---|---|---|---|---|
| S-16-26 | S | H | 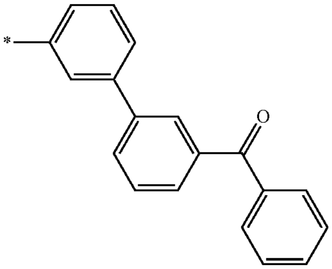 [SMILES: *c1cccc(-c2cccc(C(=O)c3ccccc3)c2)c1] | H | — | — | — |
| S-16-27 | S | H | 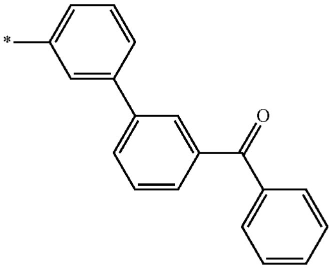 [SMILES: *c1cccc(-c2cccc(C(=O)c3ccccc3)c2)c1] | 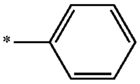 [SMILES: *c1ccccc1] | — | — | — |
| N-16-1 | $NR^3$ | H | H | H | 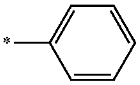 [SMILES: *c1ccccc1] | — | — |
| N-16-2 | $NR^3$ | H | 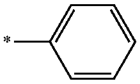 [SMILES: *c1ccccc1] | 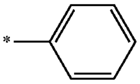 [SMILES: *c1ccccc1] | 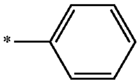 [SMILES: *c1ccccc1] | — | — |
| N-16-3 | $NR^3$ | H | 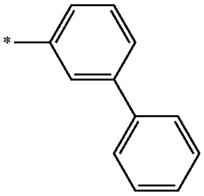 [SMILES: *c1cccc(-c2ccccc2)c1] | H | 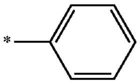 [SMILES: *c1ccccc1] | — | — |
| N-16-4 | $NR^3$ | H | 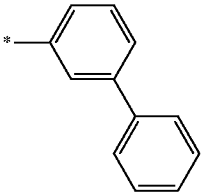 [SMILES: *c1cccc(-c2ccccc2)c1] | 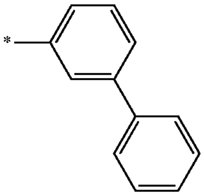 [SMILES: *c1cccc(-c2ccccc2)c1] | 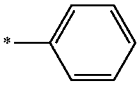 [SMILES: *c1ccccc1] | — | — |
| N-16-5 | $NR^3$ | H | 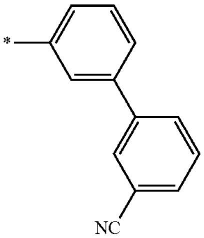 [SMILES: *c1cccc(-c2cccc(C#N)c2)c1] | H | 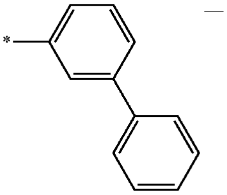 | — | — |

TABLE 53-continued
| | | | | | | | |
|---|---|---|---|---|---|---|---|
| N-16-6 | $NR^3$ | H | H | 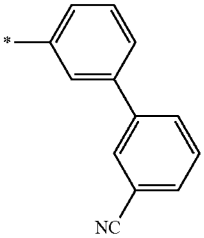 [SMILES: *c1cccc(-c2cccc(C#N)c2)c1] | 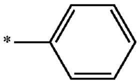 | — | — |
TABLE 54
| | | | | | | | |
|---|---|---|---|---|---|---|---|
| N-16-7 | $NR^3$ | H | 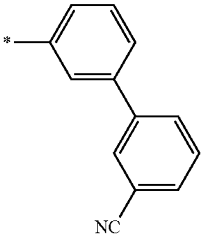 [SMILES: *c1cccc(-c2cccc(C#N)c2)c1] | 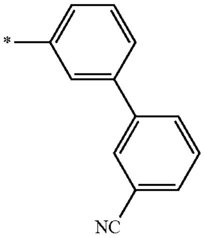 [SMILES: *c1cccc(-c2cccc(C#N)c2)c1] | 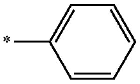 [SMILES: *c1ccccc1] | — | — |
| N-16-8 | $NR^3$ | H | 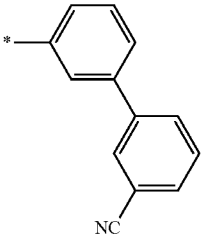 [SMILES: *c1cccc(-c2cccc(C#N)c2)c1] | 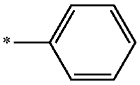 [SMILES: *c1ccccc1] | 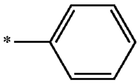 [SMILES: *c1ccccc1] | — | — |
| N-16-9 | $NR^3$ | H | 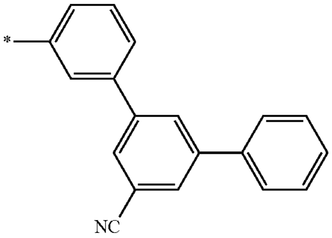 [SMILES: *c1cccc(-c2cc(C#N)cc(-c3ccccc3)c2)c1] | H | 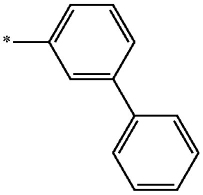 [SMILES: *c1cccc(-c2ccccc2)c1] | — | — |
| N-16-10 | $NR^3$ | H | 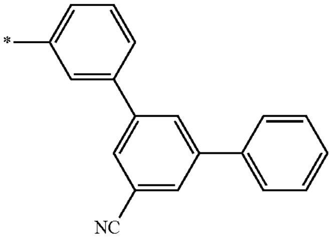 [SMILES: *c1cccc(-c2cc(C#N)cc(-c3ccccc3)c2)c1] | 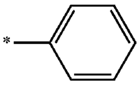 [SMILES: *c1ccccc1] | 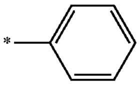 [SMILES: *c1ccccc1] | — | — |
| N-16-11 | $NR^3$ | H | 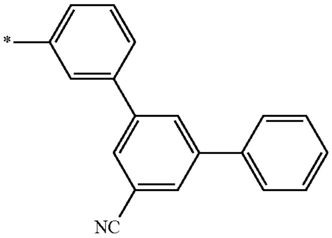 [SMILES: *c1cccc(-c2cc(C#N)cc(-c3ccccc3)c2)c1] | 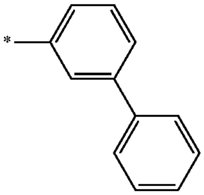 [SMILES: *c1cccc(-c2ccccc2)c1] | 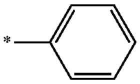 [SMILES: *c1ccccc1] | — | — |

TABLE 54-continued
| | | | | | | | |
|---|---|---|---|---|---|---|---|
| N-16-12 | $NR^3$ | H | 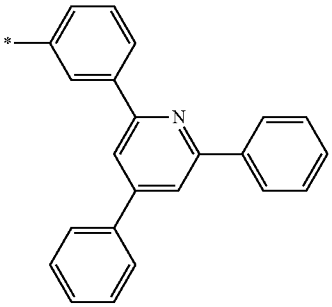 | H | 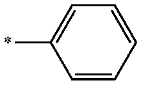 | — | — |
| N-16-13 | $NR^3$ | H | 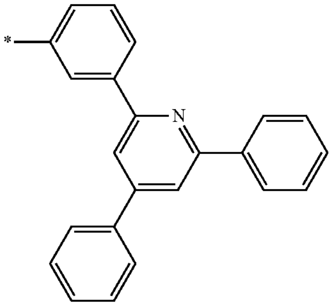 | 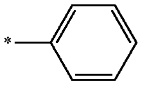 [SMILES: *c1ccccc1] | 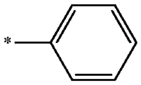 [SMILES: *c1ccccc1] | — | — |
| N-16-14 | $NR^3$ | H | 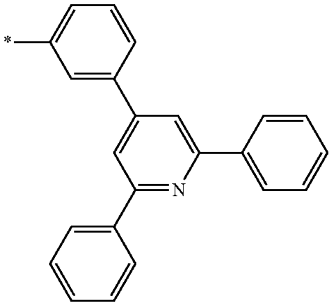 | H | 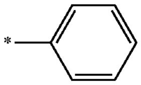 [SMILES: *c1ccccc1] | — | — |
| N-16-15 | $NR^3$ | H | 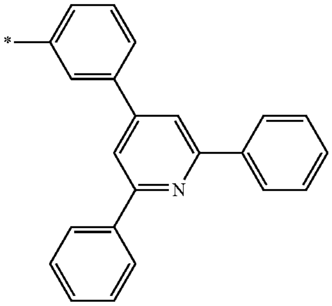 [SMILES: *c1cccc(-c2cc(-c3ccccc3)nc(-c3ccccc3)c2)c1] | 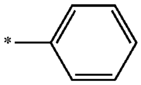 | 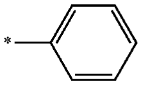 | — | — |
| N-16-16 | $NR^3$ | H | 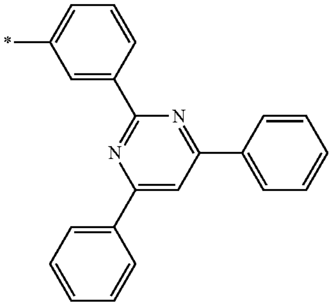 [SMILES: *c1cccc(-c2nc(-c3ccccc3)cc(-c3ccccc3)n2)c1] | H | 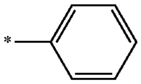 [SMILES: *c1ccccc1] | — | — |

TABLE 54-continued
| | | | | | | | |
|---|---|---|---|---|---|---|---|
| N-16-17 | $NR^3$ | H | 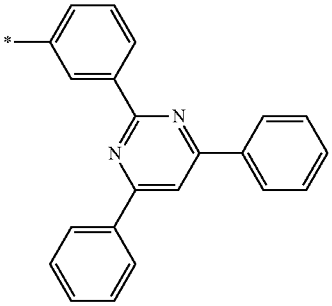 | 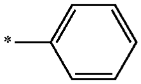 [SMILES: *c1ccccc1] | 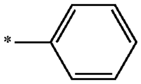 [SMILES: *c1ccccc1] | — | — |
| N-16-18 | $NR^3$ | H | 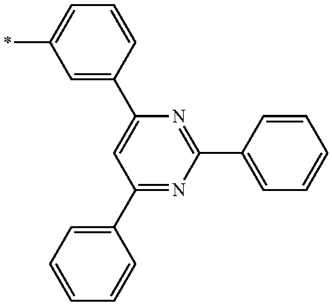 [SMILES: *c1cccc(-c2cc(-c3ccccc3)nc(-c3ccccc3)n2)c1] | H | 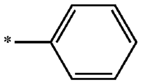 [SMILES: *c1ccccc1] | — | — |
| N-16-19 | $NR^3$ | H | 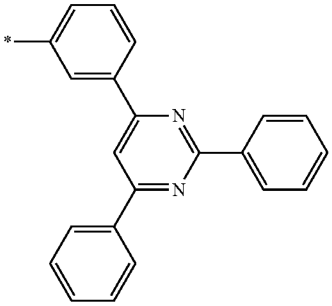 | 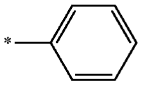 [SMILES: *c1ccccc1] | 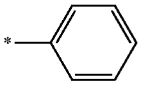 [SMILES: *c1ccccc1] | — | — |
| N-16-20 | NR* | H | 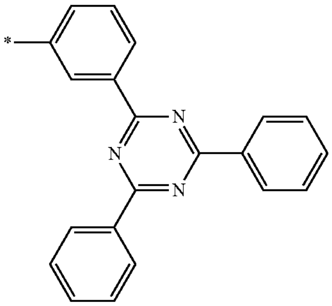 | H | 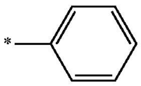 [SMILES: *c1ccccc1] | — | — |
| N-16-21 | $NR^3$ | H | 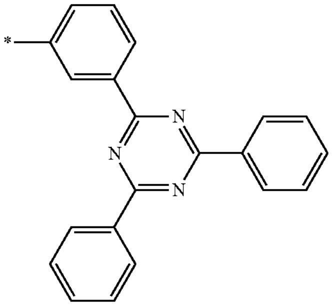 [SMILES: *c1cccc(-c2nc(-c3ccccc3)nc(-c3ccccc3)n2)c1] | 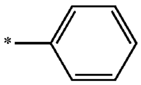 [SMILES: *c1ccccc1] | 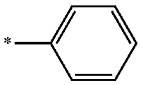 [SMILES: *c1ccccc1] | — | — |

TABLE 55
| | | | | | | | |
|---|---|---|---|---|---|---|---|
| N-16-22 | $NR^3$ | H | 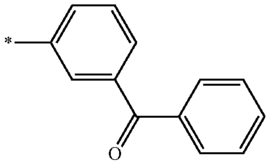 [SMILES: *c1cccc(C(=O)c2ccccc2)c1] | H | 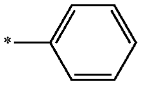 | — | — |
| N-16-23 | $NR^3$ | H | 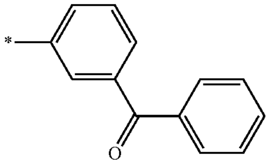 [SMILES: *c1cccc(C(=O)c2ccccc2)c1] | 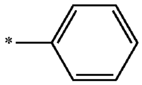 [SMILES: *c1ccccc1] | 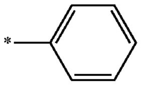 [SMILES: *c1ccccc1] | — | — |
| N-16-24 | $NR^3$ | H | 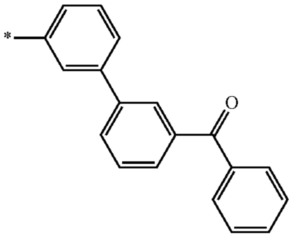 [SMILES: *c1cccc(-c2cccc(C(=O)c3ccccc3)c2)c1] | H | 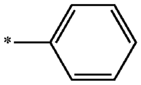 | — | — |
| N-16-25 | $NR^3$ | H | 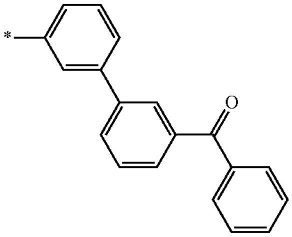 [SMILES: *c1cccc(-c2cccc(C(=O)c3ccccc3)c2)c1] | 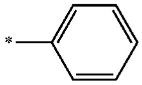 [SMILES: *c1ccccc1] | 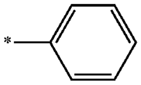 | — | — |
| C-16-1 | $CR^1R^2$ | H | H | H | — | *—Me | *—Me |
| C-16-2 | $CR^1R^2$ | H | 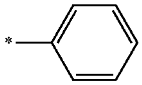 [SMILES: *c1ccccc1] | 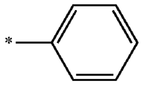 [SMILES: *c1ccccc1] | — | *—Me | *—Me |
| C-16-3 | $CR^1R^2$ | H | 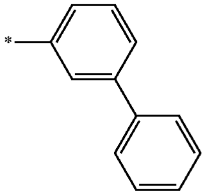 [SMILES: *c1cccc(-c2ccccc2)c1] | H | — | *—Me | *—Me |
| C-16-4 | $CR^1R^2$ | H | 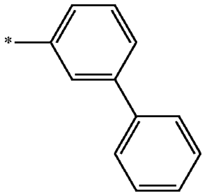 | 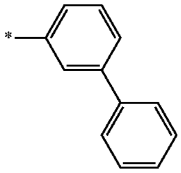 [SMILES: *c1cccc(-c2ccccc2)c1] | — | *—Me | *—Me |
| C-16-5 | $CR^1R^2$ | H | 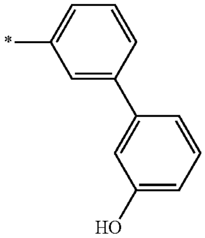 | H | — | 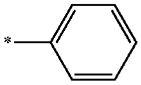 [SMILES: *c1ccccc1] | 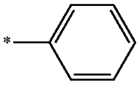 [SMILES: *c1ccccc1] |

TABLE 55-continued
| | | | | | | | |
|---|---|---|---|---|---|---|---|
| C-16-6 | $CR^1R^2$ | H | H | 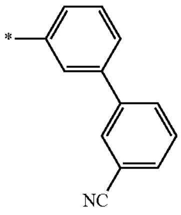 [SMILES: *c1cccc(-c2cccc(C#N)c2)c1] | — | *—Me | *—Me |
| C-16-7 | $CR^1R^2$ | H | 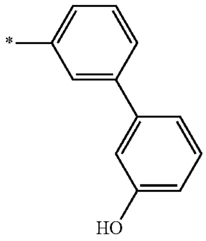 | 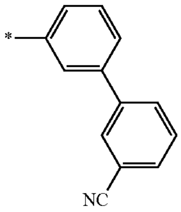 [SMILES: *c1cccc(-c2cccc(C#N)c2)c1] | — | 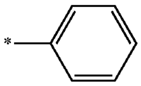 [SMILES: *c1ccccc1] | 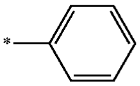 [SMILES: *c1ccccc1] |
| C-16-8 | $CR^1R^2$ | H | 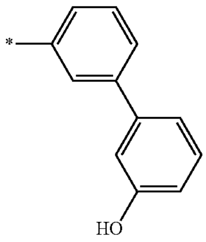 | 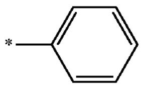 [SMILES: *c1ccccc1] | — | *—Me | *—Me |
| C-16-9 | $CR^1R^2$ | H | 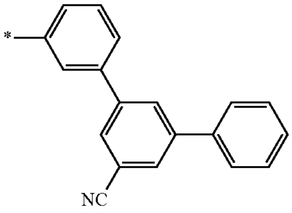 [SMILES: *c1cccc(-c2cc(C#N)cc(-c3ccccc3)c2)c1] | H | — | 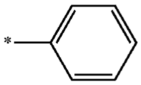 [SMILES: *c1ccccc1] | 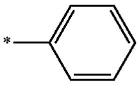 [SMILES: *c1ccccc1] |
| C-16-10 | $CR^1R^2$ | H | 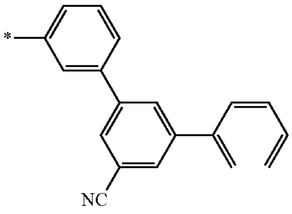 [SMILES: *c1cccc(-c2cc(C#N)cc(C(=C)/C=C\C=C)c2)c1] | 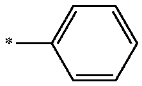 [SMILES: *c1ccccc1] | — | *—Me | *—Me |
| C-16-11 | $CR^1R^2$ | H | 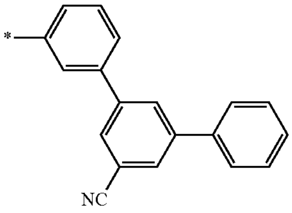 [SMILES: *c1cccc(-c2cc(C#N)cc(-c3ccccc3)c2)c1] | 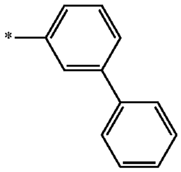 [SMILES: *c1cccc(-c2ccccc2)c1] | — | *—Me | *—Me |

TABLE 56
| | | | | | | | |
|---|---|---|---|---|---|---|---|
| C-16-12 | CR$^1$R$^2$ | H | 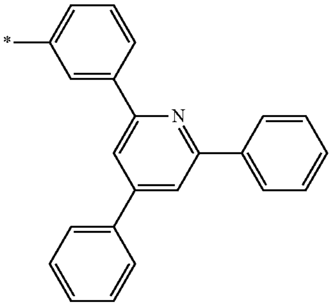 | H | — | *—Me | *—Me |
| C-16-13 | CR$^1$R$^2$ | H | 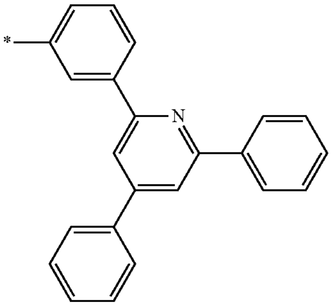 [SMILES: *c1cccc(-c2cc(-c3ccccc3)cc(-c3ccccc3)n2)c1] | 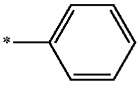 | — | *—Me | *—Me |
| C-16-14 | CR$^1$R$^2$ | H | 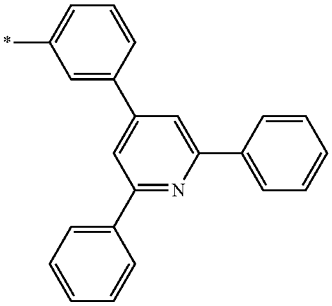 [SMILES: *c1cccc(-c2cc(-c3ccccc3)nc(-c3ccccc3)c2)c1] | H | — | *—Me | *—Me |
| C-16-15 | CR$^1$R$^2$ | H | 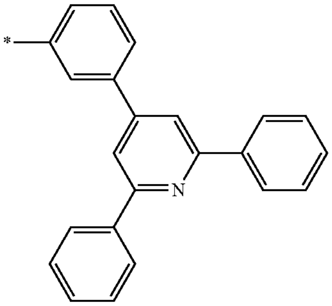 [SMILES: *c1cccc(-c2cc(-c3ccccc3)nc(-c3ccccc3)c2)c1] | 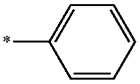 [SMILES: *c1ccccc1] | — | *—Me | *—Me |
| C-16-16 | CR$^1$R$^2$ | H | 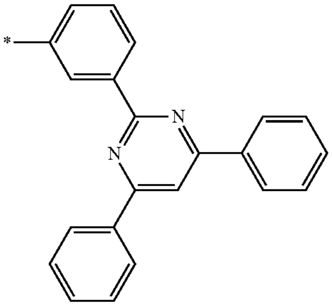 [SMILES: *c1cccc(-c2nc(-c3ccccc3)cc(-c3ccccc3)n2)c1] | H | — | 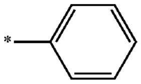 [SMILES: *c1ccccc1] | 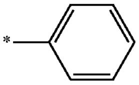 [SMILES: *c1ccccc1] |

TABLE 56-continued
| | | | | | | | |
|---|---|---|---|---|---|---|---|
| C-16-17 | $CR^1R^2$ | H | 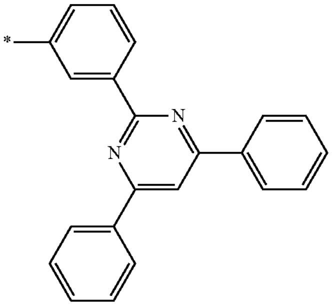 [SMILES: *c1cccc(-c2nc(-c3ccccc3)cc(-c3ccccc3)n2)c1] | 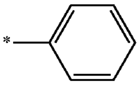 | — | *—Me | *—Me |
| C-16-18 | $CR^1R^2$ | H | 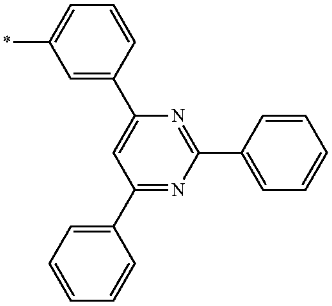 | H | — | *—Me | *—Me |
| C-16-19 | $CR^1R^2$ | H | 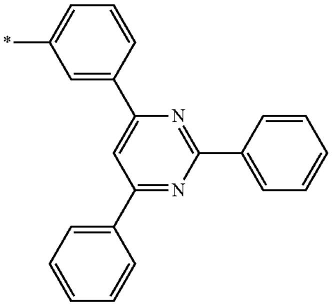 [SMILES: *c1cccc(-c2cc(-c3ccccc3)nc(-c3ccccc3)n2)c1] | 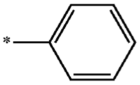 [SMILES: *c1ccccc1] | — | *—Me | *—Me |
| C-16-20 | $CR^1R^2$ | H | 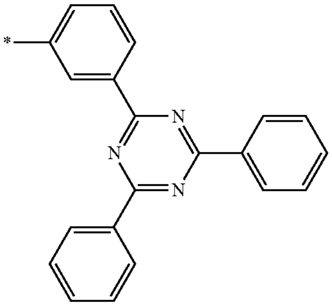 [SMILES: *c1cccc(-c2nc(-c3ccccc3)nc(-c3ccccc3)n2)c1] | H | — | *—Me | *—Me |
| C-16-21 | $CR^1R^2$ | H | 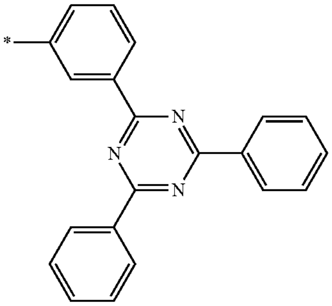 [SMILES: *c1cccc(-c2nc(-c3ccccc3)nc(-c3ccccc3)n2)c1] | 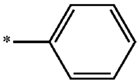 [SMILES: *c1ccccc1] | — | *—Me | *—Me |

TABLE 56-continued
| | | | | | | | |
|---|---|---|---|---|---|---|---|
| C-16-22 | $CR^1R^2$ | H | 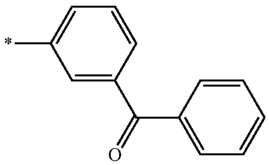 [SMILES: *c1cccc(C(=O)c2ccccc2)c1] | H | — | *—Me | *—Me |
| C-16-23 | $CR^1$ R | H | 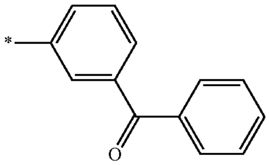 [SMILES: *c1cccc(C(=O)c2ccccc2)c1] | 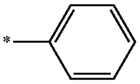 | — | 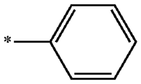 | 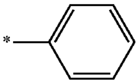 [SMILES: *c1ccccc1] |
| C-16-24 | $CR^1R^2$ | H | 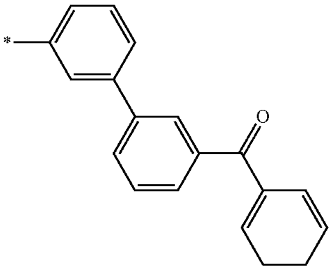 [SMILES: *c1cccc(-c2cccc(C(=O)C3=CCCC=C3)c2)c1] | H | — | *—Me | *—Me |
| C-16-25 | $CR^1R^2$ | H | 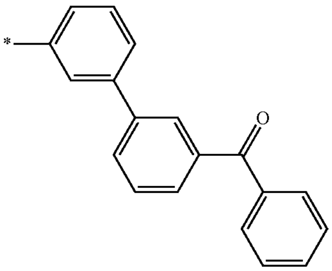 [SMILES: *c1cccc(-c2cccc(C(=O)c3ccccc3)c2)c1] | 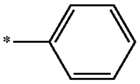 [SMILES: *c1ccccc1] | — | *—Me | *—Me |
TABLE 57
| Compound No. | Central Skeleton | Substituent |
|---|---|---|
| O-16-28 | 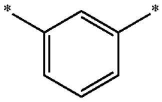 [SMILES: *c1cccc(*)c1] | 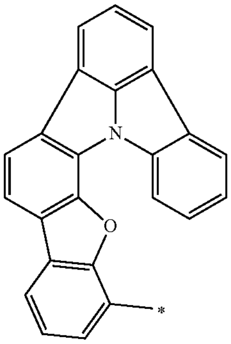 |

TABLE 57-continued
| Compound No. | Central Skeleton | Substituent |
| --- | --- | --- |
| O-16-29 | 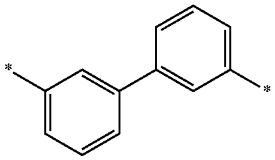 [SMILES: *c1cccc(-c2cccc(*)c2)c1] | 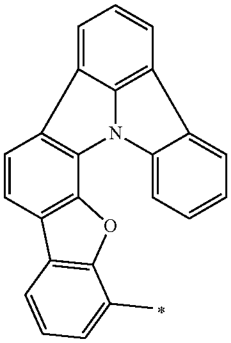 |
| O-16-30 | 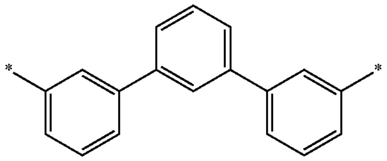 [SMILES: *c1cccc(-c2cccc(-c3cccc(*)c3)c2)c1] | 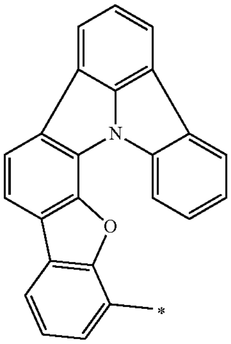 |
| O-16-31 | 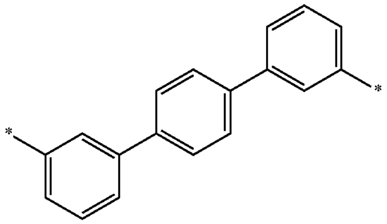 [SMILES: *c1cccc(-c2ccc(-c3cccc(*)c3)cc2)c1] | 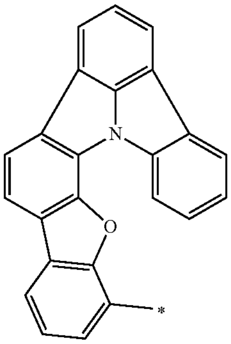 |
| O-16-32 | 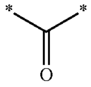 | 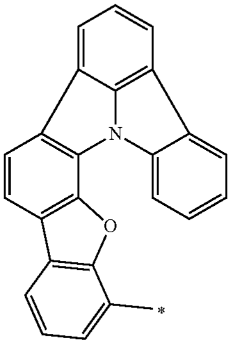 |

TABLE 57-continued
| Compound No. | Central Skeleton | Substituent |
| --- | --- | --- |
| O-16-33 | 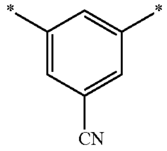 [SMILES: *c1cc(*)cc(C#N)c1] | 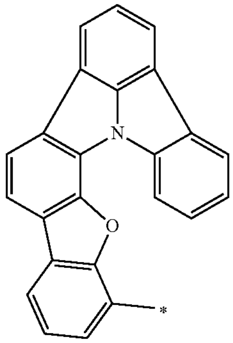 |
| 0-16-34 | 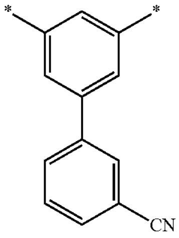 [SMILES: *c1cc(*)cc(-c2cccc(C#N)c2)c1] | 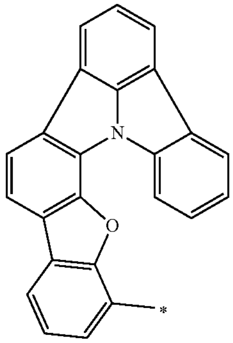 |
| O-16-35 | 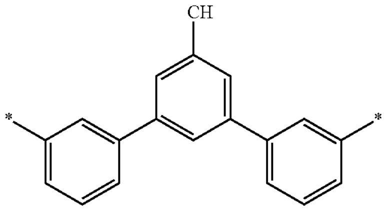 | 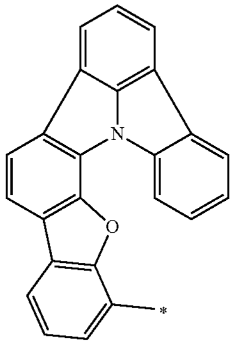 |
| O-16-36 | 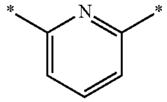 [SMILES: *c1cccc(*)n1] | 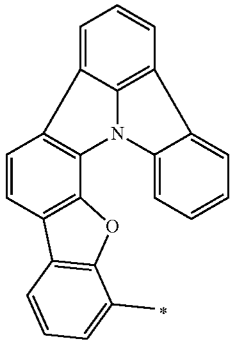 |

TABLE 57-continued
| Compound No. | Central Skeleton | Substituent |
| --- | --- | --- |
| O-16-37 | 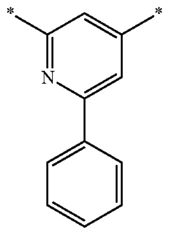 [SMILES: *c1cc(*)nc(-c2ccccc2)c1] | 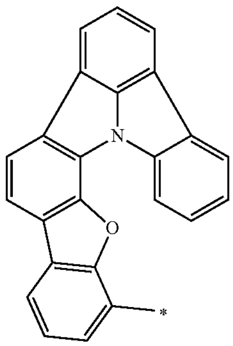 |
| O-16-38 | 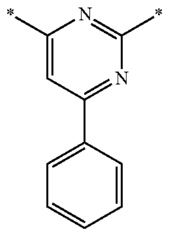 [SMILES: *c1cc(-c2ccccc2)nc(*)n1] | 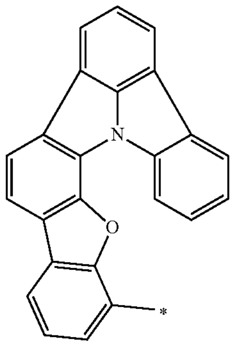 |
| O-16-39 | 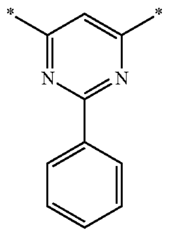 [SMILES: *c1cc(*)nc(-c2ccccc2)n1] | 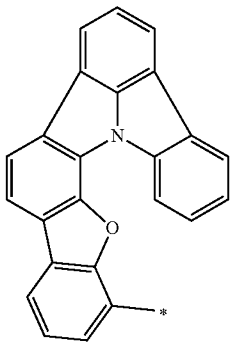 |
| 0-16-40 | 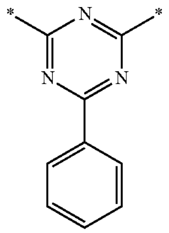 [SMILES: *c1nc(*)nc(-c2ccccc2)n1] | 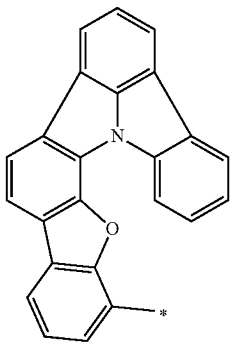 |

TABLE 57-continued
| Compound No. | Central Skeleton | Substituent |
| --- | --- | --- |
| O-16-41 | 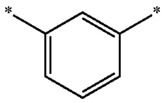 [SMILES: *c1cccc(*)c1] | 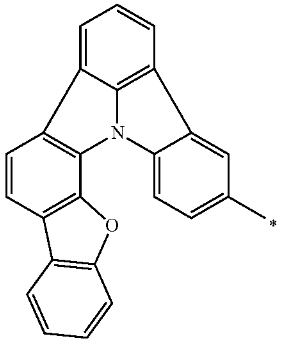 |
| O-16-42 | 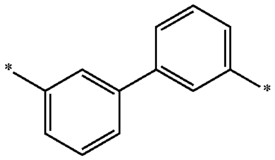 [SMILES: *c1cccc(-c2cccc(*)c2)c1] | 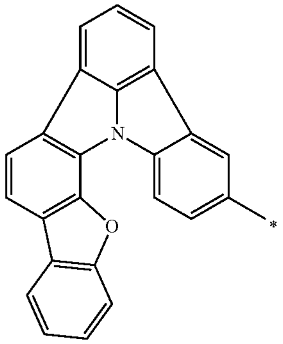 |
| O-16-43 | 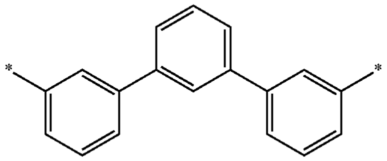 [SMILES: *c1cccc(-c2cccc(-c3cccc(*)c3)c2)c1] | 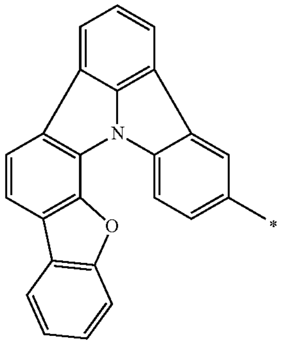 |
| O-16-44 | 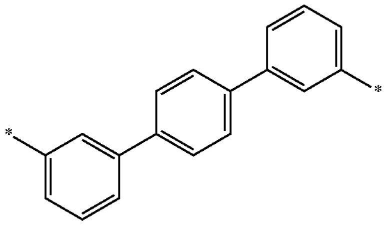 [SMILES: *c1cccc(-c2ccc(-c3cccc(*)c3)cc2)c1] | 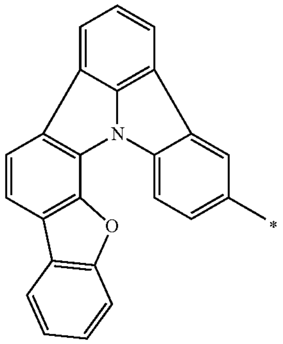 |

TABLE 57-continued
| Compound No. | Central Skeleton | Substituent |
| --- | --- | --- |
| O-16-45 | 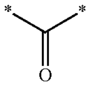 | 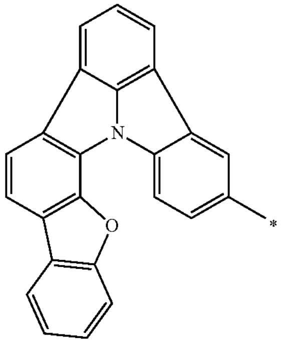 |
| O-16-46 | 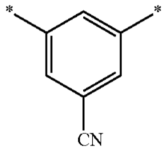 [SMILES: *c1cc(*)cc(C#N)c1] | 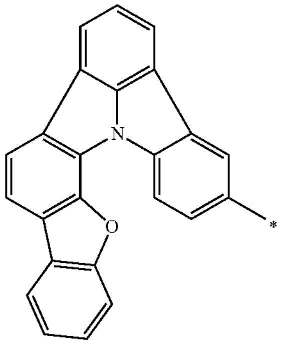 |
| O-16-47 | 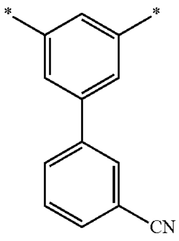 [SMILES: *c1cc(*)cc(-c2cccc(C#N)c2)c1] | 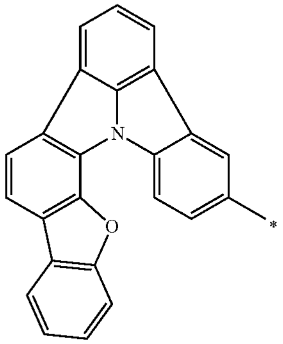 |
| O-16-48 | 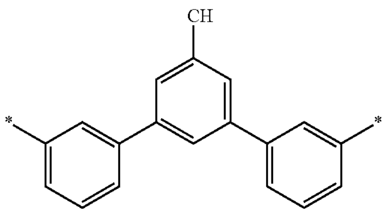 | 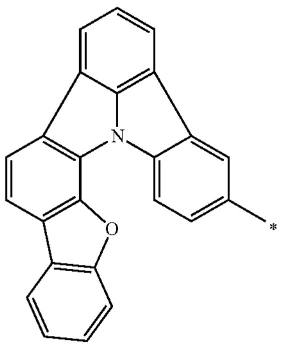 |

TABLE 57-continued
| Compound No. | Central Skeleton | Substituent |
| --- | --- | --- |
| O-16-49 | 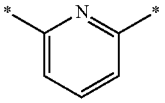 [SMILES: *c1cccc(*)n1] | 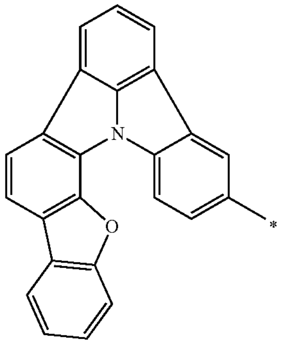 |
| O-16-50 | 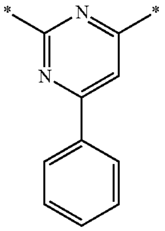 [SMILES: *c1cc(-c2ccccc2)nc(*)n1] | 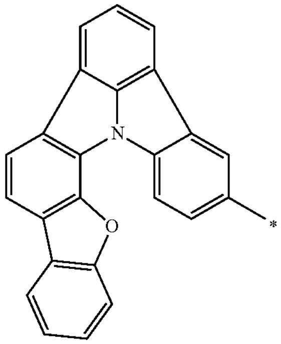 |
| O-16-51 | 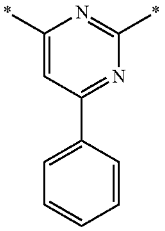 [SMILES: *c1cc(-c2ccccc2)nc(*)n1] | 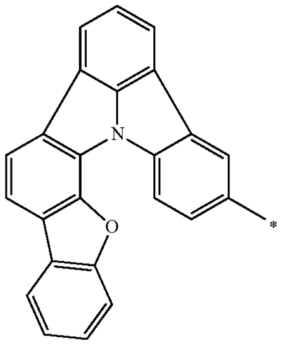 |
| O-16-52 | 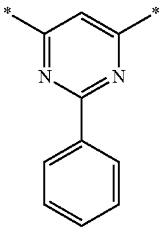 [SMILES: *c1cc(*)nc(-c2ccccc2)n1] | 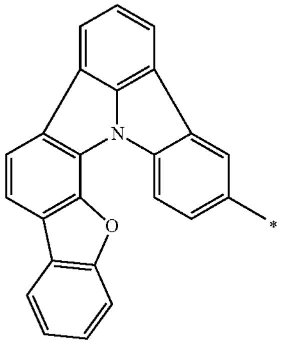 |

TABLE 57-continued
| Compound No. | Central Skeleton | Substituent |
|---|---|---|
| O-16-53 | 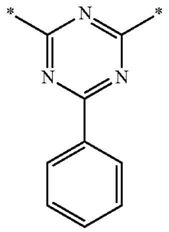 [SMILES: *c1nc(*)nc(-c2ccccc2)n1] | 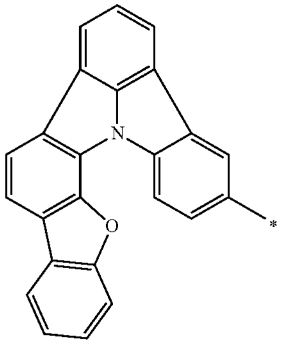 |
TABLE 58
| Compound No. | Central Sketeton | Substituent |
|---|---|---|
| O-16-54 | 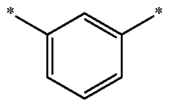 [SMILES: *c1cccc(*)c1] | 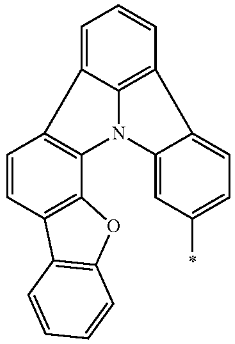 [SMILES: *c1ccc2c3cccc4c5ccc6c7ccccc7oc6c5n(c2c1)c34] |
| O-16-55 | 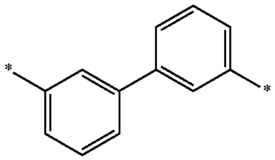 [SMILES: *c1cccc(-c2cccc(*)c2)c1] | 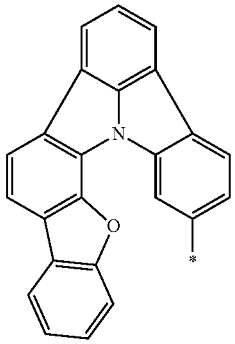 [SMILES: *c1ccc2c3cccc4c5ccc6c7ccccc7oc6c5n(c2c1)c34] |
| O-16-56 | 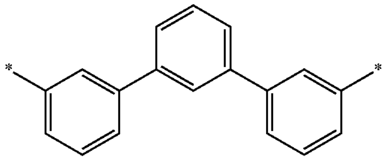 [SMILES: *c1cccc(-c2cccc(-c3cccc(*)c3)c2)c1] | 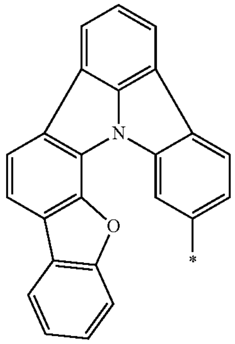 [SMILES: *c1ccc2c3cccc4c5ccc6c7ccccc7oc6c5n(c2c1)c34] |

TABLE 58-continued
| Compound No. | Central Sketeton | Substituent |
| --- | --- | --- |
| O-18-57 | 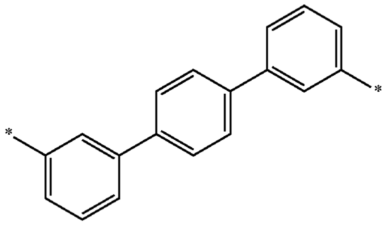 [SMILES: *c1cccc(-c2ccc(-c3cccc(*)c3)cc2)c1] | 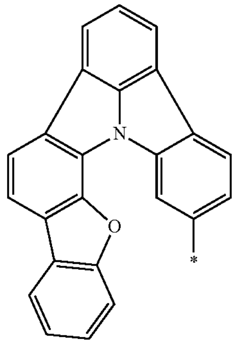 [SMILES: *c1ccc2c3cccc4c5ccc6c7ccccc7oc6c5n(c2c1)c34] |
| O-16-58 | 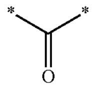 | 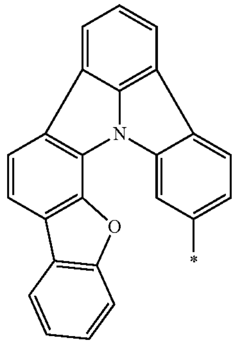 [SMILES: *c1ccc2c3cccc4c5ccc6c7ccccc7oc6c5n(c2c1)c34] |
| O-16-59 | 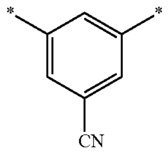 [SMILES: *c1cc(*)cc(C#N)c1] | 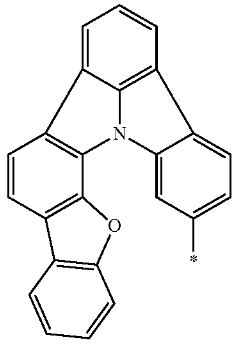 [SMILES: *c1ccc2c3cccc4c5ccc6c7ccccc7oc6c5n(c2c1)c34] |
| O-16-60 | 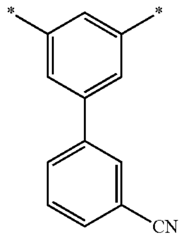 [SMILES: *c1cc(*)cc(-c2cccc(C#N)c2)c1] | 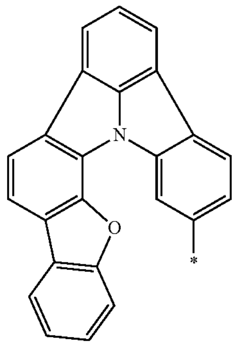 [SMILES: *c1ccc2c3cccc4c5ccc6c7ccccc7oc6c5n(c2c1)c34] |

TABLE 58-continued
| Compound No. | Central Sketeton | Substituent |
|---|---|---|
| O-16-61 | 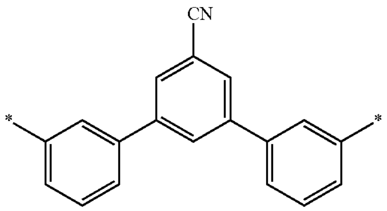 [SMILES: *c1cccc(-c2cc(C#N)cc(-c3cccc(*)c3)c2)c1] | 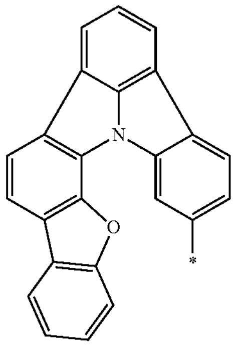 [SMILES: *c1ccc2c3cccc4c5ccc6c7ccccc7oc6c5n(c2c1)c34] |
| O-16-62 | 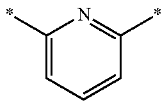 [SMILES: *c1cccc(*)n1] | 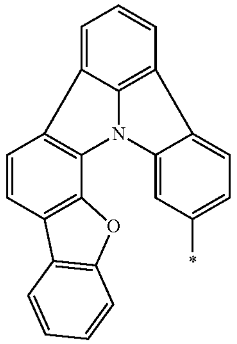 [SMILES: *c1ccc2c3cccc4c5ccc6c7ccccc7oc6c5n(c2c1)c34] |
| O-16-63 | 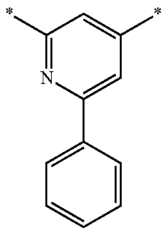 [SMILES: *c1cc(*)nc(-c2ccccc2)c1] | 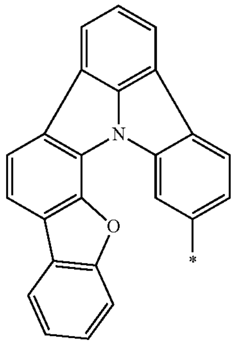 [SMILES: *c1ccc2c3cccc4c5ccc6c7ccccc7oc6c5n(c2c1)c34] |
| O-16-64 | 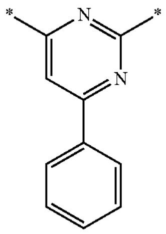 | 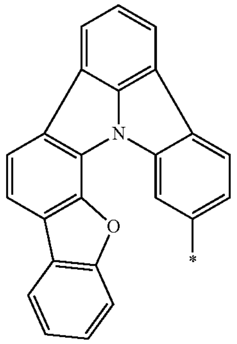 [SMILES: *c1ccc2c3cccc4c5ccc6c7ccccc7oc6c5n(c2c1)c34] |

TABLE 58-continued
| Compound No. | Central Sketeton | Substituent |
| --- | --- | --- |
| O-16-65 | 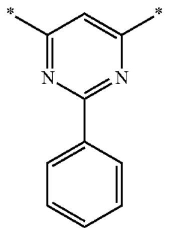 [SMILES: *c1cc(*)nc(-c2ccccc2)n1] | 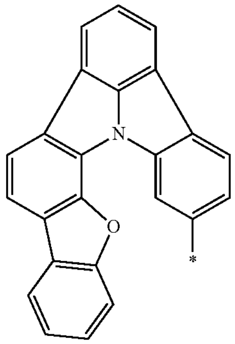 [SMILES: *c1ccc2c3cccc4c5ccc6c7ccccc7oc6c5n(c2c1)c34] |
| O-16-66 | 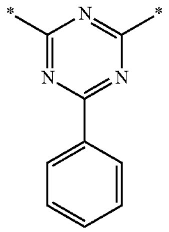 [SMILES: *c1nc(*)nc(-c2ccccc2)n1] | 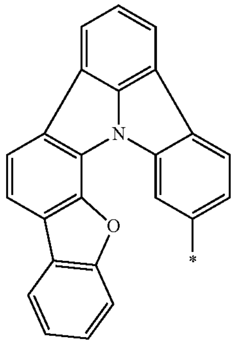 [SMILES: *c1ccc2c3cccc4c5ccc6c7ccccc7oc6c5n(c2c1)c34] |
| O-16-67 | 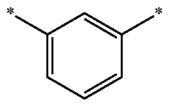 | 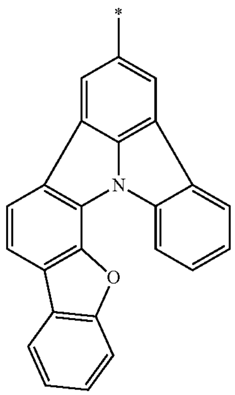 [SMILES: *c1cc2c3ccccc3n3c2c(c1)c1ccc2c4ccccc4oc2c13] |
| O-16-68 | 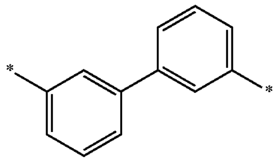 [SMILES: *c1cccc(-c2cccc(*)c2)c1] | 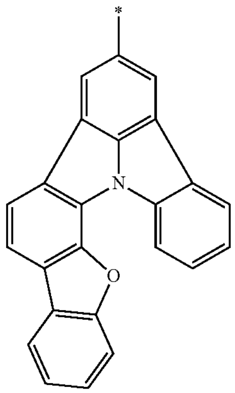 [SMILES: *c1cc2c3ccccc3n3c2c(c1)c1ccc2c4ccccc4oc2c13] |

TABLE 58-continued
| Compound No. | Central Sketeton | Substituent |
| --- | --- | --- |
| O-16-69 | 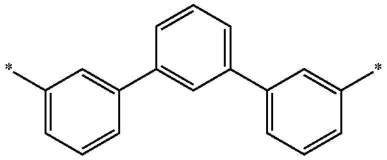 [SMILES: *c1cccc(-c2cccc(-c3cccc(*)c3)c2)c1] | 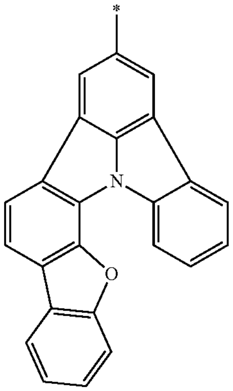 [SMILES: *c1cc2c3ccccc3n3c2c(c1)c1ccc2c4ccccc4oc2c13] |
| O-16-70 | 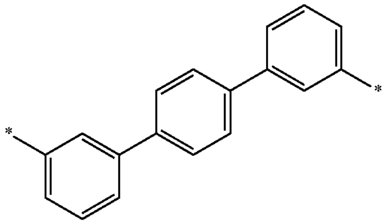 [SMILES: *c1cccc(-c2ccc(-c3cccc(*)c3)cc2)c1] | 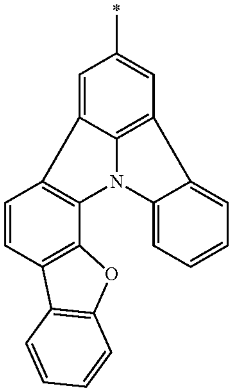 [SMILES: *c1cc2c3ccccc3n3c2c(c1)c1ccc2c4ccccc4oc2c13] |
| O-16-71 | 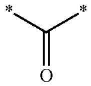 | 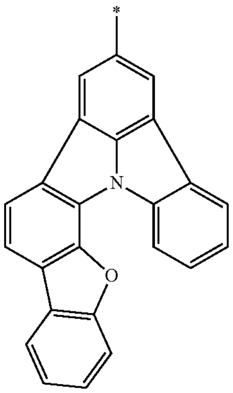 [SMILES: *c1cc2c3ccccc3n3c2c(c1)c1ccc2c4ccccc4oc2c13] |
| O-16-72 | 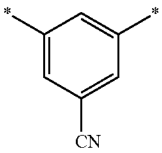 [SMILES: *c1cc(*)cc(C#N)c1] | 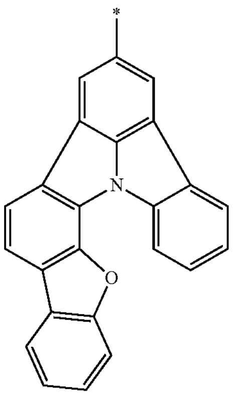 [SMILES: *c1cc2c3ccccc3n3c2c(c1)c1ccc2c4ccccc4oc2c13] |

TABLE 58-continued
| Compound No. | Central Sketeton | Substituent |
| --- | --- | --- |
| O-16-73 | 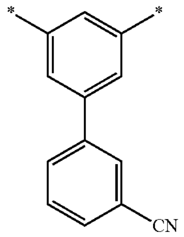 [SMILES: *c1cc(*)cc(-c2cccc(C#N)c2)c1] | 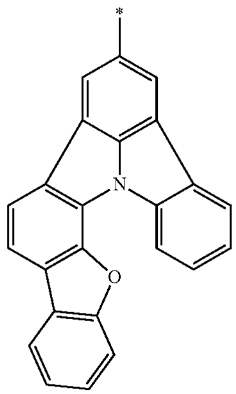 [SMILES: *c1cc2c3ccccc3n3c2c(c1)c1ccc2c4ccccc4oc2c13] |
| O-16-74 | 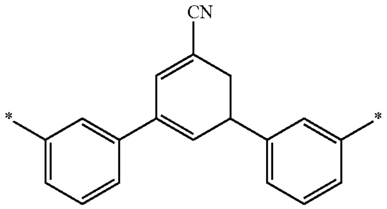 [SMILES: *c1cccc(C2=CC(c3cccc(*)c3)CC(C#N)=C2)c1] | 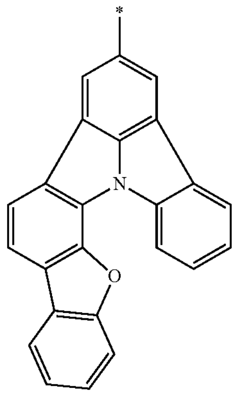 [SMILES: *c1cc2c3ccccc3n3c2c(c1)c1ccc2c4ccccc4oc2c13] |
| O-16-75 | 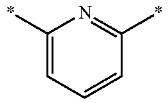 [SMILES: *c1cccc(*)n1] | 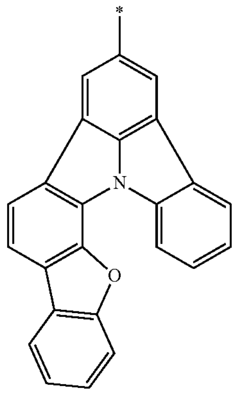 [SMILES: *c1cc2c3ccccc3n3c2c(c1)c1ccc2c4ccccc4oc2c13] |
| O-16-76 | 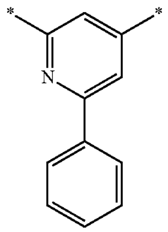 [SMILES: *c1cc(*)nc(-c2ccccc2)c1] | 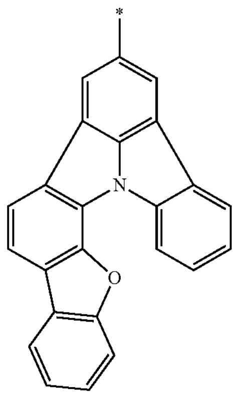 [SMILES: *c1cc2c3ccccc3n3c2c(c1)c1ccc2c4ccccc4oc2c13] |

TABLE 58-continued
| Compound No. | Central Sketeton | Substituent |
|---|---|---|
| O-16-77 | 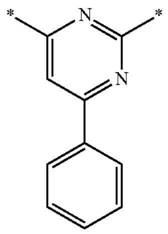 [SMILES: *c1cc(-c2ccccc2)nc(*)n1] | 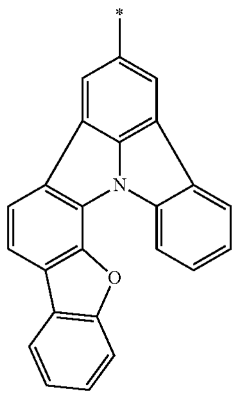 [SMILES: *c1cc2c3ccccc3n3c2c(c1)c1ccc2c4ccccc4oc2c13] |
| O-16-78 | 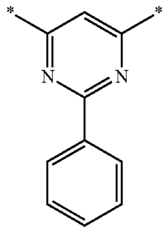 [SMILES: *c1cc(*)nc(-c2ccccc2)n1] | 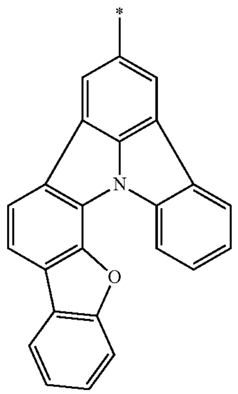 [SMILES: *c1cc2c3ccccc3n3c2c(c1)c1ccc2c4ccccc4oc2c13] |
| O-16-79 | 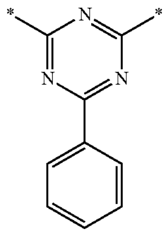 [SMILES: *c1nc(*)nc(-c2ccccc2)n1] | 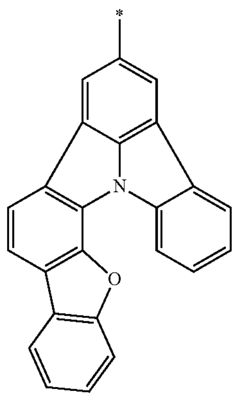 [SMILES: *c1cc2c3ccccc3n3c2c(c1)c1ccc2c4ccccc4oc2c13] |

In the compound represented by the following general formula (17), $R^{H1}$, $R^{H3}$, $R^{H4}$, $R^{H5}$, $R^{H8}$, $R^{H9}$, $R^{H11}$, $R^{H13}$ to $R^{H15}$ each represent a hydrogen atom, and the other groups are groups described in Tables below.
[Chem. 22]
(17)
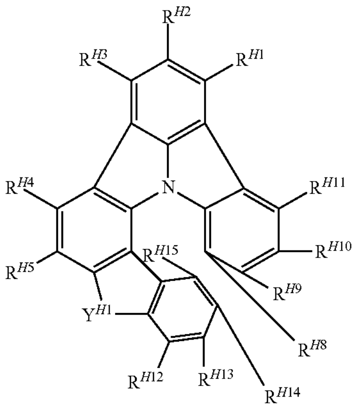
TABLE 59
| Compound No. | $Y^{H1}$ | $R^{H12}$ | $R^{H2}$ | $R^{H10}$ | $R^3$ | $R^1$ | $R^2$ |
|---|---|---|---|---|---|---|---|
| O-17-2 | O | H | 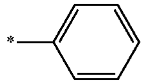 [SMILES: *c1ccccc1] | 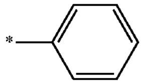 [SMILES: *c1ccccc1] | — | — | — |
| O-17-3 | O | H | 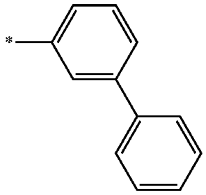 [SMILES: *c1cccc(-c2ccccc2)c1] | H | — | — | — |
| O-17-4 | O | H | 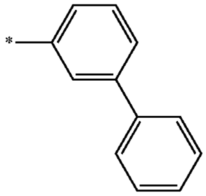 [SMILES: *c1cccc(-c2ccccc2)c1] | 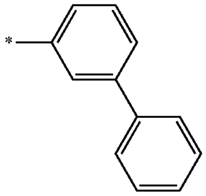 [SMILES: *c1cccc(-c2ccccc2)c1] | — | — | — |
| O-17-5 | O | 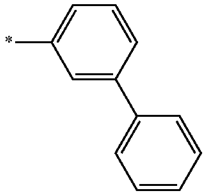 [SMILES: *c1cccc(-c2ccccc2)c1] | H | H | — | — | — |
| O-17-6 | O | H | 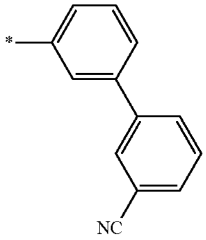 [SMILES: *c1cccc(-c2cccc(C#N)c2)c1] | H | — | — | — |

TABLE 59-continued
| Compound No. | $Y^{H1}$ | $R^{H12}$ | $R^{H2}$ | $R^{H10}$ | $R^3$ | $R^1$ | $R^2$ |
|---|---|---|---|---|---|---|---|
| O-17-7 | O | H | H | 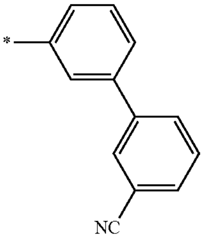 [SMILES: *c1cccc(-c2cccc(C#N)c2)c1] | — | — | — |
| O-17-8 | O | H | 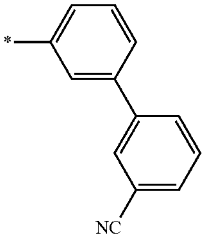 [SMILES: *c1cccc(-c2cccc(C#N)c2)c1] | 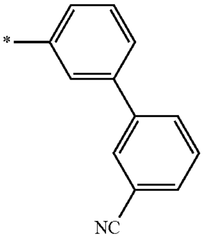 [SMILES: *c1cccc(-c2cccc(C#N)c2)c1] | — | — | — |
| O-17-9 | O | H | 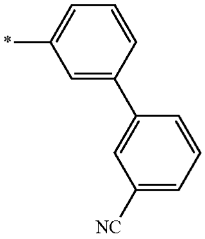 [SMILES: *c1cccc(-c2cccc(C#N)c2)c1] | 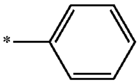 [SMILES: *c1ccccc1] | — | — | — |
| O-17-10 | O | H | 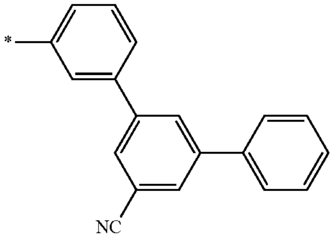 [SMILES: *c1cccc(-c2cc(C#N)cc(-c3ccccc3)c2)c1] | H | — | — | — |
| O-17-11 | O | H | 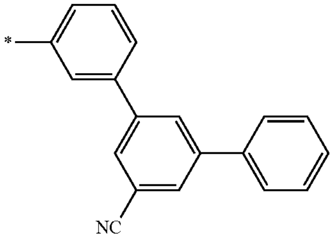 [SMILES: *c1cccc(-c2cc(C#N)cc(-c3ccccc3)c2)c1] | 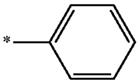 [SMILES: *c1ccccc1] | — | — | — |
| O-17-12 | O | H | 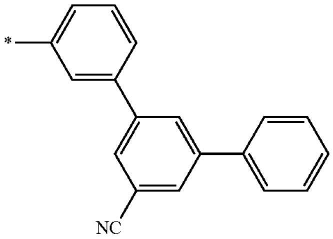 [SMILES: *c1cccc(-c2cc(C#N)cc(-c3ccccc3)c2)c1] | 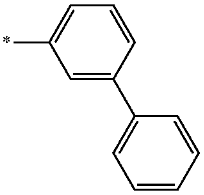 [SMILES: *c1cccc(-c2ccccc2)c1] | — | — | — |

TABLE 59-continued
| Compound No. | $Y^{H1}$ | $R^{H12}$ | $R^{H2}$ | $R^{H10}$ | $R^3$ | $R^1$ | $R^2$ |
|---|---|---|---|---|---|---|---|
| O-17-13 | O | 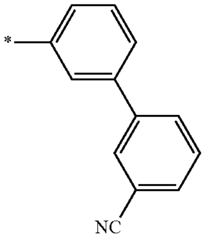 [SMILES: *c1cccc(-c2cccc(C#N)c2)c1] | 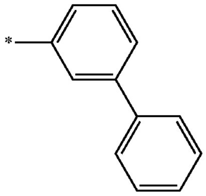 [SMILES: *c1cccc(-c2ccccc2)c1] | H | — | — | — |
| O-17-14 | O | H | 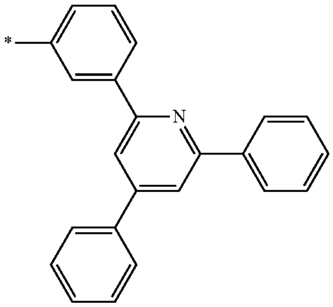 | H | — | — | — |
| O-17-15 | O | H | 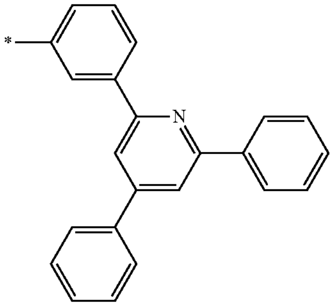 [SMILES: *c1cccc(-c2cc(-c3ccccc3)cc(-c3ccccc3)n2)c1] | 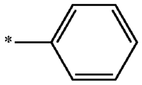 [SMILES: *c1ccccc1] | — | — | — |
| O-17-16 | O | H | 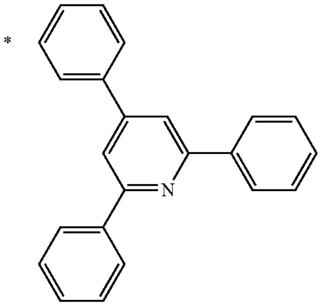 | H | — | — | — |

TABLE 60
| | | | | | | | |
|---|---|---|---|---|---|---|---|
| O-17-17 | O | H | 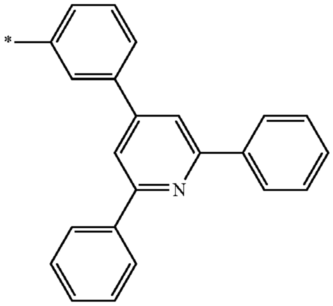 | 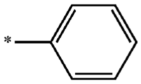 [SMILES: *c1ccccc1] | — | — | — |
| O-17-18 | O | H | 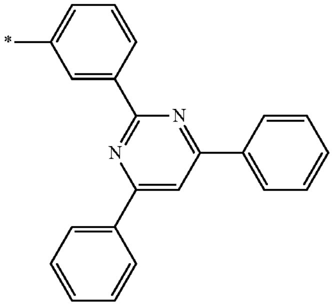 | H | — | — | — |
| O-17-19 | O | H | 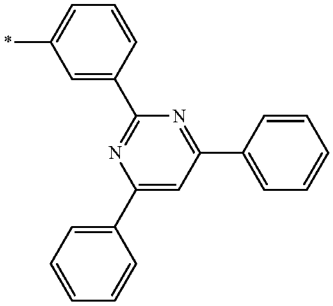 | 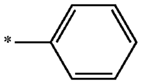 | — | — | — |
| O-17-20 | O | H | 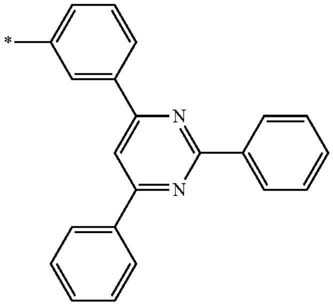 | H | — | — | — |
| O-17-21 | O | H | 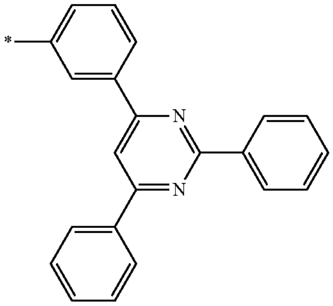 | 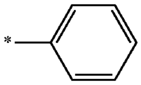 [SMILES: *c1ccccc1] | — | — | — |

TABLE 60-continued
| | | | | | | | |
|---|---|---|---|---|---|---|---|
| O-17-22 | O | H | 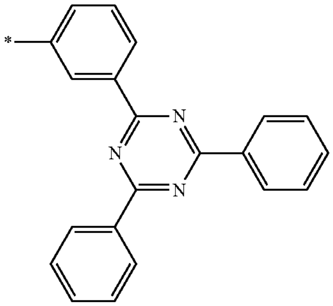 | H | — | — | — |
| O-17-23 | O | H | 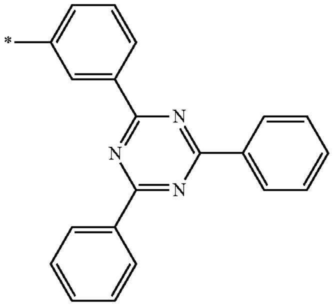 | 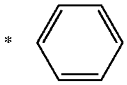 | — | — | — |
| O-17-24 | O | H | 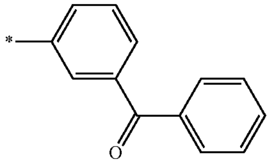 | H | — | — | — |
| O-17-25 | O | H | 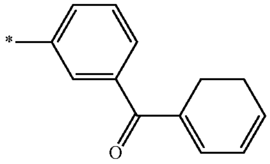 [SMILES: *c1cccc(C(=O)C2=CC=CCC2)c1] | 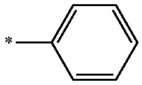 [SMILES: *c1ccccc1] | — | — | — |
| O-17-26 | O | H | 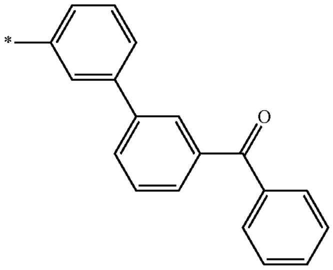 [SMILES: *c1cccc(-c2cccc(C(=O)c3ccccc3)c2)c1] | H | — | — | — |
| O-17-27 | O | H | 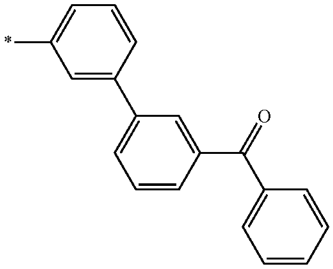 [SMILES: *c1cccc(-c2cccc(C(=O)c3ccccc3)c2)c1] | 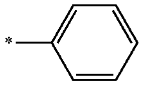 [SMILES: *c1ccccc1] | — | — | — |
| S-17-1 | S | H | H | H | — | — | — |

TABLE 60-continued
| | | | | | | | |
|---|---|---|---|---|---|---|---|
| S-17-2 | S | H | 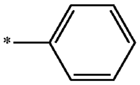 | 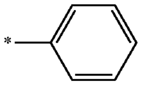 [SMILES: *c1ccccc1] | — | — | — |
| S-17-3 | S | H | 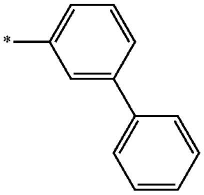 [SMILES: *c1cccc(-c2ccccc2)c1] | H | — | — | — |
| S-17-4 | S | H | 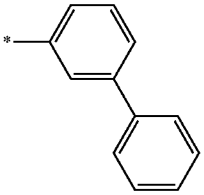 [SMILES: *c1cccc(-c2ccccc2)c1] | 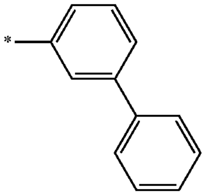 [SMILES: *c1cccc(-c2ccccc2)c1] | — | — | — |
TABLE 61
| | | | | | | | | |
|---|---|---|---|---|---|---|---|---|
| S-17-5 | S | 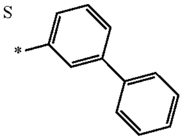 | 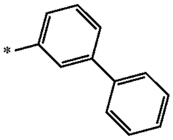 [SMILES: *c1cccc(-c2ccccc2)c1] | H | H | — | — | — |
| S-17-6 | | S | H | 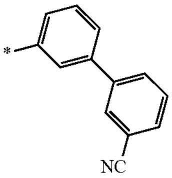 [SMILES: *c1cccc(-c2cccc(C#N)c2)c1] | H | — | — | — |
| S-17-7 | | S | H | H | 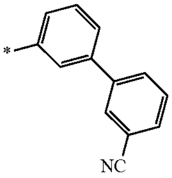 [SMILES: *c1cccc(-c2cccc(C#N)c2)c1] | — | — | — |
| S-17-8 | | S | H | 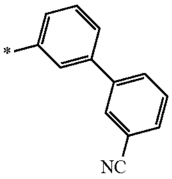 [SMILES: *c1cccc(-c2cccc(C#N)c2)c1] | 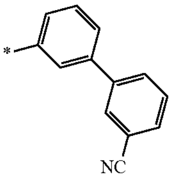 [SMILES: *c1cccc(-c2cccc(C#N)c2)c1] | — | — | — |
| S-17-9 | | S | H | 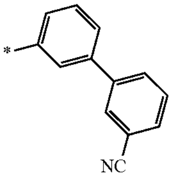 [SMILES: *c1cccc(-c2cccc(C#N)c2)c1] | 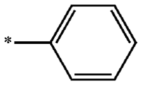 | — | — | — |

TABLE 61-continued
| | | | | | | | |
|---|---|---|---|---|---|---|---|
| S-17-10 | S | H | 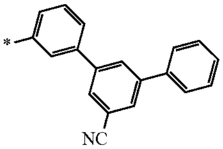 [SMILES: *c1cccc(-c2cc(C#N)cc(-c3ccccc3)c2)c1] | H | — | — | — |
| S-17-11 | S 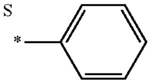 | H | 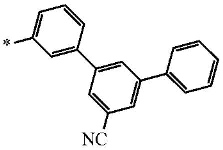 [SMILES: *c1cccc(-c2cc(C#N)cc(-c3ccccc3)c2)c1] | 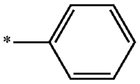 | — | — | — |
| S-17-12 | S | H | 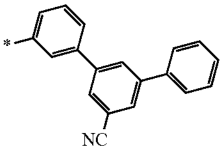 [SMILES: *c1cccc(-c2cc(C#N)cc(-c3ccccc3)c2)c1] | 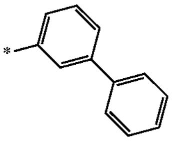 [SMILES: *c1cccc(-c2ccccc2)c1] | — | — | — |
| S-17-13 | S | 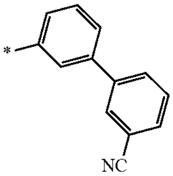 [SMILES: *c1cccc(-c2cccc(C#N)c2)c1] | 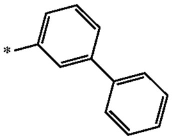 [SMILES: *c1cccc(-c2ccccc2)c1] | H | — | — | — |
| S-17-14 | S | H | 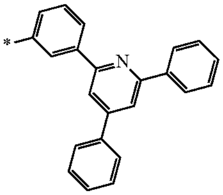 | H | — | — | — |
| S-17-15 | S | H | 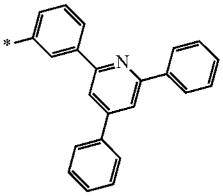 | 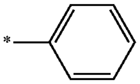 [SMILES: *c1ccccc1] | — | — | — |
| S-17-16 | S | H | 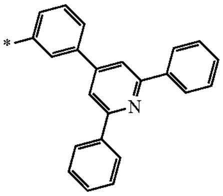 [SMILES: *c1cccc(-c2cc(-c3ccccc3)nc(-c3ccccc3)c2)c1] | H | — | — | — |
| S-17-17 | S | H | 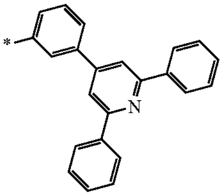 [SMILES: *c1cccc(-c2cc(-c3ccccc3)nc(-c3ccccc3)c2)c1] | 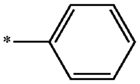 [SMILES: *c1ccccc1] | — | — | — |

TABLE 61-continued
| | | | | | | | | |
|---|---|---|---|---|---|---|---|---|
| S-17-18 | S | H | 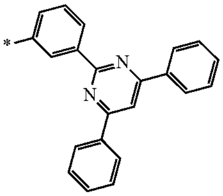 | H | | — | — | — |
| S-17-19 | S | H | 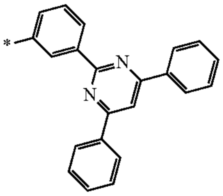 [SMILES: *c1cccc(-c2nc(-c3ccccc3)cc(-c3ccccc3)n2)c1] | 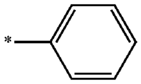 | — | 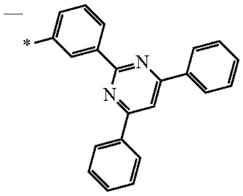 | — | — |
TABLE 62
| | | | | | | | |
|---|---|---|---|---|---|---|---|
| S-17-20 | S | H | 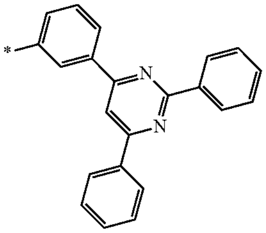 [SMILES: *c1cccc(-c2cc(-c3ccccc3)nc(-c3ccccc3)n2)c1] | H | — | — | — |
| S-17-21 | S | H | 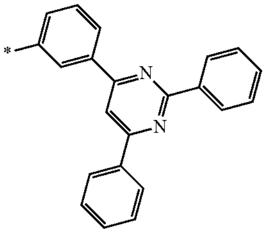 [SMILES: *c1cccc(-c2cc(-c3ccccc3)nc(-c3ccccc3)n2)c1] | 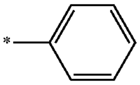 [SMILES: *c1ccccc1] | — | — | — |
| S-17-22 | S | H | 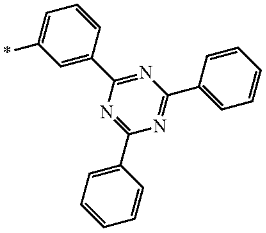 [SMILES: *c1cccc(-c2nc(-c3ccccc3)nc(-c3ccccc3)n2)c1] | H | — | — | — |
| S-17-23 | S | H | 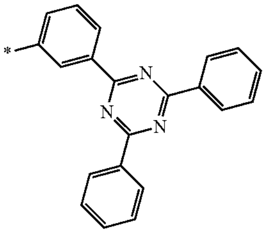 [SMILES: *c1cccc(-c2nc(-c3ccccc3)nc(-c3ccccc3)n2)c1] | 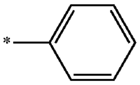 [SMILES: *c1ccccc1] | — | — | — |

TABLE 62-continued
| | | | | | | | |
|---|---|---|---|---|---|---|---|
| S-17-24 | S | H | 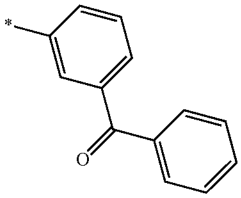 [SMILES: *c1cccc(C(=O)c2ccccc2)c1] | H | — | — | — |
| S-17-25 | S | H | 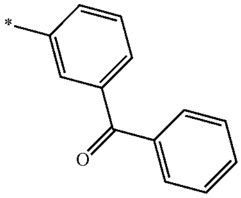 [SMILES: *c1cccc(C(=O)c2ccccc2)c1] | 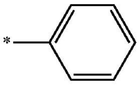 [SMILES: *c1ccccc1] | — | — | — |
| S-17-26 | S | H | 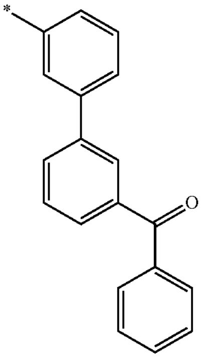 [SMILES: *c1cccc(-c2cccc(C(=O)c3ccccc3)c2)c1] | 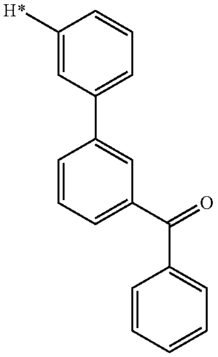 | — | — | — |
| S-17-27 | S | H | 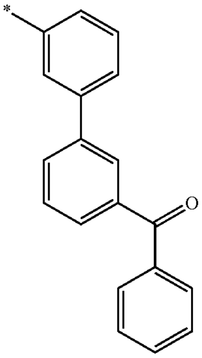 [SMILES: *c1cccc(-c2cccc(C(=O)c3ccccc3)c2)c1] | 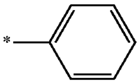 [SMILES: *c1ccccc1] | — | — | — |
| N-17-1 | $NR^3$ | H | H | H | 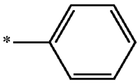 [SMILES: *c1ccccc1] | — | — |
| N-17-2 | $NR^3$ | H | 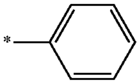 [SMILES: *c1ccccc1] | 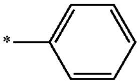 [SMILES: *c1ccccc1] | 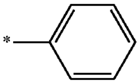 [SMILES: *c1ccccc1] | — | — |
| N-17-3 | $NR^3$ | H | 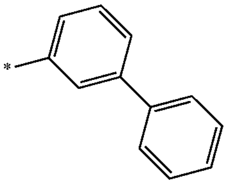 [SMILES: *c1cccc(-c2ccccc2)c1] | H | 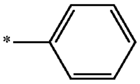 [SMILES: *c1ccccc1] | — | — |

TABLE 62-continued
| | | | | | | | |
|---|---|---|---|---|---|---|---|
| N-17-4 | $NR^3$ | H | 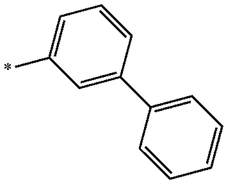 [SMILES: *c1cccc(-c2ccccc2)c1] | 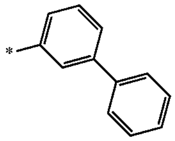 [SMILES: *c1cccc(-c2ccccc2)c1] | 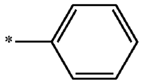 [SMILES: *c1ccccc1] | — | — |
| N-17-5 | $NR^3$ | H | 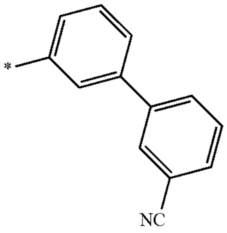 [SMILES: *c1cccc(-c2cccc(C#N)c2)c1] | H | 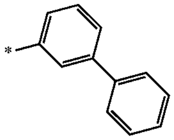 [SMILES: *c1cccc(-c2ccccc2)c1] | 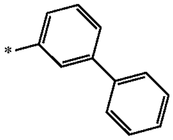 [SMILES: *c1cccc(-c2ccccc2)c1] | — |
| N-17-6 | $NR^3$ | H | H | 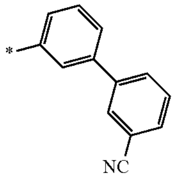 [SMILES: *c1cccc(-c2cccc(C#N)c2)c1] | 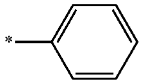 [SMILES: *c1ccccc1] | — | — |
| N-17-7 | $NR^3$ | H | 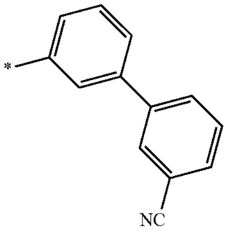 [SMILES: *c1cccc(-c2cccc(C#N)c2)c1] | 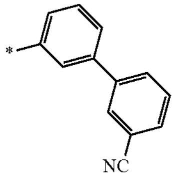 [SMILES: *c1cccc(-c2cccc(C#N)c2)c1] | 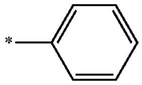 [SMILES: *c1ccccc1] | — | — |
TABLE 63
| | | | | | | | |
|---|---|---|---|---|---|---|---|
| N-17-8 | $NR^3$ | H | 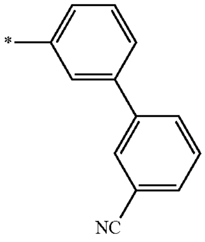 [SMILES: *c1cccc(-c2cccc(C#N)c2)c1] | 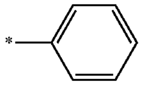 [SMILES: *c1ccccc1] | 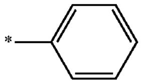 [SMILES: *c1ccccc1] | — | — |
| N-17-9 | $NR^3$ | H | 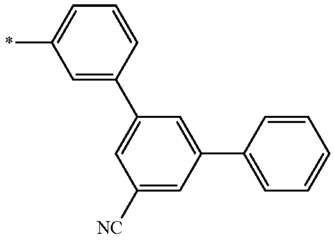 [SMILES: *c1cccc(-c2cc(C#N)cc(-c3ccccc3)c2)c1] | H | 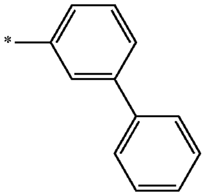 [SMILES: *c1cccc(-c2ccccc2)c1] | — | — |

TABLE 63-continued
| | | | | | | | |
|---|---|---|---|---|---|---|---|
| N-17-10 | $NR^3$ | H | 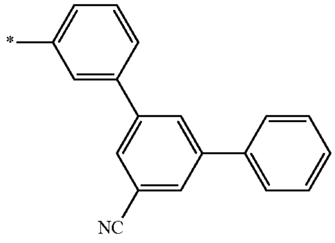 [SMILES: *c1cccc(-c2cc(C#N)cc(-c3ccccc3)c2)c1] | 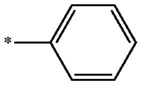 [SMILES: *c1ccccc1] | 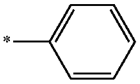 [SMILES: *c1ccccc1] | — | — |
| N-17-11 | $NR^3$ | H | 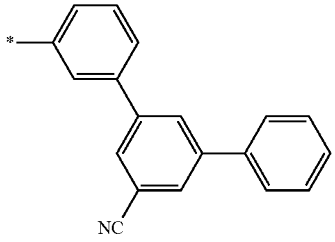 [SMILES: *c1cccc(-c2cc(C#N)cc(-c3ccccc3)c2)c1] | 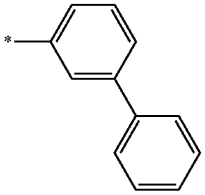 [SMILES: *c1cccc(-c2ccccc2)c1] | 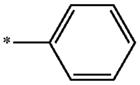 [SMILES: *c1ccccc1] | — | — |
| N-17-12 | $NR^3$ | H | 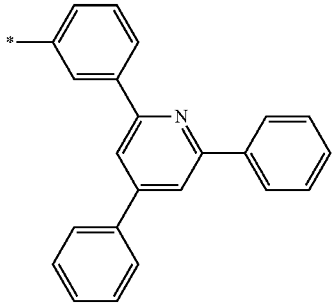 | H | 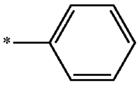 [SMILES: *c1ccccc1] | — | — |
| N-17-13 | $NR^3$ | H | 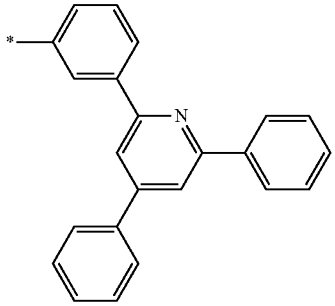 | 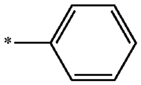 [SMILES: *c1ccccc1] | 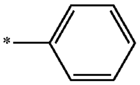 [SMILES: *c1ccccc1] | — | — |
| N-17-14 | $NR^3$ | H | 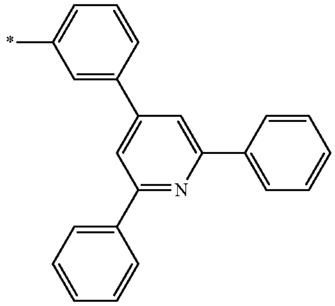 [SMILES: *c1cccc(-c2cc(-c3ccccc3)nc(-c3ccccc3)c2)c1] | H | 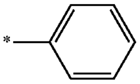 [SMILES: *c1ccccc1] | — | — |

TABLE 63-continued
| | | | | | | | |
|---|---|---|---|---|---|---|---|
| N-17-15 | $NR^3$ | H | 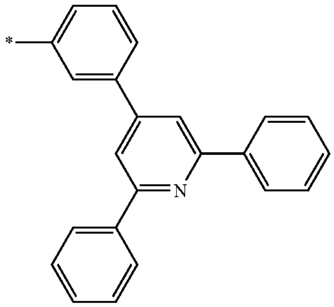 [SMILES: *c1cccc(-c2cc(-c3ccccc3)nc(-c3ccccc3)c2)c1] | 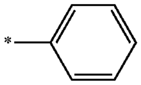 [SMILES: *c1ccccc1] | 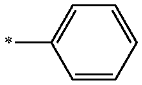 [SMILES: *c1ccccc1] | — | — |
| N-17-16 | $NR^3$ | H | 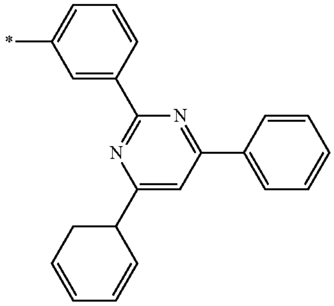 | H | 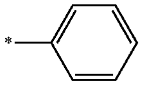 [SMILES: *c1ccccc1] | — | — |
| N-17-17 | $NR^3$ | H | 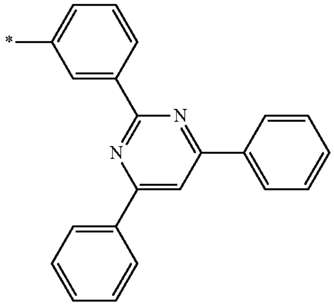 | 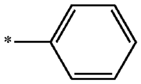 [SMILES: *c1ccccc1] | 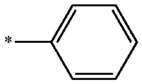 [SMILES: *c1ccccc1] | — | — |
| N-17-18 | $NR^3$ | H | 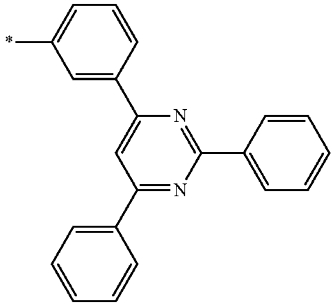 | H | 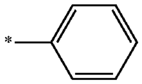 [SMILES: *c1ccccc1] | — | — |
| N-17-19 | $NR^3$ | H | 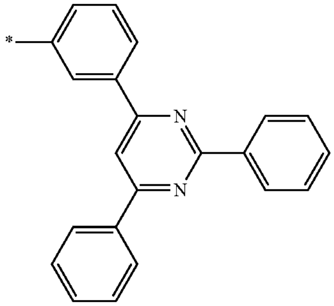 | 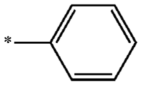 [SMILES: *c1ccccc1] | 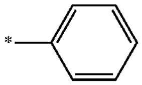 [SMILES: *c1ccccc1] | — | — |

TABLE 63-continued
| | | | | | | | |
|---|---|---|---|---|---|---|---|
| N-17-20 | $NR^3$ | H | 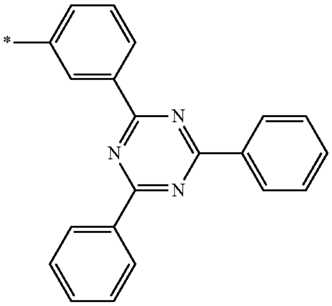 | H | 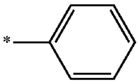 [SMILES: *c1ccccc1] | — | — |
| N-17-21 | $NR^3$ | H | 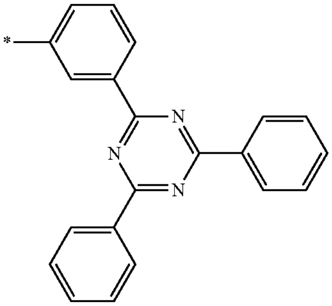 | 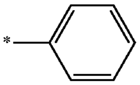 [SMILES: *c1ccccc1] | 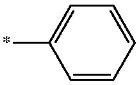 [SMILES: *c1ccccc1] | — | — |
| N-17-22 | $NR^3$ | H | 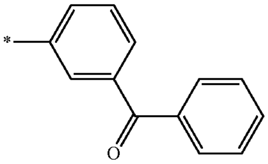 [SMILES: *c1cccc(C(=O)c2ccccc2)c1] | H | 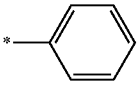 [SMILES: *c1ccccc1] | — | — |
TABLE 64
| | | | | | | | |
|---|---|---|---|---|---|---|---|
| N-17-23 | $NR^3$ | H | 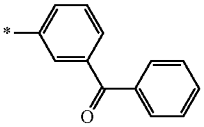 | 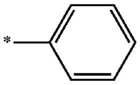 | 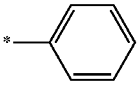 [SMILES: *c1ccccc1] | — | — |
| N-17-24 | $NR^3$ | H | 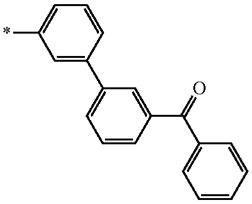 [SMILES: *c1cccc(-c2cccc(C(=O)c3ccccc3)c2)c1] | H | 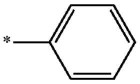 | — | — |
| N-17-25 | $NR^3$ | H | 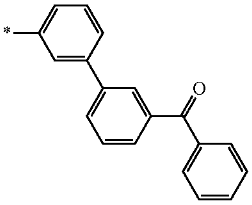 [SMILES: *c1cccc(-c2cccc(C(=O)c3ccccc3)c2)c1] | 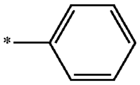 [SMILES: *c1ccccc1] | 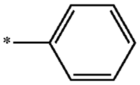 [SMILES: *c1ccccc1] | — | — |
| C-17-1 | $CR^1R^2$ | H | H | H | — | *—Me | *—Me |
| C-17-2 | $CR^1R^2$ | H | 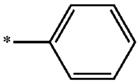 [SMILES: *c1ccccc1] | 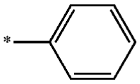 | — | *—Me | *—Me |

TABLE 64-continued
| | | | | | | | |
|---|---|---|---|---|---|---|---|
| C-17-3 | $CR^1R^2$ | H | 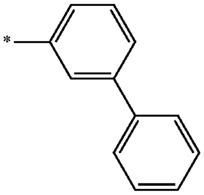 [SMILES: *c1cccc(-c2ccccc2)c1] | H | — | *—Me | *—Me |
| C-17-4 | $CR^1R^2$ | H | 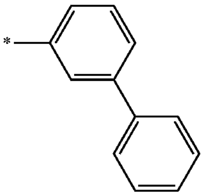 [SMILES: *c1cccc(-c2ccccc2)c1] | 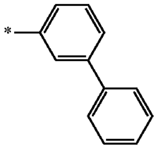 [SMILES: *c1cccc(-c2ccccc2)c1] | — | *—Me | *—Me |
| C-17-5 | $CR^1R^2$ | H | 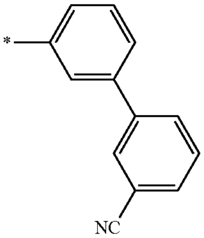 [SMILES: *c1cccc(-c2cccc(C#N)c2)c1] | H | — | 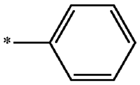 [SMILES: *c1ccccc1] | 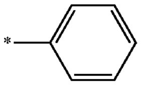 [SMILES: *c1ccccc1] |
| C-17-6 | $CR^1R^2$ | H | H | 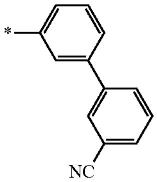 [SMILES: *c1cccc(-c2cccc(C#N)c2)c1] | — | *—Me | *—Me |
| C-17-7 | $CR^1R^2$ | H | 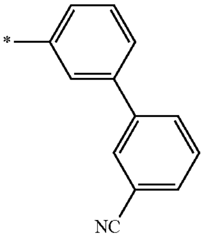 [SMILES: *c1cccc(-c2cccc(C#N)c2)c1] | 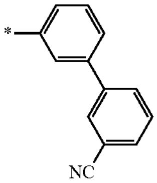 [SMILES: *c1cccc(-c2cccc(C#N)c2)c1] | — | 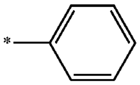 [SMILES: *c1ccccc1] | 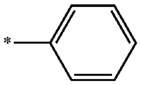 [SMILES: *c1ccccc1] |
| C-17-8 | $CR^1R^2$ | H | 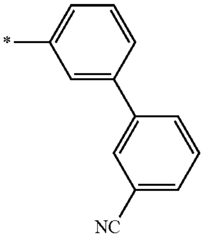 | 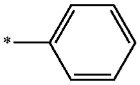 | — | *—Me | *—Me |
| C-17-9 | $CR^1R^2$ | H | 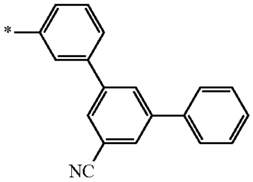 [SMILES: *c1cccc(-c2cc(C#N)cc(-c3ccccc3)c2)c1] | H | — | 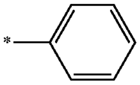 [SMILES: *c1ccccc1] | 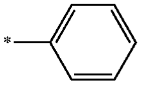 [SMILES: *c1ccccc1] |

TABLE 64-continued
| | | | | | | | |
|---|---|---|---|---|---|---|---|
| C-17-10 | $CR^1R^2$ | H | 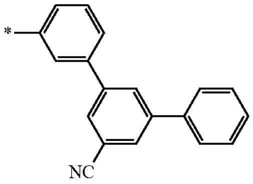 [SMILES: *c1cccc(-c2cc(C#N)cc(-c3ccccc3)c2)c1] | 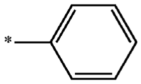 [SMILES: *c1ccccc1] | — | *—Me | *—Me |
| C-17-11 | $CR^1R^2$ | H | 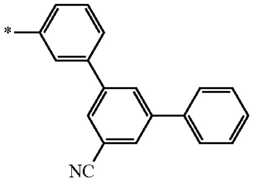 [SMILES: *c1cccc(-c2cc(C#N)cc(-c3ccccc3)c2)c1] | 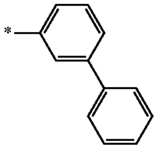 | — | *—Me | *—Me |
| C-17-12 | $CR^1R^2$ | H | 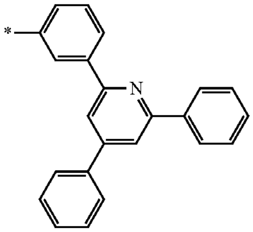 | H | — | *—Me | *—Me |
TABLE 65
| | | | | | | | |
|---|---|---|---|---|---|---|---|
| C-17-13 | $CR^1R^2$ | H | 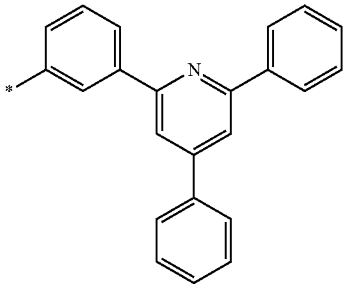 [SMILES: *c1cccc(-c2cc(-c3ccccc3)cc(-c3ccccc3)n2)c1] | 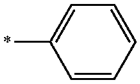 [SMILES: *c1ccccc1] | — | *—Me | *—Me |
| C-17-14 | $CR^1R^2$ | H | 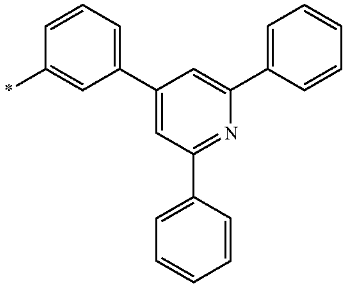 [SMILES: *c1cccc(-c2cc(-c3ccccc3)nc(-c3ccccc3)c2)c1] | H | — | *—Me | *—Me |
| C-17-15 | $CR^1R^2$ | H | 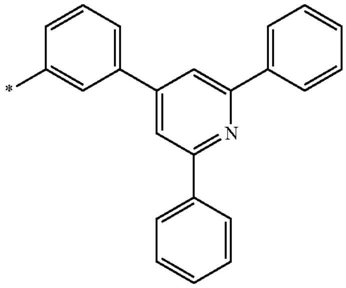 [SMILES: *c1cccc(-c2cc(-c3ccccc3)nc(-c3ccccc3)c2)c1] | 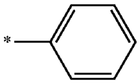 [SMILES: *c1ccccc1] | — | *—Me | *—Me |

TABLE 65-continued
| | | | | | | | |
|---|---|---|---|---|---|---|---|
| C-17-16 | $CR^1R^2$ | H | 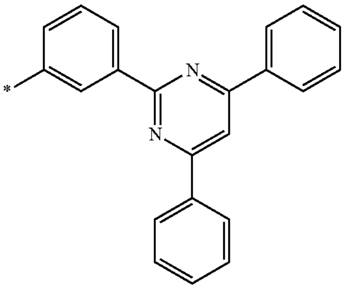 [SMILES: *c1cccc(-c2nc(-c3ccccc3)cc(-c3ccccc3)n2)c1] | H | — | 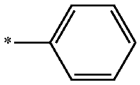 [SMILES: *c1ccccc1] | 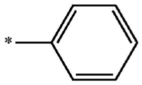 [SMILES: *c1ccccc1] |
| C-17-17 | $CR^1 R^2$ | H | 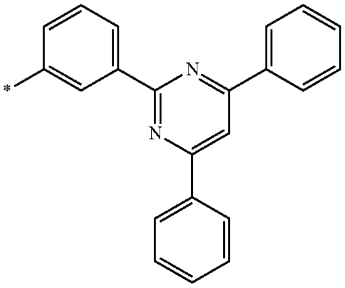 [SMILES: *c1cccc(-c2nc(-c3ccccc3)cc(-c3ccccc3)n2)c1] | 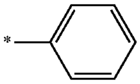 | — | *—Me | *—Me |
| C-17-18 | $CR^1R^2$ | H | 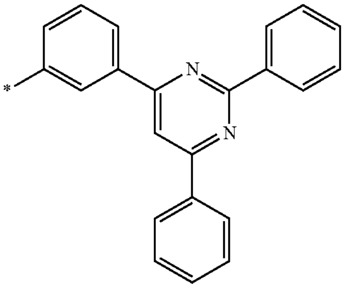 [SMILES: *c1cccc(-c2cc(-c3ccccc3)nc(-c3ccccc3)n2)c1] | H | — | *—Me | *—Me |
| C-17-19 | $CR^1 R^2$ | H | 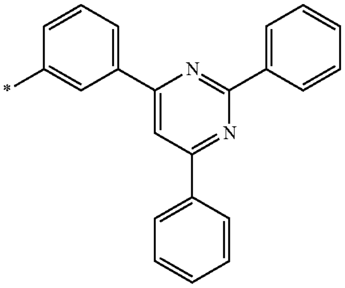 [SMILES: *c1cccc(-c2cc(-c3ccccc3)nc(-c3ccccc3)n2)c1] | 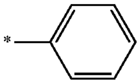 [SMILES: *c1ccccc1] | — | *—Me | *—Me |
| C-17-20 | $CR^1R^2$ | H | 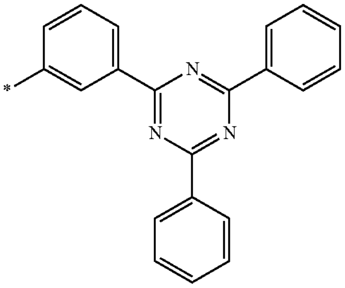 [SMILES: *c1cccc(-c2nc(-c3ccccc3)nc(-c3ccccc3)n2)c1] | H | — | *—Me | * Me |

TABLE 65-continued
| | | | | | | | |
|---|---|---|---|---|---|---|---|
| C-17-21 | $CR^1R^2$ | H | 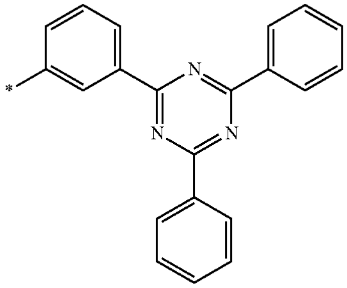 [SMILES: *c1cccc(-c2nc(-c3ccccc3)nc(-c3ccccc3)n2)c1] | 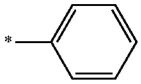 [SMILES: *c1ccccc1] | — | *—Me | *—Me |
| C-17-22 | $CR^1R^2$ | H | 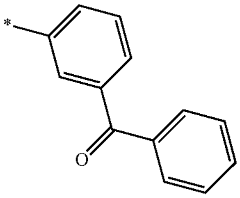 [SMILES: *c1cccc(C(=O)c2ccccc2)c1] | H | — | *—Me | *—Me |
| C-17-23 | $CR^1R^2$ | H | 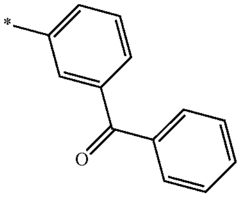 [SMILES: *c1cccc(C(=O)c2ccccc2)c1] | 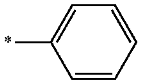 [SMILES: *c1ccccc1] | — | 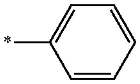 [SMILES: *c1ccccc1] | 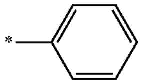 [SMILES: *c1ccccc1] |
| C-17-24 | $CR^1R^2$ | H | 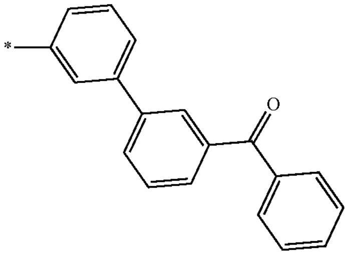 [SMILES: *c1cccc(-c2cccc(C(=O)c3ccccc3)c2)c1] | H | — | *—Me | *—Me |
| C-17-25 | $CR^1R^2$ | H | 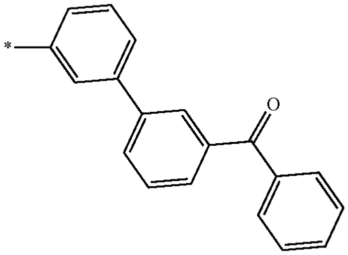 [SMILES: *c1cccc(-c2cccc(C(=O)c3ccccc3)c2)c1] | 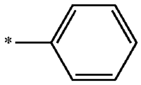 [SMILES: *c1ccccc1] | — | *—Me | *—Me |

The compounds exemplified as the compound represented by the general formula (1) can be synthesized by the methods described in, for example, WO2010/042107, WO2010/131855, JP-A-2010-087496, and the like.

The compounds represented by the general formulae (2) to (9) can be each preferably synthesized by the following scheme. However, the following synthesis scheme is one of synthesis and the synthesis can be also conducted by other known methods.

Synthesis Route of General Formula (2)

[Chem. 23]

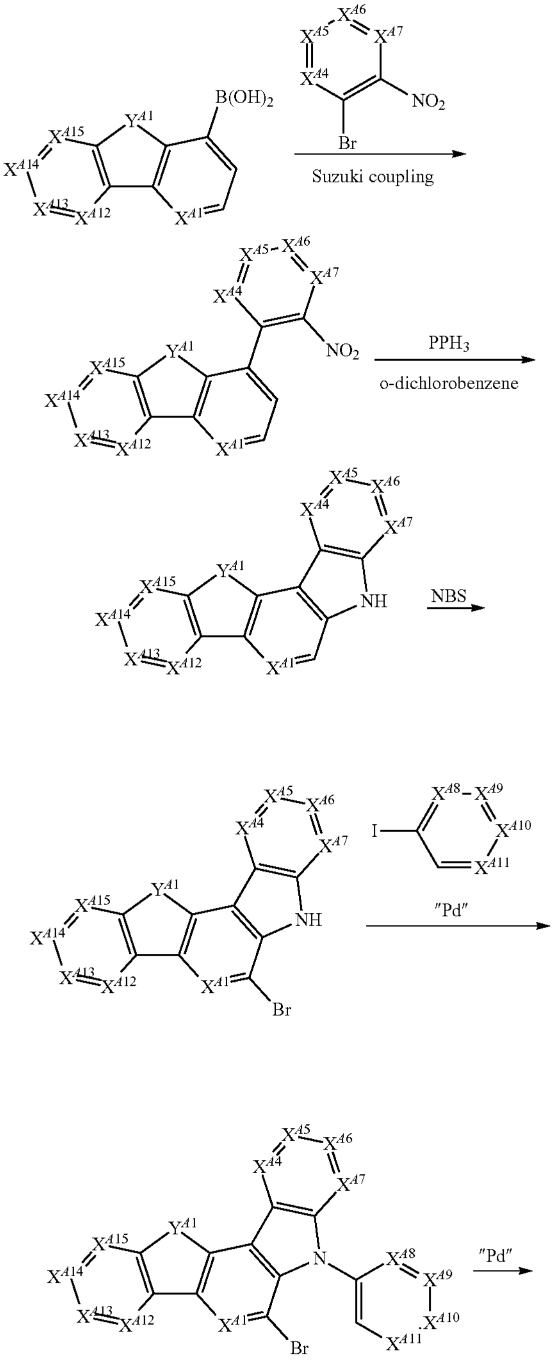

-continued

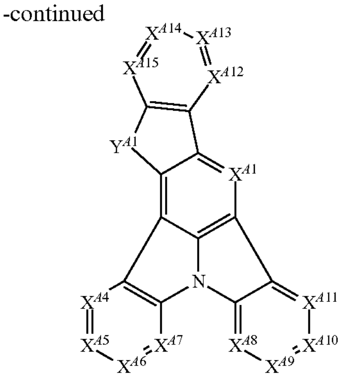

(2)

Synthesis Route of General Formula (3)

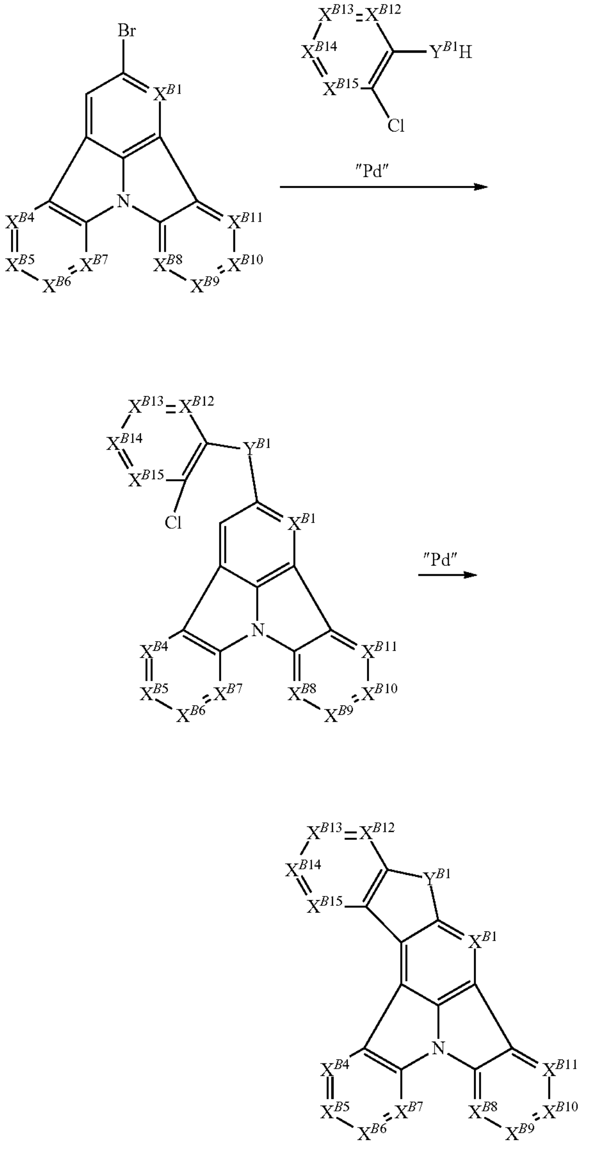

(3)

Synthesis Route of General Formula (4)
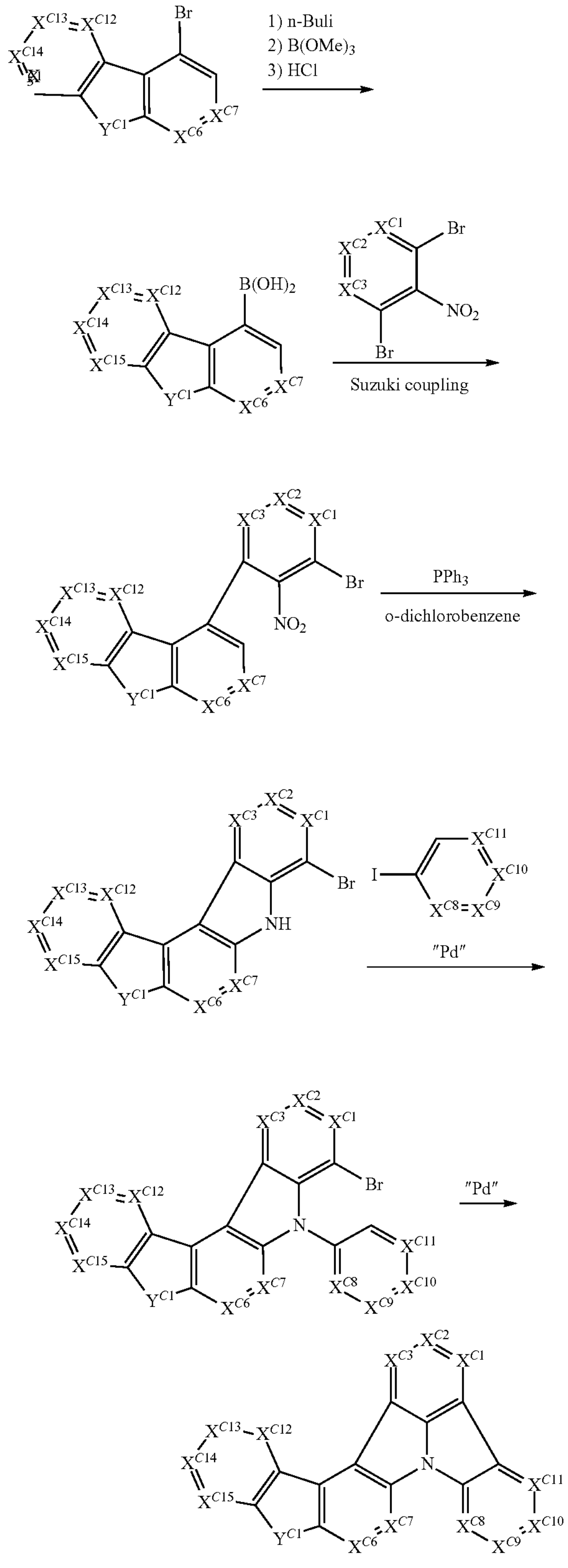
(4)
Synthesis Route of General Formula (5)
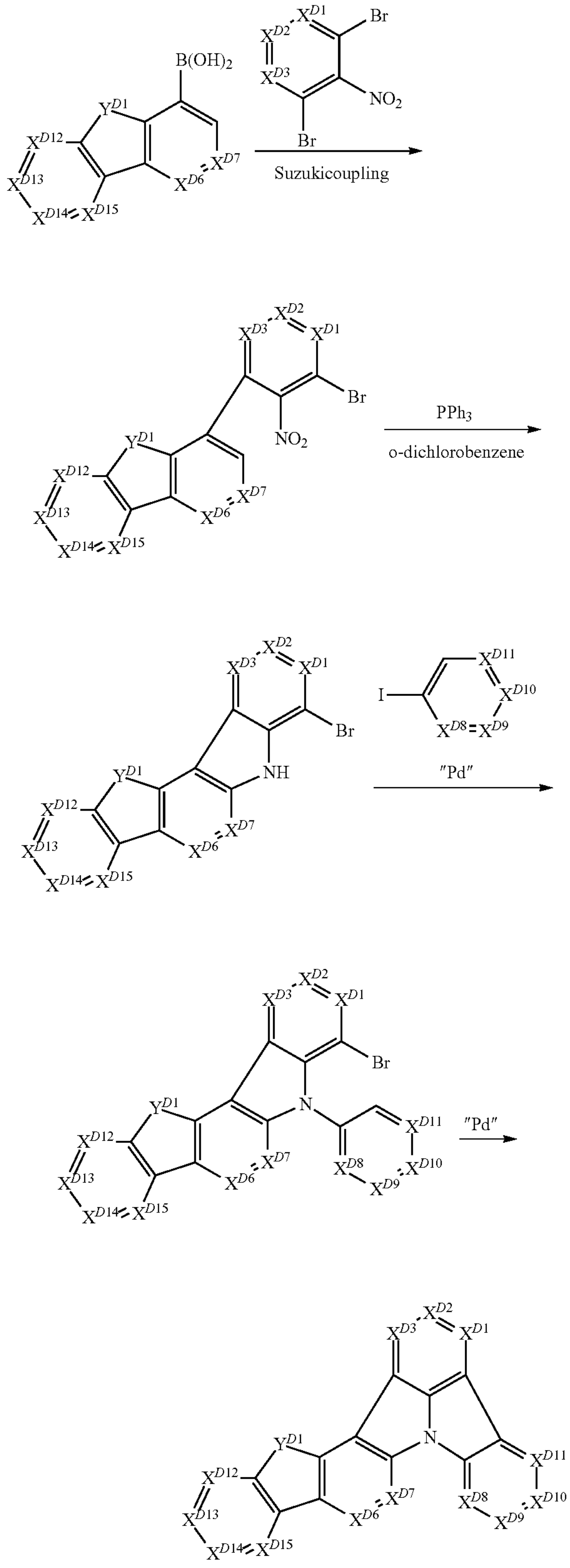
(5)

Synthesis Route of General Formula (6)
[Chem. 24-2]
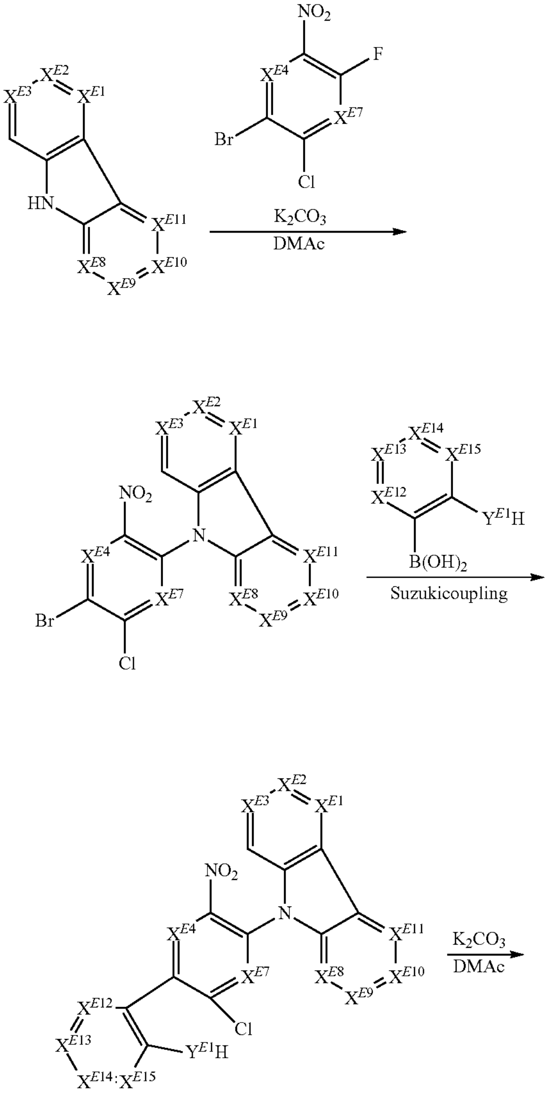
-continued
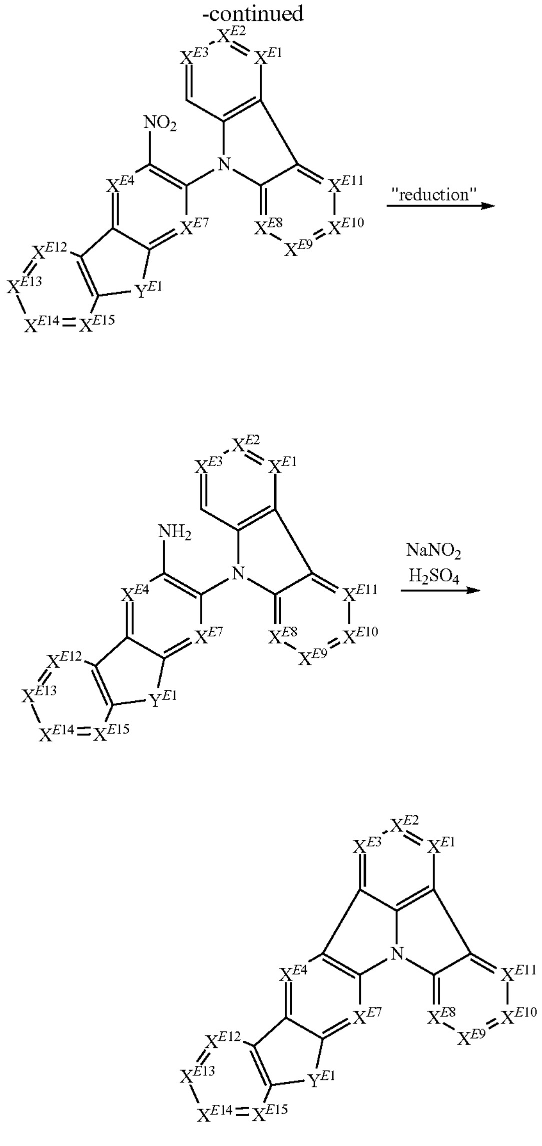
(6)
Synthesis Route of General Formula (7)
[Chem. 25]
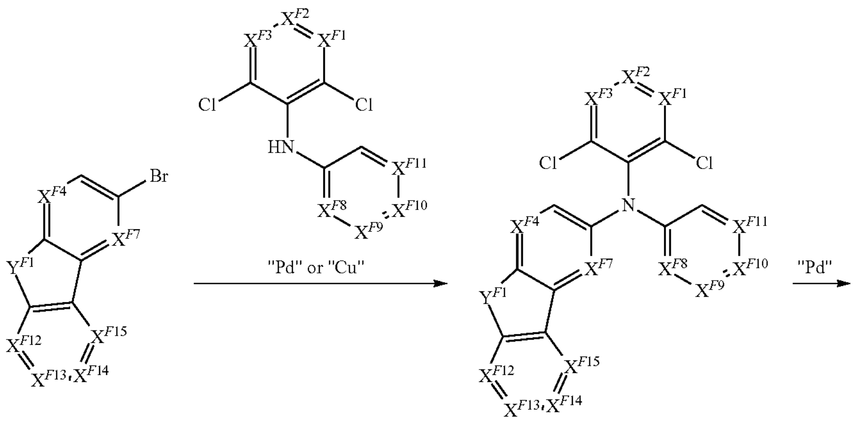

-continued
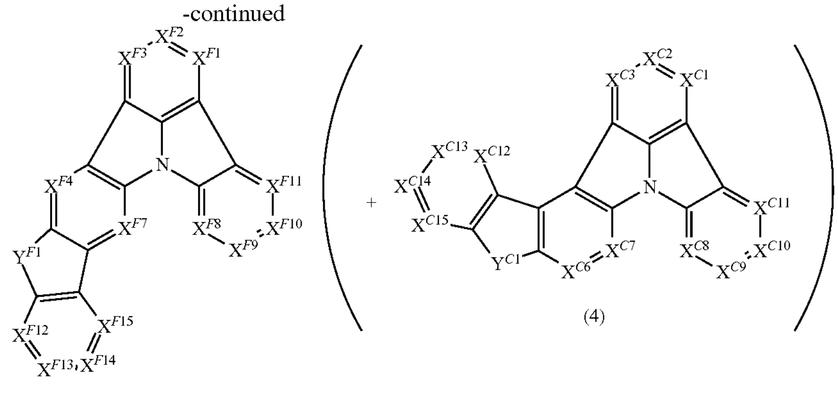
(7) (4)
Synthesis Route of General Formula (8)
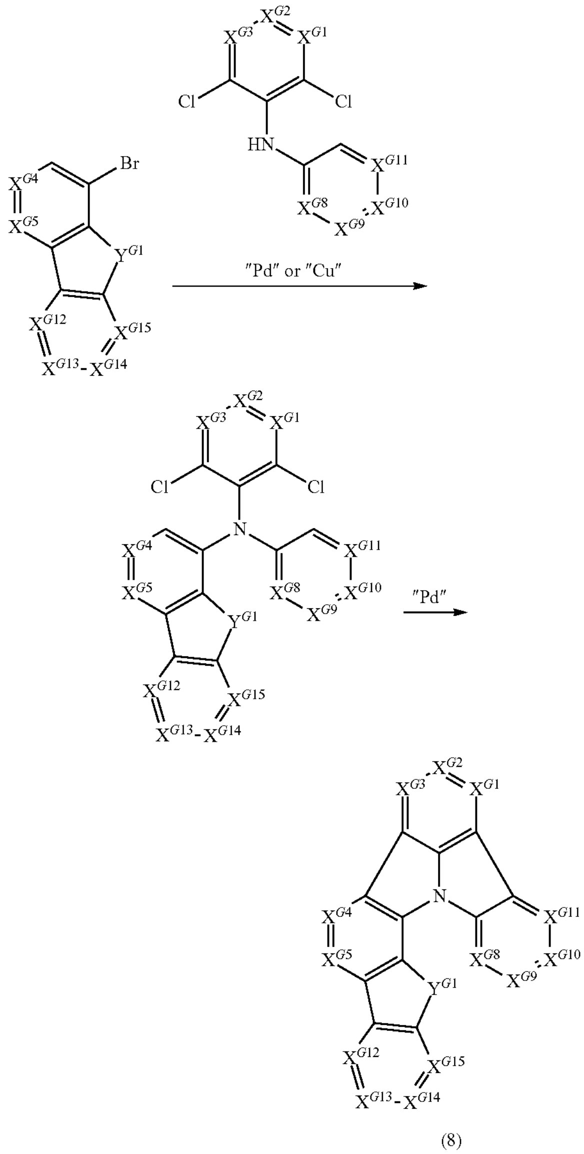
(8)
Synthesis Route of General Formula (9)
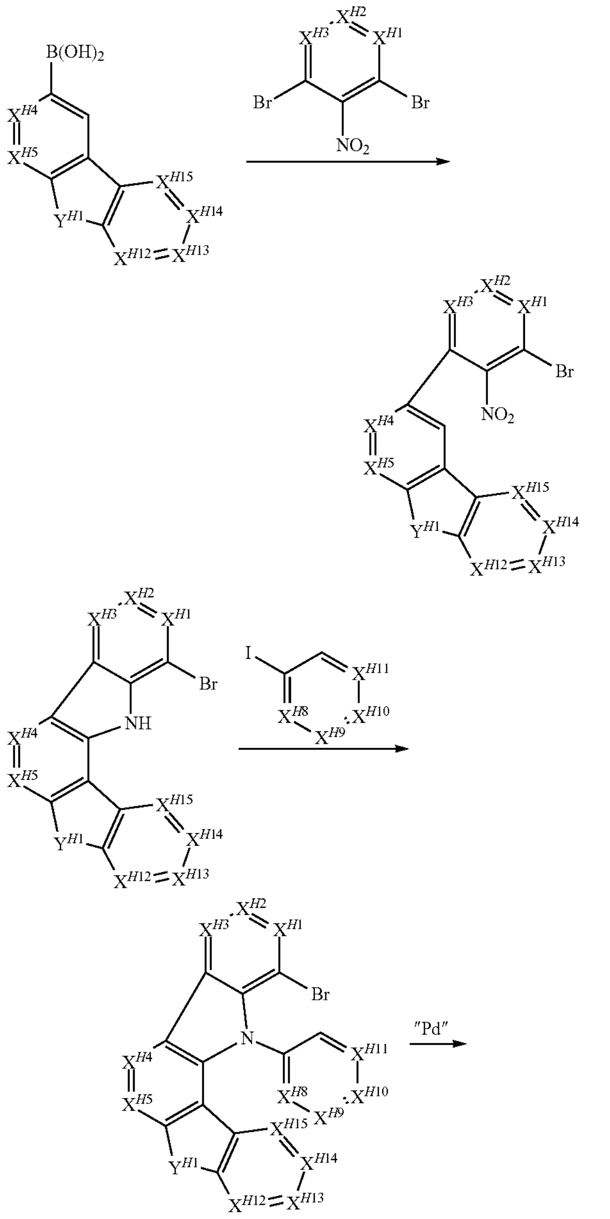

-continued

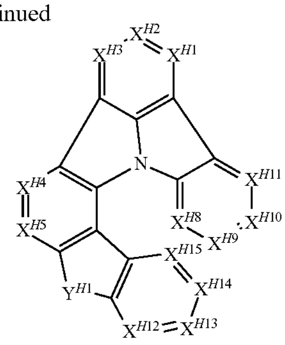

(9)

In the present invention, the compound represented by the general formula (1) is not limited in its use and can be contained in any one of the organic layers. With regard to the layer into which the compound represented by the general formula (1) is introduced, the compound is preferably contained in any one of the light emitting layer, a layer between the light emitting layer and the cathode (in particular, a layer adjacent to the light emitting layer), and a layer between the light emitting layer and the anode, more preferably contained in any one of the light emitting layer, an electron transporting layer, an electron injecting layer, an exciton blocking layer, a hole blocking layer, and an electron blocking layer, or in a plurality of layers thereof, still more preferably contained in any one of the light emitting layer, an electron transporting layer, a hole blocking layer, and a hole transporting layer, and particularly preferably contained in the light emitting layer or an electron transporting layer. Further, the compound represented by the general formula (1) may be used in a plurality of the layers. For example, the compound may be used in both of the light emitting layer and an electron transporting layer.

In the case where the compound represented by the general formula (1) is contained in the light emitting layer, the compound represented by the general formula (1) is contained in the amount of, preferably 0.1% by mass to 99% by mass, more preferably 1% by mass to 97% by mass, and still more preferably 10% by mass to 96% by mass, with respect to the total mass of the light emitting layer. In the case where the compound represented by the general formula (1) is further contained in the layers other than the light emitting layer, it is contained in the amount of, preferably 50% by mass to 100% by mass, and more preferably 85% by mass to 100% by mass, with respect to the total mass of the layers other than the light emitting layer.

(Phosphorescent Light Emitting Material)

In the present invention, the light emitting layer preferably contains at least one phosphorescent light emitting material. In the present invention, in addition to the phosphorescent light emitting material, a fluorescent light emitting material or a phosphorescent light emitting material other than the phosphorescent light emitting material contained in the light emitting layer can be used as the light emitting material.

The fluorescent light emitting material and the phosphorescent light emitting material are described in detail in, for example, paragraph Nos. [0100] to [0164] of JP-A-2008-270736 and paragraph Nos. [0088] to [0090] of JP-A-2007-266458, and the detailed descriptions in these publications can be applied to the present invention.

Examples of the phosphorescent light emitting material which can be used in the present invention include phosphorescent light emitting compounds described in patent documents, for example, U.S. Pat. Nos. 6,303,238B1, 6,097,147, WO00/57676, WO00/70655, WO01/08230, WO01/39234A2, WO01/41512A1, WO02/02714A2, WO02/15645A1, WO02/44189A1, WO05/19373A2, JP-A-2001-247859, JP-A-2002-302671, JP-A-2002-117978, JP-A-2003-133074, JP-A-2002-235076, JP-A-2003-123982, JP-A-2002-170684, EP1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP A-2006-256999, JP-A-2007-19462, JP-A-2007-84635, and JP-A-2007-96259. Above all, examples of the light emitting material which is more preferred include phosphorescent light emitting metal complex compounds such as Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes, with Ir complexes, Pt complexes, and Re complexes being particularly preferred. Above all, Ir complexes, Pt complexes, and Re complexes each including at least one coordination mode of a metal-carbon bond, a metal-nitrogen bond, a metal-oxygen bond, and a metal-sulfur bond are preferred. Furthermore, from the viewpoints of luminous efficiency, driving durability, and chromaticity, Ir complexes and Pt complexes are particularly preferred, and Ir complexes are the most preferred.

These phosphorescent light emitting metal complex compounds are preferably contained together with the compound represented by the general formula (1) in the light emitting layer.

As the phosphorescent light emitting material contained in the light emitting layer, an iridium complex represented by the general formula (E-1) shown below is preferably used. The iridium complex represented by the general formula (E-1) will be described below.

[Chem. 26]

(E-1)

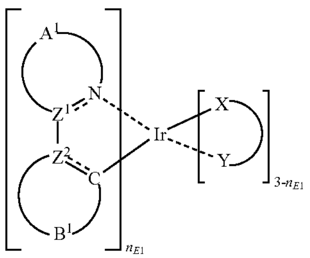

In the general formula (E-1), $Z^1$ and $Z^2$ each independently represent a carbon atom or a nitrogen atom.

$A^1$ represents an atomic group that together with $Z^1$ and a nitrogen atom forms a 5- or 6-membered hetero ring.

$B^1$ represents an atomic group that together with $Z^2$ and a carbon atom forms a 5- or 6-membered ring.

(X—Y) represents a mono-anionic bidentate ligand.

$n_{E1}$ represents an integer of 1 to 3.

$n_{E1}$ represents an integer of 1 to 3, and preferably 2 or 3.

$Z^1$ and $Z^2$ each independently represent a carbon atom or a nitrogen atom. $Z^1$ and $Z^2$ are each preferably a carbon atom.

$A^1$ represents an atomic group that together with $Z^1$ and a nitrogen atom forms a 5- or 6-membered hetero ring. Examples of the 5- of 6-membered hetero ring formed of $A^1$, $Z^1$, and a nitrogen atom include a pyridine ring, a pyrimidine ring, a pyrazine ring, a triazine ring, an imidazole ring, a pyrazole ring, an oxazole ring, a thiazole ring, a triazole ring, an oxadiazole ring, and a thiadiazole ring.

From the viewpoints of stability of complexes, control of light emitting wavelength, and luminescent quantum yield, examples of the 5- of 6-membered hetero ring formed of $A^1$, $Z^1$, and a nitrogen atom preferably include a pyridine ring, a pyrazine ring, an imidazole ring, and a pyrazole ring, more preferably include a pyridine ring, an imidazole ring, and a pyrazine ring, still more preferably include a pyridine ring and an imidazole ring, and most preferably include a pyridine ring.

The 5- of 6-membered hetero ring formed of $A^1$, $Z^1$, and a nitrogen atom may have a substituent, and as the substituent, the Substituent Group A can be applied. The substituent is appropriately selected to control the light emitting wavelength and the potentials, but in the case of shortening the wavelength, an electron donating group, a fluorine atom, and an aromatic ring group are preferred, and for example, an alkyl group, a dialkylamino group, an alkoxy group, a fluorine atom, an aryl group, a heteroaryl group, and the like are selected. Further, in the case of increasing the wavelength, an electron withdrawing group is preferred, and for example, a cyano group, a perfluoroalkyi group, and the like are preferably selected. For the purpose of adjusting the molecular interaction, an alkyl group, a cycloalkyl group, an aryl group, and the like are preferably selected.

The substituent on carbon is preferably an alkyl group, a perfluoroalkyl group, an aryl group, a heteroaryl group, a dialkylamino group, a diarylamino group, an alkoxy group, a cyano group, or a fluorine atom.

The substituent on nitrogen is preferably an alkyl group, an aryl group, or a heteroaryl group, and from the viewpoint of the stability of complexes, the substituent is preferably an alkyl group or an aryl group.

The substituents may be connected to each other to form a fused ring, and examples of the ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring. The ring thus formed may have a substituent, and examples of the substituent include the substituents on carbon atoms and the substituents on nitrogen atoms, as described above.

$B^1$ represents a 5- or 6-membered ring containing $Z^2$ and carbon atoms. Examples of the 5- or 6-membered ring formed of $B^1$, $Z^2$ and a carbon atom include a benzene ring, a pyridine ring, a pyrimidine ring, a pyrazine ring, a pyridazine ring, a triazine ring, an imidazole ring, a pyrazole ring, an oxazole ring, a thiazole ring, a triazole ring, an oxadiazol e ring, a thiadiazole ring, a thiophene ring, and a furan ring.

From the viewpoints of the stability of complexes, the control of light emitting wavelength, and the luminescent quantum yield, the 5- or 6-membered ring formed of $B^1$, $Z^2$ and a carbon atom is preferably a benzene ring, a pyridine ring, a pyrazine ring, an imidazole ring, a pyrazole ring, or a thiophene ring, more preferably a benzene ring, a pyridine ring, or a pyrazole ring, and still more preferably a benzene ring or a pyridine ring.

The 5- or 6-membered ring formed of $B^1$, $Z^2$ and a carbon atom may have a substituent, as the substituent on a carbon atom, the Substituent Group A can be applied, and as the substituent on a nitrogen atom, the Substituent Group B can be applied.

The substituent on carbon is preferably an alkyl group, a perfluoroalkyl group, an aryl group, a heteroaryl group, a dialkylamino group, a diarylamino group, an alkoxy group, a cyano group, or a fluorine atom.

The substituent on carbon is appropriately selected to control the light emitting wavelength and the potentials, but in the case of increasing the wavelength, an electron donating group and an aromatic ring group are preferred, and for example, an alkyl group, a dialkylamino group, an alkoxy group, an aryl group, a heteroaryl group, and the like are selected. Further, in the case of shortening the wavelength, an electron withdrawing group is preferred, and for example, a fluorine atom, cyano group, a perfluoroalkyl group, and the like are selected. For the purpose of adjusting the molecular interaction, an alkyl group, a cycloalkyl group, an aryl group, and the like are preferably selected.

The substituent on nitrogen is preferably an alkyl group, an aryl group, or an aromatic hetero ring group, and from the viewpoint of the stability of complexes, the substituent is preferably an alkyl group or an aryl group. The substituents may be connected to each other to form a fused ring, and examples of the ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring. The ring thus formed may have a substituent, and examples of the substituent include the substituents on carbon atoms and the substituents on nitrogen atoms, as described above.

In addition, the substituents of the 5- or 6-membered ring formed of $A^1$, $Z^1$, and a nitrogen atom and the 5- or 6-membered ring formed of $B^1$, $Z^2$, and a carbon atom may be connected to each other to form a fused ring as described above.

(X—Y) represents a mono-anionic bidentate ligand. Examples of the mono-anionic bidentate ligand described in pp. 89 to 90 of WO02/15645, Lamansky et al.

The mono-anionic bidentate ligand represented by (X—Y) is preferably a mono-anionic bidentate ligand represented by the following general formula (L-1).

[Chem. 27]

(L-1)

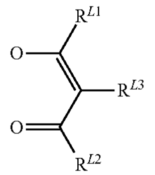

In the general formula (L-1), $R^{L1}$ and $R^{L2}$ each independently represent an alkyl group, an aryl group, or a heteroaryl group.

$R^{L3}$ represents a hydrogen atom, an alkyl group, an aryl group, or a heteroaryl group.

The alkyl group represented by $R^{L1}$ to $R^{L2}$ may have a substituent, and may be saturated or unsaturated. In the case where the alkyl group have a substituent, examples of the substituent include the following substituent Z', preferred examples of the substituent Z' include a phenyl group, a heteroaryl group, a fluorine atom, a silyl group, an amino group, a cyano group, or a group formed by a combination thereof, and more preferably a phenyl group, a fluorine atom, or a cyano group. The alkyl group represented by $R^{L1}$ to $R^{L3}$ is preferably an alkyl group having 1 to 8 carbon atoms, and more preferably an alkyl group having 1 to 5 carbon atoms.

<<Substituent Z'>

The substituents Z' represents an alkyl group (preferably having 1 to 10 carbon atoms, more preferably having 1 to 6 carbon atoms, and still more preferably having 1 to 4 carbon atoms, for example, methyl, ethyl, isopropyl, n-propyl, tert-butyl, isobutyl, n-butyl, neopentyl, n-pentyl, n-hexyl, cyclopropyl, cyclopentyl, and cyclohexyl), an alkenyl group (preferably having 2 to 8 carbon atoms, and more preferably having 2 to 5 carbon atoms, for example, vinyl), an aryl group (preferably having 6 to 30 carbon atoms, and more preferably having 6 to 20 carbon atoms, for example, a phenyl group, a naphthyl group, an anthacenyl group, a tetracenyl group, a pyrenyl group, a perylenyl group, a triphenylenyl group, and a chrysenyl group), a heteroaryl group (preferably having 4 to 30 carbon atoms, and more preferably having 4 to 20 carbon atoms, for example, pyridine, pyrazine, pyrimidine, pyridazine, triazine, thiophene, furan, oxazole, thiazole, imidazole, pyrazole, triazole, oxadiazole, and thiadiazole), an alkoxy group (preferably having 1 to 8 carbon atoms, and more preferably having 1 to 5 carbon atoms, for example, a methoxy group, an ethoxy group, an n-propyloxy group, and an iso-propyloxy group), a phenoxy group, a halogen atom (preferably a fluorine atom), a silyl group (preferably having 4 to 30 carbon atoms, and more preferably having 4 to 20 carbon atoms, for example, a trimethylsilyl group, a triethylsilyl group, and a triphenylsilyl group), an amino group (preferably having 2 to 60 carbon atoms, and more preferably having 2 to 40 carbon atoms, for example, a dimethylamino group, a diethylamino group, and a diphenylamino group), a cyano group, or a group formed by a combination thereof. A plurality of substituents Z' may be connected to each other to form an aryl ring. Examples of the aryl ring formed by a mutual combination of a plurality of substituents Z's include a phenyl ring and a pyridine ring, with a phenyl group being preferred.

The aryl groups represented by $R^{L1}$ to $R^{L3}$ may be subjected to ring fusion and may have a substituent. In the case of having a substituent, examples of the substituent include the above-described substituents Z', and the substituent Z' is preferably an alkyl group or an aryl group, and more preferably an alkyl group. The aryl group represented by $R^{L1}$ to $R^{L3}$ is preferably an aryl group having 6 to 30 carbon atoms, and more preferably an aryl group having 6 to 18 carbon atoms.

The heteroaryl groups represented by $R^{L1}$ to $R^{L3}$ may be subjected to ring fusion and may have a substituent. In the case of having a substituent, examples of the substituent include the above-described substituents Z', and the substituent Z' is preferably an alkyl group or an aryl group, and more preferably an alkyl group. The heteroaryl group represented by $R^{L1}$ to $R^{L3}$ is preferably a heteroaryl group having 4 to 12 carbon atoms, and more preferably a heteroaryl group having 4 to 10 carbon atoms.

$R^{L1}$ and $R^{L2}$ are preferably an alkyl group or an aryl group, more preferably an alkyl group or a phenyl group, and particularly preferably an alkyl group.

The alkyl group represented by $R^{L1}$ and $R^{L2}$ is preferably an alkyl group having a total carbon number of 1 to 8, and more preferably an alkyl group having a total carbon number of 1 to 5, and examples thereof include a methyl group, an ethyl group, an n-propyl group, an iso-propyl group, an iso-butyl group, a t-butyl group, an n-butyl group, and a cyclohexyl group, preferably a methyl group, an ethyl group, an iso-butyl group, and a t-butyl group, and particularly preferably a methyl group.

$R^{L3}$ is preferably a hydrogen atom, an alkyl group, or aryl group, more preferably a hydrogen atom or alkyl group, and particularly preferably a hydrogen atom.

A preferred embodiment of the iridium complex represented by the general formula (E-1) is an iridium complex material represented by the following general formula (E-2).

Next, the general formula (E-2) will be described.

[Chem. 28]

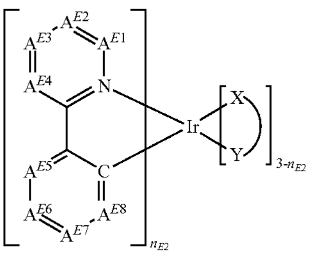

(E-2)

In the general formula (E-2), $A^{E1}$ to $A^{E8}$ each independently represent a nitrogen atom or C—$R^E$.

$R^E$ represents a hydrogen atom or a substituent.

(X—Y) represents a mono-anionic bidentate ligand.

$n_{E2}$ represents an integer of 1 to 3.

$A^{E1}$ to $A^{E8}$ each independently represent a nitrogen atom or C—$R^E$. $R^E$ represents a hydrogen atom or a substituent, and $R^E$s may be connected to each other to forma ring. Examples of the ring thus formed include the same rings as the fused rings exemplified in the general formula (E-1) as described above. Examples of the substituent represented by $R^E$ include those exemplified as the Substituent Group A.

$A^{E1}$ to $A^{E4}$ are preferably C—$R^E$, and in the case where $A^{E1}$ to $A^{E4}$ are C—$R^E$, $R^E$ of $A^{E3}$ is preferably a hydrogen atom, an alkyl group, an aryl group, an amino group, an alkoxy group, an aryloxy group, a fluorine atom, or a cyano group, more preferably a hydrogen atom, an alkyl group, an amino group, an alkoxy group, an aryloxy group, or a fluorine atom, particularly preferably a hydrogen atom or fluorine atom, and $R^E$ of $A^{E1}$, $A^{E2}$ and $A^{E4}$ is preferably a hydrogen atom, an alkyl group, an aryl group, an amino group, an alkoxy group, an aryloxy group, a fluorine atom, or a cyano group, more preferably a hydrogen atom, an alkyl group, an amino group, an alkoxy group, an aryloxy group, or a fluorine atom, and particularly preferably a hydrogen atom.

$A^{E5}$ to $A^{E8}$ are preferably C—$R^E$, in the case where $A^{E5}$ to $A^{E8}$ are C—$R^E$, $R^E$ is preferably a hydrogen atom, an alkyl group, a perfluoroalkyl group, an aryl group, an aromatic hetero ring group, a dialkylamino group, a diarylamino group, an alkyloxy group, a cyano group, or a fluorine atom, more preferably a hydrogen atom, an alkyl group, a perfluoroalkyl group, an aryl group, a dialkylamino group, a cyano group, or a fluorine atom, and still more preferably a hydrogen atom, an alkyl group, a trifluoromethyl group, or a fluorine atom. Further, if possible, the substituents may be connected to each other to form a fused ring structure. In the case where the light emitting wavelength is shifted to a short wavelength side, $A^6$ is preferably a nitrogen atom.

(X—Y) and $n_{E2}$ have the same meanings as (X—Y) and $n_{E1}$ in the general formula (E-1), and the preferred ranges thereof are also the same.

A more preferred embodiment of the compound represented by the general formula (E-2) is a compound represented by the following general formula (E-3).

[Chem. 29]

(E-3)

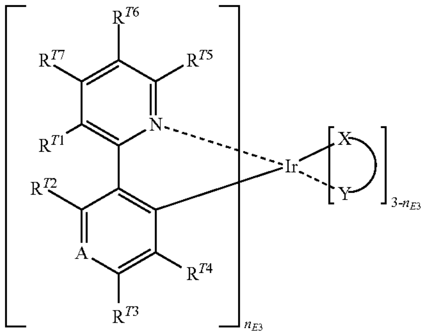

In the general formula (E-3), $R^{T1}$, $R^{T2}$, $R^{T3}$, $R^{T4}$, $R^{T5}$, $R^{T6}$ and $R^{T7}$ each independently represent a hydrogen atom, an alkyl group, a cycloalkyl group, an alkenyl group, an alkynyl group, —CN, a perfluoroalkyl group, a trifluorovinyl group, —$CO_2$R, —C(O)R, —$NR_2$, —$NO_2$, —OR, a halogen atom, an aryl group, or a heteroaryl group, and further, it may have a substituent Z. Rs each independently represent a hydrogen atom, an alkyl group, a perhaloalkyl group, an alkenyl group, an alkynyl group, a heteroalkyl group, an aryl group, or a heteroaryl group.

A represents CR' or a nitrogen atom, R' represents a hydrogen atom, an alkyl group, a cycloalkyl group, an alkenyl group, an alkynyl group, —CN, a perfluoroalkyl group, a trifluorovinyl group, —$CO_2$R, —C(O)R, —$NR_2$, —$NO_2$, —OR, a halogen atom, an aryl group, or a heteroaryl group, and further, it may have a substituent Z. Rs each independently represent a hydrogen atom, an alkyl group, a perhaloalkyl group, an alkenyl group, an alkynyl group, a heteroalkyl group, an aryl group, or a heteroaryl group.

Any two of $R^{T1}$ to $R^{T7}$, and R' may be bonded to each other to form fused 4- to 7-membered rings, the fused 4- to 7-membered rings are cycloalkyl, aryl, or heteroaryl, and the fused 4- to 7-membered rings may further have substituents Z. Above all, it is preferable that $R^{T1}$ and $R^{T7}$, or $R^{T5}$ and $T^{T6}$ be subjected to ring fusion to form a benzene ring, and it is particularly preferable that $R^{T5}$ and $R^{T6}$ be subjected to ring fusion to form a benzene ring.

Zs each independently represent a halogen atom, —R", —OR", —N(R")$_2$, —SR", —C(O)R", —C(O)OR", —C(O)N(R")$_2$, —CN, —$NO_2$, —$SO_2$, —SOR", —$SO_2$R", or —$SO_3$R", and R"s each independently represent a hydrogen atom, an alkyl group, a perhaloalkyl group, an alkenyl group, an alkynyl group, a heteroalkyl group, an aryl group, or a heteroaryl group.

(X—Y) represents a mono-anionic bidentate ligand, and $n_{E3}$ represents an integer of 1 to 3.

The alkyl group may have a substituent, and may be saturated or unsaturated, and examples of the group that may be the substituent include the above-described substituents Zs. The alkyl group represented by $R^{T1}$ to $R^{T7}$, and R' is preferably an alkyl group having a total carbon number of 1 to 8, and more preferably an alkyl group having a total carbon number of 1 to 6, and examples thereof include a methyl group, an ethyl group, an i-propyl group, a cyclohexyl group, and a t-butyl group.

The cycloalkyl group may have a substituent, and may be saturated or unsaturated, and examples of the group that may be the substitute include the above-described substituent Z. The cycloalkyl group represented by $R^{T1}$ to $R^{T7}$, and R' is preferably a cycloalkyl group having 4 to 7 ring members, more preferably a cycloalkyl group having a total carbon number of 5 to 6, and examples thereof include a cyclopenthyl group and a cyclohexyl group.

The alkenyl group represented by $R^{T1}$ to $R^{T7}$, and R' preferably has 2 to 30 carbon atoms, more preferably has 2 to 20 carbon atoms, and particularly preferably has 2 to 10 carbon atoms, and examples thereof include vinyl, allyl, 1-propenyl, 1-isopropenyl, 1-butenyl, 2-butenyl, and 3-pentenyl.

The alkynyl group represented by $R^{T1}$ to $R^{T7}$, and R' preferably has 2 to 30 carbon atoms, more preferably has 2 to 20 carbon atoms, and particularly preferably has 2 to 10 carbon atoms, and examples thereof include ethynyl, propargyl, 1-propynyl, and 3-pentynyl.

The perfluoroalkyl group represented by $R^{T1}$ to $R^{T7}$, and R' includes a group obtained by substituting all the hydrogen atoms in the above-mentioned alkyl group with fluorine atoms.

The aryl group represented by $R^{T1}$ to $R^{T7}$, and R' is preferably a substituted or unsubstituted aryl group having 6 to 30 carbon atoms, and examples thereof include a phenyl group, a tolyl group, and a naphthyl group.

The heteroaryl group represented by $R^{T1}$ to $R^{T7}$, and R' is preferably a heteroaryl group having 5 to 8 carbon atoms, and more preferably a substituted or unsubstituted 5- or 6-membered heteroaryl group, and examples thereof include a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl, group, a carbazolyl group, a dibenzofuryl group, a dibenzothienyl group, and a pyridoindolyl group. Preferred examples thereof are a pyridyl group, a pyrimidinyl group, an imidazolyl group, and a thienyl group, and more preferred examples are a pyridyl group and a pyrimidinyl group.

$R^{T1}$ to $R^{T7}$, and R' are preferably a hydrogen atom, an alkyl group, a cyano group, a trifluoromethyl group, a perfluoroalkyl group, a dialkylamino group, a fluoro group, an aryl group, or a heteroaryl group, more preferably a hydrogen atom, an alkyl group, a cyano group, a trifluoromethyl group, a fluoro group, or an aryl group, and still more preferably a hydrogen atom, an alkyl group, or an aryl group. The substituent Z is preferably an alkyl group, an alkoxy group, a fluoro group, a cyano group, or a dialkylamino group, and more preferably a hydrogen atom.

Any two of $R^{T1}$ to $R^{T7}$, and R' may be bonded to each other to form a fused 4- to 7-membered ring, the fused 4- to 7-membered ring is cycloalkyl, aryl, or heteroaryl, and the fused 4- to 7-membered ring may further have a substituent Z. The definitions and the preferred ranges of the formed cycloalkyl, aryl, and heteroaryl are the same as the cycloalkyl group, the aryl group, and the heteroaryl group defined in $R^{T1}$ to $R^{T7}$, and R'.

Further, a case where A represents CR' and 0 to 2 members of $R^{T1}$ to $R^{T7}$, and R' is/are an alkyl group or a phenyl group and the remainders are all hydrogen atoms is particularly preferred, and a case where 0 to 2 members of $R^{T1}$ to $R^{T7}$, and R' is/are an alkyl group and the remainders are all hydrogen atoms is particularly preferred.

$n_{E3}$ is preferably 2 or 3. With regard to the kind of the ligands in the complex, the ligands are preferably constituted of one or two kinds, and more preferably constituted of one kind. When a reactive group is introduced to the complex molecule, the ligand preferably includes two kinds from the viewpoint of easy synthesis.

(X—Y) has the same definition as (X—Y) in the general formula (E-1) and the preferred range thereof is also the same.

One of preferred embodiments of the compound represented by the general formula (E-3) is a compound represented by the following general formula (E-4).

[Chem. 30]

(E-4)

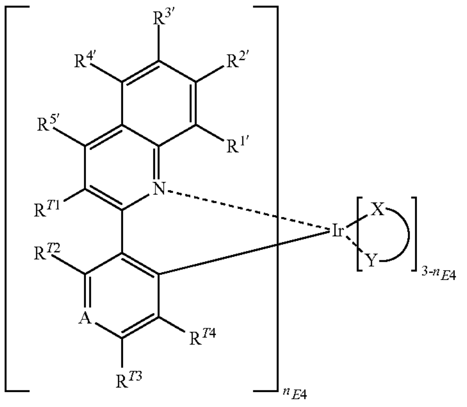

In the general formula (E-4), $R^{T1}$ to $R^{T4}$, A, (X—Y) and $n_{E4}$ have the same definitions as $R^{T1}$ to $R^{T4}$, A, (X—Y) and $n_{E3}$ in the general formula (E-3), and the preferred ranges thereof are also the same. $R^{1'}$ to $R^{5'}$ each independently represent a hydrogen atom, an alkyl group, a cycloalkyl group, an alkenyl group, an alkynyl group, —CN, a perfluoroalkyl group, a trifluorovinyl group, —$CO_2$R, —C(O)R, —$NR_2$, —$NO_2$, —OR, a halogen atom, an aryl group, or a heteroaryl group. Further, they may have a substituent Z. Rs each independently represent a hydrogen atom, an alkyl group, a perhaloalkyl group, an alkenyl group, an alkynyl group, a heteroalkyl group, an aryl group, or a heteroaryl group.

Any two of $R^{1'}$ to $R^{5'}$ may be bonded to each other to form a fused 4- to 7-membered ring, the fused 4- to 7-membered ring is cycloalkyl, aryl, or heteroaryl, and the fused 4- to 7-membered ring may further have a substituent Z.

Zs each independently represent a halogen atom, —R", —OR", —N(R")$_2$, —SR", —C(O) R", —C(O) OR", —C(O) N(R")$_2$, —CN, —$NO_2$, —$SO_2$, —SOR", —$SO_2$R", or —$SO_3$R", and R"s each independently represent a hydrogen atom, an alkyl group, a perhaloalkyl group, an alkenyl group, an alkynyl group, a heteroalkyl group, an aryl group, or a heteroaryl group.

In addition, the preferred ranges of $R^{1'}$ to $R^{5'}$ are the same as those of $R^{T1}$ to $R^{T7}$, and R' in general formula (E-3). Further, a case where A represents CR' and, 0 to 2 members of $R^{T1}$ to $R^{T4}$, R', and $R^{1'}$ to $R^{5'}$ represent(s) an alkyl group or a phenyl group, and the remainders are all hydrogen atoms is particularly preferred, and a case where 0 to 2 members of $R^{T1}$ to $R^{T4}$, R', and $R^{1'}$ to $R^{5'}$ is/are alkyl groups, and the remainders are all hydrogen atoms is still more preferred.

Preferred specific examples of the compound represented by the general formula (E-1) are listed below, but the compounds not limited thereto.

[Chem. 31]

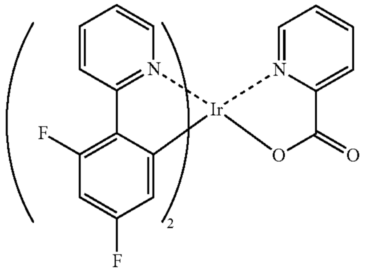

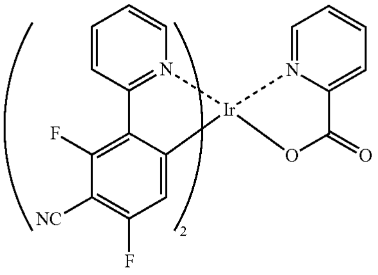

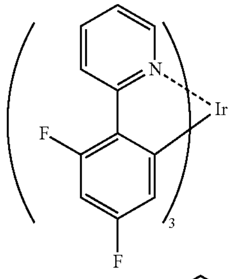
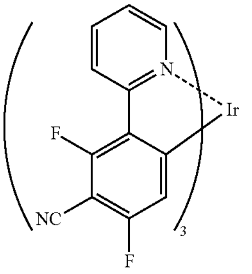

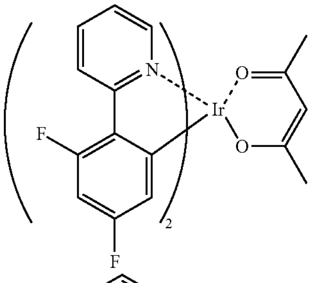

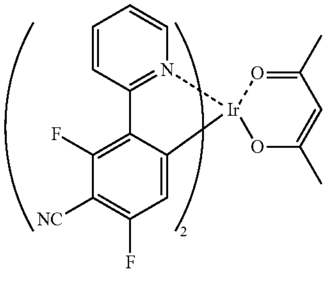

-continued
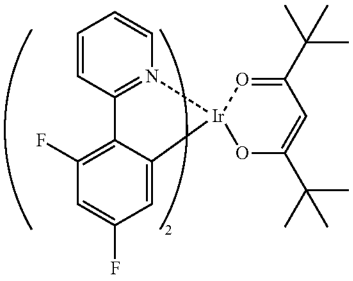
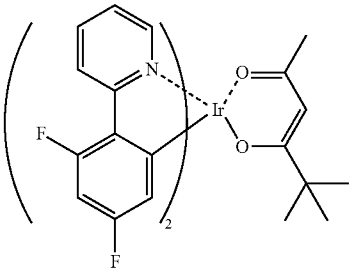
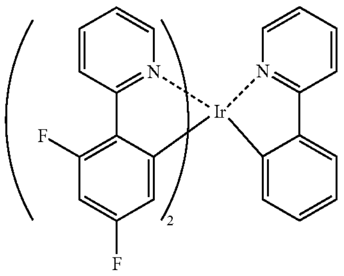
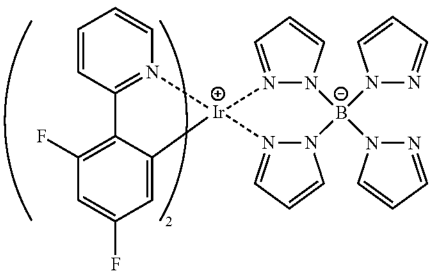
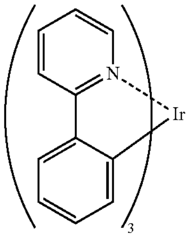
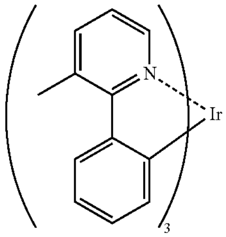
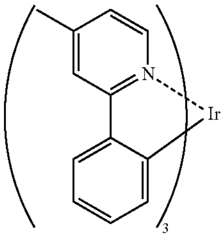
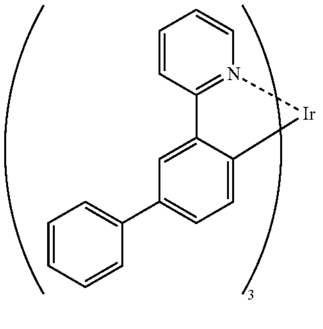
-continued
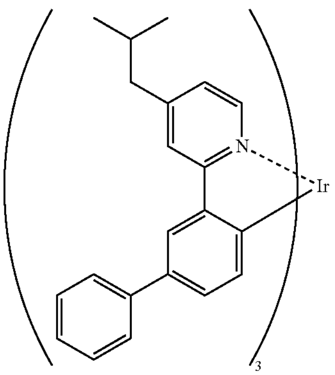
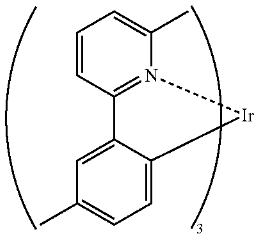
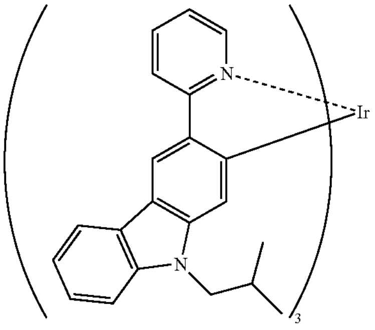
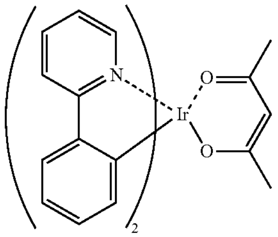
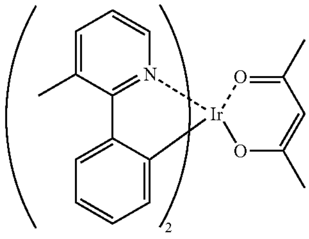
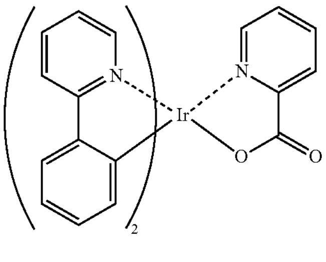

-continued
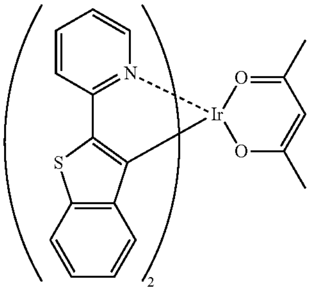
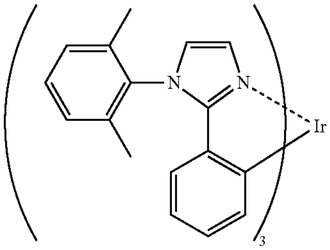
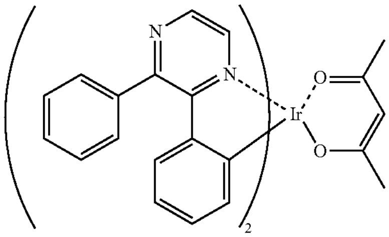
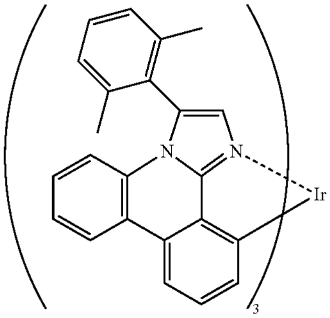
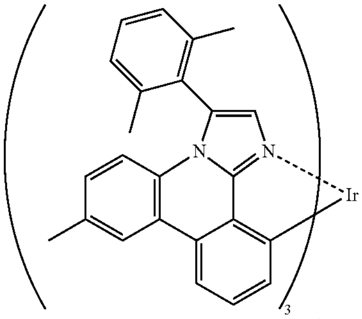
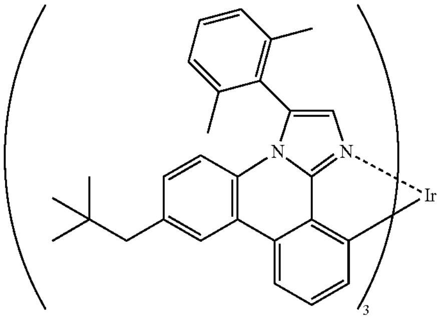
-continued
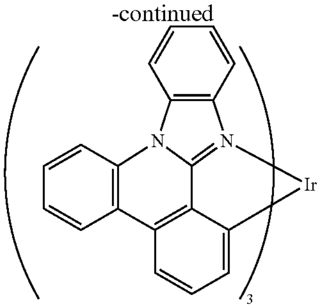
[Chem. 32]
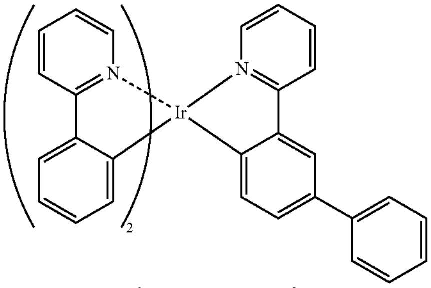
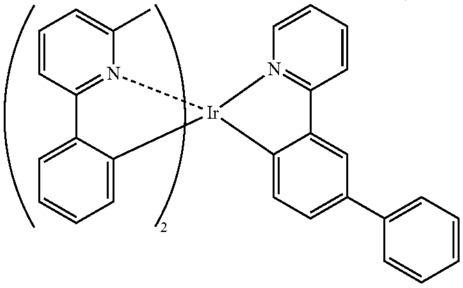
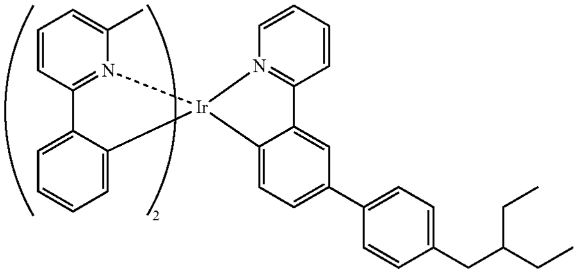
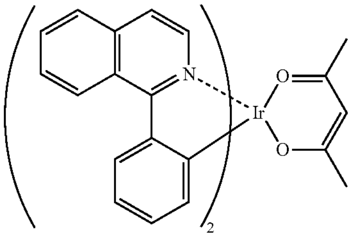
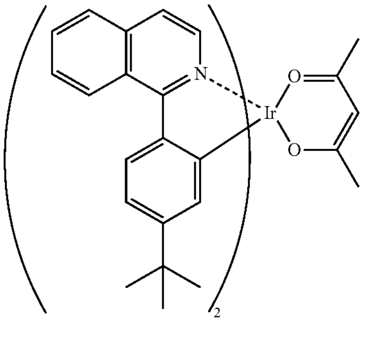

-continued
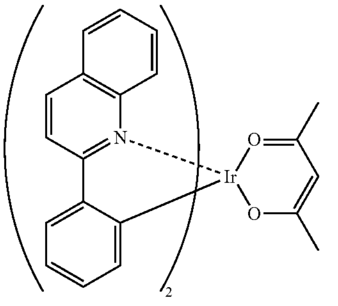
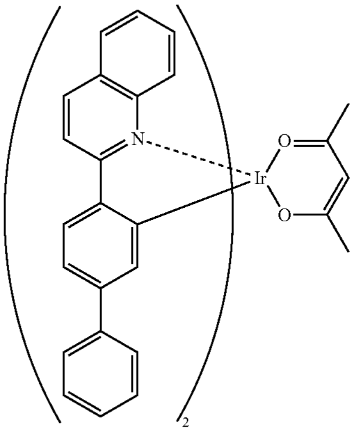
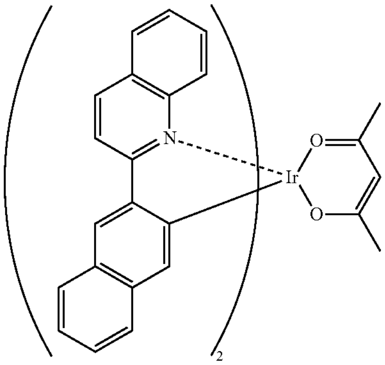
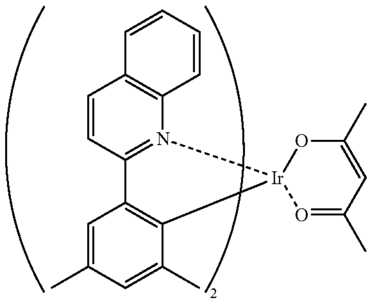
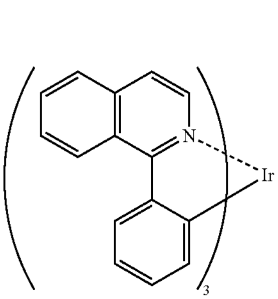
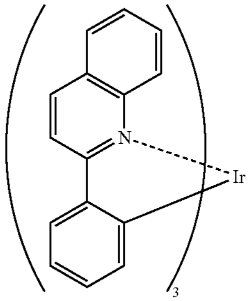
-continued
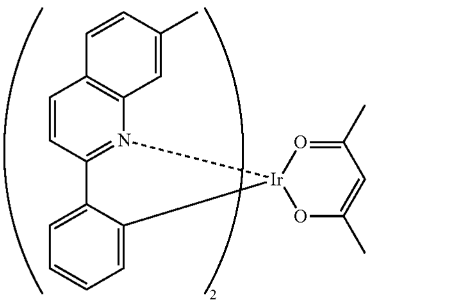
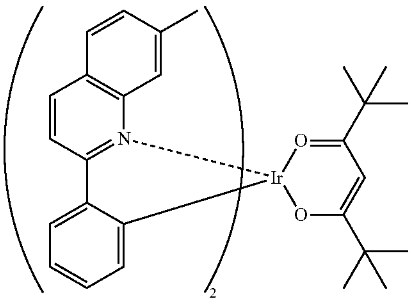
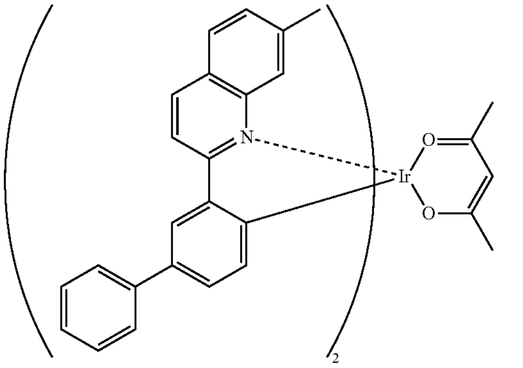
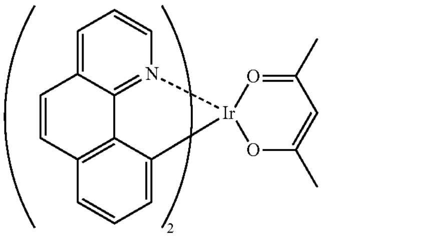
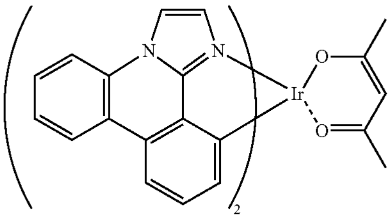
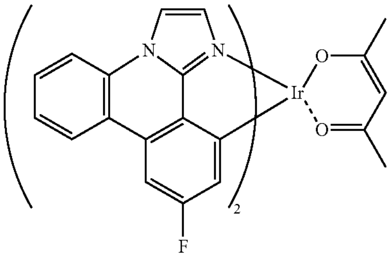

-continued
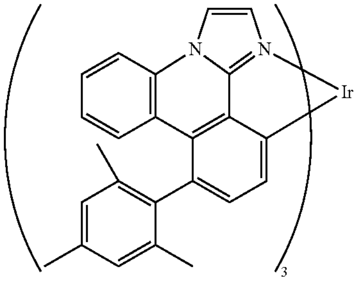
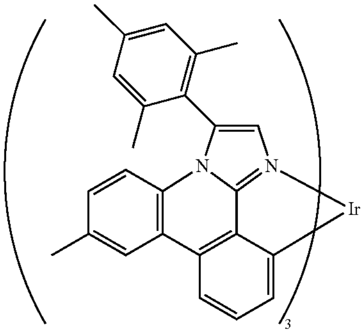
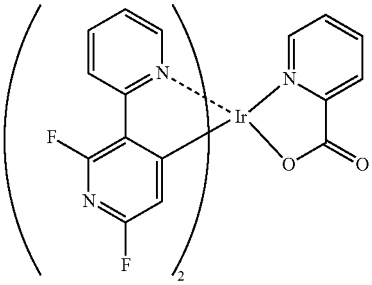
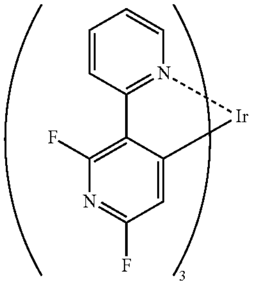
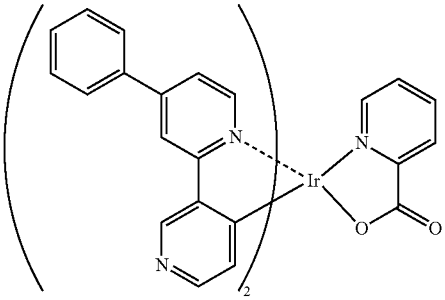
-continued
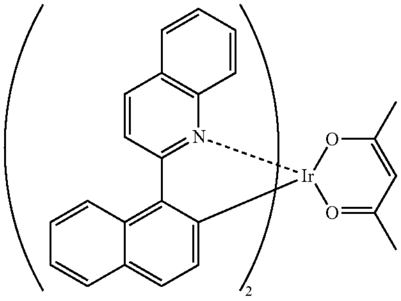
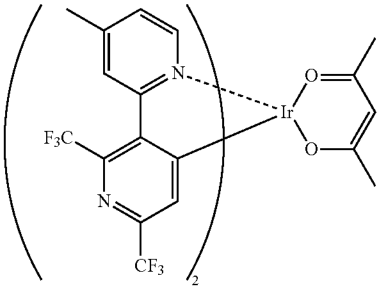
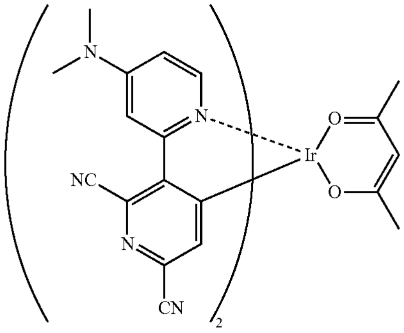
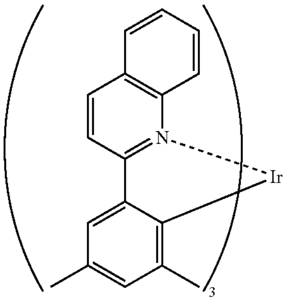
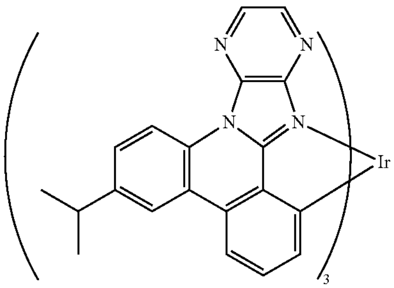

-continued

[Chem. 33]

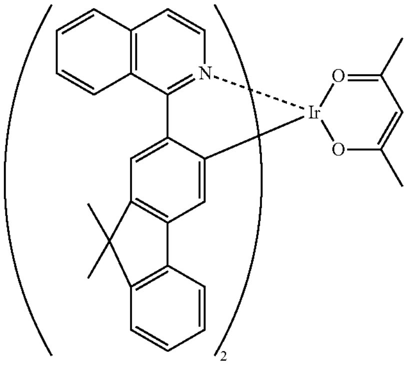

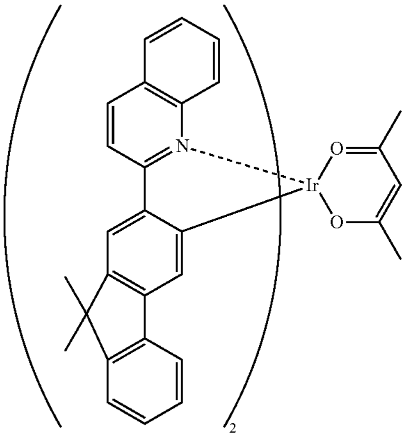

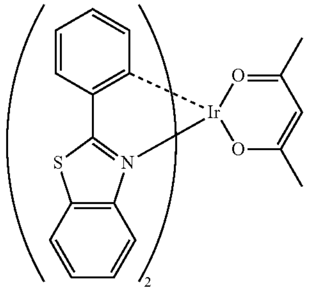

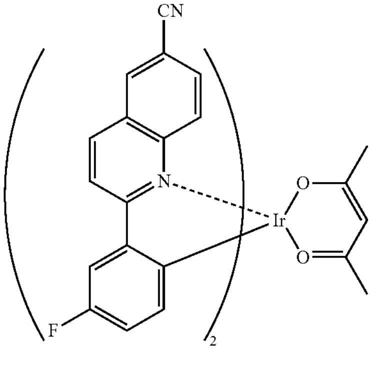

-continued

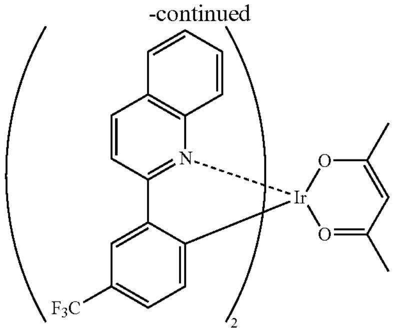

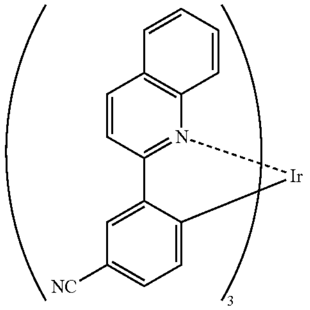

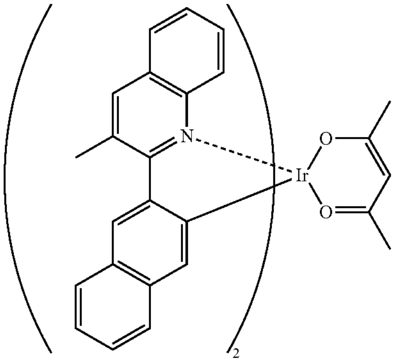

The compound exemplified as the compound represented by the general formula (E-1) can be synthesized by various methods described in JP-A-2009-99783, U.S. Pat. No. 7,279,232, and the like. After the synthesis, the compound is preferably purified by column chromatography, recrystallization, or the like, and then purified by sublimation purification. By sublimation purification, it is possible not only to separate organic impurities but also to effectively remove the inorganic salts, remaining solvent, or the like.

Although the phosphorescent light emitting material is preferably contained in the light emitting layer, the use thereof is not limited, and further, the phosphorescent light emitting material may also be contained in any further layer of the organic layers.

The phosphorescent light emitting material in the light emitting layer is preferably contained in the light emitting layer generally in an amount of 0.1% by mass to 50% b y mass with respect to the total mass of the compounds forming the light emitting layer, and from the viewpoint of durability and external quantum efficiency, the phosphorescent light emitting material is more preferably contained in an amount of 1% by mass to 50% by mass, and particularly preferably contained in an amount of 2% by mass to 40% by mass.

(3) Other Host Materials

Host materials, which can be used in the light emitting layer, other than the compound represented by the general formula (1) include a compound having the following structure as a partial structure:

conductive high-molecular oligomers such as aromatic hydrocarbon, pyrrole, indole, carbazole, azaindole, indolocarbazole, azacarbazole, triazole, oxazole, oxadiazole, pyrazole, imidazole, thiophene, polyarylalkane, pyrazoline, pyrazolone, phenylenediamine, arylamine, amino-substituted chalcone, styrylanthracene, hydrazone, stilbene, silazarie, an aromatic tertiary amine compound, a styrylamine compound, a porphyrin-based compound, a polysilane-based compound, a poly(N-viriylcarbazole), an aniline-based copolymer, a thiophene oligomer, and a polythiophene, organic silane, a carbon film, pyridine, pyrimidine, triazine, fluorenone, anthraquinodimethane, anthrone, diphenylquinone, thiopyran dioxide, carbodiimide, fluorenylidenemethane, distyrylpyrazine, a fluorine-substituted aromatic compound, heterocyclic tetracarboxylic anhydride such as naphthalene perylene, phthalocyanine, and various metal complexes typified by metal complexes of 8-quinolinol derivatives and metal complexes having metal phthalocyanine, benzoxazole, or benzothiazole as a ligand thereof, and derivatives thereof (which may have a substituent or a fused ring), and the like.

(Other Layers)

The organic electroluminescent element of the present invention may include layers other than the light emitting layer.

Examples of the organic layer other than the light emitting layer which may be included in the organic layer include a hole injecting layer, a hole transporting layer, a blocking layer (a hole blocking layer, an electron blocking layer, an exciton blocking layer, and the like), and an electron transporting layer. Specific examples of the layer configuration include those described below, but the present invention is not limited to these configurations.

Anode/Hole transporting layer/Light emitting layer/Electron transporting layer/Cathode, Anode/Hole transporting layer/Light emitting layer/Blocking layer/Electron transporting layer/Cathode, Anode/Hole transporting layer/Light emitting layer/Blocking layer/Electron transporting layer/Electron injecting layer/Cathode, Anode/Hole injecting layer/Hole transporting layer/Light emitting layer/Blocking layer/Electron transporting layer/Cathode, Anode/Hole injecting layer/Hole transporting layer/Light emitting layer/Electron transporting layer/Electron injecting layer/Cathode, Anode/Hole injecting layer/Hole transporting layer/Light emitting layer/Blocking layer/Electron transporting layer/Electron injecting layer/Cathode, Anode/Hole injecting layer/Hole transporting layer/Blocking layer/Light emitting layer/Blocking layer/Electron transporting layer/Electron injecting layer/Cathode.

The organic electroluminescent element of the present invention preferably includes at least one (A) organic layer which is preferably disposed between the anode and the light emitting layer. Examples of the (A) organic layer which is preferably disposed between the anode and the light emitting layer include an hole injecting layer, a hole transporting layer, and an electron blocking layer from the anode side.

The organic electroluminescent element of the present invention preferably includes at least one (B) organic layer which is preferably disposed between the cathode and the light emitting layer. Examples of the (B) organic layer which is preferably disposed between the cathode and the light emitting layer include an electron injecting layer, an electron transporting layer, and a hole blocking layer from the cathode side.

Specifically, an example of the preferred embodiments of the organic electroluminescent element according to the present invention is the embodiment shown in FIG. 1, in which a hole injecting layer 4, a hole transporting layer 5, a light emitting layer 6, a hole blocking layer 7, and an electron transporting layer 8 are laminated as the organic layer, in this order from the anode 3 side.

Hereinafter, the layers other than the light emitting layer which the organic electroluminescent element of the present invention may have will be described.

(A) Organic Layer Preferably Disposed Between Anode and Light Emitting Layer

First, the (A) organic layer preferably disposed between the anode and the light emitting layer will be described.

(A-1) Hole Injecting Layer and Hole Transporting Layer

The hole injecting layer and the hole transporting layer are layers having a function of receiving holes from the anode or the anode side and transporting them to the cathode side. The hole injecting material and the hole transporting material used in these layers may be either a low molecular compound or a high molecular compound.

For the hole injecting layer and the hole transporting layer, the matters described in paragraph Nos. [0165] to [0167] of JP-A-2008-270736 can be applied to the present invention.

The hole injecting layer preferably contains an electron receiving dopant. By incorporating the electron receiving dopant into the hole injecting layer, for example, there are brought such effects that the hole injecting properties are enhanced, that the driving voltage is lowered, and that the efficiency is enhanced. The electron receiving dopant may be any one of organic materials or inorganic materials so long as the material is capable of withdrawing electrons from the material to be doped and generating radical cations, and examples thereof include a TCNQ compound such as tetracyanoquinodimethane (TCNQ) and tetrafluorotetracyanoquinodimethane ($F_4$-TCNQ), a hexaazatriphenylene compound such as hexacyanohexaazatriphenylene (HAT-CN, a compound LG 101 used in Examples as described later), and molybdenum oxide. By interposing only the electron receiving dopant above, as a thin film, between the anode and the hole transporting layer, the same effect can be provided. In this case, this layer is referred to as a hole injecting layer. In addition, also by interposing the electron receiving dopant, as a thin film, between hole transporting layers, the same effect can be provided. In this case, one hole injecting layer or multiple hole injecting layers may be interposed between the hole transporting layers.

The electron receiving dopant in the hole injecting layer is preferably contained in an amount of 0.01% by mass to 50% by mass, more preferably in an amount of 0.1% by mass to 40% by mass, and more preferably in an amount of 0.2% by mass to 30% by mass, with respect to the total mass of the compounds forming the hole injecting layer. In the case of being used as a thin film, the thickness of the hole injecting layer is preferably from 1 nm to 50 nm, more preferably from 3 nm to 30 nm, and still more preferably from 5 nm to 20 nm.

(A-2) Electron Blocking Layer

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer and the anode side.

As the organic compound constituting the electron blocking layer, for example, those exemplified above as the hole transporting material can be used.

The thickness of the electron blocking layer is preferably from 1 nm to 500 nm, more preferably from 3 nm to 200 nm, and still more preferably from 5 nm to 100 nm.

The electron blocking layer may have either a single layer structure composed of one kind or two or more kinds of materials selected from the above-exemplified materials or a multilayer structure composed of a plurality of layers having the same composition or different compositions.

In order to inhibit energy transfer of excitons generated in the light emitting layer to prevent degradation of luminous efficiency, $T_1$ energy in the film state of the organic compound constituting the electron blocking layer is preferably higher than the $T_1$ energy of the light emitting material.

(A-3) Material Particularly Preferably Used in Organic Layer Preferably Disposed Between Anode and Light Emitting Layer

[Compound Represented by General Formula (M-1)]

In the organic electroluminescent element of the present invention, as a material particularly preferably used in (A) the organic layer preferably disposed between the anode and the light emitting layer, at least one compound represented by the following general formula (M-1) may be exemplified.

The compound represented by the general formula (M-1) is preferably contained in an organic layer that is located between the light emitting layer and the anode and adjacent to the light emitting layer. The use thereof is however not limited and the compound may further be contained in any layer of the organic layers. The layer into which the compound represented by the general formula (M-1) is introduced may be any one of a light emitting layer, a hole injecting layer, a hole transporting layer, an electron transporting layer, an electron injecting layer and a charge blocking layer, or the compound may be contained in a plurality of layers thereof.

The organic layer that is located between the light emitting layer and the anode and adjacent to the light emitting layer into which the compound represented by the general formula (M-1) is contained is more preferably an electron blocking layer or a hole transporting layer.

[Chem. 34]

(M-1)

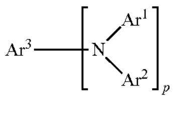

In the general formula (M-1), $Ar^1$ and $Ar^2$ each independently represent alkyl, aryl, heteroaryl, arylamino, alkylamino, morpholino, thiomorpholino, a 5- or 6-membered heterocycloalkyl containing one or more heteroatoms selected from N, O, and S, or a cycloalkyl, and may further have a substituent Z. $Ar^1$ and $Ar^2$ may be bonded to each other via a single bond, alkylene, or alkenylene (regardless of presence or absence of a fused ring) to form a fused 5- to 9-membered ring.

$Ar^3$ represents P-valent alkyl, aryl, heteroaryl or arylamino, and may further have a substituent Z.

Zs each independently represent a halogen atom, —R", —OR", —N(R")$_2$, —SR", —C(O)R", —C(O) OR", —C(O) N(R")$_2$, —CN, —$NO_2$, —$SO_2$, —SOR", —$SO_2$R", or —$SO_3$R", and R"s each independently represent a hydrogen atom, an alkyl group, a perhaloalkyl group, an alkenyl group, an alkynyl group, a heteroalkyl group, an aryl group, or a heteroaryl group.

p is an integer of 1 to 4, and when p is 2 or more, $Ar^1$s and $Ar^2$s may be the same as or different from each other, respectively.

Another preferred embodiment of the compound represented by the general formula (M-1) is a case where the compound is represented by the general formula (M-2).

[Chem. 35]

(M-2)

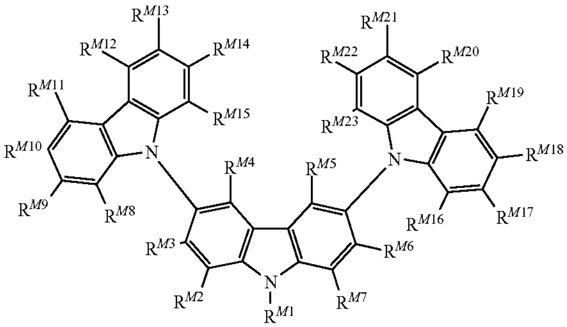

In the general formula (M-2), $R^{M1}$ represents an alkyl group, an aryl group, or a heteroaryl group.

$R^{M2}$ to $R^{M23}$ each independently represent a hydrogen atom, an alkyl group, an aryl group, a heteroaryl group, an alkoxy group, an aryloxy group, an amino group, a silyl group, a cyano group, a nitro group, or a fluorine atom.

In the general formula (M-2), $R^{M1}$ represents an alkyl group (preferably having 1 to 8 carbon atoms), an aryl group (preferably having 6 to 30 carbon atoms), or a heteroaryl group (preferably having 4 to 12 carbon atoms), and these groups may have the above-described substituent Z. $R^{M1}$ is preferably an aryl group or a heteroaryl group, and more preferably an aryl group. Examples of a preferred substituent in the case where the aryl group of $R^{M1}$ has a substituent include an alkyl group, a halogen atom, a cyano group, an aryl group and an alkoxy group, more preferably an alkyl group, a halogen atom, a cyano group, or an aryl group, and still more preferably an alkyl group, a cyano group, or an aryl group. The aryl group of $R^{M1}$ is preferably a phenyl group which may have a substituent Z, and more preferably a phenyl group which may have an alkyl, group or a cyano group.

$R^{M2}$ to $R^{23}$ each independently represent a hydrogen atom, an alkyl group (preferably having 1 to 8 carbon atoms), an aryl group (preferably having 6 to 30 carbon atoms), a heteroaryl group (preferably having 4 to 12 carbon atoms), an alkoxy group (preferably having 1 to 8 carbon atoms), an aryloxy group (preferably having 6 to 30 carbon atoms), an amino group (preferably having 0 to 24 carbon atoms), a silyl group (preferably having 0 to 18 carbon atoms), a cyano group, a nitro group, or a fluorine atom, and these groups may have the above-described substituent Z.

$R^{M2}$, $R^{M7}$, $R^{M8}$, $R^{M15}$, $R^{M16}$ and $R^{M23}$ are each preferably a hydrogen atom, or an alkyl group or an aryl group which may have a substituent Z, and more preferably a hydrogen atom.

$R^{M4}$, $R^{M5}$, $R^{M11}$, $R^{M12}$, $R^{M19}$ and $R^{M20}$ are each preferably a hydrogen atom, an alkyl group or an aryl group which may have a substituent Z, or a fluorine atom, and more preferably a hydrogen atom.

$R^{M3}$, $R^{M6}$, $R^{M9}$, $R^{M14}$, $R^{M17}$, and $R^{M22}$ are each preferably a hydrogen atom, an alkyl group or an aryl group which may have a substituent Z, a fluorine atom, or a cyano group, more preferably a hydrogen atom or an alkyl group which may have a substituent Z, and still more preferably a hydrogen atom.

$R^{M10}$, $R^{M13}$, $R^{M18}$ and $R^{M21}$ are each preferably a hydrogen atom, an alkyl group, an aryl group, a heteroaryl group, or an amino group which may have a substituent Z, a nitro group, a fluorine atom, or a cyano group, more preferably a hydrogen atom, an alkyl group, or an aryl group which may have a substituent Z, a nitro group, a fluorine atom, or a cyano group, and still more preferably a hydrogen atom or an alkyl group which may have a substituent Z. As the substituent in the case where the alkyl group has a substituent, a fluorine atom is preferred, and the carbon number in the alkyl group that may have a substituent Z is preferably from 1 to 6, and more preferably from 1 to 4.

In another preferred embodiment, the compound represented by the general formula (M-1) is represented by the following general formula (M-3).

[Chem. 36]

(M-3)

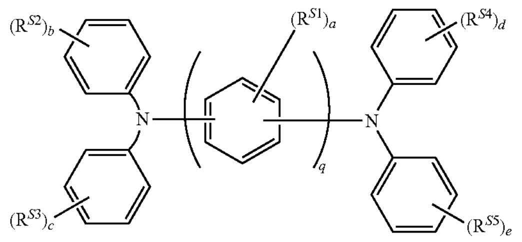

In the general formula (M-3), $R^{S1}$ to $R^{S5}$ each independently represent an alkyl group, a cycloalkyl group, an alkenyl group, an alkynyl group, —CN, a perfluoroalkyl group, a trifluorovinyl group, —$CO_2R$, —C(O)R, —$NR_2$, —$NO_2$, —OR, a halogen atom, an aryl group, or a heteroaryl group, and may further have a substituent Z. Rs each independently represent a hydrogen atom, an alkyl group, a perhaloalkyl group, an alkenyl group, an alkynyl group, a heteroalkyl group, an aryl group, or a heteroaryl group. When a plurality of $R^{S1}$ to $R^{S5}$ exist, those groups may be bonded to each other to form a ring, and may further have a substituent Z.

a represents an integer of 0 to 4, and when a plurality of $R^{S1}$s exist, the $R^{S1}$s may be the same as or different from one another, and may be bonded to each other to form a ring. b to e each independently represent an integer of 0 to 5, and when a plurality of groups exist for each $R^{S2}$ to $R^{S5}$, the groups may be the same as or different from one another, and any two thereof may be bonded to each other to form a ring.

q is an integer of 1 to 5, and when q is 2 or more, a plurality of $R^{S1}$s may be the same as or different from one another, and may be bonded to each other to form a ring.

The alkyl group may have a substituent, and may be saturated or unsaturated, and as the group that may be the substituent, the above-described Z may be exemplified. The alkyl group represented by $R^{S1}$ to $R^{S5}$ is preferably an alkyl group having a total carbon number of 1 to 8, and more preferably an alkyl group having a total carbon number of 1 to 6, and examples thereof include a methyl group, an ethyl group, an i-propyl group, a cyclohexyl group, and a t-butyl group.

The cycloalkyl group may have a substituent, and may be saturated or unsaturated, and as the group that may be the substitute, the above-described substituent Z may be exemplified. The cycloalkyl group represented by $R^{S1}$ to $R^{S5}$ is preferably a cycloalkyl group having 4 to 7 ring members, and more preferably a cycloalkyl group having a total carbon number of 5 to 6, and examples thereof include a cyclopenthyl group and a cyclohexyl group.

The alkenyl group represented by $R^{S1}$ to $R^{S5}$ preferably has 2 to 30 carbon atoms, more preferably has 2 to 20 carbon atoms, and particularly preferably has 2 to 10 carbon atoms, and examples thereof include vinyl, allyl, 1-propenyl, 1-isopropenyl, 1-butenyl, 2-butenyl, and 3-pentenyl.

The alkynyl group represented by $R^{S1}$ to $R^{S5}$ has 2 to 30 carbon atoms, more preferably has 2 to 20 carbon atoms, and particularly preferably has 2 to 10 carbon atoms, and examples thereof include ethynyl, propargyl, 1-propynyl, and 3-pentynyl.

The perfluoroalkyl group represented by $R^{S1}$ to $R^{S5}$ includes a group obtained by substituting all the hydrogen atoms in the above-mentioned alkyl group with fluorine atoms.

The aryl group represented by $R^{S1}$ to $R^{S5}$ is preferably a substituted or unsubstituted aryl group having 6 to 30 carbon atoms, and examples thereof include a phenyl group, a tolyl group, a biphenyl group, and a terphenyl group.

The heteroaryl group represented by $R^{S1}$ to $R^{S5}$ is preferably a heteroaryl group having 5 to 8 carbon atoms, more preferably a substituted or unsubstituted 5- or 6-membered heteroaryl group, and examples thereof include a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group, a carbazolyl group, a dibenzofuryl group, a dibenzothienyl group, and a pyridoindolyl group. Preferred examples thereof are a pyridyl group, a pyrimidinyl group, an imidazolyl group, and a thienyl group, and more preferred examples thereof are a pyridyl group and a pyrimidinyl group.

$R^{S1}$ to $R^{S5}$ are each preferably a hydrogen atom, an alkyl group, a cyano group, a trifluoromethyl group, a perfluoroalkyl group, a dialkylamino group, a fluoro group, an aryl group, or a heteroaryl group, more preferably a hydrogen atom, an alkyl group, a cyano group, a trifluoromethyl group, a fluoro group, or an aryl group, and still more preferably a hydrogen atom, an alkyl group, or an aryl group. The substituent Z is preferably an alkyl group, an alkoxy group, a fluoro group, a cyano group, or a dialkylamino group, and more preferably a hydrogen atom or an alkyl group.

Any two of $R^{S1}$ to $R^{S5}$ may be bonded to each other to form a fused 4- to 7-membered ring, the fused 4- to 7-membered ring is cycloalkyl, aryl, or heteroaryl, and the fused 4- to 7-membered ring may further have a substituent Z. The definitions and the preferred ranges of the formed cycloalkyl, aryl and heteroaryl are the same as the cycloalkyl group, the aryl group, and the heteroaryl group defined in $R^{S1}$ to $R^{S5}$.

In the case where the compound represented by the general formula (M-1) is used in a hole transporting layer, the compound represented by the general formula (M-1) is preferably contained in an amount of 50% by mass to 100% by mass, more preferably contained in an amount of 80% by mass to 100% by mass, and particularly preferably contained in an amount of 95% by mass to 100% by mass.

In addition, in the case where the compound represented by the general formula (M-1) is used in a plurality of organic layers, the compound is preferably contained in each layer within the above range.

Only one kind of the compound represented by the general formula (M-1) may be contained, in any one of organic layers, or a plurality of compounds represented by the general formula (M-1) may be contained in combination of any proportion thereof.

The thickness of the hole transporting layer containing the compound represented by the general formula (M-1) is preferably from 1 nm to 500 nm, more preferably from 3 nm to 200 nm, and still more preferably from 5 nm to 100 nm. In addition, the hole transporting layer is preferably provided in contact with the light emitting layer.

The minimum excited triplet ($T_1$) energy in the film state of the compound represented by the general formula (M-1) is preferably from 1.77 eV (40 kcal/mol) to 3.51 eV (81 kcal/mol), and more preferably from 2.39 eV (55 kcal/mol) to 3.25 eV (75 kcal/mol). In the organic electroluminescent element of the present invention, it is preferable that $T_1$ energy of the compound represented by the general formula (M-1) be more than $T_1$ energy of the above-mentioned phosphorescent light emitting material, from the viewpoint of luminous efficiency. In particular when the luminescent color from the organic electroluminescent element is green (the light emission peak wavelength is from 490 nm to 580 nm), from the viewpoint of luminous efficiency, $T_1$ energy is more preferably from 2.39 eV (55 kcal/mol) to 2.82 eV (65 kcal/mol).

The hydrogen atoms constituting the general formula (M-1) include hydrogen isotopes (deuterium and the like). In this case, all the hydrogen atoms in the compound may be substituted with the hydrogen isotope atoms, or the compound may be a mixture in which a part of the compound contains hydrogen isotopes.

The compound represented by the general formula (M-1) can be synthesized by combining various known synthetic methods. Most commonly, for the carbazole compound, a synthetic method may be exemplified in which a fused compound of an arylhydradine and a cyclohexane derivative is subjected to the Aza-Cope rearrangement reaction, and thereafter converted into an aromatic compound by dehydrogenating (written by L. F. Tieze and Th. Eicher, translated by Takano and Ogasawara, Seimitsu Yuuki Gousei, p. 339 (Nankodo Co., Ltd.)). For a coupling reaction of the resulting carbazole compound with a halogenated aryl compound using a palladium catalyst, a method is exemplified which is described in Tetrahedron Letters, vol. 39, p. 617 (1998), vol. 39, p. 2367 (1998), vol. 40, p. 6393 (1999), and the like. The reaction temperature and the reaction time are not particularly limited and the conditions described in the above documents may be applied.

The compound represented by the general formula (M-1) is preferably formed into a thin film by a vacuum vapor deposition process, but a wet process such as a solution coating can be suitably used. The molecular weight of the compound is preferably 2000 or less, more preferably 1200 or less, and particularly preferably 800 or less, from the viewpoint of deposition suitability and solubility. In terms of the deposition suitability, too small molecular weight causes decrease of the vapor pressure, thereby inhibiting the conversion from the vapor phase to the solid phase, so that it become difficult to form the organic layer. Accordingly, the molecular weight is preferably 250 or more, and particularly preferably 300 or more.

Specific examples of the compound represented by the general formula (M-1) are shown below, but the present invention is not limited thereto.

[Chem. 37]

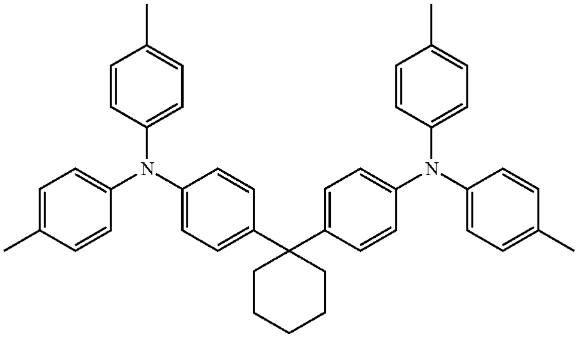

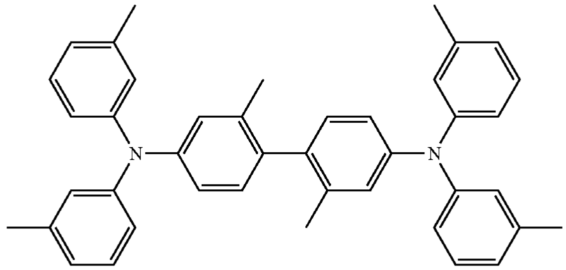

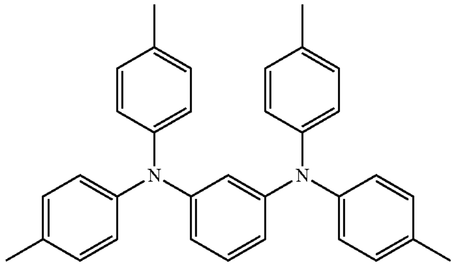

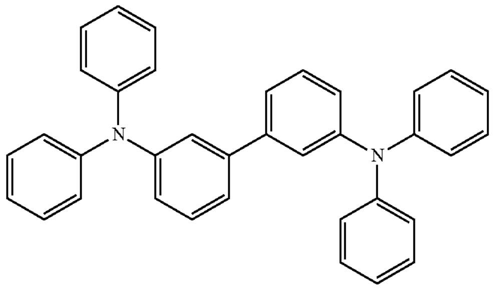

-continued
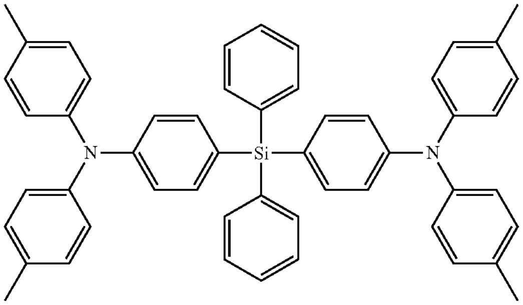
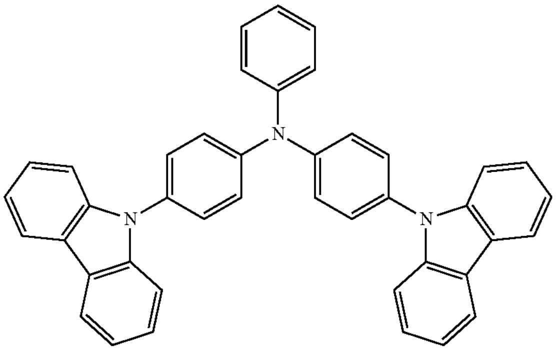
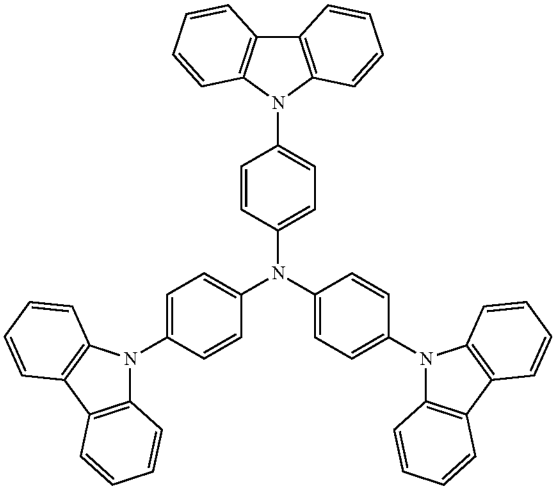
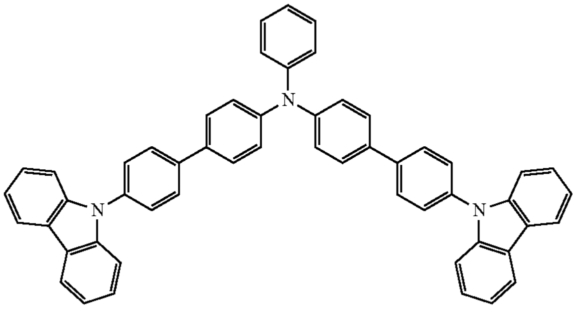
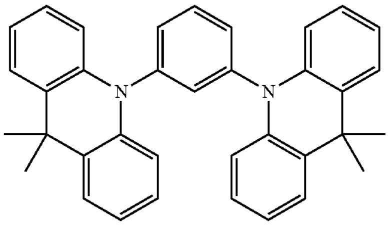
-continued
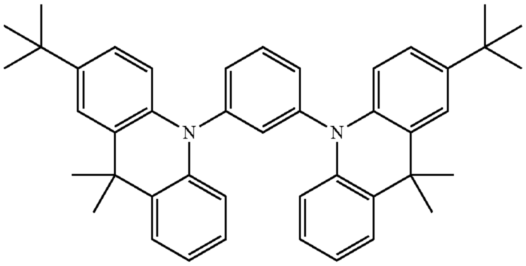
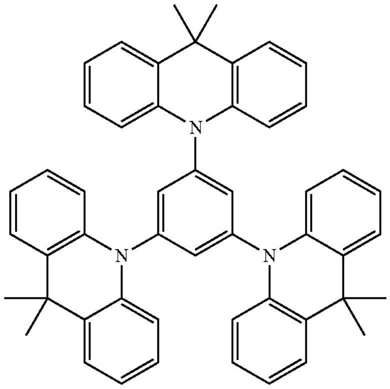
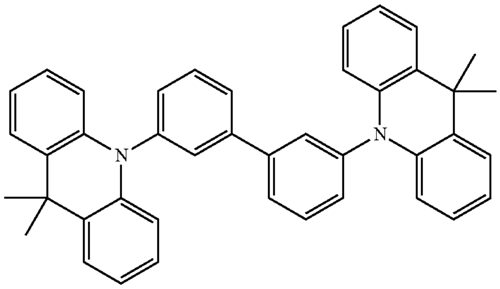
[Chem. 38]
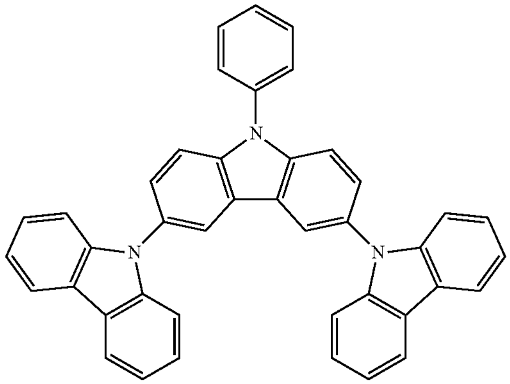

-continued
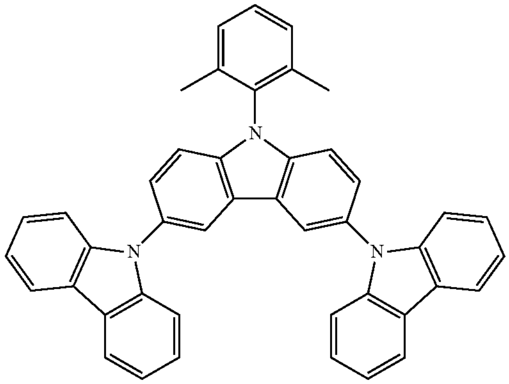
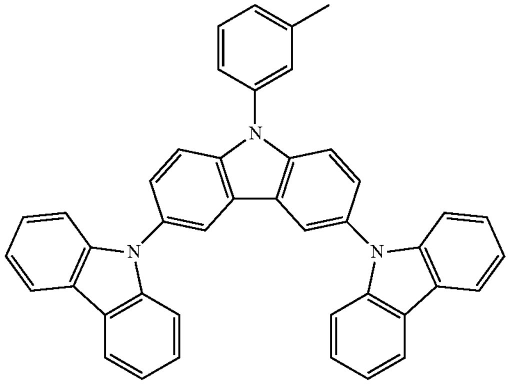
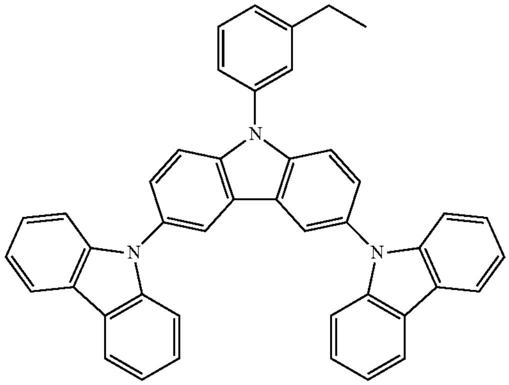
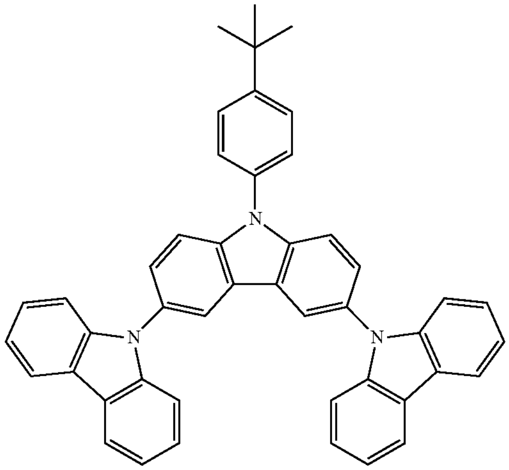
-continued
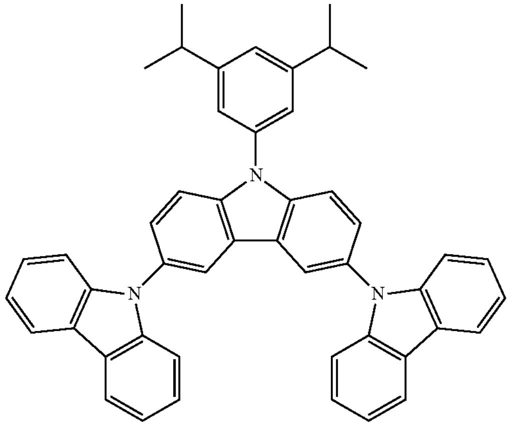
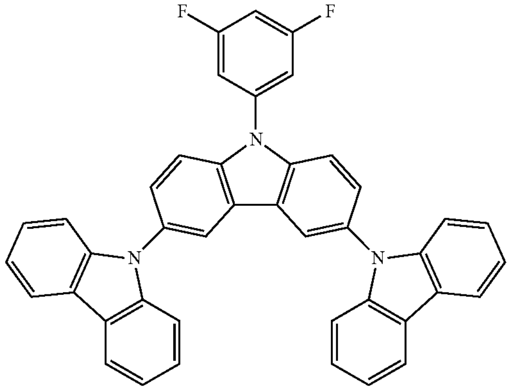
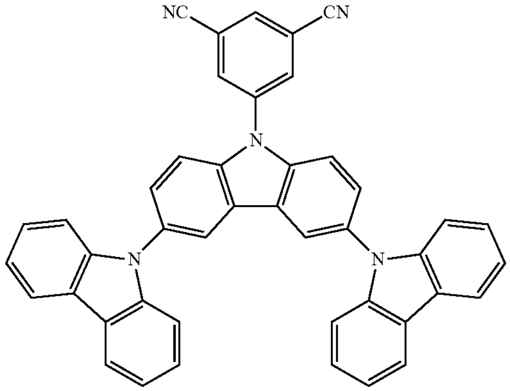
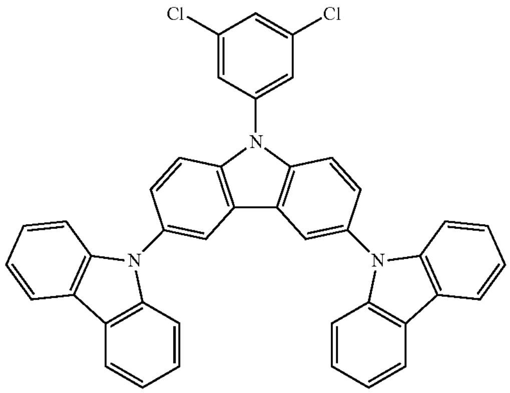

-continued
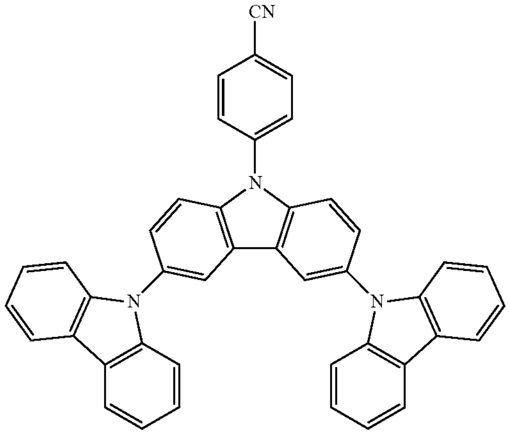
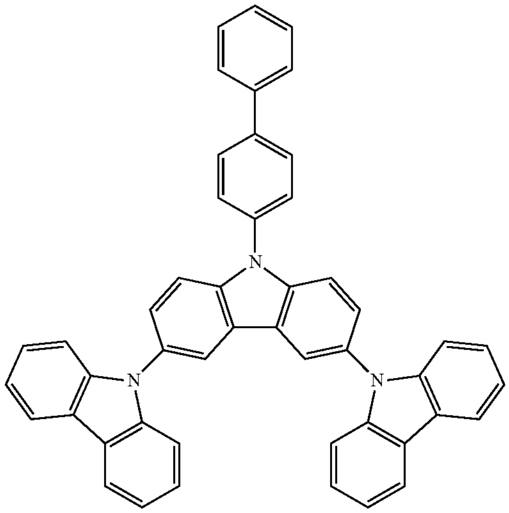
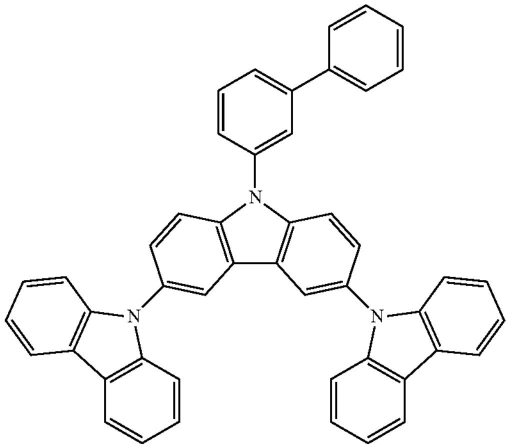
-continued
[Chem. 39]
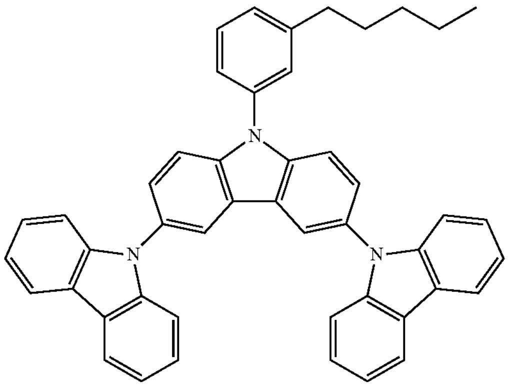
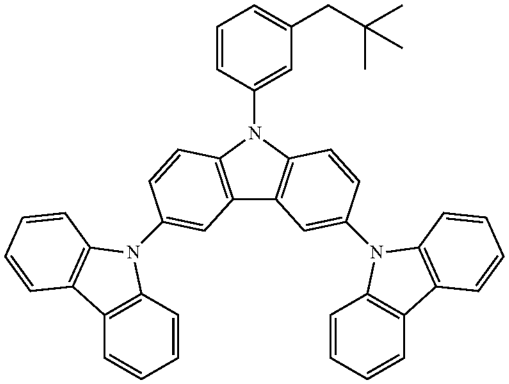
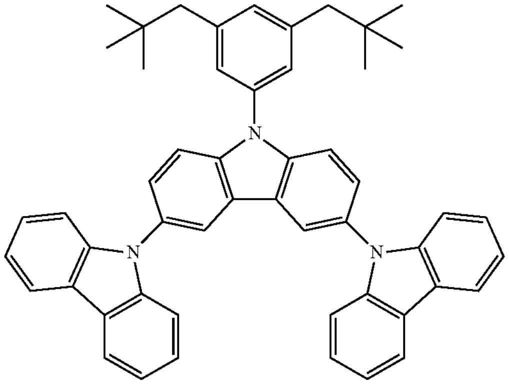
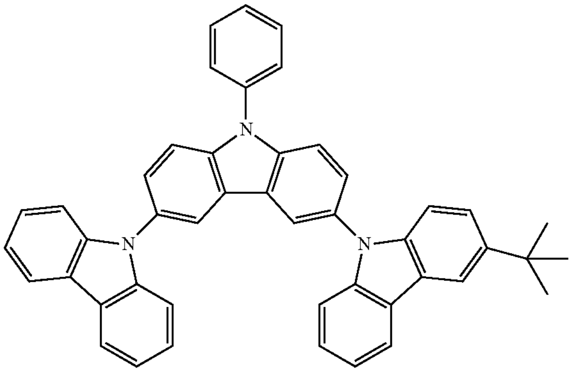

-continued
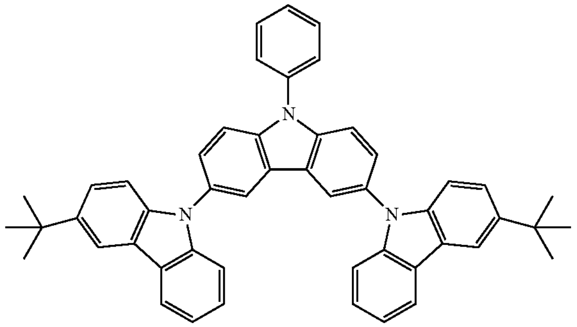
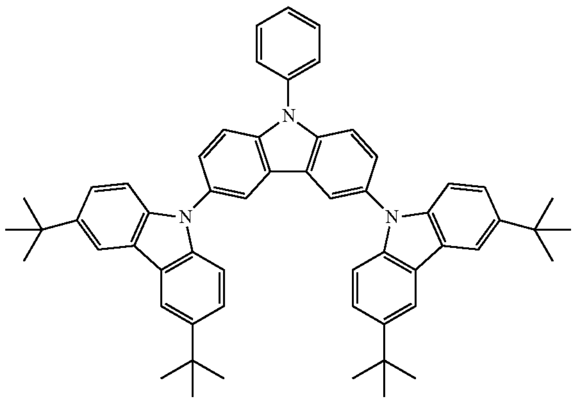
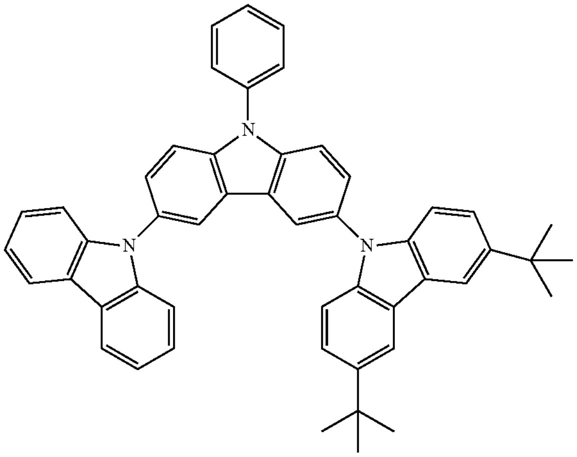
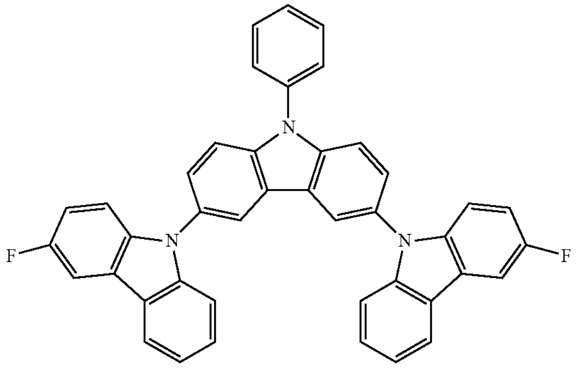
-continued
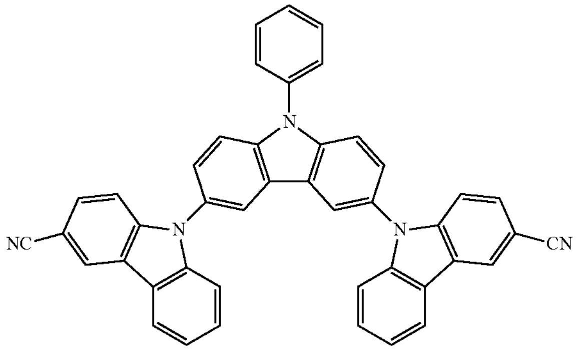
[Chem. 40]
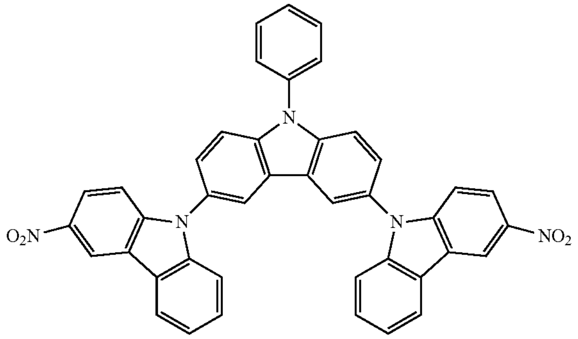
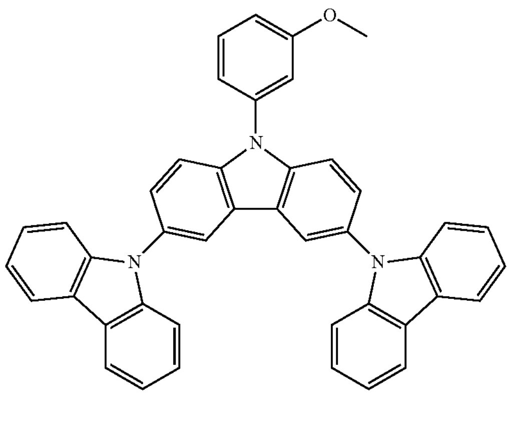
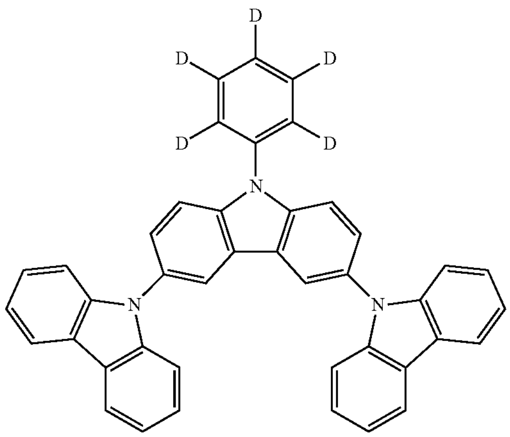

-continued
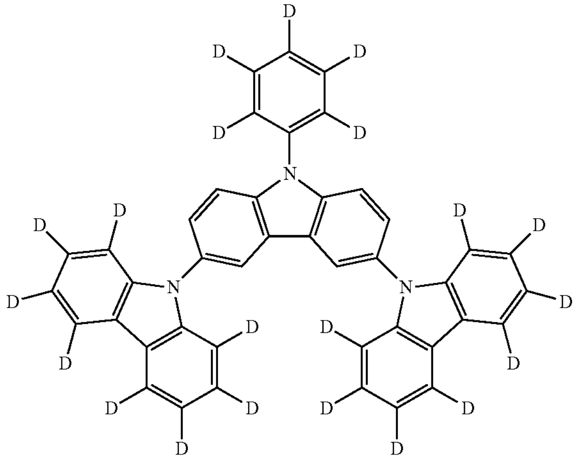
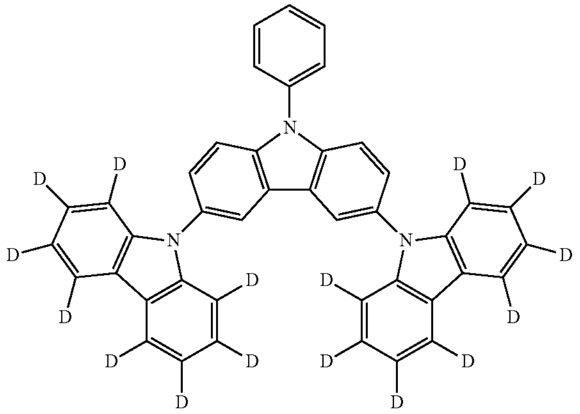
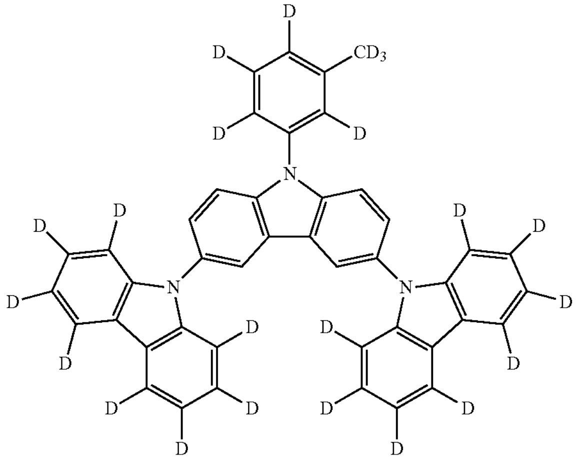
-continued
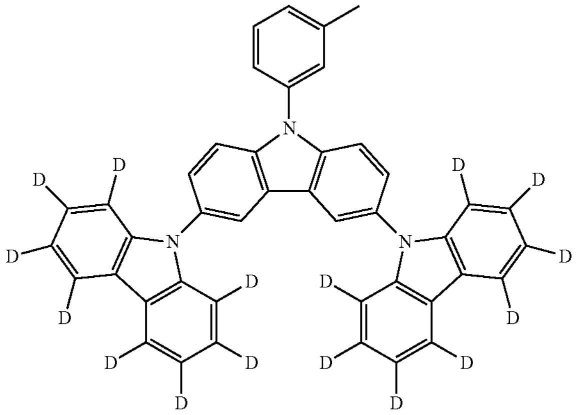
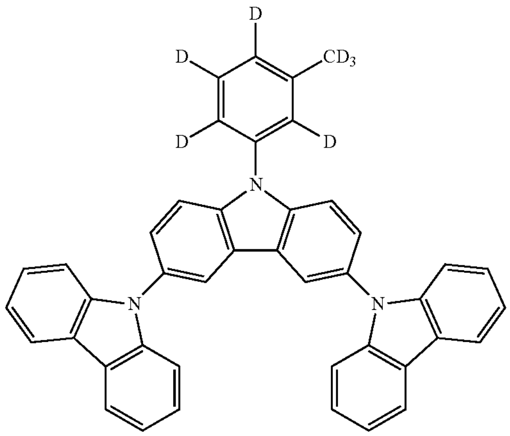
[Chem. 41]
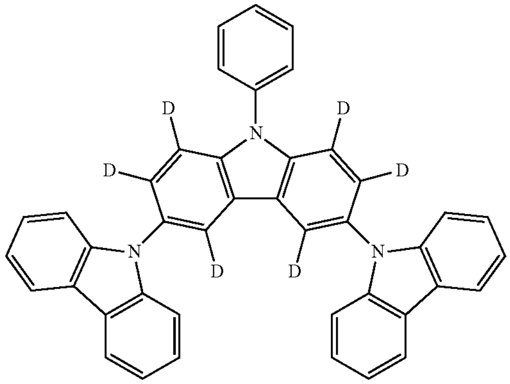
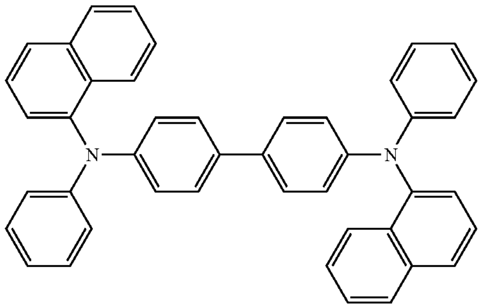

-continued

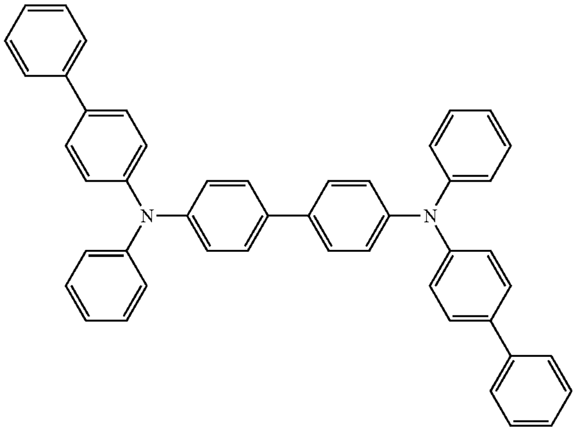

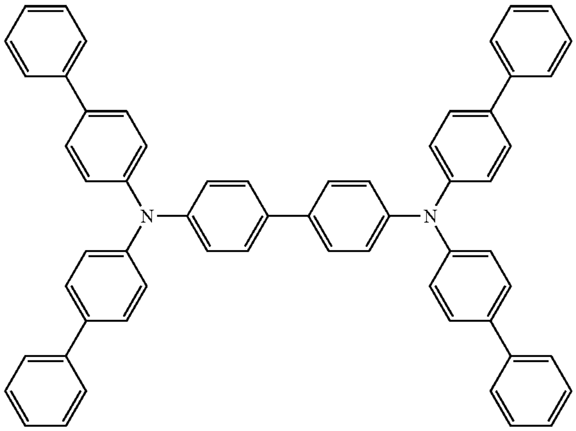

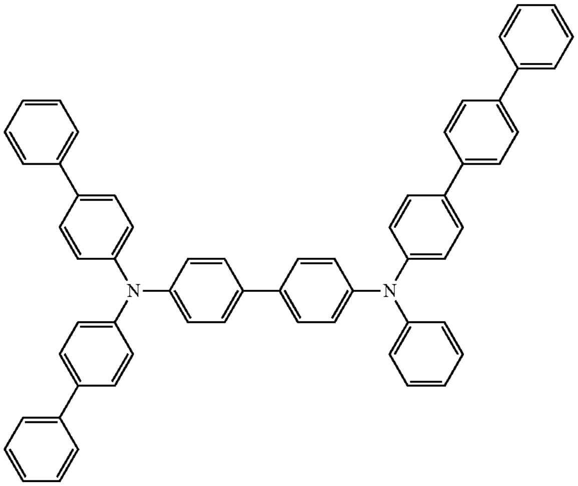

-continued

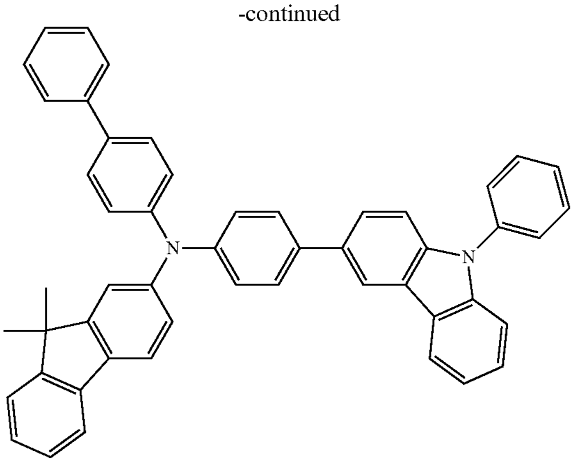

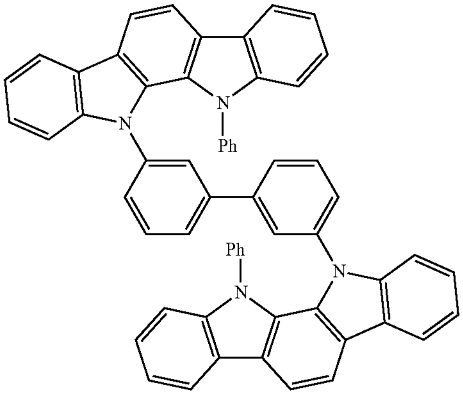

(B) Organic Layer Preferably Disposed Between Cathode and Light Emitting Layer

Next, the (B) organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, the compound represented by the general formula (1) can be used. As other electron transporting materials, any one of compounds selected from pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, aromatic ring tetracarboxylic acid anhydrides of naphthalene and perylene, phthalocyanine derivatives, various metal complexes typified by metal complexes of 8-quinolinol derivatives, metal phthalocyanine and metal complexes having benzoxazole or benzothiazole as a ligand thereof, organic silane derivatives typified by silole, and hydrocarbon compounds with fused rings such as naphthalene, anthracene, phenanthrene, triphenylene, and pyrene is preferred, and any one of compounds selected from pyridine derivatives, benzimidazole derivatives, imidazopyridine derivatives, metal complexes, and hydrocarbon compounds with fused rings are more preferred.

From the viewpoint of decreasing the driving voltage, the thickness of each of the electron injecting layer and the electron transporting layer is preferably 500 nm or less.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one kind or two or more kinds of materials selected from the above-exemplified materials or a multilayer structure composed of a plurality of layers having the same composition or different compositions.

The electron injecting layer preferably contains an electron donating dopant. By incorporating the electron donating dopant into the electron injecting layer, for example, there are brought such effects that the electron injecting properties are enhanced, that the driving voltage is lowered, and that the efficiency is enhanced. The electron donating dopant may be any one of organic materials and inorganic materials as long as it is capable of giving electrons to the material to be doped to generate radical anions. Examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably from 0.5% by mass to 30% by mass, with respect to the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order to inhibit the energy transfer of excitons generated in the light emitting layer to prevent degradation of luminous efficiency, $T_1$ energy in the film state of the organic compound constituting the hole blocking layer is preferably higher than the $T_1$ energy of the light emitting material.

As an example of the organic compound constituting the hole blocking layer, for example, the compound represented by the general formula (1) can be used.

Examples of the organic compounds constituting the hole blocking layer, other than the compound represented by the general formula (1), include aluminum complexes such as aluminum (III) tris-8-hydroxyquinoline (abbreviated as Alq) and aluminum (III) bis(2-methyl-8-quinolinato) 4-phenylphenolate (abbreviated as Balq), triazole derivatives, and phenanthroline derivatives such as 2,9-dimethyl-4,7-diphenyl-1,10-phenanthroline (abbreviated as BCP). In the present invention, the function of the hole blocking layer is not limited to the function of actually blocking the holes, and the hole blocking layer may have a function to prevent the excitons in the light emitting layer from diffusing to the electron transporting layer, or a function to block energy transfer quenching. The compound of the present invention can be preferably applied to the hole blocking layer.

The thickness of the hole blocking layer is preferably from 1 nm to 500 nm, more preferably from 3 nm to 100 nm, and still more preferably from 5 nm to 50 nm.

The hole blocking layer may have either a single layer structure composed of one kind or two or more kinds of materials selected from the above-exemplified materials or a multilayer structure composed of a plurality of layers having the same composition or different compositions.

The material which is used in the hole blocking layer preferably has higher $T_1$ energy than that of the phosphorescent light emitting material in view of color purity, luminous efficiency, and driving durability.

(B-3) Material Particularly Preferably Used in Organic Layer which is Preferably Disposed Between Cathode and Light Emitting Layer For the organic electroluminescent element of the present invention, examples of the material which is particularly preferably used in the materials for the (B) organic layer which is preferably disposed between the cathode and the light emitting layer include the compound represented by the general formula (1), an aromatic hydrocarbon compound (in particular, a compound represented by the following general formula (Tp-1)), and a compound represented by the following general formula (O-1).

The aromatic hydrocarbon compound and a compound represented by the general formula (O-1) will be described below.

[Aromatic Hydrocarbon Compound]

The aromatic hydrocarbon compound is preferably contained in an organic layer that is located between the light emitting layer and the cathode and adjacent to the light emitting layer, but is not limited in the use and may be further contained in any layer of the organic layers. The layer into which the aromatic hydrocarbon compound is introduced is anyone of a light emitting layer, a hole injecting layer, a hole transporting layer, an electron transporting layer, an electron injecting layer, an exciton blocking layer, and a charge blocking layer, or the compound may be contained in a plurality of layers.

The organic layer that is located between the light emitting layer and the cathode and adjacent to the light emitting layer, into which the aromatic hydrocarbon compound is contained, is preferably a blocking layer (a hole blocking layer or an exciton blocking layer) or an electron transporting layer, and more preferably an electron transporting layer.

In the case where the aromatic hydrocarbon compound is contained in a layer other than the light emitting layer, the compound is preferably contained in an amount of 70% by mass to 100% by mass, and more preferably 85% by mass to 100% by mass. In the case where the aromatic hydrocarbon compound is contained in the light emitting layer, the compound is preferably contained in an amount of 0.1% by mass to 99% by mass, more preferably contained in an amount of 1% by mass to 95% by mass, and more preferably contained in an amount of 10% by mass to 95% by mass, with respect to the total mass of the light emitting layer.

As the aromatic hydrocarbon compound, a hydrocarbon compound which has a molecular weight of 400 to 1200 and has a fused polycyclic skeleton having a total carbon number of 13 to 22 is preferably used. The fused polycyclic skeleton having a total carbon number of 13 to 22 is preferably any one of fluorene, anthracene, phenanthrene, tetracene, chrysene, pentacene, pyrene, perylene, and triphenylene, more preferably from the viewpoint of the $T_1$, a fluorene, triphenylene, and phenanthrene, still more preferably from the viewpoint of compound stability and electron injecting and transporting properties, triphenylene, and particularly preferably a compound represented by the following general formula (Tp-1).

The hydrocarbon compound represented by the general formula (Tp-1) has a molecular weight of preferably 400 to 1200, more preferably 400 to 1100, and still more preferably 400 to 1000. When the molecular weight is 400 or more, an amorphous thin film of good quality can be formed, and the molecular weight of 1200 or less is preferred in terms of solubility in a solvent and applicability to sublimation and deposition suitability.

The hydrocarbon compound represented by the general formula (Tp-1) is not limited in the use, and may be contained not only in the organic layer adjacent to the light emitting layer but in any layer in the organic layers.

[Chem. 42]

(Tp-1)

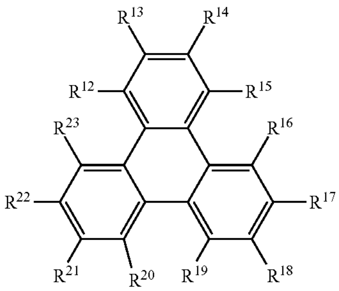

In the general formula (Tp-1), $R^{12}$ to $R^{23}$ each independently represent a hydrogen atom, an alkyl group, a phenyl group, a fluorenyl group, a naphthyl group, or a triphenylenyl group (these groups may be further substituted with an alkyl group, a phenyl group, a fluorenyl group, a naphthyl group, or a triphenylenyl group), provided that not all of $R^{12}$ to $R^{23}$ are a hydrogen atom.

Examples of the alkyl group represented by $R^{12}$ to $R^{23}$ include a methyl group, an ethyl group, an isopropyl group, an n-butyl group, a tert-butyl group, an n-octyl group, an n-decyl group, an n-hexadecyl group, a cyclopropyl group, a cyclopentyl group, and a cyclohexyl group, preferably a methyl group, an ethyl group, an isopropyl group, a tert-butyl group, and a cyclohexyl group, and more preferably a methyl group, ethyl group, and a tert-butyl group, each of which may be substituted or unsubstituted.

$R^1$ to $R^2$ may be each preferably substituted with an alkyl group having 1 to 4 carbon atoms, a phenyl group, a fluorenyl group, a naphthyl group, or a triphenylenyl group (which may be further substituted with an alkyl group, a phenyl group, a fluorenyl group, a naphthyl group, or a triphenylenyl group), and still more preferably a phenyl group, a fluorenyl group, a naphthyl group, or a triphenylenyl group.

$R^{12}$ to $R^{23}$ are each particularly preferably a benzene ring which may be substituted with a phenyl group, a fluorenyl group, a naphthyl group, or a triphenylenyl group (which may further substituted with an alkyl group, a phenyl group, a fluorenyl group, a naphthyl group, or a triphenylenyl group).

The total number of the aryl rings in the general formula (Tp-1) is preferably from 2 to 8, and more preferably from 3 to 5. When the aryl ring number is within this range, it is possible to form an amorphous thin film of high quality and to achieve good solubility in a solvent, applicability to sublimation, and deposition suitability.

$R^{12}$ to $R^{23}$ preferably each independently have a total carbon number of 20 to 50, and more preferably a total carbon number of 20 to 36. When the total carbon number is within this range, it is possible to form an amorphous thin film of high quality and to achieve good solubility in a solvent, applicability to sublimation, and deposition suitability.

The hydrocarbon compound represented by the general formula (Tp-1) is preferably a hydrocarbon compound represented by the following general formula (Tp-2).

[Chem. 43]

(Tp-2)

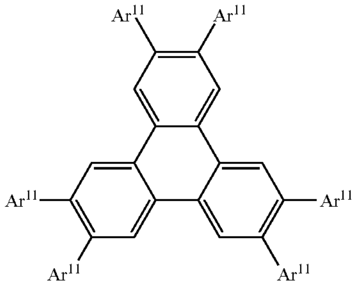

In the general formula (Tp-2), a plurality of $Ar^{11}$s are the same, and each represent an alkyl group, a phenyl group, a fluorenyl group, a naphthyl group, or a triphenylenyl group (these groups may be further substituted with an alkyl group, a phenyl group, a fluorenyl group, a naphthyl group, or a triphenylenyl group).

The hydrogen atom, the alkyl group, the phenyl group, the fluorenyl group, the naphthyl group, or the triphenylenyl group represented by $Ar^{11}$ (these groups may be further substituted with an alkyl group, a phenyl group, a fluorenyl group, a naphthyl group, or a triphenylenyl group) has the same definitions as enumerated for $R^{12}$ to $R^{23}$, and preferred ones are also the same.

The hydrocarbon compound represented by the general formula (Tp-1) is also preferably a hydrocarbon compound represented by the following general formula (Tp-3).

[Chem. 44]

General Formula (Tp-3)

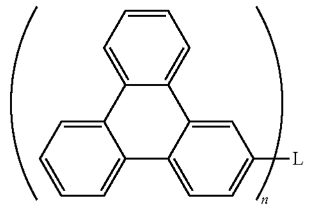

In the general formula (Tp-3), L represents an alkyl group, a phenyl group, a fluorenyl group, a naphthyl group, or a triphenylenyl group (these groups may be further substituted with an alkyl group, a phenyl group, a fluorenyl group, a naphthyl group, or a triphenylenyl group), or an n-valent linking group formed by a combination thereof. n represents an integer of 2 to 6.

The alkyl group, the phenyl group, the fluorenyl group, the naphthyl group, or the triphenylenyl group, which forms the n-valent linking group represented by L, has the same definitions as enumerated for $R^{12}$ to $R^{23}$.

L is preferably an n-valent linking group formed of a benzene ring or a fluorene ring which may be substituted by an alkyl group or a benzene ring, or a combination thereof.

Specific preferred examples of L are listed below, but L is not limited thereto. In the specific examples, the group is bonded at * to a triphenylene ring.

[Chem. 45]

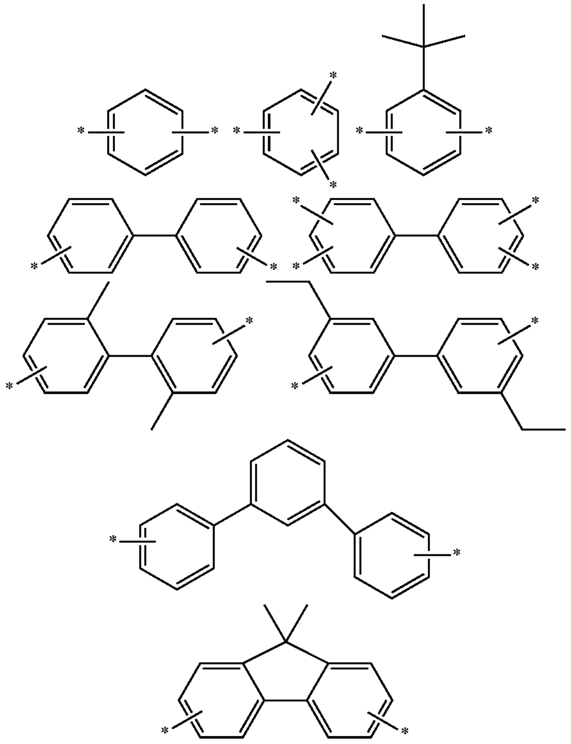

n is preferably from 2 to 5, and more preferably from 2 to 4.

The compound represented by the general formula (Tp-1) is preferably a compound represented by the following general formula (Tp-4)

[Chem. 46]

General Formula (Tp-4)

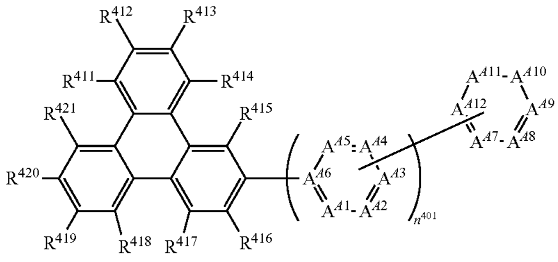

(In the general formula (Tp-4), $A^{A1}$ to $A^{A12}$ each independently represent $CR^{400}$ or a nitrogen atom. $n^{401}$ represents an integer of 0 to 8. In the case where $n^{401}$ is 0, the ring represented by $A^{A1}$ to $A^{A6}$ represents a single bond between the triphenylene ring and the ring represented by $A^{A7}$ to $A^{A12}$. In the case where $n^{401}$ is from 2 to 6, a plurality of rings represented by $A^{A1}$ to $A^{A6}$ may be different for each appearance, and a plurality of linking modes between the rings may be different for each appearance.)

Incidentally, in the present invention, the hydrogen atoms in the description of the general formula (Tp-4) include isotopes (a deuterium atom and the like), and any atoms constituting the further substituent also include the isotopes thereof.

In the general formula (Tp-4), $R^{411}$ to $R^{421}$ each independently represent a hydrogen atom, an alkyl group, a phenyl group, a fluorenyl group, a naphthyl group, or a triphenylenyl group (which may be further substituted with an alkyl group, a phenyl group, a fluorenyl group, a naphthyl group, or a triphenylenyl group).

$R^{411}$ to $R^{421}$ are each preferably a hydrogen atom, an alkyl group having 1 to 4 carbon atoms, a phenyl group, a fluorenyl group, a naphthyl group, or a triphenylenyl group (which may be further substituted with an alkyl group, a phenyl group, a fluorenyl group, a naphthyl group, or a triphenylenyl group), more preferably a hydrogen atom or a phenyl group (the phenyl group may be substituted with an alkyl group, a phenyl group, a fluorenyl group, a naphthyl group, or a triphenylenyl group), and particularly preferably a hydrogen atom.

$A^1$ to $A^{12}$ are each preferably $CR^{400}$.

In the general formula (Tp-4), the substituent represented by $R^{400}$ preferably represents a hydrogen atom, an alkyl group having 1 to 4 carbon atoms, a phenyl group, a fluorenyl group, a naphthyl group, or a triphenylenyl group (which may be further substituted with an alkyl group, a phenyl group, a fluorenyl group, a naphthyl group, or a triphenylenyl group). A plurality of $R^{400}$s may be different from each other.

Preferably, $R^{400}$ is preferably a hydrogen atom, an alkyl group having 1 to 4 carbon atoms, a phenyl group, a fluorenyl group, a naphthyl group, or a triphenylenyl group (which may be further substituted with an alkyl group, a phenyl group, a fluorenyl group, a naphthyl group, or a triphenylenyl group), more preferably a hydrogen atom, an alkyl group having 1 to 4 carbon atoms, a phenyl group (the phenyl group may be substituted with an alkyl group, a phenyl group, a fluorenyl group, a naphthyl group, or a triphenylenyl group), and particularly preferably a hydrogen atom, an alkyl group having 1 to 4 carbon atoms, a phenyl group (the phenyl group may be substituted with an alkyl group, a phenyl group, a fluorenyl group, a naphthyl group, or a triphenylenyl group).

$n^{401}$ is preferably an integer of 0 to 5, more preferably an integer of 1 to 5, and particularly preferably 2 to 4.

$n^{401}$ is an integer of 1 or more, and in the case where the linking position to the ring represented by $A^{A7}$ to $A^{12}$ is $A^{A3}$, from the viewpoint of luminous efficiency, the substituent represented by $A^{A4}$ or $A^{A5}$ is $CR^{400}$, and $R^{400}$ is preferably an alkyl group having 1 to 4 carbon atoms or a phenyl group, more preferably an alkyl group having 1 to 4 carbon atoms, and particularly preferably a methyl group.

In the general formula (Tp-4), among the 6-membered aromatic rings constituted of $A^{A1}$ to $A^{A12}$ the number of the ring containing a nitrogen atom is preferably at most one, and more preferably zero. In the general formula (Tp-4), the connection of the 6-membered aromatic rings constituted of $A^1$ to $A^{A2}$ has no restriction, but the rings preferably are connected on meta- or para-positions. Further, with regard to the compound represented by the general formula (Tp-4), the number of the aromatic rings which are sequentially connected on their para-positions is preferably three or less, including the phenyl ring which is a partial structure of the fused ring constituting the triphenylene ring.

In the case where the hydrocarbon compound represented by the general formula (Tp-1) is used in a host material of a light emitting layer or in a charge transporting material of a layer adjacent to the light emitting layer, in an organic electroluminescent element, when the energy gap in the thin film state (in the case of the light emitting material being a phosphorescent light emitting material, which is the minimum excited triplet ($T_1$) energy in the thin film state) is larger than in the light emission material, the quench of the light emission is prevented, which is advantageous in enhancing the efficiency. On the other hand, from the viewpoint of chemical stability of the compound, it is preferable that an energy gap and $T_1$ energy are not too large. The $T_1$ energy in the film state of the hydrocarbon compound represented by the general formula (Tp-1) is preferably from 1.77 eV (40 kcal/mol) to 3.51 eV (81 kcal/mol), and more preferably from 2.39 eV (55 kcal/mol) to 3.25 eV (75 kcal/mol). In the organic electroluminescent element according to the present invention, it is preferable from the viewpoint of luminous efficiency that the $T_1$ energy of the compound represented by the general formula (Tp-1) be more than the $T_1$ energy of the above-mentioned phosphorescent light emitting material. In particular, in the case where the luminescent color from the organic electroluminescent element is green (the light emission peak wavelength is from 490 nm to 580 nm), it is more preferred from the viewpoint of luminous efficiency that the $T_1$ energy is from 2.39 eV (55 kcal/mol) to 2.82 eV (65 kcal/mol).

The $T_1$ energy of the hydrocarbon compound represented by the general formula (Tp-1) can be determined by the same method as in the description of the general formula (1) above.

From the viewpoint of stable operation of the organic electroluminescent element, when being driven at a high temperature, or against the heat generation during the element driving, the glass transition temperature (Tg) of the hydrocarbon compound according to the present invention is preferably from 80° C. to 400° C., more preferably from 100° C. to 400° C., and still more preferably from 120° C. to 400° C.

Specific examples of the hydrocarbon compound represented by the general formula (Tp-1) are listed below, but the hydrocarbon compound used in the present invention is not to be limited thereto.

[Chem. 47]

TpH-1

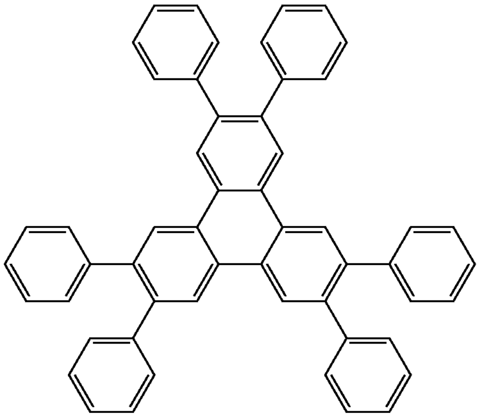

-continued

TpH-2

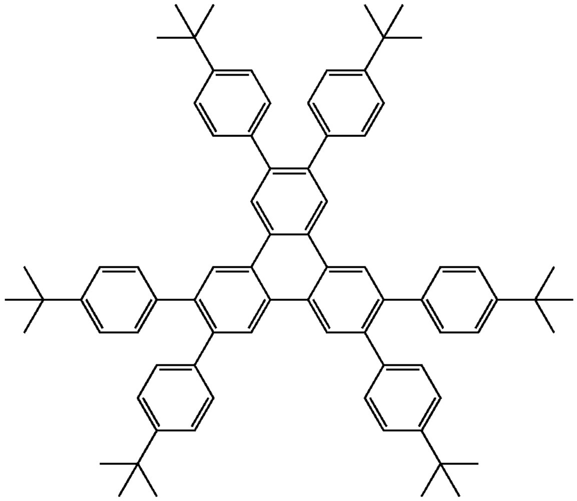

TpH-3

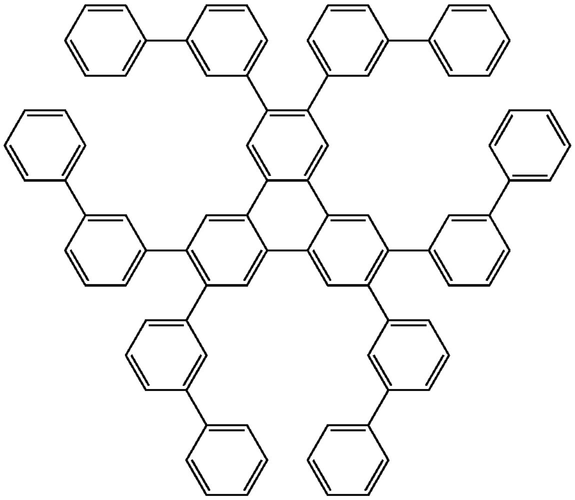

TpH-4

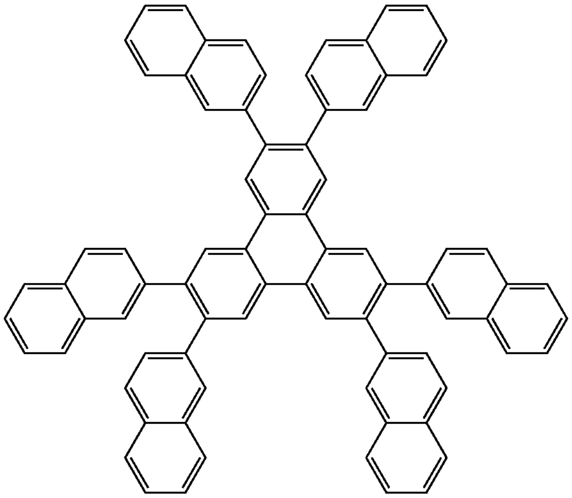

-continued
TpH-5
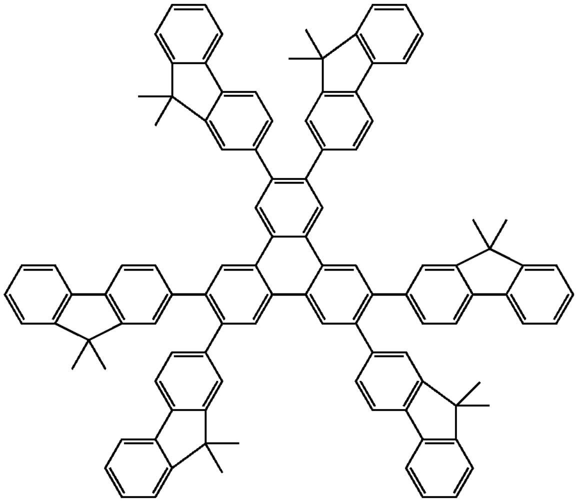
TpH-6
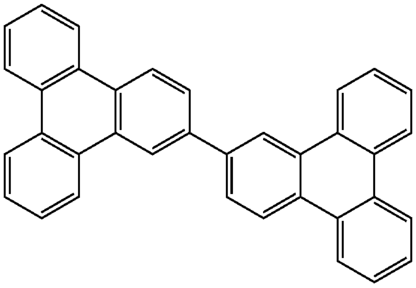
TpH-7
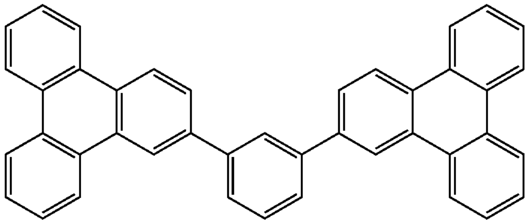
TpH-8
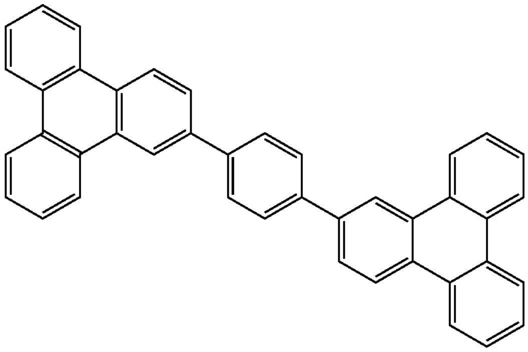
-continued
TpH-9
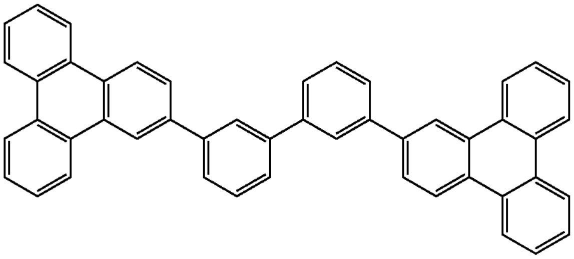
TpH-10
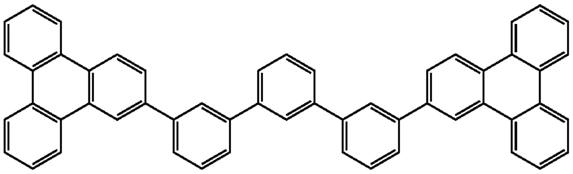
TpH-11
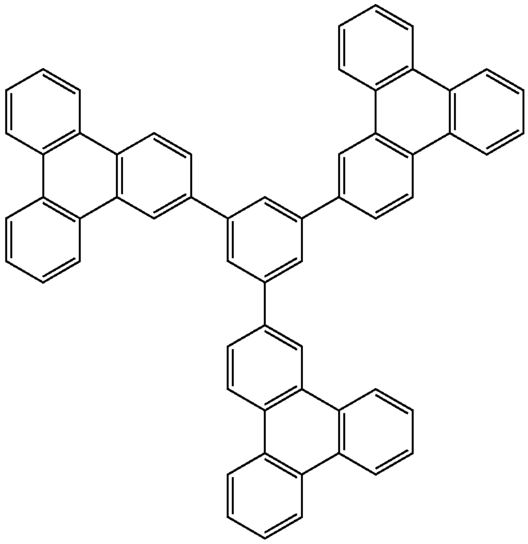
TpH-12
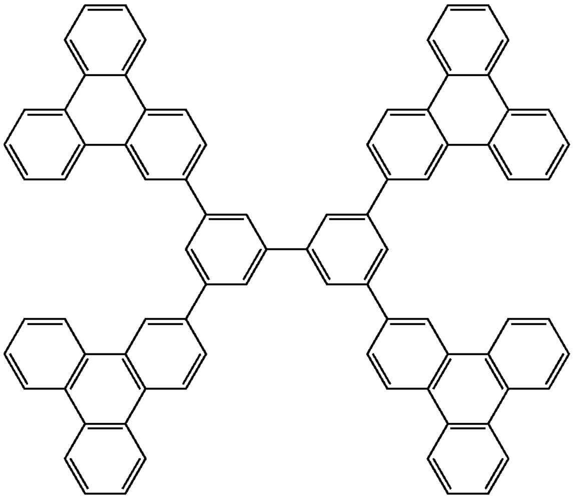

-continued
[Chem. 48]
TpH-13
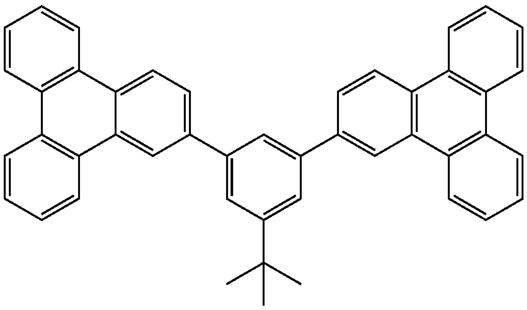
TpH-14
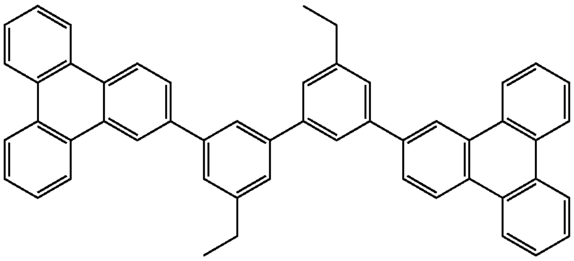
TpH-15
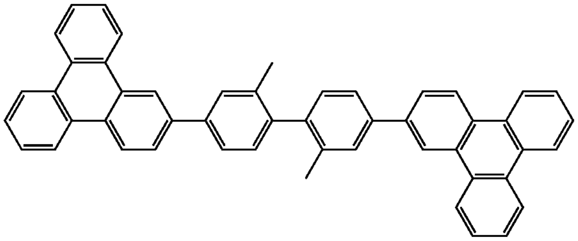
TpH-16
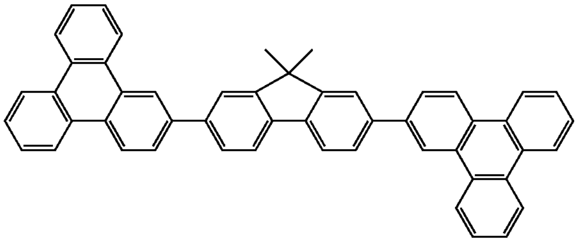
TpH-17
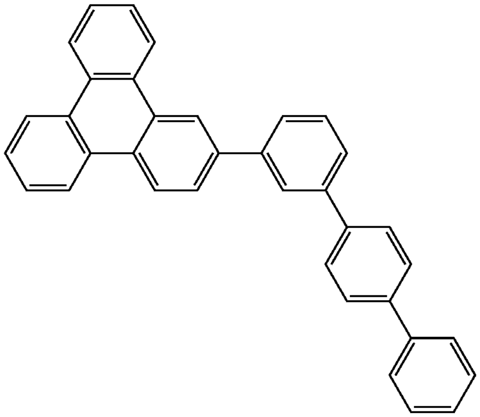
-continued
TpH-18
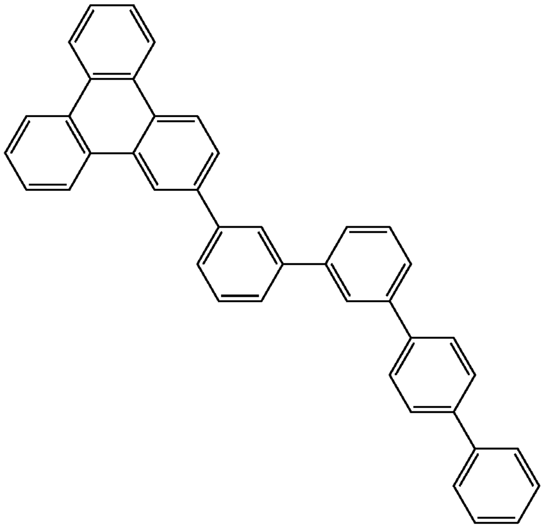
TpH-19
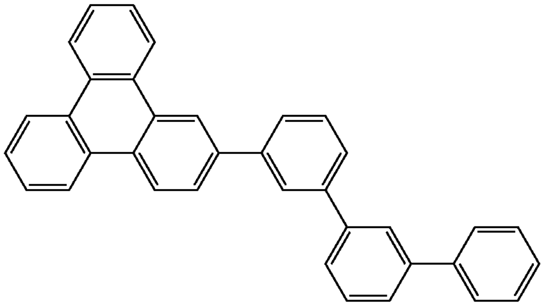
TpH-20
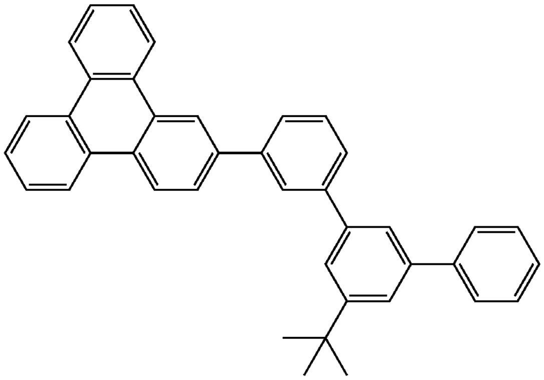

-continued

TpH-21

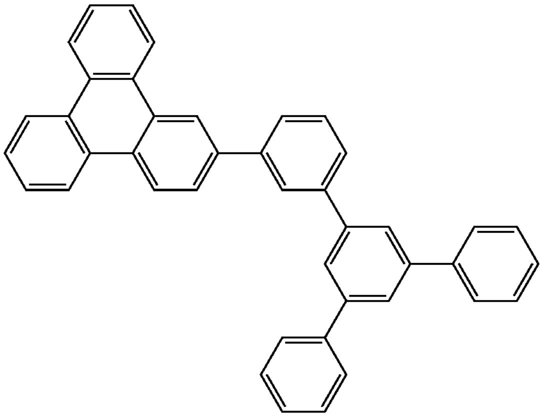

TpH-22

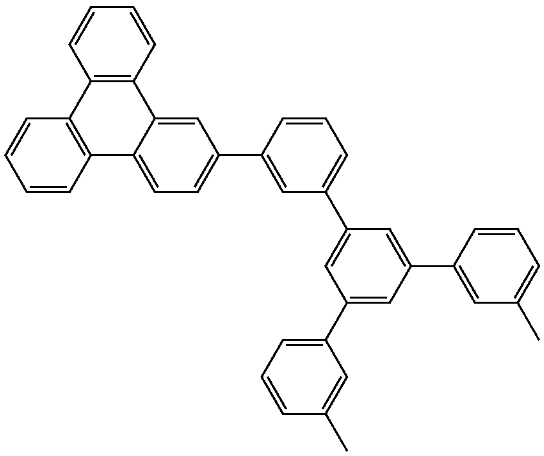

TpH-23

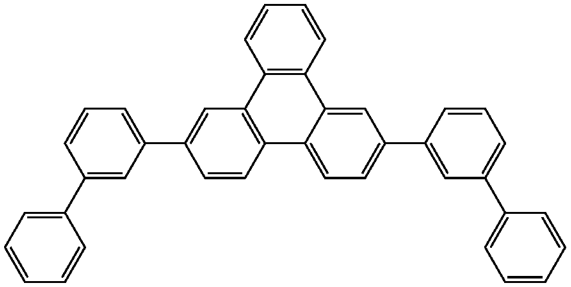

TpH-24

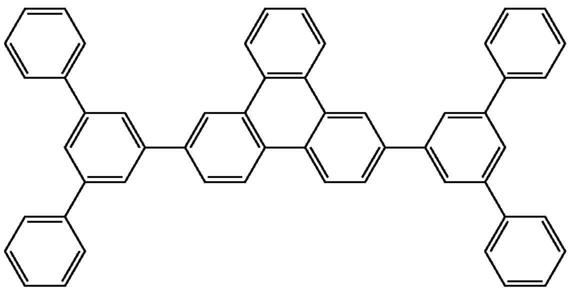

-continued

TpH-25

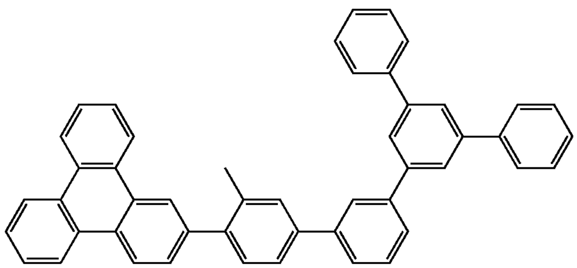

TpH-26

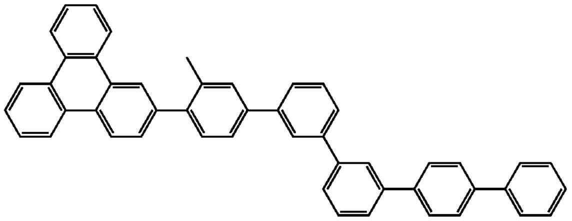

The compounds exemplified above as the hydrocarbon compound represented by general formula (Tp-1) can be synthesized by the methods described in WO05/013388, WO06/130598, WO09/021107, US2009/0009065, WO09/008311, and WO04/018587.

After the synthesis, it is preferable that the product be purified by column chromatography, recrystallization, and the like, and then purified by sublimation purification. By sublimation purification, it is possible not only to separate the organic impurities but also to effectively remove the inorganic salts, remaining solvent, and the like.

[Compound Represented by General Formula (O-1)]

As a material particularly preferably used for the material of the (B) organic layer which is preferably disposed between the cathode and the light emitting layer, the compound represented by the following general formula (O-1) is preferably used, from the viewpoint of the efficiency and the driving voltage of the organic electroluminescent element. The general formula (O-1) will be described below.

[Chem. 49]

(O-1)

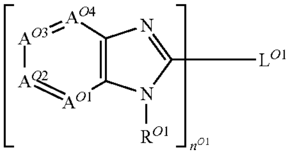

In the general formula (O-1), $R^{O1}$ represents an alkyl group, an aryl group, or a heteroaryl group. $A^{O1}$ to $A^{O4}$ each independently represent C—$R^{A}$ or a nitrogen atom. $R^{A}$ represents a hydrogen atom, an alkyl group, an aryl group, or a heteroaryl group, and a plurality of $R^{A}$s may be the same as or different from each other. $L^{O1}$ represents a divalent to hexavalent linking group composed of an aryl ring or a heteroaryl ring. $n^{O1}$ represents an integer of 2 to 6.

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have the Substituent Group A as described above. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group. Among them, an alkyl group or an aryl group are more preferred, with an aryl group being still more preferred. In the case where the aryl group of $R^{O1}$ has a plurality of substituents, a plurality of substituents may be bonded to each other to form a 5- or 6-membered ring. The aryl group of $R^{O1}$ is preferably a phenyl group which may have the Substituent Group A as described above, more preferably a phenyl group which may be substituted with an alkyl group or an aryl group, and still more preferably an unsubstituted phenyl group or a 2-phenylphenyl group.

$A^{O1}$ to $A^{O4}$ each independently represent C—$R^A$ or a nitrogen atom. It is preferable that from zero to two of $A^{O1}$ to $A^{O4}$ be a nitrogen atom, and it is more preferable that zero or one of $A^{O1}$ to $A^{O4}$ be a nitrogen atom. It is preferable that all of $A^{O1}$ to $A^{O4}$ be C—$R^A$, and $A^{O1}$ be a nitrogen atom, and $A^{O2}$ to $A^{O4}$ be C—R, it is more preferable that $A^{O1}$ be a nitrogen atom, and $A^{O2}$ to $A^{O4}$ be C—$R^A$, and it is still more preferable that $A^{O1}$ be a nitrogen atom, $A^{O2}$ to $A^{O4}$ be C—$R^A$, and $R^{As}$ be all a hydrogen atom.

$R^A$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), and may have the above-mentioned substituent Z'. In addition, a plurality of $R^A$s may be the same as or different from one another. $R^A$ is preferably a hydrogen atom or an alkyl group, and more preferably a hydrogen atom.

$L^{O1}$ represents a divalent to hexavalent linking group composed of an aryl ring (preferably having 6 to 30 carbon atoms) or a heteroaryl ring (preferably having 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have the above-mentioned substituent Z', and in the case where $L^{O1}$ has a substituent, the substituent is preferably an alkyl group, an aryl group, or a cyano group. Specific examples of $L^{O1}$ include the following.

[Chem. 50]

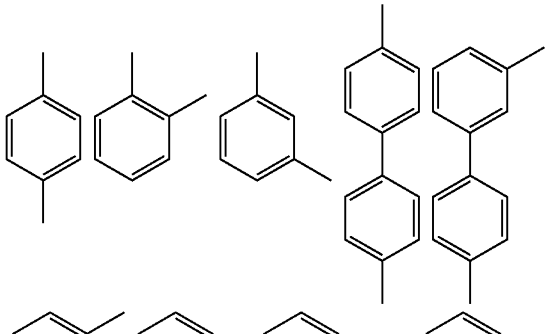

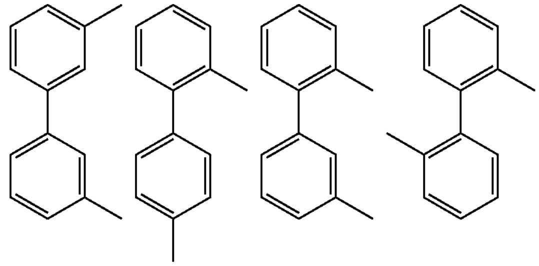

-continued

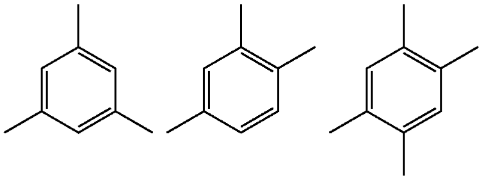

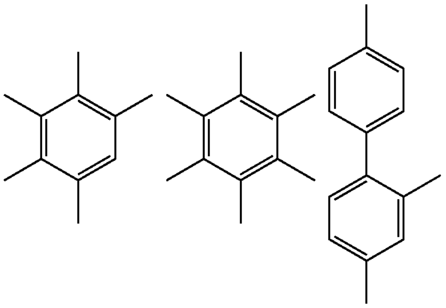

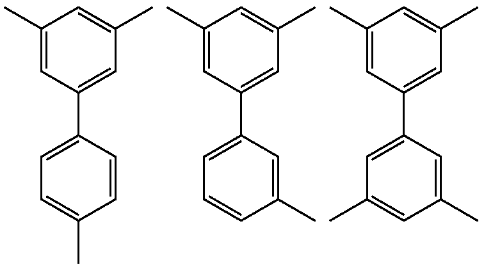

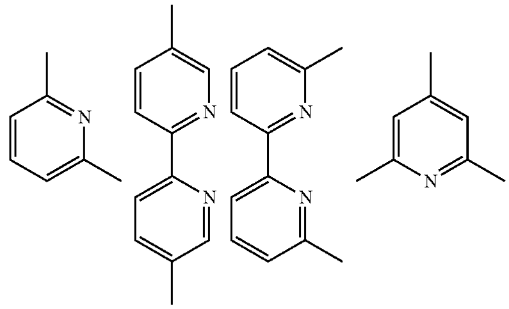

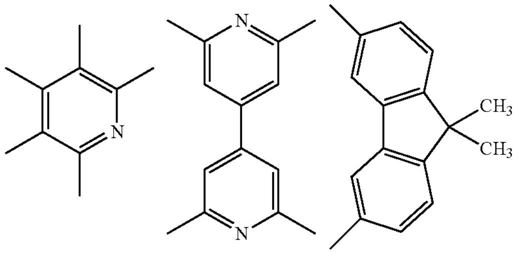

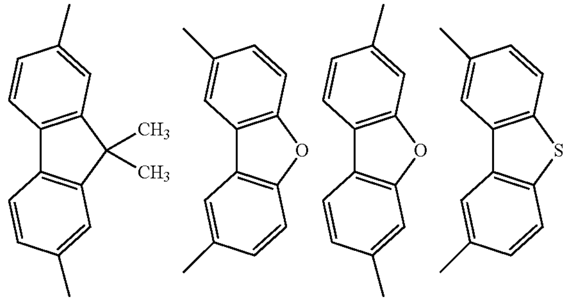

-continued

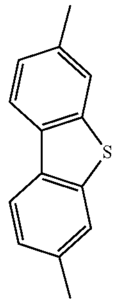

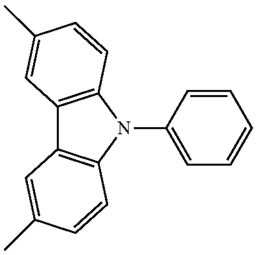

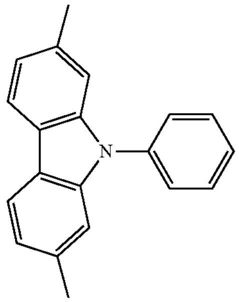

$n^{O1}$ represents an integer of 2 to 6, preferably an integer of 2 to 4, and more preferably 2 or 3. $n^{O1}$ is most preferably 3 from the viewpoint of efficiency of the organic electroluminescent element, or $n^{O1}$ is most preferably 2 from the viewpoint of durability of the organic electroluminescent element.

The compound represented by the general formula (O-1) is preferably a compound represented by the following general formula (O-2).

[Chem. 51]

(O-2)

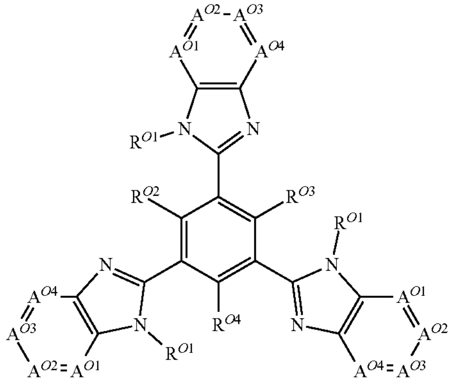

In the general formula (O-2), $R^{O1}$s each independently represent an alkyl group, an aryl group, or a heteroaryl group. $R^{O2}$ to $R^{O4}$ each independently represent a hydrogen atom, an alkyl group, an aryl group, or a heteroaryl group. $A^{O1}$ to $A^{O4}$ each independently represent C—$R^{A}$ or a nitrogen atom. $R^{A}$ represents a hydrogen atom, an alkyl group, an aryl group, or a heteroaryl group, and a plurality of $R^{A}$s may be the same as or different from one another.

$R^{O1}$ and $A^{O1}$ to $A^{O4}$ have the same definitions as $R^{O1}$ and $A^{O1}$ to $A^{O4}$ in the general formula (O-1) described above, and the preferred ranges thereof are also the same.

$R^{O2}$ to $R^{O4}$ each independently represent a hydrogen atom, an alkyl group (preferably having 1 to 8 carbon atoms), an aryl group (preferably having 6 to 30 carbon atoms), or a heteroaryl group (preferably having 4 to 12 carbon atoms), and these groups may have a substituent selected from the Substituent Group A described above. $R^{O2}$ to $R^{O4}$ are preferably a hydrogen atom, an alkyl group or an aryl group, more preferably a hydrogen atom or an aryl group, and most preferably a hydrogen atom.

The glass transition temperature (Tg) of the compound represented by the general formula (O-1) is preferably from 100° C. to 400° C., more preferably from 120° C. to 400° C., still more preferably from 140° C. to 400° C., from the viewpoint of stability at the time of storage at a high temperature, or stable operation during driving at a high temperature against heat generation during driving.

Specific examples of the compound represented by the general formula (O-1) will be shown below, but the compound used in the present invention is not limited thereto.

[Chem. 52]

OM-1

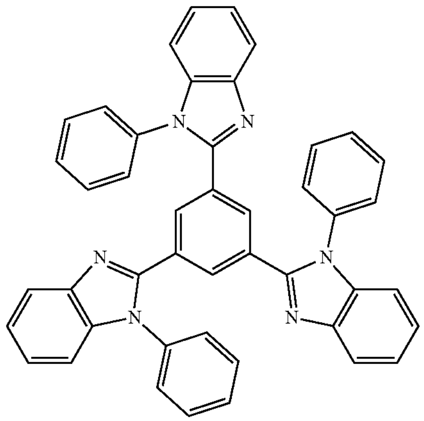

OM-2

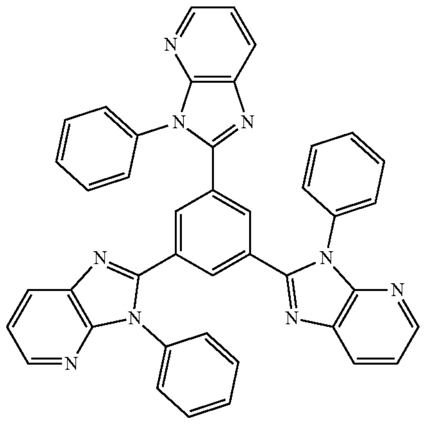

-continued
OM-3
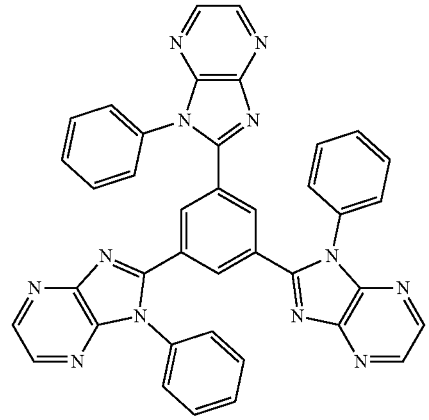
OM-4
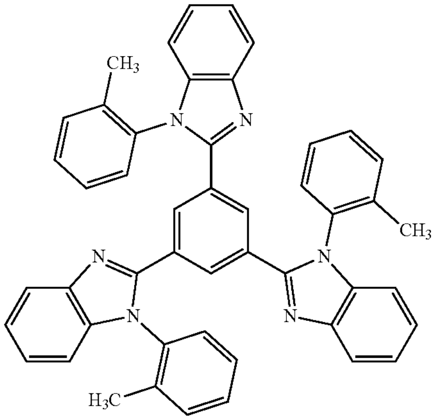
OM-5
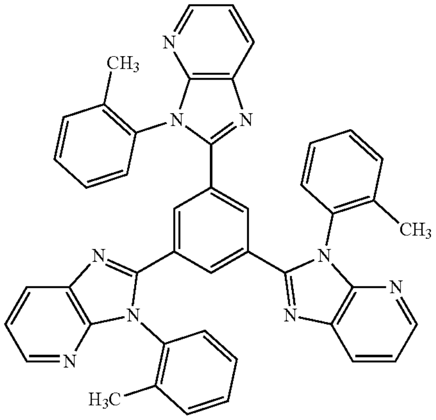
-continued
OM-6
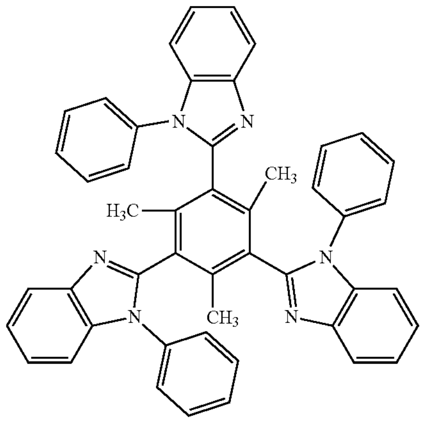
OM-7
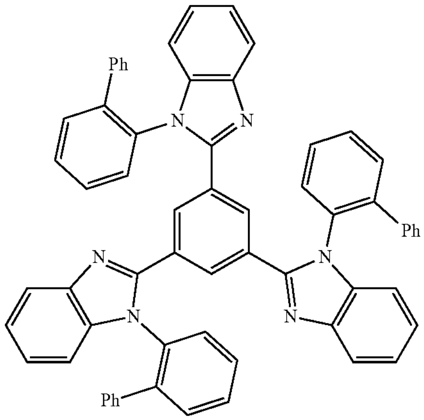
OM-8
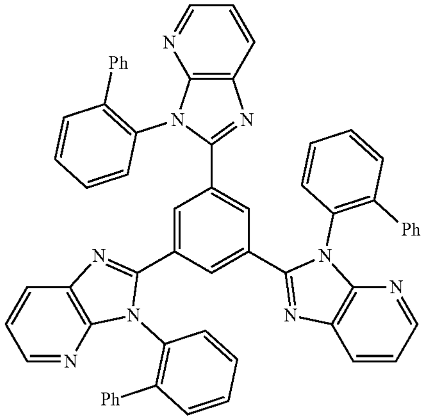

-continued
OM-9
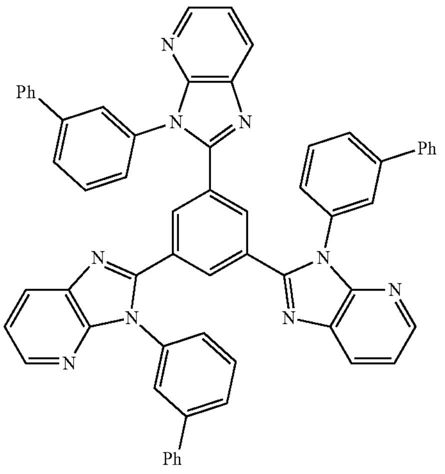
[Chem. 53-1]
OM-10
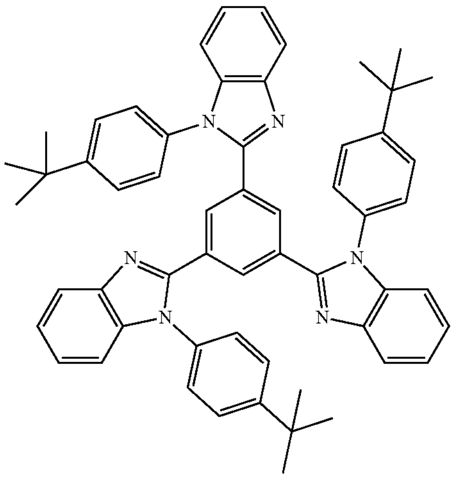
OM-11
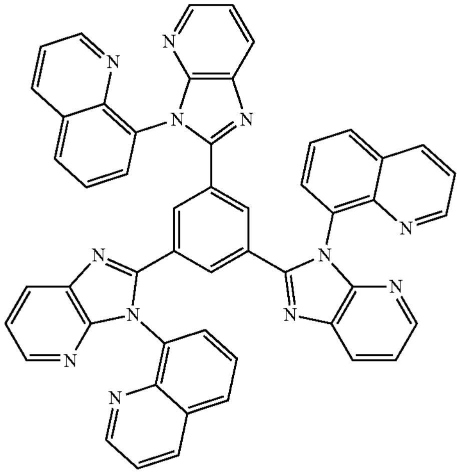
-continued
OM-12
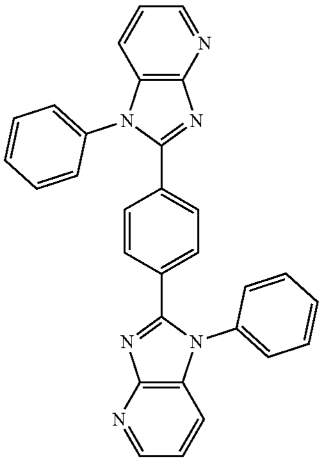
OM-13
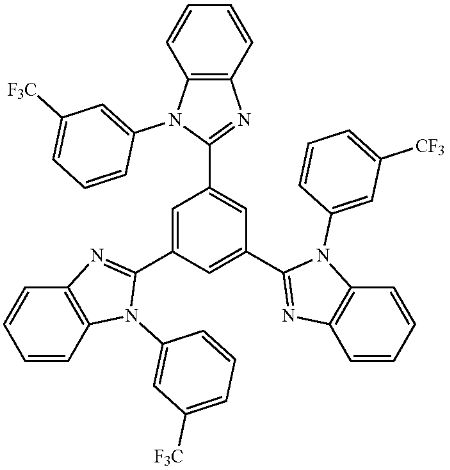
OM-14
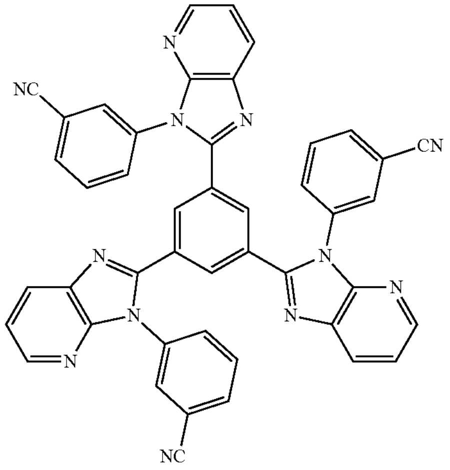

-continued

OM-15

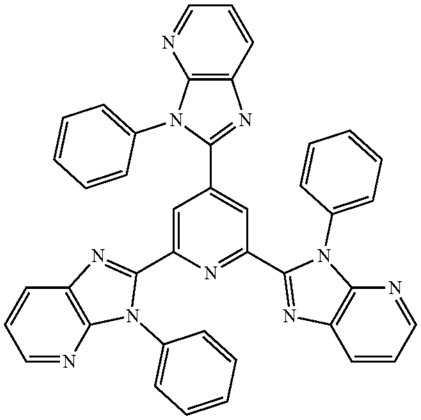

OM-16

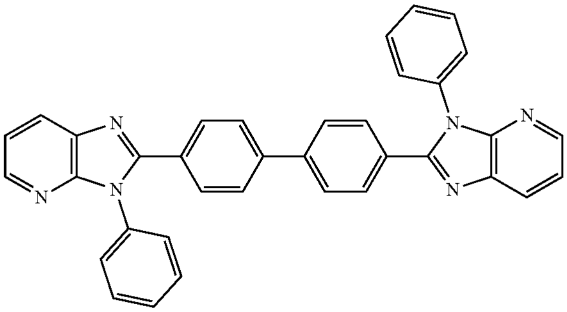

[Chem. 53-2]

OM-17

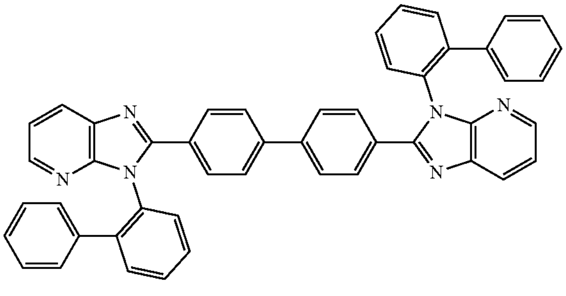

OM-18

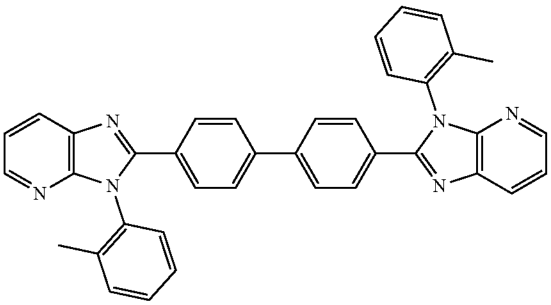

-continued

OM-19

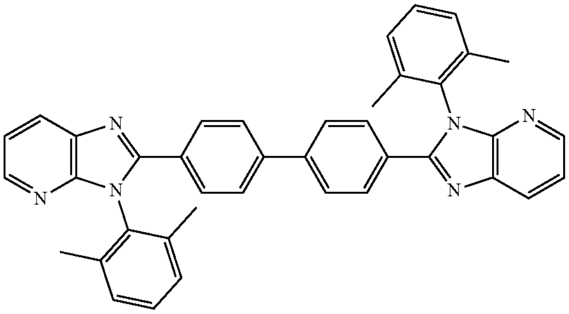

OM-20

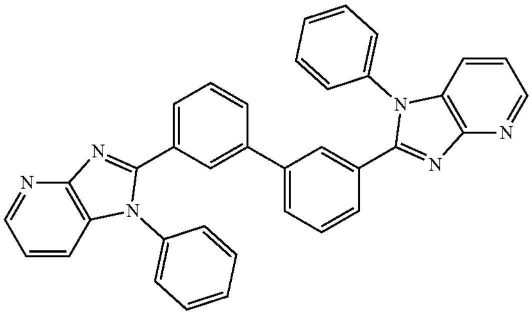

OM-21

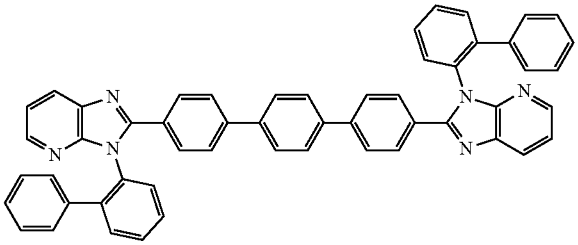

OM-22

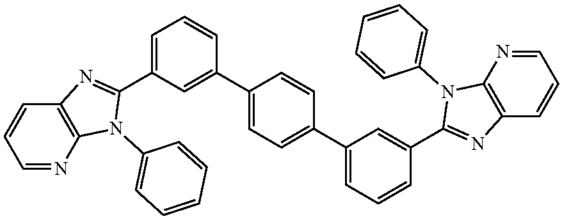

The compound represented by the general formula (O-1) can be synthesized by the method described in JP-A-2001-335776. After the synthesis, it is preferable that the product is purified by column chromatography, recrystallization, reprecipitation, and then purified by sublimation purification. By sublimation purification, it is possible not only to separate organic impurities but also to effectively remove inorganic salts, remaining solvent, moisture, or the like.

In the organic electroluminescent element of the present invention, the compound represented by the general formula (O-1) is preferably contained in an organic layer between the light emitting layer and the cathode, and more preferably contained a layer adjacent to the light emitting layer on the cathode side.

<Protective Layer>

In the present invention, the entirety of the organic electroluminescent element may be protected by a protective layer.

For the protective layer, the detailed description in paragraph Nos. [0169] to [0170] of JP-A-2008-270736 can be applied to the present invention. Incidentally, the materials for the protective layer may be either an inorganic material or an organic material.

<Sealing Enclosure>

For the organic electroluminescent element of the present invention, the entirety of the element may be sealed using a sealing enclosure.

For the sealing enclosure, the detailed description in paragraph No. [0171] of JP-A-2008-270736 can be applied to the present invention.

<Driving Method>

The organic electroluminescent element of the present invention can emit light by applying a direct current (it may include an alternate current component, if desired) voltage (usually from 2 volts to 15 volts) or a direct current between the anode and the cathode.

As a driving method of the organic electroluminescent element of the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 7% or more, and more preferably 10% or more. As for the numerical value of the external quantum efficiency, a maximum value of the external quantum efficiency obtained when the organic electroluminescent element is driven at 20° C., or a value of the external quantum efficiency in the vicinity of from 300 cd/$m^2$ to 400 cd/$m^2$ obtained when the element is driven at 20° C. can be employed.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by the light extraction efficiency. Though the light extraction efficiency in usual organic EL elements is about 20%, by adjusting the shape of a substrate, the shape of an electrode, the film thickness of an organic layer, the film thickness of an inorganic layer, the refractive index of an organic layer, the refractive index of an inorganic layer, or the like, it is possible to increase the light extraction efficiency to 20% or more.

<Light Emitting Wavelength>

The organic electroluminescent element of the present invention has no limitation in its light emitting wavelength, and may be used for red light emission, green light emission, or blue light emission among the three primary colors of light. Above all, the organic electroluminescent element of the present invention preferably have a emission peak wavelength of 400 nm to 700 nm from the viewpoint of luminous efficiency in view of the minimum excision triplet ($T_1$) energy of the compound represented by the general formula (1).

Specifically, in the organic electroluminescent element of the present invention, in the case of using the compound represented by the general formula (1) as a host material of the light emitting layer, or as an electron transporting material of the electron transporting layer or the hole blocking layer, the light emission peak wavelength of the guest material is preferably from 400 nm to 700 nm, more preferably from 450 nm to 650 nm, and particularly preferably from 480 nm to 550 nm.

<Use of Organic Electroluminescent Element of the Present Invention>

The organic electroluminescent element according to the present invention can be suitably used for display elements, displays, backlights, electrophotography, illumination light sources, recording light sources, exposure light sources, readout light sources, signs, billboards, interior decorations, optical communications, and the like. In particular, it is preferably used for devices to be driven in a region of high-intensity luminescence, such as a light emitting device, an illumination device, and a display device.

[Light Emitting Device]

The light emitting device of the present invention may include the organic electroluminescent element of the present invention.

Next, the light emitting device of the present invention will be described with reference to FIG. 2.

Figure 2:
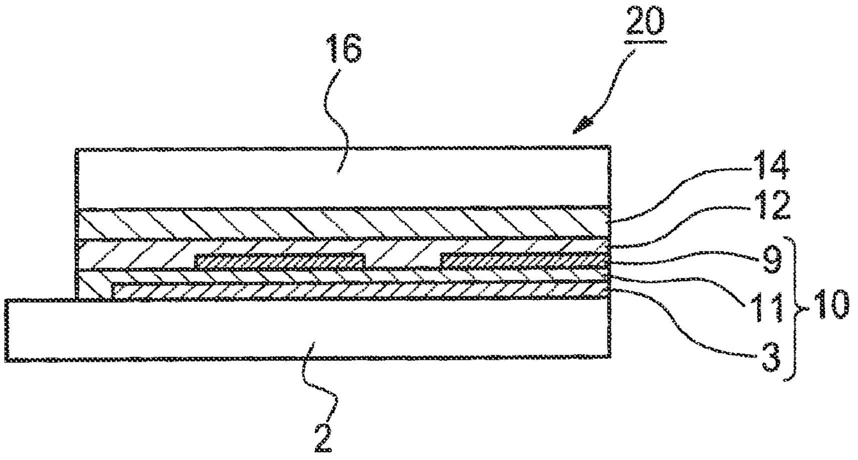
FIG. 2 is a schematic view showing one example of a light emitting device according to the present invention.

FIG. 2 is a cross-sectional view schematically showing one example of the light emitting device of the present invention. The light emitting device 20 in FIG. 2 includes a transparent substrate 2 (supporting substrate), an organic electroluminescent element 10, a sealing enclosure 16, and the like.

The organic electroluminescent element 10 is formed by laminating an anode (first electrode) 3, an organic layer 11, and a cathode (second electrode) 9 in this order on a substrate 2. In addition, a protective layer 12 is laminated on the cathode 9, and a sealing enclosure 16 is further provided via an adhesive layer 14 on the protective layer 12. Incidentally, a part of each of the electrodes 3 and 9, a diaphragm, an insulating layer, and the like are omitted.

Here, as the adhesive layer 14, a photocurable adhesive such as an epoxy resin, or a thermosetting adhesive can be used, and for example, a thermosetting adhesive sheet may also be used.

The light emitting device of the present invention is not particularly limited in its use, and it can be used as not only an illumination device but also a display device of a television set, a personal computer, a mobile phone, electronic paper, or the like.

[Illumination Device]

The illumination device of the present invention includes the organic electroluminescent element of the present invention.

Next, the illumination device of the present invention will be described with reference to FIG. 3.

Figure 3:
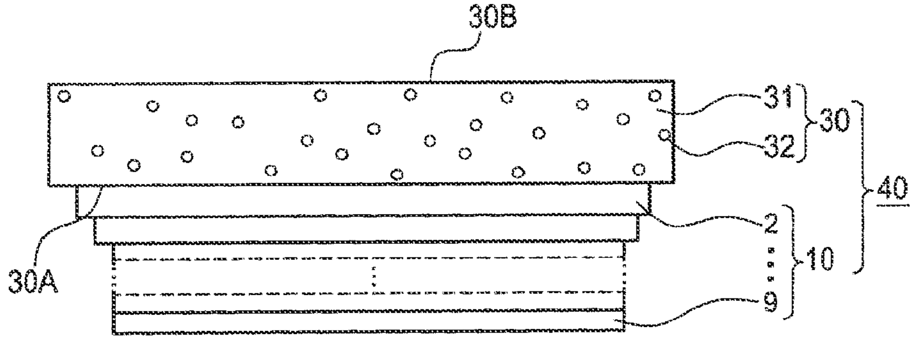
FIG. 3 is a schematic view showing one example of an illumination device according to the present invention.

FIG. 3 is a cross-sectional view schematically showing one example of the illumination device of the present invention. The illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on the light incident surface 30A of the scattering member 30, the incident light is scattered by the light scattering member 30 and the scattered light is output as illuminating light from the light output surface 30B.

[Display Device]

The display device of the present invention may include the organic electroluminescent element of the present: invention.

The display device of the present invention may be used for, for example, a display device of a television set, a personal computer, a mobile phone, electronic paper, or the like.

EXAMPLES

Hereinafter, the characteristic features of the present invention will be described in more detail with reference to Examples. The materials, use amounts, ratios, treatment details, treatment procedures, and the like shown in the following Examples can be appropriately modified so far as the gist of the present invention is not deviated. Accordingly, the scope of the present invention is not limited to the specific examples shown below.

Example 1

(Synthesis of Compound No O-10-10)

[Chem. 54]

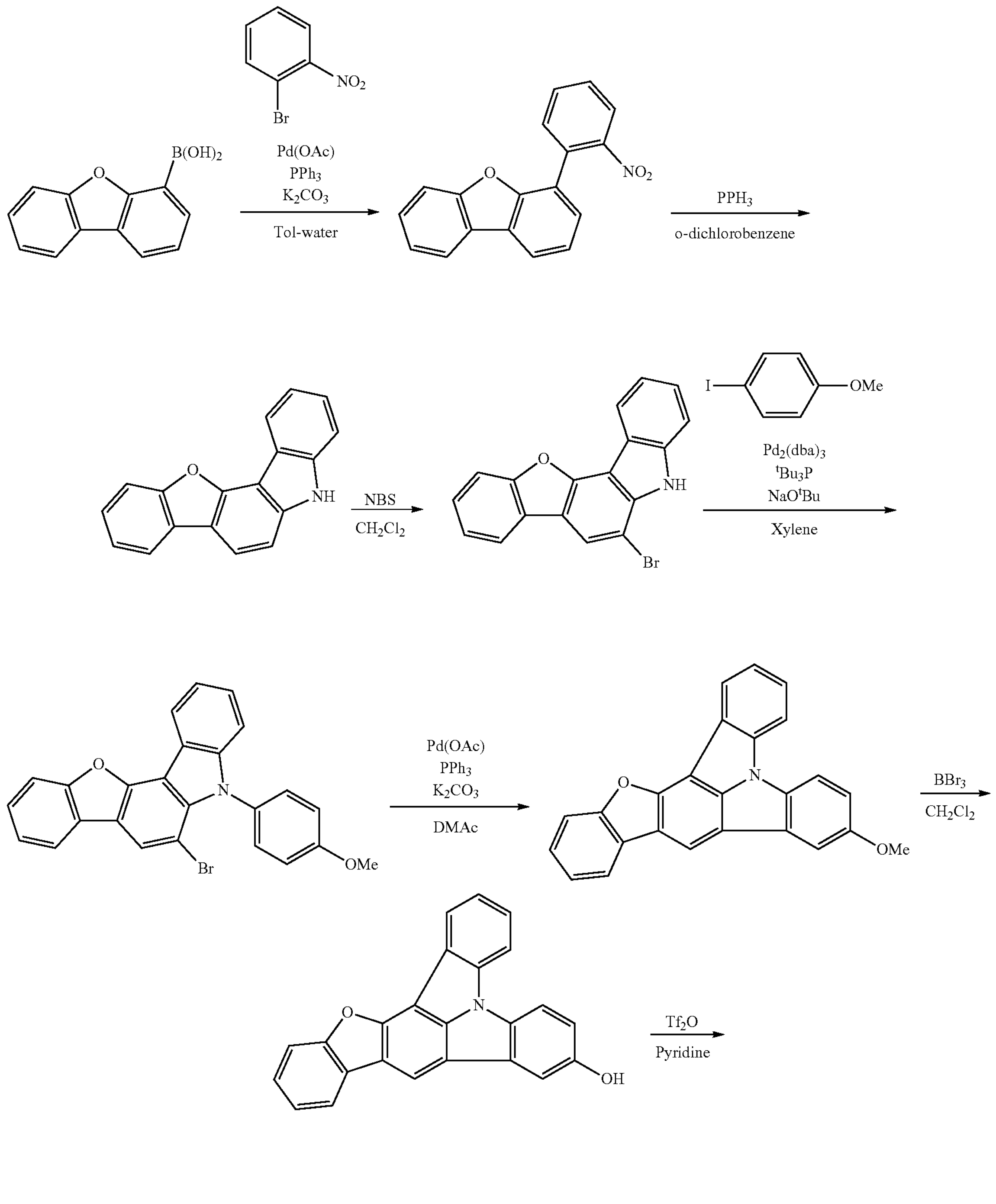

-continued

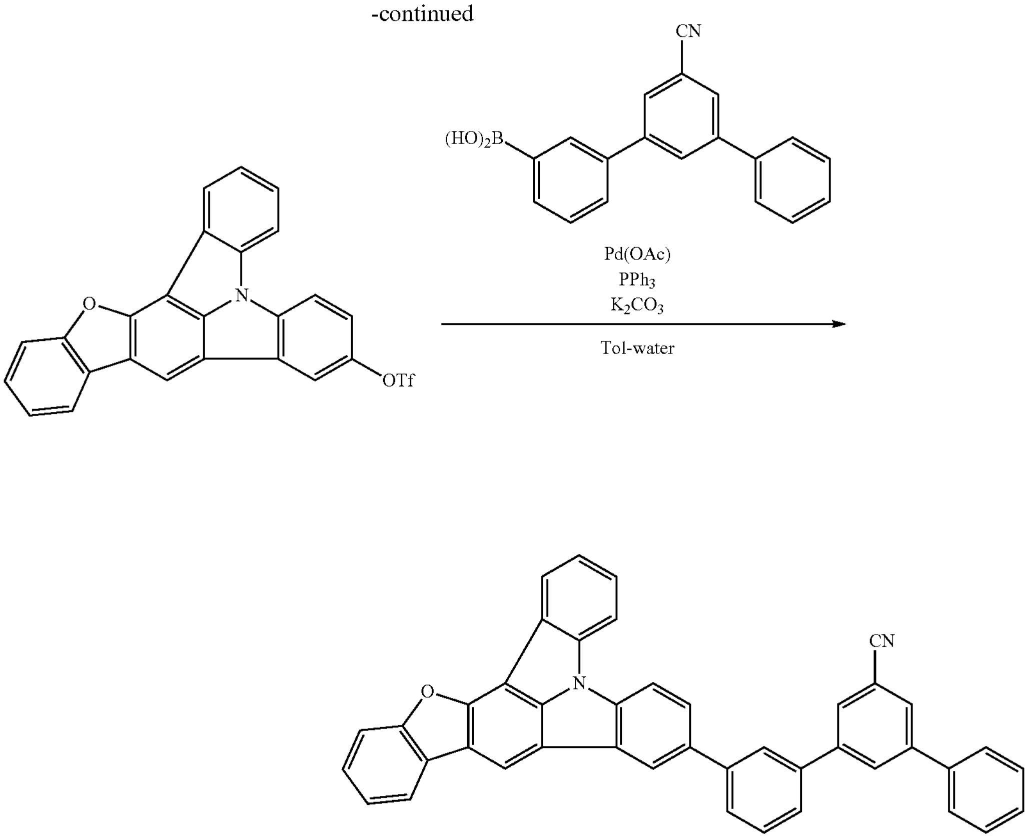

Compound No. O-10-10

According to the scheme, a compound No O-10-10 was synthesized.

The obtained compound No O-10-10 was subjected to MASS spectrum measurement to check the peaks of $[M+H]^+$.

<Fabrication and Evaluation of Organic Electroluminescent Element>

The organic materials used in the preparation of the organic electroluminescent element were all subjected to sublimation purification. The compounds used in Comparative Examples and Examples are shown below.

[Chem. 55]

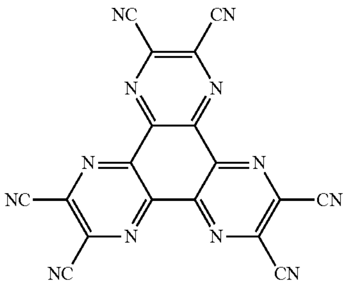

LG 101

-continued

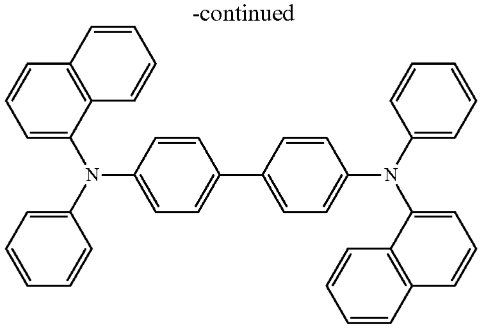

NPD

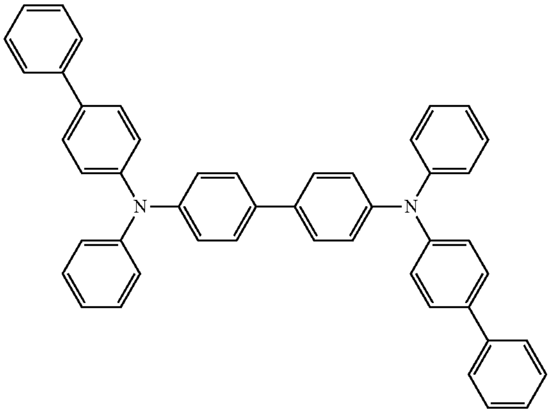

HTL-1

-continued
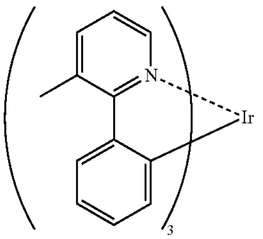
GD-1
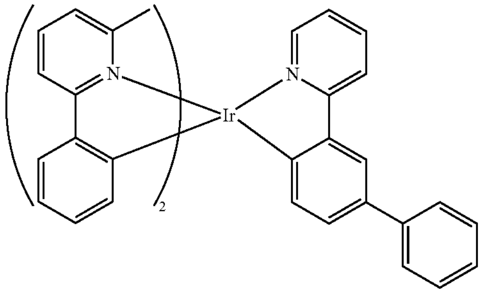
GD-2
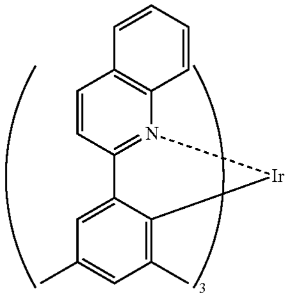
RD-1
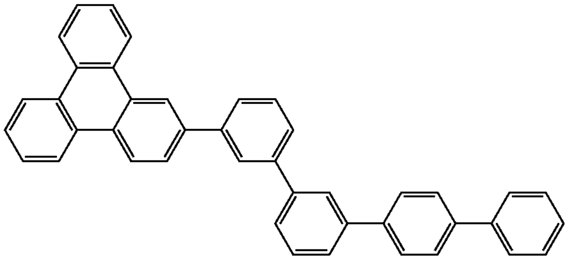
TpH-18
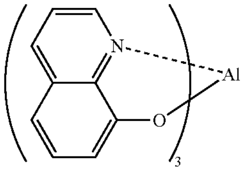
Alq
-continued
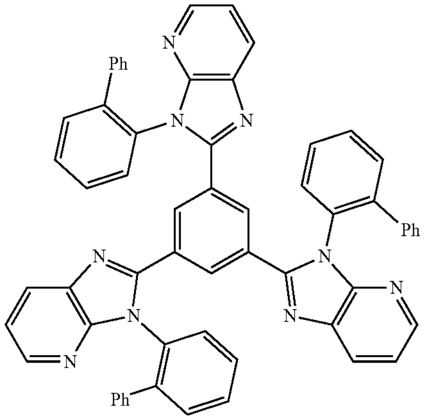
OM-8
[Chem 56]
Comparative Compound 1: Compound (4-3) described in WO2010/131855
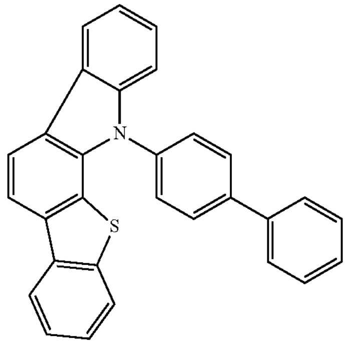 [SMILES: c1ccc(-c2ccc(-n3c4ccccc4c4ccc5c6ccccc6sc5c43)cc2)cc1]
Comparative Compound 2: Compound (1) described in JP-A-2010-087496
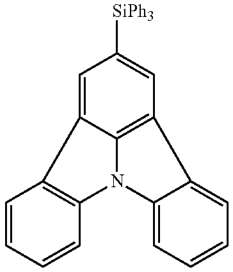

[Chem 57]
Comparative Compound 3: Compound (54) described in JP-A-2010-87496
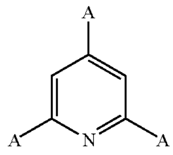
Central skeleton
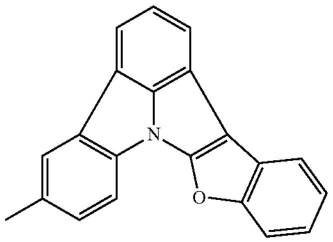
A
Comparative Compound 4: Compound (70) described in JP-A-2010-87496
Central skeleton
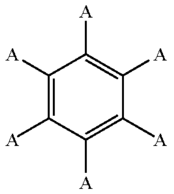
A
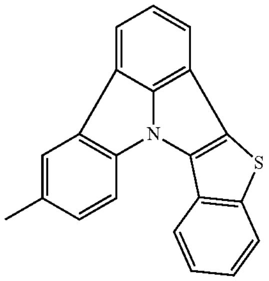
[Chem. 58]
Compound No. O-10-10
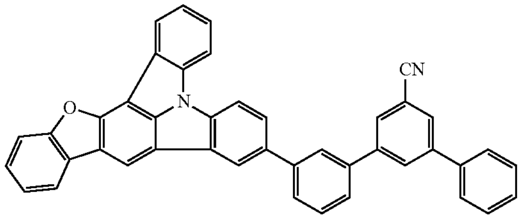
Compound No. O-10-40
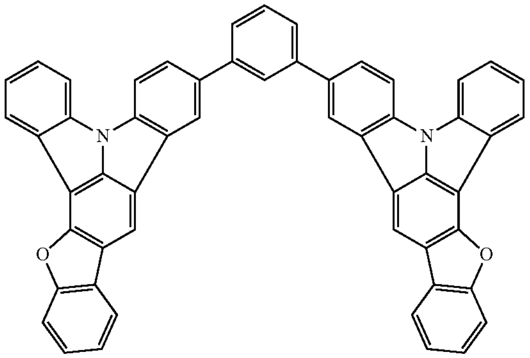
Compound No. O-10-22
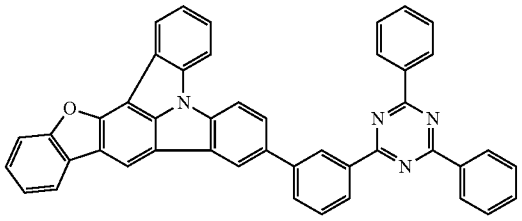
Compound No. C-10-2
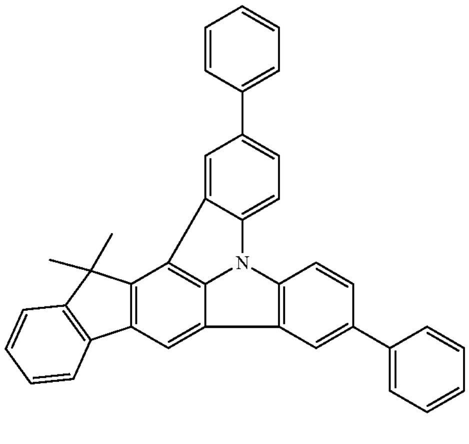

-continued
Compound No. N-11-4
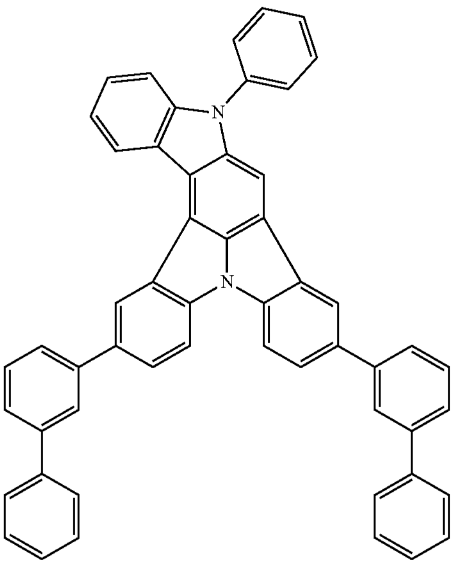
Compound No. O-11-13
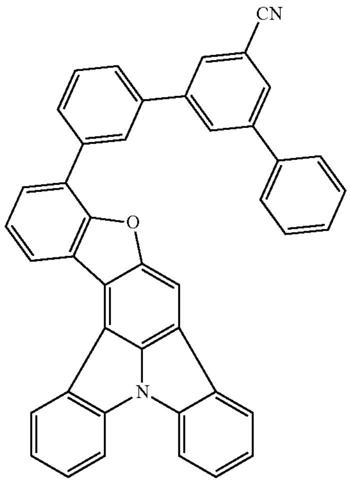
Compound No. O-12-42
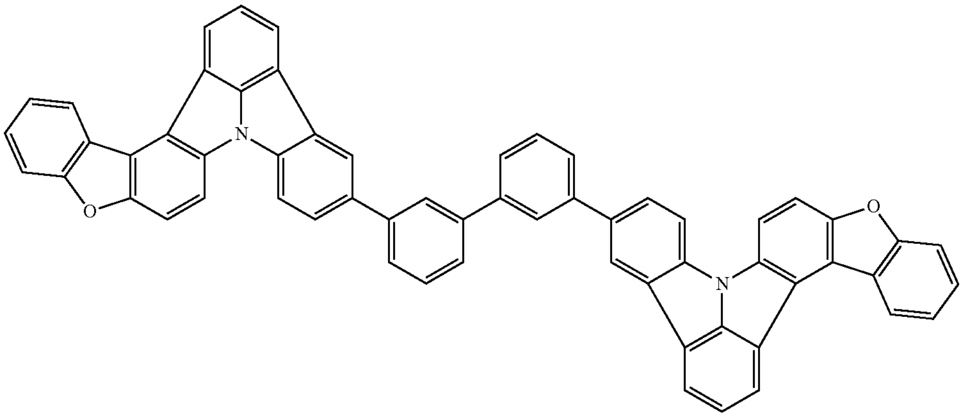
Compound No. N-13-24
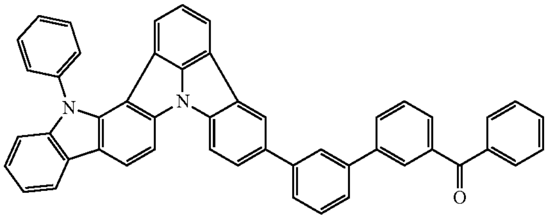
Compound No. N-13-10
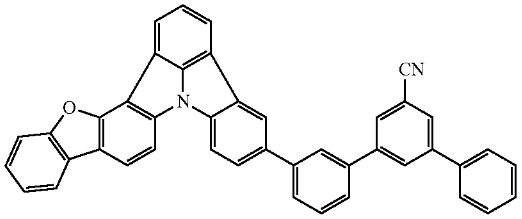

-continued
Compound No. S-13-18
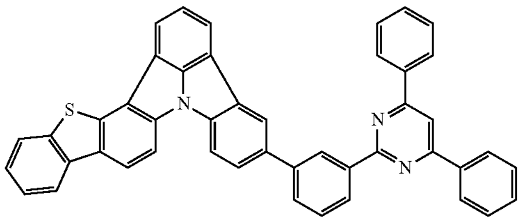
Compound No. O-14-4
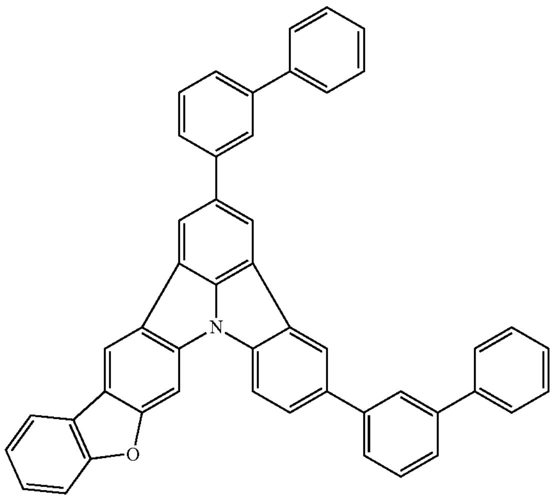
Compound No. O-14-79
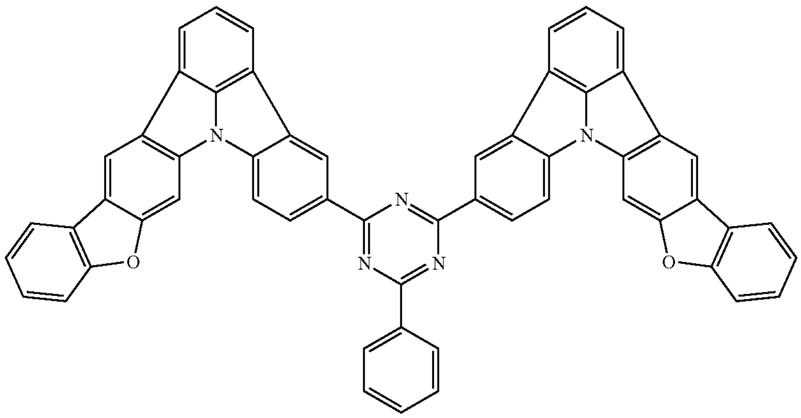
Compound No. S-15-16
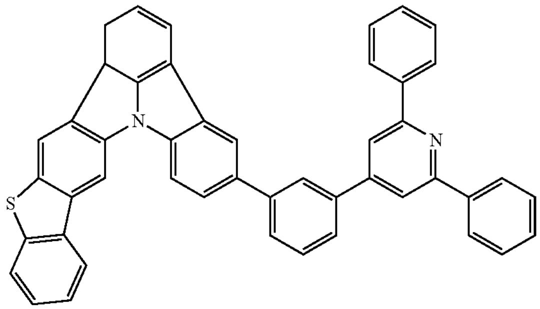
Compound No. O-16-9
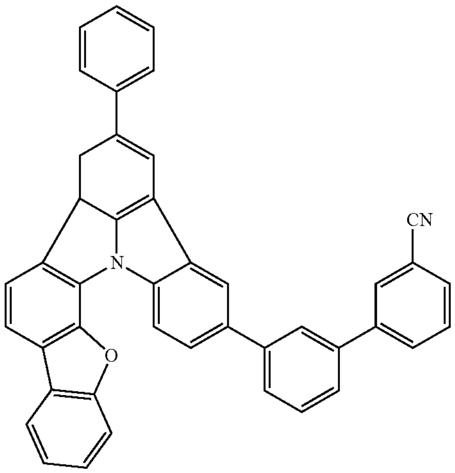

-continued

Compound No. O-16-15

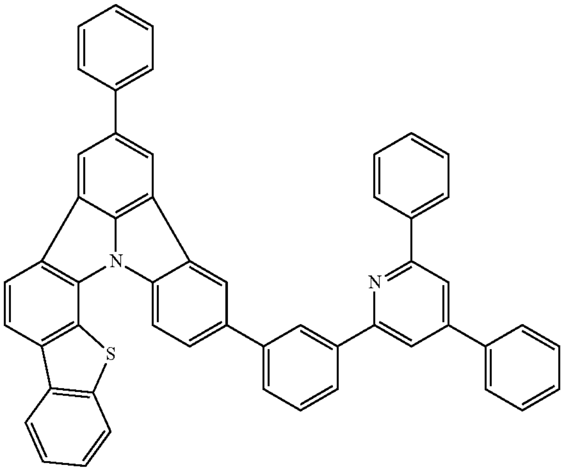

Compound No. O-17-12

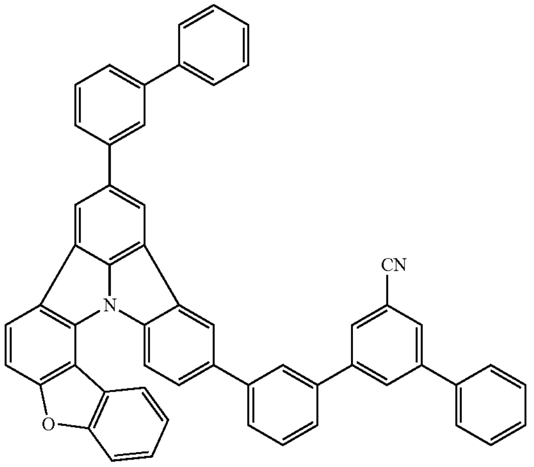

Comparative Example 1

(Fabrication of Anode)

A 0.5 mm-thick and 2.5 cm square glass substrate (manufactured by Geomatec Co., Ltd., surface resistance: 10 Ω/□) having an ITO film thereon was put in a cleaning container. After ultrasonic cleaning in 2-propanol, the glass substrate was subjected to a UV-ozone treatment for 30 minutes.

This was used as an anode (ITO film, transparent anode).

(Lamination of Organic Layers)

On the anode, first to fifth organic layers were sequentially deposited using the following compounds by a vacuum deposition method. The compound structures used in respective layers are shown below together.

First layer: LG101: film thickness: 10 nm

Second layer: NPD: film thickness: 30 nm

Third layer: Comparative Compound 1 (host material) and green phosphorescent light emitting material GD-1 (guest material) (mass ratio: 85:15): film thickness: 30 nm Fourth layer: TpH-18: film thickness: 10 nm Fifth layer: Alq: film thickness: 40 nm

[Chem. 59]

First Layer:

LG 101

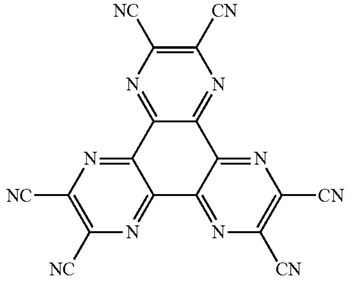

-continued

Second Layer:

NPD

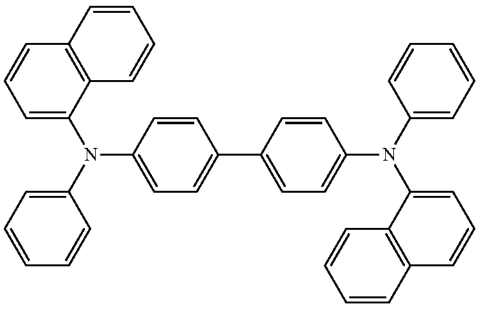

Third Layer:

Comparative Compound 1

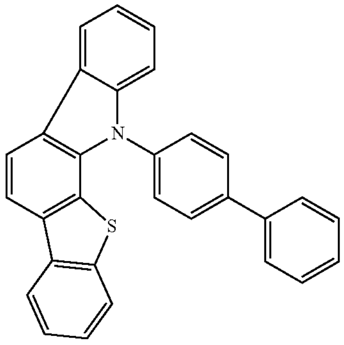

GD-1

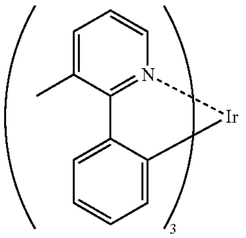

-continued

Fourth Layer:

TpH-18

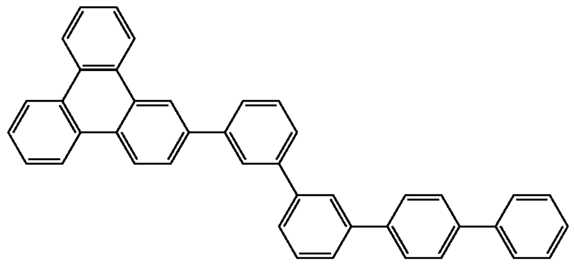

Fifth Layer:

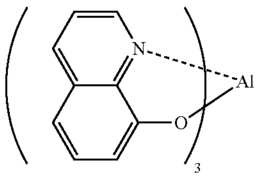

Alq (Fabrication of Cathode)

On the above lamination, 0.1 nm of lithium fluoride and 200 nm of metal aluminum were deposited in this order to form a cathode.

(Fabrication of Organic Electroluminescent Element)

A lamination which includes the anode and the cathode, and the five organic layers disposed between the anode and the cathode was placed in a glove box purged with nitrogen gas without contact with atmospheric air, and sealed in a glass sealing can using an ultraviolet cure adhesive (XNR5516HV, manufactured by Nagase-Chiba, Ltd.) to obtain an organic electroluminescent element of Comparative Example 1.

(Evaluation of Organic Electroluminescent Element)

(a) Durability

A DC voltage was applied to the organic electroluminescent element of Comparative Example 1 to allow the element to emit light continuously to attain a luminance of 8000 $cd/m^2$ at room temperature, and the time period required for the luminance to go down to 7200 $cd/m^2$ was measured. This time period was used as an index of the durability of the organic electroluminescent element.

Furthermore, in the respective Tables shown below in the respective Examples and Comparative Examples as described later, the durability at a time of using the organic electroluminescent element of Comparative Example 1 was taken as 100 and the element having a relative value of the durability of less than 100 was rated as “C”, the element having that ranging from 100 to less than 120 as “B”, and the element having that of 120 or more as “A”.

Here, a larger number of durability is more preferred.

(b) Driving Voltage

A DC voltage was applied to the organic electroluminescent element of Comparative Example 1 to allow the element to emit light to attain a luminance of 1000 $cd/m^2$. The voltage applied at this time was used as an index of the evaluation of the driving voltage.

Further, in respective Examples and Comparative Examples as described later, the applied voltage of the organic electroluminescent element of Comparative Example 1 was taken as 100 and the element having a relative value of the voltage of 100 or more was rated as “C”, the element having that ranging from 90 to less than 100 as “B”, and the element having that of less than 90 as “A”. Here, a smaller number of driving voltage is more preferred.

Examples A1 to A14 and Comparative Examples 2 to 4

The organic electroluminescent elements in Examples A1 to A14 and Comparative Example 2 were obtained by the same procedure as in Comparative Example 1, except that the compound of the present application or Comparative Compounds 2 to 4 were used instead of Comparative Compound 1 as a material for the third layer in the organic layers.

The durability and the driving voltage of these organic electroluminescent elements were measured by the same method as for the organic electroluminescent element using the Comparative Compound 1 in Comparative Example 1 above, and evaluated in accordance with the measurement criteria as described above. The results are shown in Table 66 below.

TABLE 66

| | Host material | Durability | Driving voltage |
|---|---|---|---|
| Comparative Example 1 | Comparative Compound 1 | — | — |
| Comparative Example 2 | Comparative Compound 2 | C | C |
| Comparative Example 3 | Comparative Compound 3 | C | C |
| Comparative Example 4 | Comparative Compound 4 | C | C |
| Example A1 | Compound No O-10-10 | A | A |
| Example A2 | Compound No O-10-40 | A | A |
| Example A3 | Compound No O-10-22 | A | A |
| Example A4 | Compound No C-10-2 | B | B |
| Example A5 | Compound No O-12-42 | A | B |
| Example A6 | Compound No N-13-24 | B | A |
| Example A7 | Compound No O-13-10 | A | A |
| Example A8 | Compound No S-13-18 | B | A |
| Example A9 | Compound No O-14-4 | A | B |
| Example A10 | Compound No O-14-79 | A | A |
| Example A11 | Compound No S-15-16 | A | A |
| Example A12 | Compound No O-16-9 | B | A |
| Example A13 | Compound No S-16-15 | B | B |
| Example A14 | Compound No S-17-12 | A | A |

Comparative Example 5

The organic electroluminescent element of Comparative Example 5 was fabricated in the same manner as in Comparative Example 1, except that NPD used in the second layer was changed to HTL-1, GD-1 used in the third layer was changed to GD-2, TpH-18 used in the fourth layer was changed to OM-8, and Alq used in the fifth layer was changed to OM-8. The configuration of the organic layers in Comparative Example 5 is shown below.

First layer: LG101, film thickness: 10 nm

Second layer: HTL-1, film thickness: 30 nm

Third layers: Comparative Compound 1 (host material) and green phosphorescent light emitting material GD-2 (guest material) (mass ratio: 85:15), film thickness: 30 nm Fourth layer: OM-8, film thickness: 10 nm Fifth layer: OM-8, film thickness: 40 nm Examples B1 to B14 and Comparative Examples 6 to 8

The organic electroluminescent elements of Examples B1 to B14 and Comparative Example 4 were obtained in the same manner as in Comparative Example 5, except that the compound of the present application or Comparative Compound 2 was used instead of Comparative Compound 1 as the material for the third layer in the organic layers.

The durability and the driving voltage of these organic electroluminescent elements were measured by the same method as for the organic electroluminescent element using the Comparative Compound 1 in Comparative Example 1 above, and evaluated in accordance with the measurement criteria as described above. The results are shown in Table 67 below.

TABLE 67

| | Host material | Durability | Driving voltage |
|---|---|---|---|
| Comparative Example 5 | Comparative Compound 1 | — | — |
| Comparative Example 6 | Comparative Compound 2 | C | C |
| Comparative Example 7 | Comparative Compound 3 | C | C |
| Comparative Example 8 | Comparative Compound 4 | C | C |
| Example B1 | Compound No O-10-10 | A | A |
| Example B2 | Compound No O-10-40 | A | B |
| Example B3 | Compound No O-10-22 | A | A |
| Example B4 | Compound No C-10-2 | B | B |
| Example B5 | Compound No O-12-42 | A | B |
| Example B6 | Compound No N-13-24 | B | B |
| Example B7 | Compound No O-13-10 | A | A |
| Example B8 | Compound No S-13-18 | B | A |
| Example B9 | Compound No O-14-4 | A | B |
| Example B10 | Compound No O-14-79 | A | B |
| Example B11 | Compound No S-15-16 | A | A |
| Example B12 | Compound No O-16-9 | A | A |
| Example B13 | Compound No S-16-15 | B | A |
| Example B14 | Compound No S-17-12 | A | A |

Comparative Example 9

The organic electroluminescent element of Comparative Example 9 was fabricated in the same manner as in Comparative Example 1, except that LG101 used in the first layer was changed to GD-1, GD-1 used in the third layer was changed to a red phosphorescent light emitting material RD-1, and TpH-18 used in the fourth layer was changed to Alq. The configuration of the organic layers in Comparative Example 9 is shown below.

First layer: GD-1, film thickness: 10 nm

Second layer: NPD, film thickness: 30 nm

Third layer: Comparative Compound 1 (host material) and red phosphorescent light emitting material RD-1 (guest material) (mass ratio: 90:10), film thickness: 30 nm Fourth layer: Alq, film thickness: 10 nm Fifth: Alq, film thickness: 40 nm Examples C1 to C10 and Comparative Examples 10 to 12

The organic electroluminescent elements of Examples C1 to C10 and Comparative Examples 10 to 12 were obtained in the same manner as in Comparative Example 9, except that, as the material for the third layer in the organic layers, the compound of the present application or Comparative Compound 2 was used instead of Comparative Compound 1.

The durability and the driving voltage of these organic electroluminescent elements were measured by the same method as for the organic electroluminescent element using the Comparative Compound 1 in Comparative Example 1 above, and evaluated in accordance with the measurement criteria as described above. The results are shown in Table 68 below.

TABLE 68

| | Host material | Durability | Driving voltage |
|---|---|---|---|
| Comparative Example 9 | Comparative Compound 1 | — | — |
| Comparative Example 10 | Comparative Compound 2 | C | C |
| Comparetive Example 11 | Comparative Compound 3 | C | C |
| Comparative Example 12 | Comparative Compound 4 | C | C |
| Example C1 | Compound No O-10-10 | A | B |
| Example C2 | Compound No O-10-22 | A | A |
| Example C3 | Compound No N-11-4 | B | A |
| Example C4 | Compound No O-11-13 | A | A |
| Example C5 | Compound No O-12-42 | A | B |
| Example C6 | Compound No N-13-24 | B | A |
| Example C7 | Compound No S-13-18 | A | A |
| Example C8 | Compound No O-14-79 | A | A |
| Example C9 | Compound No S-15-16 | B | B |
| Example C10 | Compound No O-16-9 | A | A |

From Tables 66 to 68 above, it can be seen that the organic electroluminescent element using the host material of the present invention has excellent durability and low driving voltage, which is thus good.

REFERENCE SIGNS LIST

2 . . . SUBSTRATE
3 . . . ANODE
4 . . . HOLE INJECTTNG LAYER
5 . . . HOLE TRANSPORTING LAYER
6 . . . LIGHT EMITTING LAYER
7 . . . HOLE BLOCKING LAYER
8 . . . ELECTRON TRANSPORTING LAYER
9 . . . CATHODE
10 . . . ORGANIC ELECTROLUMINESCENT ELEMENT (ORGANIC ET. ELEMENT)
11 . . . ORGANIC LAYER
12 . . . PROTECTIVE LAYER
14 . . . ADHESIVE LAYER
16 . . . SEALING ENCLOSURE
20 . . . LIGHT EMITTING DEVICE
30 . . . LIGHT SCATTERING MEMBER
30A . . . LIGHT INCIDENT SURFACE
30B . . . LIGHT OUTPUTTING SURFACE
31 . . . TRANSPARENT SUBSTRATE
32 . . . FINE PARTICLES
40 . . . ILLUMINATION DEVICE

The invention claimed is:

1. A compound represented by any one of the following general formulae (8) and (9):

(2)

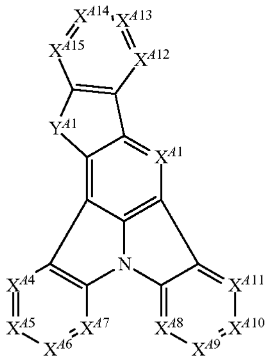

(3)

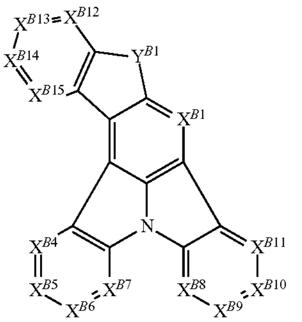

(4)

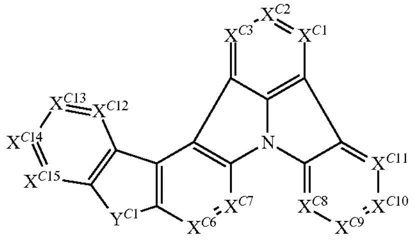

(5)

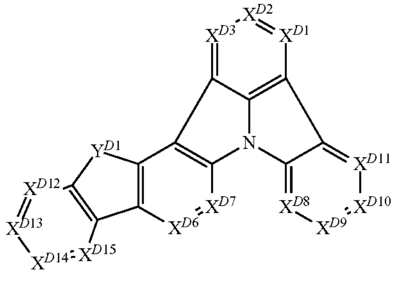

(6)

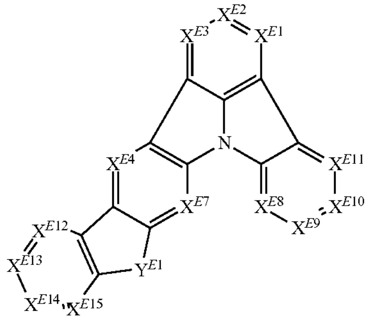

-continued (7)

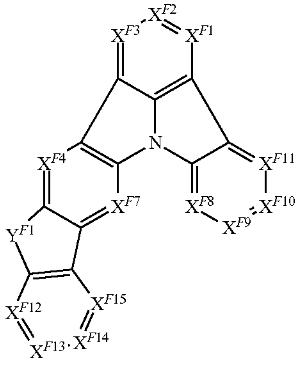

(8)

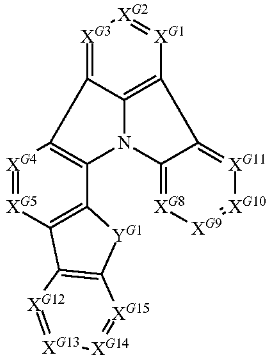

(9)

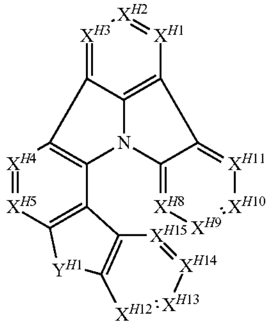

wherein $Y^{G1}$ and $Y^{H1}$ each independently represents $CR^1R^2$, $NR^3$, O, S, or Se;

$R^1$ to $R^3$ each independently represents a substituent;

$X^{G1}$ to $X^{G5}$, $X^{G8}$ to $X^{G15}$, $X^{H1}$ to $X^{H5}$, and $X^{H8}$ to $X^{H15}$ each independently represent $CR^4$ or N; and each $R^4$ independently represents a hydrogen atom or a substituent.

2. The compound according to claim 1, which is represented by any one of the following general formulae (16) and (17):

-continued
(10)
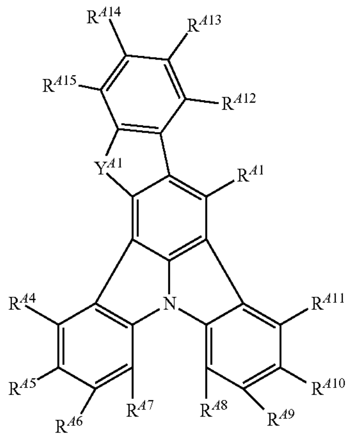
(11)
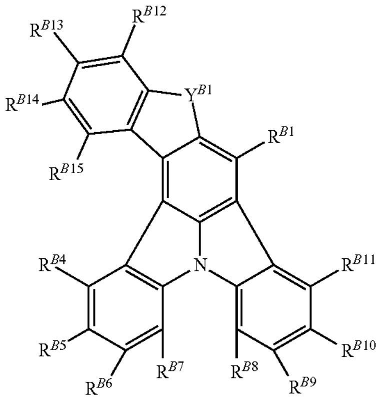
(12)
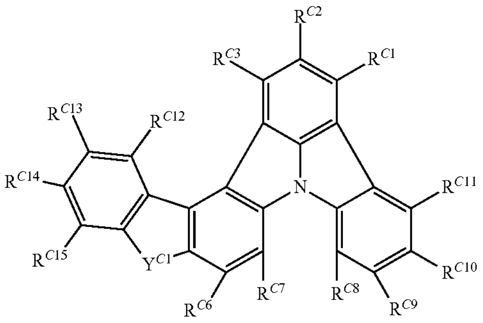
(13)
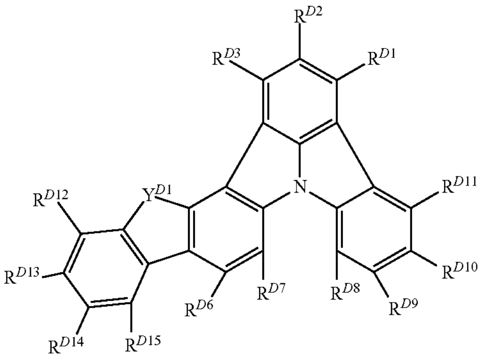
(14)
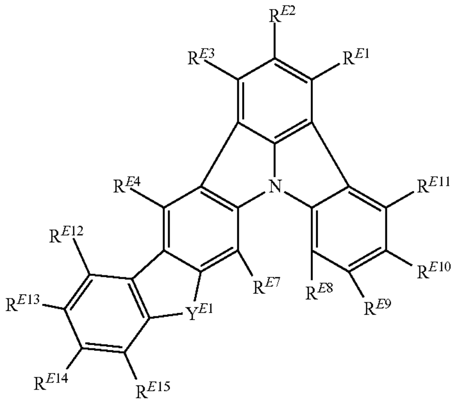
(15)
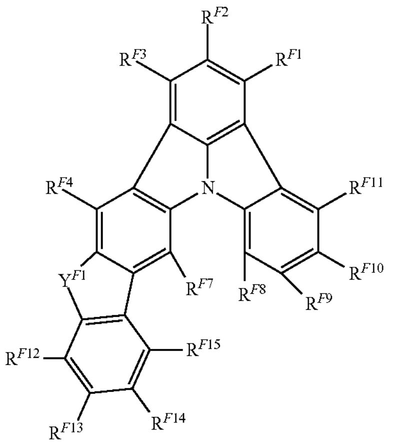
(16)
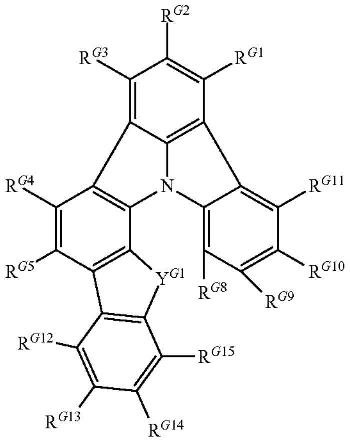

-continued (17)

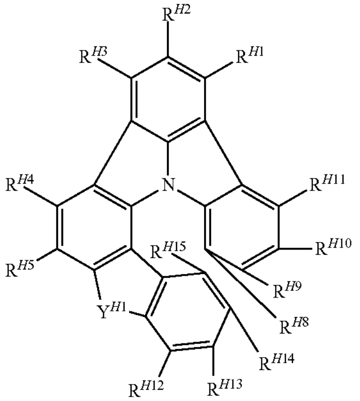

wherein $Y^{G1}$ and $Y^{H1}$ each independently represents $CR^1R^2$, $NR^3$, O, S, or Se;

$R^1$ to $R^3$ each independently represents a substituent; and $R^{G1}$ to $R^{G5}$, $R^{G8}$ to $R^{G15}$, $R^{H1}$ to $R^{H5}$, and $R^{H8}$ to $R^{H15}$ each independently represents a hydrogen atom or a substituent.

3. The compound according to claim 1, wherein the compound represented by any one of the general formulae (8) and (9) has a substituent containing at least one of a pyridine ring, a pyrimidine ring, a triazine ring, a cyano group, and a carbonyl group.

4. A compound of claim 1, wherein the compound is represented by general formula (8).

5. A compound of claim 1, wherein the compound is represented by general formula (9).

6. A material for an organic electroluminescent element, represented by any one of the following general formulae (8) and (9):

(2)

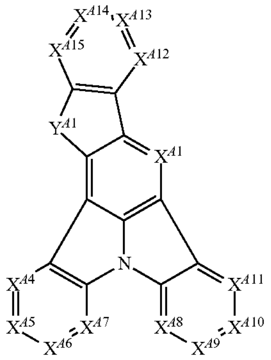

(3)

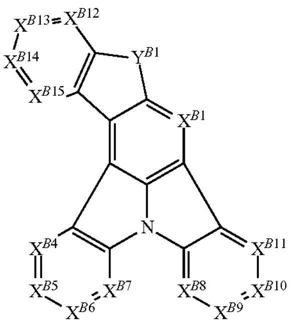

-continued (4)

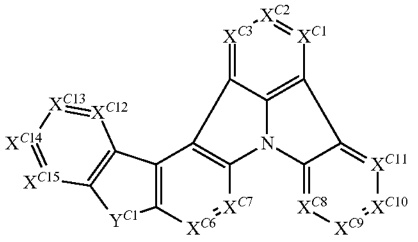

(5)

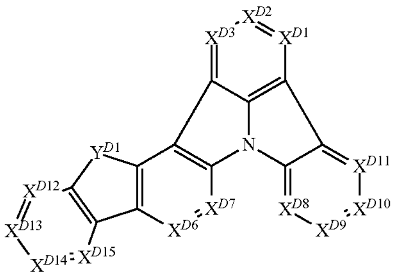

(6)

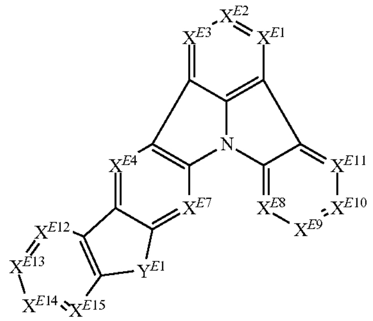

(7)

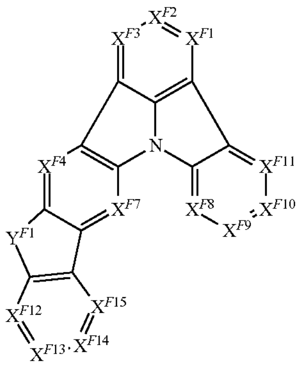

(8)

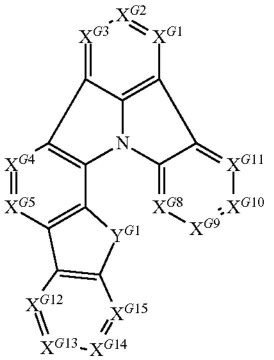

-continued (9)

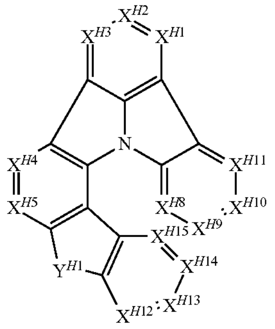

wherein $Y^{G1}$ and $Y^{H1}$ each independently represents $CR^1R^2$, $NR^3$, O, S, or Se;

$R^1$ to $R^3$ each independently represents a substituent;

$X^{G1}$ to $X^{G5}$, $X^{G8}$ to $X^{G15}$, $X^{H1}$ to $X^{H5}$, and $X^{H8}$ to $X^{H15}$ each independently represent $CR^4$ or N; and each $R^4$ independently represents a hydrogen atom or a substituent.

7. The material for an organic electroluminescent element according to claim 6, which is represented by any one of the following general formulae (16) and (17):

(10)

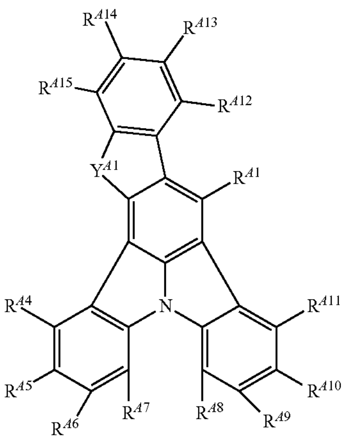

(11)

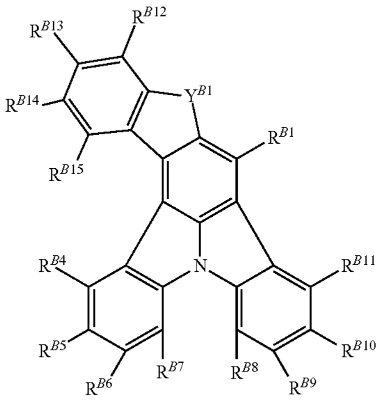

-continued (12)

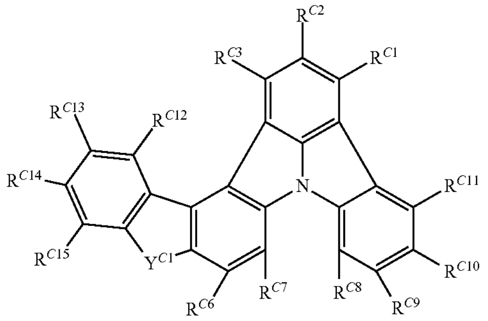

(13)

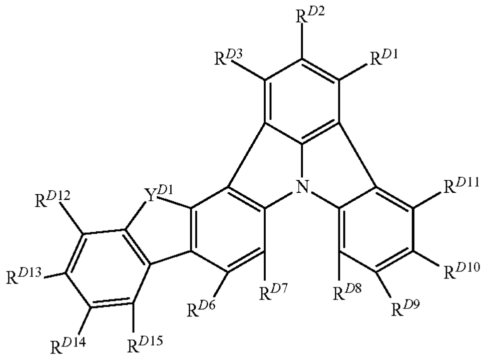

(14)

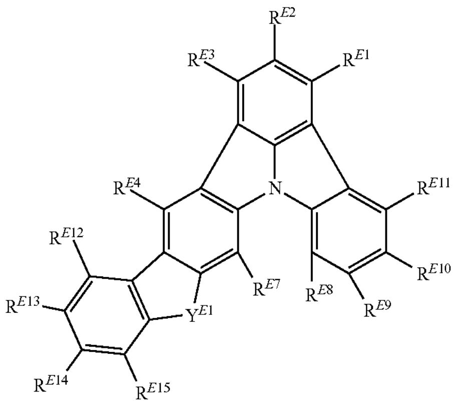

(15)

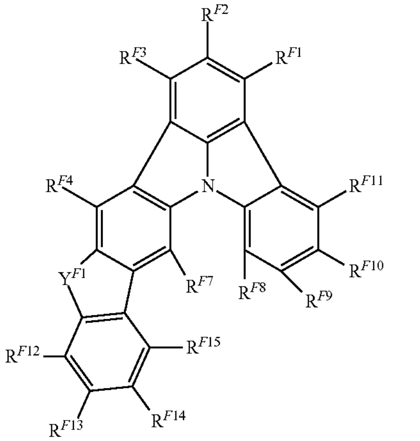

-continued (16)

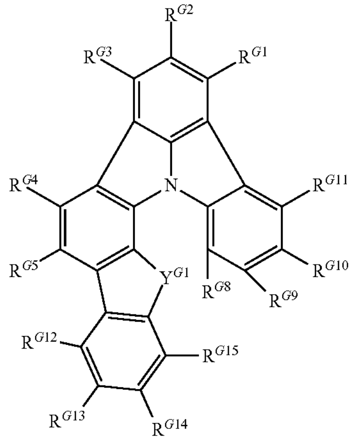

(17)

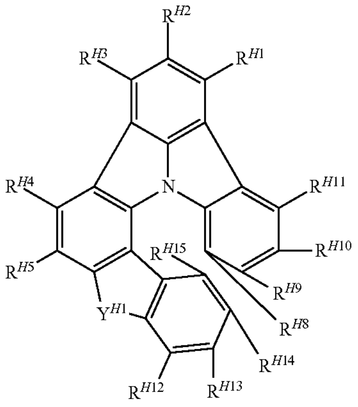

wherein $Y^{G1}$ and $Y^{H1}$ each independently represents $CR^1R^2$, $NR^3$, O, S, or Se;

$R^1$ to $R^3$ each independently represents a substituent; and $R^{G1}$ to $R^{G5}$, $R^{G8}$ to $R^{G15}$, $R^{H1}$ to $R^{H5}$, and $R^{H8}$ to each independently represents a hydrogen atom or a substituent.

8. An organic electroluminescent element comprising:

a substrate;

a pair of electrodes including an anode and a cathode, disposed on the substrate; and at least one organic layer including a light emitting layer, disposed between the electrodes, wherein at least one layer of the organic layer(s) contains a compound represented by any one of the following general formulae (8) and (9):

(2)

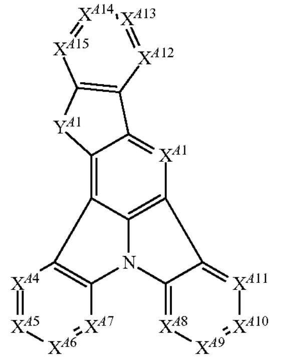

(3)

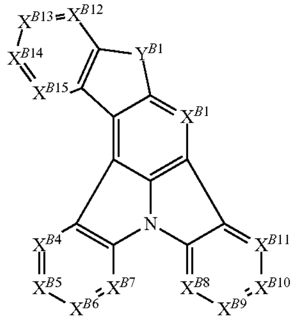

(4)

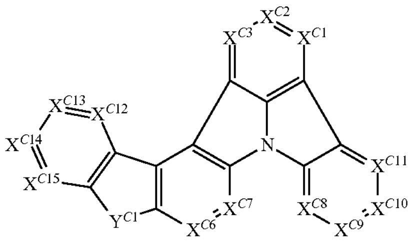

(5)

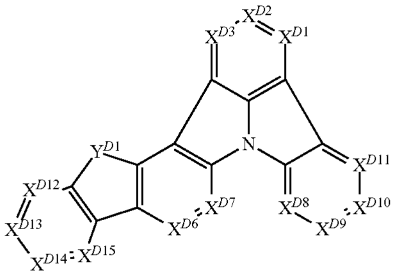

(6)

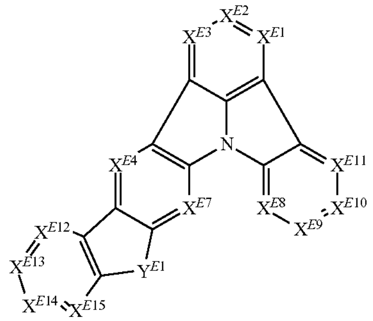

-continued (7)

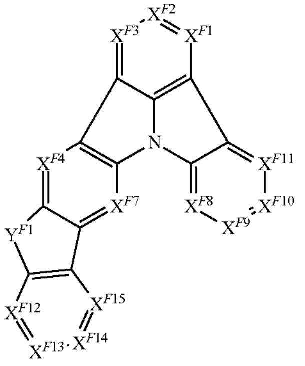

(8)

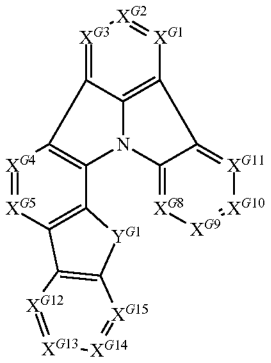

(9)

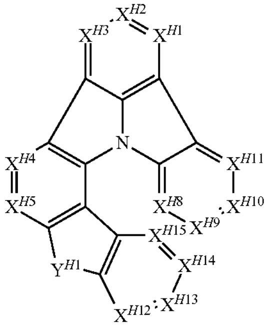

wherein $Y^{G1}$ and $Y^{H1}$ each independently represents $CR^1R^2$, $NR^3$, O, S, or Se;

$R^1$ to $R^3$ each independently represents a substituent;

$X^{G1}$ to $X^{G5}$, $X^{G8}$ to $X^{G15}$, $X^{H1}$ to $X^{H5}$, and $X^{H8}$ to $X^{H15}$ each independently represent $CR^4$ or N; and each $R^4$ independently represents a hydrogen atom or a substituent.

9. The organic electroluminescent element according to claim 8, wherein the compound is represented by any one of the following general formulae (16) and (17):

(10)

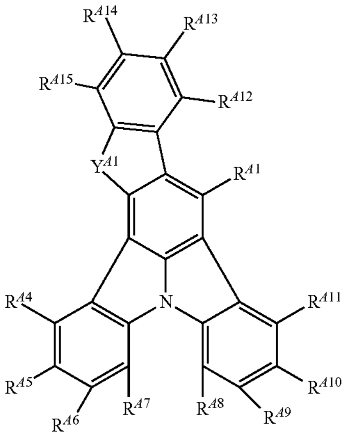

(11)

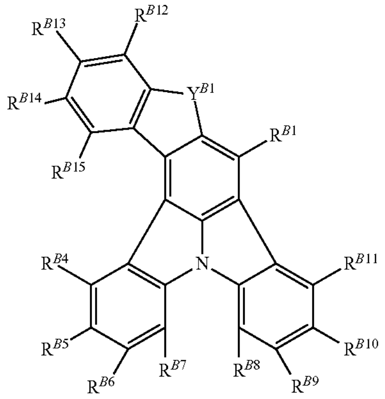

(12)

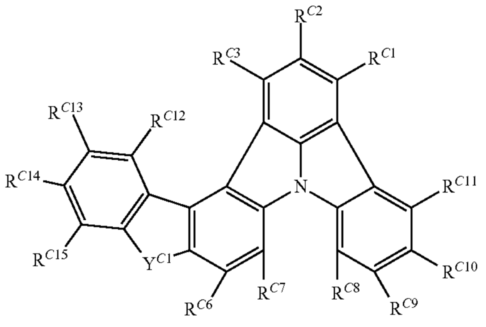

(13)

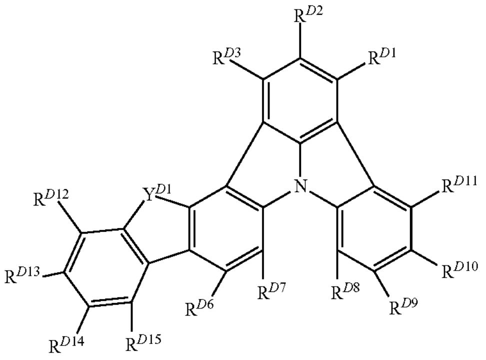

-continued (14)

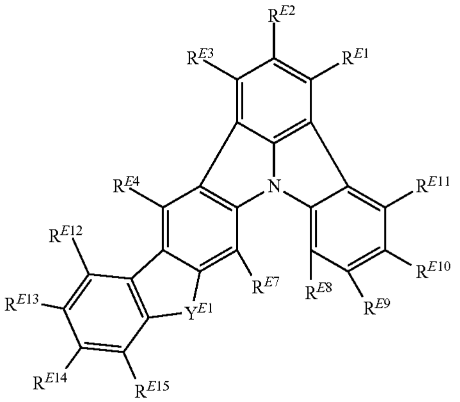

(15)

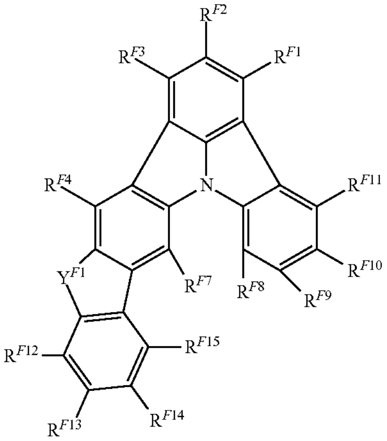

(16)

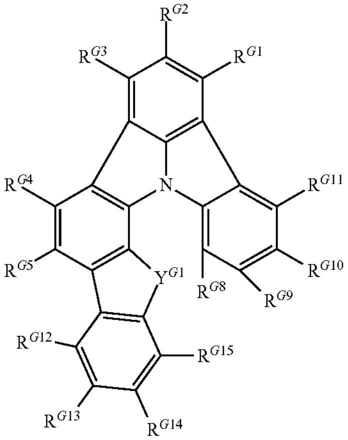

-continued (17)

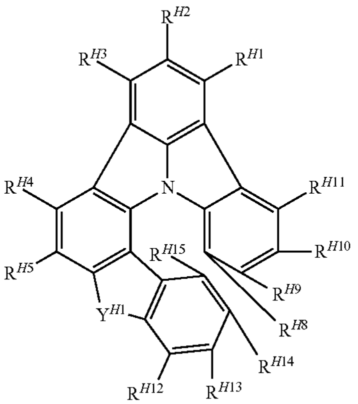

wherein $Y^{G1}$ and $Y^{H1}$ each independently represents $CR^1R^2$, $NR^3$, O, S, or Se;

$R^1$ to $R^3$ each independently represents a substituent; and $R^{G1}$ to $R^{G5}$, $R^{G8}$ to $R^{G15}$, $R^{H1}$ to $R^{H5}$, and $R^{H8}$ to $R^{H15}$ each independently represents a hydrogen atom or a substituent.

10. The organic electroluminescent element according to claim 8, wherein the light emitting layer contains at least one kind of phosphorescent light emitting material.

11. The organic electroluminescent element according to claim 10, wherein the at least one kind of phosphorescent light emitting material is an iridium complex represented by the following general formula (E-1):

(E-1)

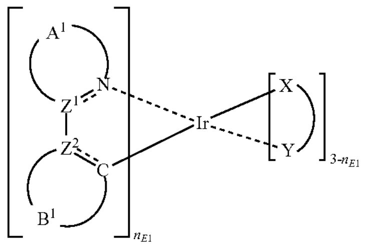

wherein $Z^1$ and $Z^2$ each independently represent a carbon atom or a nitrogen atom;

$A^1$ represent an atomic group that forms a 5- or 6-membered hetero ring together with $Z^1$ and a nitrogen atom;

$B^1$ represent an atomic group that forms a 5- or 6-membered ring together with $Z^2$ and a carbon atom;

(X-Y) represent a mono-anionic bidentate ligand; and $n_{E1}$ represents an integer of 1 to 3.

12. The organic electroluminescent element according to claim 11, wherein the iridium complex represented by the general formula (E-1) is represented by the following general formula (E-2):

(E-2)
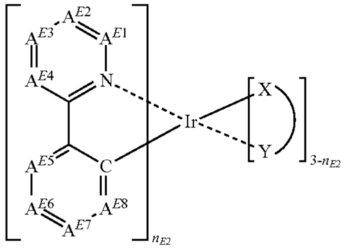
wherein $A^{E1}$ to $A^{E8}$ each independently represent a nitrogen atom or C—$R^{E}$;
$R^{E}$ represent a hydrogen atom or a substituent;
(X-Y) represent a mono-anionic bidentate ligand; and $n_{E2}$ represents an integer of 1 to 3.
13. A light emitting device, display device, or illumination device comprising the organic electroluminescent element according to claim 8.
* * * * *